(12) United States Patent
Cameron et al.

(10) Patent No.: US 11,365,261 B2
(45) Date of Patent: Jun. 21, 2022

(54) ANTI-CD38 ANTIBODIES AND METHODS OF USE

(71) Applicant: Sanofi, Paris (FR)

(72) Inventors: Béatrice Cameron, Paris (FR); Tarik Dabdoubi, Paris (FR); Cendrine Lemoine, Paris (FR); Catherine Prades, Choisy le Roi (FR)

(73) Assignee: SANOFI, Paris (FR)

( * ) Notice: Subject to any disclaimer, the term of this patent is extended or adjusted under 35 U.S.C. 154(b) by 0 days.

(21) Appl. No.: 17/503,038

(22) Filed: Oct. 15, 2021

(65) Prior Publication Data

US 2022/0041746 A1 Feb. 10, 2022

Related U.S. Application Data

(63) Continuation of application No. 16/155,807, filed on Oct. 9, 2018, now Pat. No. 11,186,649.

(60) Provisional application No. 62/676,221, filed on May 24, 2018, provisional application No. 62/570,660, filed on Oct. 11, 2017, provisional application No. 62/570,655, filed on Oct. 10, 2017.

(30) Foreign Application Priority Data

Aug. 3, 2018 (EP) .................... 18187186

(51) Int. Cl.
| | |
|---|---|
| *C07K 16/28* | (2006.01) |
| *A61K 39/395* | (2006.01) |
| *A61K 45/06* | (2006.01) |
| *A61P 35/02* | (2006.01) |
| *C07K 16/00* | (2006.01) |
| *A61P 35/00* | (2006.01) |
| *A61K 39/00* | (2006.01) |

(52) U.S. Cl.
CPC ...... *C07K 16/2896* (2013.01); *A61K 39/3955* (2013.01); *A61K 45/06* (2013.01); *A61P 35/00* (2018.01); *A61P 35/02* (2018.01); *C07K 16/00* (2013.01); *C07K 16/2809* (2013.01); *C07K 16/2818* (2013.01); *A61K 2039/505* (2013.01); *C07K 2317/21* (2013.01); *C07K 2317/31* (2013.01); *C07K 2317/33* (2013.01); *C07K 2317/51* (2013.01); *C07K 2317/515* (2013.01); *C07K 2317/524* (2013.01); *C07K 2317/526* (2013.01); *C07K 2317/565* (2013.01); *C07K 2317/567* (2013.01); *C07K 2317/622* (2013.01); *C07K 2317/64* (2013.01); *C07K 2317/76* (2013.01); *C07K 2317/92* (2013.01); *C07K 2319/33* (2013.01)

(58) Field of Classification Search
None
See application file for complete search history.

(56) References Cited

U.S. PATENT DOCUMENTS

| | | | |
|---|---|---|---|
| 9,181,349 B2 | 11/2015 | Baurin et al. | |
| 9,221,917 B2 | 12/2015 | Baurin et al. | |
| 10,882,922 B2 | 1/2021 | Yang et al. | |
| 11,129,905 B2 | 9/2021 | Yang et al. | |
| 2010/0226923 A1 | 9/2010 | Rao et al. | |
| 2012/0076782 A1 | 3/2012 | Tesar et al. | |
| 2012/0201827 A1 | 8/2012 | Elias et al. | |
| 2012/0251541 A1 | 10/2012 | Baurin et al. | |
| 2013/0345404 A1 | 12/2013 | Baurin et al. | |
| 2014/0213772 A1 | 7/2014 | Ghayur et al. | |
| 2014/0322217 A1 | 10/2014 | Moore et al. | |
| 2016/0200811 A1 | 7/2016 | Baurin et al. | |
| 2017/0320967 A1 | 11/2017 | Yang et al. | |
| 2019/0054182 A1 | 2/2019 | Yang et al. | |
| 2019/0106504 A1 | 4/2019 | Wu et al. | |
| 2020/0054765 A1 | 2/2020 | Yang et al. | |
| 2020/0140552 A1 | 5/2020 | Nabel et al. | |
| 2020/0399369 A1 | 12/2020 | Asokan et al. | |
| 2021/0061925 A1 | 3/2021 | Yang et al. | |

FOREIGN PATENT DOCUMENTS

| | | |
|---|---|---|
| CN | 105837688 A | 8/2016 |
| EP | 0308936 A2 | 3/1989 |
| EP | 1 378 520 A1 | 1/2004 |
| EP | 1 736 484 A1 | 12/2006 |
| WO | WO-1996/27011 A1 | 9/1996 |
| WO | WO-1999/051642 A1 | 10/1999 |
| WO | WO-2005/000899 A2 | 1/2005 |
| WO | WO-2005/000899 A3 | 1/2005 |
| WO | WO-2009/149189 A2 | 12/2009 |
| WO | WO-2009/149189 A3 | 12/2009 |
| WO | WO-2011/038290 A2 | 3/2011 |
| WO | WO-2011/154453 A1 | 12/2011 |

(Continued)

OTHER PUBLICATIONS

Alegre, M.L. et al. (Jun. 1, 1994). "A Non-Activating "Humanized" Anti-CD3 Monoclonal Antibody Retains Immunosuppressive Properties In Vivo," *Transplantation* 57(11):1537-1543.

(Continued)

*Primary Examiner* — Nelson B Moseley, II

(74) *Attorney, Agent, or Firm* — Morrison & Foerster LLP

(57) ABSTRACT

The disclosure provides binding proteins that bind CD38 polypeptides, e.g., human and cynomolgus monkey CD38 polypeptides. For example, the binding proteins can be monospecific, bispecific, or trispecific binding proteins with at least one antigen binding domain that binds a CD38 polypeptide. The disclosure also provides methods for making binding proteins that bind CD38 polypeptides and uses of such binding proteins.

29 Claims, 107 Drawing Sheets

Specification includes a Sequence Listing.

(56) References Cited

FOREIGN PATENT DOCUMENTS

| | | |
|---|---|---|
| WO | WO-2012/092612 A1 | 7/2012 |
| WO | WO-2012/135345 A1 | 10/2012 |
| WO | WO-2012/154312 A1 | 11/2012 |
| WO | WO-2012/158948 A1 | 11/2012 |
| WO | WO-2013/070776 A1 | 5/2013 |
| WO | WO-2013/086533 A1 | 6/2013 |
| WO | WO-2013/163427 A1 | 10/2013 |
| WO | WO-2014/089152 A1 | 6/2014 |
| WO | WO-2014/116846 A2 | 7/2014 |
| WO | WO-2014/116846 A3 | 7/2014 |
| WO | WO-2014/144299 A2 | 9/2014 |
| WO | WO-2014/144299 A3 | 9/2014 |
| WO | WO-2015/063339 A1 | 5/2015 |
| WO | WO-2015/149077 A1 | 10/2015 |
| WO | WO-2016/033690 A1 | 3/2016 |
| WO | WO-2016/116626 A1 | 7/2016 |
| WO | WO-2016/196740 A1 | 12/2016 |
| WO | WO-2017/074878 A1 | 5/2017 |
| WO | WO-2017/180913 A2 | 10/2017 |
| WO | WO-2017/180913 A3 | 10/2017 |
| WO | WO-2018-120842 A1 | 7/2018 |
| WO | WO-2018/151841 A1 | 8/2018 |
| WO | WO-2020/076853 A1 | 4/2020 |

OTHER PUBLICATIONS

Almeida, J. et al. (1999). "High-Sensitive Immunophenotyping and DNA Ploidy Studies for the Investigation of Minimal Residual Disease in Multiple Myeloma," *British J of Haematol.* 107:121-131.

Altschul, S.F. et al. (Sep. 1, 1997). "Gapped BLAST and PSI-BLAST: A New Generation of Protein Database Search Programs," *Nucleic Acids Res.* 25(17):3389-3402.

Atwell, S. et al. (Jul. 4, 1997). "Stable Heterodimers from Remodeling the Domain Interface of a Homodimer Using a Phage Display Library," *J. Mol. Biol.* 270(1):26-35.

Brandsma, A.M. et al. (Oct. 1, 2017; e-pub. Aug. 16, 2017). "Single Nucleotide Polymorphisms of the High Affinity IgG Receptor FcγRI Reduce Immune Complex Binding and Downstream Effector Functions," *The Journal of Immunology* 199(7):2432-2439.

Chai, J.G. et al. (1997). "Immobilized Anti-CD3 mAb Induces Anergy in Murine Naive and Memory CD4+ T Cells," *Int Immunol.* 9(7):935-944.

Chen, H.W. et al. (Apr. 1, 2006). "Ex Vivo Expansion of Dendritic-Cell-Activated Antigenspecific CD41\+ T Cells With Anti-CD3/CD28, Interleukin-? and Interleukin-15: Potential for Adoptive T Cell Immunotherapy," Clinical Immunology 119(1):21-31.

Chothia, C. et al. (Aug. 20, 1987). "Canonical Structures for the Hypervariable Regions of Immunoglobulins," *J. Mol. Biol.* 196(4):901-917.

Chothia, C. et al. (Dec. 21-28, 1989). "Conformations of Immunoglobulin Hypervariable Regions," *Nature* 342(6252): 877-883.

Chu, S.Y et al. (Dec. 4, 2014). "Immunotherapy with Long-Lived Anti-CD38×Anti-CD3 Bispecific Antibodies Stimulates Potent T Cell-Mediated Killing of Human Myeloma Cell Lines and CD38+ Cells in Monkeys: A Potential Therapy for Multiple Myeloma," *Blood* 124(21): 4727, 6 pages.

Colombian Opposition mailed on Mar. 15, 2019 for CO Application No. NC2018/0012107 filed on Nov. 9, 2018, twenty-one pages. (English Translation).

Deckert, J. et al. (2014; e-pub. Jul. 1, 2014). "SAR650984, a Novel Humanized CD38-Targeting Antibody, Demonstrates Potent Anti-Tumor Activity in Models of Multiple Myeloma and Other CD38+ Hematologic Malignancies," *Clin. Cancer Res* 20:4574-4583.

DiGiammarino, E. et al. (Sep.-Oct. 2011, e-pub. Sep. 1, 2011). "Ligand Association Rates to the Inner-Variable-Domain of a Dual-Variable-Domain Immunoglobulin are Significantly Impacted by Linker Design," *MAbs*. 3(5):487-494.

Esensten, J.H. et al. (May 17, 2016). "CD28 Costimulation: From Mechanism to Therapy," *Immunity* 44:973-988.

Findlay, L. et al. (2010; e-pub. Nov. 4, 2009). "Improved In Vitro Methods to Predict the In Vivo Toxicity in Man of Therapeutic Monoclonal Antibodies Including TGN1412," *J ImmunolMethods* 352:1-12.

Fournier, P. et al. (Jan. 2010). "Tumor Antigen-Dependent and Tumor Antigen-Independent Activation of Antitumor Activity in T Cells by a Bispecific Antibody-Modified Tumor Vaccine," *Clinical & Developmental Immunology* 2010(1):Article IDS 423781, 12 pages.

Garfall, A.L. et al. (Nov. 21, 2019). "Three is a Charm for an Antibody to Fight Cancer," Nature 575:450-451.

Gratama, J,W. et al. (Sep. 1, 2001). "Tetramer-Based Quantification of Cytomegalovirus (CMV)-Specific CD81 T Lymphocytes in T-Cell-Depleted Stem Cell Grafts and After Transplantation May Identify Patients at Risk for Progressive CMV Infection," *Blood* 98(5):1358-1364.

Haas, C. et al. (Mar. 31, 2005; e-pub. Nov. 25, 2004). "T-cell Triggering by CD3- and CD28-Binding Molecules Linked to a Human Virus-Modified Tumor Cell Vaccine," *Vaccine* 23(19):2439-2453.

Hartman, W.R. et al. (May 17, 2010). "CD38 Expression, Function, and Gene Resequencing in a Human Lymphoblastoid Cell Line-Based Model System," Leukemia and Lymphoma 51 (7):1315-1325.

Hinton, P.R. et al. (Jan. 1, 2006). "An Engineered Human IgG1 Antibody With Longer Serum Half-Life," *J. Immunol.* 176(1):346-356.

Hitoshi, N. et al. (Dec. 15, 1991). "Efficient Selection for High-Expression Transfectants with a Novel Eukaryotic Vector," Gene 108(2):193-199.

Hui, E. et al. (Mar. 31, 2017). "T Cell Costimulatory Receptor CD28 is a Primary Target for PD-1-Mediated Inhibition," *Science* 355(6332):1428-1433.

International Preliminary Report on Patentability dated May 11, 2018 for PCT Application No. PCT/US2016/058540 filed on Oct. 24, 2016, seven pages.

International Preliminary Report on Patentability dated Oct. 25, 2018 for PCT Application No. PCT/US2017/027488, filed on Apr. 13, 2017, thirty one pages.

International Preliminary Report on Patentability dated Apr. 8, 2021 for PCT Application No. PCT/US2019/055232, filed on Oct. 8, 2019, 7 pages.

International Search Report and Written Opinion dated Jan. 2, 2018 for PCT Application No. PCT/US2017/027488, filed on Apr. 13, 2017, forty four pages.

International Search Report and Written Opinion of the International Searching Authority dated Mar. 10, 2017 for PCT Application No. PCT/US2016/058540 filed on Oct. 24, 2016, fifteen pages.

International Search Report dated Dec. 17, 2019, for PCT Application No. PCT/US2019/055232, filed on Oct. 8, 2019, seven pages.

International Search Report dated May 17, 2019, for PCT Application No. PCT/US2018/055084, filed on Oct. 9, 2018, twelve pages.

Invitation to Pay Additional Fees and, Where Applicable, Protest Fee dated Feb. 20, 2019, for PCT Application No. PCT/US2018/055084, filed on Oct. 9, 2018, twenty three pages.

Invitation to Pay Additional Fees and, Where Applicable, Protest Fee dated Oct. 16, 2017, for PCT Application No. PCT/US2017/027488, filed on Apr. 13, 2017, twenty eight pages.

Jakob, C.G. et al. (May 1, 2013, e-pub. Apr. 2, 2013). "Structure Reveals Function of the Dual Variable Domain Immunoglobulin (DVD-Ig™) Molecule," MAbs. 5(3):358-363.

Kalim, M. et al. (2017; e-pub. Aug. 2, 2017). "Intracellular Trafficking of New Anticancer Therapeutics: Antibody-Drug Conjugates," *Drug Des. Devel. Ther.* 11:2265-2276.

Kilpatrick, K.E. et al. (Aug. 1997). "Rapid Development of Affinity Matured Monoclonal Antibodies Using RIMMS," *Hybnidoma* 16(4):381-389.

Lefranc, M.P. et al. (Jan. 2003). "IMGT Unique Numbering for Immunoglobulin and T Cell Receptor Variable Domains and Ig Superfamily V-Like Domains," *Dev. Comp. Immunol.* 27(1):55-77.

Li, T. et al. (Jun. 2, 2016). "Immuno-Targeting the Multifunctional CD38 Using Nanobody," *Scientific Reports* 6(1):27055, 11 pages.

(56) References Cited

OTHER PUBLICATIONS

Liu, Q. et al. (Sep. 2005). "Crystal Structure of Human CD38 Extracellular Domain," *Structure* 13(9):1331-1339.
Maccallum, R.M. et al. (Oct. 11, 1996). "Antibody-Antigen Interactions: Contact Analysis and Binding Site Topography," *J. Mol. Biol.* 262(5): 732-745.
Mariuzza, R.A. et al. (Jun. 1987). "The Structural Basis of Antigen-Antibody Recognition," Annual Review of Biophysics and Biophysical Chemistry 16(1):139-159.
Masui, S. et al. (Mar. 1, 2005). "An Efficient System to Establish Multiple Embryonic Stem Cell Lines Carrying an Inducible Expression Unit," *Nucleic Acids Res.* 33(4):e43, pp. 1-8.
Mateo, G. et al. (May 15, 2005). "Genetic Abnormalities and Patterns of Antigenic Expression in Multiple Myeloma," *Clin. Cancer Res.* 11(10):3661-3667.
McDermott, S.P. et al. (Jul. 15, 2010, e-published as Apr. 19, 2010). "Comparison of Human Cord Blood Engraftment Between Immunocompromised Mouse Strains," *Blood* 116(2):193-200.
McKeage, K. (Feb. 2016). "Daratumumab: First Global Approval," *Drugs.* 76(2):275-281.
Merchant, A.M. et al. (Jul. 1998). "An Efficient Route to Human Bispecific IgG," *Nature Biotechnol.* 16(7):677-681.
Moore, G. et al. (Dec. 5, 2015). "1798 Tuning T Cell Affinity Improves Efficacy and Safety of Anti-CD38×Anti-CD3 Bispecific Antibodies in Monkeys—a Potential Therapy for Multiple Myeloma," American Society of Hematology, Poster Abstract presented at 57th Annual Meeting & Exposition, Orlando, FL, three pages.
Morphosys. (Nov. 25, 2010). "R&D Day 2010," 102 pages.
Nair, J.R. et al. (2011; e-pub. Jun. 29, 2011). "CD28 Expressed on Malignant Plasma Cells Induces a Prosurvival and Immunosuppressive Microenvironment," *J Immunol.* 187:1243-1253.
Padlan, E.A. et al. (Jan. 1995). "Identification of Specificity-Determining Residues in Antibodies," *FASEB J.* 9(1):133-139.
Parslow, A.C. et al. (2016). "Antibody-Drug Conjugates for Cancer Therapy," *Biomedicines* 4:14, pp. 1-17.
Penaranda, C.I. et al. (Aug. 15, 2011). "Anti-CD3 Therapy Promotes Tolerance by Selectively Depleting Pathogenic Cells While Preserving Regulatory T Cells," *J Immunol.* 187(4):2015-2022, 19 pages.
Peters, B. et al. (Mar. 2005; e-pub. Mar. 15, 2005). "The Immune Epitope Database and Analysis Resource: From Vision to Blueprint," *PLos Biol.* 3(3):e91, pp. 0379-0381.
Ridgway, J.B. et al. (Jul. 1996). "'Knobs-Into-Holes' Engineering of Antibody CH3 Domains for Heavy Chain Heterodimerization," *Protein Eng.* 9(7):617-621.
Robillard, N. et al. (Jun. 1998). "CD28, a Marker Associated with Tumoral Expansion in Multiple Myeloma," *Clin Cancer Res.* 4:1521-1526.
Rudikoff, S. et al. (Mar. 1982). "Single Amino Acid Substitution Altering Antigen-Binding Specificity," Proc. Natl. Acad. Sci. USA 79(6):1979-1983.
Sarzotti-Kelsoe, M. et al. (Jul. 2014; e-published on Dec. 1, 2013). "Optimization and Validation of the TZM-BI Assay for Standardized Assessments of Neutralizing Antibodies Against HIV-1," *J. Immunological Methods* 409:131-146, thirty seven pages.
Sharma, P. et al. (Apr. 3, 2015). "The Future of Immune Checkpoint Therapy," *Science* 348(6230):56-61.
Shields, R.L. et al. (Mar. 2, 2001). "High Resolution Mapping of the Binding Site on Human IgG1 for FcγRI, FcγRII, FcγRI11, and FcRn and Design of IgG1 Variants with Improved Binding to the FcγR," *J. Biol. Chem.* 276(9):6591-6604.
Shultz, L.D. et al. (Jul. 2014). "Human Cancer Growth and Therapy In NOD/SCID/IL2Rγ[null] (NSG) Mice," *Cold Spring Harb. Protoc.* 2014(7):694-708.
Smith, E.J. et al. (Dec. 11, 2015). "A Novel, Native-Format Bispecific Antibody Triggering T-Cell Killing of B-Cells is Robustly Active in Mouse Tumor Models and Cynomolgus Monkeys," *Sci. Rep.* 5:17943, pp. 1-12.

Song, L.-P. et al. (Jun. 1, 2003). "A New Model of Trispecific Antibody with Cytotoxicity Against Tumor Cells," *Acta Biochimica Etbiophysica Sinica* 35(6):503-510.
Spiess, C. et al. (2015; e-pub. Jan. 27, 2015). "Alternative Molecular Formats and Therapeutic Applications for Bispecific Antibodies," *Molecular Immunology* 67(2):95-106.
Spiess, C. et al. (Sep. 13, 2013, e-published on Jul. 23, 2013). "Development of a Human IgG4 Bispecific Antibody for Dual Targeting of Interleukin-4 (IL-4) and Interleukin-13 (IL-13) Cytokines," *J. Biol. Chem.* 288:26583-26593.
Stebbings, R. et al. (Sep. 1, 2007). "'Cytokine Storm" in The Phase I Trial of Monoclonal Antibody TGN1412: Better Understanding the Causes to Improve Preclinical Testing of Immunotherapeutics," *J. Immunol.* 179(5):3325-3331.
Steinmetz, A. et al. (Mar. 16, 2016). "CODV-Ig, A Universal Bispecific Tetravalent and Multifunctional Immunoglobulin Format for Medical Applications," *MABS* 8(5):867-878, with Supplementary material, fifty nine pages.
Stevenson, G.T. (Nov.-Dec. 2006). "CD38 as a Therapeutic Target," *Mol. Med.* 12(11-12):345-346.
Suntharalingam, G. et al. (Sep. 7, 2006). "Cytokine Storm in a Phase 1 Trial of the Anti-CD28 Monoclonal Antibody TGN1412," *N Engl J Med* 355(10):1018-1028.
Tabares, P. et al. (Apr. 2014; e-pub. Feb. 1, 2014). "Human Regulatory T Cells are Selectively Activated by Low-Dose Application of the CD28 Superagonist TGN1412/TAB08," *Eur J Immunol.* 44:1225-1236.
Thompson, J.D. (Nov. 11, 1994). "CLUSTAL W: Improving the Sensitivity of Progressive Multiple Sequence Alignment Through Sequence Weighting, Position-Specific Gap Penalties and Weight Matrix Choice," *Nucleic Acids Res.* 22(22):4673-4680.
Tiller, T. et al. (Oct. 2009). "Cloning and Expression of Murine Ig Genes From Single B Cells," *J. Immunol. Methods* 350(1-2):183-193.
U.S. Appl. No. 16/596,474, filed Oct. 8, 2019, for Wu et al.
U.S. Appl. No. 17/099,439, filed Nov. 16, 2020, for Yang et al.
U.S. Appl. No. 17/515,227, filed Oct. 29, 2021, for Yang et al.
U.S. Appl. No. 17/404,908, filed Aug. 17, 2021, for Yang et al.
Waibler, Z. et al. (Mar. 5, 2008). "Signaling Signatures and Functional Properties of Anti-Human CD28 Superagonistic Antibodies," *PLoS One* 3(3):e1708, pp. 1-13.
Wang, X. (Apr. 1, 2004). "A New Recombinant Single Chain Trispecific Antibody Recruits T Lymphocytes to Kill CEA (Carcinoma Embryonic Antigen) Positive Tumor Cells In Vitro Efficiently," *Journal of Biochemistry* 135(4):555-565.
Wang, X. et al. (Jan. 2018; e-pub. Oct. 6, 2017). "IgG Fc Engineering to Modulate Antibody Effector Functions," *Protein & Cell* 9(1):63-73.
Wennerberg, A.E. et al. (Oct. 1993). "Hepatocyte Paraffin 1: A Monoclonal Antibody that Reacts with Hepatocytes and can be Used for Differential Diagnosis of Hepatic Tumors," *Am J Pathol.* 143(4):1050-1054.
Willems, A. et al. (Nov. 1, 2005; e-pub. May 13, 2005). "CD3×CD28 Cross-Interacting Bispecific Antibodies Improve Tumor Cell Dependent T-Cell Activation," *Cancer Immunology, Immunotherapy* 54(11):1059-1071.
Written Opinion of the International Searching Authority dated May 17, 2019, for PCT Application No. PCT/US2018/055084, filed on Oct. 9, 2018, fifteen pages.
Written Opinion of the International Searching Authority dated Dec. 17, 2019, for PCT Application No. PCT/US2019/055232, filed on Oct. 8, 2019, six pages.
Wu, L. et al. (Nov. 18, 2019). "Trispecific Antibodies Enhance the Therapeutic Efficacy of Tumor-Directed T Cells Through T Cell Receptor Co-Stimulation," Nat Cancer 1:86-98.
Xu, L. et al. (Oct. 6, 2017; e-pub. Sep. 20, 2017). "Trispecific Broadly Neutralizing HIV Antibodies Mediate Potent SHIV Protection in Macaques," *Science* 358(6359):85-90, 17 pages.

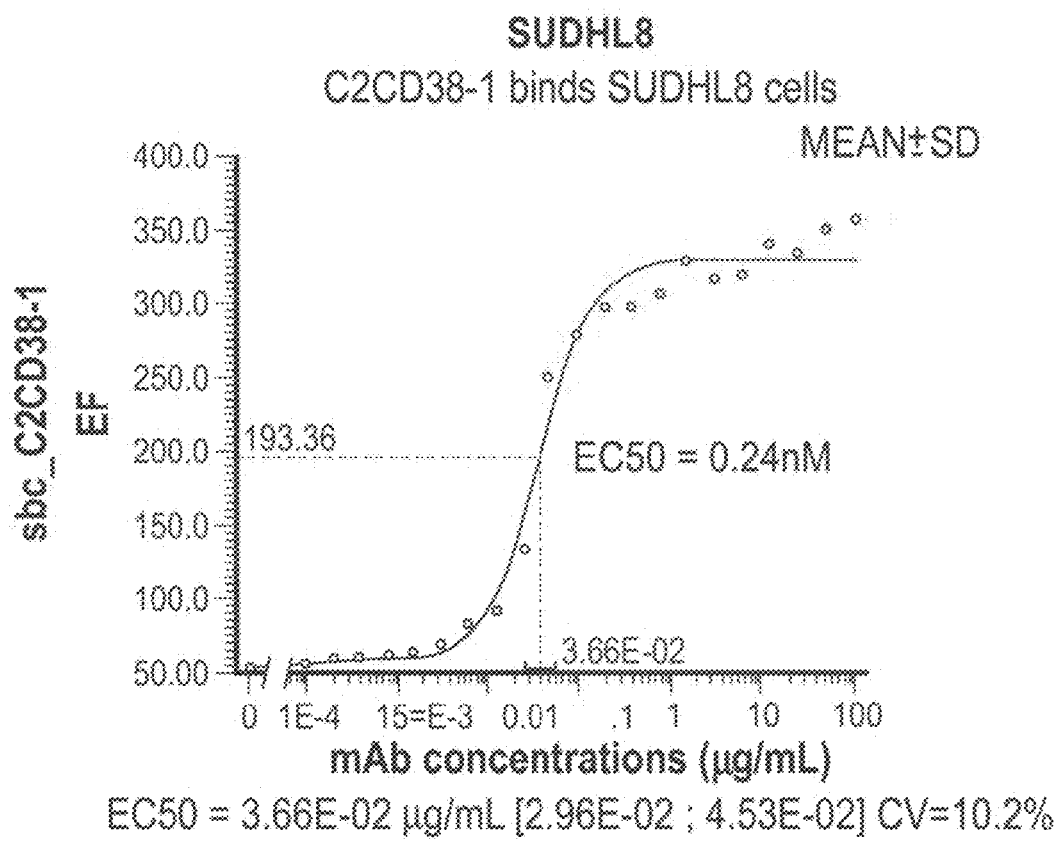
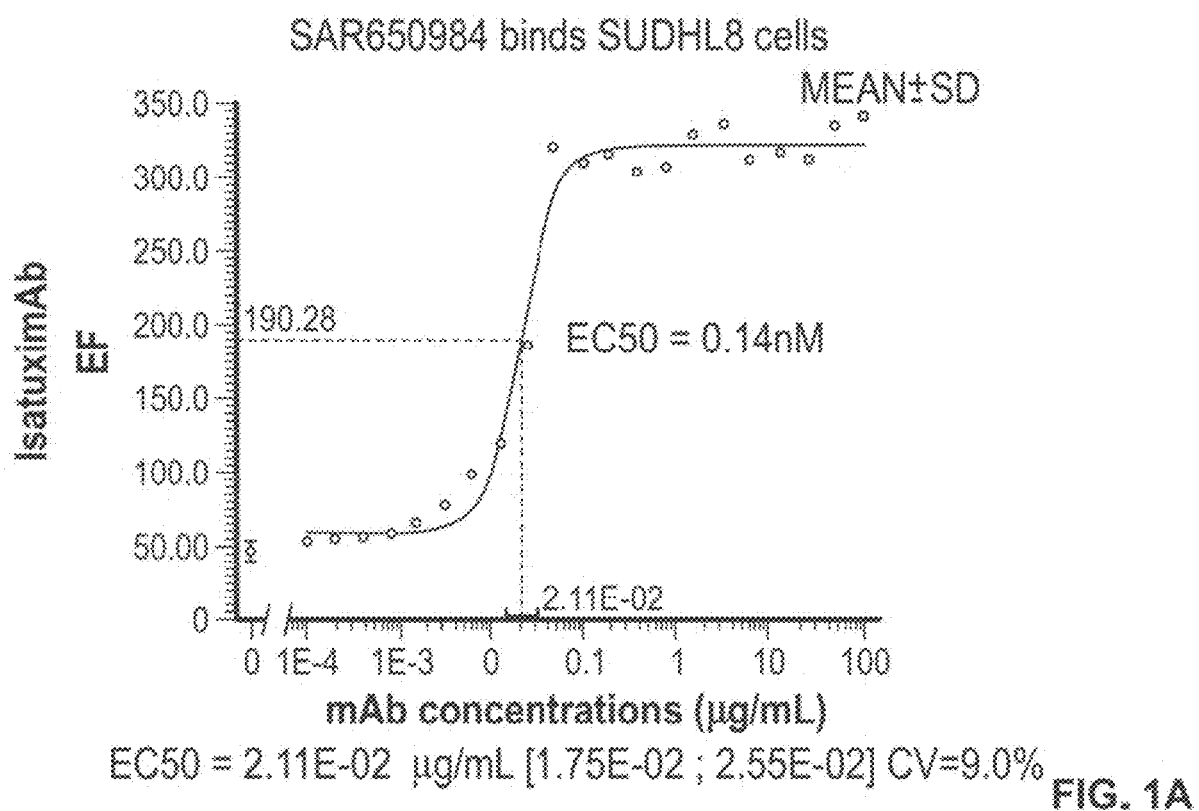
FIG. 1A

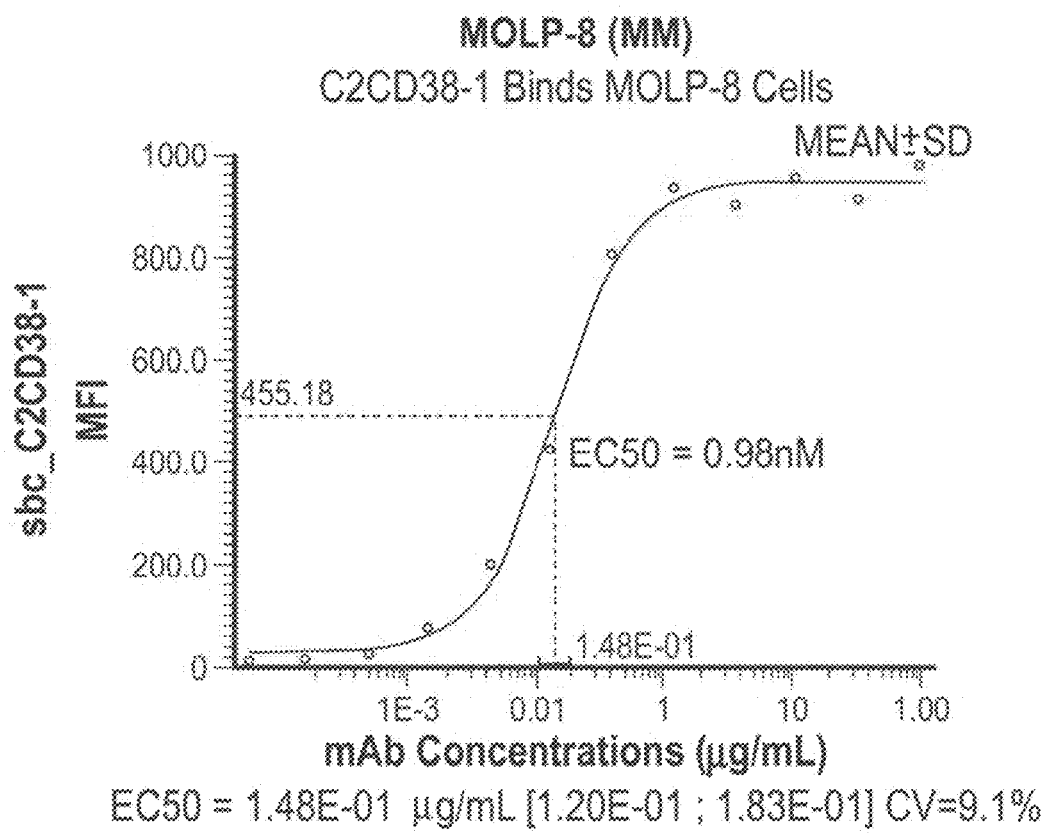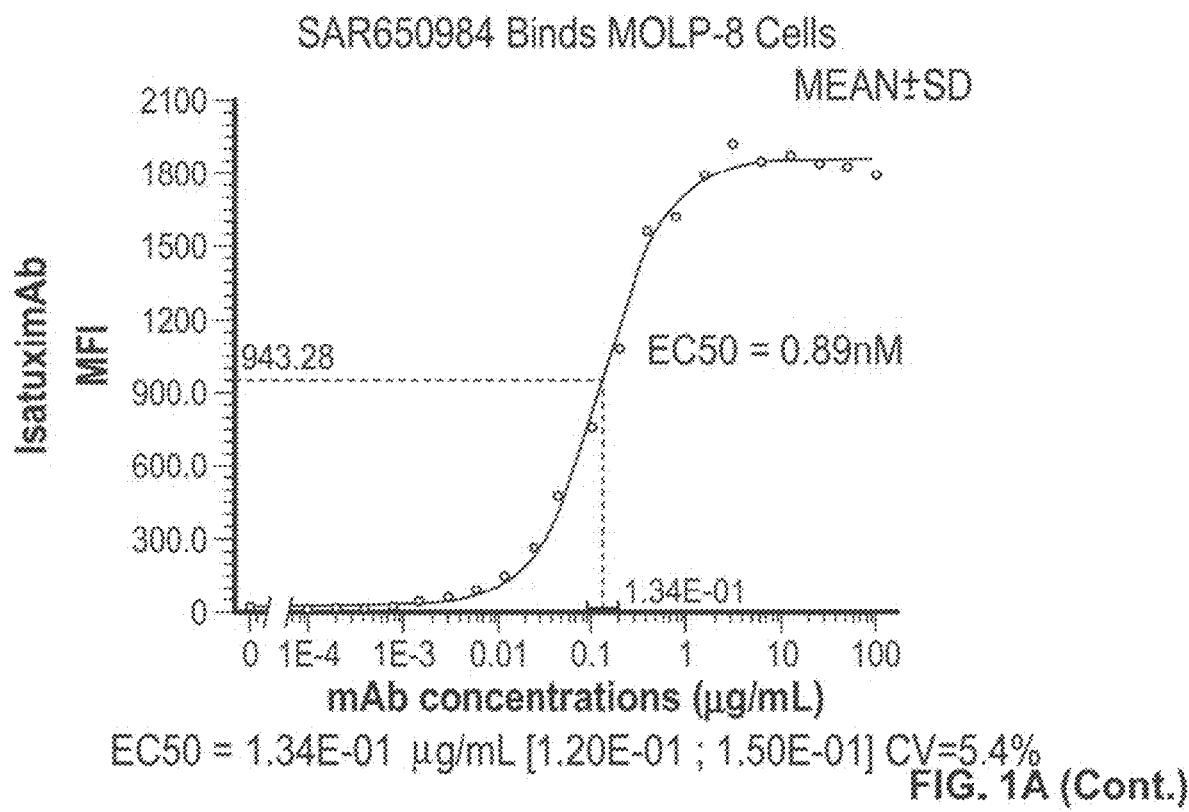
FIG. 1A (Cont.)

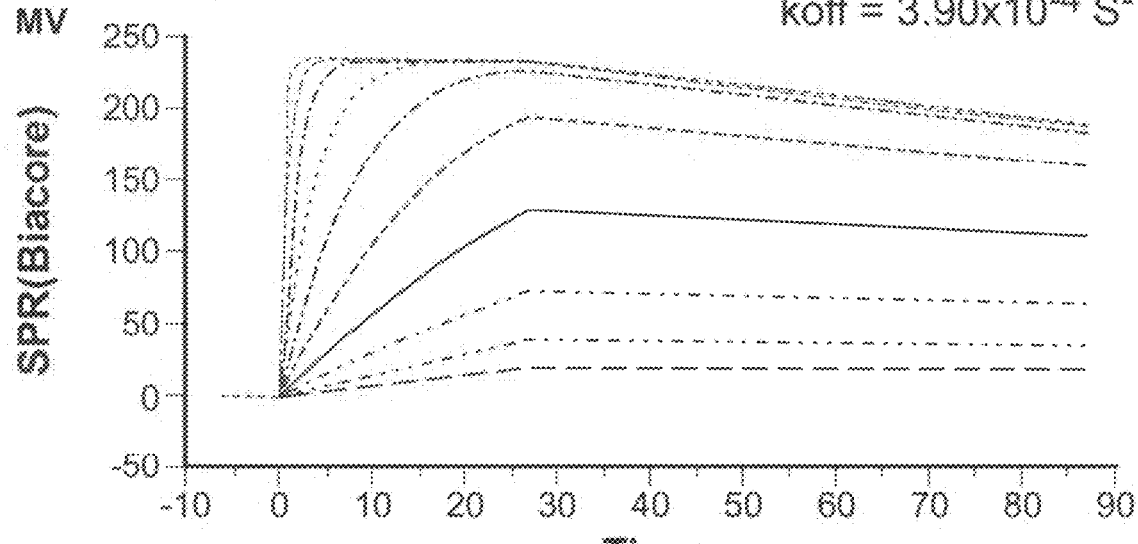
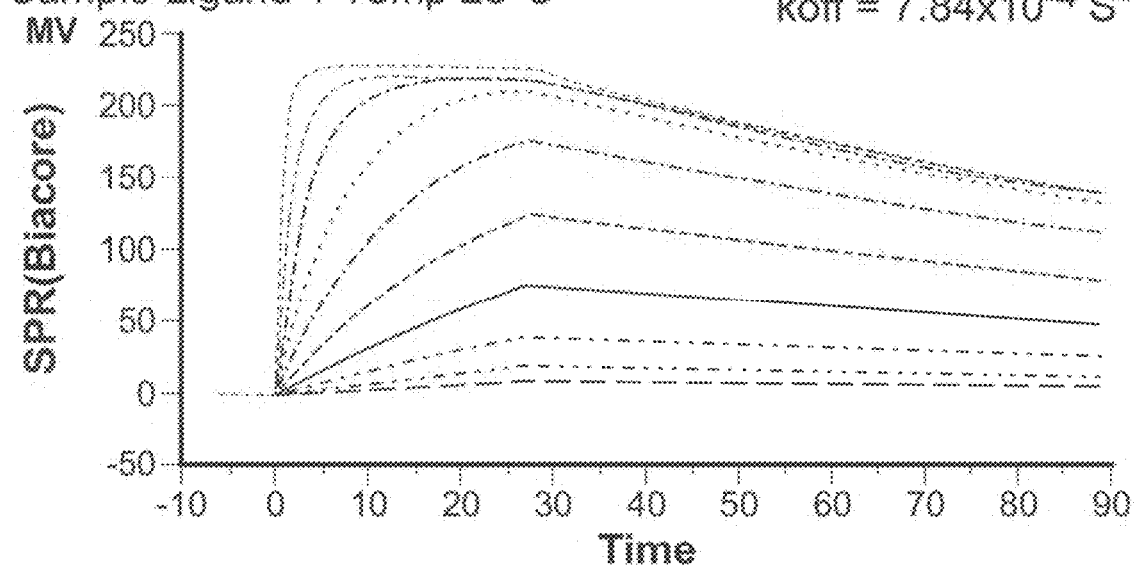
FIG. 2B

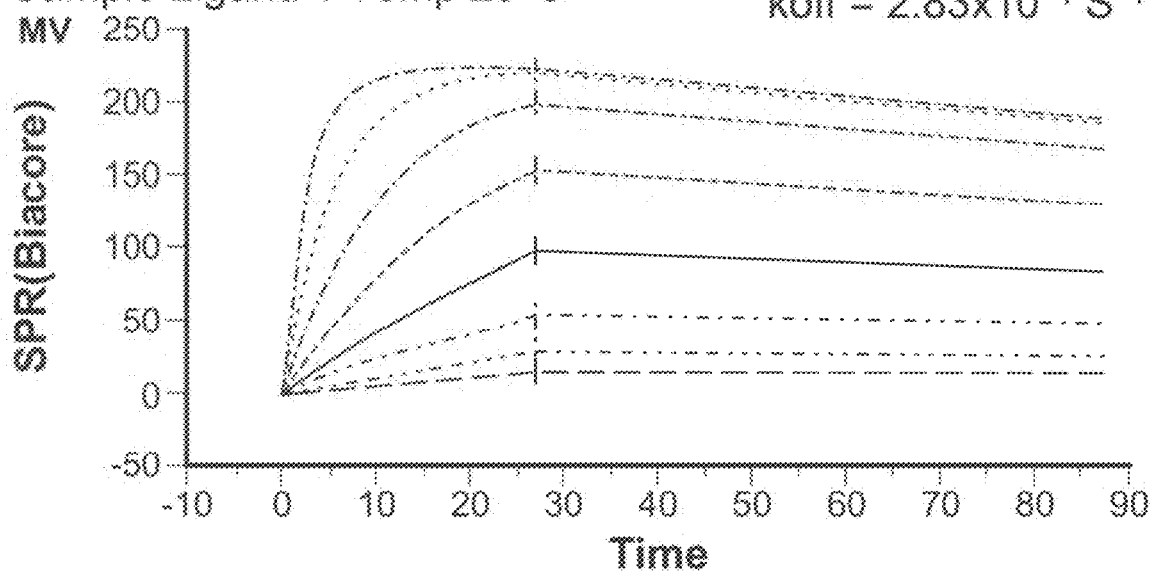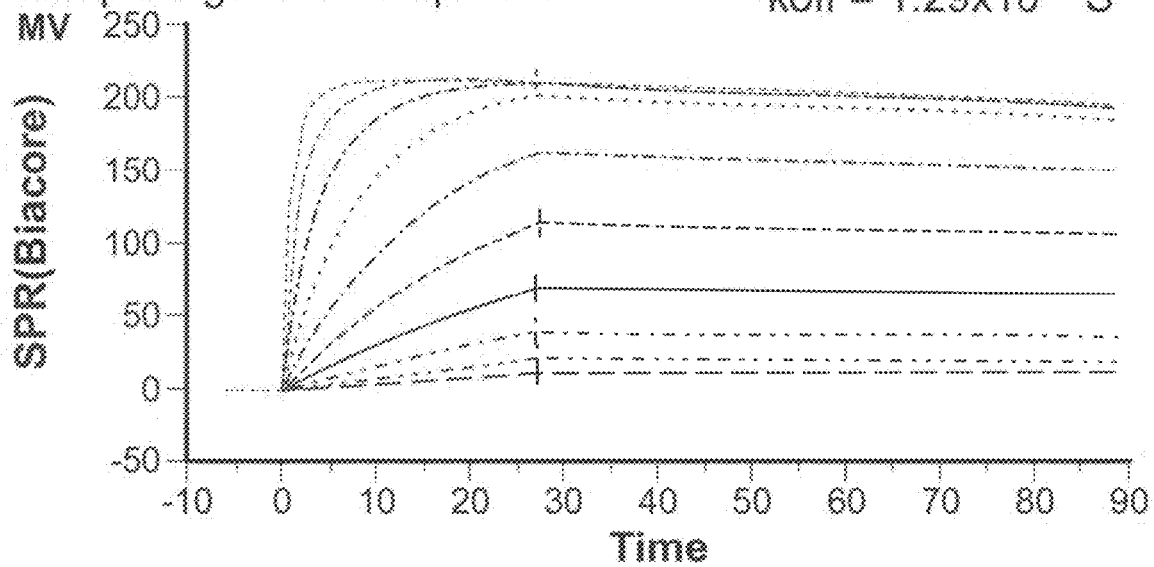
FIG. 2D

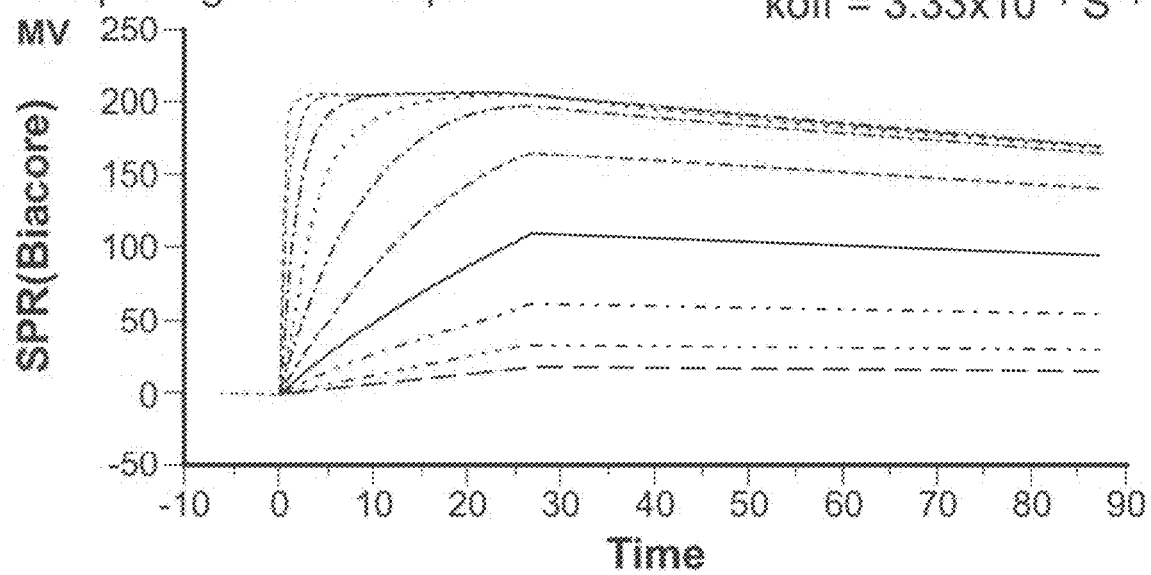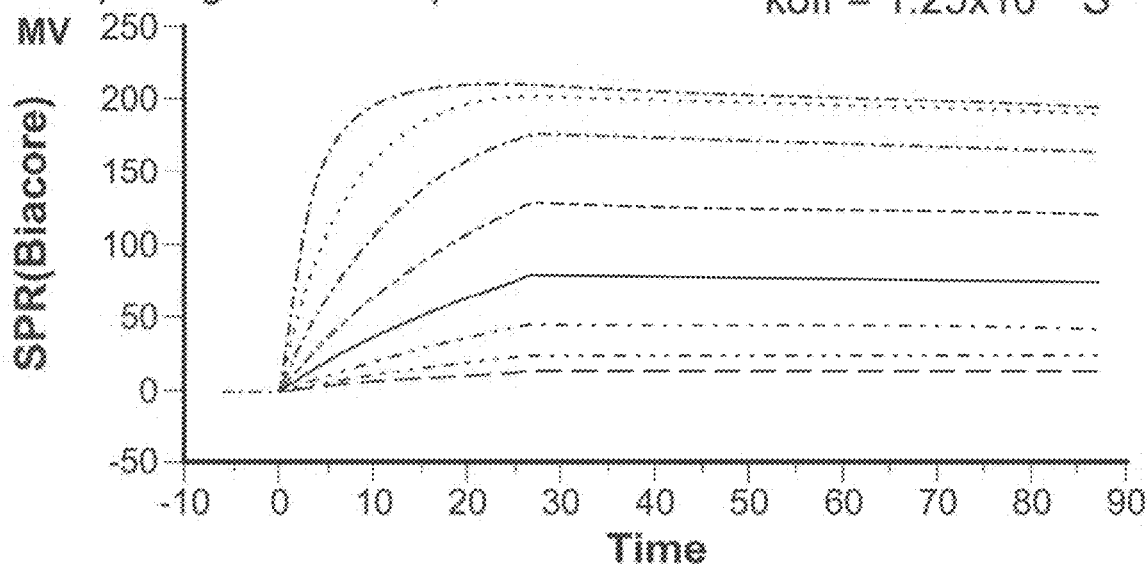
FIG. 2F

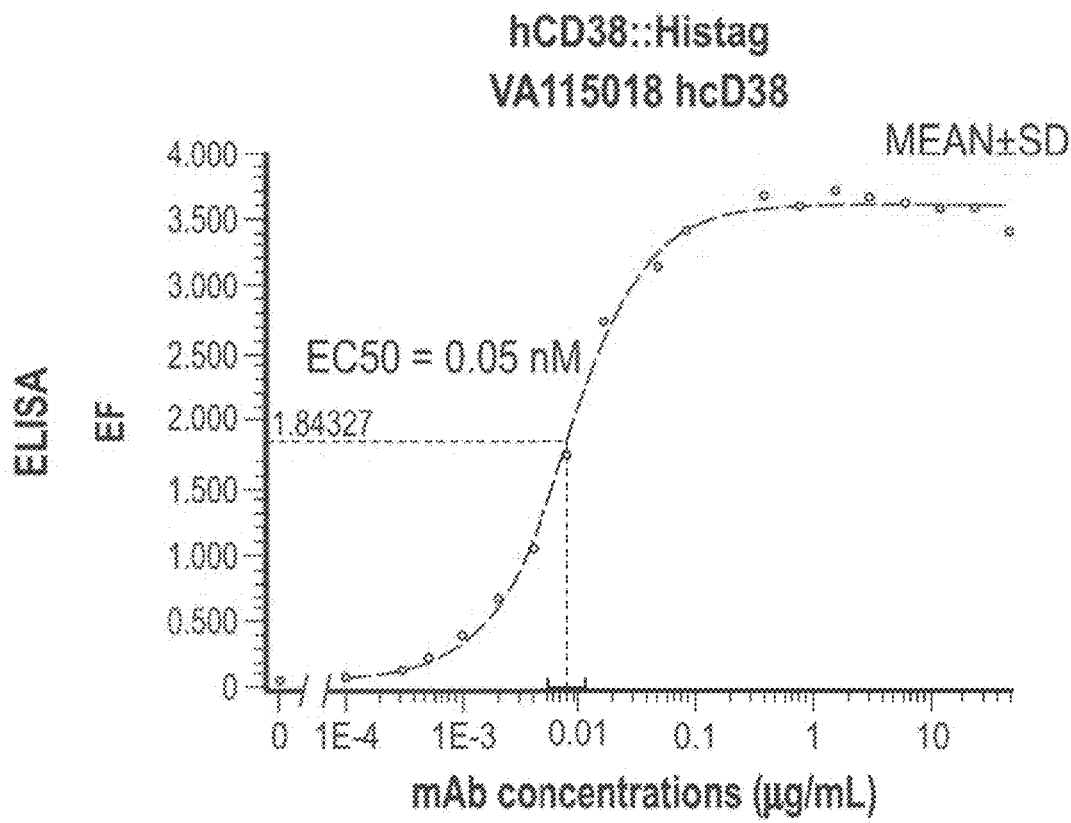
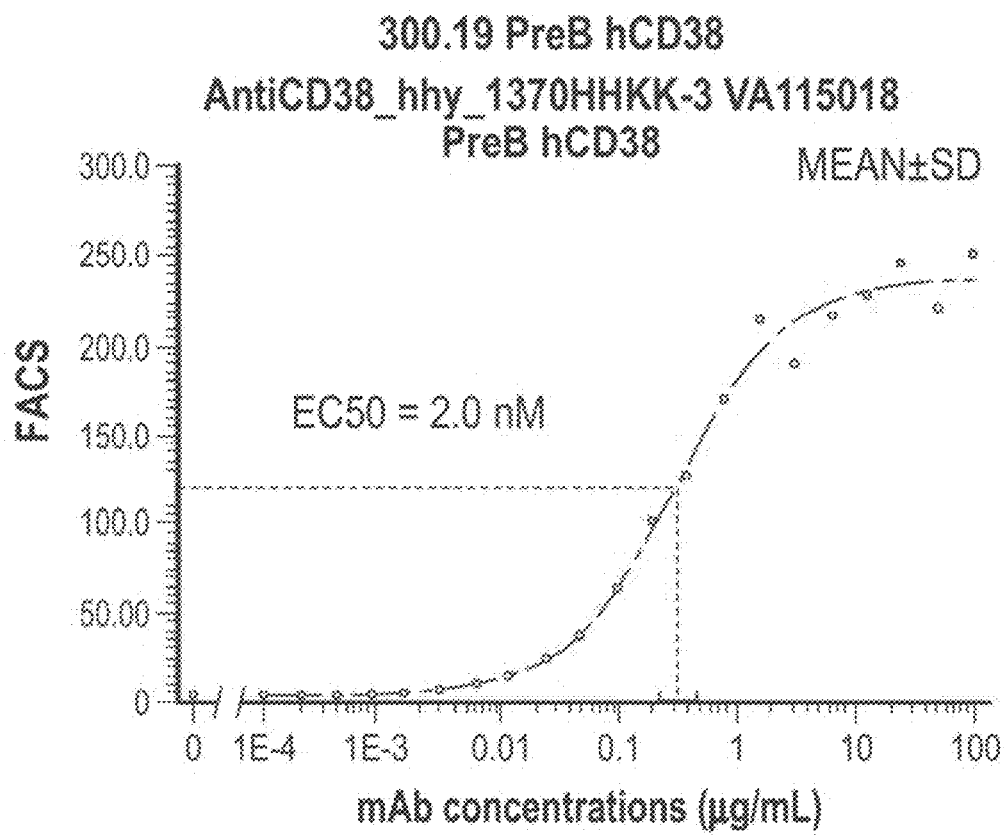
FIG. 2G

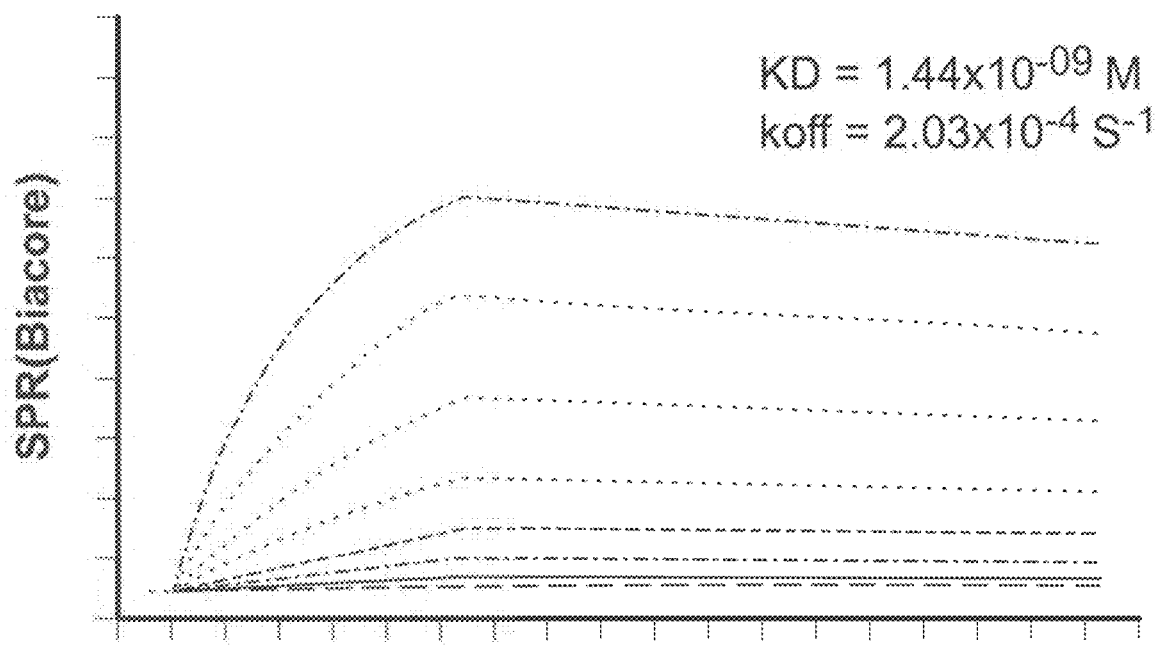
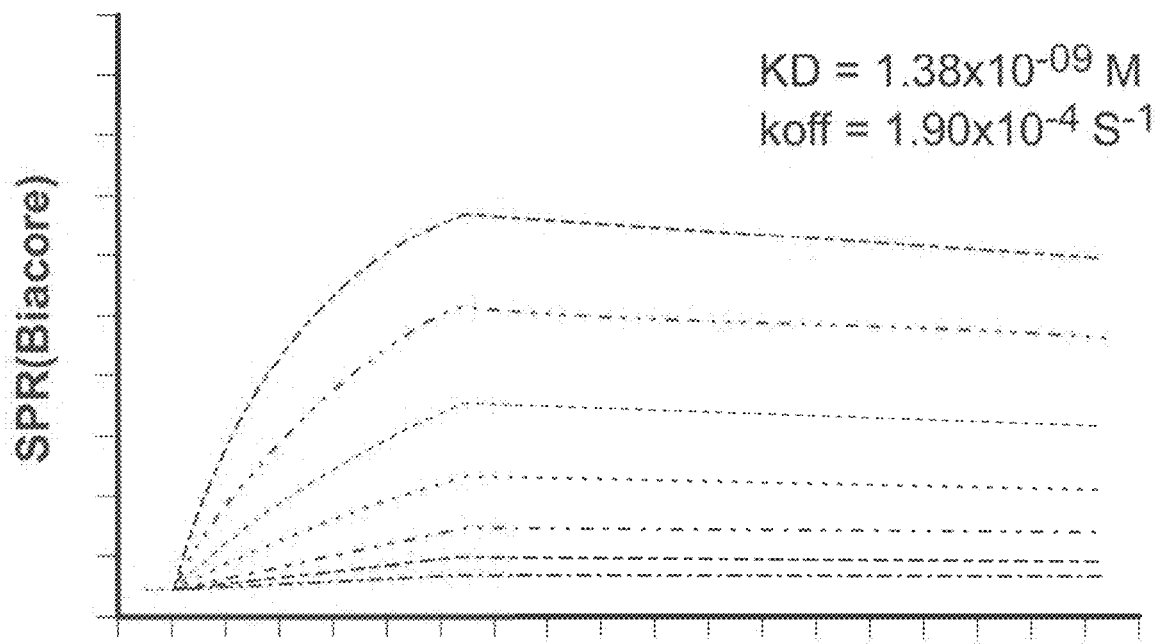
FIG. 2H

| | | ELISA EC50 nM | | SPR KD nM | | FACS EC50 nM | | Human V region identity | |
|---|---|---|---|---|---|---|---|---|---|
| | INN nomenclature | hu | cyno | hu | cyno | hu | cyno | H | L |
| AntiCD38_sbc_C2CD088-1_VL1-VH1 | -zumAb | 0.11 | 0.10 | 0.33 | 3.44 | 0.38 | 0.76 | 84.7% | 87.1% |
| AntiCD38_sbc_C2CD088-1_VL3-VH3 | -zumAb | 0.10 | 0.15 | 0.49 | 0.71 | 0.78 | 1.31 | 83.7% | 83.9% |
| AntiCD38_sbc_C2CD088-1_VL3-VH5 | -zumAb | 0.10 | 0.07 | 0.82 | 1.14 | 0.55 | 1.15 | 80.6% | 83.9% |
| AntiCD38_sbc_C2CD088-1_VL3-VH6 | -zumAb | 0.14 | 0.14 | 0.31 | 0.58 | 0.88 | 1.06 | 81.6% | 83.9% |
| AntiCD38_hhy_13704HHKK-3 | -ximAb | 0.05 | 0.09 | 1.44 | 1.38 | 2.00 | 1.14 | 89.0% | 85.6% |

FIG. 2H

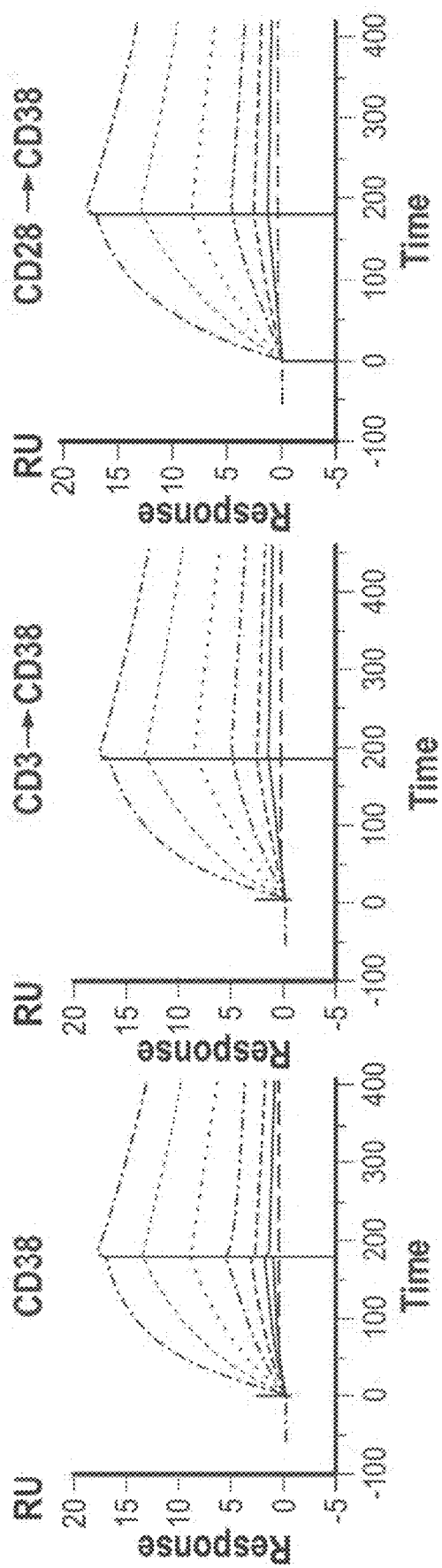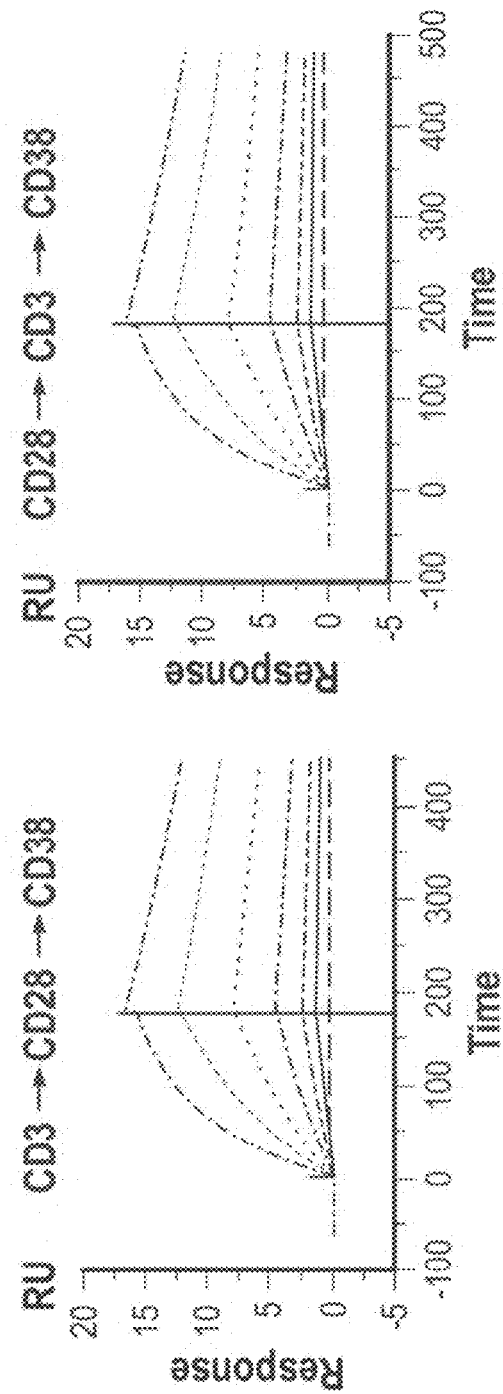
FIG. 3C

Affinity of WT TsAbs for individual targets ($K_D$ round up to integer)

| TsAbs | CD38 | CD28 | CD3 | Affinity order ranking |
|---|---|---|---|---|
| CD38$_{SB19}$CD28$_{sup}$CD3$_{mid}$ | 2 nM | 3 nM | 23 nM | • CD38 binding: MsAb ≈ TsAbs |
| CD38$_{SB19}$CD28$_{cys}$CD3$_{mid}$ | 2 nM | 17 nM | 19 nM | |
| CD38$_{VH1}$CD28$_{sup}$CD3$_{mid/low}$ | 4/6 nM | 2/4 nM | 21/76 nM | • CD28 binding: MsAb > TsAb ≥ BsAbs |
| CD38$_{VH1}$CD28$_{cys}$CD3$_{mid/low}$ | 4/6 nM | 18/34 nM | 23/59 nM | |
| CD38$_{MHY1357}$CD28$_{sup}$CD3$_{mid}$ | 1 nM | 5 nM | 48 nM | • CD3 binding: MsAb ≈ BsAb ≈ TsAb |
| CD38$_{MHY1379}$CD28$_{cys}$CD3$_{mid}$ | 1 nM | 19 nM | 44 nM | |

Impact of multi-target binding to CD38$_{SB19}$CD28$_{sup}$CD3$_{mid}$

| State of TsAb | CD38 | CD28 | CD3 | Comments |
|---|---|---|---|---|
| Single target | 2 nM | 3 nM | 23 nM | Fast kinetics of CD3 binding when all targets are present |
| All targets | 2 nM | 4 nM | 19 nM | |

FIG. 5

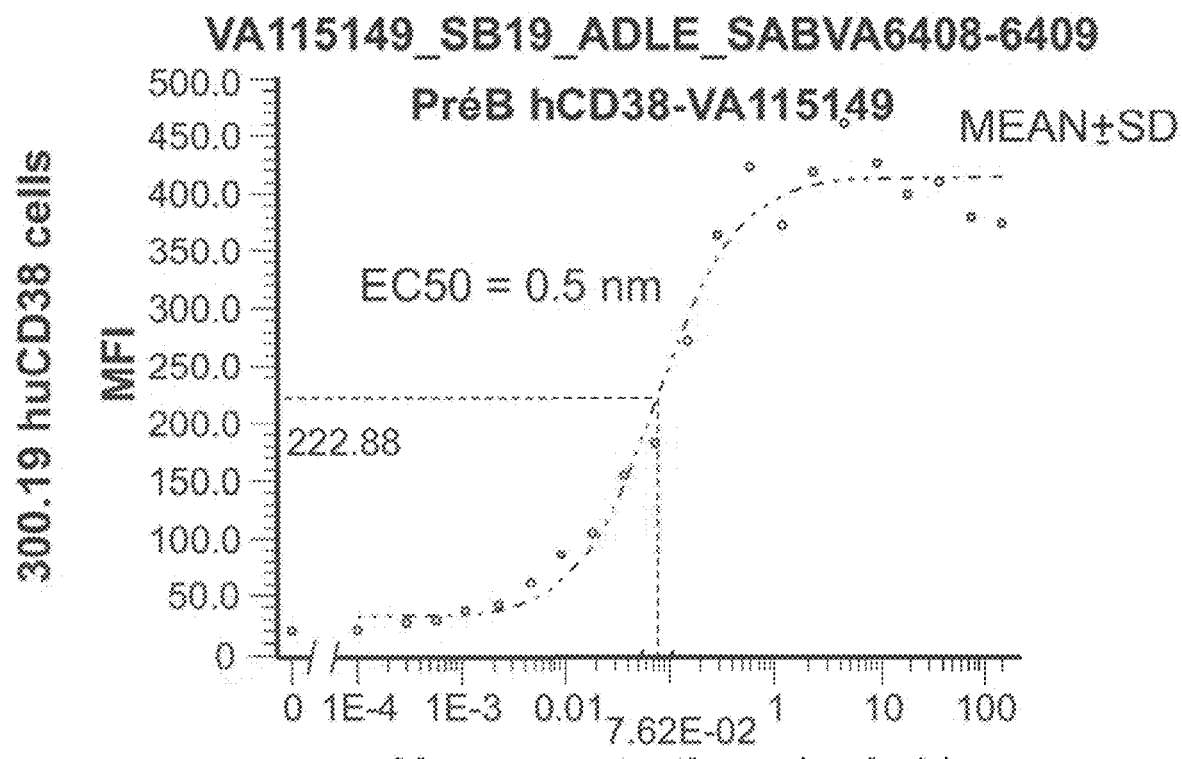
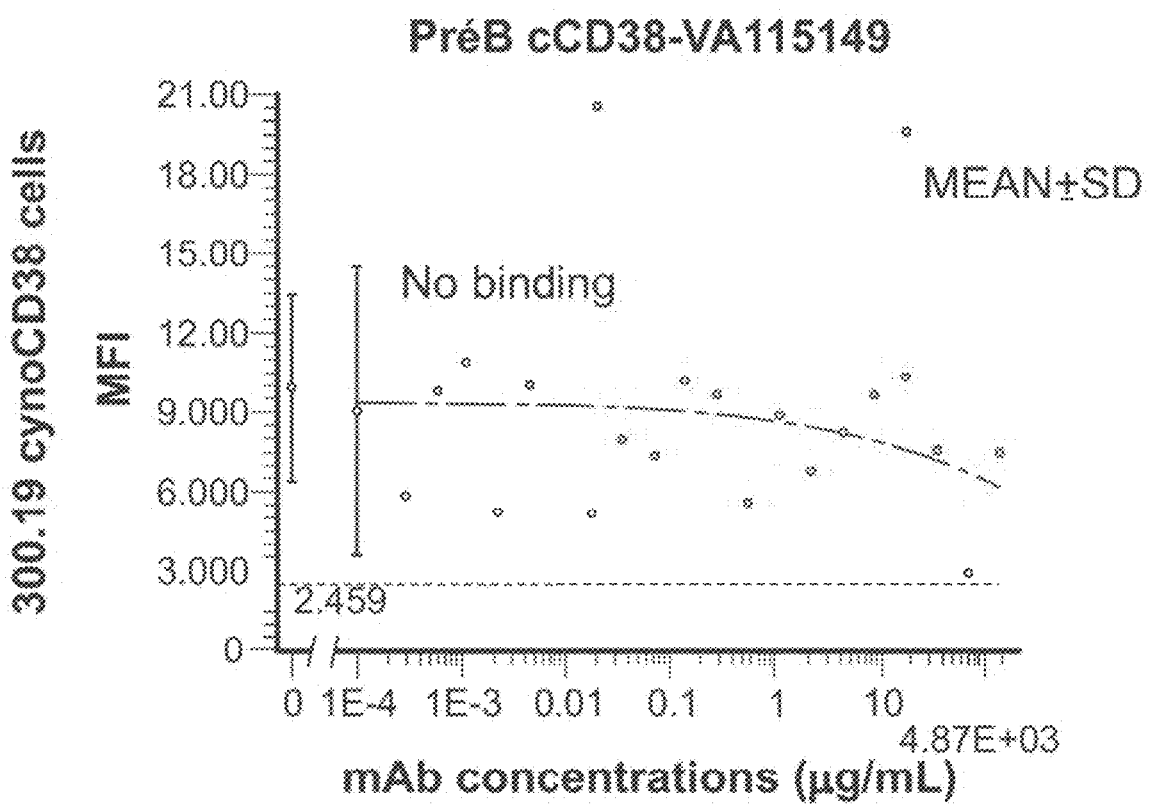
FIG. 6A (Cont.)

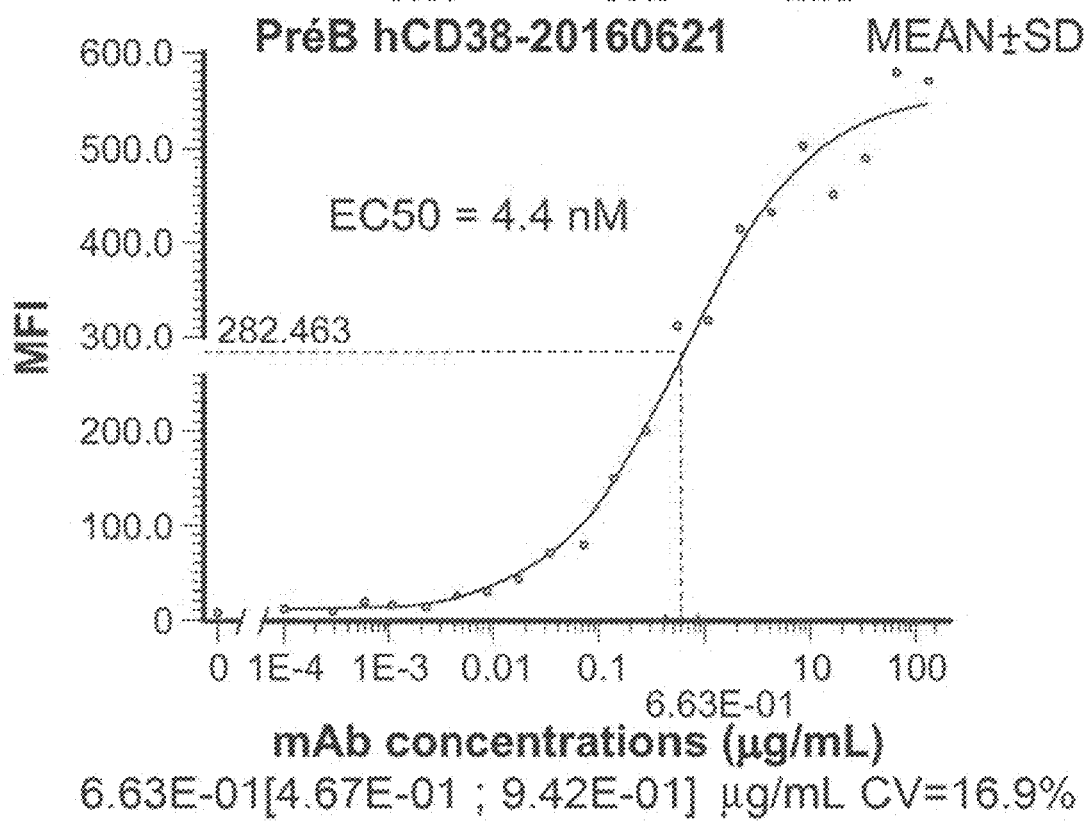
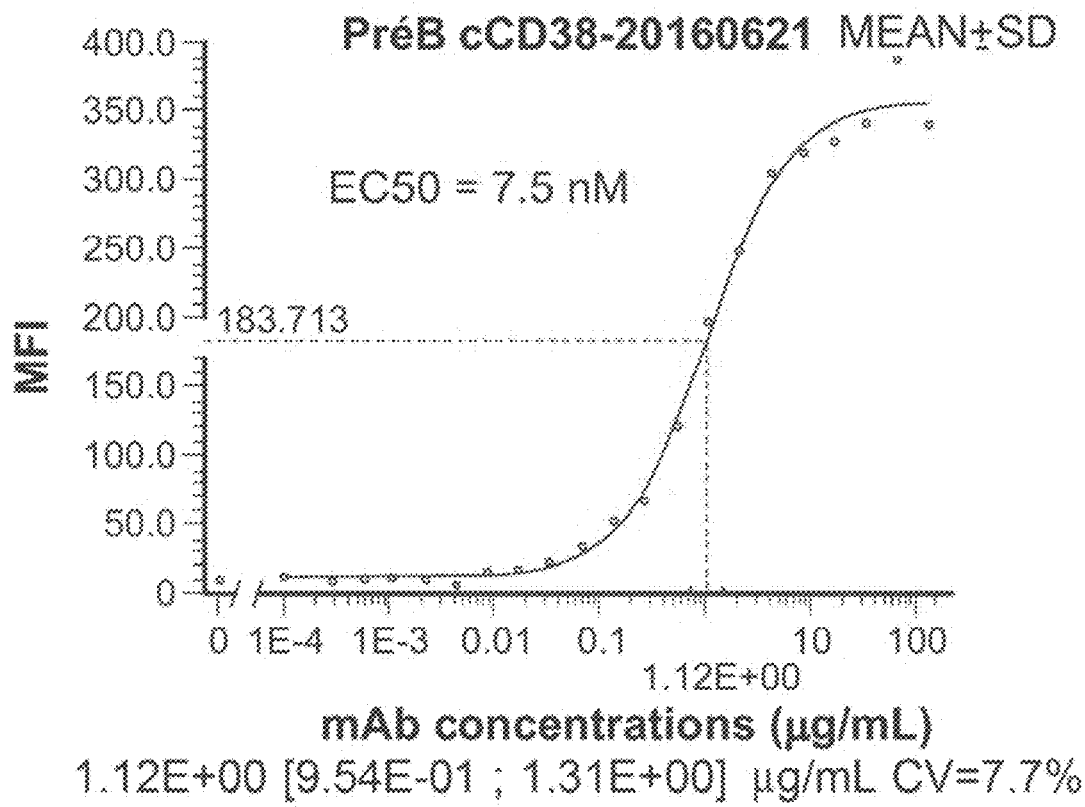
FIG. 6C

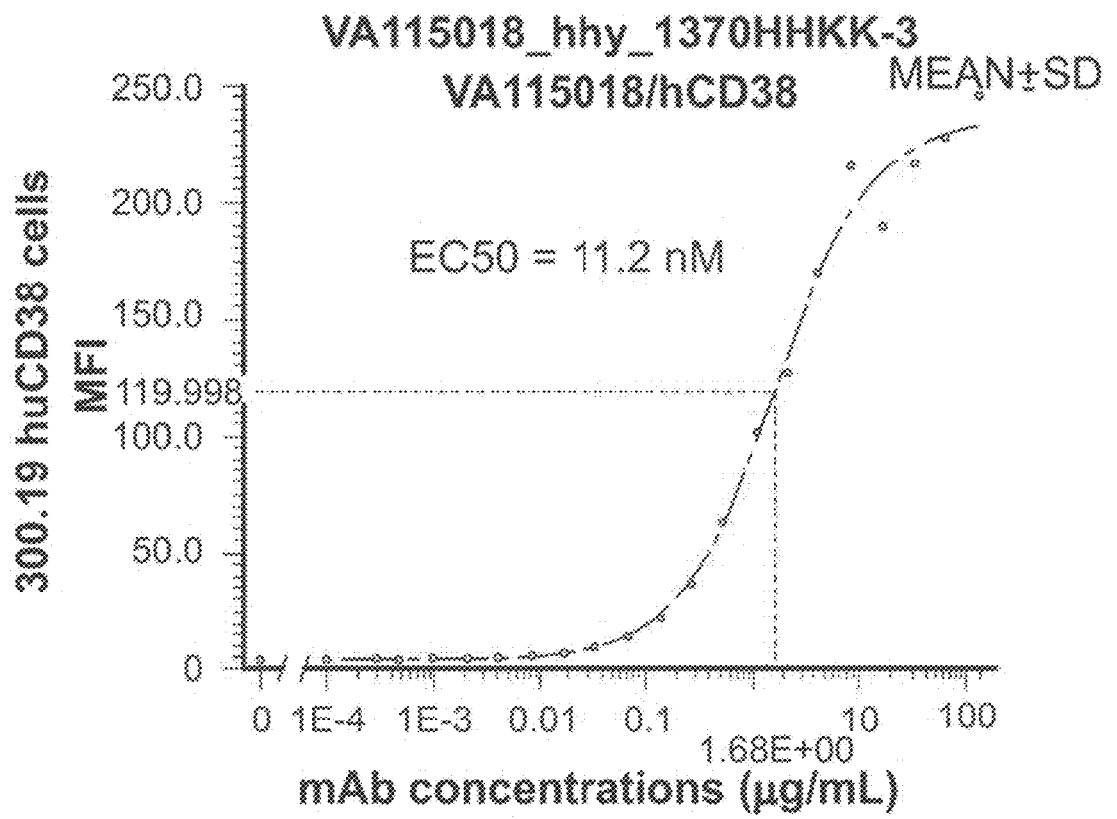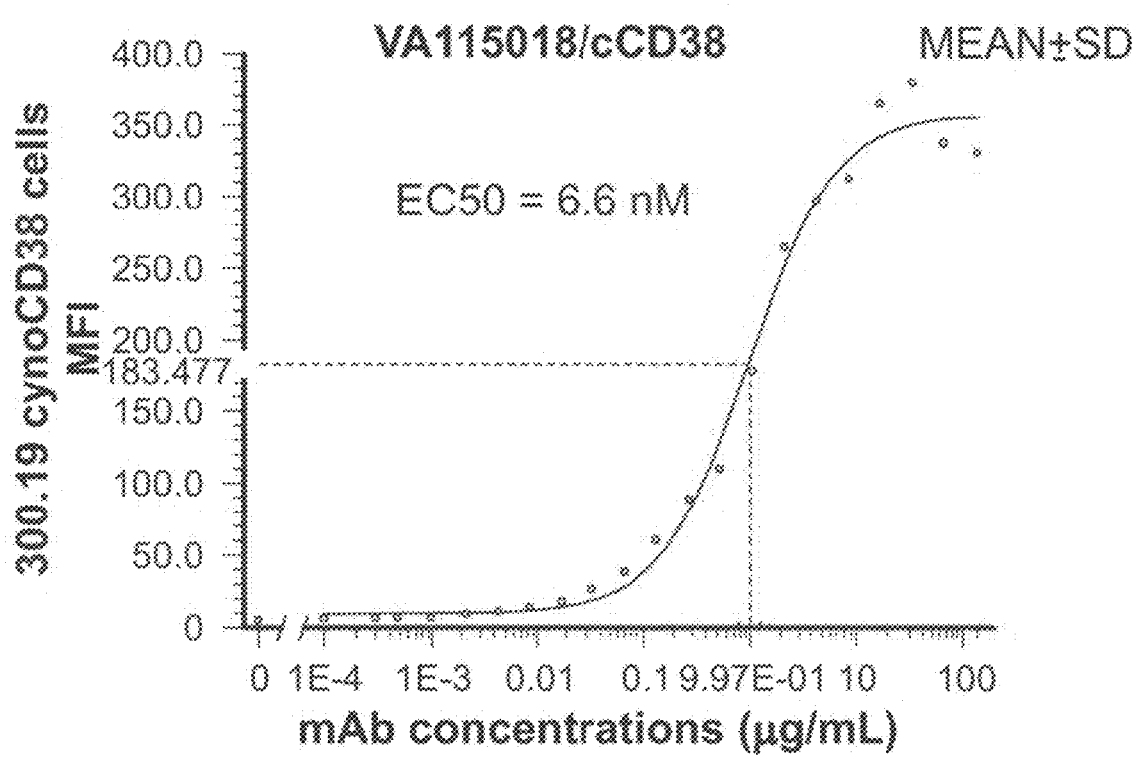
FIG. 6E (Cont.)

| TsAbs | $^1$KD value against rec. protein by SPR (nM) | $^2$Apparent KD value against rec. cells by FACS (nM) |
|---|---|---|
| CD38$_{SB19}$CD28$_{sup}$CD3$_{mid}$ | 2 | 4 |
| CD38$_{VH1}$CD28$_{sup}$CD3$_{mid/low}$ | 4/6 | 11 |
| CD38$_{VH13}$CD28$_{cvn}$CD3$_{mid/low}$ | 4/6 | 4.4 |
| CD38$_{WHY1370}$CD28$_{sup}$CD3$_{mid}$ | 1 | no accurate EC50 value could be estimated (no saturation) |

FIG. 6F

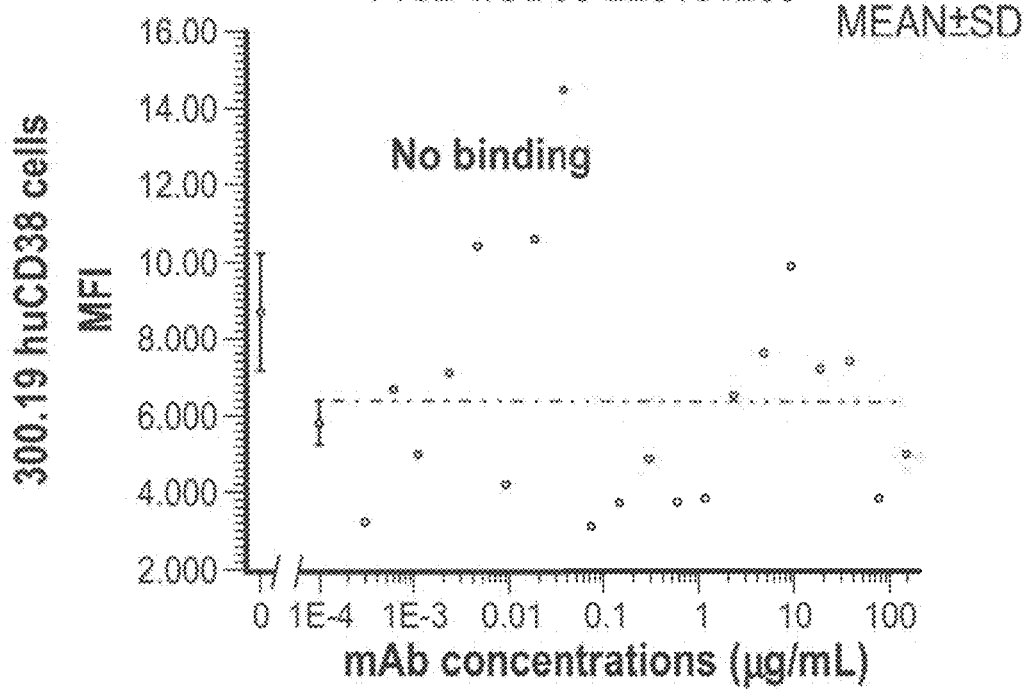
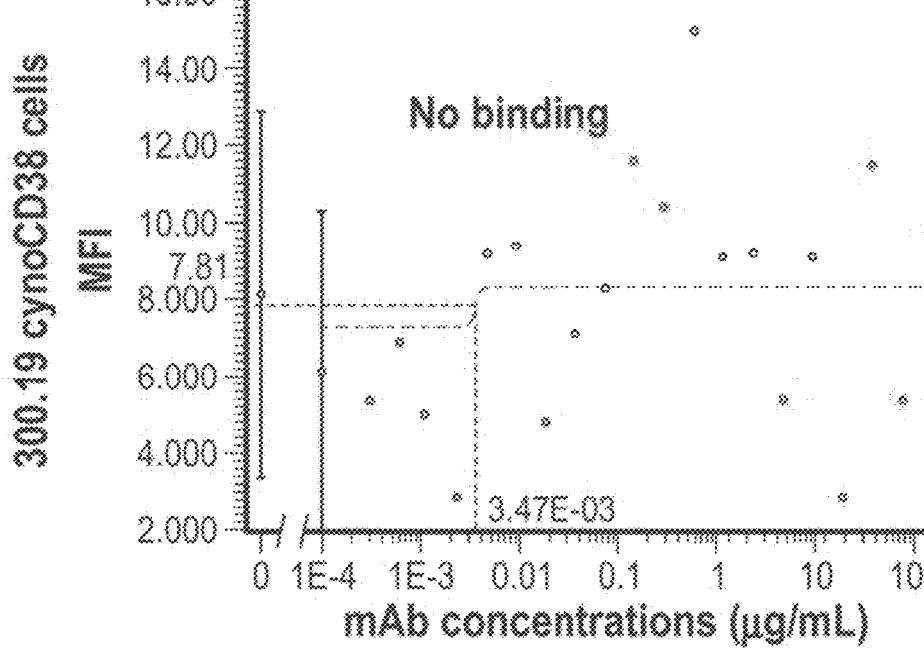
FIG. 6G

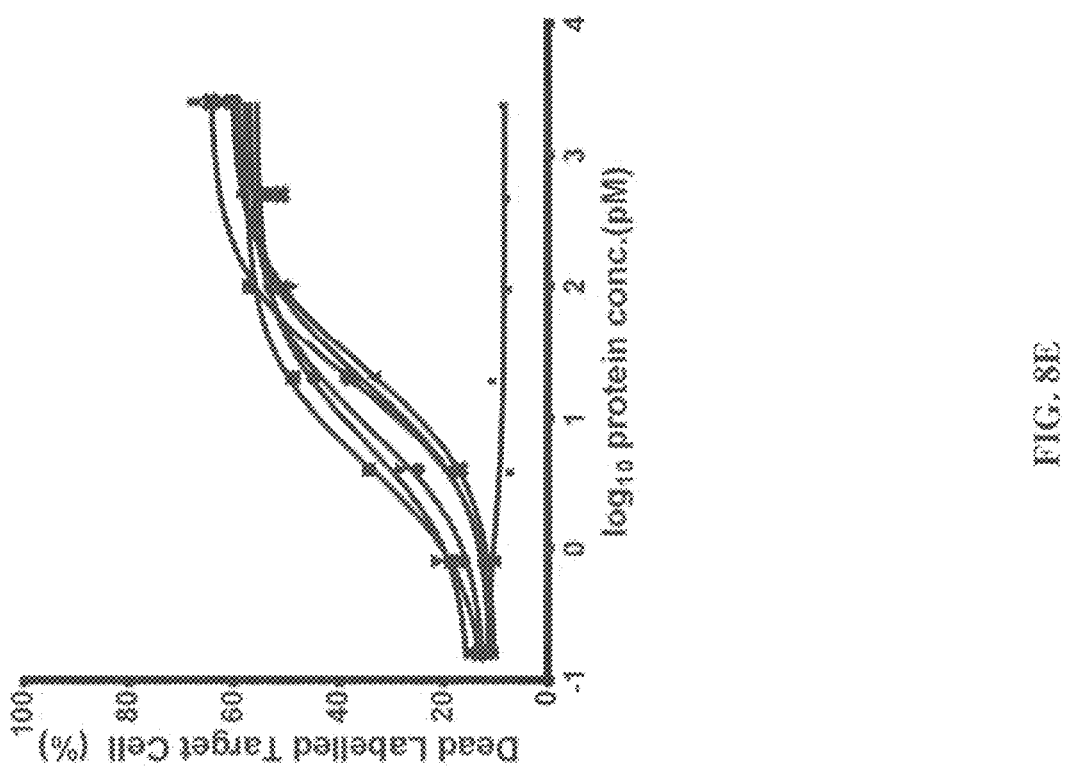
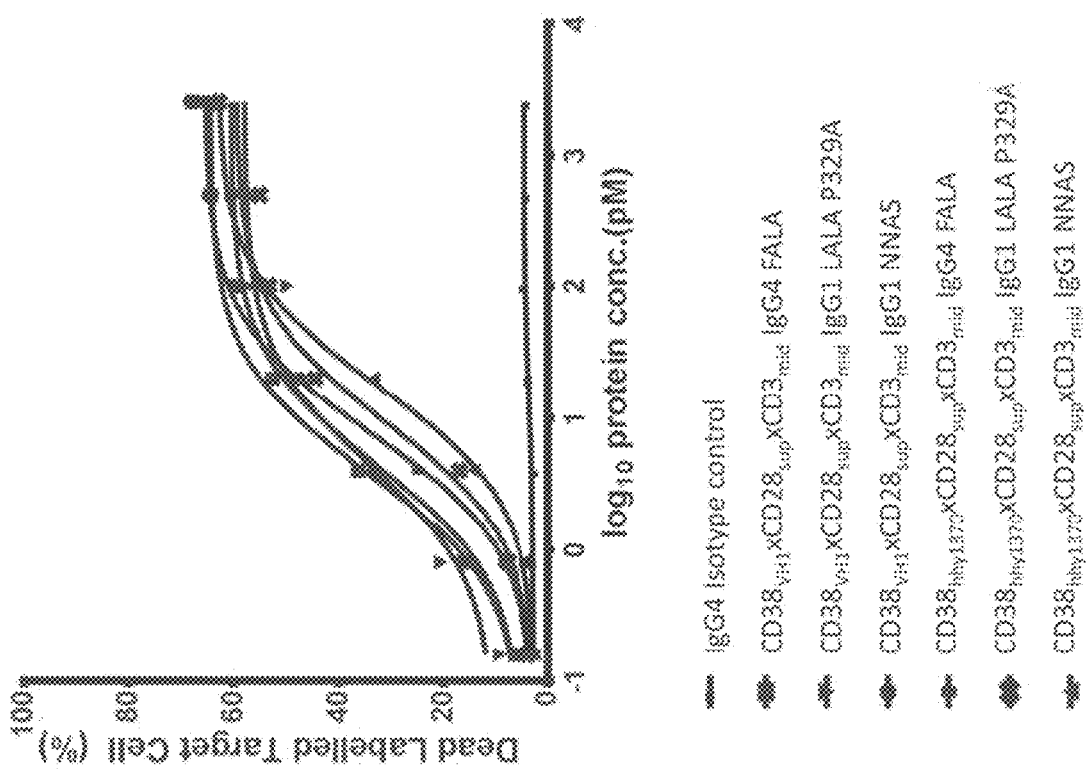
FIG. 8E

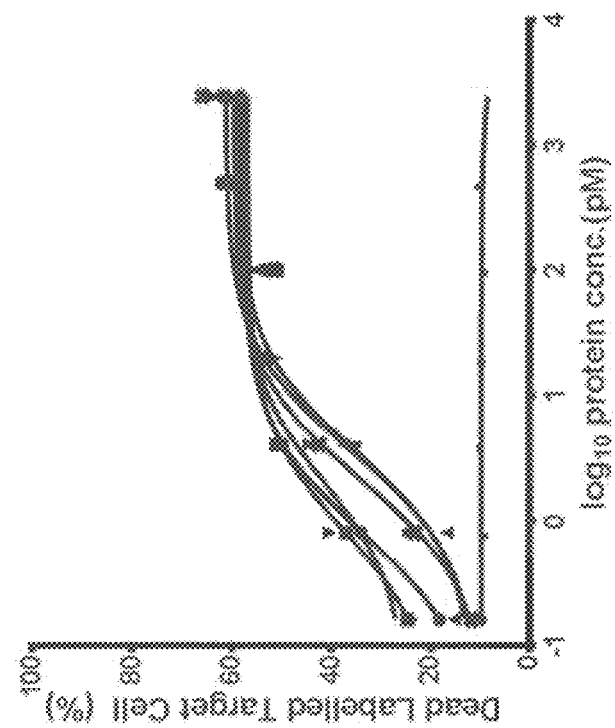
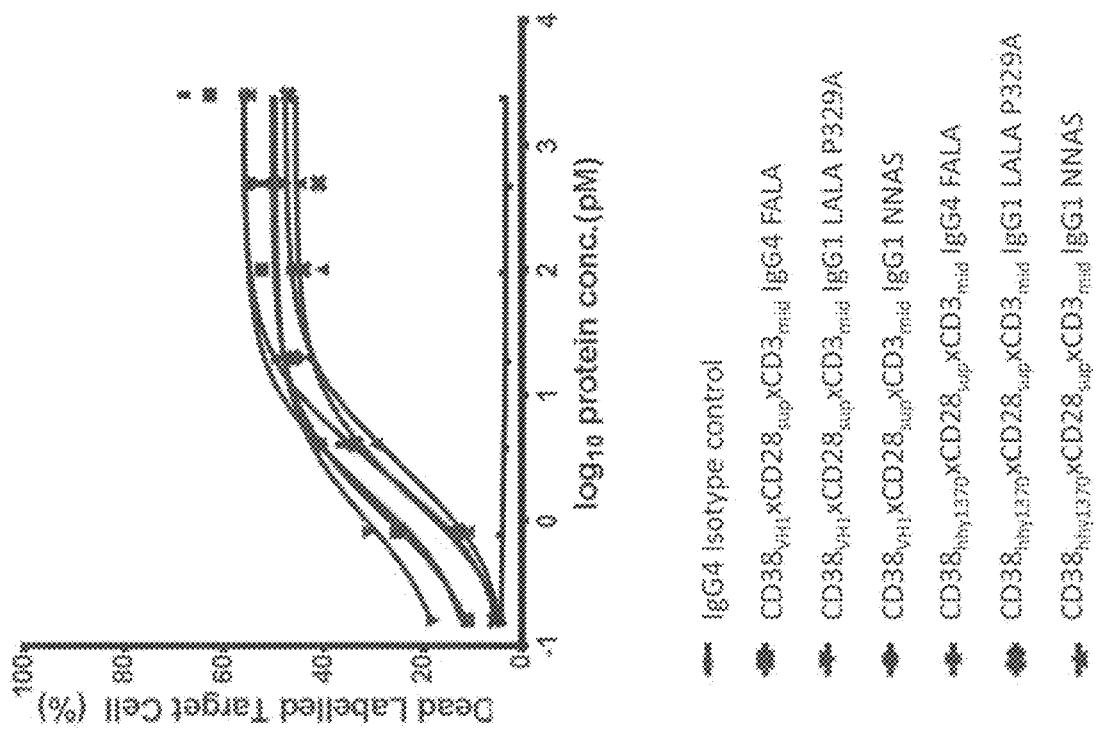
FIG. 8F

CD3

CD4+CD3+

CD8+CD3+

Day 4

Day 21

Day21_Tumor size

Day22_Terminal Tumor weight

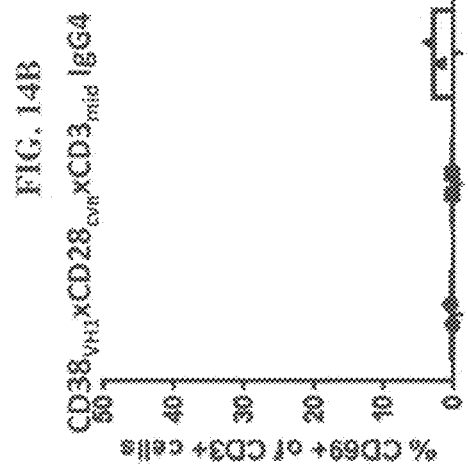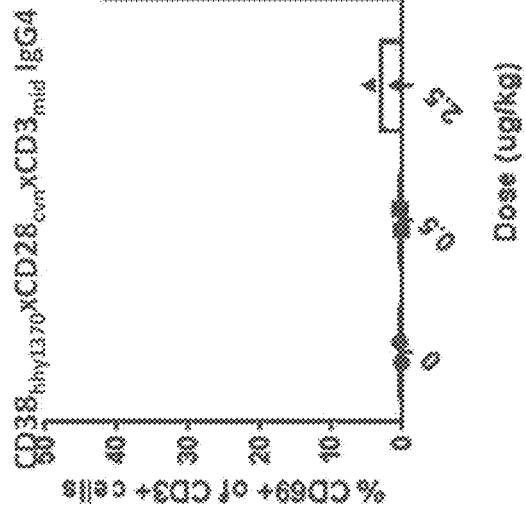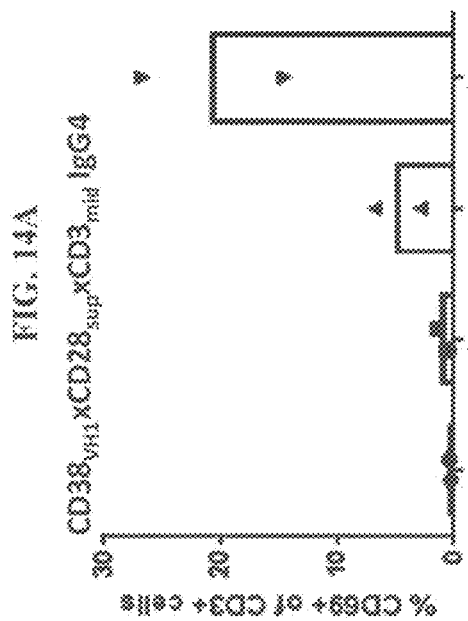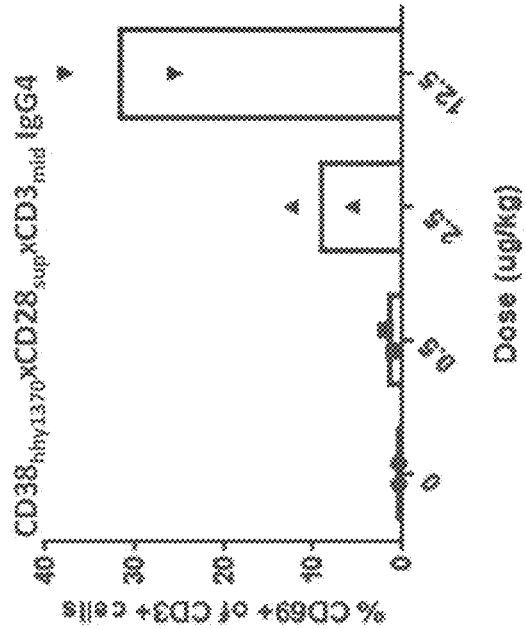

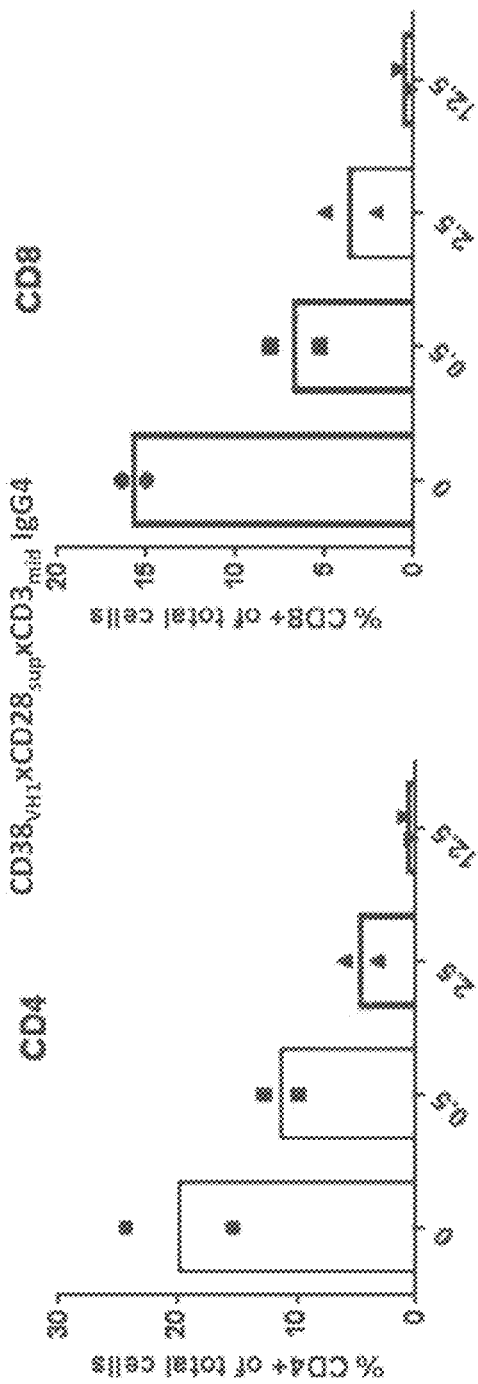
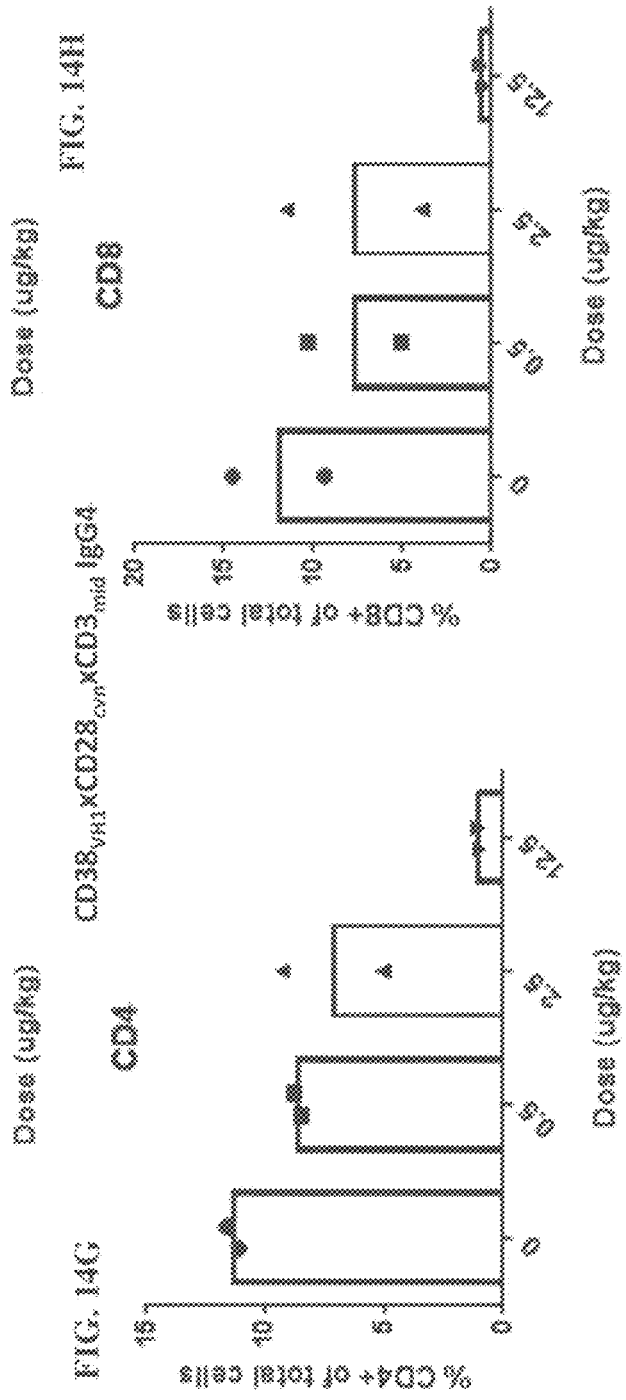

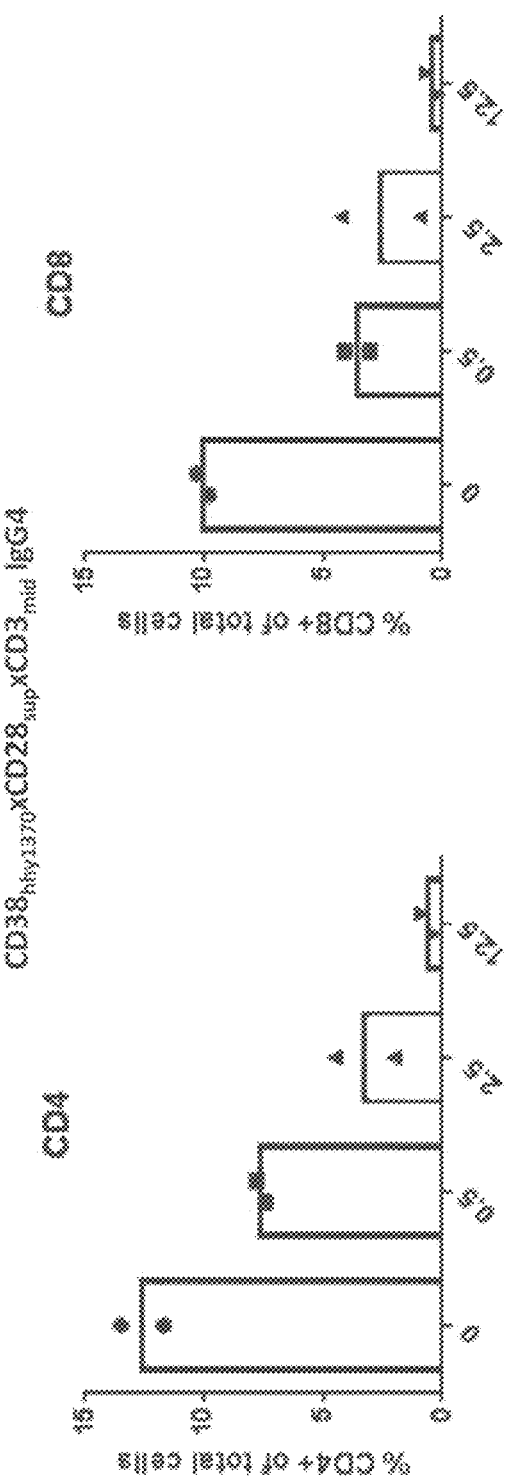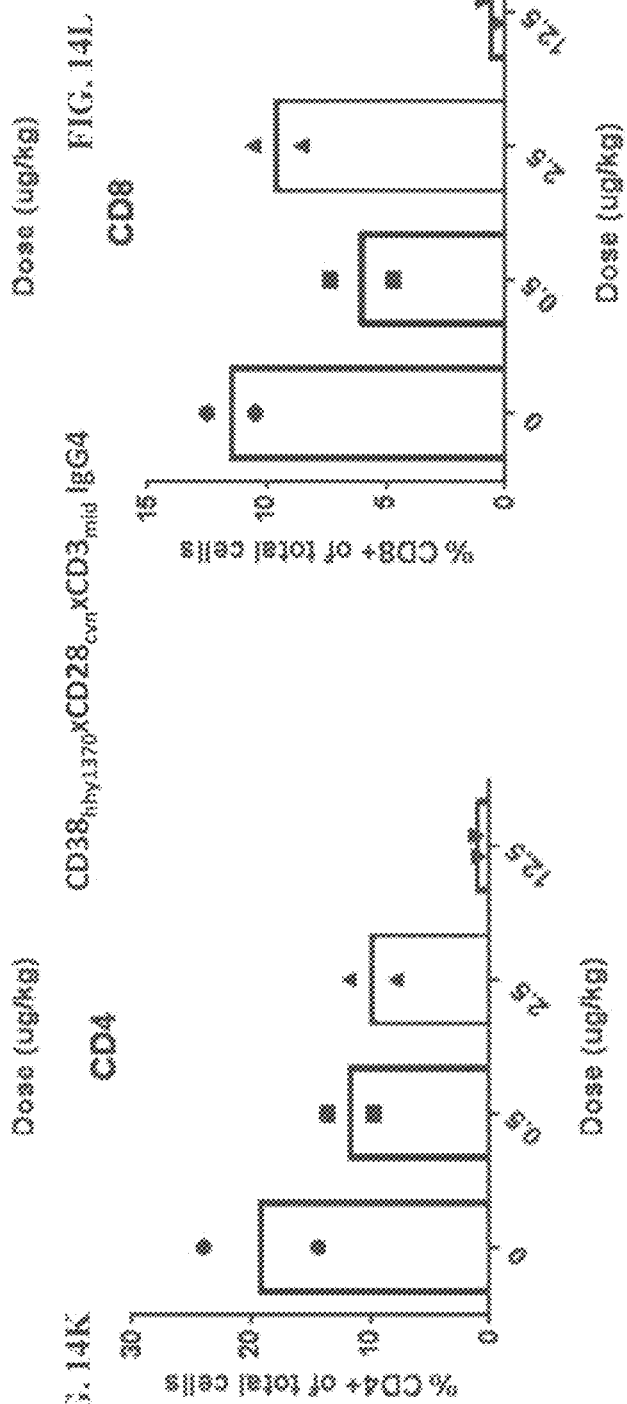

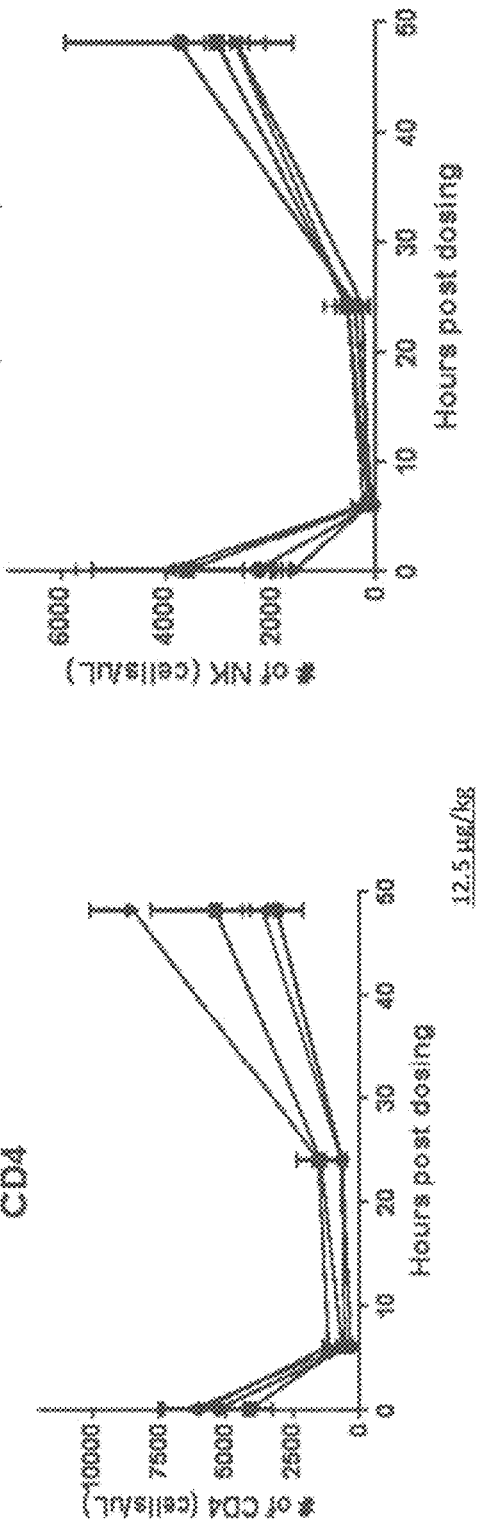
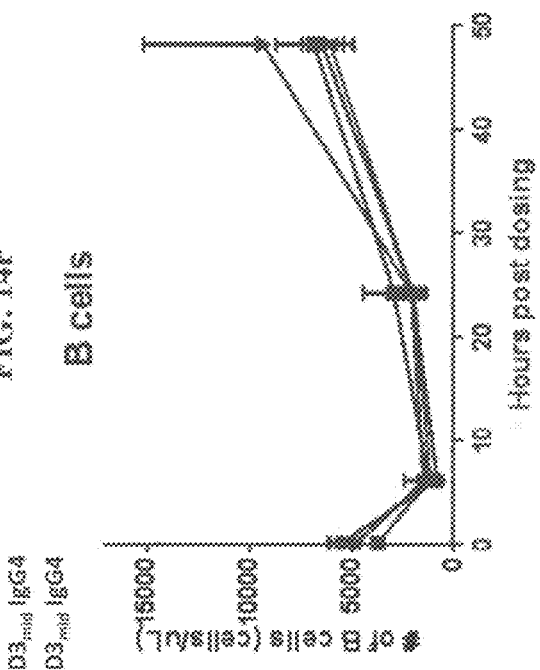
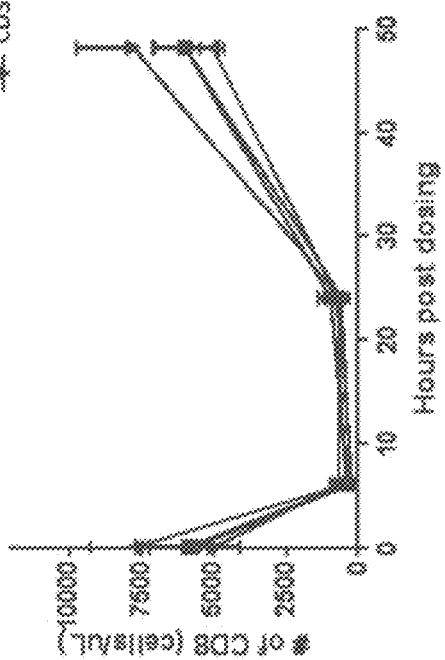
FIG. 14M, FIG. 14N, FIG. 14O, FIG. 14P

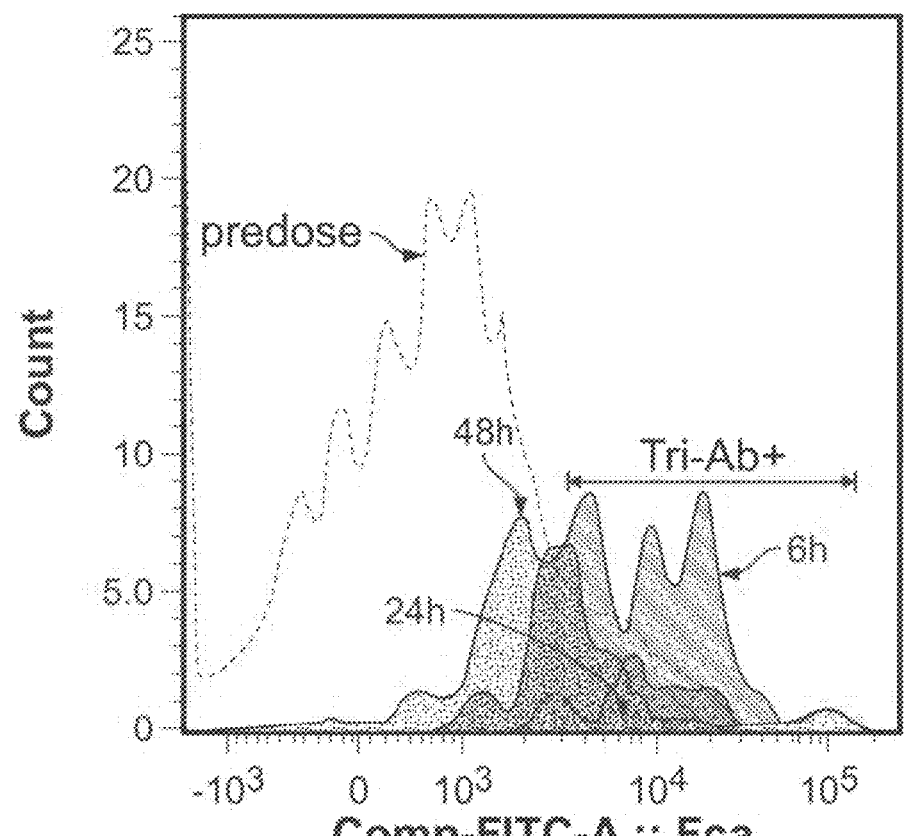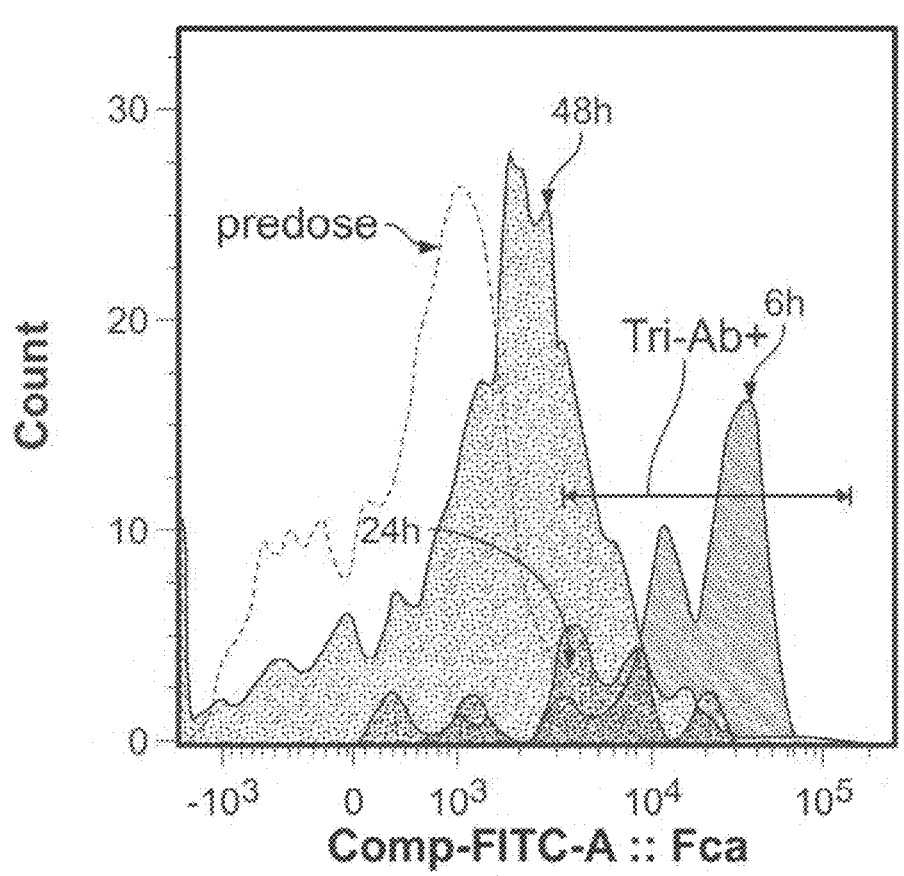
FIG. 14AE

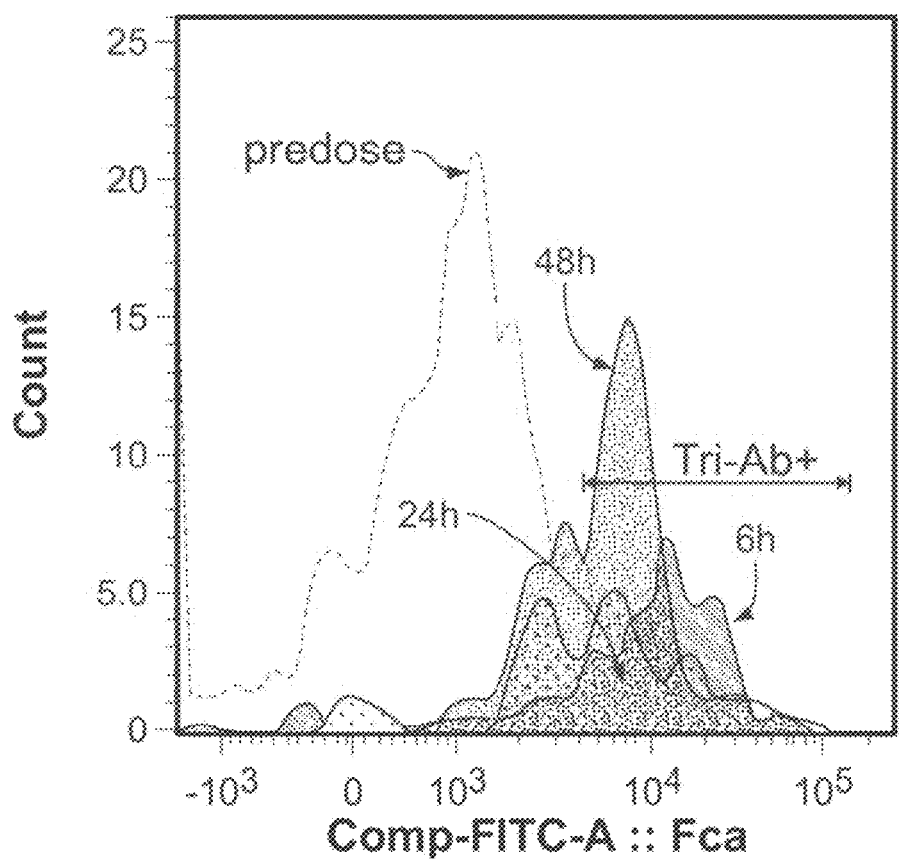
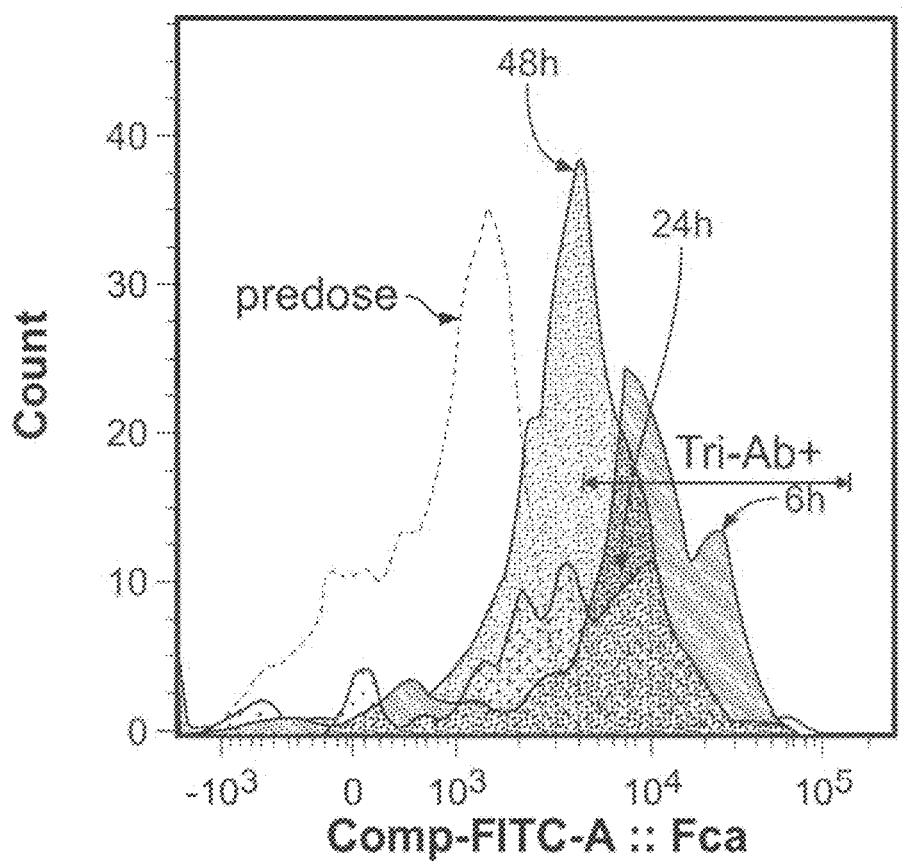
FIG. 14AG

| Antibody | Tmax (hr) | Cmax (ng/ml) | Tlast (hr) | Clast (ng/ml) | T 1/2 (hr) | AUCall (hr* ng/ml) |
|---|---|---|---|---|---|---|
| anti-hCD38$_{VH1}$/CD28$_{supV}$X CD3$_{mid}$ IgG4 | 0.083 | 460 | 72 | 16.6 | 24 | 4850 |
| anti-hCD38$_{VH1}$/CD28$_{supV}$X CD3$_{mid}$ IgG4 FALA | 0.083 | 495 | 336 | 117.1 | 234 | 61200 |
| anti-hCD38$_{VH1}$/CD28$_{supV}$X CD3$_{mid}$ IgG1 LALA P329A | 0.083 | 621 | 336 | 93.2 | 277 | 49400 |
| anti-hCD38$_{hhy1370}$/CD28$_{sup}$ pXCD3$_{mid}$ IgG4 FALA | 0.083 | 645 | 336 | 112.9 | 255 | 64500 |

FIG. 17

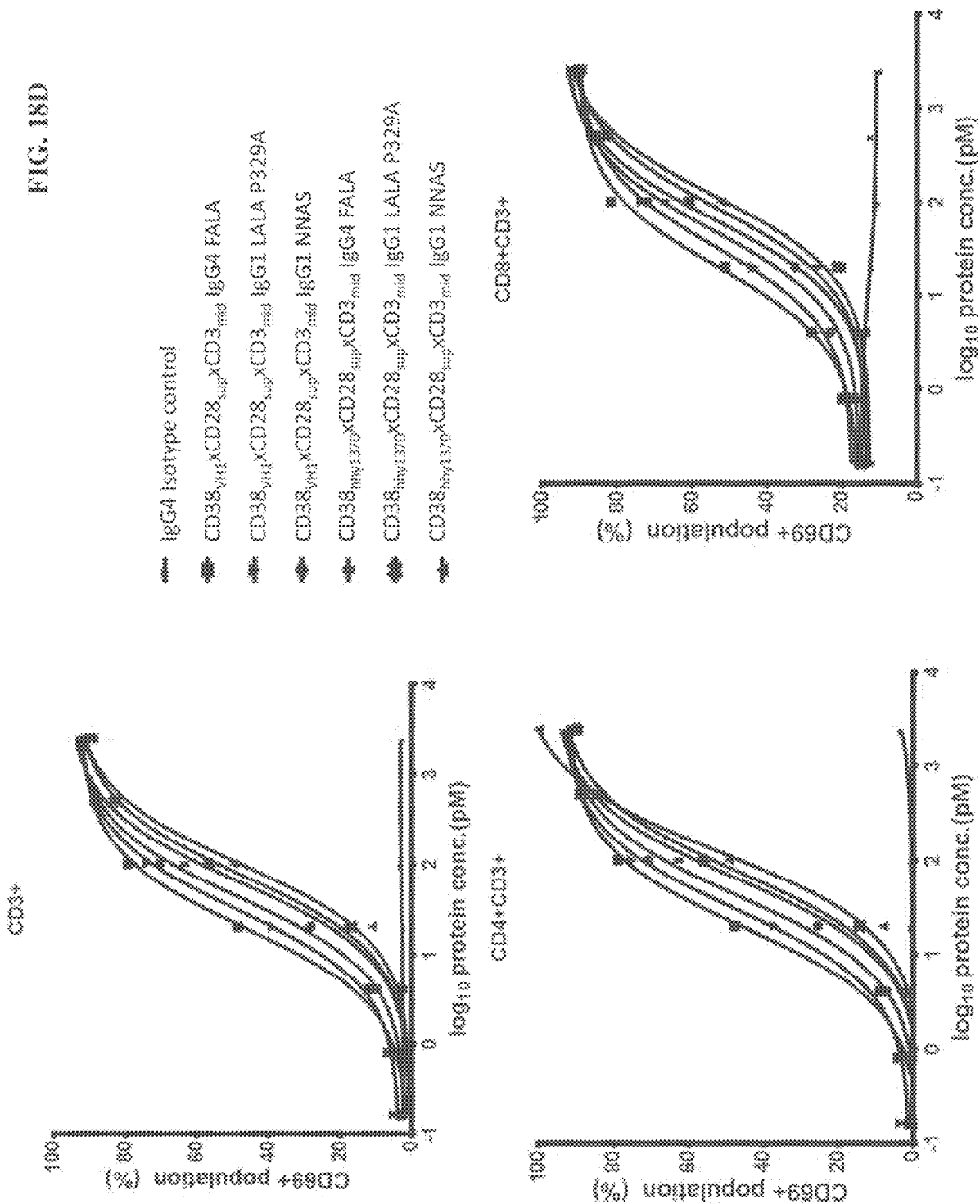

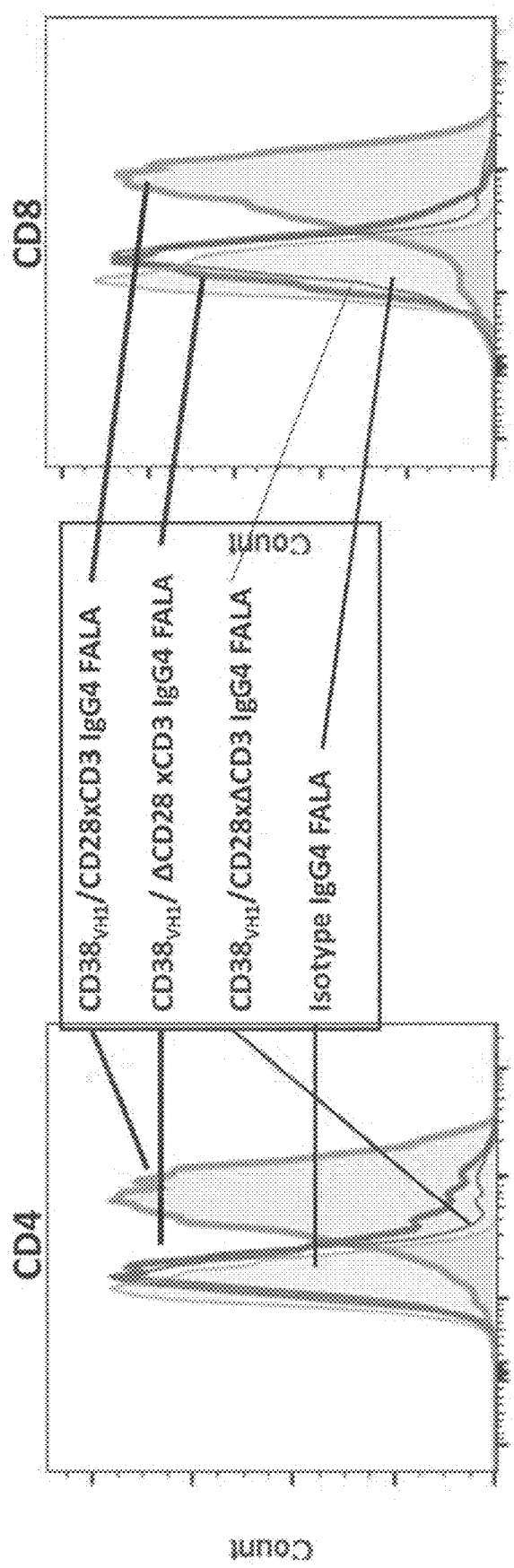
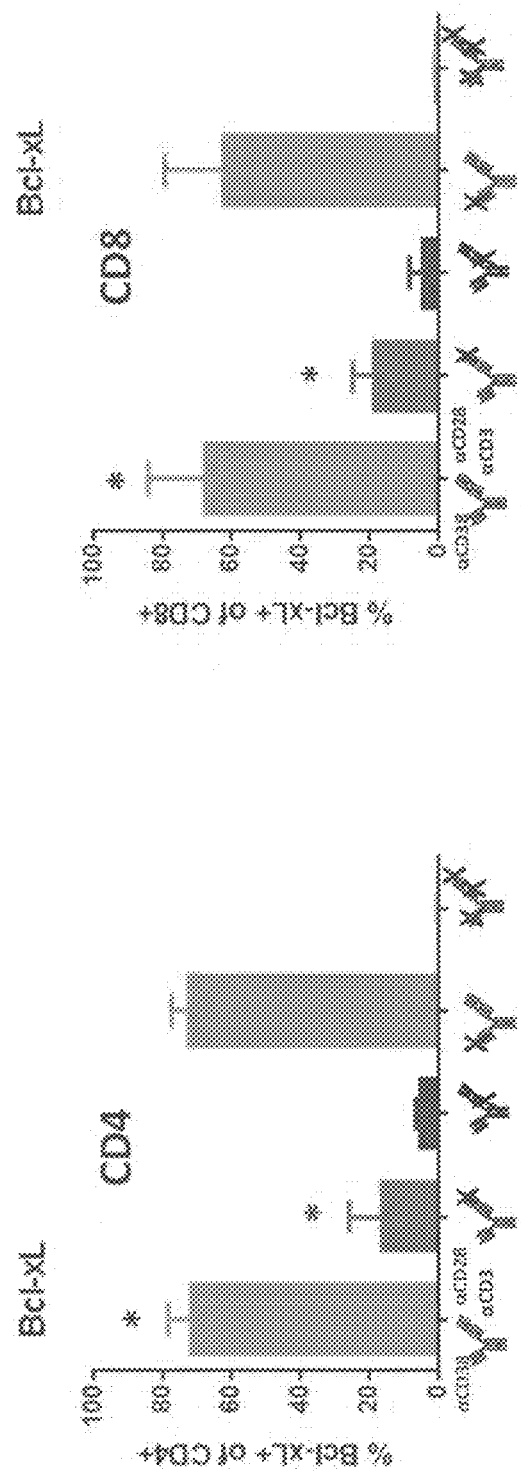
FIG. 19A
FIG. 19B

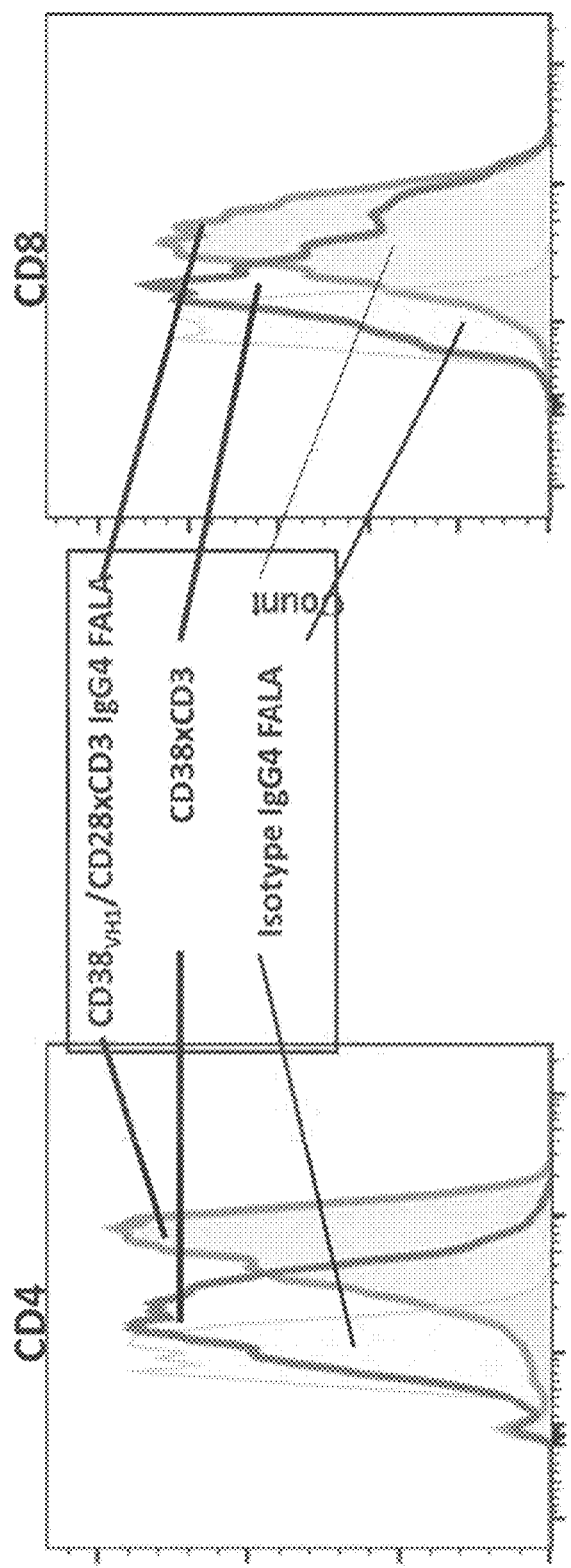
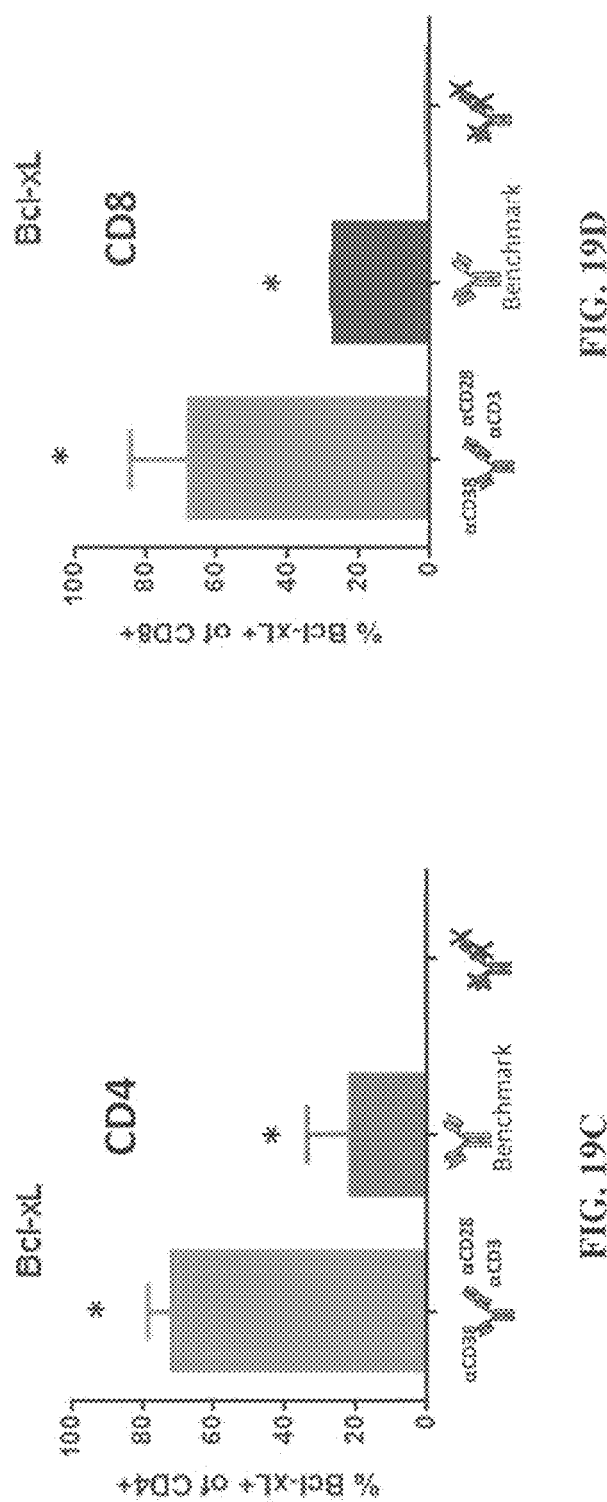
FIG. 19C
FIG. 19D

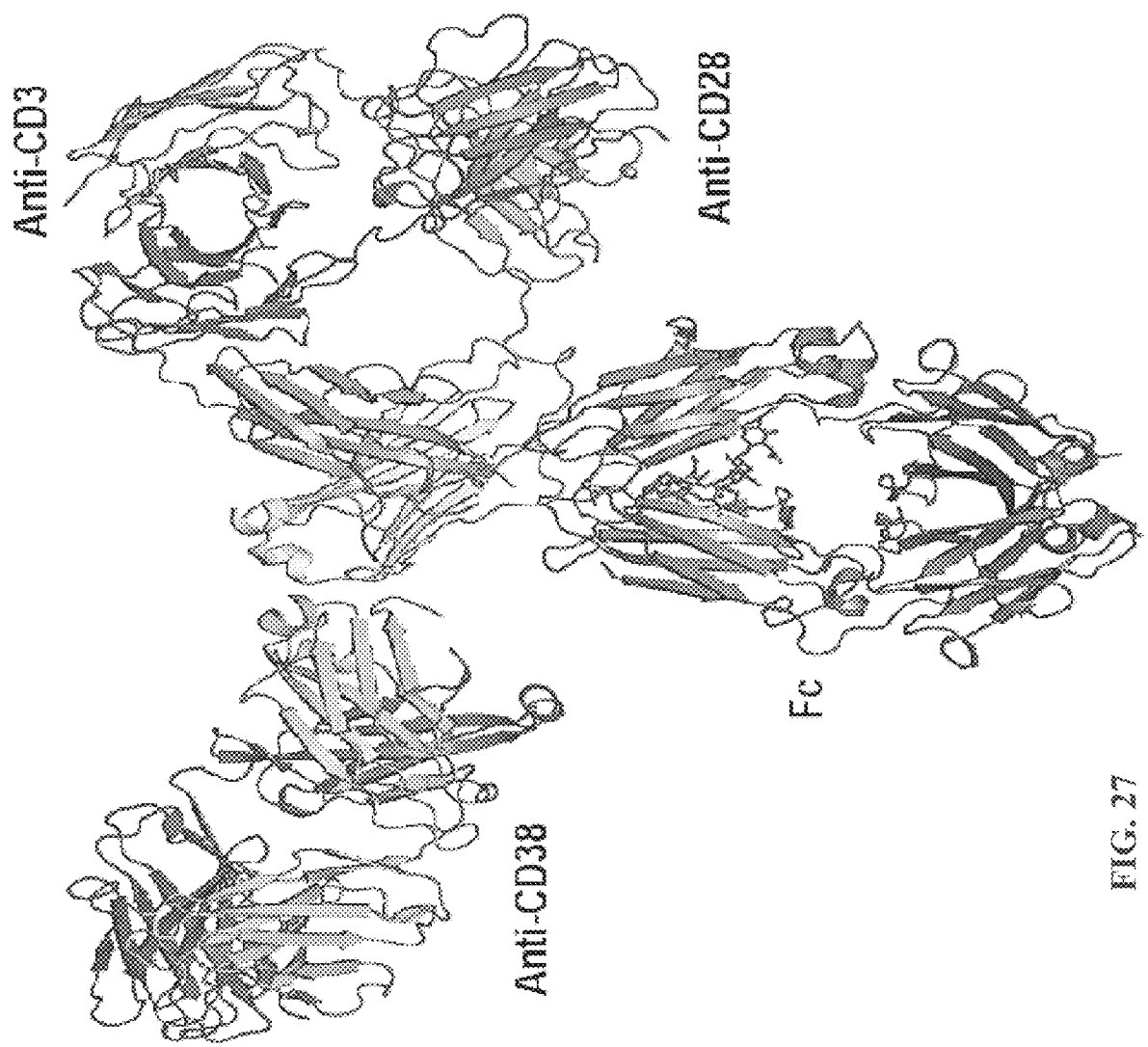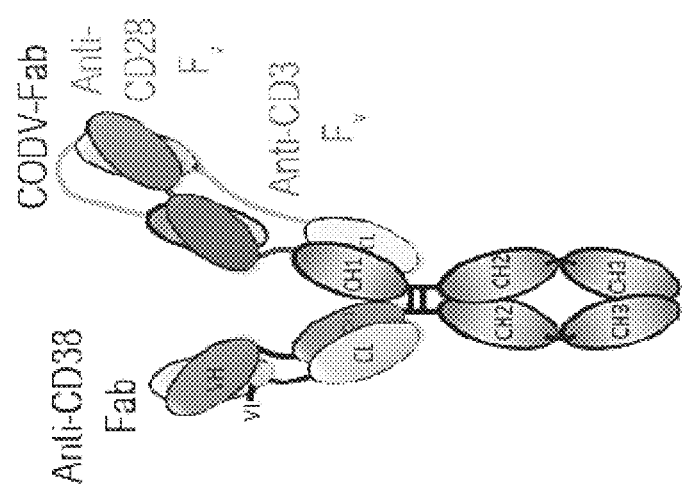
FIG. 27

Wild type

IgG1　CPPCPAPELLGGPS
IgG2　CPPCPAPPVAG-PS
IgG4　CPPCPAPEFLGGPS

Mutant

IgG1 LALA/P239A　CPPCPAPEAAGGPS
IgG4 PVA　CPPCPAPVAG-PS
IgG4 FALA　CPPCPAPEAAGGPS

ANTI-CD38 ANTIBODIES AND METHODS OF USE

CROSS REFERENCES TO RELATED APPLICATIONS

This application is a continuation of U.S. patent application Ser. No. 16/155,807, filed Oct. 9, 2018, issued as U.S. Pat. No. 11,186,649 on Nov. 30, 2021, which claims the priority benefit of U.S. Provisional Application No. 62/570,655, filed Oct. 10, 2017; U.S. Provisional Application No. 62/570,660, filed Oct. 11, 2017; U.S. Provisional Application No. 62/676,221, filed May 24, 2018; and EP Application No. EP18187186.4, filed Aug. 3, 2018; all of which are incorporated herein by reference in their entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 183952029901SEQLIST.TXT, date recorded: Jul. 27, 2021, size: 158 KB).

FIELD OF THE INVENTION

The disclosure relates to binding proteins that bind CD38 polypeptides (e.g., human and cynomolgus monkey CD38 polypeptides), including monospecific, bispecific, or trispecific binding proteins with at least one antigen binding domain that binds a CD38 polypeptide, as well as polynucleotides, host cells, methods of production, and methods of use related thereto.

BACKGROUND

Monoclonal antibody based biotherapeutics have become an important avenue for new drug development. Monoclonal antibody technology offers specific targeting, precise signaling delivery and/or payload to specific cell population, and provides long lasting biological effect through its Fc functions. Efforts in antibody engineering have allowed developing multispecific antibodies combining the specificities of multiple monoclonal antibodies for various biological applications, expanding the scope of antibody drug development.

CD38 is an attractive drug target, since it is expressed on the cell surface of a variety of lymphoid tumor cells (see Stevenson, G. T. (2006) *Mol. Med.* 12:345-346). DARZALEX● (daratumumab) is an anti-CD38 antibody approved for use in treating multiple myeloma. However, a need exists for therapeutics targeting CD38 with a different mode of action and/or improved properties, including but not limited to high affinity binding to CD38, cross-reactivity between human and cynomolgus monkey CD38 polypeptides, binding to lymphoma cells (e.g., multiple myeloma large B-cell lymphoma cell lines), and the ability to induce apoptosis and/or antibody-dependent cell-mediated cytotoxicity (ADCC) and T cell mediated anti-tumor activities.

BRIEF SUMMARY

Provided herein are binding proteins that bind CD38 polypeptides (e.g., human and cynomolgus monkey CD38 polypeptides), including monospecific, bispecific, or trispecific binding proteins with at least one antigen binding site that binds a CD38 polypeptide. Advantageously, these binding proteins have the ability to recruit T cells to the proximity of cancer cells, subsequently to activate T cells and promote the activated T cells killing of adjacent cancer cells through a Granzyme/Perforin mechanism, providing a different mode of action for anti-tumor activity from anti-CD38 antibodies such as DARZALEX● (daratumumab). Moreover, the ability to bind both human and cynomolgus monkey CD38 polypeptides allows binding proteins to be readily tested in preclinical toxicological studies, e.g., to evaluate their safety profiles for later clinical use.

In some embodiments, provided herein are monospecific binding proteins that bind to a human CD38 polypeptide. In some embodiments, the binding proteins cross-react with human and cynomolgus monkey CD38 polypeptides. In some embodiments, the binding proteins bind to human isoform A and isoform E CD38 polypeptides. In some embodiments, the binding proteins possess one or more of the following features (in any combination): binds to the extracellular domain of a human CD38 polypeptide (e.g., comprising the amino acid sequence of SEQ ID NO:1) as a purified protein, as assayed by SPR; binds to the extracellular domain of a human CD38 polypeptide (e.g., comprising the amino acid sequence of SEQ ID NO:1) as a purified protein with a $K_D$ of 1.5 nM or less, as assayed by SPR; binds to the extracellular domain of a human CD38 polypeptide (e.g., comprising the amino acid sequence of SEQ ID NO:1) expressed on the surface of a cell, as assayed by flow cytometry; binds to the extracellular domain of a human CD38 polypeptide (e.g., comprising the amino acid sequence of SEQ ID NO:1) expressed on the surface of a cell with an apparent $K_D$ of 20 nM, 15 nM, 10 nM, 5 nM, 1 nM, or less, as assayed by flow cytometry; binds to the extracellular domain of a cynomolgus monkey CD38 polypeptide (e.g., comprising the amino acid sequence of SEQ ID NO:30) as a purified protein, as assayed by SPR; binds to the extracellular domain of a cynomolgus monkey CD38 polypeptide (e.g., comprising the amino acid sequence of SEQ ID NO:30) as a purified protein with a $K_D$ of 3.5 nM or less, as assayed by SPR; binds to the extracellular domain of a cynomolgus monkey CD38 polypeptide (e.g., comprising the amino acid sequence of SEQ ID NO:30) expressed on the surface of a cell, as assayed by flow cytometry; binds to the extracellular domain of a cynomolgus monkey CD38 polypeptide (e.g., comprising the amino acid sequence of SEQ ID NO:30) expressed on the surface of a cell with an apparent $K_D$ of 7.5 nM or less, as assayed by flow cytometry; binds to the extracellular domain of a human isoform E CD38 polypeptide (e.g., comprising the amino acid sequence of SEQ ID NO:105) as a purified protein, as assayed by ELISA; binds to the extracellular domain of a human isoform E CD38 polypeptide (e.g., comprising the amino acid sequence of SEQ ID NO:105) expressed on the surface of a cell, as assayed by flow cytometry; induces apoptosis or antibody-dependent cellular cytotoxicity (ADCC) of a cell expressing CD38 on its cell surface; and has one or more mutations (e.g., in an Fc region) resulting in decreased binding to FcγRI and/or FcγRII, as compared to the same binding protein without the one or more mutations. For exemplary assays, see Examples 1.3, and 4. In some embodiments, the KD is measured at 4° C., or 25° C.

In some embodiments, provided herein are trispecific binding proteins that bind to a human CD38 polypeptide. In some embodiments, the trispecific binding proteins bind (e.g., simultaneously) to a CD38 polypeptide (e.g., expressed on the surface of a cell) and one or more other target antigens expressed on the surface of a second cell, thereby recruiting the second cell in proximity with the cell expressing the CD38 polypeptide. In some embodiments, the trispecific binding proteins bind (e.g., simultaneously) to a CD38 polypeptide (e.g., expressed on the surface of a cell) and one or two target antigens expressed on the surface of a T cell, thereby recruiting the T cell in proximity with the cell expressing the CD38 polypeptide. In some embodiments, the trispecific binding proteins activate the T cell and/or provide a CD28-mediated costimulatory signal to the T cell. In some embodiments, the trispecific binding proteins cross-react with human and cynomolgus monkey CD38 polypeptides. In some embodiments, the trispecific binding proteins bind to human isoform A and isoform E CD38 polypeptides. In some embodiments, the trispecific binding proteins possess one or more of the following features (in any combination): binds to the extracellular domain of a human CD38 polypeptide (e.g., comprising the amino acid sequence of SEQ ID NO:1) as a purified protein, as assayed by SPR; binds to the extracellular domain of a human CD38 polypeptide (e.g., comprising the amino acid sequence of SEQ ID NO:1) as a purified protein with a $K_D$ of 1.5 nM or less, as assayed by SPR; binds to the extracellular domain of a human CD38 polypeptide (e.g., comprising the amino acid sequence of SEQ ID NO:1) expressed cm the surface of a cell, as assayed by flow cytometry; binds to the extracellular domain of a human CD38 polypeptide (e.g., comprising the amino acid sequence of SEQ ID NO:1) expressed on the surface of a cell with an apparent $K_D$ of 20 nM, 15 nM, 10 nM, 5 nM, 1 nM, or less, as assayed by flow cytometry; binds to the extracellular domain of a cynomolgus monkey CD38 polypeptide (e.g., comprising the amino acid sequence of SEQ ID NO:30) as a purified protein, as assayed by SPR; binds to the extracellular domain of a cynomolgus monkey CD38 polypeptide (e.g., comprising the amino acid sequence of SEQ ID NO:30) as a purified protein with a $K_D$ of 3.5 nM or less, as assayed by SPR; binds to the extracellular domain of a cynomolgus monkey CD38 polypeptide (e.g., comprising the amino acid sequence of SEQ ID NO:30) expressed cm the surface of a cell, as assayed by flow cytometry; binds to the extracellular domain of a cynomolgus monkey CD38 polypeptide (e.g., comprising the amino acid sequence of SEQ ID NO:30) expressed on the surface of a cell with an apparent $K_D$ of 7.5 nM or less, as assayed by flow cytometry; binds to the extracellular domain of a human isoform E CD38 polypeptide (e.g., comprising the amino acid sequence of SEQ ID NO:105) as a purified protein, as assayed by ELISA; binds to the extracellular domain of a human isoform E CD38 polypeptide (e.g., comprising the amino acid sequence of SEQ ID NO:105) expressed on the surface of a cell, as assayed by flow cytometry; induces apoptosis or antibody-dependent cellular cytotoxicity (ADCC) of a cell expressing CD38 on its cell surface; and has one or more mutations (e.g., in an Fc region) resulting in decreased binding to FcγRI and/or FcγRII, as compared to the same binding protein without the one or more mutations; induces T cell (e.g., CD4+ and/or CD8+ T cell) proliferation; induces T cell (e.g., CD4+ and/or CD8+ T cell) expression of Bcl-xL; induces apoptosis of CD38+ cells; binds to CD38 expressed on the surface of a cell and one or more T cell target antigen(s) expressed on the surface of a T cell; binds to CD38 expressed on the surface of a cell, CD28 expressed on the surface of a T cell, and CD3 expressed on the surface of a T cell; stimulates activation of the T cell receptor; induces costimulation of T cell receptor signaling (e.g., as mediated by CD28); and has one or more mutations (e.g., in an Fc region) resulting in decreased induction of cytokine release (e.g., IFN-γ, IL-2, and/or TNF-α) by PBMCs, as compared to the same binding protein without the one or more mutations; induces cytokine release (e.g., IFN-γ and/or IL-6) by PBMCs in the presence of a CD38+ target cell. For exemplary assays, see Examples 1, 3, and 4. In some embodiments, the KD is measured at 4° C., or 25° C.

In some embodiments, provided herein is a binding protein comprising an antigen binding site that binds a CD38 polypeptide, wherein the antigen binding site comprises: (a) an antibody heavy chain variable (VH) domain comprising a CDR-H1 sequence comprising the amino acid sequence of GYTFTSFN (SEQ ID NO:31) or GYTFTSYA (SEQ ID NO:37), a CDR-H2 sequence comprising the amino acid sequence of IYPGNGGT (SEQ ID NO:32) or IYPGQGGT (SEQ ID NO:38), and a CDR-H3 sequence comprising the amino acid sequence of ARTGGLRRAYFTY (SEQ ID NO:33); and/or (b) an antibody light chain variable (VL) domain comprising a CDR-L1 sequence comprising the amino acid sequence of ESVDSYGNGF (SEQ ID NO:34) or QSVSSYGQGF (SEQ ID NO:39), a CDR-L2 sequence comprising the amino acid sequence of LAS (SEQ ID NO:35) or GAS (SEQ ID NO:40), and a CDR-L3 sequence comprising the amino acid sequence of QQNKEDPWT (SEQ ID NO:36). In some embodiments, the antigen binding site comprises: (a) an antibody heavy chain variable (VH) domain comprising a CDR-H1 sequence comprising the amino acid sequence of GYTFTSFN (SEQ ID NO:31) or GYTFTSYA (SEQ ID NO:37), a CDR-H2 sequence comprising the amino acid sequence of IYPGNGGT (SEQ ID NO:32) or IYPGQGGT (SEQ ID NO:38), and a CDR-H3 sequence comprising the amino acid sequence of ARTGGLRRAYFTY (SEQ ID NO:33); and/or (b) an antibody light chain variable (VL) domain comprising a CDR-L1 sequence comprising the amino acid sequence of ESVDSYGNGF (SEQ ID NO:34) or QSVSSYGQG (SEQ ID NO:132), a CDR-L2 sequence comprising the amino acid sequence of LAS (SEQ ID NO:35) or GAS (SEQ ID NO:40), and a CDR-L3 sequence comprising the amino acid sequence of QQNKEDPWT (SEQ ID NO:36). In some embodiments, the antigen binding site comprises: (a) an antibody heavy chain variable (VH) domain comprising a CDR-H1 sequence comprising die amino acid sequence of GYTFTSFN (SEQ ID NO:31), a CDR-H2 sequence comprising the amino acid sequence of IYPGNGGT (SEQ ID NO:32), and a CDR-H3 sequence comprising the amino acid sequence of ARTGGLRRAYFTY (SEQ ID NO:33); and/or (b) an antibody light chain variable (VL) domain comprising a CDR-L1 sequence comprising die amino acid sequence of ESVDSYGNGF (SEQ ID NO:34), a CDR-L2 sequence comprising the amino acid sequence of LAS (SEQ ID NO:35), and a CDR-L3 sequence comprising the amino acid sequence of QQNKEDPWT (SEQ ID NO:36). In some embodiments, the VH domain comprises the sequence, from N-terminus to C-terminus, FR1-CDR-H1-FR2-CDR-H2-FR3-CDR-H3-FR4; wherein FR1 comprises the sequence QVQLVQSGAEVVKPGASVKVSCKAS (SEQ ID NO:86), QVQLVQSGAEVVKSGASVKVSCKAS (SEQ ID NO:87), or QVQLVQSGAEVVKPGASVKMSCKAS (SEQ ID NO:88); wherein FR2 comprises the sequence MHWVKEAPGQRLEWIGY (SEQ ID NO:90) or MHWVKEAPGQGLEWIGY (SEQ ID NO:91); wherein FR3 comprises the sequence NYNQKFQGRATLTADT-SASTAYMELSSLRSEDTAVYFC (SEQ ID NO:93) or NYNQKFQGRATLTADTSASTAYMEISSLRSED-TAVYFC (SEQ ID NO:94); and wherein FR4 comprises the sequence WGQGTLVTVSS (SEQ ID NO:96). In some embodiments, the VH domain comprises the amino acid sequence of SEQ ID NO:5, and/or the VL domain comprises the amino acid sequence of SEQ ID NO:6. In some embodiments, the binding protein comprises an antibody heavy chain comprising the amino acid sequence of SEQ ID NO:7 and an antibody light chain comprising the amino acid sequence of SEQ ID NO:8. In some embodiments, the VH domain comprises the amino acid sequence of SEQ ID NO:17, and/or the VL domain comprises the amino acid sequence of SEQ ID NO:18. In some embodiments, the binding protein comprises an antibody heavy chain comprising the amino acid sequence of SEQ ID NO:19 and an antibody light chain comprising the amino acid sequence of SEQ ID NO:20. In some embodiments, the VH domain comprises the amino acid sequence of SEQ ID NO:21, and/or the VL domain comprises the amino acid sequence of SEQ ID NO:18. In some embodiments, the binding protein comprises an antibody heavy chain comprising the amino acid sequence of SEQ ID NO:22 and an antibody light chain comprising the amino acid sequence of SEQ ID NO:20. In some embodiments, the VH domain comprises the amino acid sequence of SEQ ID NO:23, and/or the VL domain comprises the amino acid sequence of SEQ ID NO:18. In some embodiments, the binding protein comprises an antibody heavy chain comprising the amino acid sequence of SEQ ID NO:24 and an antibody light chain comprising the amino acid sequence of SEQ ID NO:20. In some embodiments, the antigen binding site comprises: (a) an antibody heavy chain variable (VH) domain comprising a CDR-H1 sequence comprising the amino acid sequence of GYTFTSYA (SEQ ID NO:37), a CDR-H2 sequence comprising the amino acid sequence of IYPGQGGT (SEQ ID NO:38), and a CDR-H3 sequence comprising the amino acid sequence of ARTGGLRRAYFTY (SEQ ID NO:33); and (b) an antibody light chain variable (VL) domain comprising a CDR-L1 sequence comprising the amino acid sequence of QSVSSYGQGF (SEQ ID NO:39), a CDR-L2 sequence comprising the amino acid sequence of GAS (SEQ ID NO:40), and a CDR-L3 sequence comprising the amino acid sequence of QQNKEDPWT (SEQ ID NO:36). In some embodiments, the VH domain comprises the sequence, from N-terminus to C-terminus, FR1-CDR-H1-FR2-CDR-H2-FR3-CDR-H3-FR4; wherein FR1 comprises the sequence QVQLVQSGAEVVKPGASVKVSCKAS (SEQ ID NO:86), QVQLVQSGAEVVKSGASVKVSCKAS (SEQ ID NO:87), or QVQLVQSGAEVVKPGASVKMSCKAS (SEQ ID NO:88); wherein FR2 comprises the sequence MHWVKEAPGQRLEWIGY (SEQ ID NO:90) or MHWVKEAPGQGLEWIGY (SEQ ID NO:91); wherein FR3 comprises the sequence NYNQKFQGRATLTADTSASTAYMELSSLRSEDTAVYFC (SEQ ID NO:93) or NYNQKFQGRATLTADTSASTAYMEISSLRSEDTAVYFC (SEQ ID NO:94); and wherein FR4 comprises the sequence WGQGTLVTVSS (SEQ ID NO:96). In some embodiments, the VH domain comprises the amino acid sequence of SEQ ID NO:13, and/or the VL domain comprises the amino acid sequence of SEQ ID NO:14. In some embodiments, the binding protein comprises an antibody heavy chain comprising the amino acid sequence of SEQ ID NO:15 and an antibody light chain comprising the amino acid sequence of SEQ ID NO:16.

In some embodiments, provided herein is a binding protein comprising an antigen binding site that binds a CD38 polypeptide, wherein the antigen binding site comprises: (a) an antibody heavy chain variable (VH) domain comprising a CDR-H1 sequence comprising the amino acid sequence of GFTFSSYG (SEQ ID NO:41), a CDR-H2 sequence comprising the amino acid sequence of IWYDGSNK. (SEQ ID NO:42), and a CDR-H3 sequence comprising the amino acid sequence of ARMFRGAFDY (SEQ ID NO:43); and (b) an antibody light chain variable (VL) domain comprising a CDR-L1 sequence comprising the amino acid sequence of QGIRND (SEQ ID NO:44), a CDR-L2 sequence comprising the amino acid sequence of AAS (SEQ ID NO:45), and a CDR-L3 sequence comprising the amino acid sequence of LQDYIYYPT (SEQ ID NO:46). In some embodiments, the VH domain comprises the amino acid sequence of SEQ ID NO:9, and/or the VL domain comprises the amino acid sequence of SEQ ID NO:10. In some embodiments, the binding protein comprises an antibody heavy chain comprising the amino acid sequence of SEQ ID NO:11 and an antibody light chain comprising the amino acid sequence of SEQ ID NO:12. In some embodiments, the antigen binding site cross-reacts with an extracellular domain of a human CD38 polypeptide and an extracellular domain of a cynomolgus monkey CD38 polypeptide. In some embodiments, the antigen binding site binds a human CD38 polypeptide comprising the amino acid sequence of SEQ ID NO:1. In some embodiments, the antigen binding site binds the human CD38 polypeptide comprising the amino acid sequence of SEQ ID NO:1 with an equilibrium dissociation constant ($K_D$) of 2.1 nM or less. In some embodiments, the antigen binding site binds a human isoform E CD38 polypeptide comprising the amino acid sequence of SEQ ID NO:105. In some embodiments, the antigen binding site binds a cynomolgus monkey CD38 polypeptide comprising the amino acid sequence of SEQ ID NO:30. In some embodiments, the antigen binding site binds the cynomolgus monkey CD38 polypeptide comprising the amino acid sequence of SEQ ID NO:30 with an equilibrium dissociation constant ($K_D$) of 1.3 nM or less.

In some embodiments of any of the above embodiments, the binding protein is a chimeric or humanized antibody. In some embodiments, the binding protein is a human antibody. In some embodiments, the binding protein is a monoclonal antibody. In some embodiments, the binding protein comprises one or more full-length antibody heavy chains comprising an Fc region. In some embodiments, the Fc region is a human Fc region comprising one or more mutations that reduce or eliminate Fc receptor binding and/or effector function of the Fc region. In some embodiments, the Fc region is a human IgG1 Fc region. In some embodiments, the human IgG1 Fc region comprises amino acid substitutions at positions corresponding to positions 234, 235, and 329 of human IgG1 according to EU Index, wherein the amino acid substitutions are L234A, L235A, and P329A. In some embodiments, the human IgG1 Fc region comprises amino acid substitutions at positions corresponding to positions 298, 299, and 300 of human IgG1 according to EU Index, wherein the amino acid substitutions are S298N, T299A, and Y300S. In some embodiments, the Fc region is a human IgG4 Fc region. In some embodiments, the human IgG4 Fc region comprises amino acid substitutions at positions corresponding to positions 228 and 409 of human IgG4 according to EU Index, wherein the amino acid substitutions are S228P and R409K. In some embodiments, the human IgG4 Fc region comprises amino acid substitutions at positions corresponding to positions 234 and 235 of human IgG4 according to EU Index, wherein the amino acid substitutions are F234A and L235A. In some embodiments, the human IgG4 Fc region comprises amino acid substitutions at positions corresponding to positions 233-236 of human IgG4 according to EU Index, wherein the amino acid substitutions are E233P, F234V, L235A, and a deletion at 236. In some embodiments, the human IgG4 Fc region comprises amino acid substitutions at positions corresponding to positions 233-237 of human IgG4 according to EU Index, wherein the sequence EFLGG is replaced by PVAG. In some embodiments, the binding protein comprises an antibody F(ab), F(ab')2, Fab'-SH, Fv, or scFv fragment. In some embodiments, the binding protein is conjugated to a cytotoxic agent or label. In some embodiments, the binding protein is a bispecific binding protein comprising the first antigen binding site that binds the CD38 polypeptide and a second antigen binding site. In some embodiments, the binding protein is a trispecific binding protein comprising the first antigen binding site that binds the CD38 polypeptide, a second antigen binding site, and a third antigen binding site. In some embodiments, the first antigen binding site binds the extracellular domain of a human CD38 polypeptide, and wherein the second and third antigen binding sites each bind a T-cell surface protein. In some embodiments, the first antigen binding site binds the extracellular domain of a human CD38 polypeptide, and wherein (a) the second antigen binding site binds a human CD28 polypeptide, and the third antigen binding site binds a human CD3 polypeptide, or (b) the second antigen binding site binds a human CD3 polypeptide, and the third antigen binding site binds a human CD28 polypeptide.

In some embodiments, provided herein is a binding protein comprising three antigen binding sites that each bind one or more target proteins, wherein at least one of the three antigen binding sites cross-reacts with an extracellular domain of a human CD38 polypeptide and an extracellular domain of a cynomolgus monkey CD38 polypeptide. In some embodiments, the binding protein cross-reacts with a human CD38 polypeptide comprising the amino acid sequence of SEQ ID NO:1 or SEQ ID NO:105. In some embodiments, the binding protein cross-reacts with a cynomolgus monkey CD38 polypeptide comprising the amino acid sequence of SEQ ID NO:30. In some embodiments, the binding protein comprises an antigen binding site that cross-reacts with an extracellular domain of a human CD38 polypeptide and an extracellular domain of a cynomolgus monkey CD38 polypeptide and two antigen binding sites that each bind a T-cell surface protein. In some embodiments, the binding protein comprises an antigen binding site that cross-reacts with an extracellular domain of a human CD38 polypeptide and an extracellular domain of a cynomolgus monkey CD38 polypeptide, an antigen binding site that binds a human CD28 polypeptide, and an antigen binding site that binds a human CD3 polypeptide. In some embodiments, the binding protein comprises four polypeptide chains that form the three antigen binding sites, wherein a first polypeptide chain comprises a structure represented by the formula:

$$V_{L2}\text{-}L_1\text{-}V_{L1}\text{-}L_2\text{-}C_L \quad [I]$$

and a second polypeptide chain comprises a structure represented by the formula:

$$V_{H1}\text{-}L_3\text{-}V_{H2}\text{-}L_4\text{-}C_{H1}\text{-}hinge\text{-}C_{H2}\text{-}C_{H3} \quad [II]$$

and a third polypeptide chain comprises a structure represented by the formula:

$$V_{H3}\text{-}C_{H1}\text{-}hinge\text{-}C_{H2}\text{-}C_{H3} \quad [III]$$

and a fourth polypeptide chain comprises a structure represented by the formula:

$$V_{L3}\text{-}C_L \quad [IV]$$

wherein:
$V_{L1}$ is a first immunoglobulin light chain variable domain;
$V_{L2}$ is a second immunoglobulin light chain variable domain;
$V_{L3}$ is a third immunoglobulin light chain variable domain;
$V_{H1}$ is a first immunoglobulin heavy chain variable domain;
$V_{H2}$ is a second immunoglobulin heavy chain variable domain;
$V_{H3}$ is a third immunoglobulin heavy chain variable domain;
$C_L$ is an immunoglobulin light chain constant domain;
$C_{H1}$ is an immunoglobulin $C_{H1}$ heavy chain constant domain;
$C_{H2}$ is an immunoglobulin $C_{H2}$ heavy chain constant domain;
$CH_3$ is an immunoglobulin $C_{H3}$ heavy chain constant domain;
hinge is an immunoglobulin hinge region connecting the $C_{H1}$ and $C_{H2}$ domains; and
$L_1$, $L_2$, $L_3$ and $L_4$ are amino acid linkers;
wherein the polypeptide of formula I and the polypeptide of formula II form a cross-over light chain-heavy chain pair, and
wherein: (a) the $V_{H1}$ domain comprises a CDR-H1 sequence comprising the amino acid sequence of GYTFTSFN (SEQ ID NO:31) or GYTFTSYA (SEQ ID NO:37), a CDR-H2 sequence comprising the amino acid sequence of IYPGNGGT (SEQ ID NO:32) or IYPGQGGT (SEQ ID NO:38), and a CDR-H3 sequence comprising the amino acid sequence of ARTGGLRRAYFTY (SEQ ID NO:33), and the $V_{L1}$ domain comprises a CDR-L1 sequence comprising the amino acid sequence of ESVDSYGNGF (SEQ ID NO:34) or QSVSSYGQGF (SEQ ID NO:39), a CDR-L2 sequence comprising the amino acid sequence of LAS (SEQ ID NO:35) or GAS (SEQ ID NO:40), and a CDR-L3 sequence comprising the amino acid sequence of QQNKEDPWT (SEQ ID NO:36);
(b) the $V_{H2}$ domain comprises a CDR-H1 sequence comprising the amino acid sequence of GYTFTSFN (SEQ ID NO:31) or GYTFTSYA (SEQ ID NO:37), a CDR-H2 sequence comprising the amino acid sequence of IYPGNGGT (SEQ ID NO:32) or IYPGQGGT (SEQ ID NO:38), and a CDR-H3 sequence comprising the amino acid sequence of ARTGGLRRAYFTY (SEQ ID NO:33), and the $V_{L2}$ domain comprises a CDR-L1 sequence comprising the amino acid sequence of ESVDSYGNGF (SEQ ID NO:34) or QSVSSYGQGF (SEQ ID NO:39), a CDR-L2 sequence comprising the amino acid sequence of LAS (SEQ ID NO:35) or GAS (SEQ ID NO:40), and a CDR-L3 sequence comprising the amino acid sequence of QQNKEDPWT (SEQ ID NO:36); or
(c) the $V_{H3}$ domain comprises a CDR-H1 sequence comprising the amino acid sequence of GYTFTSFN (SEQ ID NO:31) or GYTFTSYA (SEQ ID NO:37), a CDR-H2 sequence comprising the amino acid sequence of IYPGNGGT (SEQ ID NO:32) or IYPGQGGT (SEQ ID NO:38), and a CDR-H3 sequence comprising the amino acid sequence of ARTGGLRRAYFTY (SEQ ID NO:33), and the $V_{L3}$ domain comprises a CDR-L1 sequence comprising the amino acid sequence of ESVDSYGNGF (SEQ ID NO:34) or QSVSSYGQGF (SEQ ID NO:39), a CDR-L2 sequence comprising the amino acid sequence of LAS (SEQ ID NO:35) or GAS (SEQ ID NO:40), and a CDR-L3 sequence comprising the amino acid sequence of QQNKEDPWT (SEQ ID NO:36). In some embodiments, the binding protein comprises four polypeptide chains that form the three antigen binding sites, wherein a first polypeptide chain comprises a structure represented by the formula:

$$V_{L2}\text{-}L_1\text{-}V_{L1}\text{-}L_2\text{-}C_L \qquad [\text{I}]$$

and a second polypeptide chain comprises a structure represented by the formula:

$$V_{H1}\text{-}L_3\text{-}V_{H2}\text{-}L_4\text{-}C_{H1}\text{-hinge-}C_{H2}\text{-}C_{H3} \qquad [\text{II}]$$

aid a third polypeptide chain comprises a structure represented by the formula:

$$V_{H3}\text{-}C_{H1}\text{-hinge-}C_{H2}\text{-}C_{H3} \qquad [\text{III}]$$

and a fourth polypeptide chain comprises a structure represented by the formula:

$$V_{L3}\text{-}C_L \qquad [\text{IV}]$$

wherein:
$V_{L1}$ is a first immunoglobulin light chain variable domain;
$V_{L2}$ is a second immunoglobulin light chain variable domain;
$V_{L3}$ is a third immunoglobulin light chain variable domain;
$V_{H1}$ is a first immunoglobulin heavy chain variable domain;
$V_{H2}$ is a second immunoglobulin heavy chain variable domain;
$V_{H3}$ is a third immunoglobulin heavy chain variable domain;
$C_L$ is an immunoglobulin light chain constant domain;
$C_{H1}$ is an immunoglobulin $C_{H1}$ heavy chain constant domain;
$C_{H2}$ is an immunoglobulin $C_{H2}$ heavy chain constant domain;
$C_{H3}$ is an immunoglobulin $C_{H3}$ heavy chain constant domain;
hinge is an immunoglobulin hinge region connecting the $C_{H1}$ and $C_{H2}$ domains; and
$L_1$, $L_2$, $L_3$ and $L_4$ are amino acid linkers;
wherein the polypeptide of formula I and the polypeptide of formula U form a cross-over light chain-heavy chain pair, and
wherein: (a) the $V_{H1}$ domain comprises a CDR-H1 sequence comprising the amino acid sequence of GYTFTSFN (SEQ ID NO:31) or GYTFTSYA (SEQ ID NO:37), a CDR-H2 sequence comprising the amino acid sequence of IYPGNGGT (SEQ ID NO:32) or IYPGQGGT (SEQ ID NO:38), and a CDR-H3 sequence comprising the amino acid sequence of ARTGGLRRAYFTY (SEQ ID NO:33), and the $V_{L1}$ domain comprises a CDR-L1 sequence comprising the amino acid sequence of ESVDSYGNGF (SEQ ID NO:34) or QSVSSYGQG (SEQ ID NO:132), a CDR-L2 sequence comprising the amino acid sequence of LAS (SEQ ID NO:35) or GAS (SEQ ID NO:40), and a CDR-L3 sequence comprising the amino acid sequence of QQNKEDPWT (SEQ ID NO:36);
(b) the $V_{H2}$ domain comprises a CDR-H1 sequence comprising the amino acid sequence of GYTFTSFN (SEQ ID NO:31) or GYTFTSYA (SEQ ID NO:37), a CDR-H2 sequence comprising the amino acid sequence of IYPGNGGT (SEQ ID NO:32) or IYPGQGGT (SEQ ID NO:38), and a CDR-H3 sequence comprising the amino acid sequence of ARTGGLRRAYFTY (SEQ ID NO:33), and the $V_{L2}$ domain comprises a CDR-L1 sequence comprising the amino acid sequence of ESVDSYGNGF (SEQ ID NO:34) or QSVSSYGQG (SEQ ID NO:132), a CDR-L2 sequence comprising the amino acid sequence of LAS (SEQ ID NO:35) or GAS (SEQ ID NO:40), and a CDR-L3 sequence comprising the amino acid sequence of QQNKEDPWT (SEQ ID NO:36); or
(c) the $V_{H3}$ domain comprises a CDR-H1 sequence comprising the amino acid sequence of GYTFTSFN (SEQ ID NO:31) or GYTFTSYA (SEQ ID NO:37), a CDR-H2 sequence comprising the amino acid sequence of IYPGNGGT (SEQ ID NO:32) or IYPGQGGT (SEQ ID NO:38), and a CDR-H3 sequence comprising the amino acid sequence of ARTGGLRRAYFTY (SEQ ID NO:33), and the $V_{L3}$ domain comprises a CDR-L1 sequence comprising the amino acid sequence of ESVDSYGNGF (SEQ ID NO:34) or QSVSSYGQG (SEQ ID NO:132), a CDR-L2 sequence comprising the amino acid sequence of LAS (SEQ ID NO:35) or GAS (SEQ ID NO:40), and a CDR-L3 sequence comprising the amino acid sequence of QQNKEDPWT (SEQ ID NO:36). In some embodiments, the $V_{H1}$ domain comprises a CDR-H1 sequence comprising the amino add sequence of GYTFTSFN (SEQ ID NO:31), a CDR-H2 sequence comprising the amino acid sequence of IYPGNGGT (SEQ ID NO:32), and a CDR-H3 sequence comprising the amino acid sequence of ARTGGLRRAYFTY (SEQ ID NO:33), and the $V_{L1}$ domain comprises a CDR-L1 sequence comprising the amino acid sequence of ESVDSYGNGF (SEQ ID NO:34), a CDR-L2 sequence comprising the amino acid sequence of LAS (SEQ ID NO:35), and a CDR-L3 sequence comprising the amino acid sequence of QQNKEDPWT (SEQ ID NO:36); the $V_{H1}$ domain comprises a CDR-H1 sequence comprising the amino add sequence of GYTFTSYA (SEQ ID NO:37), a CDR-H2 sequence comprising the amino acid sequence of IYPGQGGT (SEQ ID NO:38), and a CDR-H3 sequence comprising the amino acid sequence of ARTGGLRRAYFTY (SEQ ID NO:33), and the $V_{L1}$ domain comprises a CDR-L1 sequence comprising the amino acid sequence of QSVSSYGQGF (SEQ ID NO:39), a CDR-L2 sequence comprising the amino acid sequence of GAS (SEQ ID NO:40), and a CDR-L3 sequence comprising the amino acid sequence of QQNKEDPWT (SEQ ID NO:36); the $V_{H2}$ domain comprises a CDR-H1 sequence comprising the amino acid sequence of GYTFTSFN (SEQ ID NO:31), a CDR-H2 sequence comprising the amino acid sequence of IYPGNGGT (SEQ ID NO:32), and a CDR-H3 sequence comprising the amino acid sequence of ARTGGLRRAYFTY (SEQ ID NO:33), and the $V_{L1}$ domain comprises a CDR-L1 sequence comprising the amino add sequence of ESVDSYGNGF (SEQ ID NO:34), a CDR-L2 sequence comprising the amino acid sequence of LAS (SEQ ID NO:35), and a CDR-L3 sequence comprising the amino acid sequence of QQNKEDPWT (SEQ ID NO:36); the $V_{H2}$ domain comprises a CDR-H1 sequence comprising the amino acid sequence of GYTFTSYA (SEQ ID NO:37), a CDR-H2 sequence comprising the amino acid sequence of IYPGQGGT (SEQ ID NO:38), and a CDR-H3 sequence comprising the amino acid sequence of ARTGGLRRAYFTY (SEQ ID NO:33), and the $V_{L1}$ domain comprises a CDR-L1 sequence comprising the amino add sequence of QSVSSYGQGF (SEQ ID NO:39), a CDR-L2 sequence comprising the amino add sequence of GAS (SEQ ID NO:40), and a CDR-L3 sequence comprising the amino acid sequence of QQNKEDPWT (SEQ ID NO:36); the $V_{H3}$ domain comprises a CDR-H1 sequence comprising the amino acid sequence of GYTFTSFN (SEQ ID NO:31), a CDR-H2 sequence comprising the amino acid sequence of IYPGNGGT (SEQ ID NO:32), and a CDR-H3 sequence comprising the amino acid sequence of ARTGGLRRAYFTY (SEQ ID NO:33), and the $V_{L1}$ domain comprises a CDR-L1 sequence comprising the amino acid sequence of ESVDSYGNGF (SEQ ID NO:34), a CDR-L2 sequence comprising the amino acid sequence of LAS (SEQ ID NO:35), and a CDR-L3 sequence comprising the amino acid sequence of QQNKEDPWT (SEQ ID NO:36); or the $V_{H3}$ domain comprises a CDR-H1 sequence comprising the amino acid sequence of GYTFTSYA (SEQ ID NO:37), a CDR-H2 sequence comprising the amino acid sequence of IYPGQGGT (SEQ ID NO:38), and a CDR-H3 sequence composing the amino acid sequence of ARTGGLRRAYFTY (SEQ ID NO:33), and the $V_{L3}$ domain comprises a CDR-L1 sequence comprising the amino acid sequence of QSVSSYGQGF (SEQ ID NO:39), a CDR-L2 sequence comprising the amino acid sequence of GAS (SEQ ID NO:40), and a CDR-L3 sequence comprising the amino acid sequence of QQNKEDPWT (SEQ ID NO:36). In some embodiments, the $V_{H3}$ domain comprises a CDR-H1 sequence comprising the amino acid sequence of GYTFTSFN (SEQ ID NO:31), a CDR-H2 sequence comprising the amino acid sequence of IYPGNGGT (SEQ ID NO:32), and a CDR-H3 sequence comprising the amino acid sequence of ARTGGLRRAYFTY (SEQ ID NO:33), and the $V_{L1}$ domain comprises a CDR-L1 sequence comprising the amino acid sequence of ESVDSYGNGF (SEQ ID NO:34), a CDR-L2 sequence comprising the amino acid sequence of LAS (SEQ ID NO:35), and a CDR-L3 sequence comprising the amino acid sequence of QQNKEDPWT (SEQ ID NO:36); or the $V_{H1}$ domain comprises a CDR-H1 sequence comprising the amino acid sequence of GYTFTSYA (SEQ ID NO:37), a CDR-H2 sequence comprising the amino acid sequence of IYPGQGGT (SEQ ID NO:38), and a CDR-H3 sequence comprising the amino acid sequence of ARTG-GLRRAYFTY (SEQ ID NO:33), and the $V_{L}$ domain comprises a CDR-L1 sequence comprising the amino acid sequence of QSVSSYGQGF (SEQ ID NO:39), a CDR-L2 sequence comprising the amino acid sequence of GAS (SEQ ID NO:40), and a CDR-L3 sequence comprising the amino acid sequence of QQNKEDPWT (SEQ ID NO:36). In some embodiments, the $V_{H3}$ domain comprises the amino acid sequence of SEQ ID NO:5, and the $V_{L3}$ domain comprises the amino acid sequence of SEQ ID NO:6; the $V_{H3}$ domain comprises the amino acid sequence of SEQ ID NO:17, and the $V_{L3}$ domain comprises the amino acid sequence of SEQ ID NO:18; the $V_{H3}$ domain comprises the amino acid sequence of SEQ ID NO:21, and the $V_{L3}$ domain comprises the amino acid sequence of SEQ ID NO:18; the $V_{H3}$ domain comprises the amino acid sequence of SEQ ID NO:23, and the $V_{L3}$ domain comprises the amino acid sequence of SEQ ID NO:18; or the $V_{H3}$ domain comprises the amino acid sequence of SEQ ID NO:13, and the $V_{L3}$ domain comprises the amino acid sequence of SEQ ID NO:14. In some embodiments, the binding protein comprises four polypeptide chains that form the three antigen binding sites, wherein a first polypeptide chain comprises a structure represented by the formula:

$$V_{L2}\text{-}L_1\text{-}V_{L1}\text{-}L_2\text{-}C_L \quad [\text{I}]$$

and a second polypeptide chain comprises a structure represented by the formula:

$$V_{H1}\text{-}L_3\text{-}V_{H2}\text{-}L_4\text{-}C_{H1}\text{-hinge-}C_{H2}\text{-}C_{H3} \quad [\text{II}]$$

and a third polypeptide chain comprises a structure represented by the formula:

$$V_{H3}\text{-}C_{H1}\text{-hinge-}C_{H2}\text{-}C_{H3} \quad [\text{III}]$$

and a fourth polypeptide chain comprises a structure represented by the formula:

$$V_{L3}\text{-}C_L \quad [\text{IV}]$$

wherein:

$V_{L1}$ is a first immunoglobulin light chain variable domain;

$V_{L2}$ is a second immunoglobulin light chain variable domain;

$V_{L3}$ is a third immunoglobulin light chain variable domain;

$V_{H1}$ is a first immunoglobulin heavy chain variable domain;

$V_{H2}$ is a second immunoglobulin heavy chain variable domain;

$V_{H3}$ is a third immunoglobulin heavy chain variable domain;

$C_L$ is an immunoglobulin light chain constant domain;

$C_{H1}$ is an immunoglobulin $C_{H1}$ heavy chain constant domain;

$C_{H2}$ is an immunoglobulin $C_{H2}$ heavy chain constant domain;

$C_{H3}$ is an immunoglobulin $C_{H3}$ heavy chain constant domain;

hinge is an immunoglobulin hinge region connecting the $C_{H1}$ and $C_{H2}$ domains; and $L_1$, $L_2$, $L_3$ and $L_4$ are amino acid linkers;

wherein the polypeptide of formula I and the polypeptide of formula II form a cross-over light chain-heavy chain pair, and wherein (a) the $V_{H1}$ domain comprises a CDR-H1 sequence comprising the amino acid sequence of GFTFSSYG (SEQ ID NO:41), a CDR-H2 sequence comprising the amino acid sequence of IWYDGSNK (SEQ ID NO:42), and a CDR-H3 sequence comprising the amino acid sequence of ARMFRGAFDY (SEQ ID NO:43), and the $V_{L1}$ domain comprises a CDR-L1 sequence comprising the amino acid sequence of QGIRND (SEQ ID NO:44), a CDR-L2 sequence comprising the amino acid sequence of AAS (SEQ ID NO:45), and a CDR-L3 sequence comprising the amino acid sequence of LQDYIYYPT (SEQ ID NO:46);

(b) the $V_{H2}$ domain comprises a CDR-H1 sequence comprising the amino acid sequence of GFTFSSYG (SEQ ID NO:41), a CDR-H2 sequence comprising the amino acid sequence of IWYDGSNK (SEQ ID NO:42), and a CDR-H3 sequence comprising the amino acid sequence of ARMFR-GAFDY (SEQ ID NO:43), and the $V_{L1}$ domain comprises a CDR-L1 sequence comprising the amino acid sequence of QGIRND (SEQ ID NO:44), a CDR-L2 sequence comprising the amino acid sequence of AAS (SEQ ID NO:45), and a CDR-L3 sequence comprising the amino acid sequence of LQDYIYYPT (SEQ ID NO:46); or (c) the $V_{H3}$ domain comprises a CDR-H1 sequence comprising the amino acid sequence of GFTFSSYG (SEQ ID NO:41), a CDR-H2 sequence comprising the amino acid sequence of IWYDGSNK (SEQ ID NO:42), and a CDR-H3 sequence comprising the amino acid sequence of ARMFR-GAFDY (SEQ ID NO:43), and the $V_{L}$ domain comprises a CDR-L1 sequence comprising the amino acid sequence of QGIRND (SEQ ID NO:44), a CDR-L2 sequence comprising the amino acid sequence of AAS (SEQ ID NO:45), and a CDR-L3 sequence comprising the amino acid sequence of LQDYIYYPT (SEQ ID NO:46). In some embodiments, the $V_{H3}$ domain comprises a CDR-H1 sequence comprising the amino acid sequence of GFTFSSYG (SEQ ID NO:41), a CDR-H2 sequence comprising the amino acid sequence of IWYDGSNK (SEQ ID NO:42), and a CDR-H3 sequence comprising the amino acid sequence of ARMFRGAFDY (SEQ ID NO:43), and the $V_{L3}$ domain comprises a CDR-L1 sequence comprising the amino acid sequence of QGIRND (SEQ ID NO:44), a CDR-L2 sequence comprising the amino acid sequence of AAS (SEQ ID NO:45), and a CDR-L3 sequence comprising the amino acid sequence of LQDYIYYPT (SEQ ID NO:46). In some embodiments, the $V_{H3}$ domain comprises the amino acid sequence of SEQ ID NO:9, and the $V_{L3}$ domain comprises the amino acid sequence of SEQ ID NO:10. In some embodiments, the $V_{H1}$ domain comprises the amino acid sequence of SEQ ID NO:49, the $V_{L1}$ domain comprises the amino add sequence of SEQ ID NO:50, the $V_{H2}$ domain comprises the amino acid sequence of SEQ ID NO:53, and the $V_{L2}$ domain comprises the amino acid sequence of SEQ ID NO:54; the $V_{H2}$ domain comprises the amino acid sequence of SEQ ID NO:49, the $V_{L2}$ domain comprises the amino add sequence of SEQ ID NO:50, the $V_{H1}$ domain comprises the amino acid sequence of SEQ ID NO:53, and the $V_{L1}$ domain comprises the amino acid sequence of SEQ ID NO:54; the $V_{H1}$ domain comprises the amino acid sequence of SEQ ID NO:51, the $V_{L1}$ domain comprises the amino acid sequence of SEQ ID NO:52, the $V_{H2}$ domain comprises the amino add sequence of SEQ ID NO:53, and the $V_{L2}$ domain comprises the amino acid sequence of SEQ ID NO:54; the $V_{H2}$ domain comprises the amino acid sequence of SEQ ID NO:51, the $V_{L1}$ domain comprises the amino acid sequence of SEQ ID NO:52, the $V_{H1}$ domain comprises the amino acid sequence of SEQ ID NO:53, and the $V_{L1}$ domain comprises the amino acid sequence of SEQ ID NO:54 the $V_{H1}$ domain comprises the amino add sequence of SEQ ID NO:49, the $V_{L1}$ domain comprises the amino add sequence of SEQ ID NO:50, the $V_{H2}$ domain comprises the amino acid sequence of SEQ ID NO:84, and the $V_{L2}$ domain comprises the amino acid sequence of SEQ ID NO:85; the $V_{H2}$ domain comprises the amino acid sequence of SEQ ID NO:49, the $V_{L1}$ domain comprises the amino acid sequence of SEQ ID NO:50, the $V_{H1}$ domain comprises the amino acid sequence of SEQ ID NO:84, and the $V_{L1}$ domain comprises the amino acid sequence of SEQ ID NO:85; the $V_{H1}$ domain comprises the amino acid sequence of SEQ ID NO:51, the $V_{L1}$ domain comprises the amino acid sequence of SEQ ID NO:52, the $V_{H2}$ domain comprises the amino acid sequence of SEQ ID NO:84, and the $V_{L1}$ domain comprises the amino acid sequence of SEQ ID NO:85; or the $V_{H2}$ domain comprises the amino acid sequence of SEQ ID NO:51, the $V_{L2}$ domain comprises the amino acid sequence of SEQ ID NO:52, the $V_{H1}$ domain comprises the amino acid sequence of SEQ ID NO:84, and the $V_{H1}$ domain comprises the amino acid sequence of SEQ ID NO:85. In some embodiments, the $V_{H1}$ domain comprises the amino acid sequence of SEQ ID NO:49, the $V_{L1}$ domain comprises the amino acid sequence of SEQ ID NO:50, the $V_{H2}$ domain comprises the amino acid sequence of SEQ ID NO:53, the $V_{L1}$ domain comprises the amino acid sequence of SEQ ID NO:54, the $V_{H3}$ domain comprises the amino add sequence of SEQ ID NO:13, and the $V_{L3}$ domain comprises the amino add sequence of SEQ ID NO:14; or the $V_{H1}$ domain comprises the amino acid sequence of SEQ ID NO:49, the $V_{L1}$ domain comprises the amino acid sequence of SEQ ID NO:50, the $V_{H2}$ domain comprises the amino add sequence of SEQ ID NO:53, the $V_{H3}$ domain comprises the amino acid sequence of SEQ ID NO:54, the $V_{L3}$ domain comprises the amino acid sequence of SEQ ID NO:9, and the $V_{H1}$ domain comprises the amino acid sequence of SEQ ID NO:10. In some embodiments, at least one of $L_1$, $L_2$, $L_3$ or $L_4$ is independently 0 amino acids in length. In some embodiments, $L_1$, $L_2$, $L_3$ or $L_4$ are each independently at least one amino acid in length. In some embodiments, (a) $L_1$, $L_2$, $L_3$ and $L_4$ each independently are zero amino acids in length or comprise a sequence selected from the group consisting of GGGGSGGGGS (SEQ ID NO:55), GGGGSGGGGSGGGGS (SEQ ID NO:56), S, RT, TKGPS (SEQ ID NO:57), GQPKAAP (SEQ ID NO:58), and GGSGSSGSGG (SEQ ID NO:59); or (b) $L_1$, $L_2$, $L_3$ and $L_4$ each independently comprise a sequence selected from the group consisting of GGGGSGGGGS (SEQ ID NO:55), GGGGSGGGGSGGGGS (SEQ ID NO:56), S, RT, TKGPS (SEQ ID NO:57), GQPKAAP (SEQ ID NO:58), and GGSGSSGSGG (SEQ ID NO:59). In some embodiments, $L_1$ comprises the sequence GQPKAAP (SEQ ID NO:58), $L_2$ comprises the sequence TKGPS (SEQ ID NO:57), $L_3$ comprises the sequence S, and $L_4$ comprises the sequence RT; $L_1$ comprises the sequence GGGGSGGGGS (SEQ ID NO:55), $L_2$ comprises the sequence GGGGSGGGGS (SEQ ID NO:55), $L_3$ is 0 amino acids in length, and $L_4$ is 0 amino acids in length; $L_1$ comprises the sequence GGSGSSGSGG (SEQ ID NO:59), $L_2$ comprises the sequence GGSGSSGSGG (SEQ ID NO:59), $L_3$ is 0 amino acids in length, and $L_4$ is 0 amino acids in length; or $L_1$ comprises the sequence GGGGSGGGGSGGGGS (SEQ ID NO:56), $L_2$ is 0 amino acids in length, $L_3$ comprises the sequence GGGGSGGGGSGGGGS (SEQ ID NO:56), and $L_4$ is 0 amino acids in length. In some embodiments, the hinge-$C_{H2}$-$C_{H3}$ domains of the second and the third polypeptide chains are human IgG4 hinge-$C_{H2}$-$C_{H3}$ domains, and wherein the hinge-$C_{H2}$-$C_{H3}$ domains each comprise amino acid substitutions at positions corresponding to positions 234 and 235 of human IgG4 according to EU Index, wherein the amino acid substitutions are F234A and L235A. In some embodiments, the hinge-$C_{H2}$-$C_{H3}$ domains of the second and the third polypeptide chains are human IgG4 hinge-$C_{H2}$-$C_{H3}$ domains, and wherein the hinge-$C_{H2}$-$C_{H3}$ domains each comprise amino acid substitutions at positions corresponding to positions 233-236 of human IgG4 according to EU Index, wherein the amino acid substitutions are E233P, F234V, L235A, and a deletion at 236. In some embodiments, the hinge-$C_{H2}$-$C_{H3}$ domains of the second and the third polypeptide chains are human IgG4 hinge-$C_{H2}$-$C_{H3}$ domains, and wherein the hinge-$C_{H2}$-$C_{H3}$ domains each comprise amino acid substitutions at positions corresponding to positions 228 and 409 of human IgG4 according to EU index, wherein the amino acid substitutions are S228P and R409K. In some embodiments, the hinge-$C_{H2}$-$C_{H3}$ domains of the second and the third polypeptide chains are human IgG1 hinge-$C_{H2}$-$C_{H3}$ domains, and wherein the hinge-$C_{H2}$-$C_{H3}$ domains each comprise amino acid substitutions at positions corresponding to positions 234, 235, and 329 of human IgG1 according to EU Index, wherein the amino acid substitutions are L234A, L235A, and P329A. In some embodiments, the hinge-$C_{H2}$-$C_{H3}$ domains of the second and the third polypeptide chains are human IgG1 hinge-$C_{H2}$-$C_{H3}$ domains, and wherein the hinge-$C_{H2}$-$C_{H3}$ domains each comprise amino acid substitutions at positions corresponding to positions 298.299, and 300 of human IgG1 according to EU Index, wherein the amino acid substitutions are S298N, T299A, and Y300S. In some embodiments, the hinge-$C_{H2}$-$C_{H3}$; domain of the second polypeptide chain comprises amino acid substitutions at positions corresponding to positions 349, 366, 368, and 407 of human IgG1 or IgG4 according to EU Index, wherein the amino acid substitutions are Y349C, T366S, L368A, and Y407V; and wherein the hinge-$C_{H2}$-$C_{H3}$ domain of the third polypeptide chain comprises amino acid substitutions at positions corresponding to positions 354 and 366 of human IgG1 or IgG4 according to EU Index, wherein the amino acid substitutions are S354C and T366W. In some embodiments, the hinge-$C_{H2}$-$C_{H3}$ domain of the second polypeptide chain comprises amino acid substitutions at positions corresponding to positions 3S4 and 366 of human IgG1 or IgG4 according to ELI index, wherein the amino acid substitutions are S354C and T366W; and wherein the hinge-$C_{H2}$-$C_{H3}$ domain of the third polypeptide chain comprises amino acid substitutions at positions corresponding to positions 349, 366, 368, and 407 of human IgG1 or IgG4 according to EU Index, wherein the amino acid substitutions are Y349C, T366S, L368A, and Y407V. In some embodiments, the first polypeptide chain comprises the amino acid sequence of SEQ ID NO:61, the second polypeptide chain comprises the amino acid sequence of SEQ ID NO:60, the third polypeptide chain comprises the amino acid sequence of SEQ ID NO:62, and the fourth polypeptide chain comprises the amino acid sequence of SEQ ID NO:63. In some embodiments, the first polypeptide chain comprises the amino acid sequence of SEQ ID NO:61, the second polypeptide chain comprises the amino acid sequence of SEQ ID NO:64, the third polypeptide chain comprises the amino acid sequence of SEQ ID NO:65, and the fourth polypeptide chain comprises the amino acid sequence of SEQ ID NO:63. In some embodiments, the first poly peptide chain comprises the amino acid sequence of SEQ ID NO:61, the second polypeptide chain comprises the amino acid sequence of SEQ ID NO:66, the third polypeptide chain comprises the amino acid sequence of SEQ ID NO:67, and the fourth polypeptide chain comprises the amino acid sequence of SEQ ID NO:63. In some embodiments, the first polypeptide chain comprises the amino acid sequence of SEQ ID NO:61, the second polypeptide chain comprises the amino add sequence of SEQ ID NO:60, the third polypeptide chain comprises the amino acid sequence of SEQ ID NO:68, and the fourth polypeptide chain comprises the amino acid sequence of SEQ ID NO:69. In some embodiments, the first polypeptide chain comprises the amino acid sequence of SEQ ID NO:61, the second polypeptide chain comprises the amino add sequence of SEQ ID NO:64, the third polypeptide chain comprises the amino acid sequence of SEQ ID NO:70, and the fourth polypeptide chain comprises the amino acid sequence of SEQ ID NO:69. In some embodiments, the first polypeptide chain comprises the amino acid sequence of SEQ ID NO:61, the second polypeptide chain comprises the amino acid sequence of SEQ ID NO:66, the third polypeptide chain comprises the amino add sequence of SEQ ID NO:71, and the fourth polypeptide chain comprises the amino add sequence of SEQ ID NO:69.

In some embodiments, provided herein is a binding protein comprising three antigen binding sites that each bind one or more target proteins, wherein the binding protein comprises four polypeptide chains that form the three antigen binding sites, wherein a first polypeptide chain comprises a structure represented by the formula:

$$V_{L2}\text{-}L_1\text{-}V_{L1}\text{-}L_2\text{-}C_L \quad [\text{I}]$$

and a second polypeptide chain comprises a structure represented by the formula:

$$V_{H1}\text{-}L_3\text{-}V_{H2}\text{-}L_4\text{-}C_{H1}\text{-}\text{hinge-}C_{H2}\text{-}C_{H3} \quad [\text{II}]$$

and a third polypeptide chain comprises a structure represented by the formula:

$$V_{H3}\text{-}C_{H1}\text{-}\text{hinge-}C_{H2}\text{-}C_{H3} \quad [\text{III}]$$

and a fourth polypeptide chain comprises a structure represented by the formula:

$$V_{L3}\text{-}C_L \quad [\text{IV}]$$

wherein:
$V_{L1}$ is a first immunoglobulin light chain variable domain;
$V_{L2}$ is a second immunoglobulin light chain variable domain;
$V_{L3}$ is a third immunoglobulin light chain variable domain;
$V_{H1}$ is a first immunoglobulin heavy chain variable domain;
$V_{H2}$ is a second immunoglobulin heavy chain variable domain;
$V_{H3}$ is a third immunoglobulin heavy chain variable domain;
$C_L$ is an immunoglobulin light chain constant domain;
$C_{H1}$ is an immunoglobulin $C_{H1}$ heavy chain constant domain;
$C_{H2}$ is an immunoglobulin $C_{H2}$ heavy chain constant domain;
$C_{H3}$ is an immunoglobulin $C_{H3}$ heavy chain constant domain;
hinge is an immunoglobulin hinge region connecting the $C_{H1}$ and $C_{H2}$ domains; and
$L_1$, $L_2$, $L_3$, and $L_4$ are amino acid linkers;
wherein the polypeptide of formula I and the polypeptide of formula II form a cross-over light chain-heavy chain pair; and
wherein (a) the hinge-$C_{H2}$-$C_{H3}$ domains of the second and the third polypeptide chains are human IgG1 hinge-$C_{H2}$-$C_{H3}$ domains, and wherein the hinge-$C_{H2}$-$C_{H3}$ domains each comprise amino acid substitutions at positions corresponding to positions 298, 299, and 300 of human IgG1 according to EU Index, wherein the amino acid substitutions are S298N, T299A, and Y300S; or (b) the hinge-$C_{H2}$-$C_{H3}$ domains of the second and the third polypeptide chains are human IgG4 hinge-$C_{H2}$-$C_{H1}$ domains, and wherein the hinge-$C_{H2}$-$C_{H3}$ domains each comprise amino acid substitutions at positions corresponding to positions 233-236 of human IgG4 according to EU Index, wherein the amino acid substitutions are E233P, F234V, L235A, aid a deletion at 236. In some embodiments, the human IgG4 hinge-$C_{H2}$-$C_{H3}$ domains comprise amino acid substitutions at positions corresponding to positions 233-237 of human IgG4 according to EU Index, wherein the sequence EFLGG is replaced by PVAG. In some embodiments, at least one pair of $V_{H1}$ and $V_{L1}$, $V_{H2}$ and $V_{L2}$, and $V_{H3}$ and $V_{L3}$ forms an antigen binding site that binds a CD38 polypeptide. In some embodiments, one, two, or three pairs of $V_{H1}$ and $V_{L1}$, $V_{H2}$ and $V_{L2}$, and $V_{H1}$ and $V_{L3}$ form an antigen binding site that binds an antigen target selected from the group consisting of A2AR, APRIL, ATPDase, BAFF, BAFFR, BCMA, BlyS, BTK, BTLA, B7DC, B7H1, B7H4, B7H5, B7H6, B7H7, B7RP1, B7-4, C3, C5, CCL2, CCL3, CCL4, CCL5, CCL7, CCL8, CCL11, CCL15, CCL17, CCL19, CCL20, CCL21, CCL24, CCL25, CCL26, CCR3, CCR4, CD3, CD19, CD20, CD23, CD24, CD27, CD28, CD38, CD39, CD40, CD70, CD80, CD86, CD122, CD137, CD137L, CD152, CD154, CD160, CD272, CD273, CD274, CD275, CD276, CD278, CD279, CDH1, chitinase, CLEC9, CLEC91, CRTH2, CSF-1, CSF-2, CSF-3, CX3CL1, CXCL12, CXCL13, CXCR3, DNGR-1, ectonucleoside triphosphate diphosphohydrolase 1, EGFR, ENTPD1, FCER1A, FCER1, FLAP, FOLH1, Gi24, GITR, GITRL, GM-CSF, Her2, HHLA2, HMGB1, HVEM, ICO-SLG, IDO, IFNα, IgE, IGF1R, IL2Rbeta, IL1, IL1A, IL1B, IL1F10, IL2, IL4, IL4Ra, IL5, IL5R, IL6, IL7, IL7Ra, IL8, IL9, IL9R, IL10, rhIL10, IL12, IL13, IL13Ra1, IL13Ra2, IL15, IL17, IL17Rb, IL18, IL22, IL23, IL25, IL27, IL33, IL35, ITGB4, ITK, KIR, LAG3, LAMP1, leptin, LPFS2, MHC class IL NCR3LG1, NKG2D, NTPDase-1, OX40, OX40L, PD-1H, platelet receptor, PROM1, S152, SISP1, SLC, SPG64, ST2, STEAP2, Syk kinase, TACI, TDO, T14, TIGIT, TIM3, TLR, TLR2, TLR4, TLR5, TLR9, TMEF1, TNFa, TNFRSF7, Tp55, TREM1, TSLP, TSLPR, TWEAK, VEGF, VISTA, Vstm3, WUCAM, and XCR1. In some embodiments, a first pair of $V_{H1}$ and $V_{L1}$, $V_{H2}$ and $V_{L2}$, and $V_{H3}$ and $V_{L3}$ forms an antigen binding site that binds a human CD3 polypeptide, a second pair of $V_{H1}$ and $V_{L1}$, $V_{H2}$ and $V_{L2}$, and $V_{H3}$ and $V_{L3}$ forms an antigen binding site that binds a human CD28 polypeptide, and a third pair of $V_{H1}$ and $V_{L1}$, $V_{H1}$ and $V_{L2}$, and $V_{H3}$ and $V_{L3}$ forms an antigen binding site that binds a human antigen target selected from the group consisting of A2AR, APRIL, ATPDase, BAFF, BAFFR, BCMA, BlyS, BTK, BTLA, B7DC, B7H1, B7H4, B7H5, B7H6, B7H7, B7RP1, B7-4, C3, C5, CCL2, CCL3, CCL4, CCL5, CCL7, CCL8, CCL11, CCL15, CCL17, CCL19, CCL20, CCL21, CCL24, CCL25, CCL26, CCR3, CCR4, CD3, CD19, CD20, CD23, CD24, CD27, CD28, CD38, CD39, CD40, CD70, CD80, CD86, CD122, CD137, CD137L, CD152, CD154, CD160, CD272, CD273, CD274, CD275, CD276, CD278, CD279, CDH1, chitinase, CLEC9, CLEC91, CRTH2, CSF-1, CSF-2, CSF-3, CX3CL1, CXCL12, CXCL13, CXCR3, DNGR-1, ectonucleoside triphosphate diphosphohydrolase 1, EGFR, ENTPD1, FCER1A, FCER1, FLAP, FOLH1, Gi24, GITR, GITRL, GM-CSF, Her2, HHLA2, HMGB1, HVEM, ICOSLG, IDO, IFNα, IgE, IGF1R, IL2Rbeta, IL1, IL1A, IL1B, IL1F10, IL2, IL4, IL4Ra, IL5, IL5R, IL6, IL7, IL7Ra, IL8, IL9, IL9R, IL10, rhIL10, IL12, IL13, IL13Ra1, IL13Ra2, IL15, IL17, IL17Rb, IL18, IL22, IL23, IL25, IL27, IL33, IL35, ITGB4, ITK, KIR LAG3, LAMP1, leptin, LPFS2, MHC class II, NCR3LG1, NKG2D, NTPDase-1, OX40, OX40L, PD-1H, platelet receptor, PROM1, S152, SISP1, SLC, SPG64, ST2, STEAP2, Syk kinase, TACI, TOO, T14, TIGIT, TIM3, TLR, TLR2, TLR4, TLR5, TLR9, TMEF1, TNFa, TNFRSF7, Tp55, TREM1, TSLP, TSLPR, WEAK, VEGF, VISTA, Vstm3, WUCAM, and XCR1.

In some embodiments, provided herein is a kit of polynucleotides, comprising: (a) a first polynucleotide comprising the sequence of SEQ ID NO:73, a second polynucleotide comprising the sequence of SEQ ID NO:72, a third polynucleotide comprising the sequence of SEQ ID NO:74, and a fourth polynucleotide comprising the sequence of SEQ ID NO:75; (b) a first polynucleotide comprising the sequence of SEQ ID NO:73, a second polynucleotide comprising the sequence of SEQ ID NO:76, a third polynucleotide comprising the sequence of SEQ ID NO:77, and a fourth polynucleotide comprising the sequence of SEQ ID NO:75; (c) a first polynucleotide comprising the sequence of SEQ ID NO:73, a second polynucleotide comprising the sequence of SEQ ID NO:78, a third polynucleotide comprising the sequence of SEQ ID NO:79, and a fourth polynucleotide comprising the sequence of SEQ ID NO:75, (d) a first polynucleotide comprising the sequence of SEQ ID NO:73, a second polynucleotide comprising the sequence of SEQ ID NO:72, a third polynucleotide comprising the sequence of SEQ ID NO:80, and a fourth polynucleotide comprising the sequence of SEQ ID NO:81; (e) a first polynucleotide comprising the sequence of SEQ ID NO:73, a second polynucleotide comprising the sequence of SEQ ID NO:76, a third polynucleotide comprising the sequence of SEQ ID NO:82, and a fourth polynucleotide comprising the sequence of SEQ ID NO:81; or (f) a first polynucleotide comprising the sequence of SEQ ID NO:73, a second polynucleotide comprising the sequence of SEQ ID NO:78, a third polynucleotide comprising the sequence of SEQ ID NO:83, and a fourth polynucleotide comprising the sequence of SEQ ID NO:81.

In some embodiments, provided herein is a polynucleotide comprising the binding protein of any one of the above embodiments. In some embodiments, provided herein is a vector comprising a polynucleotide comprising the binding protein of any one of the above embodiments.

In some embodiments, provided herein is a host cell comprising the kit of polynucleotides, polynucleotide, or vector of any one of the above embodiments. In some embodiments, provided herein is a method of producing a binding protein, the method comprising culturing the host cell of any one of the above embodiments such that the binding protein is produced. In some embodiments, the method further comprises recovering the binding protein from the host cell.

In some embodiments, provided herein is a pharmaceutical composition comprising the binding protein of any one of the above embodiments and a pharmaceutically acceptable carrier.

In some embodiments, provided herein is a method of preventing and/or treating cancer in a patient comprising administering to the patient a therapeutically effective amount of at least one binding protein of any one of the above embodiments or the pharmaceutical composition of any one of the above embodiments. In some embodiments, the binding protein is a trispecific binding protein comprising a first antigen binding site that binds CD3, a second antigen binding site that binds CD28, and a third antigen binding site that binds the extracellular domain of a human CD38 polypeptide. In some embodiments, the at least one binding protein is co-administered with a chemotherapeutic agent. In some embodiments, the cancer is multiple myeloma. In some embodiments, the cancer is acute myeloid leukemia (AML), acute lymphoblastic leukemia (ALL), chronic lymphocytic leukemia (CLL), or a B cell lymphoma. In some embodiments, the patient is a human. In some embodiments, the patient is selected for treatment because cells of the cancer express a human CD38 isoform E polypeptide (e.g., as set forth in SEQ ID NO:105) on their edit surface. In some embodiments, the cancer cells express CD38 and CD28. In some embodiments, the cancer cells express CD38 and do not express CD28.

In some embodiments, provided herein is at least one binding protein of any one of the above embodiments or the pharmaceutical composition of any one of the above embodiments for use in preventing and/or treating cancer in a patient (e.g., a patient in need thereof, such as a patient with cancer). In some embodiments, provided herein is at least one binding protein of any one of the above embodiments or the pharmaceutical composition of any one of the above embodiments for use in the manufacture of a medicament for preventing and/or treating cancer in a patient (e.g., a patient in need thereof, such as a patient with cancer). In some embodiments of any of the above embodiments, the binding protein is a trispecific binding protein comprising a first antigen binding site that binds CD3, a second antigen binding site that binds CD28, and a third antigen binding site that binds the extracellular domain of a human CD38 polypeptide. In some embodiments, the at least one binding protein is to be co-administered with a chemotherapeutic agent. In some embodiments, the cancer is multiple myeloma. In some embodiments, the cancer is acute myeloid leukemia (AML), acute lymphoblastic leukemia (ALL), chronic lymphocytic leukemia (CLL), or a B cell lymphoma, in some embodiments, the patient is a human, in some embodiments, the patient is selected for treatment because cells of the cancer express a human CD38 isoform E polypeptide (e.g., as set forth in SEQ ID NO:105) on their cell surface. In some embodiments, the cancer cells express CD38 and CD28. In some embodiments, the cancer cells express CD38 and do not express CD28.

It is to be understood that one, some, or all of the properties of the various embodiments described herein may be combined to form other embodiments of the present invention. These and other aspects of the invention will become apparent to one of skill in the art. These and other embodiments of the invention are further described by the detailed description that follows.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1A shows; the binding of anti-CD38 antibodies mAb1 (top) and isatuximab (bottom) to SU-DHL-8 human lymphoma cells or MOLP-8 human multiple myeloma cells using flow cytometry.

FIGS. 2A-2I show the results of assays characterizing the binding of anti-CD38 antibodies to human and cynomolgus monkey CD38 polypeptides FIG. 2A shows the binding of humanized anti-CD38 antibody mAb2 to soluble human CD38 (top, "hCD38::Histag") or cynomolgus monkey CD38 (top. "cynoCD38::Histag") by ELISA, as well as the binding of mAb2 to the surface of cells expressing human CD83 (bottom, as indicated) or cynomolgus monkey CD38 (bottom, as indicated) by flow cytometry. FIG. 2B shows the binding of mAb2 to human CD38 (top) or cynomolgus monkey CD38 (bottom) by surface plasmon resonance (SPR). FIG. 2C shows the binding of humanized anti-CD38 antibody mAb3 to soluble human CD38 (top, "hCD38::Histag") or cynomolgus monkey CD38 (top, "cynoCD38::Histag") by ELISA, as well as the binding of mAb3 to the surface of cells expressing human CD83 (bottom, as indicated) or cynomolgus monkey CD38 (bottom, as indicated) by flow cytometry. FIG. 2D shows the binding of mAb3 to human CD38 (top) or cynomolgus monkey CD38 (bottom) by SPR FIG. 2E shows the binding of humanized anti-CD38 antibody mAb5 to soluble human CD38 (top, "hCD38::Histag") or cynomolgus monkey CD38 (top, "cynoCD38::Histag") by ELISA, as well as the binding of mAb5 to the surface of cells expressing human CD83 (bottom, as indicated) or cynomolgus monkey CD38 (bottom, as indicated) by flow cytometry. FIG. 2F shows the binding of mAb5 to human CD38 (top) or cynomolgus monkey CD38 (bottom) by SPR. FIG. 2G shows the binding of human anti-CD38 antibody hhy 1370 to soluble human CD38 (top, "hCD38::Histag") or cynomolgus monkey CD38 (top, "cynoCD38::Histag") by ELISA, as well as the binding of hhy 1370 to the surface of cells expressing human CD83 (bottom, as indicated) or cynomolgus monkey CD38 (bottom, as indicated) by flow cytometry. FIG. 2H shows the binding of hhy 1370 to human CD38 (top) or cynomolgus monkey CD38 (bottom) by SPR. FIG. 2I summarizes the binding data from the ELISA, SPR, and FACS experiments, as well as the percentage identity of each antibody VH ("H") or VL ("L") domain to human V region sequence from top to bottom it corresponds to mAb2, mAb3, mAb 4, mAb 5, and mAb6 last line (1195 HHKK-3 has not been described by its VL/VH amino acid sequence in the text below).

FIG. 2M shows the percentage of apoptotic cells induced by each antibody. FIGS. 2N-2Q show dose-dependent induction of apoptosis in in SU-DHL-8 lymphoma cells by anti-CD38 antibodies mAb2 (FIG. 2N), mAb3 (FIG. 2O), mAb4 (FIG. 2P), and mAb5 (FIG. 2Q), as well as the IC50 for each antibody.

FIGS. 6B-6D compare the apparent affinities of trispecific binding protein $CD38_{VH1} \times CD28_{sup} \times CD3_{mid}$, $CD38_{VH1} \times CD28_{evn} \times CD3_{mid}$, or monospecific anti-CD38 antibody mAb2 for binding to cells expressing human or cynomolgus monkey CD38 polypeptides, as assayed by flow cytometry. FIG. 6B shows the binding of trispecific binding protein $CD38_{VH1} \times CD28_{sup} \times CD3_{mid}$ to cells expressing human (top) or cynomolgus monkey (bottom) CD38 polypeptides. FIG. 6C shows the binding of trispecific binding protein CD38$_{VH1}$×CD28$_{evn}$×CD3$_{mid}$ to cells expressing human (top) or cynomolgus monkey (bottom) CD38 polypeptides. FIG. 6D shows the binding of monospecific anti-CD38 antibody mAb2 to cells expressing human (top) or cynomolgus monkey (bottom) CD38 polypeptides.

FIG. 6F summarizes the binding affinity of the indicated anti-CD38×anti-CD28×anti-CD3 trispecific binding proteins for human CD38, as measured by SPR or flow cytometry (FACS).

FIG. 6G shows the apparent affinity of trispecific binding protein ΔCD38$_{VH1}$×CD28$_{sup}$×CD3$_{mid}$ lacking the anti-CD38 antigen binding domain for binding to cells expressing human (top) or cynomolgus monkey (bottom) CD38 polypeptides, as assayed by flow cytometry.

FIGS. 8E & 8F show the results of antibody-mediated specific killing of CD38$^+$ cells by PBMCs from two different donors using the indicated anti-CD38×CD28×CD3 trispecific binding proteins with variant Fc regions and control antibodies. Representative results using CD38$^+$ KMS-11 (FIG. 8D) and U266 (FIG. 8E) cell lines are shown, and EC50 values are provided in Tables Q2 and Q3.

FIG. 9A shows the activation (CD69$^+$) of human CD3$^+$ T cells. FIG. 9B shows the activation (CD69$^+$) of human CD3$^+$ CD4$^+$ T cells.

FIG. 10 shows the activation (CD69$^+$) of human CD3$^+$ CD8$^+$ T cells.

FIG. 11A shows the results using 5 µg/mL of the indicated antibodies. FIG. 11B shows the results using 25 ng/mL of the indicated antibodies.

FIG. 12A shows the change in tumor volume in mice treated with the indicated concentrations of the anti-CD38$_{(VH1)}$×CD28$_{(sup)}$×CD3$_{(mid)}$ trispecific binding protein vs. mice treated with an anti-CD3/CD38 bispecific antibody. FIG. 12B shows the average tumor volume at day 18 in mice treated with the indicated concentrations of the anti-CD38$_{(VH1)}$×CD28$_{(sup)}$×CD3$_{(mid)}$ trispecific binding protein vs. mice treated with an anti-CD3/CD38 bispecific antibody. FIG. 12C shows the average terminal tumor weight in mice treated with the indicated concentrations of the anti-CD38$_{(VH1)}$×CD28$_{(sup)}$×CD3$_{(mid)}$ trispecific binding protein vs. mice treated with an anti-CD3/CD38 bispecific antibody. FIG. 12D shows the average tumor growth curve over the length of the experiment in mice treated with the indicated concentrations of the anti-CD38$_{(VH1)}$×CD28$_{(sup)}$×CD3$_{(mid)}$ trispecific binding protein vs. mice treated with an anti-CD3/CD38 bispecific antibody. FIG. 12E shows the average change in body weight at multiple time points over the length of the experiment of mice treated with the indicated concentrations of the anti-CD38$_{(VH1)}$×CD28$_{(sup)}$×CD3$_{(mid)}$, trispecific binding protein vs, mice treated with an anti-CD3/CD38 bispecific antibody.

FIG. 13A shows the change in tumor volume in mice treated with the indicated concentrations of the anti-CD38$_{(VH1)}$×CD28$_{(sup)}$×CD3$_{(mid)}$ trispecific binding protein vs. mice treated with an anti-CD3/CD38 bispecific antibody. FIG. 13B shows the tumor volume at day 4 in mice treated with the indicated concentrations of the anti-CD38$_{(VH1)}$×CD28$_{(sup)}$×CD3$_{(mid)}$ trispecific binding protein vs. mice treated with an anti-CD3/CD38 bispecific antibody. FIG. 13C shows the tumor volume at day 21 in mice treated with the indicated concentrations of the anti-CD38$_{(VH1)}$×CD28$_{(sup)}$×CD3$_{(mid)}$ trispecific binding protein vs. mice treated with an anti-CD3/CD38 bispecific antibody. FIG. 13D shows the average tumor volume at day 21 in mice treated with the indicated concentrations of the anti-CD38$_{(VH1)}$×CD28$_{(sup)}$×CD3$_{(mid)}$ trispecific binding protein vs. mice treated with an anti-CD3/CD38 bispecific antibody. FIG. 13E shows the average terminal tumor weight in mice treated with the indicated concentrations of the anti-CD38$_{(VH1)}$×CD28$_{(sup)}$×CD3$_{(mid)}$ trispecific binding protein vs. mice treated with an anti-CD3/CD38 bispecific antibody. FIG. 13F shows the average tumor volume at multiple time points over the length of the experiment in mice treated with the indicated concentrations of the anti-CD38$_{(VH1)}$×CD28$_{(sup)}$×CD3$_{(mid)}$ trispecific binding protein vs. mice treated with an anti-CD3/CD38 bispecific antibody.

FIG. 14A shows T cell activation (CD69$^+$) of circulating CD3$^+$ T cells after administration of different doses of the anti-CD38$_{(VH1)}$×CD28$_{(sup)}$×CD3$_{(mid)}$ trispecific binding protein. FIG. 14B shows T cell activation (CD69$^+$) of circulating CD3$^+$ T cells after administration of different doses of the anti-CD38$_{(VH1)}$×CD28$_{(sup)}$×CD3$_{(mid)}$ trispecific binding protein. FIG. 14C shows T cell activation (CD69$^+$) of circulating CD3$^+$ T cells after administration of different doses of the anti-CD38$_{(hhy1370)}$×CD28$_{(sup)}$×CD3$_{(mid)}$ trispecific binding protein. FIG. 14D shows T cell activation (CD69$^+$) of circulating CD3$^+$ T cells after administration of different doses of the anti-CD38$_{(hhy1370)}$×CD28$_{(evn)}$×CD3$_{(mid)}$ trispecific binding protein. FIG. 14E shows the changes in percentage of circulating CD4$^+$ T cells after administration of the indicated doses of the anti-CD38$_{(VH1)}$×CD28$_{(VH1)}$×CD3$_{(mid)}$, trispecific binding protein. FIG. 14F shows the changes in percentage of circulating CD8$^+$ T cells after administration of the indicated doses of the anti-CD38$_{(VH1)}$×CD28$_{(sup)}$×CD3$_{(mid)}$ trispecific binding protein. FIG. 14G shows the changes in percentage of circulating CD4$^+$ T cells after administration of the indicated doses of the anti-CD38$_{(VH1)}$×CD28$_{(evn)}$×CD3$_{(mid)}$ trispecific binding protein. FIG. 14H shows the changes in percentage of circulating CD8$^+$ T cells after administration of the indicated doses of the anti-CD38$_{(VH1)}$×CD28$_{(evn)}$×CD3$_{(mid)}$ trispecific binding protein. FIG. 14I shows the changes in percentage of circulating CD4$^+$ T cells after administration of the indicated doses of the anti-CD38$_{(VH1)}$×CD28$_{(sup)}$×CD3$_{(mid)}$ trispecific binding protein. FIG. 14J shows the changes in percentage of circulating CD8$^+$ T cells after administration of the indicated doses of the anti-CD38$_{(hhy1370)}$×CD28$_{(sup)}$×CD3$_{(mid)}$ trispecific binding protein. FIG. 14K show s the changes in percentage of circulating CD4$^+$ T cells after administration of the indicated doses of the anti-CD38$_{(hhy1370)}$×CD28$_{(evn)}$×CD3$_{(mid)}$ trispecific binding protein. FIG. 14L shows the changes in percentage of circulating CD8$^+$ T cells after administration of the indicated doses of the anti-CD38$_{(hhy1370)}$×CD28$_{(evn)}$×CD3$_{(mid)}$ trispecific binding protein. FIG. 14M shows the changes in total CD4$^+$ T cells 6,24, and 48 hours after administration of 12.5 µg/kg of the indicated trispecific binding proteins. FIG. 14N shows the changes in total NK cells 6,24, and 48 hours after administration of 12.5 µg/kg of the indicated trispecific binding proteins. FIG. 14O shows the changes in total CD8$^+$ T cells 6, 24, and 48 hours after administration of 12.5 µg/kg of the indicated trispecific binding proteins. FIG. 14P shows the changes in total B cells 6,24, and 48 hours after administration of 12.5 µg/kg of the indicated trispecific binding proteins. FIG. 14G shows the changes in cytokine levels 24 hours after administration of the three ascending doses (0.5, 2.5, 12.5 µg/kg) of the indicated trispecific binding proteins (results shown from all test animals).

FIGS. 14Z & 14AA show the amount of blood T cells in non-human primates over time after administration of anti-CD38$_{(VH1)}$×CD28$_{(sup)}$×CD3$_{(mid)}$ or anti-CD38$_{(VH1)}$×CD28$_{(evn)}$×CD3$_{(mid)}$ trispecific binding proteins.

FIGS. 14AB & 14AC show the amount of blood T cells in non-human primates over time after administration of anti-CD38$_{(HHY1370)}$×CD28$_{(sup)}$×CD3$_{(mid)}$ or anti-CD38$_{(HHY1370)}$×CD28$_{(evn)}$×CD3$_{(mid)}$ trispecific binding proteins.

FIGS. 14AD & 14AE show the amount of CD4+ T cells with trispecific binding protein bound after administration of 100 µg/kg dose in non-human primates.

FIGS. 14AF & 14AG show the amount of CD8+ T cells with trispecific binding protein bound after administration of 100 µg/kg dose in non-human primates.

FIG. 17 summarizes PK parameters of the indicated trispecific binding proteins (CD38$_{VH1}$×CD28$_{sup}$×CD3$_{mid}$ IgG4, CD38$_{VH1}$×CD28$_{sup}$×CD3$_{mid}$ IgG4 FALA, CD38$_{VH1}$×CD28$_{sup}$×CD3$_{mid}$ IgG1 LALA P329A, and CD38$_{HHY1370}$×CD28$_{sup}$×CD3$_{mid}$ IgG4 FALA) in NSG mice.

FIG. 18D shows in vitro activation of human PBMCs by CD38$_{VH1}$×CD28$_{sup}$×CD3$_{mid}$ and CD38$_{HHY1370}$×CD28$_{sup}$×CD3$_{mid}$ trispecific binding proteins, as well as IgG1 and IgG4 Fc variants thereof.

FIGS. 19A & 19B show that induction of Bcl-xL in CD4+ (FIG. 19A) or CD8+ (FIG. 19B) T cells by trispecific binding protein CD38$_{VH1}$×CD28$_{sup}$×CD3$_{mid}$ requires both CD3 and CD28 antigen binding domains. Bar graph=mean and s.d. from 3 PBMC donors. *p=≤0.009.

FIGS. 19C & 19D show that CD38$_{VH1}$×CD28×CD3 with IgG4 FALA variant Fc upregulates Bcl-xL in CD4+(FIG. 19C) or CD8+(FIG. 19D) T cells greater than a benchmark bispecific antibody. Bar graph-mean and s.d. from 3 PBMC donors. *p=≤0.045

FIG. 19F shows the release of cytokines TNF, IFNg, IL-2, IL-6, and IL-10 by CD38$_{VH1}$×CD28$_{sup}$CD3$_{mid}$ trispecific binding proteins, as compared to binding proteins with mutated anti-CD28, anti-CD38, or anti-CD28, anti-CD38, and anti-CD3, as well as the benchmark.

FIG. 27 shows the configuration of the trispecific antibody, color-coded by parental antibody (left) Dark shades (purple or green) denote heavy chain peptides: light shades denote light chain peptides. Also shown is a structure model of the $CD38_{VH1}/CD28_{sup} \times CD3_{mid}$ trispecific Ab based on crystal structures of anti-CD38 VH1 Fab and $CD28_{sup}/CD3_{mid}$ CODV Fab (right).

FIG. 28A) and low (KMS-11; FIG. 28B) CD38 surface expression were lysed efficiently by human PBMCs (E:T=10:1) incubated with various concentrations of the trispecific Ab. Contribution to the killing activity by each binding site was demonstrated by binding site KO mutations, as indicated.

FIG. 31A) or the CD38/CD28×CD3 trispecific Ab (FIG. 31B) using human PBMCs incubated with RPMI-8226 myeloma cell line labeled with CellTracker™ deep red dye. Images presented were collected after 24 hour incubation. Scale bar 50 µm.

FIG. 32 shows alternative mutations in the Fc region of IgG4 prepared for analysis in Fc receptor binding assays. Shown are SEQ ID NOs: 111*116 (top to bottom, respectively).

DETAILED DESCRIPTION

Figure 1B:
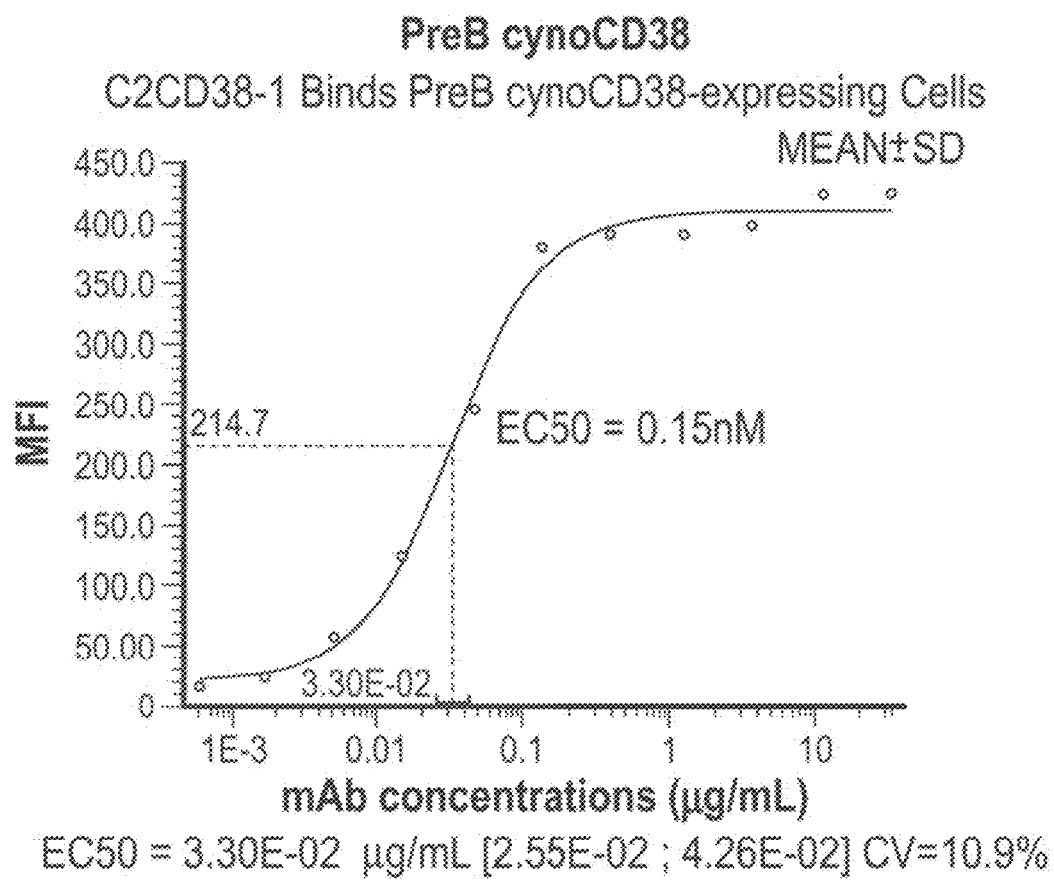
FIG. 1B shows the results of flow cytometry binding assays examining binding of anti-CD38 antibodies mAb1 or isatuximab (no binding observed) to cells expressing cynomolgus monkey CD38 on their surface.

The disclosure provides binding protein comprising at least one antigen binding site that binds a CD38 polypeptide.

I. General Definitions

As utilized in accordance with the present disclosure, the following terms, unless otherwise indicated, shall be understood to have the following meanings. Unless otherwise required by context, singular terms shall include pluralities and plural terms shall include the singular. As used in this specification and the appended claims, the singular forms "a", "an" and "the" include plural referents unless the content clearly dictates otherwise. Thus, for example, reference to "a molecule" optionally includes a combination of two or more such molecules, and the like.

It is understood that aspects and embodiments of the present disclosure described herein include "comprising," "consisting." and "consisting essentially of" aspects and embodiments.

The term "polynucleotide" as used herein refers to single-stranded or double-stranded nucleic acid polymers of at least 10 nucleotides in length. In certain embodiments, the nucleotides comprising the polynucleotide can be ribonucleotides or deoxyribonucleotides or a modified form of either type of nucleotide. Such modifications include base modifications such as bromouridine, ribose modifications such as arabinoside and 2',3'-dideoxyribose, and internucleotide linkage modifications such as phosphorothioate, phosphorodithioate, phosphoroselenoate, phosphorodiselenoate, phosphoroanilothioate, phoshoraniladate and phosphoroamidate. The term "polynucleotide" specifically includes single-stranded and double-stranded forms of DNA.

An "isolated polynucleotide" is a polynucleotide of genomic, cDNA, or synthetic origin or some combination thereof, which: (1) is not associated with all or a portion of a polynucleotide in which the isolated polynucleotide is found in nature, (2) is linked to a polynucleotide to which it is not linked in nature, or (3) does not occur in nature as part of a larger sequence.

An "isolated polypeptide" is one that: (1) is free of at least some other polypeptides with which it would normally be found, (2) is essentially free of other polypeptides from the same source, e.g., from the same species, (3) is expressed by a cell from a different species, (4) has been separated from at least about 50 percent of polynucleotides, lipids, carbohydrates, or other materials with which it is associated in nature, (5) is not associated (by covalent or noncovalent interaction) with portions of a polypeptide with which the "isolated polypeptide" is associated in nature, (6) is operably associated (by covalent or noncovalent interaction) with a polypeptide with which it is not associated in nature, or (7) does not occur in nature. Such an isolated polypeptide can be encoded by genomic DNA, cDNA, mRNA or other RNA, of synthetic origin, or any combination thereof. Preferably, the isolated polypeptide is substantially free from polypeptides or other contaminants that are found in its natural environment that would interfere with its use (therapeutic, diagnostic, prophylactic, research or otherwise).

Naturally occurring antibodies typically comprise a tetramer. Each such tetramer is typically composed of two identical pairs of polypeptide drains, each pair having one full-length "light" chain (typically having a molecular weight of about 25 kDa) and one full-length "heavy" chain (typically having a molecular weight of about 50-70 kDa). The terms "heavy drain" and "light chain" as used herein refer to any immunoglobulin polypeptide having sufficient variable domain sequence to confer specificity for a target antigen. The amino-terminal portion of each light and heavy chain typically includes a variable domain of about 100 to 110 or more amino acids that typically is responsible for antigen recognition. The carboxy-terminal portion of each chain typically defines a constant domain responsible for effector function. Thus, in a naturally occurring antibody, a full-length heavy chain immunoglobulin polypeptide includes a variable domain ($V_H$) and three constant domains ($C_{H1}$, $C_{H2}$, and $C_{H3}$), wherein the $V_H$ domain is at the amino-terminus of the polypeptide and the $C_{H3}$ domain is at the carboxyl-terminus, and a full-length light drain immunoglobulin polypeptide includes a variable domain ($V_L$) and a constant domain ($C_L$), wherein the $V_L$ domain is at the amino-terminus of the polypeptide and the $C_L$ domain is at the carboxyl-terminus.

Human light chains are typically classified as kappa and lambda light chains, and human heavy chains are typically classified as mu, delta, gamma, alpha, or epsilon, and define the antibody's isotype as IgM, IgD, IgG, IgA, and IgE, respectively. IgG has several subclasses, including, but not limited to, IgG1, IgG2, IgG3, and IgG4. IgM has subclasses including, but not limited to, IgM1 and IgM2. IgA is similarly subdivided into subclasses including, but not limited to, IgA1 and IgA2. Within full-length light and heavy chains, the variable and constant domains typically are joined by a "J" region of about 12 or more amino acids, with the heavy chain also including a "D" region of about 10 more amino acids. See, e.g., FUNDAMENTAL IMMUNOLOGY (Paul, W., ed., Raven Press, 2nd ed., 1989), which is incorporated by reference in its entirety for all purposes. The variable regions of each light-heavy chain pair typically form an antigen binding site. The variable domains of naturally occurring antibodies typically exhibit the same general structure of relatively conserved framework regions (FR) joined by three hypervariable regions, also called complementarity determining regions or CDRs. The CDRs from the two chains of each pair typically are aligned by the framework regions, which may enable binding to a specific epitope. From the amino-terminus to the carboxyl-terminus, both light and heavy chain variable domains typically comprise the domains FR1, CDR1, FR2, CDR2, FR3, CDR3, and FR4.

The term "CDR set" refers to a group of three CDRs that occur in a single variable region capable of binding the antigen. The exact boundaries of these CDRs have been defined differently according to different systems. The system described by Kabat (Kabat et al, SEQUENCES OF PROTONS OF IMMUNOLOGICAL INTEREST (National institutes of Health, Bethesda, Md. (1987) and (1991)) not only provides an unambiguous residue numbering system applicable to any variable region of an antibody, but also provides precise residue boundaries defining the three CDRs. These CDRs may be referred to as Kabat CDRs. Chothia and coworkers (Chothia and Lesk, 1987, *J. Mol. Biol.* 196: 901-17; Chothia et al., 1989, *Nature* 342: 877-83) found that certain sub-portions within Kabat CDRs adopt nearly identical peptide backbone conformations, despite having great diversity at the level of amino acid sequence. These sub-portions were designated as L1, L2, and L3 or H1, H2, and H3 where the "L" and the "H" designates the light chain and the heavy chain regions, respectively. These regions may be referred to as Chothia CDRs, which have boundaries that overlap with Kabat CDRs. Other boundaries defining CDRs overlapping with the Kabat CDRs have been described by Padlan, 1995, *FASEB J.* 9: 133-39, MacCallum, 1996, *J. Mol. Biol.* 262(5): 732-45; and Lefranc, 2003, *Dev. Comp. Immunol.* 27; 55-77. Still other CDR boundary definitions may not strictly follow one of the herein systems, but will nonetheless overlap with the Kabat CDRs, although they may be shortened or lengthened in light of prediction or experimental findings that particular residues or groups of residues or even entire CDRs do not significantly impact antigen binding. The methods used herein mas' utilize CDRs defined according to any of these systems, although certain embodiments use Kabat or Chothia defined CDRs. Identification of predicted CDRs using the amino acid sequence is well known in the field, such as in Martin, A. C. "Protein sequence and structure analysis of antibody variable domains," In *Antibody Engineering*, Vol. 2, Konlermann R., Dübel S., eds. Springer-Verlag, Berlin, p. 33-51 (2010). The amino acid sequence of the heavy and/or light chain variable domain may be also inspected to identify the sequences of the CDRs by other conventional methods, e.g., by comparison to known amino acid sequences of other heavy and light chain variable regions to determine the regions of sequence hypervariability. The numbered sequences may be aligned by eye, or by employing an alignment program such as one of the CLUSTAL suite of programs, as described in Thompson, 1994, *Nucleic Adds Res.* 22: 4673-80. Molecular models are conventionally used to correctly delineate framework and CDR regions and thus correct the sequence-based assignments.

In some embodiments, CDR/FR definition in an immunoglobulin light or heavy chain is to be determined based on IMGT definition (Lefranc et al. Dev. Comp. Immunol., 2003, 27(1):55-77; www.imgt.org).

The term "Fc" as used herein refers to a molecule comprising the sequence of a non-antigen-binding fragment resulting from digestion of an antibody or produced by other means, whether in monomeric or multimeric form, and can contain the hinge region. The original immunoglobulin source of the native Fc is preferably of human origin and can be any of the immunoglobulins. Fc molecules are made up of monomeric polypeptides that can be linked into dimeric or multimeric forms by covalent (i.e., disulfide bonds) and noncovalent association. The number of intermolecular disulfide bonds between monomeric subunits of native Fc molecules ranges from 1 to 4 depending on class (e.g., IgG, IgA, and IgE) or subclass (e.g., IgG1, IgG2, IgG3, IgA1, IgGA2, and IgG4). One example of a Fc is a disulfide-bonded dimer resulting from papain digestion of an IgG. The term "native Fc" as used herein is generic to the monomeric, dimeric, and multimeric forms.

A F(ab) fragment typically includes one light chain and the $V_H$ and $C_{H1}$ domains of one heavy chain, wherein the $V_H$-$C_{H1}$ heavy chain portion of the F(ab) fragment cannot form a disulfide bond with another heavy chain polypeptide. As used herein, a F(ab) fragment can also include one light chain containing two variable domains separated by an amino acid linker and one heavy chain containing two variable domains separated by an amino acid linker and a $C_{H1}$ domain.

A F(ab') fragment typically includes one light chain and a portion of one heavy chain that contains more of the constant region (between the $C_{H1}$ and $C_{H2}$ domains), such that an interchain disulfide bond can be formed between two heavy chains to form a $F(ab')_2$ molecule.

The term "binding protein" as used herein refers to a non-naturally occurring (or recombinant or engineered) molecule that specifically binds to at least one target antigen, e.g., a CD38 polypeptide of the present disclosure A "recombinant" molecule is one that has been prepared, expressed, created, or isolated by recombinant means.

One embodiment of the disclosure provides binding proteins having biological and immunological specificity to between one and three target antigens. Another embodiment of the disclosure provides nucleic acid molecules comprising nucleotide sequences encoding polypeptide chains that form such binding proteins. Another embodiment of the disclosure provides expression vectors comprising nucleic acid molecules comprising nucleotide sequences encoding polypeptide chains that form such binding proteins. Yet another embodiment of the disclosure provides host cells that express such binding proteins (i.e., comprising nucleic acid molecules or vectors encoding polypeptide chains that form such binding proteins).

The term "swapability" as used herein refers to the interchangeability of variable domains within the binding protein format and with retention of folding and ultimate binding affinity. "Full swapability" refers to the ability to swap the order of both $V_{H1}$ and $V_{H2}$ domains, and therefore the order of $V_{L1}$ and $V_{L1}$ domains, in the polypeptide chain of formula I or the polypeptide chain of formula II (i.e., to reverse the order) while maintaining full functionality of the binding protein as evidenced by the retention of binding affinity. Furthermore, it should be noted that the designations $V_H$ and $V_L$ refer only to the domain's location on a particular protein chain in the final format. For example, $V_{H1}$ and $V_{H2}$ could be derived from $V_{L1}$ and $V_{L1}$ domains in parent antibodies and placed into the $V_{H1}$ and $V_{H2}$ positions in the binding protein. Likewise, $V_{L1}$ and $V_{L1}$ could be derived from $V_{H1}$ and $V_{H2}$ domains in parent antibodies and placed in the $V_{H1}$ and $V_{H2}$ positions in the binding protein. Thus, the $V_H$ and $V_L$ designations refer to the present location and not the original location in a parent antibody. $V_H$ and $V_L$ domains are therefore "swappable."

The term "antigen" or "target antigen" or "antigen target" as used herein refers to a molecule or a portion of a molecule that is capable of being bound by a binding protein, and additionally is capable of being used in an animal to produce antibodies capable of binding to an epitope of that antigen. A target antigen may have one or more epitopes. With respect to each target antigen recognized by a binding protein, the binding protein is capable of competing with an intact antibody that recognizes the target antigen.

"CD38" is cluster of differentiation 38 polypeptide and is a glycoprotein found on the surface of many immune cells. In some embodiments, a binding protein of the present disclosure binds the extracellular domain of one or more CD38 polypeptide. Exemplary CD38 extracellular domain polypeptide sequences include, but are not limited to, the extracellular domain of human CD38 (e.g., as represented by SEQ ID NO:1) and the extracellular domain of cynomolgus monkey CD38 (e.g., as represented by SEQ ID NO:30).

The term "T-cell engager" refers to binding proteins directed to a host's immune system, more specifically the T cells' cytotoxic activity as well as directed to a tumor target protein.

The term "monospecific binding protein" refers to a binding protein that specifically binds to one antigen target.

The term "monovalent binding protein" refers to a binding protein that has one antigen binding site.

The term "bispecific binding protein" refers to a binding protein that specifically binds to two different antigen targets. In some embodiments, a bispecific binding protein binds to two different antigens. In some embodiments, a bispecific binding protein binds to two different epitopes on the same antigen.

The term "bivalent binding protein" refers to a binding protein that has two binding sites.

The term "trispecific binding protein" refers to a binding protein that specifically binds to three different antigen targets, in some embodiments, a trispecific binding protein binds to three different antigens. In some embodiments, a trispecific binding protein binds to one, two, or three different epitopes on the same antigen.

The term "trivalent binding protein" refers to a binding protein that has three binding sites. In particular embodiments the trivalent binding protein can bind to one antigen target. In other embodiments, the trivalent binding protein can bind to two antigen targets. In other embodiments, the trivalent binding protein can bind to three antigen targets.

An "isolated" binding protein is one that has been identified and separated and/or recovered from a component of its natural environment. Contaminant components of its natural environment are materials that would interfere with diagnostic or therapeutic uses for the binding protein, and may include enzymes, hormones, and other proteinaceous or non-proteinaceous solutes. In some embodiments, the binding protein will be purified: (1) to greater than 95% by weight of anti bods' as determined by the Lowry method, and most preferably more than 99% by weight (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated binding proteins include the binding protein in situ within recombinant cells since at least one component of the binding protein's natural environment will not be present.

The terms "substantially pure" or "substantially purified" as used herein refer to a compound or species that is the predominant species present (i.e., on a molar basis it is more abundant than any other individual species in the composition). In some embodiments, a substantially purified fraction is a composition wherein the species comprises at least about 50% (on a molar basis) of all macromolecular species present. In other embodiments, a substantially pure composition will comprise more than about 80%, 85%, 90%, 95%, or 99% of all macromolar species present in the composition. In still other embodiments, the species is purified to essential homogeneity (contaminant species cannot be detected in the composition by conventional detection methods) wherein the composition consists essentially of a single macromolecular species.

The term "epitope" includes any determinant, preferably a polypeptide determinant, capable of specifically binding to an immunoglobulin or T-cell receptor. In certain embodiments, epitope determinants include chemically active surface groupings of molecules such as amino acids, sugar side chains, phosphoryl groups, or sulfonyl groups, and, in certain embodiments, may have specific three-dimensional structural characteristics and/or specific charge characteristics. An epitope is a region of an antigen that is bound by an antibody or binding protein. In certain embodiments, a binding protein is said to specifically bind an antigen when it preferentially recognizes its target antigen in a complex mixture of proteins and/or macromolecules. In some embodiments, a binding protein is said to specifically bind an antigen when the equilibrium dissociation constant is $\leq 10^{-8}$ M, more preferably when the equilibrium dissociation constant is $\leq 10^{-9}$ M, and most preferably when the dissociation constant is $\leq 10^{-10}$ M.

The dissociation constant ($K_D$) of a binding protein can be determined, for example, by surface plasmon resonance. Generally, surface plasmon resonance analysis measures real-time binding interactions between ligand (a target antigen on a biosensor matrix) and analyte (a binding protein in solution) by surface plasmon resonance (SPR) using the BIAcore system (Pharmacia Biosensor; Piscataway, N.J.). Surface plasmon analysis can also be performed by immobilizing the analyte (binding protein on a biosensor matrix) and presenting the ligand (target antigen). The term "$K_D$," as used herein refers to the dissociation constant of the interaction between a particular binding protein and a target antigen.

The term "binds to" as used herein in reference to a binding protein refers to the ability of a binding protein or an antigen-binding fragment thereof to bind to an antigen containing an epitope with an Kd of at least about $1 \times 10^{-6}$ M, $1 \times 10^{-7}$ M, $1 \times 10^{-8}$ M, $1 \times 10^{-9}$ M, $1 \times 10^{-10}$ M, $1 \times 10^{-11}$ M, $1 \times 10^{-12}$ M, or more, and/or to bind to an epitope with an affinity that is at least two-fold greater than its affinity for a nonspecific antigen. In some embodiments, a binding protein of the present disclosure binds to two or more antigens, e.g., a human and a cynomologus monkey CD38 polypeptide.

In some embodiments, an antigen binding domain and/or binding protein of the present disclosure "cross reacts" with human and cynomolgus monkey CD38 polypeptides, e.g., CD38 extracellular domains, such as SEQ ID NO:1 (human CD38 isoform A), SEQ ID NO:105 (human CD38 isoform E) and SEQ ID NO:30 (cynomolgus monkey CD38). A binding protein binding to antigen 1 (Ag1) is "cross-reactive" to antigen 2 (Ag2) when the EC50s are in a similar range for both antigens. In the present application, a binding protein binding to Ag1 is cross-reactive to Ag2 when the ratio of affinity of Ag2 to affinity of Ag1 is equal or less than 10 (for instance 5, 2, 1 or 0.5), affinities being measured with the same method for both antigens.

A binding protein binding to Ag1 is "not significantly cross-reactive" to Ag2 when the affinities are very different for the two antigens. Affinity for Ag2 may not be measurable if the binding response is too low. In the present application, a binding protein binding to Ag1 is not significantly cross-reactive to Ag2, when the binding response of the binding protein to Ag2 is less than 5% of the binding response of the same binding protein to Ag1 in the same experimental setting and at the same antibody concentration. In practice, the binding protein concentration used can be the $EC_{50}$ or the concentration required to reach the saturation plateau obtained with Ag1.

The term "linker" as used herein refers to one or more amino acid residues inserted between immunoglobulin domains to provide sufficient mobility for the domains of the light and heavy chains to fold into cross over dual variable region immunoglobulins. A linker is inserted at the transition between variable domains or between variable and constant domains, respectively, at the sequence level. The transition between domains can be identified because the approximate size of the immunoglobulin domains are well understood. The precise location of a domain transition can be determined by locating peptide stretches that do not form secondary structural elements such as beta-sheets or alphahelices as demonstrated by experimental data or as can be assumed by techniques of modeling or secondary structure prediction. The linkers described herein are referred to as $L_1$, which is located on the light chain between the C-terminus of the $V_{L1}$ and the N-terminus of the $V_{L1}$ domain; and $L_2$, which is located on the light chain between the C-terminus of the $V_{L1}$ and the N-terminus of the $C_L$ domain. The heavy chain linkers are know n as $L_3$, which is located between the C-terminus of the $V_{H1}$ and the N-terminus of the $V_{H2}$ domain; and $L_4$, which is located between the C-terminus of the $V_{H1}$ and the N-terminus of the $C_{H1}$ domain.

The term "vector" as used herein refers to any molecule (e.g., nucleic acid, plasmid, or virus) that is used to transfer coding information to a host cell. The term "vector" includes a nucleic acid molecule that is capable of transporting another nucleic acid to which it has been linked. One type of vector is a "plasmid," which refers to a circular double-stranded DNA molecule into which additional DNA segments may be inserted. Another type of vector is a viral vector, wherein additional DNA segments may be inserted into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell and thereby are replicated along with the host genome. In addition, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. The terms "plasmid" and "vector" may be used interchangeably herein, as a plasmid is the most commonly used form of vector. How ever, the disclosure is intended to include other forms of expression vectors, such as viral vectors (e.g., replication defective retroviruses, adenoviruses, and adeno-associated viruses), which serve equivalent functions.

The phrase "recombinant host cell" (or "host cell") as used herein refers to a cell into which a recombinant expression vector has been introduced. A recombinant host cell or host cell is intended to refer not only to the particular subject cell, but also to the progeny of such a cell. Because certain modifications may occur in succeeding generations due to either mutation or environmental influences, such progeny may not, in fact, be identical to the parent cell, but such cells are still included within the scope of the term "host cell" as used herein. A wide variety of host cell expression systems can be used to express the binding proteins, including bacterial, yeast, baculoviral, and mammalian expression systems (as well as phage display expression systems). An example of a suitable bacterial expression vector is pUC19. To express a binding protein recombinantly, a host cell is transformed or transfected with one or more recombinant expression vectors carrying DNA fragments encoding the polypeptide chains of the binding protein such that the polypeptide chains are expressed in the host cell and, preferably, secreted into the medium in which the host cells are cultured, from which medium the binding protein can be recovered.

The term "transformation" as used herein refers to a change in a cell's genetic characteristics, and a cell has been transformed when it has been modified to contain a new DNA. For example, a cell is transformed where it is genetically modified from its native state. Following transformation, the transforming DNA may recombine with that of the cell by physically integrating into a chromosome of the cell, or may be maintained transiently as an episomal element without being replicated, or may replicate independently as a plasmid. A cell is considered to have been stably transformed when the DNA is replicated with the division of the cell. The term "transfection" as used herein refers to the uptake of foreign or exogenous DNA by a cell, and a cell has been "transfected" when the exogenous DNA has been introduced inside the cell membrane. A number of transfection techniques are well known in the art. Such techniques can be used to introduce one or more exogenous DNA molecules into suitable host cells.

The term "naturally occurring" as used herein and applied to an object refers to the fact that the object can be found in nature and has not been manipulated by man. For example, a polynucleotide or polypeptide that is present in an organism (including viruses) that can be isolated from a source in nature and that has not been intentionally modified by man is naturally-occurring. Similarly, "non-naturally occurring" as used herein refers to an object that is not found in nature or that has been structurally modified or synthesized by man.

As used herein, the twenty conventional amino acids and their abbreviations follow conventional usage. Stereoisomers (e.g., D-amino acids) of the twenty conventional amino acids; unnatural amino acids and analogs such as α-, α-di-substituted amino acids, N-alkyl amino acids, lactic acid, and other unconventional amino acids may also be suitable components for the polypeptide chains of the binding proteins. Examples of unconventional amino acids include; 4-hydroxyproline, γ-carboxyglulamate, ε-N,N,N-trimelhyllysine, ε-N-acetyllysine, O-phosphoserine, N-acetylserine, N-formylmethionine, 3-methylhistidine, 5-hydroxy lysine, σ-N-methylarginine, and other similar amino acids and imino acids (e.g., 4-hydroxy proline). In the polypeptide notation used herein, the left-hand direction is the amino terminal direction and the right-hand direction is the carboxyl-terminal direction, in accordance with standard usage and convention.

Naturally occurring residues may be divided into classes based on common side chain properties;

(1) hydrophobic: Met, Ala, Val, Leu, Ile, Phe, Trp, Tyr, Pro;

(2) polar hydrophilic: Arg, Asn, Asp, Gin, Glu, His, Lys, Ser, Thr;

(3) aliphatic: Ala, Gly, Ile, Leu, Val, Pro;

(4) aliphatic hydrophobic: Ala, He, Leu, Val, Pro;

(5) neutral hydrophilic: Cys, Ser, Thr, Asn, Gin;

(6) acidic: Asp, Glu;

(7) basic: His, Lys, Arg;

(8) residues that influence chain orientation: Gly, Pro;

(9) aromatic: His, Trp, Tyr, Phe; and

(10) aromatic hydrophobic: Phe, Trp, Tyr.

Conservative amino acid substitutions may involve exchange of a member of one of these classes with another member of the same class. Non-conservative substitutions may involve the exchange of a member of one of these classes for a member from another class.

A skilled artisan will be able to determine suitable variants of the polypeptide chains of the binding proteins using well-known techniques. For example, one skilled in the art may identify suitable areas of a poly peptide chain that may be changed without destroying activity by targeting regions not believed to be important for activity. Alternatively, one skilled in the art can identify residues and portions of the molecules that are conserved among similar polypeptides. In addition, even areas that may be important for biological activity or for structure may be subject to conservative amino acid substitutions without destroying the biological activity or without adversely affecting the polypeptide structure.

The term "patient" as used herein includes human and animal subjects (e.g., mammals, such as dogs, pigs, horses, cats, cows, etc.).

The terms "treatment" or "treat" as used herein refer to both therapeutic treatment and prophylactic or preventative measures. Those in need of treatment include those having a disorder as well as those prone to have the disorder or those in which the disorder is to be prevented. In particular embodiments, binding proteins can be used to treat humans with cancer, or humans susceptible to cancer, or ameliorate cancer in a human subject. The binding proteins can also be used to prevent cancer in a human patient. In particular embodiments, the cancer is multiple myeloma, acute lymphoblastic leukemia, chronic lymphocytic leukemia, acute myeloid leukemia, lymphoma, breast cancer such as Her2+ breast cancer, prostate cancer, germinal center B-cell lymphoma or B-cell acute lymphoblastic leukemia.

The terms "pharmaceutical composition" or "therapeutic composition" as used herein refer to a compound or composition capable of inducing a desired therapeutic effect when properly administered to a patient.

The term "pharmaceutically acceptable carrier" or "physiologically acceptable carrier" as used herein refers to one or more formulation materials suitable for accomplishing or enhancing the delivery of a binding protein.

The terms "effective amount" and "therapeutically effective amount" when used in reference to a pharmaceutical composition comprising one or more binding proteins refer to an amount or dosage sufficient to produce a desired therapeutic result. More specifically, a therapeutically effective amount is an amount of a binding protein sufficient to inhibit, for some period of time, one or more of the clinically defined pathological processes associated with the condition being treated. The effective amount may vary depending on the specific binding protein that is being used, and also depends on a variety of factors and conditions related to the patient being treated and the severity of the disorder. For example, if the binding protein is to be administered in vivo, factors such as the age, weight and health of the patient as well as dose response curves and toxicity data obtained in preclinical animal work would be among those factors considered. The determination of an effective amount or therapeutically effective amount of a given pharmaceutical composition is well within the ability of those skilled in the art.

One embodiment of the disclosure provides a pharmaceutical composition comprising a pharmaceutically acceptable carrier and a therapeutically effective amount of a binding protein.

II. Anti-CD38 Binding Proteins

Certain aspects of the present disclosure relate to binding proteins that comprise an antigen binding site that binds a CD38 polypeptide (e.g., human and cynomolgus monkey CD38 polypeptides). In some embodiments, the binding proteins are monospecific and/or monovalent, bispecific and/or bivalent, trispecific and/or trivalent, or multispecific and/or multivalent.

A variety of features of exemplary monospecific, bispecific, or trispecific binding proteins are described herein. For example, in some embodiments, a binding protein or antigen-binding fragment thereof cross-reacts with human CD38 (e.g., a human CD38 isoform A and/or isoform E polypeptide) and cynomolgus monkey CD38. In some embodiments, a binding protein induces apoptosis of a CD38+ cell, in some embodiments, a binding protein recruits a T cell to a CD38+ cell and optionally activates the T cell (e.g., though TCR stimulation and/or costimulation).

In some embodiments, the binding proteins comprise an antigen binding site comprising: an antibody heavy chain variable (VH) domain comprising a CDR-H1 sequence comprising the amino acid sequence of GYTFTSFN (SEQ ID NO:31) or GYTFTSYA (SEQ ID NO:37), a CDR-H2 sequence comprising the amino acid sequence of IYPGNGGT (SEQ ID NO:32) or IYPGQGGT (SEQ ID NO:38), and a CDR-H3 sequence comprising the amino acid sequence of ARTGGLRRAYFTY (SEQ ID NO:33); or an antibody light chain variable (VL) domain comprising a CDR-L1 sequence comprising the amino acid sequence of ESVDSYGNGF (SEQ ID NO:34) or QSVSSYGQGF (SEQ ID NO:39), a CDR-L2 sequence comprising the amino acid sequence of LAS (SEQ ID NO:35) or GAS (SEQ ID NO:40), and a CDR-L3 sequence comprising the amino acid sequence of QQNKEDPWT (SEQ ID NO:36). In some embodiments, the binding proteins comprise an antigen binding site comprising: an antibody heavy chain variable (VH) domain comprising a CDR-H1 sequence comprising the amino acid sequence of GYTFTSFN (SEQ ID NO:31) or GYTFTSYA (SEQ ID NO:37), a CDR-H2 sequence comprising the amino acid sequence of IYPGNGGT (SEQ ID NO:32) or IYPGQGGT (SEQ ID NO:38), and a CDR-H3 sequence comprising the amino acid sequence of ARTGGLRRAYFTY (SEQ ID NO:33); or an antibody light chain variable (VL) domain comprising a CDR-L1 sequence comprising the amino acid sequence of ESVDSYGNGF (SEQ ID NO:34) or QSVSSYGQG (SEQ ID NO:132), a CDR-L2 sequence comprising the amino add sequence of LAS (SEQ ID NO:35) or GAS (SEQ ID NO:40), and a CDR-L3 sequence comprising the amino acid sequence of QQNKEDPWT (SEQ ID NO:36). In some embodiments, the binding proteins comprise 1, 2, 3, 4, 5, or 6 CDRs from an antibody VH and/or VL domain sequence of mAb1, mAb2, mAb3, mAb4, mAb5, mAb6, mAb2×CD28sup×CD3mid IgG4 FALA, mAb2×CD28sup×CD3mid IgG1LALA P329A, mAb2×CD28sup×CD3mid IgG1 NNSA mAb6×CD28sup×CD3mid IgG4 FALA, mAb6×CD28sup×CD3mid IgG1LALA P329A, or mAb6×CD28sup×CD3mid IgG1 NNSA as shown in Table G, H, or I.

In some embodiments, the binding proteins comprise an antigen binding site comprising: an antibody heavy chain variable (VH) domain comprising a CDR-H1 sequence comprising the amino acid sequence of GYTFTSFN (SEQ ID NO:31) or GYTFTSYA (SEQ ID NO:37), a CDR-H2 sequence comprising the amino add sequence of IYPGNGGT (SEQ ID NO:32) or IYPGQGGT (SEQ ID NO:38), and a CDR-H3 sequence comprising the amino add sequence of ARTGGLRRAYFTY (SEQ ID NO: 33); and an antibody light chain variable (VL) domain comprising a CDR-L1 sequence comprising the amino acid sequence of ESVDSYGNGF (SEQ ID NO:34) or QSVSSYGQGF (SEQ ID NO:39), a CDR-L2 sequence comprising the amino acid sequence of LAS (SEQ ID NO:35) or GAS (SEQ ID NO:40), and a CDR-L3 sequence comprising the amino acid sequence of QQNKEDPWT (SEQ ID NO:36).

In some embodiments, the binding proteins comprise an antigen binding site comprising: an antibody heavy chain variable (VH) domain comprising a CDR-H1 sequence comprising the amino add sequence of GYTFTSFN (SEQ ID NO:31), a CDR-H2 sequence comprising the amino add sequence of IYPGNGGT (SEQ ID NO:32), and a CDR-H3 sequence comprising the amino acid sequence of ARTG-GLRRAYFTY (SEQ ID NO:33); or an antibody light chain variable (VL) domain comprising a CDR-L1 sequence comprising the amino add sequence of ESVDSYGNGF (SEQ ID NO:34), a CDR-L2 sequence comprising the amino add sequence of IAS (SEQ ID NO:35), and a CDR-L3 sequence comprising the amino acid sequence of QQNKEDPWT (SEQ ID NO:36). In some embodiments, the binding proteins comprise an antigen binding site comprising: an antibody heavy chain variable (VH) domain comprising a CDR-H1 sequence comprising the amino acid sequence of GYTFTSFN (SEQ ID NO:31), a CDR-H2 sequence comprising the amino add sequence of IYPGNGGT (SEQ ID NO:32), and a CDR-H3 sequence comprising the amino add sequence of ARTGGLRRAYFTY (SEQ ID NO:33); and an antibody light chain variable (VL) domain comprising a CDR-L1 sequence comprising the amino acid sequence of ESVDSYGNGF (SEQ ID NO:34), a CDR-L2 sequence comprising the amino acid sequence of LAS (SEQ ID NO:35), and a CDR-L3 sequence comprising the amino acid sequence of QQNKEDPWT (SEQ ID NO:36). In other embodiments, the binding proteins comprise an antigen binding site comprising: an antibody heavy chain variable (VH) domain comprising a CDR-H1 sequence comprising the amino acid sequence of GYTFTSYA (SEQ ID NO:37), a CDR-H2 sequence comprising the amino acid sequence of IYPGQGGT (SEQ ID NO:38), and a CDR-H3 sequence comprising the amino acid sequence of ARTGGLRRAY-FTY (SEQ ID NO:33); or an antibody light chain variable (VL) domain comprising a CDR-L1 sequence comprising the amino acid sequence of QSVSSYGQGF (SEQ ID NO:39), a CDR-L2 sequence comprising the amino acid sequence of GAS (SEQ ID NO:40), and a CDR-L3 sequence comprising the amino acid sequence of QQNKEDPWT (SEQ ID NO:36). In some embodiments, the binding proteins comprise an antigen binding site comprising, an antibody heavy chain variable (VH) domain comprising a CDR-H1 sequence comprising the amino acid sequence of GYTFTSYA (SEQ ID NO:37), a CDR-H2 sequence comprising the amino acid sequence of IYPGQGGT (SEQ ID NO:38), and a CDR-H3 sequence comprising the amino acid sequence of ARTGGLRRAYFTY (SEQ ID NO:33), and an antibody light chain variable (VL) domain comprising a CDR-L1 sequence comprising the amino acid sequence of QSVSSYGQGF (SEQ ID NO:39), a CDR-L2 sequence comprising the amino acid sequence of GAS (SEQ ID NO:40), and a CDR-L3 sequence comprising the amino acid sequence of QQNKEDPWT (SEQ ID NO:36).

In some embodiments, the VH domain comprises the sequence, from N-terminus to C-terminus, FR1-CDR-H1-FR2 CDR-H2-FR3-CDR-H3-FR4; where FR1 comprises the sequence QVQLVQSGAEVVKPGASVKVSCKAS (SEQ ID NO:86), QVQLVQSGAEVVKS-GASVKVSCKAS (SEQ ID NO:87), or QVQLVQS-GAEVVKPGASVKMSCKAS (SEQ ID NO:88); where FR2 comprises the sequence MHWVKEAPGQRLEWIGY (SEQ ID NO:90) or MHWVKEAPGQGLEWIGY (SEQ ID NO:91), where FR3 comprises the sequence NYNQKFQGRATLTADTSASTAYMELSSLRSED-TAVYFC (SEQ ID NO: 93) or NYNQKFQGRATLTADT-SASTAYMEISSLRSEDTAVYFC (SEQ ID NO:94); and where FR4 comprises the sequence WGQGTLVTVSS (SEQ ID NO:96). In some embodiments, the VL domain comprises the sequence, from N-terminus to C-terminus, FR1-CDR-L1-FR2-CDR-L2-FR3-CDR-L3-FR4; where FR1 comprises the sequence DIVLTQSPATLSLSPGER-ATISCRAS (SEQ ID NO:97); where FR2 comprises the sequence MHWYQQKPGQPPRLLIY (SEQ ID NO:99); where FR3 comprises the sequence SRATGI-PARFSGSGSGTDFTLTISPLEPEDFAVYYC (SEQ ID NO:101); and where FR4 comprises the sequence FGGGTKLEIK (SEQ ID NO:103).

In some embodiments, the VH domain comprises an amino acid sequence that is at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the amino acid sequence of SEQ ID NO:5; and/or the VL domain comprises an amino acid sequence that is at least 85%, at least 86%, at least 87%, at least 88%, at least 89%, at least 90%, at least 91% at least 92%, at least 93%, at least 94% at least 95%, at least 96%, at least 97%, at least 98%, at least 99%, or 1.00% identical to the amino acid sequence of SEQ ID NO:6. In some embodiments, the YH domain comprises an amino acid sequence that is at least 85%, at least 86%, at least 87%, at least 88%, at least 89%, at least 90%, at least 91%, at least 92% at least 93% at least 94%, at least 95%, at least 96% at least 97%, at least 98%, at least 99% or 100% identical to the amino acid sequence of SEQ ID NO:17; and/or the VL domain comprises an amino acid sequence that is at least 85%, at least 86%, at least 87% at least 88%, at least 89%, at least 90%, at least 91% at least 92%, at least 93%, at least 94% at least 95%, at least 96%, at least 97%, at least 98%, at least 99%, or 100% identical to the amino acid sequence of SEQ ID NO:18. In some embodiments, the VH domain comprises an amino acid sequence that is at least 85%, at least 86% at least 87% at least 88%, at least 89%, at least 90%, at least 91%, at least 92% at least 93%, at least 94% at least 95%, at least 96% at least 97% at least 98%, at least 99%, or 100% identical to the amino acid sequence of SEQ ID NO:21; and/or the VL domain comprises an amino acid sequence that is at least 85% at least 86%, at least 87%, at least 88%, at least 89%, at least 90%, at least 91%, at least 92%, at least 93%, at least 94%, at least 95%, at least 96% at least 97%, at least 98%, at least 99%, or 100% identical to the amino acid sequence of SEQ ID NO:18. In some embodiments, the VH domain comprises an amino acid sequence that is at least 85% at least 86% at least 87%, at least 88% at least 89% at least 90%, at least 91% at least 92%, at least 93%, at least 94%, at least 95% at least 96%, at least 97% at least 98%, at least 99%, or 100% identical to the amino acid sequence of SEQ ID NO:23; and/or the VL domain comprises an amino acid sequence that is at least 85%, at least 86%, at least 87%, at least 88% at least 89% at least 90%, at least 91%, at least 92% at least 93% at least 94%, at least 95%, at least 96%, at least 97%, at least 98% at least 99%, or 100% identical to the amino acid sequence of SEQ ID NO:18. In some embodiments, the VH domain comprises an amino acid sequence that is at least 85%, at least 86%, at least 87%, at least 88% at least 89%, at least 90%, at least 91%, at least 92% at least 93% at least 94%, at least 95%, at least 96% at least 97%, at least 98%, at least 99%, or 100*% identical to the amino acid sequence of SEQ ID NO:13; and/or the VL domain comprises an amino acid sequence that is at least 85%, at least 86%, at least 87%, at least 88%, at least 89% at least 90%, at least 91%, at least 92% at least 93%, at least 94% at least 95%, at least 96%, at least 97%, at least 98% at least 99%, or 100% identical to the amino acid sequence of SEQ ID NO:14.

In some embodiments, the VH domain comprises an amino acid sequence that is at least 85%, at least 86%, at least 87% at least 88%, at least 89%, at least 90%, at least 91%, at least 92%, at least 93%, at least 94%, at least 95%, at least 96%, at least 97%, at least 98%, at least 99%, or 100% identical to the amino acid sequence of SEQ ID NO:5; and the VL domain comprises an amino acid sequence that is at least 85% at least 86%, at least 87%, at least 88%, at least 89%, at least 90%, at least 91%, at least 92% at least 93% at least 94%, at least 95%, at least 96%, at least 97%, at least 98%, at least 99%, or 100% identical to the amino acid sequence of SEQ ID NO:6. In some embodiments, the VH domain comprises an amino acid sequence that is at least 85%, at least 86%, at least 87% at least 88% at least 89%, at least 90%, at least 91% at least 92%, at least 93%, at least 94%, at least 95%, at least 96%, at least 97% at least 98%, at least 99%, or 100% identical to the amino acid sequence of SEQ ID NO:17; and the VL domain comprises an amino acid sequence that is at least 85% at least 86% at least 87%, at least 88% at least 89%, at least 90%, at least 91% at least 92% at least 93% at least 94%, at least 95% at least 96% at least 97%, at least 98% at least 99%, or 100% identical to the amino acid sequence of SEQ ID NO:18. In some embodiments, the VH domain comprises an amino acid sequence that is at least 85%, at least 86%, at least 87%, at least 88% at least 89%, at least 90%, at least 91%, at least 92% at least 93%, at least 94% at least 95%, at least 96%, at least 97%, at least 98%, at least 99%, or 100% identical to the amino acid sequence of SEQ ID NO:21; and the VL domain comprises an amino acid sequence that is at least 85%, at least 86% at least 87%, at least 88%, at least 89% at least 90% at least 91%, at least 92% at least 93% at least 94%, at least 95%, at least 96%, at least 97%, at least 98%, at least 99%, or 100% identical to the amino acid sequence of SEQ ID NO:18. In some embodiments, the VH domain comprises an amino acid sequence that is at least 85%, at least 86%, at least 87%, at least 88%, at least 89% at least 90% at least 91%, at least 92% at least 93% at least 94%, at least 95%, at least 96%, at least 97%, at least 98%, at least 99%, or 100% identical to the amino acid sequence of SEQ ID NO:23; and the VL domain comprises an amino acid sequence that is at least 85%, at least 86% at least 87% at least 88%, at least 89% at least 90% at least 91%, at least 92% at least 93% at least 94%, at least 95%, at least 96%, at least 97%, at least 98%, at least 99%, or 100% identical to the amino acid sequence of SEQ ID NO:18. In some embodiments, the VH domain comprises an amino acid sequence that is at least 85%, at least 86%, at least 87%, at least 88%, at least 89% at least 90% at least 91%, at least 92% at least 93%, at least 94%, at least 95%, at least 96%, at least 97%, at least 98%, at least 99%, or 100% identical to the amino acid sequence of SEQ ID NO:13; and the VL domain comprises an amino acid sequence that is at least 85%, at least 86% at least 87% at least 88%, at least 89%, at least 90% at least 91%, at least 92%, at least 93%, at least 94%, at least 95%, at least 96%, at least 97%, at least 98%, at least 99%, or 100% identical to the amino acid sequence of SEQ ID NO:14.

In some embodiments, the VH domain comprises the amino acid sequence of SEQ ID NO:5; and the VL domain comprises the amino acid sequence of SEQ ID NO:6. In some embodiments, the VH domain comprises the amino acid sequence of SEQ ID NO:17; and the VL domain comprises the amino acid sequence of SEQ ID NO:18. In some embodiments, the VH domain comprises the amino acid sequence of SEQ ID NO:21; and the VL domain comprises the amino acid sequence of SEQ ID NO:18. In some embodiments, the VH domain comprises the amino acid sequence of SEQ ID NO:23; and the VL domain comprises the amino acid sequence of SEQ ID NO:18. In some embodiments, the VH domain comprises the amino acid sequence of SEQ ID NO:13; and the VL domain comprises the amino acid sequence of SEQ ID NO:14.

In some embodiments, a binding protein of the present disclosure comprises an antibody heavy chain comprising the amino acid sequence of SEQ ID NO:7 and/or an antibody light chain comprising the amino acid sequence of SEQ ID NO:8. In some embodiments, a binding protein of the present disclosure comprises an antibody heavy chain comprising the amino acid sequence of SEQ ID NO:19 and/or an antibody light chain comprising the amino acid sequence of SEQ ID NO:20. In some embodiments, a binding protein of the present disclosure comprises an antibody heavy chain comprising the amino acid sequence of SEQ ID NO:22 and/or an antibody light chain comprising the amino add sequence of SEQ ID NO:20. In some embodiments, a binding protein of the present disclosure comprises an antibody heavy chain comprising the amino acid sequence of SEQ ID NO:24 and/or an antibody light chain comprising the amino acid sequence of SEQ ID NO:20. In some embodiments, a binding protein of the present disclosure comprises an antibody heavy chain comprising the amino acid sequence of SEQ ID NO:15 and/or an antibody light chain comprising the amino acid sequence of SEQ ID NO:16.

In some embodiments, a binding protein of the present disclosure comprises an antibody heavy chain comprising the amino acid sequence of SEQ ID NO:7 and an antibody light chain comprising the amino acid sequence of SEQ ID NO:8. In some embodiments, a binding protein of the present disclosure comprises an antibody heavy chain comprising the amino acid sequence of SEQ ID NO:19 and an antibody light chain comprising the amino acid sequence of SEQ ID NO:20. In some embodiments, a binding protein of the present disclosure comprises an antibody heavy chain comprising the amino acid sequence of SEQ ID NO:22 and an antibody light chain comprising the amino acid sequence of SEQ ID NO:20. In some embodiments, a binding protein of the present disclosure comprises an antibody heavy chain comprising the amino acid sequence of SEQ ID NO:24 and an antibody light chain comprising the amino acid sequence of SEQ ID NO:20. In some embodiments, a binding protein of the present disclosure comprise an antibody heavy chain comprising the amino acid sequence of SEQ ID NO:15 and an antibody light drain comprising the amino acid sequence of SEQ ID NO:16.

In some embodiments, the binding proteins comprise an antigen binding site comprising, an antibody heavy chain variable (VH) domain comprising a CDR-H1 sequence comprising the amino acid sequence of GFTFSSYG (SEQ ID NO:41), a CDR-H2 sequence comprising the amino acid sequence of IWYDGSNK (SEQ ID NO:42), and a CDR-H3 sequence comprising the amino acid sequence of ARMFRGAFDY (SEQ ID NO:43); or an antibody light chain variable (VL) domain comprising a CDR-1.1 sequence comprising the amino acid sequence of QGIRND (SEQ ID NO:44), a CDR-L2 sequence comprising the amino acid sequence of AAS (SEQ ID NO:45), and a CDR-L3 sequence comprising the amino acid sequence of LQDYIYYPT (SEQ ID NO:46). In some embodiments, the binding proteins comprise an antigen binding site comprising: an antibody heavy chain variable (VH) domain comprising a CDR-H1 sequence comprising the amino acid sequence of GFTFSSYG (SEQ ID NO:41), a CDR-H2 sequence comprising the amino acid sequence of IWYDGSNK (SEQ ID NO:42), and a CDR-H3 sequence comprising the amino acid sequence of ARMFRGAFDY (SEQ ID NO:43); and an antibody light chain variable (VL) domain comprising a CDR-L1 sequence comprising the amino acid sequence of QGIRND (SEQ ID NO:44), a CDR-L2 sequence comprising the amino acid sequence of AAS (SEQ ID NO:45), and a CDR-L3 sequence comprising the amino acid sequence of LQDYIYYPT (SEQ ID NO:46).

In some embodiments, the VH domain comprises the sequence, from N-terminus to C-terminus, FR1-CDR-H1-FR2-CDR-H2-FR3-CDR-H3-FR4; where FR1 comprises the sequence QVQLVESGGGVVQPGRSLRLSCAAS (SEQ ID NO:89); where FR2 comprises the sequence MHWVRQAPGKGLEWVAV (SEQ ID NO:92); where FR3 comprises the sequence YYADSVKGRFTISGDNSKNT-LYLQMNSLRAEDTAVYYC (SEQ ID NO:95); and where FR4 comprises the sequence WGQGTLVTVSS (SEQ ID NO:96). In some embodiments, the VL domain comprises the sequence, from N-terminus to C-terminus, FR1-CDR-L1-FR2-CDR-L2-FR3-CDR-L3-FR4; where FR1 comprises the sequence AIQMTQSPSSLSASVGDRVTIT-CRAS (SEQ ID NO:98); where FR2 comprises the sequence GWYQQKPGKAPKLLIY (SEQ ID NO:100); where FR3 comprises the sequence SLQSGVPSRFSGSGSGTDFTLTISGLQPEDSATYYC (SEQ ID NO:102); and where FR4 comprises the sequence WGQGTLVTVSS (SEQ ID NO:104).

In some embodiments, the VH domain comprises an amino acid sequence that is at least 85% at least 86%, at least 87%, at least 88%, at least 89%, at least 90%, at least 91%, at least 92%, at least 93%, at least 94%, at least 95V at least 96%, at least 97%, at least 98%, at least 99%, or 100*% identical to the amino acid sequence of SEQ ID NO:9; and/or the VL domain comprises an amino acid sequence that is at least 85%, at least 86%, at least 87%, at least 88%, at least 89%, at least 90%, at least 91% at least 92%, at least 93%, at least 94V at least 95%, at least 96%, at least 97V at least 98%, at least 99%, or 100% identical to the amino acid sequence of SEQ ID NO:10.

In some embodiments, the VH domain comprises an amino acid sequence that is at least 85% at least 86% at least 87%, at least 88% at least 89% at least 90%, at least 91V at least 92% at least 93%, at least 94%, at least 95% at least 96%, at least 97%, at least 98V at least 99%, or 100% identical to the amino acid sequence of SEQ ID NO:9; and the VL domain comprises an amino acid sequence that is at least 85%, at least 86%, at least 87%, at least 88%, at least 89%, at least 90%, at least 91%, at least 92%, at least 93% at least 94%, at least 95%, at least 96%, at least 97% at least 98%, at least 99%, or 100% identical to the amino acid sequence of SEQ ID NO:10. In some embodiments, the VH domain comprises the amino acid sequence of SEQ ID NO:9; and the VL domain comprises the amino add sequence of SEQ ID NO:10.

In some embodiments, a binding protein of the present disclosure comprises an antibody heavy chain comprising the amino add sequence of SEQ ID NO:11 or an antibody light chain comprising the amino add sequence of SEQ ID NO:12. In some embodiments, a binding protein of the present disclosure comprises an antibody heavy chain comprising the amino acid sequence of SEQ ID NO:11 and an antibody light chain comprising the amino acid sequence of SEQ ID NO:12.

In some embodiments, a binding protein of the present disclosure comprises 1, 2, 3, 4, 5, or 6 CDR sequences of an antibody sequence shown in Table G. In some embodiments, a binding protein of the present disclosure comprises 1, 2, 3, 4, 5, or 6 CDR sequences, a VH domain sequence, and/or a VL domain sequence of an antibody sequence shown in Table H. In some embodiments, a binding protein of the present disclosure comprises 1, 2, 3, 4, 5, or 6 CDR sequences, a VH domain sequence, and/or a VL domain sequence of an antibody sequence shown in Table I. In some embodiments, a binding protein of the present disclosure comprises 1, 2, 3, or 4 polypeptide sequences shown in Table I.

TABLE G

CDR sequences of anti-CD38 binding proteins.

| Ab | CDR_H1 | CDR_H2 | CDR_H3 | CDR_L1 | CDR_L2 | CDR_L3 |
|---|---|---|---|---|---|---|
| mAb1 | GYTFTSFN (SEQ ID NO: 31) | IYPGNGGT (SEQ ID NO: 32) | ARTGGLRRAYFTY (SEQ ID NO: 33) | ESVDSYGNGF (SEQ ID NO: 34) | LAS (SEQ ID NO: 35) | QQNKEDPWT (SEQ ID NO: 36) |
| mAb2 | GYTFTSYA (SEQ ID NO: 37) | IYPGQGGT (SEQ ID NO: 38) | ARTGGLRRAYFTY (SEQ ID NO: 33) | QSVSSYGQGF (SEQ ID NO: 39) | GAS (SEQ ID NO: 40) | QQNKEDPWT (SEQ ID NO: 36) |
| mAb3 | GYTFTSFN (SEQ ID NO: 31) | IYPGNGGT (SEQ ID NO: 32) | ARTGGLRRAYFTY (SEQ ID NO: 33) | ESVDSYGNGF (SEQ ID NO: 34) | LAS (SEQ ID NO: 35) | QQNKEDPWT (SEQ ID NO: 36) |
| mAb4 | GYTFTSFN (SEQ ID NO: 31) | IYPGNGGT (SEQ ID NO: 32) | ARTGGLRRAYFTY (SEQ ID NO: 33) | ESVDSYGNGF (SEQ ID NO: 34) | LAS (SEQ ID NO: 35) | QQNKEDPWT (SEQ ID NO: 36) |
| mAb5 | GYTFTSFN (SEQ ID NO: 31) | IYPGNGGT (SEQ ID NO: 32) | ARTGGLRRAYFTY (SEQ ID NO: 33) | ESVDSYGNGF (SEQ ID NO: 34) | LAS (SEQ ID NO: 35) | QQNKEDPWT (SEQ ID NO: 36) |
| mAb6 | GFTFSSYG (SEQ ID NO: 41) | IWYDGSNK (SEQ ID NO: 42) | ARMFRGAFDY (SEQ ID NO: 43) | QGIRND (SEQ ID NO: 44) | AAS (SEQ ID NO: 45) | LQDYIYYPT (SEQ ID NO: 46) |

TABLE H

Variable domain sequences of anti-CD38 (mAb1-7) and other binding proteins.

| Ab | VH (protein) | VL (protein) |
|---|---|---|
| mAb1 | QVQLQQSGAELVRSGASVKMS CKASGYTFTSFNMKWVKETPG QGLEWIGYIYPGNGGTSTAYMQIS FKGKATLTADTSSSTAYMQIS SLTSEDSAVYFCARTGGLRRA YFTYWGQGTLVTVSS (SEQ ID NO: 5) | DIVLTQSPASLAVSLGQRA TISCRASESVDSYGKGFMH WYQQKPGQPPKLLIYLASN LESGVPARFSGSGSRTDFT LTIDPVEADDAATYYCQQN KEDPWTFGGGTKLEIK (SEQ ID NO: 6) |
| mAb2 | QVQLVQSGAEVVKPGASVKVS CKASGYTFTSYAMHWVKEAPG QRLEWIGYIYFGQGGTNYNQK FQGRATLTADTSASTAYMELS SLRSEDTAVYFCARTGGLRRA YFTYWGQGTLVTVSS (SEQ ID NO: 13) | DIVLTQSPATLSLSPGERA TISCRASQSVSSYGQGFMH WYQQKPGQPPRLLIYGASS RATGIPARFSGSGSGTDFT LTISPLEPEDFAVYYCQQN KEDPWTFGGGTKLEIK (SEQ ID NO: 14) |
| mAb3 | QVQLVQSGAEVVKPGASVKVS CKASGYTFTSFNMHWVKEAPG QRLEWIGYIYPGNGGTNYNQK FQGRATLTADTSASTAYMELS SLRSEDTAVYFCARTGGLRRA YFTYWGQGTLVTVSS (SEQ ID NO: 17) | DIVLTQSPATLSLSPGERA TISCRASESVDSYGNGFMH WYQQKPGQPPRLLIYLASS RATGIPARFSGSGSGTDFT DLTISPLEPEFAYYYCQQN KEDPWTFGGGTKLEIK (SEQ ID NO: 18) |
| mAb4 | QVQLVQSGAEVVKSGASVKVS CKASGYTFTSFNMHWVKEAPG QGLEWIGYIYPGNGGTNYNQK FQGRATLTADTSASTAYMEIS SLRSEDTAVYFCARTGGLRRA YFTYWGQGTLVTVSS (SEQ ID NO: 21) | DIVLTQSPATLSLSPGERA TISCRASESVDSYGNGFMH QWYQQKPGPPRLLIYLASS RATGIPARFSGSGSGTDFT DLTISPLEPEFAYYYCQQN KEDPWTFGGGTKLEIK (SEQ ID NO: 18) |
| mAb5 | QVQLVQSGAEVVKPGASVKMS CKASGYTFTSFNMHWVKEAPG QRLEWIGYIYPGNGGTNYNQK FQGRATLTADTSASTAYMEIS SLRSEDTAVYFCARTGGERRA YFTYWGQGTLVTVSS (SEQ ID NO: 23) | DIVLTQSPATLSLSPGERA TISCRASESVDSYGNGFMH WYQQKPGQPPRLLIYLASS RATGIPARFSGSGSGTDFT LTISPLEPEDFAYYYCQQN KEDPWTFGGGTKLEIK (SEQ ID NO: 18) |
| mAb6 | QVQLVESGGGVVQPGRSLRLS SCAAGFTFSSYGMHWVRQAPG VKGLEWAVIWDGSNKYYADS VKGRFTISGDNSKNTLYLQMN SLRAEDTAVYYCARMFRGAFD YWGQGTLVTVSS (SEQ ID NO: 9) | AIQMTQSPSSLSASVGDRV TITCRASQGIRNDLGWYQQ KPGKAPKLLIYAASSLSQG VPSRFSGSGSGTDFTLTIS GLQPEDSATYYCLQDYIYY PTFGQGTKVEIK (SEQ ID NO: 10) |
| mAb7 | QVQLVQSGAEVAKPGTSVKLS CKASGYTFTDYWMQWVKQRPG QGLEWIGTIYPGDGDTGYAQK FQGKATLTADKSSKTVYMHLS SLASEDSAVYYCARGDYYGSN SLDYWGQGTSYTVSS (SEQ ID NO: 47) | DIVMTQSHLSMSTSLGDPV KSITCASQDVSTVVAWYQQ KPGQSPRRLIYSASYRYIG VPDRFTGSGAGTDFTFTIS SLASEDLAVYYCQQHYSPP YTFGGGTRLEIK (SEQ ID NO: 48) |
| Anti-CD28$_{sup}$ | QVQLYQSGAEVVKSGASVKVS CKASGYTFTSYYIHWVRQAPG QGLEWIGSIYPGNVNTNYAQK FQGRATLTVDTSISTAYMELS RLRSDDTAVYYCTRSHYGLDW NFDVWGKGTTVTVSS (SEQ ID NO: 49) | DIQMTQSPSSLSASVGDRV TITCQASQNIYVWLNWYQQ KPGKAPKLLIYKASNLHTG VPSRFSGSGSGTDFTLTIS SLQPEDIATYYCQQGQTYP YTFGQGTKVEIK (SEQ ID NO: 50) |
| Anti-CD28$_{cva}$ | QVQLQESGPGLVKPSQTLSLT CTVSGFSLSDYGVHWVRQPPG KGLEWLGVIWAGGGTNYNPSL KSRKTISKDTSKNQVSLKLSS VTAADTAVYYCARDKGYSYYY SMDYWGQGTTVTVSS (SEQ ID NO: 51) | DIVLTQSPASLAVSPGQRA TITCRASESVEYYVTSLMQ WYQQKPGQPPKLLIFAASN VESGVPARFSGSGSGTDFT LTINPVEANDVANYYCQQS RKVPYTFGQGTKLEIK (SEQ ID NO: 52) |
| Anti-CD3$_{mid}$ | QVQLVESGGGVVQPGRSLRLS CAASGFTFTKAWMHWVRQAPG KQLEWVAQIKDKSNSYATYYA DSVKGRFTISRDDSKNTLYLQ MNSLRAEDTAVYYCRGVYYAL SPFDYWGQGTLVTVSS (SEQ ID NO: 53) | DIVMTQTPLSLSVTPGQPA SISCKSSQSLVHNNANTYL SWYLQKPGQSPQSLIYKVS NRFSGVPDRFSGSGSTDF TLKISRVEAEDVGVYYCGQ GTQYPFTFGSGTKVEIK (SEQ ID NO: 54) |
| Anti-Cd3$_{low}$ | QVQLVESGGGVVQPGRSLRLS CAASGFTFTKAWMHWVRQAPG KGLEWVAQIKDKSNSYATYYA DSVKGRFTISRDDSKNTLYLQ MNSLRAEDTAVYYCRGVYYAL SPFDYWGQGTLVTVSS (SEQ ID NO: 84) | DIVMTQTPLSLSVTPGQPA SISCKSSQSLVHNNGNTYL SWYLQKPGQSPQLLIYKVS NRFSGVPDRFSGSGSGTDF TLKISRVEAEDVGVYYCGQ GTQYPFTFGGGTKVEIK (SEQ ID NO: 85) |

Note: CDR sequences are bolded and underlined in amino acid sequences above.

TABLE I

Full-length sequences of binding proteins.

mAb2xCD28supxCD3mid IgG4 FALA

| | | |
|---|---|---|
| CD28supxCD3mid IgG4(hole) FALA Heavy Chain 1 (e.g., a second polypeptide chain of a trispecific binding protein of the present disclosure) | QVQLVQSGAEVVKPGASVKV SCKASGYTFTSYYIHWVRQA POQGLEWIGSIYPGNVNTNY AQKFQGRATLTVDTSISTAY MELSRLRSDDTAVYYCTRSH YGLDWNFDVWGKGTTVTVSS SQVQLVESGGGVVQPGRSLR LSCAASGFTFTKAWMHWVRQ APGKQLEWVAQIKDKSNSYA TYYADSVKGRFTISRDDSKN TLYLQMNSLRAEDTAVYYCR GVYYALSPFDYWGQGTLVTV SSRTASTKGPSVFPLAPCSR STSESTAALGCLVKDYFPEP VTVSWNSGALTSGVHTFPAV LQSSGLYSLSSVVTVPSSSL GTKTYTCNVDHKPSNTKVDK RVESKYGPPCPPCPAPEAAG GPSVFLFPPKPKDTLMISRT PEVTCVVVDVSQEDPEVQFN WYVDGVEVHNAKTKPREEQF NSTYRVVSVLTVLHQDWLNG KEYKCKVSNKGLPSSIEKTI SKAKGQPREPQVCTLPPSQE EMTKNQVSLSCAVKGFYPSD IAVEWESNGQPENNYKTTPP VLDSDGSFFLVSKLTVDKSR WQEGNVTSCSVMHEALHNHY TQKSLSLSLG | SEQ ID NO: 60 |
| CD28supxCD3mid Light Chain 1 (e.g., a first polypeptide chain of a trispecific binding protein of the present disclosure) | DIVMTQTPLSLSVTPGQPAS ISCKSSQSLVHNNANTYLSW YLQKPGQSPQSLIYKVSNRF SGVPDRFSGSGSGTDFTLKI SRYEAEDVGVYYCGQGTQYP FTFGSGTKVEIKGQPKAAPD IQMTQSPSSLSASVGDRVTI TCQASQNIYVWLNWYQQKPG KAPKLLIYKASNLHTGVPSR FSGSGSGTDPTLTISSLQPE DIATYYCQQGQTYPYTFGQG TKLEIKTKGPSRTVAAPSVF IFPPSDEQLKSGTASVVCLL NNFYPRKAKVQWKVDNAEQS GNSQESVTEQPSKDSTYSLS STLTLSKADYEYKHKVACEV THQGLSSPVTKSKNRGEC | SEQ ID NO: 61 |

TABLE I-continued

Full-length sequences of binding proteins.

| | | |
|---|---|---|
| mAb2 IgG4(knob) FALA Heavy Chain 2 (e.g., a third polypeptide chain of a trispecific binding protein of the present disclosure) | QVQLVQSGAEVVKPGASVKV SCKASGYTFTSYAMHWVKEA PGQRLEWKIYIYPGQGGTNY NQKFQGRATLTADTSASTAY MELSSLRSEDTAVYFCARTG GLRRAYFTYWGQGTLVTVSS ASTKGPSVFPLAPCSRSTSE STAALGCLVKDYFPEPVTVS WNSGALTSGVHTFPAVLQSS GLYSLSVVTVPSSSLGTKTY TCNVDHKPSNTKVDKRVESK YGPPCPPCPAPEAAGGPSVF LFPPKPKDTLMISRTPEVTC VVVDVSQEDPEVQFNWYVDG VBVHNAKTKPREEQFNSTYR VVSVLTVLHQDWLNGKEYKC KVSNKGLPSSIEKTISKAKG QPREPQVYTLPPCQEEMTKN QVSLWCLVKGFYPSDIAVEW ESNGQPENNYKTTPPVLDSD GSFFLYSKLTVDKSRWQEGN VFSCSVMHEALFINHYTQKS LSLSLG | SEQ ID NO: 62 |
| mAb2 Light Chain 2 (e.g., a fourth polypeptide chain of a trispecific binding protein of the present disclosure) | DIVLTQSPATLSLSPGERAT ISCRASQSVSSYGQGFMHWY QQKPGQPPRLLIYGASSRAT GIPARFSGSGSGTDFTLTIS PLEPEDFAVYYCQQNKEDPW TFGGGTKLEIKRTVAAPSVF IFPPSDEQLKSGTASVVCLL NNFYPREAKVQWKVDNALQS GNSQESVTEQDSKDSTYSLS STLTLSKADYEKHKVYACEV THQGLSSPVTKSFNRGEC | SEQ ID NO: 63 | mAb2xCD28supxCD3mid IgG1LALA P329A

| | | |
|---|---|---|
| CD28supxCD3mid IgG1(hole) LALA P329A Heavy Chain 1 (e.g., a second polypeptide chain of a trispecific binding protein of the present disclosure) | QVQLVQSGAEVVKPGASVKV SCKASGYTFTSYYIHWVRQA PGQGLEWIGSIYPGNVNTNY AQKFQGRATLTVDTSISTAY MELSRLRSDDTAVYYCTRSH YGLDWNFDVWGKGTTVTVSS SQVQLVESGGGVVQPGRSLR LSCAASGFTFTKAWMHWVRQ APGKQLEWVAQIKDKSNSYA TYYADSVKGRFTISRDDSKN TLYLQMNSLRAEDTAVYYCR GVYYALSPFDYWGQGTLVTV SSRTASTKGPSVFPLAPSSK STSGGTAALGCLVKDYFPEP VTVSWNSGALTSGVHTFPAV LQSSGLYSLSSVVTVPSSSL GTQTYICNVNHKPSNTKVDK KVEPKSCDKTHTCPPCPAPE AAGGPSVFLFPPKPKDTLMI SRTPEVTCVVVDVSHEDPEV KFNWYVDGVEVHNAKTKPRE EQYNSTYRVVSVLFVLHQDW LNGKEYKCKVSNKALAAPIE KTISKAKGQPREPQVCTLPP SRDELTKNQVSLSCAVKGFY PSDIAVEWESNGQPENNYKT TPPVLDSDGSFFLVSKLTVD KSRWQQGNVFSCSVMHEALH NHYTQKSLSLSPG | SEQ ID NO: 64 |
| CD28supxCD3mid Light Chain 1 (e.g. a first polypeptide chain of a trispecific binding protein of the present disclosure) | See above. | SEQ ID NO: 61 |

| | | |
|---|---|---|
| mAb2 IgG1(knob) LALA P329A Heavy Chain 2 (e.g., a third polypeptide chain of a trispecific binding protein of the present disclosure) | QVQLVQSGAEVVKPGASVKV SCKASGYTFTSYAMHWVKEA PGQRLEWIGYIYPGQGGTNY NQKFQGRATLTADTSASTAY MELSSLRSEDTAVYFCARTG GLRRAYFTYWGQGTLVTVSS ASTKGPSYFPLAPSSKSTSG GTAALGCLVKDYFPEPVTVS WNSGALTSGVHTFPAVLQSS GLYSLSSVVTVPSSSLGTQT YICNVNHKPSNTKVDKKVEP KSCDKTHTCPPCPAPEAAGG PSVFLFPPKPKDTLMISRTP EVTCVVVDVSHEDPEVKFNW YVDGVEVHNAKTKPREEQYN STYRVVSVLTVLHQDWLNGK EYKCKVSNKALAAPIEKTIS KAKGQPREPQVYTLPPCRDE LTKNQVSLWCLVKGFYPSDI AVEWESNGQPENNYKTTPPV LDSDGSFFLYSKLTVDKSRW QQGNVFSCSVMHEALHNHYT QKSLSLSPG | SEQ ID NO: 65 |
| mAb2 Light Chain 2 (e.g., a fourth polypeptide chain of a trispecific binding protein of the present disclosure) | See above. | SEQ ID NO: 63 | mAb2xCD28supxCD3mid IgG1 NNSA

| | | |
|---|---|---|
| CD28supxCD3mid IgG1(hole) NNSA Heavy Chain 1 (e.g., a second polypeptide chain of a trispecific binding protein of the present disclosure) | QVQLVQSGAEVVKPGASVKV SCKASGYTFTSYYIHWVRQA PGQGLEWIGSIYPGNVNTNY AQKFQGRATLTVDTSISTAY MELSRLRSDDTAVYYCTRSH YGLDWNFDVWGKGTTVTVSS SQVQLVESGGGVVQPGRSLR LSCAASGFTFTKAWMHWVRQ APGKQLEWVAQIKDKSNSYA TYYADSVKGRFTISRDDSKN TLYLQMNSLRAEDTAVYYCR GVYYALSPFDYWGQGTLVTV SSRTASTKGPSVFPLAPSSK STSGGTAALGCLVKDYFPEP VTVSWNSGALTSGVHTFPAV LQSSGLYSLSSVVTVPSSSL GTQTYICNVNHKPSNTKVDK KVEPKSCDKTHTCPPCPAPE LLGGPSVFLFPPKPKDTLMI SRTPEVTCVVVDVSHEDPEV KFNWYVDGVEVHNAKTKPRE EQYNNASRVVSVLTVLHQDW LNGKEYKCKVSNKALPAPIE KTISKAKGQPREPQVCTLPP SRDELTKNQVSLSCAVKGFY PSDIAVEWESNGQPENNYKT TPPVLDSDGSFFLVSKLTVD KSRWQQGNVFSCSVMHEALH NHYTQKSLSLSPG | SEQ ID NO: 66 |
| CD28supxCD3mid Light Chain 1 (e.g., a First polypeptide chain of a trispecific binding protein of the present disclosure) | See above. | SEQ ID NO: 61 |

TABLE I-continued

Full-length sequences of binding protiens.

| | | |
|---|---|---|
| mAb2 IgG1(knob) NNSA Heavy Chain 2 (e.g.. a third polypeptide chain of a trispecific binding protein of the present disclosure) | QVQLVQSGAEVVKPGASVKV SCKASGYTFTSYAMHWVKEA PGQRLEWIGYIYPGQGGTNY NQKFQGRATLTADTSASTAY MELSSLRSEDTAVYFCARTG GLRRAYFTYWGQGTLVTVSS ASTKGPSVFPLAPSSKSTSG GTAALGCLVKDYFPEPVTVS WNSGALTSGVHTFPAVLQSS GLYSLSSVVTVPSSSLGTQT YICNVNHKPSNTKVDKKVEP KSCDKTHTCPPCPAPELLGG PSVFLFPPKPKDTLMISRTP EVTCVVVDVSHEDPEVKFNW YVDGVEVHNAKTKPREEQYN NASRVVSVLTVLHQDWLNGK EYKCKVSNKALPAPIEKTIS KAKGQPREPQVYTLPPCRDE LTKNQVSLWCLVKGFYPSDI AVEWESNGQPENNYKTTPPV LDSDGSFFLYSKLTVDKSRW QQGNVFSCSVMHEALHNHYT QKSLSLSPG | SEQ ID NO: 67 |
| CD38VH1 Light Chain 2 (e.g.,a fourth polypeptide chain of a trispecific binding protein of the present disclosure) | See above. | SEQ ID NO: 63 | mAb6xCD28supxCD3mid IgG4 FALA

| | | |
|---|---|---|
| CD28supxCD3mid IgG4(hole) FALA Heavy Chain 1 (e.g., a second polypeptide chain of a trispecific binding protein of the present disclosure) | See above. | SEQ ID NO: 60 |
| CD28supxCD3mid Chain 1 (e.g., a first polypeptide chain of a trispecific binding protein of the present disclosure) | See above. | SEQ ID NO: 61 |
| mAb6 IgG4(knob) FALA Heavy Chain 2 (e.g., a third polypeptide chain of a trispecific binding protein of the present disclosure) | QVQLVESGGGVVQPGRSLRL SCAASGFTFSSYGMHWVRQA PGKGLEWVAVIWYDGSNKYY ADSVKGRFTISGDNSKNTLY LQMNSLRAEDTAVYYCARMF RGAFDYWGQGTLVTVSSAST KGPSVFPLAPCSRSTSESTA ALGCLVKDYFPEPVTVSWNS GALTSCVHTFPAVLQSSGLY SLSSVVTVPSSSLGTKTYTC NVDHKPSNTKVDKRVESKYG PPCPPCPAPEAAGGPSVFLF PPKPKDTLMISRTPEVTCVV VDVSQEDPEVQFNWYVDGVE VHNAKTKPREEQFNSTYRVV SVLTVLHQDWLNGKEYKCKV SNKGLPSSIEKTISKAKGQP REPQVYTLPPCQEEMTKNQV SLWCLVKGFYPSDIAVEWES NGQPENNYKTTPPVLDSDGS FFLYSKLTVDKSRWQEGNVF SCSVMHEALHNHYTQKSLSL SLG | SEQ ID NO: 68 |

TABLE I-continued

Full-length sequences of binding protiens.

| | | |
|---|---|---|
| mAb6 Light2 (e.g. a fourth polypeptide chain of a trispecific binding protein of present disclosure) | AIQMTQSPSSLSASVGDRVT ITCRASQGIRNDLGWYQQKP GKAPKLLIYAASSLQSGVPS RFSGSGSGTDFTLTISGLQP EDSATYYCLQDYIYYPTFGQ GTKVEIKRTVAAPSVFIFPP SDEQLKSGTASVVCLLNNFY PREAKVQWKVDNALQSGNSQ ESVTEQDSKDSTYSLSSTLT LSKADYEKHKVYACEVTHQG LSSPVTKSFNRGEC | SEQ ID NO: 69 | mAb6xCD28supxCD3mid IgG1LALA P329A

| | | |
|---|---|---|
| CD28supxCD3mid IgG1(hole) LALA P329A Heavy Chain 1 (e.g., a second polypeptide chain of a trispecific binding protein of the present disclosure) | See above. | SEQ ID NO: 64 |
| CD28supxCD3mid Light Chain 1 (e.g., a first polypeptide chain of a trispecific binding protein of the present disclosure) | See above. | SEQ ID NO: 61 |
| mAb6 IgG1(knob) LALA P329A Heavy Chain 2 (e.g., third polypeptide chain of a trispecific binding protein of the present disclosure) | QVQLVESGGGVVQPGRSLRL SCAASGFTFSSYGMHWVRQA PGKGLEWVAVIWYDGSNKYY ADSVKGRFTISGDNSKNTLY LQMNSLRAEDTAVYYCARMF RGAFDYWGQGTLVTVSSAST KGPSVFPLAPSSKSTSGGTA ALGCLVKDYFPEPVTVSWNS GALTSGVHTFPAVLQSSGLY SLSSVVTVPSSSLGTQTYIC NVNHKPSNTKVDKKVEPKSC DKTHTCPPCPAPEAAGGPSV FLFPPKPKDTLMISRTPEVT CVVVDVSHEDPEVKFNWYVD GVEVHNAKTKPREEQYNSTY RVVSVLTVLHQDWLNGKEYK CKVSNKALAAPIEKTISKAK GQPREPQVYTLPPCRDELTK NQVSLVVCLVKGFYPSDIAV EWESNGQPENNYKTTPPVLD SDGSFFLYSKLTVDKSRWQQ GNVFSCSVMHEALHNHYTQK SLSLSPG | SEQ ID NO: 70 |
| mAb6 Light2 (e.g., a fourth polypeptide chain of a trispecific binding protein of the present disclosure) | See above. | SEQ ID NO: 69 | mAb6xCD28supxCD3mid IgG1 NNSA

| | | |
|---|---|---|
| CD28supxCD3mid IgG1(hole) NNSA Heavy Chain 1 (e.g., a second polypeptide chain of a trispecific binding protein of the present disclosure) | See above. | SEQ ID NO: 66 |

TABLE I-continued

Full-length sequences of binding proteins.

| | | |
|---|---|---|
| CD28supxCD3mid Light Chain 1 (e.g., a first polypeptide chain of a trispecific binding protein of the present disclosure) | See above. | SEQ ID NO: 61 |
| mAb6 IgG1(knob) NNSA Heavy Chain 2 (e.g., a third polypeptide chain of a trispecific binding protein of the present disclosure) | QVQLVESGGGVVQPGRSLRL SCAASGFTSSYGMHWVRQA PGKGLEWVAVIWYDGSNKYY ADSVKGRFTISGDNSKNTLY LQMNSLRAEDTAVYYCARMF RGAFDYWGQGTLVTVSSAST KGPSVFPLAPSSKSTSGGTA ALGCLVKDYFPEPVTVSWNS GALTSGVHTFPAVLQSSGLY SLSSVVTVPSSSLGTQTYIC NVNHKPSNTKVDKKVEPKSC DKTHTCPPCPAPELLGGPSV FLFPPKPKDTLMISRTPEVT CVVVDVSHEDPEVKFNWYVD GVEVHNAKTKPREEQYNNAS RVVSVLTVLHQDWLNGKEYK CKVSNKALPAPIEKTLSKAK GQPREPQVYTLPPCRDELTK NQVSLWCLVKGFYPSDIAVE WESNGQPENNYKTTPPVLDS DGSFFLYSKLTVDKSRWQQG NVFSGSVMHEALHNHYTQKS LSLSPG | SEQ ID NO: 71 |
| mAb6 Light2 (e.g., a fourth polypeptide chain of a trispecific binding protein of the present disclosure) | See above. | SEQ ID NO: 69 | mAb1 monovalent antibody

| | | |
|---|---|---|
| mAb1 heavy chain | QVQLQQSGAE LVRSGASVKM SCKASGYTFTSFNMHWVKET PGQGLEWIGYIYPGNGGTNY NQKFKGKATLTADTSSSTAY MQISSLTSEDSAVYFCARTG GLRRAYFTYWGQGTLVTVSS ASTKGPSVFPLAPSSKSTSG GTAALGCLVKDYFPEPVTVS WNSGALTSGVHTFPAVLQSS GLYSLSSVVTVPSSSLGTQT YICNVNHKPSNTKVDKKVEP KSCDKTHTCPPCPAPELLAG PDVFLFPPKPKDTLMISRTP EVTCVVVDVSHEDPEVKFNW YVDGVEVHNAKTKPREEQYN STYRVVSVLTVLHQDWLNGK EYKCKVSNKALPLPEEKTIS KAKGQPREPQVYTLPPSRDE LTKNQVSLTCLVKGFYPSDI AVEWESNGQPENNYKTTPPV LDSDGSFFLYSKLTVDKSRW QQGNVFSCSVMHEALHNHYT QKSLSLSPG | SEQ ID NO: 7 |
| mAb1 light chain | DIVLTQSPASLAVSLGQRAT ISCRASESVDSYGNGFMHWY QQKPGQPPKLLIYLASNLES GVPARFSGSGSRTDFTLTID PVEADDAATYYCQQNKEDPW TFGGGTKLEIKRTVAAPSVF IFPPSDEQLKSGTASVVCLL NNFYPREAKVQWKVDNALQS GNSQESVTEQDSKDSTYSLS STLTLSKADYEKHKVYACEV THQGLSSPVTKSFNRGEC | SEQ ID NO: 8 | mAb2 monovalent antibody

| | | |
|---|---|---|
| mAb2 heavy chain | QVQLVQSGAEVVKPGASVKV SCKASGYTFISYAMHWVKEA PGQRLEWIGYIYPGQGGTNY NQKFQGRATLTADTSASTAY MELSSLRSEDTAVYFCARTG GLRRAYFTYWGQGTLVTVSS ASTKGPSVFPLAPSSKSTSG GTAALGCLVKDYFPEPVTVS WNSGALTSGVHTFPAVLQSS GLYSLSSVVTVPSSSLGTQT YICNVNHKPSNTKVDKKVEP KSCDKTHTCPPCPAPELLAG PDVFLFPPKPKDTLMISRTP EVTCVVVDVSHEDPEVKFNW YVDGVEVHNAKTKPREEQYN STYRVVSVLTVLHQDWLNGK EYKCKVSNKALPLPEEKTIS KAKGQPREPQVYTLPPSRDE LTKNQVSLTCLVKGFYPSDI AVEWESNGQPENNYKTTPPV LDSDGSFFLYSKLTVDKSRW QQGNVFSCSVMHEALHNHYT QKSLSLSPG | SEQ ID NO: 15 |
| mAb2 light chain | DIVLTQSPATLSLSPGERAT ISCRASQSVSSYGQGFMHWY QQKPGQPPRLLIYGASSRAT GIPARFSGSGSGTDFTLTIS PLEPEDFAVYYCQQNKEDPW TFGGGTKLEIKRTVAAPSVF IFPPSDEQLKSGTASVVCLL NNFYPREAKVQWKVDNALQS GNSQESVTEQDSKDSTYSLS STLTLSKADYEKHKVYACE VTHQGLSSPVTKSFNRGEC | SEQ ID NO: 16 | mAb3 monovalent antibody

| | | |
|---|---|---|
| mAb3 heavy chain | QVQLVQSGAEVVKPGASVKV SCKASGYTFTSFNMHWVKEA PGQRLEWIGYIYPGNGGTNY NQKFQGRATLTADTSASTAY MELSSLRSEDTAVYFCARTG GLRRAYFTYWGQGTLVTVSS ASTKGPSVFPLAPSSKSTSG GTAALGCLVKDYFPEPVTVS WNSGALTSGVHTFPAVLQSS GLYSLSSVVTVPSSSLGTQT YICNVNHKPSNTKVDKKVEP KSCDKTHTCPPCPAPELLAG PDVFLFPPKPKDTLMISRTP EVTCVVVDVSHEDPEVKFNW YVDGVEVHNAKTKPREEQYN STYRVVSVLTVLHQDWLNGK EYKCKVSNKALPLPEEKTIS KAKGQPREPQVYTLPPSRDE LTKNQVSLTCLVKGFYPSDI AVEWESNGQPENNYKTTPPV LDSDGSFFLYSKLTVDKSRW QQGNVFSCSVMHEALHNHYT QKSLSLSPG | SEQ ID NO: 19 |
| mAb3 light chain | DIVLTQSPATLSLSPGERAT ISCRASESVDSYGNGFMHWY QQKPGQPPRLLIYLASSRAT GIPARFSGSGSGTDFTLTIS PLEPEDFAVYYCQQNKEDPW TFGGGTKLEIKRTVAAPSVF IFPPSDEQLKSGTASVVCLL NNFYPREAKVQWKVDNALQS GNSQESVTEQDSKDSTYSLS STLTLSKADYEKHKVYACEV THQGLSSPVTKSFNRGEC | SEQ ID NO: 20 |

TABLE I-continued

Full-length sequences of binding protiens.

mAb4 monovalent antibody

| mAb4 heavy chain | QVQLVQSGAEVVKSGASVKV SCKASGYTFTSFNMHWVKEA PGQGLEWIGYIYPGNGGTNY NQKFQGRATLTADTSASTAY MEISSLRSEDTAVYFCARTG GLRRAYFTYWGQGTLYTVSS ASTKGPSVFPLAPSSKSTSG GTAALGCLVKDYFPEPVTVS WNSGALTSGVHTFPAVLQSS GLYSLSSVVTVPSSSLGTQT YICNVNHKPSNTKVDKKVEP KSCDKTHTCPPCPAPELLAG PDVFLFPPKPKDTLMISRTP EVTCVVVDVSHEDPEVKFNW YVDGVEVHNAKTKPREEQYN STYRVVSVLTVLHQDWLNGK EYKCKVSNKALPLPEEKTIS KAKGQPREPQVYTLPPSRDE LTKNQVSLTCLVKGFYPSDI AVEWESNGQPENNYKTTPPV LDSDGSFFLYSRLTVDKSRW QQGNVFSCSVMHEALHNHYT QKSLSLSPG | SEQ ID NO: 22 |
| --- | --- | --- |
| mAb4 light chain | DTVLTQSPATLSLSPGERAT ISCRASESVDSYGNGFMHWY QQKPGQPPRLLIYLASSRAT GIPARFSGSGSGTDFTLTIS PLEPEDFAVYYCQQNKEDPW TFGGGTKLEIKRTVAAPSVF IFPPSDEQLKSGTASVVCLL NNFYPREAKVQWKVDNALQS GNSQESVTEQDSKDSTYSLS STLTLSKADYEKHKVYACEV THQGLSSPVTKSFNRGEC | SEQ ID NO: 20 | mAb5 monovalent antibody

| mAb5 heavy chain | QVQLVQSGAEVVKPGASVKM SCKASGYTFTSFNMHWVKEA PGQRLEWIGYIYPGNGGTNY NQKFQGRATLTADTSASTAY MEISSLRSEDTAVYFCARTG GLRRAYFTYWGQGTLVTVSS ASTKGPSVFPLAPSSKSTSG GTAALGCLVKDYFPEPVTVS WNSGALTSGVHTFPAVLQSS GLYSLSSVVTVPSSSLGTQT YICNVNHKPSNTKVDKKVEP KSCDKTHTCPPCPAPELLAG PDVFLFPPKPKDTLMISRTP EVTCVVVDVSHEDPEVKFNW YVDGVEVHNAKTKPREEQYN STYRVVSVLTVLHQDWLNGK EYKCKVSNKALPLPEEKTIS KAKGQPREPQVYTLPPSRDE LTKNQVSLTCLVKGFYPSDI AVEWESNGQPENNYKTTPPV LDSDGSFFLYSKLTVDKSRW QQGNVFSCSVMHEALHNHYT QKSLSLSPG | SEQ ID NO: 24 |
| --- | --- | --- |
| mAb5 light chain | DIVLTQSPATLSLSPGERAT ISCRASESVDSYGNGFMHWY QQKPGQPPRLLIYLASSRAT GIPARFSGSGSGTDFTLTIS PLEPEDFAVYYCQQNKEDPW TFGGGTKLEIKRTVAAPSVF IFPPSDEQLKSGTASVVCLL NNFYPREAKVQWKVDNALQS GNSQESVTEQDSKDSTYSLS STLTLSKADYEKHKVYACEV THQGLSSPVTKSFNRGEC | SEQ ID NO: 20 | mAb6 monovalent antibody

| mAb6 heavy chain | QVQLVESGGGVVQPGRSLRL SCAASGFTFSSYGMHWVRQA PGKGLEWVAVIWYDGSNKYY ADSVKGRFTISGDNSKNTLY LQMNSLRAEDTAVYYCARMF RGAFDYWGQGTLVTVSSAST KGPSVFPLAPSSKSTSGGTA ALGCLVKDYFPEPVTVSWNS GALTSGVHTFPAVLQSSGLY SLSSVVTVPSSSLGTQTYIC NVNHKPSNTKVDKKVEPKSC DKTHTCPPCPAPELLAGPDV FLFPPKPKDTLMISRTPEVT CVVVDVSHEDPEVKFNWYVD GVEVHNAKTKPREEQYNSTY RVVSVLTVLHQDWLNGKEYK CKVSNKAEPLPEEKTISKAK GQPREPQVYTLPPSRDELTK NQVSLTCLVKGFYPSDIAVE WESNGQPENNYKTTPPVLDS DGSFFLYSKLTVDKSRWQQG NVFSCSVMHEALHNHYTQKS LSLSPG | SEQ ID NO: 21 |
| --- | --- | --- |
| mAb6 light chain | AIQMTQSPSSLSASVGDRVT ITCRASQGIRNDLGWYQQKP GKAPKLLIYAASSLQSGVPS RFSGSGSGTDFTLTISGLQP EDSATYYCLQDYIYYPTFGQ GTKVEIKRTVAAPSVFIFPP SDEQLKSGTASVVCLLNNFY PREAKVQWKVDNALQSGNSQ ESVTEQDSKDSTYSLSSTLT LSKADYEKHKVYACEVTHQG LSSPYTKSPNRGEC | SEQ ID NO: 12 | mAb7 monovalent antibody

| mAb7 heavy chain | QVQLVQSGAEVAKPGTSVKL SCKASGYTFTDYWMQWVKQR PGQGLEWIGTIYPGDGDTGY AQKFQGKATLTADKSSKTVY MHLSSLASEDSAVYYCARGD YYGSNSLDYWGQGTSVTVSS ASTKGPSVFPLAPSSKSTSG GTAALGCLVKDYFPEPVTVS WNSGALTSGVHTFPAVLQSS GLYSLSSVVTVPSSSLGTQT YICNVNHKPSNTKVDKKVEP KSCDKTHTCPPCPAPELLGG PSVFLFPPKPKDTLMISRTP EVTCVVVDVSHEDPEVKFNW YVDGVEYHNAKTKPREEQYN STYRVVSVLTVLHQDWLNGK EYKCKVSNKALPAPIEKTIS KAKGQPREPQVYTLPPSRDE LTKNQVSLTCCVKGFYPSDI AVEWESNGQPENNYKTTPPV LDSDGSFFLYSKLTVDKSRW QQGNVFSCSVMHEALHNHYT QKSLSLSPGK | SEQ ID NO: 107 |
| --- | --- | --- |
| mAb7 light chain | DIVMTQSHLSMSTSLGDPVS ITCKASQDVSTVVAWYQQKP GQSPRRLIYSASYRYIGVPD RFTGSGAGTDFTFTISSVQA EDLAVYYCQQHYSPPYTFGG GTKLEIKRTVAAPSVFIFPP SDEQLKSGTASVVCLLNNFY PREAKVQWKVDNALQSGNSQ ESVTEQDSKDSTYSLSSTLT LSKADYEKHKVYACEVTHQG LSSPVTKSFNRGEC | SEQ ID NO: 106 |

TABLE J

Full-length polynucleotide sequences of binding proteins.

| mAb2xCD28supxCD3mid IgG4 FALA | | |
|---|---|---|
| CD28supxCD3mid IgG4(hole) FALA Heavy Chain 1 (e.g., encoding a second polypeptide chain of a trispecific binding protein of the present disclosure) | CAGGTGCAGCTGGTGCAGTCTGGC CCGAGGTCGTGAAACCTGGCGCCTC TGTGAAGGTGTCCTGCAAGGCCAGC GGCTACACCTTTACCAGCTACACA TCCACTGGGTGCGCCAGGCCCCTGG ACAGGGACTCGAATGGATCGGCAGC ATCTACCCCGGCAACGTGAACACCA ACTACGCCCAGAAGTTCCACGGCAG AGCCACCCTGACCGTGGACACCAGC ATCAGCACCGCCTACATGGAACTGA GCCGCCTGAGAAGCGACGACACCGC CGTGTACTACTGCACCCGGTCCCAC TACGCCTGGATTGGAACTTCGACG TGTGGGCAAGGGCACCACCGTGAC AGTGTCTAGCAGCCAGGTGCAGCTG GTGGAATCTGGCGGCGGAGTGGTGC AGCCTGGCAGAAGCCTGAGACTGAG CTGTGCCGCCAGCGGCTTCACCTTC ACCAAGGCCTGGATGCACTGGGTGC GCCAGGCCCCTGGAAAGCAGCTGGA ATGGGTGGCCCAGATCAAGGACAAG AGCAACAGCTACGCCACCTACTACG CCGACAGCGTGAAGGGCCGGTTCAC CATCAGCCGGGACGACGCCAAGAAC ACCCTGTACCTGCAGATGAACAGCC TGCGGGCCGAGGACACCGCCGTGTA CTACTGTCGGGGCGTGTACTATGCC CTGAGCCCCTTCGATTACTGGGGCC AGGGAACCCTCGTGACCGTCTTCTA GTCGGACCGCCAGCACAAAGGGCCC ATCGGTGTTCCCTCTGGCCCCTTGC AGCAGAAGCACCAGCGAATCTACAG CCGCCCTGGGCTGCCTCGTGAAGGA CTACTTTCCCGAGCCCGTGACCGTG TCCTGGAACTCTGGCGCTCTGACAA GCGGCGTGCACACCTTTCCAGCCGT GCTCCAGAGCAGCGGCCTGTACTCT CTGAGCAGCGTCGTGACAGTGCCCA GCAGCAGCCTGGGCACCAAGACCTA CACCTGTAACGTGGACCACAAGCCC AGCAACACCAAGGTGGACAAGCGGG TGGAATCTAAGTACGGCCCTCCCTG CCCTCCTTGCCCAGCCCCTGAAGCT GCCGGCGGACCCTCCGTGTTCCTGT TCCCCCCAAAGCCCAAGGACACCCT GATGATCAGCCGGACCCCCGAAGTG ACCTGCGTGGTGGTGGATGTGTCCC AGGAAGATCCCGAGGTGCAGTTCAA TTGGTACGTGGACGGCGTGGAAGTG CACAACGCCAAGACCAAGCCCAGAG AGGAACAGTTCAACAGCACCTACCG GGTGGTGTCCGTGCTGACCGTGCTG CACCAGGACTGGCTGAACGGCAAAG ACTACAAGTGCAAGGTGTCCAACAA GGGCCTGCCCAGCTCCATCGAGAAA ACCATCAGCAAGGCCAAGGGCCAGC CCCGCGAGCCTCAAGTGTGTACCCT GCCCCCTAGCCAGGAAGAGATGACC AAGAACCAGGTGTCCCTGAGCTGTG CCGTGAAAGGCTTCTACCCCAGCGA CATTGCCGTGGAATGGGAGAGCAAC GGCCAGCCCGAGAACAACTACAAGA CCACCCCCCCTGTGCTGGACAGCGA CGGCTCATTCTTCCTGGTGTCCAAG CTGACCGTGGACAAGAGCCGGTGGC AGGAAGGCAACGTGTTCAGCTGCTC CGTGATGCACGAGGCCCTGCACAAC CACTACACCCAGAAGTCCCTGTCTC TGTCCCTGGGC | SEQ ID NO: 72 |
| CD28supxCD3mid Light Chain 1 (e.g., encoding a first polypeptide chain of a | GACATCGTGATGACCCAGACCCCCCS GCCTGCCAGCATCAGCTGCAAGAGC AGCCAGAGCCTGGTGCACAACAACG CCAACACCTACCTGAGCTGGTATCT | SEQ ID NO: 73 |
| trispecific binding protein of the present disclosure) | GCAGAAGCCCGGCCAGAGCCCCCAG TCCCTGATCTACAAGGTGTCCAACA GATTCAGCGGCGTGCCCGACAGATT CTCCGGCAGCGGCTCTGGCACCGAC TTCACCCTGAAGATCAGCCGGGTGG AAGCCGAGGACGTGGGCGTGTACTA TTGTGGCCAGGGCACCCAGTACCCC TTCACCTTTGGCAGCGGCACCAAGG TGGAAATCAAGGGCCAGCCCAAGGC CGCCCCGACATCCAGATGACCCAG AGCCCCAGCAGCCTGTCTGCCACCG TGGGCGACAGAGTGACCATCACCTG TCAGGCCGCCAGAACATCTACGTG TGGCTGAACTGGTATCAGCAGAAGC CCGGCAAGGCCCCCAAGCTGCTGAT CTACAAGGCCAGCAACCTGCACACC GGCGTGCCCAGCAGATTTTCTGGCA GCGGCTCCGGCACCGACTTCACCCT GACAATCAGCTCCCTGCAGCCCGAG GACATTGCCACCTACTACTGCCAGC AGGGCCAGACCTACCCCTACACCTT TGGCCAGGGCACCAAGCTGGAAATC AAGACCAAGGGCCCCAGCCGTACGG TGGCCGCTCCCAGCGTGTTCATCTT CCCACCTAGCGACGAGCAGCTGAAG TCCGGCACAGCCTCTGTCGTGTGCC TGCTGAACAACTTCTACCCCCGCGA GGCCAAAGTGCAGTGGAAGGTGGAC AACGCCCTGCAGAGCGGCAACAGCC AGGAAAGCGTGACCGAGCAGGACAG CAAGGACTCCACCTACAGCCTGAGC AGCACCCTGACACTGAGCAAGGCCG ACTACGAGAAGCACAAGGTGTACGC CTGCGAAGTGACCCACCAGGGCCTG TCTAGCCCCGTGACCAAGAGCTTCA ACCGGGGCGAGTCT | |
| mAb2 IgG4(knob) FALA Heavy Chain 2 (e.g., encoding a third polypeptide chain of a trispecific binding protein of the present disclosure) | CAGGTGCAGCTGGTGCAGTCTGGC CCGAAGTCGTGAAACCTGGCGCCTC CGTGAAGGTGTCCTGCAAGGCCAGC GGCTACACCTTTACCAGCTACGCCA TGCACTGGGTCAAAGAGGCCCCTGG CCAGAGACTGGAATGGATGGCTAC ATCTACCCCGGCCAGGGCGGCACCA ACTACAACCAGAAGTTCCAGGGCAG AGCCACCCTGACCGCCGATACAAGC GCCAGCACCGCCTACATGGAACTGA GCAGCCTGCGGAGCGAGGATACCGC CGTGTACTTCTGTGCCAGAACAGGC GGCCTGAGGCGGGCCTACTTTACCT ATTGGGGCCAGGGCACCCTCGTGAC CGTGTCTAGCGCTAGCACAAAGGGC CCATCGGTGTTCCCTCTGGCCCCTT GCAGCAGAAGCACCAGCGAATCTAC AGCGCCCTGGGCTGCCTCGTGAAG GACTACTTTCCCGAGCCCGTGACCG TGTCCTGGAACTCTGGCGCTCTGAC AAGCGGCGTGCACACCTTTCCAGCC GTGCTCCAGAGCAGCGGCCTGTACT CTCTGAGCAGCGTCGTGACAGTGCC CAGCAGCAGCCTGGGCACCAAGACC TACACCTGTAACGTGGACCACAAGC CCAGCAACACCAAGGTGGACAAGCG GGTGGAATCTAAGTACGGCCCTCCC TGCCCTCCTTGCCCAGCCCCTGAAG CTGCCGGCGGACCCTCCGTGTTCCT GTTCCCCCCAAAGCCCAAGGACACC CTGATGATCAGCCGGACCCCCGAAG TGACCTGCGTGGTGGTGGATGTGTC CCAGGAAGATCCCGAGGTGCAGTTC AATTGGTACGTGGACGGCGTGGAAG TGCACAACGCCAAGACCAAGCCCAG AGAGGAACAGTTCAACAGCACCTAC CGGGTGGTGTCCGTGCTGACCGTGC TGCACCAGGACTGGCTGAACGGCAA AGAGTACAAGTGCAAGGTGTCCAAC AAGGGCCTGCCCAGCTCCATCGAGA | SEQ ID NO: 74 |

TABLE J-continued

Full-length polynucleotide sequences of binding proteins.

| | | |
|---|---|---|
| | AAACCATCAGCAAGGCCAAGGGCCA GCCCCGCGAGCCTCAAGTGTATACC CTGCCCCCTTGCCAGGAAGAGATGA CCAAGAACCAGGTGTCCCTGTGGTG TCTCGTGAAAGGCTTCTACCCCAGC GACATTGCCGTGGAATGGGAGAGCA ACGGCCAGCCCGAGAACAACTACAA GACCACCCCCCCTGTGCTGGACAGC GACGGCTCATTCTTCCTGTACTCCA AGCTGACCGTGGACAAGAGGCGGTG GCAGGAAGGCAAGGTGTTCAGCTGC TCCGTGATGCACGAGGCCCTGCACA ACCACTACACCCAGAAGTCCCTGTC TCTGTCCCTGGGC | |
| mAb2 Light Chain 2 (e.g., encoding a fourth polypeptide chain of a trispecific binding protein of the present disclosure) | GACATCGTGCTGACACAGAGCCCTG CCACCCTGTCTCTGAGCCCTGGCGA GAGAGCCACCATCAGCTGTAGAGCC AGCCAGAGCGTGTCCAGCTACGGCC AGGGCTTCATGCACTGGTATCAGCA GAAGCCCGGCCAGCCCCCCAGACTG CTGATCTATGGCGCCAGCAGCAGAG CCACAGGCATCCCCGCCAGATTTTC TGGCTCTGGCAGCGGCACCGACTTC ACCCTGACAATCAGCCCCCTGGAAC CCGAGGACTTCGCCGTGTACTACTG CCAGCAGAACAAAGAGGACCCCTGG ACCTTCGGCGGAGGCACCAAGCTGG AAATCAAGCGTACGGTGGCCGCTCC CAGCGTGTTCATCTTCCCACCTAGC GACGAGCAGCTGAAGTCCGGCACAG CCTCTGTCGTGTGCCTGCTGAACAA CTTCTACCCCCGCGAGGCCAAGGTG CAGTGGAAGGTGGACAATGCCCTGC AGAGCGGCAACAGCCAGGAAAGCGT GACCGAGCAGGACAGCAAGGACTCC ACCTACAGCCTGAGCAGCACCCTGA CCCTGTCCAAGGCCGATTACGAGAA GCACAAGGTGTACGCCTGCGAAGTG ACCCACCAGGGCCTGTCTAGCCCCG TGACCAAGAGCTTCAACCGGGGCGA GTGC | SEQ ID NO: 75 | mAb2xCD28supxCD3mid IgG1LALA P329A

| | | |
|---|---|---|
| CCD28supxCD3mid IgG1(hole) LALA P329A Heavy Chain 1 (e.g., encoding a second polypeptide chain of a trispecific binding protein of the present disclosure) | CAGGTGCAGCTGGTGCAGTCTGGCG CCGAGGTCGTGAAACCTGGCGCCTC TGTGAAGGTGTCCTGCAAGGCCAGC GGCTACACCTTTACCAGCTACTACA TCCACTGGGTGCGCCAGGCCCCTGG ACAGGGACTGGAATGGATGGGCAAC ATCTACCCTGGCAACGTGAAGACCA ACTACGCCCAGAAGTTCCAGGGCAG AGCCACCCTGACCGTGGACACCAGC ATCAGCACCGCCTACATGGAACTGA GCCGGCTGAGAAGCGACGACACCGC CGTGTACTACTGCACCCGGTCCCAC TACGGCCTGGATTGGAACTTCGACG TGTGGGGCCAAGGCACCACCGTGAC AGTGTCTAGCAGCCAGGTGCAGCTG GTGGAATCTGGCGGCGGAGTGGTGC AGCCTGGCAGAAGCCTGAGACTGAG CTGTGCCGCCAGCGGCTTCACCTTC ACCAAGGCCTGGATGCACTGGGTGC GCCAGGCCCCTGGAAAGCAGCTGGA ATGGGTGGCCCAGATCAAGGACAAG AGCAACAGCTACGCCACCTACTACG CCGACAGCGTGAAGGGCCGGTTCAC CATCAGCCGGGACGACAGCAAGAAC ACCCTGTACCTGCAGATGAACAGCC TGCGGGCCGAGGACACCGCCGTGTA CTACTGTCGGGGCGTGTACTATGCC CTGAGCCCCTTCGATTACTGGGGCC AGGGAACCCTCGTGACCGTGTCTAG TCGGACCGCCAGCACAAAGGGCCCC AGCGTGTTCCCTCTGGCCCCTAGCA GCAAGAGCACATCTGGCGGAACAGC | SEQ ID NO: 76 |
| | CGCCCTGGGCTGCCTCGTGAAGGAC TACTTTCCCGAGCCCGTGACCGTGT CCTGGAATTCTGGCGCCCTGACCAG CGGCGTGCACACCTTTCCAGCTGTG CTGCAGTCCAGCGGCCTGTACAGCC TGAGCAGCGTCGTGACAGTGCCCAG CAGCTCTCTGGGCACCCAGACCTAC ATCTGCAACGTGAACCACAAGCCCA GCAACACCAAGGTGGACAAGAAGGT GGAACCCAAGAGCTGCGACAAGACC CACACCTGTCCCCCTTGTCCTGCCC CCGAAGCCGCCGGAGGCCCTTCCGT GTTCCTGTTCCCCCCAAAGCCCAAG GACACCCTGATGATCAGCCGGACCC CCGAAGTGACCTGCGTGGTGGTGGA TGTGTCCCACGAGGACCCTGAAGTG AAGTTCAATTGGTACGTGGACGGCG TGGAAGTGCACAACGCCAAGACCAA GCCAAGAGAGGAACAGTACAACAGC ACCTACCGGGTGGTGTCCGTGCTGA CCGTGCTGCACCAGGACTGGCTGAA CGGCAAAGAGTACAAGTGCAAGGTG TCCAACAAGGCCCTGGCCGCCCCCA TCGAGAAAACCATCAGCAAGGCCAA GGGCCAGCCCCGCGAACCCCAGGTG TGCACACTGCCCCCAAGCAGGACG AGCTGACCAAGAACCAGGTGTCCCT GAGCTGTGCCGTGAAAGGCTTCTAC CCCTCCGATATCGCCGTGGAATGGC AGAGCAACGGCCAGCCCGAGAACAA CTACAAGACCACCCCCCCTGTGCTG GACAGCGACGGCTCATTCTTCCTGG TGTCCAAGCTGACAGTGGACAAGTC CCGGTGGCAGCAGGGCAACGTGTTC AGCTGCTCCGTGATGCACGAGGCCC TGCACAACCACTACACCCAGAAGTC CCTGAGCCTGAGCCCCGGC | |
| CD28supxCD3mid Light Chain 1 (e.g., encoding a first polypeptide chain of a trispecific binding protein of the present disclosure) | See above. | SEQ ID NO: 73 |
| mAb2 IgG1(knob) LALA P329A Heavy Chain 2 (e.g., encoding a third polypeptide chain of a trispecific binding protein of the present disclosure) | CAGGTGCAGCTGGTGCAGTCTGGCG CCGAAGTCGTGAAACCTGGCGCCTC CGTGAAGGTGTCCTGCAAGGCCAGG GGCTACACCTTTACCAGCTACGCCA TGCACTGGGTGCAAAGAGGGCCCTGG CCAGAGACTGGAATGGATCGGCTAC ATCTACCCCGGCCAGGGCGGCACCA ACTACAACCAGAACTTCCAGGGCAG AGCCACCCTGACCGCCGATACAAGC GCCAGCACCGCCTACATGGAACTGA GCAGCCTGCGGAGCGAGGATACCGC CGTGTACTTCTGTGCCAGAACAGGC GGCCTGAGGCGGGCCTACTTTACCT ATTGGGGCCAGGGCACCCTCGTGAC CGTGTCTAGCGCTAGCACAAAGGGC CCCAGCGTGTTCCCTCTGGCCCCTA GCAGCAAGAGCACATCTGGCGGAAC AGCCGCCCTGGGCTGCCTCGTGAAG GACTACTTTCCCGAGCCCGTGACCG TGTCCTGGAATTCTGGCGCCCTGAC CAGCGGCCTGCACACCTTTCCAGCT GTGCTGCAGTCCAGCGCCCTGTACA GCCTGAGCAGCGTCGTGACAGTGCC CAGGAGCTCTCTGGGCACCCAGACC TACATCTGCAACGTGAACCACAAGC CCAGCAACACCAAGGTGGACAAGAA GGTGGAACCCAAGAGCTGCGACAAG ACCCACACCTGTCCCCCTTGTCCTG CCCCCGAAGCCGCCGGAGGCCCTTC | SEQ ID NO: 77 |

TABLE J-continued

Full-length polynucleotide sequences of binding proteins.

|  |  |  |
| --- | --- | --- |
|  | CGTGTTCCTGTTCCCCCCAAAGCCC | |
|  | AAGGACACCCTGATGATCAGCCGGA | |
|  | CCCCCGAAGTGACCTGCGTGGTGGT | |
|  | GGATGTGTCCCACGAGGACCCTGAA | |
|  | GTGAAGTTCAATTGGTACGTGGACG | |
|  | GCGTGGAAGTGCACAACGCCAAGAC | |
|  | CAAGCCAAGAGAGGAACAGTACAAC | |
|  | AGCACCTACCGGGTGGTGTCCGTGC | |
|  | TGACCGTGCTGCACCAGGACTGGCT | |
|  | GAACGGCAAAGAGTACAAGTGCAAG | |
|  | GTGTCCAACAAGGCCCTGGCCGCCC | |
|  | CCATCGAGAAACCATCAGCAAGGC | |
|  | CAAGGGCCAGCCCCGCGAACCCCAG | |
|  | GTGTACACACTGCCCCCATGCAGGG | |
|  | ACGAGCTGACCAAGAACCAGGTGTC | |
|  | CCTGTGGTGTCTGGTGAAAGGCTTC | |
|  | TACCCCTCCGATATCGCCGTGGAAT | |
|  | GGGAGAGCAACGGCCAGCCCGAGAA | |
|  | CAACTACAAGACCACCCCCCCTGTG | |
|  | CTGGACAGCGACGGCTCATTCTTCC | |
|  | TGTACTCCAAGCTGACAGTGGACAA | |
|  | GTCCCGGTGGCAGCAGGGCAACGTG | |
|  | TTCAGCTGCTCCGTGATGCACGAGG | |
|  | CCCTGCACAACCACTACACCCAGAA | |
|  | GTCCCTGAGCCTGAGCCCCGGC | |
| mAb2 Light Chain 2 (e.g., encoding a fourth polypeptide chain of a trispecific binding protein of the present | See above. | SEQ ID NO: 75 | mAb2xCD28supxCD3mid IgG1 NNSA

| CD28supxCD3mid IgG1(hole) NNSA Heavy Chain 1 (e.g., encoding a second polypeptide chain of a trispecific binding protein of the present disclosure) | CAGGTGCAGCTGGTGCAGTCTGGCG CCGAGGTCGTGAAACCTGGCGCCTC TGTGAAGGTGTCCTGCAAGGCCAGC GGCTACACCTTTACCAGCTACTACA TCCACTGGGTGCGCCAGGCCCCTGG ACAGGGACTGGAATGGATCGGCAGC ATCTACCCCGGCAACGTGAACACCA ACTACGCCCAGAAGTTCCAGGGCAG AGCCACCCTGACCGTGGACACCAGC ATCAGCACCGCCTACATGGAACTGA GCCGGCTGAGAAGCGACGACACCGC CGTGTACTACTGCACCCGGTCCCAC TACGGCCTGGATTGGAACTTCGACG TGTGGGGCAAGGGCACCACCGTGAC AGTGTCTAGCGCCAGTGCAGCTG GTGGAATCTGGCGGCGGAGTGGTGC AGCCTGGCAGAAGCCTGAGACTGAG CTGTGCCGCCAGCGGCTTCACCTTC ACCAAGGCCTGGATGCACTGGGTGC GCCAGGCCCCTGGAAAGCAGCTGGA ATGGGTGGCCCAGATCAAGGACAAG AGCAACAGCTACGCCACCTACTACG CCGACAGCGTGAAGGGCCGGTTCAC CATCAGCCGGGACGACAGCAAGAAC ACCCTGTACCTGCAGATGAACAGCC TGCGGGCCGAGGACACCGCCGTGTA CTACTGTGCGGGCGTGTACTATGCC CTGAGCCCCTTCGATTACTGGGGCC AGGGAACCCTCGTGACCGTGTCTAG TCGGACCGCCAGCACAAAGGGCCCC AGCGTGTTCCCTCTGGCCCCTAGCA GCAAGAGCACATCTGGCGGAACAGC CGCCCTGGGCTGCCTCGTGAAGGAC TAGTTTCCCGAGCCCGTGACCGTGT CCTGGAATTCTGGCGCCCTGACCAG CGGCGTGCACACCTTTCCAGCTGTG CTGCAGTCCAGCGGCCTGTACAGCC TGAGCAGCGTCGTGACAGTGCCCAG CAGCTCTCTGGGCACCCAGACCTAC ATCTGCAACGTGAATCACAAGCCCA GCAACACCAAGGTGGACAAGAAGGT | SEQ ID NO: 78 |
| --- | --- | --- |

TABLE J-continued

Full-length polynucleotide sequences of binding proteins.

|  |  |  |
| --- | --- | --- |
|  | GGAACCCAAGAGCTGCGACAAGACC | |
|  | CACACCTGTCCCCCTTGTCCTGCCC | |
|  | CCGAACTGCTGGGAGGCCCTTCCGT | |
|  | GTTCCTGTTCCCCCCAAAGCCCAAG | |
|  | GACACCCTGATGATCAGCCGGACCC | |
|  | CCGAAGTGACCTGCGTGGTGGTGGA | |
|  | TGTGTCCCACGAGGACCCTGAAGTG | |
|  | AAGTTCAATTGGTACGTGGACGGCG | |
|  | TGGAAGTGCACAACGCCAAGACCAA | |
|  | GCCAAGAGAGGAACAGTACAACAAT | |
|  | GCCTCCGGGTGGTGTCCGTGCTGA | |
|  | CCGTGCTGCACCAGGACTGGCTGAA | |
|  | CGGCAAAGAGTACAAGTGCAAGGTG | |
|  | TCCAACAAGGCCTGCCTGCCCCCAT | |
|  | CGAGAAACCCATCAGCAAGGCCAAG | |
|  | GGCCAGCCCCGCGAACCCCAGGTGT | |
|  | GCACACTGCCCCCCAAGCAGGGACGA | |
|  | GCTGACCAAGAACCAGGTGTCCCTG | |
|  | ACCTGTGCCGTGAAAGGCTTCTACC | |
|  | CCTCCGATATCGCCGTGGAATGGGA | |
|  | GAGCAACGGCCAGCCCGAGAACAAC | |
|  | TACAAGACCACCCCCCCTGTGCTGG | |
|  | ACAGCGACGGCTCATTCTTCCTGGT | |
|  | GTCCAAGCTGACAGTGGACAAGTCC | |
|  | CGGTGGCAGCAGGGCAACGTGTTCA | |
|  | GCTGCTCCGTGATGCACGAGGCCCT | |
|  | GCACAACCACTACACCCAGAAGTCC | |
|  | CTGAGCCTGAGCCCCGGC | |
| CD28supxCD3mid Light Chain 1 (e.g., encoding a first polypeptide chain of a trispecific binding protein of the present disclosure) | See above. | SEQ ID NO: 73 |
| mAb2 IgG1(knob) NNSA Heavy Chain 2 (e.g., encoding a third polypeptide chain of a trispecific binding protein of the present disclosure) | CAGGTGCAGCTGGTGCAGTCTGGCG CCGAAGTCGTGAAACCTGGCGCCTC CGTGAAGGTGTCCTGCAAGGCCAGC GGCTACACCTTTACCAGCTACGCCA TGCACTGGGTGCAAAGAGGCCCCTGG CCAGAGACTGGAATGGATCGGCTAC ATCTACCCCGGCCAGGGCGGCACCA ACTACAACCAGAAGTTCCAGGGCAG AGCCACCCTGACCGCCGATACAAGC GCCAGCACCGGCTACATGGAACTGA GCAGCCTGCGGAGCGAGGATACCGC CGTGTACTTCTGTGCCAGAACAGGC GGCCTGAGCGGGGCCTACTTTACCT ATTGGGGCCAGGGCACCCTCGTGAC CGTGTCTAGCGCTAGCACAAAGGGC CCATCGGTCTTCCCCCTGGCACCCT CCTCCAAGAGCACCTCTGGGGGCAC AGCGGCCCTGGGCTGCCTGGTCAAG GACTACTTCCCCGAACCGGTGACGG TGTCGTGGAACTCAGGCGCCCTGAC CAGCGGCGTGCACACCTTCCCGGCT GTCCTACAGTCCTCAGGACTCTACT CCCTCAGCAGCGTGGTGACCGTGCC CTCCAGCAGCTTGGGCACCCAGACC TACATCTGCAACGTGAATCACAAGC CCAGCAACACCAAGGTGGACAAGAA AGTTGAGCCCAAATCTTGTGACAAA ACTCACACATGCCCACCGTGCCCAG CACCTGAACTCCTGGGGGGACCGTC AGTCTTCCTCTTCCCCCCAAAACCC AAGGACACCCTCATGATCTCCCGGA CCCCTGAGGTCACATGCGTGGTGGT GGACGTGAGCCACGAAGACCCTGAG GTCAAGTTCAACTGGTATGTTGACG GCGTGGAGGTGCATAATGCCAAGAC AAAGCCGCGGGAGGAGCAGTACAAC AATGCCTCCGTGTGGTCAGCGTCC TCACCGTCCTGCACCAGGACTGGCT | SEQ ID NO: 79 |

TABLE J-continued

Full-length polynucleotide sequences of binding proteins.

| | | |
|---|---|---|
| | GAATGGCAAGGAGTACAAGTGCAAG<br>GTCTCCAACAAAGCCCTCCCAGCCC<br>CCATCGAGAAAACCATCTCCAAAGC<br>CAAAGGGCAGCCCCGAGAACCACAG<br>GTGTACACCCTGCCCCCATGCCGGG<br>ATCAGCTGACCAAGAATCAAGTCAG<br>CCTGTGGTGCCTGGTAAAAGGCTTC<br>TATCCCAGCGACATCGCCGTGGAGT<br>GGGAGAGCAATGGGCAGCCGGAGAA<br>CAACTACAAGACCACGCCTCCCGTG<br>CTGGACTCCGACGGCTCCTTCTTCC<br>TCTACTCAAAACTCACCGTGGACAA<br>GAGCAGGTGGCAGCAGGGGAACGTC<br>TTCTCATGCTCCGTGATGCATGAGG<br>CTCTGCACAACCACTACACGCAGAA<br>GAGCCTCTCCCTGTCTCCGGGT | |
| mAb2 Light Chain 2<br>(e.g., encoding a<br>fourth polypeptide<br>chain of a<br>trispecific<br>binding protein of<br>the present<br>disclosure) | See above. | SEQ ID<br>NO: 75 |
| mAb6xCD28supxCD3mid IgG4 FALA | | |
| CD28supxCD3mid<br>IgG4(hole) FALA<br>Heavy Chain 1<br>(e.g., encoding a<br>second polypeptide<br>chain of a<br>trispecific<br>binding protein of<br>the present<br>disclosure) | See above. | SEQ ID<br>NO: 72 |
| CD28supxCD3mid<br>Light Chain 1<br>(e.g., encoding a<br>first polypeptide<br>chain of a<br>trispecific<br>binding protein of<br>the present<br>disclosure) | See above. | SEQ ID<br>NO: 73 |
| mAb6 IgG4(knob)<br>FALA Heavy Chain 2<br>(e.g., encoding a<br>third polypeptide<br>chain of a<br>trispecific<br>binding protein of<br>the present<br>disclosure) | CAGGTGCAGCTGGTGGAAAGCGGCG<br>GAGGCGTGGTGCAGCCTGGCAGGTC<br>TCTGAGACTGAGCTGTGCCGCCAGC<br>GGCTTCACCTTCAGCAGCTACGGAA<br>TGCACTGGGTGCGCCAGGCCCCTGG<br>CAAAGGACTGGAATGGGTGGCCGTG<br>ATTTGGTACGACGGCAGCAACAAGT<br>ACTACGCCGACAGCGTGAAGGGCCG<br>GTTCACCATCAGCGGCGACAACAGC<br>AAGAACACCCTGTAGCTGCAAGATGA<br>ACAGCCTGCGGGCCGAGGACACCGC<br>CGTGTACTACTGCGCCAGAATGTTC<br>AGAGGCGCCTTCGACTACTGGGGCC<br>AGGGCACACTCGTGACCGTGTCTAG<br>TGCGTCGACCAAGGGCCCATCGGTG<br>TTCCCTCTGGCCCCTTGCAGCAGAA<br>GCACCAGCGAATCTACAGCCGCCCT<br>GGGCTGCCTCGTGAAGGACTACTTT<br>CCCGAGCCCGTGACCGTGTCCTGGA<br>ACTCTGGCGCTCTGACAAGCGGCGT<br>GCACACCTTTCCAGCCGTGCTCCAG<br>AGCAGCGGCCTGTACTCTCTGAGCA<br>GCGTCGTGACAGTGCCCAGCAGCAG<br>CCTGGGCACCAAGACCTACACCTGT<br>AACGTGGACCACAAGCCCAGCAACA<br>CCAAGGTGGACAAGCGGGTGGAATC<br>TAAGTACGGCCCTCCCTGCCCTCCT<br>TGCCCAGCCCCTGAAGCTGCCGGCC | SEQ ID<br>NO: 80 |
| | GACCCTCCGTGTTCCTGTTCCCCCC<br>AAAGCCCAAGGACACCCTGATGATC<br>AGCCGGACCCCCGAAGTGACCTGCG<br>TGGTGGTGGATGTGTCCCAGGAAGA<br>TCCCGAGGTGCAGTTCAATTGGTAC<br>GTGGACGGCGTGGAAGTGCACAACG<br>CCAAGACCAAGCCCAGAGAGGAACA<br>GTTCAACAGCACCTACCGGGTGGTG<br>TCCGTGCTGACCGTGCTGCACCAGG<br>ACTGGCTGAACGGCAAAGAGTACAA<br>GTGCAAGGTGTCCAACAAGGGCCTG<br>CCCAGCTCCATCGAGAAAACCATCA<br>GCAAGGCCAAGGGCCAGCCCCGCGA<br>GCCTCAAGTGTATACCCTGCCCCCT<br>TGCCAGGAAGAGATGACCAAGAACC<br>AGGTGTCCCTGTGGTGTCTCGTGAA<br>AGGCTTCTACCCCAGCGACATTGCC<br>GTGGAATGGGAGAGCAACGGCCAGC<br>CCGAGAACAACTACAAGACCACCCC<br>CCCTGTGCTGGACAGCGACGGCTCA<br>TTCTTCCTGTACTCCAAGCTGACCG<br>TGGACAAGAGCCGGTGGCAGGAAGG<br>CAACGTGTTCAGCTGCTCCGTGATG<br>CACGAGGCCCTGCACAACCACTACA<br>CCCAGAAGTCCCTGTCTCTGTCCCT<br>GGGC | |
| mAb6 Light2<br>(e.g., encoding a<br>fourth polypeptide<br>chain of a<br>trispecific<br>binding protein of<br>the present<br>disclosure) | GCCATCCAGATGACCCAGAGCCCCA<br>GCAGCCTGTCTGCCAGCGTGGGCGA<br>CAGAGTGACCATCACCTGTAGAGCC<br>AGCCAGGGCATCCGGAACGACCTGG<br>GCTGGTATCAGCAGAAGCCTGGCAA<br>GGCCCCCAAGCTGCTGATCTACGCC<br>GCTAGCTCTCTGCAGTCCGGCGTGG<br>CCAGCAGATTTTCTGGCAGCGGCTC<br>CGGCACCGACTTCACCCTGACAATC<br>TCTGGCCTGCAGCCCGAGGACAGCG<br>CCACCTACTACTGTCTGCAAGACTA<br>CATCTACTACCCCACCTTCGGCCAG<br>GGCACCAAGGTGGAAATCAAGCGTA<br>CGGTGGCCGCTCCCAGCGTGTTCAT<br>CTTCCCACCTAGCGACGAGCAGCTG<br>AAGTCCGGCACAGCCTCTGTCGTGT<br>GCCTGCTGAACAACTTCTACCCCCG<br>CGAGGCCAAAGTGCAGTGGAAGGTG<br>GACAACGCCCTGCAGAGCGGCAACA<br>GCCAGGAAAGCGTGACCGAGCAGGA<br>CAGCAAGGACTCCAGCTACAGCCTG<br>AGCAGCAGCCTGACACTGAGCAAGG<br>CCGACTACGAGAAGCACAAGGTGTA<br>CGCCTGCGAAGTGACCCACCAGGGC<br>CTGTCTAGCCCCGTGACCAAGAGCT<br>TCAACCGGGGCGAGTGT | SEQ ID<br>NO: 81 |
| mAb6xCD28supxCD3mid IgG1LALA P329A | | |
| CD28supxCD3mid<br>IgG1(hole) LALA<br>P329A Heavy Chain<br>1 (e.g., encoding<br>a second<br>polypeptide<br>chain of a<br>trispecific<br>binding protein of<br>the present<br>disclosure) | See above. | SEQ ID<br>NO: 76 |
| CD28supxCD3mid<br>Light Chain 1<br>(e.g., encoding a<br>first polypeptide<br>chain of a<br>trispecific<br>binding protein of<br>the present<br>disclosure) | See above. | SEQ ID<br>NO: 73 |

TABLE J-continued

Full-length polynucleotide sequences of binding proteins.

| | | |
|---|---|---|
| mAb6 IgG1(knob) LALA P329A Heavy Chain 2 (e.g., encoding a third polypeptide chain of a trispecific binding protein of the present disclosure) | CAGGTGCAGCTGGTGGAAAGCGGCG GAGGCGTGGTGCAGCCTGGCAGGT TCTGAGACTGAGCTGTGCCGCCAGC GGCTTCACCTTCAGCAGCTACGGAA TGCACTGGGTGCGCCAGGCCCCTGG CAAAGGACTGGAATGGGTGGCCGTG ATTTGGTACGACGGCAGCAACAAGT ACTACGCCGACAGCGTGAAGGGCCG GTTCACCATCAGCGGCGACAACAGC AAGAACACCCTGTACCTGCAGATGA ACAGCCTGCGGGCCGAGGACACCGC CGTGTACTACTGCGCCAGAATGTTC AGAGGCGCCTTCGACTACTGGGGCC AGGGCACACTCGTGACCGTGTCTAG TGCGTCGACCAAGGGCCCCAGCGTG TTCCCTCTGGCCCCTAGCAGCAAGA GCACATCTGGCGGAACAGCCGCCCT GGGCTGCCTCGTGAAGGACTACTTT CCCGAGCCCGTGACCGTGTCCTGGA ATTCTGGCGCCCTGACCAGCGGCGT GCACACCTTTCCAGCTGTGCTGCAG TCCAGCGGCCTGTACAGCCTGAGCA GCGTCGTGACAGTGCCCAGCAGCTC TCTGGGCACCCAGACCTACATCTGC AACGTGAACCACAAGCCCAGCAACA CCAAGGTGGACAAGAAGGTGGAACC CAAGAGCTGCGACAAGACCCACACC TGTCCCCCTTGTCCTGCCCCCGAAG CCGCCGGAGGCCCTTCCGTGTTCCT GTTCCCCCCAAAGCCCAAGGACACC CTGATGATCAGCCGGACCCCCGAAG TGACCTGCGTGGTGGTGGATGTGTC CCACGAGGACCCTGAAGTGAAGTTC AATTGGTACGTGGACGGCGTGGAAG TGCACAACGCCAAGACCAAGCCAAG AGAGGAACAGTACAACAGCACCTAC CGGGTGGTGTCCGTGCTGACCGTGC TGCACCAGGACTGGCTGAACGGCAA AGAGTACAAGTGCAAGGTGTCCAAC AAGGCCCTGGCCGCCCCCATCGAGA AAACCATCAGCAAGGCCAAGGGCCA GCCCCGCGAACCCCAGGTGTACACA CTGCCCCCATGCAGGGACGAGCTGA CCAAGAACCAGGTGTCCCTGTGGTG TCTGGTGAAAGGCTTCTACCCCTCC GATATCGCCGTGGAATGGGAGAGCA ACGGCCAGCCCGAGAACAACTACAA GACCACCCCCCCTGTGCTGGACAGC GACGGCTCATTCTTCCTGTACTCCA AGCTGACAGTGGACAAGTCCCGGTG GCAGCAGGGCAACGTGTTCAGCTGC TCCGTGATGCAGGAGGCCCTGCACA ACCACTACACCCAGAAGTCCCTGAG CCTGAGCCCCGGC | SEQ ID NO: 82 |
| mAb6 Light2 (e.g., encoding a fourth polypeptide chain of a trispecific binding protein of the present disclosure) | See above. | SEQ ID NO: 81 | mAb6xCD28supxCD3mid IgG1 NNSA

| | | |
|---|---|---|
| CD28supxCD3mid IgG1(hole) NNSA Heavy Chain 1 (e.g., encoding a second polypeptide chain of a trispecific binding protein of the present disclosure) | See above. | SEQ ID NO: 78 |
| CD28supxCD3mid Light Chain 1 (e.g., encoding a first polypeptide chain of a trispecific binding protein of the present disclosure) | See above. | SEQ ID NO: 73 |
| mAb6 IgG1(knob) NNSA Heavy Chain 2 (e.g., encoding a third polypeptide chain of a trispecific binding protein of the present disclosure) | CAGGTGCAGCTGGTGGAAAGCGGCG GAGGCGTGGTGCAGCCTGGCAGGT TCTGAGACTGAGCTGTGCCGCCAGC GGCTTCACCTTCAGCAGCTAGGGAA TGCACTGGGTGCGCCAGGCCCCTGG CAAAGGACTGGAATGGGTGGCCGTG ATTTGGTACGACGGCAGCAACAAGT ACTACGCCGACAGCGTGAAGGGCCG GTTCACCATCAGCGGCGACAACAGC AAGAACACCCTGTACCTGCAGATGA ACAGCCTGCGGGCCGAGGACACCGC CGTGTACTACTGCGCCAGAATGTTC AGAGGCGCCTTCGACTACTGGGGCC AGGGCACACTCGTGACCGTGTCTAG TGCGTCGACCAAGGGCCCATCGGTC TTCCCCCTGGCACCCTCCTCCAAGA GCACCTCTGGGGGCACAGCGGCCCT GGGCTGCCTGGTCAAGGACTACTTC CCCGAACCGGTGACGGTGTCGTGGA ACTCAGGCGCCCTGACCAGCGGCGT GCACACCTTCCCGGCTGTCCTACAG TCCTCAGGACTCTACTCCCTCAGCA GCGTGGTGACCGTGCCCTCCAGCAG CTTGGGCACCCAGACCTACATCTGC AACGTGAATCACAAGCCCAGCAACA CCAAGGTGGACAAGAAAGTTGAGCC CAAATCTTGTGACAAAACTCACACA TGCCCACCGTGCCCAGCACCTGAAC TCCTGGGGGGACCGTCAGTCTTCCT CTTCCCCCCAAAACCCAAGGACACC CTCATGATCTCCCGGACCCCTGAGG TCACATGCGTGGTGGTGGACGTGAG CCACGAAGACCCTGAGGTCAAGTTC AACTGGTATGTTGACGGCGTGGAGG TGCATAATGCCAAGACAAAGCCGCG GGAGGAGCAGTACAACATGCCTCC CGTGTGGTCAGCGTCCTCACCGTCC TGCACCAGGACTGGCTGAATGGCAA GGAGTACAAGTGCAAGGTCTCCAAC AAAGCCCTCCCAGCCCCCATCGAGA AAACCATCTCCAAAGCCAAAGGGCA GCCCCGAGAACCACAGGTGTACACC CTGCCCCCATGCCGGGATGAGCTGA CCAAGAATCAAGTCAGCCTGTGGTG CCTGGTAAAAGGCTTCTATCCCAGC GACATCGCCGTGGAGTGGGAGAGCA ATGGGCAGCCGGAGAACAACTACAA GACCACGCCTCCCGTGCTGGACTCC GACGGCTCCTTCTTCCTCTACTCAA AACTCACCGTGGACAAGAGCAGGTG GCAGCAGGGGAACGTCTTCTCATGC TCCGTGATGCATGAGGCTCTGCACA ACCACTACACGCAGAAGAGCCTCTC CCTGTCTCCGGGT | SEQ ID NO: 83 |
| mAb6 Light2 (e.g., encoding a fourth polypeptide chain of a trispecific binding protein of the present disclosure) | See above. | SEQ ID NO: 81 |

CD38 Polypeptides

In some embodiments, a binding protein of the present disclosure comprises an antigen binding site that binds an extracellular domain of a human CD38 polypeptide and an extracellular domain of a cynomolgus monkey CD38 polypeptide. Exemplary assays for determining whether an antigen binding site binds an antigen are described herein and known in the art. In some embodiments, binding is determined by ELISA assay, e.g., as described infra. In some embodiments, binding is determined by SPR assay, e.g., as described infra. In some embodiments, binding is determined by flow cytometry assay using cells expressing a CD38 polypeptide on their cell surface, e.g., as described infra. See, e.g., Examples 1, 3, and 4.

In some embodiments, a binding protein of the present disclosure binds a purified polypeptide or fragment thereof comprising the amino acid sequence of SEQ ID NO:1 and/or 30 (e.g., as measured by ELISA or SPR). In some embodiments, a binding protein of the present disclosure binds a polypeptide or comprising the amino acid sequence of SEQ ID NO:1 and/or 30 when expressed on the surface of a cell (e.g., as measured by flow cytometry).

In some embodiments, a binding protein of the present disclosure binds to a CD38 isoform A polypeptide (e.g., comprising the amino acid sequence of SEQ ID NO:1). In some embodiments, a binding protein of the present disclosure binds to a CD38 isoform E polypeptide (e.g., comprising the amino acid sequence of SEQ ID NO:105 and not comprising the full amino acid sequence of SEQ ID NO:1, consisting of the amino acid sequence of SEQ ID NO:105, or consisting essentially of the amino acid sequence of SEQ ID NO:105). In some embodiments, a binding protein of the present disclosure binds to a CD38 isoform A polypeptide (e.g., comprising the amino acid sequence of SEQ ID NO:1) and a CD38 isoform E polypeptide (e.g., comprising the amino acid sequence of SEQ ID NO:105 and not comprising the full amino acid sequence of SEQ ID NO:1, consisting of the amino acid sequence of SEQ ID NO:105, or consisting essentially of the amino acid sequence of SEQ ID NO:105). Without wishing to be bound by theory, it is thought that binding to a CD38 isoform E polypeptide can be advantageous, e.g., in targeting a binding protein of the present disclosure to cell(s) expressing a CD38 isoform E polypeptide.

```
Human CD38 isofom A extracellular domain
polypeptide sequence
                                      (SEQ ID NO: 1)
RWRQQWSGPGTTKRFPETVLARCVKYTEIHPEMRHVDCQSVWDAFKGAF

ISKHPCNITEEDYQPLMKLGTQTVPCNKILLWSRIKDLAHQFTQVQRDM

FTLEDTLLGYLADDLTWCGEFNTSKINYQSCPDWRKDCSNNPVSVFWKT

VSRRFAEAACDVVHVMLNGSRSKIFDKNSTFGSVEVHNLQPEKVQTLEA

WVIHGGREDSRDLCQDPTIKELESIISKRNIQFSCKNIYRPDKFLQCVK

NPEDSSCTSEI

Human CD38 isoform E polypeptide sequence
                                    (SEQ ID NO: 105)
RWRQQWSPGTTKRFPETVLARCVKYTEIHPEMRHVDCQSVWDAFKGAFI

SKHPCNITEEDYQPLMKLGTQTVPCNKILLWSRIKDLAHQFTQVQRDMF

TLEDTLLGYLADDLTWCGEFNTSKINYQSCPDWRKDCSNNPVSVFWKTV

SRRHFWECGSP
```

```
In some embodiments, the extracellular domain of a
human CD38 polypeptide comprises the amino acid
sequence of SEQ ID NO: 1. In some embodiments,
the extracellular domain of a cynomolgus monkey
CD38 polypeptide comprises the amino acid
sequence of SEQ ID NO: 30.

Cynomolgus monkey CD38 polypeptide sequence
                                      (SEQ ID NO: 30)
RWRQQWSGSGTTSRFPETVLARCVKYTEVHPEMRHVDCQSVWDAFKGAF

ISKYPCNITEEDYQPLVKLGTQTVPCNKTLLWSRIKDLAHQFTQVQRDM

FTLEDMLLGYLADDLTWCGEFNTFEINYQSCPDWRKDCSNNPVSVFWKT

VSRRFAETACGVVHVMLNGSRSKIFDKNSTFGSVEVHNLQPEKVQALEA

WVIHGGREDSRDLCQDPTIKELESIISKRNIRFFCKNIYRPDKFLQCVK

NPEDSSCLSGI
```

Multispecific (e.g., Bispecific, Trispecific, or Multispecific) Binding Proteins that Bind CD38 Polypeptides In some embodiments, a binding protein of the present disclosure is a bispecific binding protein comprising an antigen binding site that binds one or more CD38 polypeptides and a second antigen binding site that binds a different target antigen. In some embodiments, a binding protein of the present disclosure is a bispecific binding protein comprising an antigen binding site that binds one or more CD38 polypeptides and a second antigen binding site that binds one or more CD38 polypeptides.

In some embodiments, a landing protein of the present disclosure is a trispecific binding protein comprising an antigen binding site that binds one or more CD38 polypeptides, a second antigen binding site, and a third antigen binding site. For example, in some embodiments, one of the antigen binding sites binds one or more CD38 polypeptide(s) (e.g., the extracellular domain of a human and/or cynomolgus monkey CD3S polypeptide), and one or two of the antigen binding sites binds a T-cell surface protein. In some embodiments, one of the antigen binding sites binds one or more CD38 polypeptide(s) (e.g., the extracellular domain of a human and/or cynomolgus monkey CD38 polypeptide), one of the antigen binding sites binds a human CD3 polypeptide, and one of the antigen binding sites binds a human CD28 polypeptide. Human CD3 and CD28 polypeptides are known in the art. The amino acid sequences of exemplary and non-limiting antibody variable domains that bind human CD3 and CD28 poly peptides are provided herein.

In some embodiments, provided herein are binding proteins comprising three antigen binding sites that each bind one or more target proteins. In some embodiments, at least one of the three antigen binding sites binds an extracellular domain of a human CD38 polypeptide and an extracellular domain of a cynomolgus monkey CD38 polypeptide. In some embodiments, the human CD38 polypeptide comprises the amino acid sequence of SEQ ID NO:1, and/or the cynomolgus monkey CD38 polypeptide comprises the amino acid sequence of SEQ ID NO:30. In some embodiments, the binding protein comprises an antigen binding site that binds an extracellular domain of a human CD38 polypeptide and an extracellular domain of a cynomolgus monkey CD38 polypeptide and two antigen binding sites that each bind a T-cell surface protein (e.g., a human CD28 polypeptide and/or a human CD3 polypeptide).

In some embodiments, a binding protein of the present disclosure binds one or more tumor target proteins (e.g., one or more CD38 polypeptide(s)) and one or more T cell target proteins. In some embodiments, the binding protein is capable of binding one tumor target protein (e.g., one or mom CD38 polypeptide(s)) and two different epitopes on a single T cell target protein. In some embodiments, the binding protein is capable of binding one tumor target protein (e.g., one or more CD38 polypeptide(s)) and two different T cell target proteins (e.g., CD28 and CD3). In some embodiments, the binding protein is capable of binding one T cell target protein and two different epitopes on a single tumor target protein (e.g., one or more CD38 polypeptide(s). In some embodiments, the binding protein is capable of binding one T cell target protein and two different tumor target proteins (e.g., one or more CD38 polypeptide(s) and another tumor target protein). In some embodiments, the first and second polypeptide chains of the binding protein form two antigen binding sites that target two T cell target proteins, and the third and fourth polypeptide chains of the binding protein form an antigen binding site that binds one or more CD38 polypeptide(s). In some embodiments, the first and second polypeptide chains of the binding protein form two antigen binding sites that target two tumor target proteins (e.g., one or more CD38 polypeptide(s) and another tumor target protein), and the third and fourth polypeptide chains of the binding protein form an antigen binding site that binds a T cell target protein. In some embodiments, the one or more T cell target proteins are one or more of CD3 and CD28.

In some embodiments, the binding proteins specifically bind to one or more CD38 polypeptide(s) and one or more target protein on a T-cell including a T cell receptor complex. These T-cell engager binding proteins are capable of recruiting T cells transiently to target cells and, at the same time, activating the cytolytic activity of the T cells. Examples of target proteins on T cells include but are not limited to CD3 and CD28, among others. Further examples of such antigen targets or target proteins are provided supra. In some embodiments, the trispecific binding proteins may be generated by combining the antigen binding domains of two or more monospecific antibodies (parent antibodies) into one antibody.

Bispecific Binding Protein Formats

In some embodiments, the binding protein of the disclosure is a bispecific and/or bivalent binding protein comprising four polypeptide chains that form four antigen binding sites that bind one or more (e.g., two) different antigen targets or target proteins (e.g., having a structure described in International Publication No. WO2012/135345). In some embodiments, the binding protein is bivalent and/or bispecific. In some embodiments, the binding protein is tetravalent and/or tetraspecific. In some embodiments, the binding protein is tetravalent and/or bispecific. In some embodiments, at least one of the antigen binding sites binds a CD38 polypeptide (e.g., the extracellular domain of human and/or cynomolgus monkey CD38 polypeptides).

In some embodiments, the binding protein comprises two poly peptide chains having a structure represented by the formula:

$$V_{L1}\text{-}L_1\text{-}V_{L2}\text{-}L_2\text{-}C_L \qquad [\text{I}]$$

and two polypeptide chains have a structure represented by the formula:

$$V_{H2}\text{-}L_3\text{-}V_{H1}\text{-}L_4\text{-}C_{H1}\text{-}Fc \qquad [\text{II}]$$

wherein:

$V_{L1}$ is a first immunoglobulin light chain variable domain;

$V_{L2}$ is a second immunoglobulin light chain variable domain;

$V_{H1}$ is a first immunoglobulin heavy chain variable domain;

$V_{H2}$ is a second immunoglobulin heavy chain variable domain;

$C_L$ is an immunoglobulin light chain constant domain;

$C_{H1}$ is the immunoglobulin $C_{H1}$ heavy chain constant domain;

Fc comprises an immunoglobulin hinge region and $C_{H2}$, $C_{H3}$ immunoglobulin heavy chain constant domains;

$L_1$, $L_2$, $L_3$, and $L_4$ are amino acid linkers;

and wherein the polypeptides of formula I and the polypeptides of formula II form a cross-over light chain-heavy chain pair. In some embodiments, $V_{H1}$ and $V_{L1}$ form an antigen binding domain that binds a CD38 polypeptide, and $V_{H2}$ and $V_{L2}$ form an antigen binding domain that binds another antigen target. In some embodiments, $V_{H2}$ and $V_{L2}$ form an antigen binding domain that binds a CD38 polypeptide, and $V_{H1}$ and $V_{L1}$ form an antigen binding domain that binds another antigen target.

In some embodiments, the binding protein comprises two polypeptide chains that form two antigen binding sites, wherein a first polypeptide chain comprises $$V_{L1}\text{-}L_1\text{-}V_{L2}\text{-}L_2\text{-}CL\text{-}Fc$$

and a second polypeptide chain comprises $$V_{H2}\text{-}L_3\text{-}V_{H1}\text{-}L_4\text{-}C_{H1}\text{-}Fc$$

wherein:

$V_{L1}$ is a first immunoglobulin light chain variable domain;

$V_{L2}$ is a second immunoglobulin light chain variable domain;

$V_{H1}$ is a first immunoglobulin heavy chain variable domain;

$V_{H2}$ is a second immunoglobulin heavy chain variable domain;

CL is an immunoglobulin light chain constant domain;

$C_{H1}$ is the immunoglobulin CH1 heavy chain constant domain;

$C_{H2}$ is an immunoglobulin $C_{H2}$ heavy chain constant domain;

$C_{H3}$ is an immunoglobulin $C_{H3}$ heavy chain constant domain;

Fc comprises an immunoglobulin hinge region and $C_{H2}$, $C_{H3}$ immunoglobulin heavy chain constant domains; and $L_1$, $L_2$, $L_3$, and $L_4$ are amino acid linkers;

wherein the first and second polypeptides form a cross-over light chain-heavy chain pair. In some embodiments, $V_{H1}$ and $V_{L1}$ form an antigen binding domain that binds a CD38 polypeptide, and $V_{H2}$ and $V_{L1}$ form an antigen binding domain that binds another antigen target. In some embodiments, $V_{H2}$ and $V_{L2}$ form an antigen binding domain that binds a CD38 polypeptide, and $V_{H1}$ and $V_{L1}$ form an antigen binding domain that binds another antigen target.

In some embodiments, the binding protein comprises three polypeptide chains that form two antigen binding sites, wherein a first polypeptide chain comprises $$V_{L1}\text{-}L_1\text{-}V_{L2}\text{-}L_2\text{-}CL$$

a second polypeptide chain comprises $$V_{H2}\text{-}L_3\text{-}V_{H1}\text{-}L_4\text{-}C_{H1}\text{-}Fc$$

a third polypeptide chain comprises an antibody Fc region wherein:

$V_{L1}$ is a first immunoglobulin light chain variable domain;
$V_{L2}$ is a second immunoglobulin light chain variable domain;
$V_{H1}$ is a first immunoglobulin heavy chain variable domain;
$V_{H2}$ is a second immunoglobulin heavy chain variable domain;
CL is an immunoglobulin light chain constant domain;
$C_{H1}$ is the immunoglobulin CH1 heavy chain constant domain;
$C_{H2}$ is an immunoglobulin $C_{H2}$ heavy chain constant domain;
$C_{H3}$ is an immunoglobulin $C_{H3}$ heavy chain constant domain;
Fc comprises an immunoglobulin hinge region and $C_{H2}$, $C_{H3}$ immunoglobulin heavy chain constant domains; and
$L_1$, $L_2$, $L_3$, and $L_4$ are amino acid linkers;
wherein the first and second polypeptides form a crossover light chain-heavy chain pair. In some embodiments, $V_{H1}$ and $V_{L1}$ form an antigen binding domain that binds a CD38 polypeptide, and $V_{H2}$ and $V_{L2}$ form an antigen binding domain that binds another antigen target. In some embodiments, $V_{H2}$ and $V_{L2}$ form an antigen binding domain that binds a CD38 polypeptide, and $V_{H1}$ and $V_{L1}$ form an antigen binding domain that binds another antigen target.

In some embodiments, the binding protein comprises a first polypeptide chain comprising a structure represented by the formula:

$$V_{L1}\text{-}L_1\text{-}V_{L2}\text{-}L_2\text{-}C_L \quad [\text{I}]$$

and a second polypeptide chain comprising a structure represented by the formula:

$$V_{H2}\text{-}L_3\text{-}V_{H1}\text{-}L_4\text{-}C_{H1} \quad [\text{II}]$$

wherein:

$V_{L1}$ is a first immunoglobulin light chain variable domain;
$V_{L1}$ is a second immunoglobulin light chain variable domain;
$V_{H1}$ is a first immunoglobulin heavy chain variable domain;
$V_{H2}$ is a second immunoglobulin heavy chain variable domain;
$C_L$ is an immunoglobulin light chain constant domain;
$C_{H1}$ is an immunoglobulin $C_{H1}$ heavy chain constant domain; and
$L_1$, $L_2$, $L_3$ and $L_4$ are amino acid linkers;
wherein the polypeptide of formula I and the polypeptide of formula II form a cross-over light chain-heavy chain pair. In some embodiments, $V_{H1}$ and $V_{L1}$ form an antigen binding domain that binds a CD38 polypeptide, and $V_{H2}$ and $V_{L1}$ form an antigen binding domain that binds another antigen target. In some embodiments, $V_{H2}$ and $V_{L2}$ form an antigen binding domain that binds a CD38 polypeptide, and $V_{H1}$ and $V_{L1}$ form an antigen binding domain that binds another antigen target.

In any of the bispecific binding proteins described supra, the target antigen other than CD38 can be any of the following exemplary antigen targets: A2AR, APRIL, ATP-Dase, BAFF, BAFFR, BCMA, BlyS, BTK, BTLA, B7DC, B7H1, B7H4 (also known as VTCN1), B7H5, B7H6, B7H7, B7RP1, B7-4, C3, C5, CCL2 (also known as MCP-1), CCL3 (also known as MIP-1a), CCL4 (also known as MIP-1 b), CCL5 (also known as RANTES), CCL7 (also known as MCP-3), CCL8 (also known as mcp-2), CCL11 (also known as eotaxin), CCL15 (also known as MIP-1d), CCL17 (also known as TARC), CCL19 (also known as MIP-3b), CCL20 (also known as MIP-3a), CCL21 (also known as MIP-2), CCL24 (also known as MPIF-2/eotaxin-2), CCL25 (also known as TECK), CCL26 (also known as eotaxin-3), CCR3, CCR4, CD3, CD19, CD20, CD23 (also known as FCER2, a receptor for IgE), CD24, CD27, CD28, CD38, CD39, CD40, CD70, CD80 (also known as B7-1), CD86 (also known as B7-2), CD122, CD137 (also known as 41BB), CD137L, CD152 (also known as CTLA4), CD154 (also known as CD40L), CD160, CD272, CD273 (also known as PDL2), CD274 (also known as PDL1), CD275 (also known as B7H2), CD276 (also known as B7H3), CD278 (also known as ICOS), CD279 (also known as PD-1), CDH1 (also known as E-cadherin), chitinase, CLEC9, CLEC91, CRTH2 CSF-1 (also known as M-CSF), CSF-2 (also known as GM-CSF), CSF-3 (also known as GCSF), CX3CL1 (also known as SCYD1), CXCL12 (also known as SDF1), CXCL13, CXCR3, DNGR-1, ectonucleoside triphosphate diphosphohydrolase 1, EGFR, ENTPD1, FCER1A, FCER1, FLAP, FOLH1, Gi24, GITR, GITRL, GM-CSF, Her2, HHLA2, HMGB1, HVEM, ICOSLG, IDO, IFNα, IgE, IGF1R, IL2Rbeta, IL1, IL1A, IL1B, IL1F10, IL2, IL4, IL4Ra, IL5, IL5R, IL6, IL7, IL7Ra, IL8, IL9, IL9R, IL10, rhIL10, IL12, IL13, IL13Ra1, IL13Ra2, IL5, IL17, IL17Rb (also known as a receptor for IL25), IL18, IL22, IL23, IL25, IL27, IL33, IL35, ITGB4 (also known as b4 integrin), ITK, KIR, LAG3, LAMP1, leptin, LPFS2, MHC class II, NCR3LG1, NKG2D, NTPDase-1, OX40, OX40L, PD-1H, platelet receptor, PROM1, S152, SISP1, SLC, SPG64, ST2 (also known as a receptor for IL33), STEAP2, Syk kinase, TACI, TDO, T14, TIGIT, TIM3, TLR, TLR2, TLR4, TLR5, TLR9, TMEF1, TNFa, TNFRSF7, Tp55, TREM1, TSLP (also known as a co-receptor for IL7Ra), TSLPR, TWEAK, VEGF, VISTA, Vstm3, WUCAM, and XCR1 (also known as GPR5/CCXCR1). In some embodiments, one or more of the above antigen targets are human antigen targets.

In any of the bispecific binding proteins described supra, any linker or combination of linkers described herein may be used. For example, in some embodiments, at least one of $L_1$, $L_2$, $L_3$ or $L_4$ is independently 0 amino acids in length. In some embodiments, $L_1$, $L_2$, $L_3$ or $L_4$ are each independently at least one amino add in length. In some embodiments, $L_1$, $L_2$, $L_3$ and $L_4$ each independently are zero amino acids in length or comprise a sequence selected from the group consisting of GGGGSGGGGS (SEQ ID NO:55), GGGGSGGGGSGGGGS (SEQ ID NO:56), S, RT, TKGPS (SEQ ID NO:57), GQPKAAP (SEQ ID NO:58), and GGSGSSGSGG (SEQ ID NO:59). In some embodiments, $L_1$, $L_2$, $L_3$ and $L_4$ each independently comprise a sequence selected from the group consisting of GGGGSGGGGS (SEQ ID NO:55), GGGGSGGGGSGGGGS (SEQ ID NO:56), S, RT, TKGPS (SEQ ID NO:57), GQPKAAP (SEQ ID NO:58), and GGSGSSGSGG (SEQ ID NO:59). In some embodiments, $L_1$ comprises the sequence GQPKAAP (SEQ ID NO:58), $L_2$ comprises the sequence TKGPS (SEQ ID NO:57), $L_3$ comprises the sequence S, and $L_4$ comprises the sequence RT. In some embodiments, $L_1$ comprises the sequence GGGGSGGGGS (SEQ ID NO:55), $L_2$ comprises the sequence GGGGSGGGGS (SEQ ID NO:55), $L_3$ is 0 amino acids in length, and $L_4$ is 0 amino acids in length. In some embodiments, $L_1$ comprises the sequence GGSGSSGSGG (SEQ ID NO:59), $L_2$ comprises the sequence GGSGSSGSGG (SEQ ID NO:59), $L_3$ is 0 amino acids in length, and L₄ is 0 amino adds in length. In some embodiments, L₁ comprises the sequence GGGGSGGGGSGGGGS (SEQ ID NO:56), L₂ is 0 amino acids in length, L₃ composes the sequence GGGGSGGGGSGGGGS (SEQ ID NO:56), and L₄ is 0 amino acids in length.

Trispecific Binging Proteins that Bind to CD38 Polypeptides

In some embodiments, the binding protein of the disclosure is a trispecific and/or bivalent binding protein comprising four polypeptide chains that form three antigen binding sites that bind one or more (e.g., three) different antigen targets or target proteins. In some embodiments, at least one of the antigen binding sites binds a CD38 polypeptide (e.g., the extracellular domain of human and/or cynomolgus monkey CD38 polypeptides). In some embodiments, a first polypeptide chain comprises a structure represented by the formula:

$$V_{L2}\text{-}L_1\text{-}V_{L1}\text{-}L_2\text{-}C_L \qquad [I]$$

and a second polypeptide chain comprises a structure represented by the formula:

$$V_{H1}\text{-}L_3\text{-}V_{H2}\text{-}L_4\text{-}C_{H1}\text{-}\text{hinge-}C_{H2}\text{-}CH_3 \qquad [II]$$

and a third polypeptide chain comprises a structure represented by the formula:

$$V_{H3}\text{-}C_{H1}\text{-}\text{hinge-}C_{H2}\text{-}C_{H3} \qquad [III]$$

and a fourth polypeptide chain comprises a structure represented by the formula:

$$V_{L3}\text{-}C_L \qquad [IV]$$

wherein:
$V_{L1}$ is a first immunoglobulin light chain variable domain;
$V_{L2}$ is a second immunoglobulin light chain variable domain;
$V_{L3}$ is a third immunoglobulin light chain variable domain;
$V_{H1}$ is a first immunoglobulin heavy chain variable domain;
$V_{H2}$ is a second immunoglobulin heavy chain variable domain;
$V_{H3}$ is a third immunoglobulin heavy chain variable domain;
$C_L$ is an immunoglobulin light chain constant domain;
$C_{H1}$ is an immunoglobulin $C_{H1}$ heavy chain constant domain;
$C_{H2}$ is an immunoglobulin $C_{H2}$ heavy chain constant domain;
$C_{H3}$ is an immunoglobulin $C_{H3}$ heavy chain constant domain;
hinge is an immunoglobulin hinge region connecting the $C_{H1}$ and $C_{H1}$ domains; and
$L_1$, $L_2$, $L_3$ and $L_4$ are amino acid linkers;
wherein the polypeptide of formula I and the polypeptide of formula II form a cross-over light chain-heavy chain pair.

In some embodiments, the binding protein of the disclosure is a trispecific and/or trivalent binding protein comprising four polypeptide chains that form three antigen binding sites that bind one or more (e.g., three) different antigen targets or target proteins. In some embodiments, at least one of the antigen binding sites binds a CD38 polypeptide (e.g., the extracellular domain of human and/or cynomolgus monkey CD38 polypeptides). In some embodiments, a first polypeptide chain comprises a structure represented by the formula:

$$V_{L2}\text{-}L_1\text{-}V_{L1}\text{-}L_2\text{-}C_L \qquad [I]$$

and a second polypeptide chain comprises a structure represented by the formula:

$$V_{H1}\text{-}L_3\text{-}V_{H2}\text{-}L_4\text{-}C_{H1} \qquad [II]$$

and a third polypeptide chain comprises a structure represented by the formula:

$$V_{H3}\text{-}C_{H1} \qquad [III]$$

and a fourth polypeptide chain comprises a structure represented by the formula:

$$V_{L3}\text{-}C_L \qquad [IV]$$

wherein:
$V_{L1}$ is a first immunoglobulin light chain variable domain;
$V_{L2}$ is a second immunoglobulin light chain variable domain;
$V_{L3}$ is a third immunoglobulin light chain variable domain;
$V_{H1}$ is a first immunoglobulin heavy chain variable domain;
$V_{H2}$ is a second immunoglobulin heavy chain variable domain;
$V_{H3}$ is a third immunoglobulin heavy chain variable domain;
$C_L$ is an immunoglobulin light chain constant domain;
$C_{H1}$ is an immunoglobulin $C_{H1}$ heavy chain constant domain; and
$L_1$, $L_2$, $L_3$ and $L_4$ are amino acid linkers;
and wherein the polypeptide of formula I and the polypeptide of formula II form a cross-over light chain-heavy chain pair. In some embodiments, the second and the third polypeptide chain further comprise an Fc region linked to $C_{H1}$, the Fc regions comprising an immunoglobulin hinge region and $C_{H2}$ and $C_{H3}$ immunoglobulin heavy chain constant domains.

In some embodiments, the first polypeptide chain and the second polypeptide chain have a cross-over orientation that forms two distinct antigen binding sites. In some embodiments, the VH1 and VL1 form a binding pair and form the first antigen binding site. In some embodiments, the VH2 and VL2 form a binding pair and form the second antigen binding site. In some embodiments, the first antigen binding site binds a CD3 polypeptide (e.g., human CD3), and the second antigen binding site binds a CD28 polypeptide (e.g., human CD28). In some embodiments, the second antigen binding site binds a CD3 polypeptide (e.g., human CD3), and the first antigen binding site binds a CD28 polypeptide (e.g., human CD28). In some embodiments, the third polypeptide and the fourth polypeptide form a third antigen binding site. In some embodiments, the VH3 and VL3 form a binding pair and form the third antigen binding site. In some embodiments, the third antigen binding site binds a CD38 polypeptide (e.g., human and optionally cynomolgus monkey CD38). Exemplary tending protein formats with cross-over orientations contemplated for use herein are also described in U.S. patent application Ser. No. 15/487,243 and International Application No. PCT/US2017/027488.

In some embodiments in any of the bispecific, trispecific, or multispecific binding proteins described herein, an antigen binding site binds a CD38 polypeptide (e.g., human and optionally cynomolgus monkey CD38). In some embodiments, other (e.g., not binding to CD38) antigen binding site(s) of any of the bispecific, trispecific, or multispecific binding proteins described herein bind to CD28 or CD3. In some embodiments, the $V_{H1}$ domain comprises a CDR-H1 sequence comprising the amino acid sequence of GYTFTSFN (SEQ ID NO:31) or GYTFTSYA (SEQ ID NO:37), a CDR-H2 sequence comprising the amino acid sequence of IYPGNGGT (SEQ ID NO:32) or IYPGQGGT (SEQ ID NO:38), and a CDR-H3 sequence comprising the amino acid sequence of ARTGGLRRAYFTY (SEQ ID NO:33), and the $V_{L1}$ domain comprises a CDR-L1 sequence comprising the amino acid sequence of ESVDSYGNGF (SEQ ID NO:34) or QSVSSYGQGF (SEQ ID NO:39), a CDR-L2 sequence comprising the amino acid sequence of LAS (SEQ ID NO:35) or GAS (SEQ ID NO:40), and a CDR-L3 sequence comprising the amino acid sequence of QQNKEDPWT (SEQ ID NO:36). In some embodiments, the $V_{H5}$ domain comprises a CDR-H1 sequence comprising the amino add sequence of GYTFTSFN (SEQ ID NO:31) or GYTFTSYA (SEQ ID NO:37), a CDR-H2 sequence comprising the amino acid sequence of IYPGNGGT (SEQ ID NO:32) or IYPGQGGT (SEQ ID NO:38), and a CDR-H3 sequence comprising the amino acid sequence of ARTGGLRRAYFTY (SEQ ID NO:33), and the $V_{L2}$ domain comprises a CDR-L1 sequence comprising the amino add sequence of ESVDSYGNGF (SEQ ID NO:34) or QSVSSYGQGF (SEQ ID NO:39), a CDR-1.2 sequence comprising the amino acid sequence of LAS (SEQ ID NO:35) or GAS (SEQ ID NO:40), and a CDR-L3 sequence comprising the amino acid sequence of QQNKEDPWT (SEQ ID NO:36). In some embodiments, the $V_{H3}$ domain comprises a CDR-H1 sequence comprising the amino acid sequence of GYTFTSFN (SEQ ID NO:31) or GYTFTSYA (SEQ ID NO:37), a CDR-H2 sequence comprising the amino add sequence of IYPGNGGT (SEQ ID NO:32) or IYPGQGGT (SEQ ID NO:38), and a CDR-H3 sequence comprising the amino add sequence of ARTGGLRRAYFTY (SEQ ID NO:33), and the $V_{L3}$ domain comprises a CDR-L1 sequence comprising the amino add sequence of ESVDSYGNGF (SEQ ID NO:34) or QSVSSYGQGF (SEQ ID NO:39), a CDR-1.2 sequence comprising the amino acid sequence of LAS (SEQ ID NO:35) or GAS (SEQ ID NO:40), and a CDR-L3 sequence comprising the amino acid sequence of QQNKEDPWT (SEQ ID NO:36). In some embodiments, the $V_{H1}$ domain comprises a CDR-H1 sequence comprising the amino acid sequence of GYTFTSFN (SEQ ID NO:31) or GYTFTSYA (SEQ ID NO:37), a CDR-H2 sequence comprising the amino add sequence of IYPGNGGT (SEQ ID NO:32) or IYPGQGGT (SEQ ID NO:38), and a CDR-H3 sequence comprising the amino % acid sequence of ARTGGLRRAYFTY (SEQ ID NO:33), and the $V_{L1}$ domain comprises a CDR-L1 sequence comprising the amino acid sequence of ESVDSYGNGF (SEQ ID NO:34) or QSVSSYGQG (SEQ ID NO:132), a CDR-L2 sequence comprising the amino acid sequence of LAS (SEQ ID NO:35) or GAS (SEQ ID NO:40), and a CDR-L3 sequence comprising the amino acid sequence of QQNKEDPWT (SEQ ID NO:36). In some embodiments, the $V_{H2}$ domain comprises a CDR-H1 sequence comprising the amino acid sequence of GYTFTSFN (SEQ ID NO:31) or GYTFTSYA (SEQ ID NO:37), a CDR-H2 sequence comprising the amino acid sequence of IYPGNGGT (SEQ ID NO:32) or IYPGQGGT (SEQ ID NO:38), and a CDR-H3 sequence comprising the amino acid sequence of ARTGGLRRAYFTY (SEQ ID NO:33), and the $V_u$ domain comprises a CDR-L1 sequence comprising the amino acid sequence of ESVDSYGNGF (SEQ ID NO:34) or QSVSSYGQG (SEQ ID NO:132), a CDR-L2 sequence comprising the amino acid sequence of LAS (SEQ ID NO:35) or GAS (SEQ ID NO:40), and a CDR-L3 sequence comprising the amino acid sequence of QQNKEDPWT (SEQ ID NO:36). In some embodiments, the $V_{H3}$ domain comprises a CDR-H1 sequence comprising the amino acid sequence of GYTFTSFN (SEQ ID NO:31) or GYTFTSYA (SEQ ID NO:37), a CDR-H2 sequence comprising the amino acid sequence of IYPGNGGT (SEQ ID NO:32) or IYPGQGGT (SEQ ID NO:38), and a CDR-H3 sequence comprising the amino acid sequence of ARTGGLRRAYFTY (SEQ ID NO:33), and the $V_{L3}$ domain comprises a CDR-L1 sequence comprising the amino acid sequence of ESVDSYGNGF (SEQ ID NO:34) or QSVSSYGQG (SEQ ID NO:132), a CDR-L2 sequence comprising the amino acid sequence of LAS (SEQ ID NO:3S) or GAS (SEQ ID NO:40), and a CDR-L3 sequence comprising the amino acid sequence of QQNKEDPWT (SEQ ID NO:36).

In some embodiments, the $V_{H1}$ domain comprises a CDR-H1 sequence comprising the amino acid sequence of GFTFSSYG (SEQ ID NO:41), a CDR-H2 sequence comprising the amino acid sequence of IWYDGSNK (SEQ ID NO:42), and a CDR-H3 sequence comprising the amino acid sequence of ARMFRGAFDY (SEQ ID NO:43), and/or the $V_{L1}$ domain comprises a CDR-L1 sequence comprising the amino acid sequence of QGIRND (SEQ ID NO:44), a CDR-L2 sequence comprising the amino acid sequence of AAS (SEQ ID NO:45), and a CDR-L3 sequence comprising the amino acid sequence of LQDYIYYPT (SEQ ID NO:46). In some embodiments, the $V_{H2}$ domain comprises a CDR-H1 sequence comprising the amino acid sequence of GFTFSSYG (SEQ ID NO:41), a CDR-H2 sequence comprising the amino acid sequence of IWYDGSNK (SEQ ID NO:42), and a CDR-H3 sequence comprising the amino acid sequence of ARMFRGAFDY (SEQ ID NO:43), and/or the $V_{L2}$ domain comprises a CDR-L1 sequence comprising the amino acid sequence of QGIRND (SEQ ID NO:44), a CDR-L2 sequence comprising the amino acid sequence of AAS (SEQ ID NO:45), and a CDR-L3 sequence comprising the amino acid sequence of LQDYIYYPT (SEQ ID NO:46). In some embodiments, the $V_{H3}$ domain comprises a CDR-H1 sequence comprising the amino acid sequence of GFTFSSYG (SEQ ID NO:41), a CDR-H2 sequence comprising the amino acid sequence of IWYDGSNK (SEQ ID NO:42), and a CDR-H3 sequence comprising the amino acid sequence of ARMFRGAFDY (SEQ ID NO:43), and/or the $V_{L3}$ domain comprises a CDR-L1 sequence comprising the amino acid sequence of QGIRND (SEQ ID NO:44), a CDR-L2 sequence comprising the amino acid sequence of AAS (SEQ ID NO:45), and a CDR-L3 sequence comprising the amino acid sequence of LQDYIYYPT (SEQ ID NO:46). In some embodiments, the $V_{H1}$ domain comprises a CDR-H1 sequence comprising the amino acid sequence of GFTFSSYG (SEQ ID NO:41), a CDR-H2 sequence comprising the amino acid sequence of IWYDGSNK (SEQ ID NO:42), and a CDR-H3 sequence comprising the amino acid sequence of ARMFRGAFDY (SEQ ID NO:43), and the $V_{L1}$ domain comprises a CDR-L1 sequence comprising the amino acid sequence of QGIRND (SEQ ID NO:44), a CDR-L2 sequence comprising the amino acid sequence of AAS (SEQ ID NO:45), and a CDR-L3 sequence comprising the amino acid sequence of LQDYIYYPT (SEQ ID NO:46). In some embodiments, the $V_{H2}$ domain comprises a CDR-H1 sequence comprising the amino acid sequence of GFTFSSYG (SEQ ID NO:41), a CDR-H2 sequence comprising the amino acid sequence of IWYDGSNK (SEQ ID NO:42), and a CDR-H3 sequence comprising the amino acid sequence of ARMFRGAFDY (SEQ ID NO:43), and the $V_{L2}$ domain comprises a CDR-L1 sequence comprising the amino acid sequence of QGIRND (SEQ ID NO:44), a CDR-L2 sequence comprising the amino acid sequence of AAS (SEQ ID NO:45), and a CDR-L3 sequence comprising the amino acid sequence of LQDYIYYPT (SEQ ID NO:46).

In some embodiments, the $V_{H1}$ domain comprises a CDR-H1 sequence comprising the amino acid sequence of GFTFSSYG (SEQ ID NO:41), a CDR-H2 sequence comprising the amino acid sequence of IWYDGSNK (SEQ ID NO:42), and a CDR-H3 sequence comprising the amino acid sequence of ARMFRGAFDY (SEQ ID NO:43), and the $V_{L3}$ domain comprises a CDR-L1 sequence comprising the amino acid sequence of QGIRND (SEQ ID NO:44), a CDR-L2 sequence comprising the amino acid sequence of AAS (SEQ ID NO:45), and a CDR-L3 sequence comprising the amino acid sequence of LQDYIYYPT (SEQ ID NO:46).

In some embodiments, the $V_{H1}$ domain comprises a CDR-H1 sequence comprising the amino acid sequence of GYTFTSFN (SEQ ID NO:31), a CDR-H2 sequence comprising the amino acid sequence of IYPGNGGT (SEQ ID NO:32), and a CDR-H3 sequence comprising the amino acid sequence of ARTGGLRRAYFTY (SEQ ID NO:33), and/or the $V_{L1}$ domain comprises a CDR-L1 sequence comprising the amino acid sequence of ESVDSYGNGF (SEQ ID NO:34), a CDR-L2 sequence comprising the amino acid sequence of LAS (SEQ ID NO:35), and a CDR-L3 sequence comprising the amino acid sequence of QQNKEDPWT (SEQ ID NO:36). In some embodiments, the $V_{H1}$ domain comprises a CDR-H1 sequence comprising the amino acid sequence of GYTFTSYA (SEQ ID NO:37), a CDR-H2 sequence comprising the amino acid sequence of IYPGQGGT (SEQ ID NO:38), and a CDR-H3 sequence comprising the amino acid sequence of ARTGGLRRAYFTY (SEQ ID NO:33), and/or the $V_{L1}$ domain comprises a CDR-L1 sequence comprising the amino acid sequence of QSVSSYGQGF (SEQ ID NO:39), a CDR-L2 sequence comprising the amino acid sequence of GAS (SEQ ID NO:40), and a CDR-L3 sequence comprising the amino acid sequence of QQNKEDPWT (SEQ ID NO:36). In some embodiments, the $V_{H1}$ domain comprises a CDR-H1 sequence comprising the amino acid sequence of GYTFTSFN (SEQ ID NO:31), a CDR-H2 sequence comprising the amino acid sequence of IYPGNGGT (SEQ ID NO:32), and a CDR-H3 sequence comprising the amino acid sequence of ARTGGLRRAYFTY (SEQ ID NO:33), and/or the $V_{L2}$ domain comprises a CDR-L1 sequence comprising the amino acid sequence of ESVDSYGNGF (SEQ ID NO:34), a CDR-L2 sequence comprising the amino acid sequence of LAS (SEQ ID NO:35), and a CDR-L3 sequence comprising the amino acid sequence of QQNKEDPWT (SEQ ID NO:36). In some embodiments, the $V_{H1}$ domain comprises a CDR-H1 sequence comprising the amino acid sequence of GYTFTSYA (SEQ ID NO:37), a CDR-H2 sequence comprising the amino acid sequence of IYPGQGGT (SEQ ID NO:38), and a CDR-H3 sequence comprising the amino acid sequence of ARTGGLRRAYFTY (SEQ ID NO:33), and/or the $V_{L2}$ domain comprises a CDR-L1 sequence comprising the amino acid sequence of QSVSSYGQGF (SEQ ID NO:39), a CDR-L2 sequence comprising the amino acid sequence of GAS (SEQ ID NO:40), and a CDR-L3 sequence comprising the amino add sequence of QQNKEDPWT (SEQ ID NO:36). In some embodiments, the $V_{H3}$ domain comprises a CDR-H1 sequence comprising the amino acid sequence of GYTFTSFN (SEQ ID NO:31), a CDR-H2 sequence comprising the amino acid sequence of IYPGNGGT (SEQ ID NO:32), and a CDR-H3 sequence comprising the amino acid sequence of ARTGGLRRAYFTY (SEQ ID NO:33), and/or the $V_{L3}$ domain comprises a CDR-L1 sequence comprising the amino add sequence of ESVDSYGNGF (SEQ ID NO:34), a CDR-L2 sequence comprising the amino acid sequence of LAS (SEQ ID NO:35), and a CDR-L3 sequence comprising the amino acid sequence of QQNKEDPWT (SEQ ID NO:36). In some embodiments, the $V_{H3}$ domain comprises a CDR-H1 sequence comprising the amino acid sequence of GYTFTSYA (SEQ ID NO:37), a CDR-H2 sequence comprising the amino acid sequence of IYPGQGGT (SEQ ID NO:38), and a CDR-H3 sequence comprising the amino acid sequence of ARTGGLRRAYFTY (SEQ ID NO:33), and/or the $V_{L3}$ domain comprises a CDR-L1 sequence comprising the amino acid sequence of QSVSSYGQGF (SEQ ID NO:39), a CDR-L2 sequence comprising the amino acid sequence of GAS (SEQ ID NO:40), and a CDR-L3 sequence comprising the amino acid sequence of QQNKEDPWT (SEQ ID NO:36).

In some embodiments, the $V_{H1}$ domain comprises a CDR-H1 sequence comprising the amino acid sequence of GYTFTSFN (SEQ ID NO:31), a CDR-H2 sequence comprising the amino acid sequence of IYPGNGGT (SEQ ID NO:32), and a CDR-H3 sequence comprising the amino acid sequence of ARTGGLRRAYFTY (SEQ ID NO:33), and the $V_{L1}$ domain comprises a CDR-L1 sequence comprising the amino acid sequence of ESVDSYGNGF (SEQ ID NO:34), a CDR-L2 sequence comprising the amino acid sequence of LAS (SEQ ID NO:35), and a CDR-L3 sequence comprising the amino acid sequence of QQNKEDPWT (SEQ ID NO:36). In some embodiments, the $V_{H1}$ domain comprises a CDR-H1 sequence comprising the amino acid sequence of GYTFTSYA (SEQ ID NO:37), a CDR-H2 sequence comprising the amino acid sequence of IYPGQGGT (SEQ ID NO:38), and a CDR-H3 sequence comprising the amino acid sequence of ARTGGLRRAYFTY (SEQ ID NO:33), and the $V_{L1}$ domain comprises a CDR-L1 sequence comprising the amino acid sequence of QSVSSYGQGF (SEQ ID NO:39), a CDR-L2 sequence comprising the amino acid sequence of GAS (SEQ ID NO:40), and a CDR-L3 sequence comprising the amino acid sequence of QQNKEDPWT (SEQ ID NO:36). In some embodiments, the $V_{H2}$ domain comprises a CDR-H1 sequence comprising the amino acid sequence of GYTFTSFN (SEQ ID NO:31), a CDR-H2 sequence comprising the amino acid sequence of IYPGNGGT (SEQ ID NO:32), and a CDR-H3 sequence comprising the amino acid sequence of ARTGGLRRAYFTY (SEQ ID NO:33), and the $V_{L1}$ domain comprises a CDR-L1 sequence comprising the amino acid sequence of ESVDSYGNGF (SEQ ID NO:34), a CDR-L2 sequence comprising the amino acid sequence of LAS (SEQ ID NO:35), and a CDR-L3 sequence comprising the amino acid sequence of QQNKEDPWT (SEQ ID NO:36). In some embodiments, the $V_{(12}$ domain comprises a CDR-H1 sequence comprising the amino acid sequence of GYTFTSYA (SEQ ID NO:37), a CDR-H2 sequence comprising the amino acid sequence of IYPGQGGT (SEQ ID NO:38), and a CDR-H3 sequence comprising the amino acid sequence of ARTGGLRRAYFTY (SEQ ID NO:33), and the $V_{L2}$ domain comprises a CDR-L1 sequence comprising the amino add sequence of QSVSSYGQGF (SEQ ID NO:39), a CDR-L2 sequence comprising the amino acid sequence of CAS (SEQ ID NO:40), and a CDR-L3 sequence comprising the amino add sequence of QQNKEDPWT (SEQ ID NO:36). In some embodiments, the $V_{H3}$ domain comprises a CDR-H1 sequence comprising the amino add sequence of GYTFTSFN (SEQ ID NO:31), a CDR-H2 sequence comprising the amino acid sequence of IYPGNGGT (SEQ ID NO:32), and a CDR-H3 sequence comprising the amino acid sequence of ARTGGLRRAYFTY (SEQ ID NO:33), and the $V_{L3}$ domain comprises a CDR-L1 sequence comprising the amino add sequence of ESVDSYGNGF (SEQ ID NO:34), a CDR-L2 sequence comprising the amino acid sequence of LAS (SEQ ID NO:35), and a CDR-L3 sequence comprising the amino add sequence of QQNKEDPWT (SEQ ID NO:36). In some embodiments, the V$_{H3}$ domain comprises a CDR-H1 sequence comprising the amino acid sequence of GYTFTSYA (SEQ ID NO:37), a CDR-H2 sequence comprising the amino add sequence of IYPGQGGT (SEQ ID NO:38), and a CDR-H3 sequence comprising the amino acid sequence of ARTGGLRRAYFTY (SEQ ID NO:33), and the V$_{L3}$ domain comprises a CDR-L1 sequence comprising the amino acid sequence of QSVSSYGQGF (SEQ ID NO:39), a CDR-L2 sequence comprising the amino acid sequence of GAS (SEQ ID NO:40), and a CDR-L3 sequence comprising the amino add sequence of QQNKEDPWT (SEQ ID NO:36)

In some embodiments, the V$_{H3}$ domain comprises a CDR-H1 sequence comprising the amino add sequence of GYTFTSFN (SEQ ID NO:31), a CDR-H2 sequence comprising the amino acid sequence of IYPGNGGT (SEQ ID NO:32), and a CDR-H3 sequence comprising the amino acid sequence of ARTGGLRRAYFTY (SEQ ID NO:33), and/or the V$_{L3}$ domain comprises a CDR-L1 sequence comprising the amino acid sequence of ESVDSYGNGF (SEQ ID NO:34), a CDR-L2 sequence comprising the amino add sequence of LAS (SEQ ID NO:35), and a CDR-L3 sequence comprising the amino acid sequence of QQNKEDPWT (SEQ ID NO:36). In some embodiments, the V$_{H3}$ domain comprises a CDR-H1 sequence comprising the amino acid sequence of GYTFTSYA (SEQ ID NO:37), a CDR-H2 sequence comprising the amino add sequence of IYPGQGGT (SEQ ID NO:38), and a CDR-H3 sequence comprising the amino acid sequence of ARTGGLRRAYFTY (SEQ ID NO:33), and/or the V$_{L3}$ domain comprises a CDR-L1 sequence comprising the amino acid sequence of QSVSSYGQGF (SEQ ID NO:39), a CDR-L2 sequence comprising the amino acid sequence of GAS (SEQ ID NO:40), and a CDR-L3 sequence comprising the amino acid sequence of QQNKEDPWT (SEQ ID NO:36).

In some embodiments, the V$_{H3}$ domain comprises the amino add sequence of SEQ ID NO:5, or the V$_{L3}$ domain comprises the amino acid sequence of SEQ ID NO:6. In some embodiments, the V$_{H1}$ domain comprises the amino acid sequence of SEQ ID NO:17, or the V$_{L3}$ domain comprises the amino acid sequence of SEQ ID NO:18. In some embodiments, the V$_{H3}$ domain comprises the amino add sequence of SEQ ID NO:21, or the V$_{L3}$ domain comprises the amino add sequence of SEQ ID NO:18. In some embodiments, the V$_{H3}$ domain comprises the amino acid sequence of SEQ ID NO:23, or the V$_{L3}$ domain comprises the amino acid sequence of SEQ ID NO:18. In some embodiments, the V$_{H3}$ domain comprises the amino acid sequence of SEQ ID NO:13, or the V$_{L3}$ domain comprises the amino add sequence of SEQ ID NO:14.

In some embodiments, the V$_{H3}$ domain comprises the amino add sequence of SEQ ID NO:5, and/or the V$_{L3}$ domain comprises the amino acid sequence of SEQ ID NO:6. In some embodiments, the V$_{H1}$ domain comprises the amino add sequence of SEQ ID NO:17, and the V$_{L3}$ domain comprises the amino acid sequence of SEQ ID NO:18. In some embodiments, the V$_{H3}$ domain comprises the amino acid sequence of SEQ ID NO:21, and the V$_{L3}$ domain comprises the amino acid sequence of SEQ ID NO:18. In some embodiments, the V$_{H3}$ domain comprises the amino acid sequence of SEQ ID NO:23, and the V$_{L3}$ domain comprises the amino add sequence of SEQ ID NO:18. In some embodiments, the V$_{H3}$ domain comprises the amino acid sequence of SEQ ID NO:13, and the V$_{L3}$ domain comprises the amino acid sequence of SEQ ID NO:14.

In some embodiments, the V$_{H3}$ domain comprises a CDR-H1 sequence comprising the amino acid sequence of GFTFSSYG (SEQ ID NO:41), a CDR-H2 sequence comprising the amino acid sequence of IWYDGSNK (SEQ ID NO:42), and a CDR-H3 sequence comprising the amino acid sequence of ARMFRGAFDY (SEQ ID NO:43), and/or die V$_{L3}$ domain comprises a CDR-L1 sequence comprising the amino add sequence of QGIRND (SEQ ID NO:44), a CDR-L2 sequence comprising the amino acid sequence of AAS (SEQ ID NO:45), and a CDR-L3 sequence comprising the amino add sequence of LQDYIYYPT (SEQ ID NO:46).

In some embodiments, the V$_{H3}$ domain comprises the amino add sequence of SEQ ID NO:9, and/or the V$_{L3}$ domain comprises the amino acid sequence of SEQ ID NO:10.

In some embodiments of any of the trispecific binding proteins of the present disclosure, one antigen binding domain binds to a CD3 polypeptide (e.g., human CD3) and one antigen binding domain binds to a CD28 polypeptide (e.g., human CD28). In some embodiments, the V$_{H1}$ domain comprises three CDRs from SEQ ID NOs:49 or 5 J as shown in Table H, and the V$_{L1}$ domain comprises three CDRs from SEQ ID NOs:50 or 52 as shown in Table H. In some embodiments, the V$_{H2}$ domain comprises three CDRs from SEQ ID NOs:49 or 51 as shown in Table H, and the V$_{L2}$ domain comprises three CDRs from SEQ ID NOs:50 or 52 as shown in Table H. In some embodiments, the V$_{H1}$ domain comprises three CDRs from SEQ ID NOs:53 or 84 as shown in Table H, and the V$_{L1}$ domain comprises three CDRs from SEQ ID NOs:54 or 85 as shown in Table H. In some embodiments, the V$_{H2}$ domain comprises three CDRs from SEQ ID NOs:53 or 84 as shown in Table H, and the V$_{L2}$ domain comprises three CDRs from SEQ ID NOs:54 or 85 as shown in Table H.

In some embodiments, the V$_{H1}$ domain comprises the amino acid sequence of SEQ ID NO:49, the V$_{L1}$ domain comprises the amino acid sequence of SEQ ID NO:50, the V$_{H1}$ domain comprises the amino acid sequence of SEQ ID NO:53, and the V$_{L2}$ domain comprises the amino acid sequence of SEQ ID NO:54. In some embodiments, the V$_{H2}$ domain comprises the amino acid sequence of SEQ ID NO:49, the V$_{L2}$ domain comprises the amino acid sequence of SEQ ID NO:50, the V$_{H1}$ domain comprises the amino acid sequence of SEQ ID NO:53, and the V$_{L1}$ domain comprises the amino acid sequence of SEQ ID NO:54. In some embodiments, the V$_{H1}$ domain comprises the amino acid sequence of SEQ ID NO:51, the V$_{L1}$ domain comprises the amino acid sequence of SEQ ID NO:52, the V$_{H2}$ domain comprises the amino acid sequence of SEQ ID NO:53, and the V$_{L2}$ domain comprises the amino acid sequence of SEQ ID NO:54. In some embodiments, the V$_{H1}$ domain comprises the amino acid sequence of SEQ ID NO:51, the V$_{L2}$ domain comprises the amino acid sequence of SEQ ID NO:52, the V$_{H1}$ domain comprises the amino acid sequence of SEQ ID NO:53, and the V$_{L1}$ domain comprises the amino acid sequence of SEQ ID NO:54.

In some embodiments, the V$_{H1}$ domain comprises the amino acid sequence of SEQ ID NO:49, the V$_{L1}$ domain comprises the amino acid sequence of SEQ ID NO:50, the V$_{H1}$ domain comprises the amino acid sequence of SEQ ID NO:53, the V$_{L2}$ domain comprises the amino acid sequence of SEQ ID NO:54, the V$_{H1}$ domain comprises the amino acid sequence of SEQ ID NO:13, and the V$_{L3}$ domain comprises the amino acid sequence of SEQ ID NO:14. In some embodiments, the V$_{H1}$ domain comprises the amino add sequence of SEQ ID NO:49, the V$_{L1}$ domain comprises the amino acid sequence of SEQ ID NO:50, the V$_{H1}$ domain comprises the amino add sequence of SEQ ID NO:53, the V$_{L2}$ domain comprises the amino add sequence of SEQ ID NO:54, the V$_{H1}$ domain comprises the amino acid sequence of SEQ ID NO:9, and the V$_{L3}$ domain comprises the amino acid sequence of SEQ ID NO:10.

In certain embodiments, the first polypeptide chain comprises a polypeptide sequence that is at least 95% identical to the amino acid sequence of SEQ ID NO:61, the second polypeptide chain comprises a polypeptide sequence that is at least 95% identical to the amino acid sequence of SEQ ID NO:60, the third polypeptide chain comprises a polypeptide sequence that is at least 95% identical to the amino acid sequence of SEQ ID NO:62, and the fourth polypeptide chain comprises a polypeptide sequence that is at least 95% identical to the amino acid sequence of SEQ ID NO:63. In certain embodiments, the first polypeptide chain comprises a polypeptide sequence that is at least 95% identical to the amino acid sequence of SEQ ID NO:61, the second polypeptide chain comprises a polypeptide sequence that is at least 95% identical to the amino acid sequence of SEQ ID NO:64, the third polypeptide chain comprises a polypeptide sequence that is at least 95% identical to the amino acid sequence of SEQ ID NO:65, and the fourth polypeptide chain comprises a polypeptide sequence that is at least 95% identical to the amino acid sequence of SEQ ID NO:63. In certain embodiments, the first polypeptide chain comprises a polypeptide sequence that is at least 95% identical to the amino acid sequence of SEQ ID NO:61, the second polypeptide chain comprises a polypeptide sequence that is at least 95% identical to the amino acid sequence of SEQ ID NO:66, the third polypeptide chain comprises a polypeptide sequence that is at least 95% identical to the amino acid sequence of SEQ ID NO:67, and the fourth polypeptide chain comprises a polypeptide sequence that is at least 95% identical to the amino acid sequence of SEQ ID NO:63. In certain embodiments, the first poly peptide chain comprises a polypeptide sequence that is at least 95% identical to the amino acid sequence of SEQ ID NO:61, the second polypeptide chain comprises a polypeptide sequence that is at least 95% identical to the amino acid sequence of SEQ ID NO:60, the third polypeptide chain comprises a polypeptide sequence that is at least 95% identical to the amino acid sequence of SEQ ID NO:68, and the fourth polypeptide chain comprises a polypeptide sequence that is at least 95% identical to the amino acid sequence of SEQ ID NO:69. In certain embodiments, the first polypeptide chain comprises a polypeptide sequence that is at least 95% identical to the amino acid sequence of SEQ ID NO:61, the second polypeptide chain comprises a polypeptide sequence that is at least 95% identical to the amino acid sequence of SEQ ID NO:64, the third poly peptide chain comprises a polypeptide sequence that is at least 95% identical to the amino acid sequence of SEQ ID NO:70, and the fourth polypeptide chain comprises a polypeptide sequence that is at least 95% identical to the amino acid sequence of SEQ ID NO:69. In certain embodiments, the first polypeptide chain comprises a polypeptide sequence that is at least 95% identical to the amino acid sequence of SEQ ID NO:61, the second polypeptide chain comprises a polypeptide sequence that is at least 95% identical to the amino acid sequence of SEQ ID NO:66, the third polypeptide chain comprises a polypeptide sequence that is at least 95% identical to the amino acid sequence of SEQ ID NO:71, and the fourth polypeptide chain comprises a polypeptide sequence that is at least 95% identical to the amino acid sequence of SEQ ID NO: 69.

In certain embodiments, the first polypeptide chain comprises the amino acid sequence of SEQ ID NO:61, the second polypeptide chain comprises the amino acid sequence of SEQ ID NO:60, the thud polypeptide chain comprises the amino acid sequence of SEQ ID NO:62, and the fourth polypeptide chain comprises the amino acid sequence of SEQ ID NO:63. In certain embodiments, the first polypeptide chain comprises the amino acid sequence of SEQ ID NO:61, the second polypeptide chain comprises the amino acid sequence of SEQ ID NO:64, the third polypeptide chain comprises the amino acid sequence of SEQ ID NO:65, and the fourth polypeptide chain comprises the amino acid sequence of SEQ ID NO:63. In certain embodiments, the first polypeptide chain comprises the amino acid sequence of SEQ ID NO:61, the second polypeptide chain comprises the amino acid sequence of SEQ ID NO:66, the third polypeptide chain comprises the amino acid sequence of SEQ ID NO:67, and the fourth polypeptide chain comprises the amino acid sequence of SEQ ID NO:63. In certain embodiments, the first polypeptide chain comprises the amino acid sequence of SEQ ID NO:61, the second polypeptide chain comprises the amino acid sequence of SEQ ID NO:60, the third polypeptide chain comprises the amino acid sequence of SEQ ID NO:68, and the fourth polypeptide chain comprises the amino acid sequence of SEQ ID NO:69. In certain embodiments, the first polypeptide chain comprises the amino acid sequence of SEQ ID NO:61, the second poly peptide chain comprises the amino acid sequence of SEQ ID NO:64, the third polypeptide chain comprises the amino acid sequence of SEQ ID NO:70, and the fourth polypeptide chain comprises the amino acid sequence of SEQ ID NO:69. In certain embodiments, the first polypeptide chain comprises the amino acid sequence of SEQ ID NO:61, the second polypeptide chain comprises the amino add sequence of SEQ ID NO:66, the third polypeptide chain comprises the amino acid sequence of SEQ ID NO:71, and the fourth polypeptide chain comprises the amino acid sequence of SEQ ID NO: 69.

In any of the trispecific binding proteins described supra, the target antigen other than CD38 can be any of the following exemplary antigen targets: A2AR, APRIL, ATPDase, BAFF, BAFFR, BCMA, BlyS, BTK, BTLA, B7DC, B7H1, B7H4 (also known as VTCN1), B7H5, B7H6, B7H7, B7RP1, B7-4, C3, C5, CCL2 (also known as MCP-1), CCL3 (also known as MIP-Ja), CCL4 (also known as MIP-1b), CCL5 (also known as RANTES), CCL7 (also known as MCP-3), CCL8 (also known as mcp-2), CCL11 (also known as eotaxin), CCL15 (also known as MIP-1d), CCL17 (also known as TARC), CCL19 (also known as MIP-3b), CCL20 (also known as MIP-3a), CCL21 (also known as MIP-2), CCL24 (also known as MPIF-2/eotaxin-2), CCL25 (also known as TECK), CCL26 (also known as eotaxin-3), CCR3, CCR4, CD3, CD19, CD20, CD23 (also known as FCER2, a receptor for IgE), CD24, CD27, CD28, CD38, CD39, CD40, CD70, CD80 (also known as B7-1), CD86 (also known as B7-2), CD122, CD137 (also known as 41BB), CD137L, CD152 (also known as CTLA4), CD154 (also known as CD40L), CD160, CD272, CD273 (also known as PDL2), CD274 (also known as PDL1), CD275 (also known as B7H2), CD276 (also known as B7H3), CD278 (also known as ICOS), CD279 (also known as PD-1), CDH1 (also known as E-cadherin), chitinase, CLEC9, CLEC91, CRTH2, CSF-1 (also known as M-CSF), CSF-2 (also known as GM-CSF), CSF-3 (also known as GCSF), CX3CL1 (also known as SCYD1), CXCL12 (also known as SDF1), CXCL13, CXCR3, DNGR-1, ectonucleoside triphosphate diphosphohydrolase 1, EGFR, ENTPD1, FCER1A, FCER1, FLAP, FOLH1, Gi24, GITR, GITRL, GM-CSF, Her2, HHLA2, HMGB1, HVEM, ICOSLG, IDO, IFNα, IgE, IGF1R, IL2Rbeta, IL1, IL1A, IL1B, IL1F10, IL2, IL4, IL4Ra, IL5, IL5R, IL6, IL7, IL7Ra, IL8, IL9, IL9R, IL10, rhIL10, IL12, IL13, IL13R&1, IL13Ra2, IL15, IL17, IL17Rb (also known as a receptor for IL25), IL18, IL22, IL23, IL25, IL27, IL33, IL35, ITGB4 (also known as b4 integrin), ITK, KIR, LAG3, LAMP1, leptin, LPFS2, MHC class II, NCR3LG1, NKG2D, NTPDase-1, OX40, OX40L, PD-1H, platelet receptor, PROM1, S152, SISP1, SLC, SPG64, ST2 (also known as a receptor for IL33), STEAP2, Syk kinase, TACI, TDO, T14, TIGIT, TIM3, TLR, TLR2, TLR4, TLR5, TLR9, TMEF1, TNFa, TNFRSF7, Tp55, TREM1, TSLP (also known as a co-receptor for IL7Ra), TSLPR, WEAK, VEGF, VISTA, Vstm3, WUCAM, and XCR1 (also known as GPR5/CCXCR1). In some embodiments, one or more of the above antigen targets are human antigen targets.

In some embodiments, a binding protein of the present disclosure is an antibody. In some embodiments, the antibody is a monoclonal antibody. In some embodiments, the antibody is a chimeric, humanized, or human antibody.

The binding proteins of the disclosure may be prepared using domains or sequences obtained or derived from any human or non-human antibody, including, for example, human, murine, or humanized antibodies.

Linkers

In some embodiments, the linkers $L_1$, $L_2$, $L_3$ and $L_4$ range from no amino acids (lengths)) to about 100 amino acids long, or less than 100, 50, 40, 30, 20, or 15 amino acids or less. The linkers can also be 10, 9, 8, 7, 6, 5, 4, 3, 2, or 1 amino acids long. $L_1$, $L_2$, $L_3$ and $L_4$ in one binding protein may all have the same amino acid sequence or may all have different amino acid sequences.

Examples of suitable linkers include a single glycine (Gly) residue; a diglycine peptide (Gly-Gly); a tripeptide (Gly-Gly-Gly); a peptide with four glycine residues; a peptide with five glycine residues; a peptide with six glycine residues; a peptide with seven glycine residues; and a peptide with eight glycine residues. Other combinations of amino acid residues may be used such as the peptide GGGGSGGGGS (SEQ ID NO:55), the peptide GGGGSGGGGSGGGGS (SEQ ID NO:56), the peptide TKGPS (SEQ ID NO:57), the peptide GQPKAAP (SEQ ID NO:58), and the peptide GGSGSSGSGG (SEQ ID NO:59). The examples listed above are not intended to limit the scope of the disclosure in any way, and linkers comprising randomly selected amino acids selected from the group consisting of valine, leucine, isoleucine, serine, threonine, lysine, arginine, histidine, aspartate, glutamate, asparagine, glutamine, glycine, and proline have been shown to be suitable in the binding proteins. For additional descriptions of linker sequences, see, e.g., WO2012135345 and International Application No. PCT/US2017/027488.

The identity and sequence of amino acid residues in the linker may vary depending on the type of secondary structural element necessary to achieve in the linker. For example, glycine, serine, and alanine are best for linkers having maximum flexibility. Some combination of glycine, proline, threonine, and serine are useful if a more rigid and extended linker is necessary. Any amino acid residue may be considered as a linker in combination with other amino acid residues to construct larger peptide linkers as necessary depending on the desired properties.

In some embodiments, at least one of $L_1$, $L_2$, $L_3$ or $L_4$ is independently 0 amino acids in length. In some embodiments, $L_1$, $L_2$, $L_3$ or $L_4$ are each independently at least one amino acid in length. In some embodiments, the length of $L_1$ is at least twice the length of $L_3$. In some embodiments, the length of $L_2$ is at least twice the length of $L_4$. In some embodiments, the length of $L_1$ is at least twice the length of $L_3$, and the length of $L_2$ is at least twice the length of $L_4$. In some embodiments, $L_1$ is 3 to 12 amino acid residues in length, $L_2$ is 3 to 14 amino acid residues in length, $L_3$ is 1 to 8 amino acid residues in length, and $L_4$ is 1 to 3 amino acid residues in length. In some embodiments, $L_1$ is 5 to 10 amino acid residues in length, $L_2$ is 5 to 8 amino acid residues in length, $L_3$ is 1 to 5 amino acid residues in length, and $L_4$ is 1 to 2 amino acid residues in length. In some embodiments, $L_1$ is 7 amino acid residues in length, $L_2$ is 5 amino acid residues in length, $L_3$ is 1 amino acid residue in length, and $L_4$ is 2 amino acid residues in length. In some embodiments, $L_1$ is 10 amino acid residues in length, $L_2$ is 10 amino acid residues in length, $L_1$ is 0 amino acid residue in length, and $L_4$ is 0 amino acid residues in length. In some embodiments, $L_1$, $L_2$, $L_3$, and $L_4$ each have an independently selected length from 0 to 15 amino acids (e.g., 0.1, 2, 3, 4, 5, 6, 7, 8, 9, 10, 11, 12, 13, 14, or 15 amino acids), wherein at least two of the linkers have a length of 1 to 15 amino acids (e.g., 1, 2, 3, 4, 5, 6, 7, 8, 9, 10, 11, 12, 13, 14, or 15 amino acids). In some embodiments, $L_1$, $L_2$, $L_3$, and $L_4$ are each 0 amino acids in length.

In some embodiments, $L_1$, $L_2$, $L_3$, and/or $L_4$ comprise a sequence derived from a naturally occurring sequence at the junction between an antibody variable domain and an antibody constant domain (e.g., as described in WO2012/135345). For example, in some embodiments, the linker comprises a sequence found at the transition between an endogenous $V_H$ and $C_{H1}$ domain, or between an endogenous $V_L$ and $C_L$ domain (e.g., kappa or lambda). In some embodiments, the linker comprises a sequence found at the transition between an endogenous human $V_M$ and $C_{H1}$ domain, or between an endogenous human $V_L$ and $C_L$ domain (e.g., human kappa or lambda).

In some embodiments, $L_1$, $L_2$, $L_3$ and $L_4$ each independently are zero amino acids in length or comprise a sequence selected from the group consisting of GGGGSGGGGS (SEQ ID NO:55), GGGGSGGGGSGGGGS (SEQ ID NO:56), S, RT, TKGPS (SEQ ID NO:57), GQPKAAP (SEQ ID NO:58), and GGSGSSGSGG (SEQ ID NO:59). In some embodiments, $L_1$, $L_2$, $L_3$ and $L_4$ each independently comprise a sequence selected from the group consisting of GGGGSGGGGS (SEQ ID NO:55), GGGGSGGGGSGGGGS (SEQ ID NO:56), S, RT, TKGPS (SEQ ID NO:57), GQPKAAP (SEQ ID NO:58), and GGSGSSGSGG (SEQ ID NO:59).

In some embodiments, $L_1$ comprises the sequence GQPKAAP (SEQ ID NO:58), $L_2$ comprises the sequence TKGPS (SEQ ID NO:57), $L_3$ comprises the sequence S, and $L_4$ comprises the sequence RT. In some embodiments, $L_1$ comprises the sequence GGGGSGGGGS (SEQ ID NO:55), $L_2$ comprises the sequence GGGGSGGGGS (SEQ ID NO:55), $L_3$ is 0 amino acids in length, and $L_4$ is 0 amino acids in length. In some embodiments, $L_1$ comprises the sequence GGSGSSGSGG (SEQ ID NO:59), $L_2$ comprises the sequence GGSGSSGSGG (SEQ ID NO:59), $L_3$ is 0 amino adds in length, and $L_4$ is 0 amino acids in length. In some embodiments, $L_t$ comprises the sequence GGGGSGGGGSGGGGS (SEQ ID NO:56), $L_2$ is 0 amino acids in length, $L_3$ comprises the sequence GGGGSGGGGSGGGGS (SEQ ID NO:56), and $L_4$ is 0 amino acids in length.

Fc Regions and Constant Domains

In some embodiments, a binding protein of the present disclosure comprises a full-length antibody heavy chain or a polypeptide chain comprising an Fc region. In some embodiments, the Fc region is a human Fc region, e.g., a human IgG1, IgG2, IgG3, or IgG4 Fc region. In some embodiments, the Fc region includes an antibody hinge, $C_{H1}$, $C_{H2}$, $C_{H3}$, and optionally $C_{H4}$ domains. In some embodiments, the Fc region is a human IgG1 Fc region. In some embodiments, the Fc region is a human IgG4 Fc region. In some embodiments, the Fc region includes one or more of the mutations described infra.

In some embodiments, a binding protein of the present disclosure includes one or two Fc variants. The term "Fc variant" as used herein refers to a molecule or sequence that is modified from a native Fc but still comprises a binding site for the salvage receptor, FcRn (neonatal Fc receptor). Exemplary Fc variants, and their interaction with the salvage receptor, are known in the art. Thus, the term "Fc variant" can comprise a molecule or sequence that is humanized from a non-human native Fc. Furthermore, a native Fc comprises regions that can be removed because they provide structural features or biological activity that are not required for the antibody-like binding proteins of the invention. Thus, the term "Fc variant" comprises a molecule or sequence that lacks one or more native Fc sites or residues, or in which one or more Fc sites or residues has be modified, that affect or are involved in: (1) disulfide bond formation, (2) incompatibility with a selected host cell, (3) N-terminal heterogeneity upon expression in a selected host cell, (4) glycosylation, (5) interaction with complement, (6) binding to an Fc receptor other than a salvage receptor, or (7) antibody-dependent cellular cytotoxicity (ADCC).

In some embodiments, the Fc region comprises one or more mutations that reduce or eliminate Fc receptor binding and/or effector function of the Fc region (e.g., Fc receptor-mediated antibody-dependent cellular phagocytosis (ADCP), complement-dependent cytotoxicity (CDC), and/or antibody-dependent cellular cytotoxicity (ADCC)).

In some embodiments, the Fc region is a human IgG1 Fc region comprising one or more amino acid substitutions at positions corresponding to positions 234,235, and/or 329 of human IgG1 according to EU Index. In some embodiments, the amino acid substitutions are L234A, L235A, and/or P329A. In some embodiments, the Fc region is a human IgG1 Fc region comprising amino acid substitutions at positions corresponding to positions 298,299, and/or 300 of human IgG1 according to EU Index. In some embodiments, the amino acid substitutions are S298N, T299A, and/or Y300S.

In some embodiments, the Fc region is a human IgG4 Fc region comprising one or more mutations that reduce or eliminate FcγI and/or FcγII binding. In some embodiments, the Fc region is a human IgG4 Fc region comprising one or more mutations that reduce or eliminate FcγI and/or FcγII binding but do not affect FcRn binding. In some embodiments, the Fc region is a human IgG4 Fc region comprising amino acid substitutions at positions corresponding to positions 228 and/or 409 of human IgG4 according to EU Index. In some embodiments, the amino acid substitutions are S228P and/or R409K. In some embodiments, the Fc region is a human IgG4 Fc region comprising amino acid substitutions at positions corresponding to positions 234 and/or 235 of human IgG4 according to EU Index. In some embodiments, the amino acid substitutions are F234A and/or L235A. In some embodiments, the Fc region is a human IgG4 Fc region comprising amino acid substitutions at positions corresponding to positions 228, 234, 235, and/or 409 of human IgG4 according to EU Index. In some embodiments, the amino acid substitutions are S228P, F234A, L235A, and/or R409K. In some embodiments, the Fc region is a human IgG4 Fc region comprising amino acid substitutions at positions corresponding to positions 233-236 of human IgG4 according to EU Index. In some embodiments, the amino acid substitutions are E233P, F234V, L235A, and a deletion at 236. In some embodiments, the Fc region is a human IgG4 Fc region comprising amino acid mutations at substitutions corresponding to positions 228, 233-236, and/or 409 of human IgG4 according to EU Index. In some embodiments, the amino acid mutations are S228P, E233P, F234V, L235A, and a deletion at 236; and/or R409K.

In some embodiments, a binding protein of the present disclosure comprises one or more mutations to improve purification, e.g., by modulating the affinity for a purification reagent. For example, it is known that heterodimeric binding proteins can be selectively purified away from their homodimeric forms if one of the two Fc regions of the heterodimeric form contains mutation(s) that reduce or eliminate binding to Protein A, because the heterodimeric form will have an intermediate affinity for Protein A-based purification than either homodimeric form and can be selectively eluted from Protein A, e.g., by use of a different pH (See e.g., Smith, E. J. et al. (2015) Sci. Rep. 5:17943). In some embodiments, the mutation comprises substitutions at positions corresponding to positions 435 and 436 of human IgG1 or IgG4 according to EU Index, wherein the amino acid substitutions are H435R and Y436F. In some embodiments, the binding protein comprises a second polypeptide chain further comprising a first Fc region linked to $C_{H1}$, the first Fc region comprising an immunoglobulin hinge region and $C_{H2}$ and $C_{H3}$ immunoglobulin heavy chain constant domains, and a third polypeptide drain further comprising a second Fc region linked to $C_{H1}$, the second Fc region comprising an immunoglobulin hinge region and $C_{H2}$ and $C_{H3}$ immunoglobulin heavy chain constant domains; and wherein only one of the first and the second Fc regions comprises amino acid substitutions at positions corresponding to positions 435 and 436 of human IgG1 or IgG4 according to EU Index, wherein the amino acid substitutions are H435R and Y436F. In some embodiments, a binding protein of the present disclosure comprises knob and hole mutations and one or more mutations to improve purification. In some embodiments, the first and/or second Fc regions are human IgG1 Fc regions. In some embodiments, the first and/or second Fc regions are human IgG4 Fc regions.

To improve the yields of some binding proteins (e.g., bispecific or trispecific binding proteins), the $C_{H1}$ domains can be altered by the "knob-into-holes" technology which is described in detail with several examples in, for example, International Publication No. WO 96/027011, Ridgway et al., 1996, Protein Eng. 9: 617-21; and Merchant et al., 1998, Nat. Biotechnol. 16: 677-81. Specifically, the interaction surfaces of the two $C_{H3}$ domains are altered to increase the heterodimerisation of both heavy chains containing these two $C_{H3}$ domains. Each of the two $C_{H3}$ domains (of the two heavy chains) can be the "knob," while the other is the "hole." The introduction of a disulfide bridge further stabilizes the heterodimers (Merchant et al., 1998; Atwell et al., 1997, J. Mol. Biol. 270: 26-35) and increases the yield. In particular embodiments, the knob is on the second pair of polypeptides with a single variable domain. In other embodiments, the knob is on the first pair of polypeptides having the cross-over orientation. In yet other embodiments, the $C_{H3}$ domains do not include a knob in hole.

In some embodiments, a landing protein of the present disclosure (e.g., a trispecific binding protein) comprises a "knob" mutation on the second polypeptide chain and a "hole" mutation on the third polypeptide chain. In some embodiments, a binding protein of the present disclosure comprises a "knob" mutation on the third polypeptide chain and a "hole" mutation on the second polypeptide chain. In some embodiments, the "knob" mutation comprises substitution(s) at positions corresponding to positions 354 and/or 366 of human IgG1 or IgG4 according to EU Index. In some embodiments, the amino add substitutions are S354C, T366W, T366Y, S354C and T366W, or S354C and T366Y. In some embodiments, the "knob" mutation comprises substitutions at positions corresponding to positions 354 and 366 of human IgG1 or IgG4 according to EU Index. In some embodiments, the amino acid substitutions are S354C and T366W. In some embodiments, the "hole" mutation comprises substitution(s) at positions corresponding to positions 407 and, optionally, 349,366, and/or 368 and of human IgG1 or IgG4 according to EU Index. In some embodiments, the amino acid substitutions are Y407V or Y407T and optionally Y349C, T366S, and/or L368A. In some embodiments, the "hole" mutation comprises substitutions at positions corresponding to positions 349,366,368, and 407 of human IgG1 or IgG4 according to EU Index. In some embodiments, the amino acid substitutions are Y349C, T366S, L368A, and Y407V.

In some embodiments, the second polypeptide chain further comprises a first Fc region linked to CH1, the first Fc region comprising an immunoglobulin hinge region and CH2 and CH3 immunoglobulin heavy chain constant domains, wherein the first Fc region comprises amino acid substitution(s) at positions corresponding to positions 366 and optionally 354 of human IgG1 or IgG4 according to EU Index w herein the amino acid substitutions are T366W or T366Y and optionally S354C; and wherein the third polypeptide chain further comprises a second Fc region linked to CH1, the second Fc region comprising an immunoglobulin hinge region and CH2 and CH3 immunoglobulin heavy chain constant domains, wherein the second Fc region comprises amino acid substitution(s) at positions corresponding to positions 407 and optionally 349.366, and/or 368 and of human IgG1 or IgG4 according to EU Index, wherein the amino acid substitutions are Y407V or Y407T and optionally Y349C, T366S, and/or L368A.

In some embodiments, the second polypeptide chain further comprises a first Fc region linked to CH1, the first Fc region comprising an immunoglobulin hinge region and CH2 and CH3 immunoglobulin heavy chain constant domains, wherein the first Fc region comprises amino acid substitution(s) at positions corresponding to positions 407 and optionally 349,366, and/or 368 and of human IgG1 or IgG4 according to EU Index, wherein the amino acid substitutions are Y407V or Y407T and optionally Y349C, T366S, and/or L368A; and wherein the third polypeptide chain further comprises a second Fc region linked to CH1, the second Fc region comprising an immunoglobulin hinge region and CH2 and CH3 immunoglobulin heavy chain constant domains, wherein the second Fc region comprises amino acid substitutions) at positions corresponding to positions 366 and optionally 354 of human IgG1 or IgG4 according to EU Index, wherein the amino acid substitutions are T366W or T366Y and optionally S354C.

In some embodiments, the second polypeptide chain further comprises a first Fc region linked to CH1, the first Fc region comprising an immunoglobulin hinge region and CH2 and CH3 immunoglobulin heavy chain constant domains, wherein the first Fc region comprises amino acid substitution at position corresponding to position 366 of human IgG1 or IgG4 according to EU Index, wherein the amino acid substitution is T366W; and wherein the third polypeptide chain further comprises a second Fc region linked to CH1, the second Fc region comprising an immunoglobulin hinge region and CH2 and CH3 immunoglobulin heavy chain constant domains, wherein the second Fc region comprises amino acid substitution(s) at positions corresponding to positions 366,368, and/or 407 and of human IgG1 or IgG4 according to EU Index, wherein the amino acid substitutions are T366S, L368A, and/or Y407V.

In some embodiments, the second poly peptide chain further comprises a first Fc region linked to CH1, the first Fc region comprising an immunoglobulin hinge region and CH2 and CH3 immunoglobulin heavy chain constant domains, wherein the first Fc region comprises amino acid substitution(s) at positions corresponding to positions 366, 368, and/or 407 of human IgG1 or IgG4 according to EU Index, wherein the amino acid substitutions are T366S, L368A, and/or Y407V; and wherein the third polypeptide chain further comprises a second Fc region linked to CH1, the second Fc region comprising an immunoglobulin hinge region and CH2 and CH3 immunoglobulin heavy chain constant domains, wherein the second Fc region comprises amino acid substitution at position corresponding to position 366 of human IgG1 or IgG4 according to EU Index, wherein the amino acid substitution is T366W.

In some embodiments, the second polypeptide chain further comprises a first Fc region linked to CH1, the first Fc region comprising an immunoglobulin hinge region and CH2 and CH3 immunoglobulin heavy chain constant domains, wherein the first Fc region comprises amino acid substitutions at positions corresponding to positions 354 and 366 of human IgG1 or IgG4 according to EU Index, wherein the amino acid substitutions are S354C and T366W; and wherein the third polypeptide chain further comprises a second Fc region linked to Oil, the second Fc region comprising an immunoglobulin hinge region and CH2 and CH3 immunoglobulin heavy chain constant domains, wherein the second Fc region comprises amino acid substitutions at positions corresponding to positions 349, 366, 368, and 407 of human IgG1 or IgG4 according to EU Index, wherein the amino acid substitutions are Y349C, T366S, L368A, and Y407V. In some embodiments, the second polypeptide chain further comprises a first Fc region linked to CH1, the first Fc region comprising an immunoglobulin hinge region and CH2 and CH3 immunoglobulin heavy chain constant domains, wherein the first Fc region comprises amino acid substitutions at positions corresponding to positions 349,366,368, and 407 of human IgG1 or IgG4 according to EU Index, wherein the amino acid substitutions are Y349C, T366S, L368A, and Y407V; and wherein the third polypeptide chain further comprises a second Fc region linked to CH1, the second Fc region comprising an immunoglobulin hinge region and CH2 and CH3 immunoglobulin heavy chain constant domains, wherein the second Fc region comprises amino acid substitutions at positions corresponding to positions 3S4 and 366 of human IgG1 or IgG4 according to EU Index, wherein the amino acid substitutions are S354C and T366W. In some embodiments, the first and/or second Fc regions are human IgG1 Fc regions. In some embodiments, the first and/or second Fc regions are human IgG4 Fc regions.

In some embodiments, the second poly peptide chain further comprises a first Fc region linked to CH1, wherein the first Fc region is a human IgG4 Fc region comprising an immunoglobulin hinge region and CH2 and CH3 immunoglobulin heavy chain constant domains, wherein the first Fc region comprises amino acid substitutions at positions corresponding to positions 228,354,366, and 409 of human IgG4 according to EU Index, wherein the amino acid substitutions are S228P, S354C, T366W, and R409K; and wherein the third polypeptide chain further comprises a second Fc region linked to CH1, wherein the second Fc region is a human IgG4 Fc region comprising an immunoglobulin hinge region and CH2 and CH3 immunoglobulin heavy chain constant domains, wherein the second Fc region comprises amino acid substitutions at positions corresponding to positions 228, 349, 366, 368, 407, and 409 of human IgG4 according to EU Index, wherein the amino acid substitutions are S228P, Y349C, T366S, L368A, Y407V, and R409K. In some embodiments, the second polypeptide chain further comprises a first Fc region linked to CH1, wherein the first Fc region is a human IgG4 Fc region comprising an immunoglobulin hinge region and CH2 and CH3 immunoglobulin heavy chain constant domains, wherein the first Fc region comprises amino acid substitutions at positions corresponding to positions 228, 349, 366, 368, 407, and 409 of human IgG4 according to EU Index, wherein the amino acid substitutions are S228P, Y349C, T366S, L368A, Y407V, and R409K; and wherein the third polypeptide chain further comprises a second Fc region linked to CH1, wherein the second Fc region is a human IgG4 Fc region comprising an immunoglobulin hinge region and CH2 and CH3 immunoglobulin heavy chain constant domains, wherein the second Fc region comprises amino acid substitutions at positions corresponding to positions 228, 354, 366, and 409 of human IgG4 according to EU Index, wherein the amino add substitutions are S228P, S354C, T366W, and R409K.

In some embodiments, the second polypeptide chain further comprises a first Fc region linked to CH1, wherein the first Fc region is a human IgG4 Fc region comprising an immunoglobulin hinge region and CH2 and CH3 immunoglobulin heavy chain constant domains, wherein the first Fc region comprises amino acid substitutions at positions corresponding to positions 234, 235. 354, and 366 of human IgG4 according to EU index, wherein the amino acid substitutions are F234A, L235A, S354C, and T366W; and wherein the third polypeptide chain further comprises a second Fc region linked to CH1, wherein the second Fc region is a human IgG4 Fc region comprising an immunoglobulin hinge region and CH2 and CH3 immunoglobulin heavy chain constant domains, wherein the second Fc region comprises amino acid substitutions at positions corresponding to positions 234,235,349, 366.368, and 407 of human IgG4 according to EU Index, wherein the amino acid substitutions are F234A, L235A, Y349C, T366S, L368A, and Y407V. In some embodiments, the second polypeptide chain further comprises a first Fc region linked to CH1, wherein the first Fc region is a human IgG4 Fc region comprising an immunoglobulin hinge region and CH2 and CH3 immunoglobulin heavy chain constant domains, wherein the first Fc region comprises amino acid substitutions at positions corresponding to positions 234, 235, 349, 366.368, and 407 of human IgG4 according to EU Index, wherein the amino acid substitutions are F234A, L235A Y349C, T366S, L368A, and Y407V; and wherein the third polypeptide chain further comprises a second Fc region linked to CH1, wherein the second Fc region is a human IgG4 Fc region comprising an immunoglobulin hinge region and CH2 and CH3 immunoglobulin heavy chain constant domains, wherein the second Fc region comprises amino acid substitutions at positions corresponding to positions 234, 235, 354, and 366 of human IgG4 according to EU Index, wherein the amino acid substitutions are F234A, L235A, S354C, and T366W.

In some embodiments, the second polypeptide chain further comprises a first Fc region linked to CH1, wherein the first Fc region is a human IgG4 Fc region comprising an immunoglobulin hinge region and CH2 and CH3 immunoglobulin heavy chain constant domains, wherein the first Fc region comprises amino acid substitutions at positions corresponding to positions 228,234,235,354, 366, and 409 of human IgG4 according to EU Index, wherein the amino acid substitutions are S228P, F234A, L235A, S354C, T366W, and R409K; and wherein the third polypeptide chain further comprises a second Fc region linked to CH1, wherein the second Fc region is a human IgG4 Fc region comprising an immunoglobulin hinge region and CH2 and CH3 immunoglobulin heavy chain constant domains, wherein the second Fc region comprises amino acid substitutions at positions corresponding to positions 228, 234, 235, 349, 366, 368, 407, and 409 of human IgG4 according to EU Index, wherein the amino acid substitutions are S228P, F234A, L235A, Y349C, T366S, L368A, Y407V, and R409K. In some embodiments, the second polypeptide drain further comprises a first Fc region linked to CH1, wherein the first Fc region is a human IgG4 Fc region comprising an immunoglobulin hinge region and CH2 and CH3 immunoglobulin heavy chain constant domains, wherein the first Fc region comprises amino acid substitutions at positions corresponding to positions 228, 234.235, 349, 366, 368, 407, and 409 of human IgG4 according to EU Index, wherein the amino acid substitutions are S228P, F234A, L235A, Y349C, T366S, L368A, Y407V, and R409K; and wherein the third polypeptide chain further comprises a second Fc region linked to CH1, wherein the second Fc region is a human IgG4 Fc region comprising an immunoglobulin hinge region and CH2 and CH3 immunoglobulin heavy chain constant domains, wherein the second Fc region comprises amino acid substitutions at positions corresponding to positions 228, 234, 235, 354, 366, and 409 of human IgG4 according to EU Index, wherein the amino acid substitutions are S228P, F234A, L235A, S354C, T366W, and R409K.

In some embodiments, a binding protein of the present disclosure comprises one or more mutations to improve serum half-life (See e.g., Hinton, P. R. et al. (2006) J. Immunol 176(1):346-56). In some embodiments, the mutation comprises substitutions at positions corresponding to positions 428 and 434 of human IgG1 or IgG4 according to EU Index, wherein the amino acid substitutions are M428L and N434S. In some embodiments, the binding protein comprises a second polypeptide chain further comprising a first Fc region linked to CH1, the first Fc region comprising an immunoglobulin hinge region and CH2 and CH3 immunoglobulin heavy chain constant domains, and a third polypeptide chain further comprising a second Fc region linked to CH1, the second Fc region comprising an immunoglobulin hinge region and CH2 and CH3 immunoglobulin heavy chain constant domains, wherein the first and/or second Fc regions comprise amino acid substitutions at positions corresponding to positions 428 and 434 of human IgG1 or IgG4 according to EU Index, wherein the amino acid substitutions are M428L and N434S. In some embodiments, a binding protein of the present disclosure comprises knob and hole mutations and one or more mutations to improve serum half-life. In some embodiments, the first and/or second Fc regions are human IgG1 Fc regions. In some embodiments, the first and/or second Fc regions are human IgG4 Fc regions.

In some embodiments, a binding protein of the present disclosure comprises one or more mutations to improve stability, e.g., of the hinge region and/or dimer interface of IgG4 (See e.g., Spiess, C. et al (2013) J. Biol. Chem. 288:26583-26593). In some embodiments, the mutation comprises substitutions at positions corresponding to positions 228 and 409 of human IgG4 according to EU Index, wherein the amino acid substitutions are S228P and R409K. In some embodiments, the binding protein comprises a second polypeptide chain further comprising a first Fc region linked to $C_{H1}$, the first Fc region comprising an immunoglobulin hinge region and $C_{H2}$ and $C_{H3}$ immunoglobulin heavy drain constant domains, and a third polypeptide chain further comprising a second Fc region linked to $C_{H1}$, the second Fc region comprising an immunoglobulin hinge region and $C_{H1}$ and $C_{H3}$ immunoglobulin heavy chain constant domains; wherein the first and second Fc regions are human IgG4 Fc regions; and wherein the first and the second Fc regions each comprise amino acid substitutions at positions corresponding to positions 228 and 409 of human IgG4 according to EU Index, wherein the amino acid substitutions are S228P and R409K. In some embodiments, a binding protein of the present disclosure comprises knob and hole mutations and one or more mutations to improve stability. In some embodiments, the first and/or second Fc regions are human IgG4 Fc regions.

In some embodiments, a binding protein of the present disclosure comprises one or more mutations to improve purification, e.g., by modulating the affinity for a purification reagent. For example, it is known that heterodimeric binding proteins can be selectively-purified away from their homodimeric forms if one of the two Fc regions of the heterodimeric form contains mutation(s) that reduce or eliminate binding to Protein A, because the heterodimeric form will have an intermediate affinity for Protein A-based purification than either homodimeric form and can be selectively eluted from Protein A, e.g., by use of a different pH (See e.g., Smith, E. J, et al. (2015) Sci. Rep. 5:17943). In some embodiments, the mutation comprises substitutions at positions corresponding to positions 435 and 436 of human IgG1 or IgG4 according to EU Index, wherein the amino acid substitutions are H435R and Y436F. In some embodiments, the binding protein comprises a second polypeptide drain further comprising a first Fc region linked to $C_{H1}$, the first Fc region comprising an immunoglobulin hinge region and $C_{H2}$ and $C_{H3}$ immunoglobulin heavy chain constant domains, and a third polypeptide chain further comprising a second Fc region linked to $C_{H1}$, the second Fc region comprising an immunoglobulin hinge region and $C_{H2}$ and $C_{H3}$ immunoglobulin bean chain constant domains; and wherein only one of the first and the second Fc regions comprises amino acid substitutions at positions corresponding to positions 435 and 436 of human IgG1 or IgG4 according to EU Index, wherein the amino acid substitutions are H435R and Y436F. In some embodiments, a binding protein of the present disclosure comprises knob and bole mutations and one or more mutations to improve purification. In some embodiments, the first and/or second Fc regions are human IgG1 Fc regions. In some embodiments, the first and/or second Fc regions are human IgG4 Fc regions.

In some embodiments, a binding protein of the present disclosure comprises one or more mutations to improve serum half-life (See e.g., Hinton, P. R. et al. (2006) J. Immunol. 176(1):346-56). In some embodiments, the mutation comprises substitutions at positions corresponding to positions 428 and 434 of human IgG1 or IgG4 according to EU Index, wherein the amino acid substitutions are M428L and N434S. In some embodiments, the binding protein comprises a second polypeptide chain further comprising a first Fc region linked to CH1, the first Fc region comprising an immunoglobulin hinge region and CH2 and CH3 immunoglobulin heavy chain constant domains, and a third polypeptide chain further comprising a second Fc region linked to CH1, the second Fc region comprising an immunoglobulin hinge region and CH2 and CH3 immunoglobulin heavy chain constant domains, wherein the first and/or second Fc regions comprise amino acid substitutions at positions corresponding to positions 428 and 434 of human IgG1 or IgG4 according to EU Index, wherein the amino acid substitutions are M428L and N434S. In some embodiments, a binding protein of the present disclosure comprises knob and hole mutations and one or more mutations to improve serum half-life. In some embodiments, the first and/or second Fc regions are human IgG1 Fc regions. In some embodiments, the first and/or second Fc regions are human IgG4 Fc regions.

In some embodiments, a binding protein of the present disclosure comprises one or more mutations to reduce effector function, e.g., Fc receptor-mediated antibody-dependent cellular phagocytosis (ADCP), complement-dependent cytotoxicity (CDC), and/or antibody-dependent cellular cytotoxicity (ADCC). In some embodiments, the second polypeptide chain further comprises a first Fc region linked to $C_{H1}$, the first Fc region comprising an immunoglobulin hinge region and $C_{H2}$ and $C_{H3}$ immunoglobulin heavy chain constant domains; wherein the third polypeptide chain further comprises a second Fc region linked to $C_{H1}$, the second Fc region comprising an immunoglobulin hinge region and $C_{H2}$ and $C_{H3}$ immunoglobulin heavy chain constant domains; wherein the first and second Fc regions are human IgG1 Fc regions; and wherein the first and the second Fc regions each comprise amino acid substitutions at positions corresponding to positions 234 and 235 of human IgG1 according to EU Index, wherein the amino acid substitutions are L234A and L235A. In some embodiments, the Fc regions of the second and the third polypeptide chains are human IgG1 Fc regions, and wherein the Fc regions each comprise amino acid substitutions at positions corresponding to positions 234 and 235 of human IgG1 according to EU Index, wherein the amino acid substitutions are L234A and L235A. In some embodiments, the second polypeptide chain further comprises a first Fc region linked to $C_{H1}$, the first Fc region comprising an immunoglobulin hinge region and $C_{H2}$ and $C_{H3}$ immunoglobulin heavy chain constant domains; wherein the third polypeptide chain further comprises a second Fc region linked to $C_{H1}$, the second Fc region comprising an immunoglobulin hinge region and $C_{H2}$ and $C_{H3}$ immunoglobulin heavy chain constant domains; wherein the first and second Fc regions are human IgG1 Fc regions; and wherein the first and the second Fc regions each comprise amino acid substitutions at positions corresponding to positions 234,235, and 329 of human IgG1 according to EU Index, wherein the amino acid substitutions are L234A, L235A, and P329A. In some embodiments, the Fc regions of the second and the third polypeptide chains are human IgG1 Fc regions, and wherein the Fc regions each comprise amino acid substitutions at positions corresponding to positions 234, 235, and 329 of human IgG1 according to EU Index, wherein the amino acid substitutions are L234A, L235A, and P329A. In some embodiments, the Fc regions of the second and the third polypeptide chains are human IgG4 Fc regions, and the Fc regions each comprise amino acid substitutions at positions corresponding to positions 234 and 235 of human IgG4 according to EU Index, wherein the amino acid substitutions are F234A and L235A. In some embodiments, the binding protein comprises a second polypeptide chain further comprising a first Fc region linked to $C_{H1}$, the first Fc region comprising an immunoglobulin lunge region and $C_{H1}$ and $C_{H1}$ immunoglobulin heavy chain constant domains, and a third polypeptide chain further comprising a second Fc region linked to $C_{H1}$, the second Fc region comprising an immunoglobulin hinge region and $C_{H2}$ and $C_{H1}$ immunoglobulin heavy chain constant domains; and wherein the first and the second Fc regions each comprise amino acid substitutions at positions corresponding to positions 234 and 235 of human IgG4 according to EU Index, wherein the amino acid substitutions are F234A and L235A.

In some embodiments, a binding protein of the present disclosure comprises knob and hole mutations and one or more mutations to reduce effector function. In some embodiments, the first and or second Fc regions are human IgG1 Fc regions. In some embodiments, the first and/or second Fc regions are human IgG4 Fc regions. For further description of Fc mutations at position 329, see, e.g., Shields, R. L. et al. (2001) *J. Biol. Chem.* 276:6591-6604 and WO1999051642.

In some embodiments, the types of mutations described supra can be combined in any order or combination. For example, a binding protein of the present disclosure can comprise two or more of the "knob" and "hole" mutations, the one or more mutations to improve serum half-life, the one or more mutations to improve IgG4 stability, the one or more mutations to improve purification, and/or the one or more mutations to reduce effector function described supra.

In some embodiments, a binding protein of the present disclosure comprises an antibody fragment, including but not limited to antibody F(ab), F(ab')$_2$, Fab'-SH, Fv, or scFv fragments.

Assays

The present disclosure provides antigen binding proteins that bind human and/or cynomolgus CD38 polypeptides, induce T cell (e.g., CD4+ and/or CD8+ T cell) proliferation, and/or induce apoptosis of CD38+ cells. Exemplary assays for measuring these parameters and identifying such binding proteins are provided herein. For example, in some embodiments, binding affinity between a binding protein or antigen-binding fragment thereof and a purified CD38 polypeptide is measured by SPR (e.g., as described infra), and binding affinity between a binding protein or antigen-binding fragment thereof and a CD38 polypeptide expressed on the surface of a cell is measured by flow cytometry (e.g., as described infra).

In some embodiments, the antigen binding site of a binding protein of the present disclosure binds the human CD38 polypeptide comprising the amino acid sequence of SEQ ID NO:1 with an equilibrium dissociation constant ($K_D$) of 20 nM or less, 15 nM or less, 12 nM or less, 10 nM or less, 5 nM or less, 2 nM or less, 1 nM or less, or 0.8 nM or less, as measured by a flow cytometry assay using cells that express the human CD38 polypeptide comprising the amino acid sequence of SEQ ID NO:1 on their cell surface, e.g., as described infra. In some embodiments, the antigen binding site binds the cynomolgus monkey CD38 polypeptide comprising the amino acid sequence of SEQ ID NO:30 with an equilibrium dissociation constant ($K_D$) of 20 nM or less, 15 nM or less, 12 nM or less, 10 nM or less, 5 nM or less, 2 nM or less, 1 nM or less, or 0.75 nM or less, as measured by a flow cytometry assay using cells that express the cynomolgus monkey CD38 polypeptide comprising the amino acid sequence of SEQ ID NO:30 on their cell surface, e.g., as described infra. In some embodiments, the antigen binding site binds the human CD38 polypeptide comprising the amino acid sequence of SEQ ID NO:1 with an equilibrium dissociation constant ($K_D$) of 20 nM or less, 15 nM or less, 12 nM or less, 10 nM or less, 5 nM or less, 2 nM or less, 1 nM or less, or 0.83 nM or less, as measured by an SPR assay using the human CD38 polypeptide comprising the amino acid sequence of SEQ ID NO:1, e.g., as described infra. In some embodiments, the antigen binding site binds the cynomolgus monkey CD38 polypeptide comprising the amino acid sequence of SEQ ID NO:30 with an equilibrium dissociation constant ($K_D$) of 20 nM or less, 15 nM or less, 12 nM or less, 10 nM or less, 5 nM or less, 3.5 nM or less, 1.5 nM or less, or 1.0 nM or less, as measured by an SPR assay using the cynomolgus monkey CD38 polypeptide comprising the amino acid sequence of SEQ ID NO:30, e.g., as described infra. As demonstrated herein, in some embodiments, a binding protein of the present disclosure may possess one or more of the exemplary binding properties described herein. In some embodiments, the KD is measured at 4° C. or 25° C.

In some embodiments, a monospecific binding protein of the present disclosure possesses one or more of the following features: binds to the extracellular domain of a human CD38 poly peptide (e.g., comprising the amino acid sequence of SEQ ID NO: 1) as a purified protein, as assayed by SPR or ELISA; binds to the extracellular domain of a human CD38 polypeptide (e.g., comprising the amino acid sequence of SEQ ID NO:1) as a purified protein with a $K_D$ of 20 nM or less, 15 nM or less, 12 nM or less, 10 nM or less, 5 nM or less, 2 nM or less, or 1.5 nM or less, as assayed by SPR or ELISA; binds to the extracellular domain of a human CD38 polypeptide (e.g., comprising the amino acid sequence of SEQ ID NO:1) expressed on the surface of a cell, as assayed by flow cytometry; binds to the extracellular domain of a human CD38 polypeptide (e.g., comprising the amino acid sequence of SEQ ID NO:1) expressed on the surface of a cell with an apparent $K_D$ of 20 nM or less, 15 nM or less, 12 nM or less, 10 nM or less, 5 nM or less, 2 nM or less, or 1 nM or less, as assayed by flow cytometry; binds to the extracellular domain of a cynomolgus monkey CD38 polypeptide (e.g., comprising the amino acid sequence of SEQ ID NO:30) as a purified protein, as assayed by SPR or ELISA; binds to the extracellular domain of a cynomolgus monkey CD38 polypeptide (e.g., comprising the amino acid sequence of SEQ ID NO:30) as a purified protein with a $K_D$ of 20 nM or less, 15 nM or less, 12 nM or less, 10 nM or less, 5 nM or less, 2 nM or less, 1 nM or less, as assayed by SPR or ELISA; binds to the extracellular domain of a cynomolgus monkey CD38 poly peptide (e.g., comprising the amino acid sequence of SEQ ID NO:30) expressed on the surface of a cell, as assayed by flow cytometry; binds to the extracellular domain of a cynomolgus monkey CD38 polypeptide (e.g., comprising the amino acid sequence of SEQ ID NO:30) expressed on the surface of a cell with an apparent $K_D$ of 20 nM or less, 15 nM or less, 12 nM or less, 10 nM or less, 5 nM or less, 2 nM or less, 1 nM or less, as assayed by flow cytometry; binds (o the extracellular domain of a human isoform E CD38 polypeptide (e.g., comprising the amino acid sequence of SEQ ID NO:105) as a purified protein, as assayed by SPR or ELISA, binds to the extracellular domain of a human isoform E CD38 polypeptide (e.g., comprising the amino acid sequence of SEQ ID NO:105) expressed on the surface of a cell, as assayed by flow cytometry, induces apoptosis or antibody-dependent cellular cytotoxicity (ADCC) of a cell expressing CD38 on its cell surface; and has one or more mutations (e.g., in an Fc region) resulting in decreased binding to FcγRI and/or FcγRII, as compared to the same binding protein without the one or more mutations. In some embodiments, a binding protein of the present disclosure binds a CD38 poly peptide (e.g., human or cynomolgus monkey) expressed on the surface of a cell with an EC50 of 20 nM or less, 15 nM or less, 12 nM or less, 10 nM or less, 5 nM or less, 2 nM or less, or 1 nM or less, as assayed by flow cytometry. In some embodiments, a binding protein of the present disclosure binds a CD38 polypeptide (e.g., human or cynomolgus monkey) as a purified protein with an EC50 of 20 nM or less, 15 nM or less, 12 nM or less, 10 nM or less, 5 nM or less, 2 nM or less, or 1 nM or less, as assayed by ELISA. In some embodiments, the KD is measured at 4° C., or 25° C.

In some embodiments, a trispecific binding protein of the present disclosure possesses one or more of the following features, induces T cell (e.g., CD4+ and/or CD8+ T cell) proliferation; induces 7 cell (e.g., CD4+ and/or CD8+ T cell) expression of Bcl-xL, induces apoptosis of CD38+ cells (e.g., as measured by Annexin V staining and/or propidium iodide uptake); binds to CD38 expressed on the surface of a cell and one or more T cell target antigen(s) expressed on the surface of a T cell; binds to CD38 expressed on the surface of a cell, CD28 expressed on the surface of a T cell, and CD3 expressed on the surface of a T cell; stimulates activation of the T cell receptor (e.g., as measured by CD69 expression); induces costimulation of T cell receptor signaling (e.g., as mediated by CD28); has one or more mutations (e.g., in an Fc region) resulting in decreased induction of cytokine release (e.g., IFN-γ, IL-2, and/or TNF-α) by PBMCs, as compared to the same binding protein without the one or more mutations; induces cytokine release (e.g., IFN-γ and/or IL-6) by PBMCs in the presence of a CD38+ target cell (e.g., as measured by immunoassay); binds to the extracellular domain of a human CD38 polypeptide (e.g., comprising the amino acid sequence of SEQ ID NO:1) as a purified protein, as assayed by SPR or ELISA; binds to the extracellular domain of a human CD38 polypeptide (e.g., comprising the amino acid sequence of SEQ ID NO:1) as a purified protein with a $K_D$ of 1.5 nM or less, as assayed by SPR or ELISA; binds to the extracellular domain of a human CD38 polypeptide (e.g. comprising the amino acid sequence of SEQ ID NO:1) expressed on the surface of a cell, as assayed by flow cytometry; binds to the extracellular domain of a human CD38 polypeptide (e.g., comprising the amino acid sequence of SEQ ID NO:1) expressed on the surface of a cell with an apparent $K_D$ of 12 nM or less, as assayed by flow cytometry, binds to the extracellular domain of a cynomolgus monkey CD38 polypeptide (e.g., comprising the amino acid sequence of SEQ ID NO:30) as a purified protein, as assayed by SPR or ELISA; binds to the extracellular domain of a cynomolgus monkey CD38 poly peptide (e.g., comprising the amino acid sequence of SEQ ID NO:30) as a purified protein with a $K_D$ of 3.5 nM or less, as assayed by SPR or ELISA; binds to the extracellular domain of a cynomolgus monkey CD38 polypeptide (e.g., comprising the amino acid sequence of SEQ ID NO:30) expressed on the surface of a cell, as assayed by flow cytometry; binds to the extracellular domain of a cynomolgus monkey CD38 polypeptide (e.g., comprising the amino acid sequence of SEQ ID NO:30) expressed on the surface of a cell with an apparent $K_D$ of 7.5 nM or less, as assayed by flow cytometry; binds to the extracellular domain of a human isoform E CD38 polypeptide (e.g., comprising the amino acid sequence of SEQ ID NO:105) as a purified protein, as assayed by SPR or ELISA, binds to the extracellular domain of a human isoform E CD38 polypeptide (e.g., comprising the amino acid sequence of SEQ ID NO:105) expressed on the surface of a cell, as assayed by flow cytometry; induces apoptosis or antibody-dependent cellular cytotoxicity (ADCC) of a cell expressing CD38 on its cell surface; and has one or more mutations (e.g., in an Fc region) resulting in decreased binding to FcγRI and/or FcγRII, as compared to the same binding protein without the one or more mutations. In some embodiments, a binding protein of the present disclosure binds a CD38 poly peptide (e.g., human or cynomolgus monkey) expressed on the surface of a cell with an EC50 of 20 nM or less, 15 nM or less, 12 nM or less, 10 nM or less, 5 nM or less, 2 nM or less, or 1 nM or less, as assayed by flow cytometry. In some embodiments, a binding protein of the present disclosure binds a CD38 polypeptide (e.g., human or cynomolgus monkey) as a purified protein with an EC50 of 20 nM or less, 15 nM or less, 12 nM or less, 10 nM or less, 5 nM or less, 2 nM or less, or 1 nM or less, as assayed by ELISA.

Nucleic Acids

Standard recombinant DNA methodologies are used to construct the polynucleotides that encode the polypeptides which form the binding proteins, incorporate these polynucleotides into recombinant expression vectors, and introduce such vectors into host cells. See e.g., Sambrook et ah, 2001, MOLECULAR CLONING: A LABORATORY MANUAL (Cold Spring Harbor Laboratory Press, 3rd ed). Enzymatic reactions and purification techniques may be performed according to manufacturer's specifications, as commonly accomplished in the art, or as described herein. Unless specific definitions are provided, the nomenclature utilized in connection with, and the laboratory procedures and techniques of, analytical chemistry, synthetic organic chemistry, and medicinal and pharmaceutical chemistry described herein are those well-known and commonly used in the art. Similarly, conventional techniques may be used for chemical syntheses, chemical analyses, pharmaceutical preparation, formulation, delivery, and treatment of patients.

Other aspects of the present disclosure relate to isolated nucleic acid molecules comprising a nucleotide sequence encoding any of the binding proteins described herein. In some embodiments, the isolated nucleic acid molecules comprise a sequence that is at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to SEQ ID NOs:60-83 and/or shown in Table J.

Certain aspects of the present disclosure relate to kits of polynucleotides. In some embodiments, one or more of the polynucleotides is a vector (e.g., an expression vector). The kits may find use, inter alia, in producing one or more of the binding proteins described herein, e.g., a trispecific binding protein of the present disclosure. In some embodiments, the kit comprises one, two, three, or four polynucleotides shown in Table J (e.g., of mAb2×CD28sup×CD3mid IgG4 FALA, mAb2×CD28sup×CD3mid IgG1LALA P329A, mAb2× CD28sup×CD3mid IgG1 NNSA, mAb6CD28sup×CD3mid IgG4 FALA, mAb6×CD28sup×CD3mid IgG1LALA P329A, or mAb6×CD28sup×CD3mid IgG1 NNSA). In some embodiments, a kit of polynucleotides comprises: a first polynucleotide comprising the sequence of SEQ ID NO:73, a second polynucleotide comprising the sequence of SEQ ID NO:72, a third polynucleotide comprising the sequence of SEQ ID NO:74, and a fourth polynucleotide comprising the sequence of SEQ ID NO:75. In some embodiments, a kit of polynucleotides comprises: a first polynucleotide comprising the sequence of SEQ ID NO:73, a second polynucleotide comprising the sequence of SEQ ID NO:76, a third poly nucleotide comprising the sequence of SEQ ID NO:77, and a fourth polynucleotide comprising the sequence of SEQ ID NO:75. In some embodiments, a kit of polynucleotides comprises, a first polynucleotide comprising the sequence of SEQ ID NO:73, a second polynucleotide comprising the sequence of SEQ ID NO:78, a third polynucleotide comprising the sequence of SEQ ID NO:79, and a fourth polynucleotide composing the sequence of SEQ ID NO:75. In some embodiments, a kit of polynucleotides comprises: a first polynucleotide comprising the sequence of SEQ ID NO:73, a second polynucleotide comprising the sequence of SEQ ID NO:72, a third polynucleotide comprising the sequence of SEQ ID NO:80, and a fourth polynucleotide comprising the sequence of SEQ ID NO:81. In some embodiments, a kit of polynucleotides comprises: a first polynucleotide comprising the sequence of SEQ ID NO:73, a second polynucleotide comprising the sequence of SEQ ID NO:76, a third poly nucleotide comprising the sequence of SEQ ID NO:82, and a fourth polynucleotide comprising the sequence of SEQ ID NO:81. In some embodiments, a kit of polynucleotides comprises: a first polynucleotide comprising the sequence of SEQ ID NO:73, a second polynucleotide comprising the sequence of SEQ ID NO:78, a third polynucleotide comprising the sequence of SEQ ID NO:83, and a fourth polynucleotide comprising the sequence of SEQ ID NO:81.

In some embodiments, the isolated nucleic acid is operably linked to a heterologous promoter to direct transcription of the binding protein-coding nucleic acid sequence. A promoter may refer to nucleic acid control sequences which direct transcription of a nucleic acid. A first nucleic acid sequence is operably linked to a second nucleic acid sequence when the first nucleic acid sequence is placed in a functional relationship with the second nucleic acid sequence. For instance, a promoter is operably linked to a coding sequence of a binding protein if the promoter affects the transcription or expression of the coding sequence. Examples of promoters may include, but are not limited to, promoters obtained from the genomes of viruses (such as polyoma vims, fowlpox virus, adenovirus (such as Adenovirus 2), bovine papilloma virus, avian sarcoma virus, cytomegalovirus, a retrovirus, hepatitis-B virus, Simian Virus 40 (SV40), and the like), from heterologous eukaryotic promoters (such as the actin promoter, an immunoglobulin promoter, from heat-shock promoters, and the like), the CAG-promoter (Niwa et al., Gene 108(2): 193-9.1991), the phosphoglycerate kinase (PGK)-promoter, a tetracycline-inducible promoter (Masui et al., Nucleic Acids Res. 33:e43, 2005), the lac system, the trp system, the tac system, the trc system, major operator and promoter regions of phage lambda, the promoter for 3-phosphoglycerate kinase, the promoters of yeast acid phosphatase, and the promoter of the yeast alpha-mating factors. Polynucleotides encoding binding proteins of the present disclosure may be under the control of a constitutive promoter, an inducible promoter, or any other suitable promoter described herein or other suitable promoter that will be readily recognized by one skilled in the art.

In some embodiments, the isolated nucleic acid is incorporated into a vector. In some embodiments, the vector is an expression vector. Expression vectors may include one or more regulatory sequences operatively linked to the polynucleotide to be expressed. The term "regulatory sequence" includes promoters, enhancers and other expression control elements (e.g., polyadenylation signals). Examples of suitable enhancers may include, but are not limited to, enhancer sequences from mammalian genes (such as globin, elastase, albumin, α-fetoprotein, insulin and the like), and enhancer sequences from a eukaryotic cell virus (such as SV40 enhancer on the late side of the replication origin (bp 100-270), the cytomegalovirus early promoter enhancer, the polyoma enhancer on tire late side of the replication origin, adenovirus enhancers, and the like). Examples of suitable vectors may include, for example, plasmids, cosmids, episomes, transposons, and viral vectors (e.g., adenoviral, vaccinia viral, Sindbis-viral, measles, herpes viral, lentiviral, retroviral, adeno-associated viral vectors, etc.). Expression vectors can be used to transfect host cells, such as, for example, bacterial cells, yeast cells, insect cells, and mammalian cells. Biologically functional viral and plasmid DMA vectors capable of expression and replication in a host are known in the art, and can be used to transfect any cell of interest.

Other aspects of the present disclosure relate to a vector system comprising one or more vectors encoding a first, second, third, and fourth polypeptide chain of any of the binding proteins described herein. In some embodiments, the vector system comprises a first vector encoding the first poly peptide chain of the binding protein, a second vector encoding the second polypeptide chain of the binding protein, a third vector encoding the third polypeptide chain of the binding protein, and a fourth vector encoding the fourth polypeptide chain of the binding protein. In some embodiments, the vector system comprises a first vector encoding the first and second polypeptide chains of the binding protein, and a second vector encoding the third and fourth polypeptide chains of the binding protein. In some embodiments, the vector system comprises a first vector encoding the first and third polypeptide chains of the binding protein, and a second vector encoding the second and fourth polypeptide chains of the binding protein. In some embodiments, the vector system comprises a first vector encoding the first and fourth poly peptide chains of the binding protein, and a second vector encoding the second and third polypeptide chains of the binding protein. In some embodiments, the vector system comprises a first vector encoding the first, second, third, and fourth polypeptide chains of the binding protein. The one or more vectors of the vector system may be any of the vectors described herein. In some embodiments, the one or more vectors are expression vectors.

Isolated Host Cells

Other aspects of the present disclosure relate to an isolated host cell comprising one or more isolated polynucleotides, polynucleotide kits, vectors, and/or vector systems described herein. In some embodiments, the host cell is a bacterial cell (e.g., an *E. coli* cell). In some embodiments, the host cell is a yeast cell (e.g., an *S. cerevisiae* cell). In some embodiments, the host cell is an insect cell. Examples of insect host cells may include, for example, *Drosophila* cells (e.g., S2 cells), *Trichoplusia ni* cells (e.g., High Five™ cells), and *Spodoptera frugiperda* cells (e.g., Sf21 or Sf9 cells). In some embodiments, the host cell is a mammalian cell Examples of mammalian host cells may include, for example, human embryonic kidney cells (e.g., 293 or 293 cells subcloned for growth in suspension culture), Expi293™ cells, CHO cells, baby hamster kidney cells (e.g., BHK, ATCC CCL 10), mouse sertoli cells (e.g., TM4 cells), monkey kidney cells (e.g., CV1 ATCC CCL 70), African green monkey kidney cells (e.g., VERO-76, ATCC CRL-1587), human cervical carcinoma cells (e.g., HE1A, ATCC CCL 2), canine kidney cells (e.g. MDCK, ATCC CCL 34), buffalo rat liver cells (e.g., BRL 3A, ATCC CRL 1442), human lung cells (e.g., W138, ATCC CCL 75), human liver cells (e.g., Hep G2, HB 8065), mouse mammary tumor cells (e.g., MMT 060562, ATCC CCL51), TRI cells, MRC 5 cells, FS4 cells, a human hepatoma line (e.g., Hep G2), and myeloma cells (e.g., NS0 and Sp2/0 cells).

Other aspects of the present disclosure relate to a method of producing any of the binding proteins described herein. In some embodiments, the method includes a) culturing a host cell (e.g., any of the host cells described herein) comprising an isolated nucleic acid, vector, and/or vector system (e.g., any of the isolated nucleic acids, vectors, and/or vector systems described herein) under conditions such that the host cell expresses the binding protein; and b) isolating the binding protein from the host cell. Methods of culturing host cells under conditions to express a protein are well known to one of ordinary skill in the art. Methods of isolating proteins from cultured host cells are well known to one of ordinary skill in the art, including for example, by affinity chromatography (e.g., two step affinity chromatography comprising protein A affinity chromatography followed by size exclusion chromatography).

In some embodiments, a binding protein of the present disclosure is purified by protein A affinity chromatography, kappa light chain affinity chromatography (e.g., using a KappaSelect resin according to manufacturer's instructions; GE Healthcare), and optionally lambda light chain affinity chromatography (e.g., using a LambdaFabSelect resin according to manufacturer s instructions; GE Healthcare). In some embodiments, a binding protein of the present disclosure is purified by Protein A affinity chromatography, lambda light chain affinity chromatography (e.g., using a LambdaFabSelect resin according to manufacturer's instructions; GE Healthcare), and optionally kappa light chain affinity chromatography (e.g., using a KappaSelect resin according to manufacturer's instructions; GE Healthcare). In some embodiments, the binding protein comprises two Fc regions, each comprising a $C_{H3}$ domain, and only one of the $C_{H3}$ domains comprises amino acid substitutions at positions corresponding to positions 435 and 436 of human IgG1 or IgG4 according to EU Index, wherein the amino acid substitutions are H435R and Y436F. In some embodiments, a binding protein of the present disclosure is purified by protein A affinity chromatography, then kappa light chain affinity chromatography (e.g., using a KappaSelect resin according to manufacturer s instructions; GE Healthcare), then optionally lambda light chain affinity chromatography (e.g. using a LambdaFabSelect resin according to manufacturer's instructions; GE Healthcare) in sequence. In some embodiments, a binding protein of the present disclosure is purified by Protein A affinity chromatography, then lambda light chain affinity chromatography (e.g., using a Lambda-FabSelect resin according to manufacturer's instructions; GE Healthcare), then optionally kappa light drain affinity chromatography (e.g., using a KappaSelect resin according to manufacturer's instructions; GE Healthcare) in sequence. For example, in some embodiments, the binding protein is contacted with Protein A, eluted from Protein A under conditions suitable for isolating the binding protein away from binding proteins comprising either 0 or 2 $C_{H3}$ domains comprising the amino acid substitutions are H435R and Y436F, contacted with a kappa light chain affinity medium (e.g., as used in the KappaSelect resin; GE Healthcare), and eluted from the kappa light chain affinity medium under conditions suitable for isolating the binding protein aw ay from binding proteins comprising only lambda $C_L$ domains (e.g., according to manufacturer's instructions) Conditions suitable for the Protein A elution are known in the art, including without limitation a stepwise elution gradient from pH4.5-2.8. In some embodiments. Protein A or a Protein A variant useful for protein purification is employed. In some embodiments, the Protein A is attached to a substrate or resin, e.g., as pan of a chromatography medium. In some embodiments, after elution from the kappa light chain affinity medium, the binding protein is contacted with a lambda light chain affinity medium (e.g., as used in the Lambda-FabSelect resin; GE Healthcare), and eluted from the lambda light chain affinity medium under conditions suitable for isolating the binding protein away from binding proteins comprising only kappa $C_L$ domains (e.g., according to manufacturer's instructions). In some embodiments, a binding protein of the present disclosure is detected using H1C chromatography. In some embodiments, the binding protein comprises: a first polypeptide chain that comprises a lambda $C_L$ domain; a $C_{H3}$ domain of a second polypeptide chain that comprises amino acid substitutions at positions corresponding to positions 354 and 366 of human IgG1 or IgG4 according to EU Index, wherein the amino acid substitutions are S354C and T366W; a $C_{H3}$ domain of a third polypeptide chain that comprises amino acid substitutions at positions corresponding to positions 349, 366, 368, 407, 435, and 436 of human IgG1 or IgG4 according to EU Index, wherein the amino acid substitutions are Y349C, T366S, L368A, Y407V, H435R, and Y436F; and a fourth polypeptide chain that comprises a kappa $C_L$ domain. In some embodiments, the binding protein is produced by a host cell. In some embodiments, the binding protein is purified from a cell culture medium or host cell extract. In some embodiments, the binding proteins are secreted by a host cell or produced and extracted from a host cell (e.g., before being contacted with Protein A). In some embodiments, the binding protein is in a cell culture medium or host cell extract when contacted with Protein A. In some embodiments, the binding protein is purified aw ay from other binding proteins, polypeptides, and/or other cellular components.

III. Trispecific Binding Proteins

In some embodiments, the binding protein of the disclosure is a trispecific and/or trivalent binding protein comprising four polypeptide chains that form three antigen binding sites that bind one or more (e.g., three) different antigen targets or target proteins, in some embodiments, a first polypeptide chain comprises a structure represented by the formula:

$$V_{L2}\text{-}L_1\text{-}V_{L1}\text{-}L_2\text{-}C_L \quad [\text{I}]$$

and a second polypeptide chain comprises a structure represented by the formula:

$$V_{H1}\text{-}L_3\text{-}V_{H2}\text{-}L_4\text{-}C_{H1}\text{-hinge-}C_{H2}\text{-}C_{H3} \quad [\text{II}]$$

and a third polypeptide chain comprises a structure represented by the formula:

$$V_{H3}\text{-}C_{H1}\text{-hinge-}C_{H2}\text{-}C_{H3} \quad [\text{III}]$$

and a fourth polypeptide chain comprises a structure represented by the formula:

$$V_{L3}\text{-}C_L \quad [\text{IV}]$$

wherein:
  $V_{L1}$ is a first immunoglobulin light chain variable domain;
  $V_{L2}$ is a second immunoglobulin light chain variable domain;
  $V_{L3}$ is a third immunoglobulin light chain variable domain;
  $V_{H1}$ is a first immunoglobulin heavy chain variable domain;
  $V_{H2}$ is a second immunoglobulin heavy chain variable domain;

V$_{H3}$ is a third immunoglobulin heavy chain variable domain;

C$_L$ is an immunoglobulin light chain constant domain;

C$_{H1}$ is an immunoglobulin C$_{H1}$ heavy chain constant domain;

C$_{H2}$ is an immunoglobulin C$_{H2}$ heavy chain constant domain;

C$_{H3}$ is an immunoglobulin C$_{H3}$ heavy chain constant domain;

hinge is an immunoglobulin hinge region connecting the C$_{H1}$ and C$_{H2}$ domains; and L$_1$, L$_2$, L$_3$ and L$_4$ are amino acid linkers;

wherein the polypeptide of formula I and the polypeptide of formula II form a cross-over light chain-heavy chain pair. In some embodiments, the first polypeptide chain and the second polypeptide chain have a cross-over orientation that forms two distinct antigen binding sites. As described above, the second and third polypeptide chains include an Fc region (e.g., comprising the hinge-C$_{H2}$-C$_{H3}$ domains). In some embodiments, one or both Fc regions are human IgG4 Fc regions comprising amino acid substitutions at positions corresponding to positions 233-236 of human IgG4 according to EU Index. In some embodiments, the amino acid substitutions are E233P, F234V, L235A, and a deletion at 236. In some embodiments, the Fc regions are human IgG4 Fc regions comprising amino acid mutations at substitutions corresponding to positions 228, 233-236, and/or 409 of human IgG4 according to EU Index. In some embodiments, the amino acid mutations are S228P; E233P, F234V, L235A, and a deletion at 236; and/or R409K. In some embodiments, one or both Fc regions are human IgG1 Fc regions comprising one or more amino acid substitutions at positions corresponding to positions 234,235, and/or 329 of human IgG1 according to EU index. In some embodiments, the amino acid substitutions are L234A, L235A, and/or P329A. In some embodiments, the Fc regions are human IgG1 Fc regions comprising amino acid substitutions at positions corresponding to positions 298, 299, and/or 300 of human IgG1 according to EU Index. In some embodiments, the amino acid substitutions are S298N, T299A, and/or Y300S.

In some embodiments, the binding protein of the disclosure is a trispecific and/or trivalent binding protein comprising four polypeptide chains that form three antigen binding sites that bind one or more (e.g., three) different antigen targets or target proteins. In some embodiments, at least one of the antigen binding sites binds a GD38 polypeptide (e.g., the extracellular domain of human and/or cynomolgus monkey CD38 polypeptides). In some embodiments, a first polypeptide chain comprises a structure represented by the formula:

$$V_{L2}\text{-}L_1\text{-}V_{L1}\text{-}L_2\text{-}C_L \quad \text{[I]}$$

and a second poly peptide chain comprises a structure represented by the formula:

$$V_{H1}\text{-}L_3\text{-}V_{H2}\text{-}L_4\text{-}C_{H1} \quad \text{[II]}$$

and a third polypeptide chain comprises a structure represented by the formula:

$$V_{H3}\text{-}C_{H1} \quad \text{[III]}$$

and a fourth polypeptide chain comprises a structure represented by the formula:

$$V_{L3}\text{-}C_1 \quad \text{[IV]}$$

wherein:

V$_{L1}$ is a first immunoglobulin light chain variable domain;

V$_{L2}$ is a second immunoglobulin light chain variable domain;

V$_{L3}$ is a third immunoglobulin light chain variable domain;

V$_{H1}$ is a first immunoglobulin heavy chain variable domain;

V$_{H2}$ is a second immunoglobulin heavy chain variable domain;

V$_{H3}$ is a third immunoglobulin heavy chain variable domain;

C$_L$ is an immunoglobulin light chain constant domain;

C$_{H1}$ IS an immunoglobulin C$_{H1}$ heavy chain constant domain; and

L$_1$, L$_2$, L$_3$ and L$_4$ are amino acid linkers;

and wherein the polypeptide of formula I and the polypeptide of formula U form a cross-over light chain-heavy chain pair. In some embodiments, the second and the third polypeptide chain further comprise an Fc region linked to C$_{H1}$, the Fc regions comprising an immunoglobulin hinge region and C$_{H2}$ and C$_{H3}$ immunoglobulin heavy chain constant domains. In some embodiments, one or both Fc regions are human IgG4 Fc regions comprising amino acid substitutions at positions corresponding to positions 233-236 of human IgG4 according to EU Index. In some embodiments, the amino acid substitutions are E233P, F234V, L235A, and a deletion at 236. In some embodiments, the Fc regions are human IgG4 Fc regions comprising amino acid mutations at substitutions corresponding to positions 228, 233-236, and/or 409 of human IgG4 according to EU Index. In some embodiments, the amino acid mutations are S228P; E233P, F234V, L235A, and a deletion at 236; and/or R409K. In some embodiments, one or both Fc regions are human IgG1 Fc regions comprising one or more amino acid substitutions at positions corresponding to positions 234,235, and/or 329 of human IgG1 according to EU Index. In some embodiments, the amino acid substitutions are L234A, L235A, and or P329A. In some embodiments, the Fc regions are human IgG1 Fc regions comprising amino acid substitutions at positions corresponding to positions 298,299, and/or 300 of human IgG1 according to EU Index. In some embodiments, the amino acid substitutions are S298N, T299A, and/or Y300S.

In some embodiments, the VH1 and VL1 form a binding pair and form a first antigen binding site. In some embodiments, the VH2 and VL2 form a binding pair and form a second antigen binding site. In some embodiments, the VH3 and VL3 form a binding pair and form a third antigen binding site. The binding proteins can also be used for cell activation, tumor targeting, neutralization of cytokine activities, neutralization of viral infection, combination of multiple signaling events, to treat cancer, arthritis, and/or inflammatory disorders. For example, in some embodiments, a binding protein specifically binds one, two, or three antigen targets selected from A2AR, APRIL, ATPDase, BAFF, BAFFR, BCMA, BlyS, BIX, BTLA, B7DC, B7H1, B7H4 (also known as VTCN1), B7H5, B7H6, B7H7, B7RP1, B7-4, C3, C5, CCL2 (also known as MCP-1), CCL3 (also known as MIP-1a), CCL4 (also know n as MIP-1b), CCL5 (also known as R ANTES), CCL7 (also known as MCP-3), CCL8 (also known as mcp-2), CCL11 (also known as eotaxin), CCL15 (also known as MIP-1d), CCL17 (also known as TARC), CCL19 (also known as MIP-3b), CCL20 (also known as MIP-3a), CCL21 (also known as MIP-2), CCL24 (also known as MPIF-2/eotaxin-2), CCL25 (also known as TECK), CCL26 (also known as eotaxin-3), CCR3, CCR4, CD3, CD19, CD20, CD23 (also known as FCER2, a receptor for IgE), CD24, CD27, CD28, CD38, CD39, CD40, CD70, CD80 (also known as B7-1), CD86 (also known as B7-2), CD122, CD137 (also known as 41BB), CD137L, CD152 (also known as CTLA4), CD154 (also known as CD40L), CD160, CD272, CD273 (also known as PDL2), CD274 (also known as PDL1), CD275 (also known as B7H2), CD276 (also known as B7H3), CD278 (also known as ICOS), CD279 (also known as PD-1), CDH1 (also known as E-cadherin), chitinase, CLEC9, CLEC91, CRTH2, CSF-1 (also known as M-CSF), CSF-2 (also known as GM-CSF), CSF-3 (also known as GCSF), CX3CL1 (also known as SCYD1), CXCL12 (also known as SDF1), CXCL13, CXCR3, DNGR-1, ectonucleoside triphosphate diphosphohydrolase 1, EGFR, ENTPD1, FCER1A, FCER1, FLAP, FOLH1, Gi24, GITR, GITRL, GM-CSF, Her2, HHLA2, HMGB1, HVEM, ICOSLG, IDO, IFNα, IgE, IGF1R, IL2Rbeta, IL1, IL1A, IL1B, IL1F10, IL2, IL4, IL4Ra, IL5, IL5R, IL6, IL7, IL7Ra, IL8, IL9, IL9R, IL10, rhIL10, IL12, IL13, IL13Ra1, IL13Ra2, IL15, IL17, IL17Rb (also known as a receptor for IL25), IL18, IL22, IL23, IL25, IL27, IL33, IL35, ITGB4 (also known as b4 integrin), ITK, KIR, LAG3, LAMP1, leptin, LPFS2, MHC class II, NCR3LG1, NKG2D, NTPDase-1, OX40, OX40L, PD-1H, platelet receptor, PROM1, S152, SISP1, SLC, SPG64, ST2 (also known as a receptor for IL33), STEAP2, Syk kinase, TACI, TDO, T14, TIGIT, TIM3, TLR, TLR2, TLR4, TLR5, TLR9, TMEF1, TNFa, TNFRSF7, Tp55, TREM1, TSLP (also known as a co-receptor for IL7Ra), TSLPR, TWEAK, VEGF, VISTA, Vstm3, WUCAM and XCR1 (also known as GPR5/CCXCR1). In some embodiments, one or more of the above antigen targets are human antigen targets.

In some embodiments, one of the three antigen binding sites binds a CD3 polypeptide (e.g., a human CD3 polypeptide), one of the three antigen binding sites binds a CD28 polypeptide (e.g., a human CD28 polypeptide), and one of the three antigen binding sites binds a third polypeptide. In some embodiments, the antigen binding site that specifically binds an antigen target other than CD3 or CD28 binds an antigen target selected from A2AR, APRIL, ATPDase, BAPF, BAFFR, BCMA, BlyS, BTK, BTLA, B7DC, B7H1, B7H4 (also known as VTCN1), B7H5, B7H6, B7H7, B7RP1, B7-4, C3, C5, CCL2 (also known as MCP-1), CCL3 (also known as MIP-1a), CCL4 (also known as MIP-1b), CCL5 (also known as RANTES), CCL7 (also known as MCP-3), CCL8 (also known as mcp-2), CCL11 (also known as eotaxin), CCL15 (also known as MIP-1d), CCL17 (also known as TARC), CCL19 (also known as MIP-3b), CCL20 (also known as MIP-3a), CCL21 (also known as MIP-2), CCL24 (also known as MPIF-2/eotaxin-2), CCL25 (also known as TECK), CCL26 (also known as eotaxin-3), CCR3, CCR4, CD19, CD20, CD23 (also known as FCER2, a receptor for IgE), CD24, CD27, CD38, CD39, CD40, CD70, CD80 (also known as B7-1), CD86 (also known as B7-2), CD122, CD137 (also known as 41BB), CD137L, CD152 (also known as CTLA4), CD154 (also known as CD40L), CD160, CD272, CD273 (also known as PDL2), CD274 (also known as PDL1), CD275 (also known as B7H2), CD276 (also known as B7H3), CD278 (also known as ICOS), CD279 (also known as PD-1), CDH1 (also known as E-cadhenn), chitinase, CLEC9, CLEC91, CRTH2, CSF-1 (also known as M-CSF), CSF-2 (also known as GM-CSF), CSF-3 (also known as GCSF), CX3CL1 (also known as SCYD1), CXCL12 (also known as SDF1), CXCL13, CXCR3, DNGR-1, ectonucleoside triphosphate diphosphohydrolase 1, EGFR, ENTPD1, FCER1A, FCER1, FLAP, FOLH1, Gi24, GITR, GITRL, GM-CSF, Her2, HHLA2, HMGB1, HVEM, ICOSLG, IDO, IFNα, IgE, IGF1R, IL2Rbeta, IL1, IL1A, IL1B, IL1F10, IL2, IL4, IL4Ra, IL5, IL5R, IL6, IL7, IL7Ra, IL8, IL9, IL9R, IL10, rhIL10, IL12, IL13, IL13Ra1, IL13Ra2, IL15, IL17, IL17Rb (also known as a receptor for IL25), IL18, IL22, IL23, IL25, IL27, IL33, IL35, ITGB4 (also known as b4 integrin), ITK, KIR, LAG3, LAMP1, leptin, LPFS2, MHC class II, NCR3LG1, NKG2D, NTPDase-1, OX40, OX40L, PD-1H, platelet receptor, PROM1, S152, SISP1, SLC, SPG64, ST2 (also known as a receptor for IL33), STEAP2, Syk kinase, TACI, TDO, T14, TIGIT, TIM3, TLR, TLR2, TLR4, TLR5, TLR9, TMEF1, TNFa, TNFRSF7, Tp53, TREM1, TSLP (also known as a co-receptor for IL7Ra), TSLPR, TWEAK, VEGF, VISTA, Vstm3, WUCAM, and XCR1 (also known as GPR5/CCXCR1). In some embodiments, one or more of the above antigen targets are human antigen targets.

In any of the trispecific binding proteins described supra, any linker or combination of linkers described herein may be used. For example, in some embodiments, at least one of $L_1$, $L_2$, $L_3$ or $L_4$ is independently 0 amino acids in length. In some embodiments, $L_1$, $L_2$, $L_3$ or $L_4$ are each independently at least one amino acid in length. In some embodiments, $L_1$, $L_2$, $L_3$ and $L_4$ each independently are zero amino acids in length or comprise a sequence selected from the group consisting of GGGGSGGGGS (SEQ ID NO:55), GGGGSGGGGSGGGGS (SEQ ID NO:56), S, RT, TKGPS (SEQ ID NO:57), GQPKAAP (SEQ ID NO:58), and GGSGSSGSGG (SEQ ID NO:59). In some embodiments, $L_1$, $L_2$, $L_3$, and $L_4$ each independently comprise a sequence selected from the group consisting of GGGGSGGGGS (SEQ ID NO:55), GGGGSGGGGSGGGGS (SEQ ID NO:56), S, RT, TKGPS (SEQ ID NO:57), GQPKAAP (SEQ ID NO:58), and GGSGSSGSGG (SEQ ID NO:59). In some embodiments, $L_1$ comprises the sequence GQPKAAP (SEQ ID NO:58), $L_2$ comprises the sequence TKGPS (SEQ ID NO:57), $L_3$ comprises the sequence S, and $L_4$ comprises the sequence RT. In some embodiments, $L_1$ comprises the sequence GGGGSGGGGS (SEQ ID NO:55), $L_2$ comprises the sequence GGGGSGGGGS (SEQ ID NO:55), $L_3$ is 0 amino acids in length, and $L_4$ is 0 amino acids in length. In some embodiments, $L_1$ comprises the sequence GGSGSSGSGG (SEQ ID NO:59), $L_2$ comprises the sequence GGSGSSGSGG (SEQ ID NO:59), $L_3$ is 0 amino acids in length, and $L_4$ is 0 amino acids in length. In some embodiments, $L_1$ comprises the sequence GGGGSGGGGSGGGGS (SEQ ID NO:56), $L_2$ is 0 amino acids in length, $L_3$ comprises the sequence GGGGSGGGGSGGGGS (SEQ ID NO:56), and $L_4$ is 0 amino acids in length.

IV. Uses for Binding Proteins

The binding proteins can be employed in any known assay method, such as competitive binding assays, direct and indirect sandwich assays, and immunoprecipitation assay s for the detection and quantitation of one or more target antigens. The binding proteins will bind the one or more target antigens with an affinity that is appropriate for the assay method being employ ed.

For diagnostic applications, in certain embodiments, binding proteins can be labeled with a delectable moiety. The detectable moiety can be any one that is capable of producing, either directly or indirectly, a detectable signal. For example, the detectable moiety can be a radioisotope, such as $^3H$, $^{14}C$, $^{32}P$, $^{35}S$, $^{125}I$, $^{99}Tc$, $^{111}In$, or $^{67}Ga$; a fluorescent or chemiluminescent compound, such as fluorescein isothiocyanate, rhodamine, or luciferin; or an enzyme, such as alkaline phosphatase, β-galactosidase, or horseradish peroxidase.

The binding proteins are also useful for in vivo imaging. A binding protein labeled with a detectable moiety can be administered to an animal, preferably into the bloodstream, and the presence and location of the labeled antibody in the host assayed. The binding protein can be labeled with any moiety that is detectable in an animal, whether by nuclear magnetic resonance, radiology, or other detection means known in the art.

For clinical or research applications, in certain embodiments, binding proteins can be conjugated to a cytotoxic agent. A variety of antibodies coupled to cytotoxic agents (i.e., antibody-drug conjugates) have been used to target cytotoxic pay loads to specific tumor cells. Cytotoxic agents and linkers that conjugate the agents to an antibody are known in the art; sec, e.g., Parslow, A. C. et al. (2016) Biomedicines 4.14 and Kalim, M. et al. (2017) Drug Des. Devel. Ther. 11:2265-2276.

The disclosure also relates to a kit comprising a binding protein and other reagents useful for detecting target antigen levels in biological samples. Such reagents can include a delectable label, blocking serum, positive and negative control samples, and detection reagents, in some embodiments, the kit comprises a composition comprising any binding protein, poly nucleotide, vector, vector system, and/or host cell described herein. In some embodiments, the kit comprises a container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition effective for treating, preventing and/or diagnosing a condition and may have a sterile access port (for example the container may be an intravenous solution bag or a vial having a stopper pierceable by a hypodermic injection needle). In some embodiments, the label or package insert indicates that the composition is used for preventing, diagnosing, and/or treating the condition of choice. Alternatively, or additionally, the article of manufacture or kit may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

In some embodiments, a binding protein of the present disclosure is administered to a patient in need thereof for the treatment or prevention of cancer. In some embodiments, die present disclosure relates to a method of preventing and/or heating a proliferative disease or disorder (e.g., cancer). In some embodiments, the method comprises administering to a patient a therapeutically effective amount of at least one of the binding proteins, or pharmaceutical compositions related thereto, described herein. In some embodiments, the present disclosure relates to uses of at least one of the binding proteins, or pharmaceutical compositions related thereto, described herein for preventing and/or treating a proliferative disease or disorder (e.g., cancer) in a patient in need thereof. In some embodiments, the present disclosure relates to at least one of the binding proteins, or pharmaceutical compositions related thereto, described herein for use in the manufacture of a medicament for preventing and/or treating a proliferative disease or disorder (e.g., cancer) in a patient in need thereof. In some embodiments, the patient is a human. In some embodiments, the binding protein comprises one antigen binding site that binds a T-cell surface protein and another antigen binding site that binds the extracellular domain of a human CD38 polypeptide, e.g., as described in section II supra. In some embodiments, the binding protein comprises an antigen binding site that binds the extracellular domain of a human CD38 polypeptide, an antigen binding site that binds a human CD28 polypeptide, and an antigen binding site that binds a human CD3 polypeptide.

In some embodiments, cells of the cancer express a human CD38 isoform A polypeptide on their cell surface (e.g., comprising the amino acid sequence of SEQ ID NO:1). In some embodiments, cells of the cancer express a human CD38 isoform E polypeptide on their cell surface (e.g., comprising the amino acid sequence of SEQ ID NO:105). In some embodiments, the patient is selected for treatment on the basis that the cells of the cancer express a human CD38 isoform E polypeptide on their cell surface (e.g., comprising the amino acid sequence of SEQ ID NO:105). In some embodiments, the cancer cells express CD38 and CD28. In some embodiments, the cancer cells express CD38 and do not express CD28.

In some embodiments, the cancer is multiple myeloma, acute lymphoblastic leukemia, chronic lymphocytic leukemia, acute myeloid leukemia, lymphoma breast cancer such as Her2+ breast cancer, prostate cancer, germinal center B-cell lymphoma or B-cell acute lymphoblastic leukemia. In certain embodiments, the cancer is multiple myeloma, in certain embodiments, the cancer is acute myeloid leukemia (AML), acute lymphoblastic leukemia (ALL), chronic lymphocytic leukemia (CLL), or a B cell lymphoma.

In certain embodiments, the cancer is multiple myeloma. Anti-CD38 antibodies have been tested for the treatment of multiple myeloma, such as daratumumab and isatuximab. However, while multiple myeloma is considered treatable, relapse is inevitable in almost all patients, leading to the development of treatment-refractory disease. In some embodiments, the cancer is relapsed or refractory multiple myeloma. In some embodiments, the patient has been treated with a prior multiple myeloma treatment. In some embodiments, a binding protein of the present disclosure is administered to the patient as a $1^{st}$, $2^{nd}$, or $3^{rd}$ line treatment for multiple myeloma. Without wishing to be bound to theory, it is thought that an anti-CD38×anti-CD28×anti-CD3 binding protein of the present disclosure may be useful in treating multiple myeloma, e.g., by recruiting T cells to tumor cells via anti-CD38 (or anti-CD28/anti-CD38), activation of engaged T cells via anti-CD3/anti-CD28, and/or killing of tumor cells through perform/granzyme-based mechanisms. CD28 has been reported as a novel cancer marker for multiple myeloma. See Hair, J. R. et al. (2011) J. Immunol. 187:1243-1253.

In some embodiments, the at least one binding protein is administered (or is to be administered) in combination with one or more anti-cancer therapies (e.g., any anti-cancer therapy known in the art, such as a chemotherapeutic agent or therapy). In some embodiments, the at least one binding protein is administered (or is to be administered) before the one or more anti-cancer therapies. In some embodiments, the at least one binding protein is administered (or is to be administered) concurrently with the one or more anti-cancer therapies. In some embodiments, the at least one binding protein is administered (or is to be administered) after the one or more anti-retroviral therapies.

V. Binding Protein Therapeutic Compositions and Administration Thereof

Therapeutic or pharmaceutical compositions comprising binding proteins are within the scope of the disclosure. Such therapeutic or pharmaceutical compositions can comprise a therapeutically effective amount of a binding protein, or binding protein-drug conjugate, in admixture with a pharmaceutically or physiologically acceptable formulation agent selected for suitability with the mode of administration.

Acceptable formulation materials preferably are nontoxic to recipients at the dosages and concentrations employ ed.

The pharmaceutical composition can contain formulation materials for modifying, maintaining, or preserving, for example, the pH, osmolality, viscosity, clarity, color, isotonicity, odor, sterility, stability, rate of dissolution or release, adsorption, or penetration of the composition. Suitable formulation materials include, but are not limited to, amino acids (such as glycine, glutamine, asparagine, arginine, or lysine), antimicrobials, antioxidants (such as ascorbic acid, sodium sulfite, or sodium hydrogen-sulfite), buffers (such as borate, bicarbonate, Tris-HC), citrates, phosphates, or other organic acids), bulking agents (such as mannitol or glycine), chelating agents (such as ethylenediamine tetraacetic acid (EDTA)), complexing agents (such as caffeine, polyvinylpyrrolidone, beta-cyclodextrin, or hydroxypropyl-beta-cyclodextrin), fillers, monosaccharides, disaccharides, and other carbohydrates (such as glucose, mannose, or dextrins), proteins (such as serum albumin, gelatin, or immunoglobulins), coloring, flavoring and diluting agents, emulsifying agents, hydrophilic polymers (such as poly vinylpyrrolidone), low molecular weight polypeptides, salt-forming counterions (such as sodium), preservatives (such as benzalkonium chloride, benzoic add, salicylic add, thimerosal, phenethyl alcohol, methylparaben, propylparaben, chlorhexidine, sorbic acid, or hydrogen peroxide), solvents (such as glycerin, propylene glycol, or polyethylene glycol), sugar alcohols (such as mannitol or sorbitol), suspending agents, surfactants or wetting agents (such as pluronics; PEG; sorbitan esters; polysorbates such as polysorbate 20 or polysorbate 80; triton; tromethamine; lecithin; cholesterol or tyloxapal), stability enhancing agents (such as sucrose or sorbitol), tonicity enhancing agents (such as alkali metal halides—preferably sodium or potassium chloride—or mannitol sorbitol), delivery vehicles, diluents, excipients and/or pharmaceutical adjuvants (see, e.g., REMINGTON'S PHARMACEUTICAL SCIENCES (18th Ed., A. R. Gennaro, ed, Mack Publishing Company 1990), and subsequent editions of the same, incorporated herein by reference for any purpose).

The optimal pharmaceutical composition will be determined by a skilled artisan depending upon, for example, the intended route of administration, delivery format, and desired dosage. Such compositions can influence the physical state, stability, rate of in vivo release, and rate of in vivo clearance of the binding protein.

The primary vehicle or carrier in a pharmaceutical composition can be either aqueous or non-aqueous in nature. For example, a suitable vehicle or carrier for injection can be water, physiological saline solution, or artificial cerebrospinal fluid, possibly supplemented with other materials common in compositions for parenteral administration. Neutral buffered saline or saline mixed with serum albumin are further exemplary vehicles. Other exemplary pharmaceutical compositions comprise Tris buffer of about pH 7.0-8.5, or acetate buffer of about pH 4.0-5.5, which can further include sorbitol or a suitable substitute. In one embodiment of the disclosure, binding protein compositions can be prepared for storage by mixing the selected composition having the desired degree of purity with optional formulation agents in the form of a lyophilized cake or an aqueous solution. Further, the binding protein can be formulated as a lyophilizate using appropriate excipients such as sucrose.

The pharmaceutical compositions of the disclosure can be selected for parenteral delivery or subcutaneous. Alternatively, the compositions can be selected for inhalation or for delivery through the digestive tract, such as orally. The preparation of such pharmaceutically acceptable compositions is within the skill of the art.

The formulation components are present in concentrations that are acceptable to the site of administration. For example, buffers are used to maintain the composition at physiological pH or at a slightly lower pH, typically within a pH range of from about 5 to about 8.

When parenteral administration is contemplated, the therapeutic compositions for use can be in the form of a pyrogen-free, parenterally acceptable, aqueous solution comprising the desired binding protein in a pharmaceutically acceptable vehicle. A particularly suitable vehicle for parenteral injection is sterile distilled water in which a binding protein is formulated as a sterile, isotonic solution, properly preserved. Yet another preparation can involve the formulation of the desired molecule with an agent, such as injectable microspheres, bio-erodible particles, polymeric compounds (such as polylactic acid or polyglycolic acid), beads, or liposomes, that provides for the controlled or sustained release of the product which can then be delivered via a depot injection. Hyaluronic acid can also be used, and this can have the effect of promoting sustained duration in the circulation. Other suitable means for the introduction of the desired molecule include implantable drug delivery devices.

In one embodiment, a pharmaceutical composition can be formulated for inhalation. For example, a binding protein can be formulated as a dry pow der for inhalation. Binding protein inhalation solutions can also be formulated with a propellant for aerosol delivery. In yet another embodiment, solutions can be nebulized.

It is also contemplated that certain formulations can be administered orally. In one embodiment of the disclosure, binding proteins that are administered in this fashion can be formulated with or without those carriers customarily used in the compounding of solid dosage forms such as tablets and capsules. For example, a capsule can be designed to release the active portion of the formulation at the point in the gastrointestinal tract when bioavailability is maximized and pre-systemic degradation is minimized. Additional agents can be included to facilitate absorption of the binding protein. Diluents, flavorings, low melting point waxes, vegetable oils, lubricants, suspending agents, tablet disintegrating agents, and binders can also be employed.

Another pharmaceutical composition can involve an effective quantity of binding proteins in a mixture with non-toxic excipients that are suitable for the manufacture of tablets. By dissolving the tablets in sterile water, or another appropriate vehicle, solutions can be prepared in unit-dose form. Suitable excipients include, but are not limited to, inert diluents, such as calcium carbonate, sodium carbonate or bicarbonate, lactose, or calcium phosphate, or binding agents, such as starch, gelatin, or acacia; or lubricating agents such as magnesium stearate, stearic acid, or talc.

Additional pharmaceutical compositions of the disclosure will be evident to those skilled in the art, including formulations involving binding proteins in sustained- or controlled-delivery formulations. Techniques for formulating a variety of other sustained- or controlled-delivery means, such as liposome carriers, bio-erodible microparticles or porous beads and depot injections, are also known to those skilled in the art. Additional examples of sustained-release preparations include semipermeable polymer matrices in the form of shaped articles, e.g. films, or microcapsules. Sustained release matrices can include polyesters, hydrogels, polylactides, copolymers of L-glutamic acid and gamma ethyl-L-glutamate, poly(2-hydroxyethyl-methacrylate), ethylene vinyl acetate, or poly-D(-)-3-hydroxybutyric acid. Sustained-release compositions can also include liposomes, which can be prepared by any of several methods known in the art.

Pharmaceutical compositions to be used for in vivo administration typically must be sterile. This can be accomplished by filtration through sterile filtration membranes. Where the composition is lyophilized, sterilization using this method can be conducted either prior to, or following, lyophilization and reconstitution. The composition for parenteral administration can be stored in lyophilized form or in a solution. In addition, parenteral compositions generally are placed into a container having a sterile access port, for example, an intravenous solution bag or vial having a stopper pierceable by a hypodermic injection needle.

Once the pharmaceutical composition has been formulated, it can be stored in sterile vials as a solution, suspension, gel, emulsion, solid, or as a dehydrated or lyophilized powder. Such formulations can be stored either in a ready-to-use form or in a form (e.g., lyophilized) requiring reconstitution prior to administration.

The disclosure also encompasses kits for producing a single-dose administration unit. The kits can each contain both a first container having a dried protein and a second container having an aqueous formulation. Also included within the scope of this disclosure are kits containing single and multi-chambered pre-filled syringes (e.g., liquid syringes and lyosyringes).

The effective amount of a binding protein pharmaceutical composition to be employed therapeutically will depend, for example, upon the therapeutic context and objectives. One skilled in the art will appreciate that the appropriate dosage levels for treatment will thus vary depending, in part, upon the molecule delivered, the indication for which the binding protein is being used, the route of administration, and the size (body-weight, body surface, or organ size) and condition (the age and general health) of the patient. Accordingly, the clinician can titer the dosage and modify the route of administration to obtain the optimal therapeutic effect.

Dosing frequency will depend upon the pharmacokinetic parameters of the binding protein in the formulation being used. Typically, a clinician will administer the composition until a dosage is reached that achieves the desired effect. The composition can therefore be administered as a single dose, as two or more doses (which may or may not contain the same amount of the desired molecule) over time, or as a continuous infusion via an implantation device or catheter. Further refinement of the appropriate dosage is routinely made by those of ordinary skill in the art and is within the ambit of tasks routinely performed by them. Appropriate dosages can be ascertained through use of appropriate dose-response data.

The route of administration of the pharmaceutical composition is in accord with known methods, e.g., orally; through injection by intravenous, intraperitoneal, intracerebral (intraparenchymal), intracerebroventricular, intramuscular, intraocular, intraarterial, intraportal, or intralesional routes; by sustained release systems; or by implantation devices. Where desired, the compositions can be administered by bolus injection or continuously by infusion, or by implantation device.

The composition can also be administered locally via implantation of a membrane, sponge, or other appropriate material onto which the desired molecule has been absorbed or encapsulated. Where an implantation device is used, the device can be implanted into any suitable tissue or organ, and delivery of the desired molecule can be via diffusion, timed-release bolus, or continuous administration.

EXAMPLES

The Examples that follow are illustrative of specific embodiments of the disclosure, and various uses thereof. They are set forth for explanatory purposes only, and should not be construed as limiting the scope of the invention in any way.

The following terminology may be used interchangeably in the Examples and Drawings herein to refer to specific anti-CD38 antigen binding domains or antibodies.
antiCD38_C2-CD38-1: mAb1
antiCD38_C2-CD38-1_VH1-VL1 or $CD38_{VH1}$: mAb2
antiCD38_C2-CD38-1_VH3-VL3: mAb3
antiCD38_C2-CD38-1_VH5-VL3: mAb4
antiCD38_C2-CD38-1_VH6-VL3: mAb5
antiCD38_1370 or $CD38_{HHY1370}$: mAb6
antiCD38_SB19 or isatuximab, mAb7.

Example 1: Generation and Characterization of Monoclonal Anti-CD38 Antibodies

The Examples that follow describe the generation and characterization of monoclonal anti-CD38 antibodies. Advantageously, antibodies provided herein cross-react with human and monkey CD38 proteins, thereby providing molecules that can be used for both safety and clinical studies. These antibodies are also capable of killing CD38+ cells by apoptosis and antibody-dependent cell-mediated cytotoxicity (ADCC).

This Example describes an efficient workflow for generating CD38-specific and cross-reactive monoclonal antibodies from single murine B cells.

Materials and Methods
Generation of Monoclonal Antibodies
Antibodies to human CD38 were generated using the human CD38 extracellular domain R45-1300 (SEQ ID NO:1). See Q. Liu, I. Krilksunov, R. Graeff, C. Munshi, H. C. Lee, and Q. Hao 2005 Structure 13:1331-1339. The immunogen was administered directly, with an adjuvant to stimulate the immune response, to either normal BalbC mice or transgenic Trianni Mice™ (Trianni, San Francisco, Calif.) comprising DNA encoding human Immunoglobulin heavy and kappa light chain variable regions.

Various recombinant CD38 proteins derived from isoform A with different tag and point mutations were used (SEQ ID NOs:2, 3, 4, and 28), and a tagged version of CD38 isoform E (SEQ ID NO:105) encompassing CD38 extracellular domain from R45-P203. The proteins were produced by transient expression in mammalian cells. Coding DNA sequences were cloned into mammalian expression plasmids under CMV enhancer/promoter and SV40 polyA signals. HEK293 cells (Invitrogen; #K9000-10) were transiently transfected with the expression plasmids using FreeStyle™ MAX 293 Expression System according to the manufacturers instructions.

Immunization of Mice and Single B Cell Selection
Anti-CD38 antibodies were also isolated directly from antigen-positive B cells without fusion to myeloma cells. Using this method, several anti-CD38 antibodies were obtained, such as mAb1 (see SEQ ID Nos. 5 and 6 for VH and VL sequences, respectively, and SEQ ID Nos. 7 and 8 for heavy chain and light chain sequences, respectively). Briefly, 6-8 weeks old female BALB/c mice (S082342; Charles River Labs, Bar Harbor, Me.) each received three rounds of immunization over a course of 41 days using the classical method as described by A. Wennerberg et al. (1993 Am. J. Pathol. 143:1050-1054). Antigen was administered intraperitoneally to ventral site of mice. Three days after the last injection, mice were sacrificed and spleens were isolated aseptically and washed with fresh RPMI medium. Lymphocytes were released from the spleens and single-cell suspension was washed twice with RPMI medium before being sorted using a four colour sorting strategy including a panel of fluorescent antibodies and dual human and monkey CD38 proteins and then were separated using flow cytometric cell sorting to isolate human/monkey cross reactive IgG-CD38 specific B cells. Single cells were directly sorted into PCR tubes to amplify cognate pair of VH and VL genes by RT-PCR (T. Tiller, C. Busse and H. Wardemann 2009 J. Immunol. Methods 350:183-193). Resulting DNA was sequenced.

Resulting DNA was cloned into a mammalian expression vector encoding respectively the human IgG1 or human Ck domains for transient expression in HEK293 cells using FreeStyle™ MAX 293 Expression System according to the manufacturer s instructions. Batches were purified by protein A affinity chromatography (MabSelect, GE Heathcare). The eluate was dialyzed against PBS before sterile filtration and storage at 4° C.

Generation of Antibodies by Immunization in Human Immunoglobulin Transgenic Mice and Selection Using Hybridoma Technology Immunizations, fusion and screening were performed using P3X63-Ag8.653 myeloma cells with the extracellular domain of human CD38 as described in Kilpatrick et al. 1997 Hybridoma 16; 381389. Using the RIMMS method described by Kilpatrick et al. 6-8 week old female transgenic Trianni Mice™ comprising ON A encoding human Immunoglobulin heavy and kappa light chain variable regions each received four rounds of immunization over a course of 14 days at intervals of 3-4 days. CD38 protein emulsified in RIBI's adjuvant (Sigma #T2684) was administered subcutaneously to six sites proximal to draining lymph nodes, along the back of the mice and to six juxtaposed sites along abdomen. Four days after the last injection, mice were sacrificed. Bilateral popliteal, superficial inguinal, axillary and branchial lymph nodes were isolated aseptically and washed with fresh RPMI medium. Lymphocytes were released from the lymph nodes and single-cell suspension was washed twice with RPMI medium before being fused with P3X63-AG8.653 myeloma cells using polyethylene glycol. After fusion, the cell mixture was incubated in an incubator at 37° C. for 16-24 hours. The resulting cell preparation was transferred into selective semi-solid medium and aseptically plated out into 100 mm Petri plates and incubated at 37° C. Ten days after initiation of selection, the plates were examined for hybridoma growth, and visible colonies were picked-up and placed into 96-well plates containing 200 µL of growth medium. The 96-well plates were kept in an incubator at 37° C. for 2 to 4 days. Using this technique, and the immunogen described above, several anti-CD38 chimeric antibodies were obtained such as mAb 6 (see SEQ ID Nos: 9 and 10 for VH and VL sequences, respectively, and SEQ ID Nos: 11 and 12 for heavy chain and light chain sequences, respectively. The VH and VL sequences were retrieved by RT-PCR and mAb 6 was produced by transient expression as described above.

Binding Affinity to Soluble CD38 Extracellular Domains

The binding properties of the anti-huCD38 mabs were evaluated using a BIAcore 2000 (BIAcore Inc., Uppsala, Ni). Briefly, a CM5 BIAcore biosensor chip was docked into the instrument and activated with 250 µL of 1:1 NHS/EDC at room temperature. A mouse anti-human Fc IgG1 (GE Healthcare #BR-1008-39) (13.5 µg/mL in 0.05M acetate buffer. pH5) were immobilized on the activated chips in (low cells 1. The immobilization was carried out at a flow rate of 5 µL/min. The chip was then blocked by injection of 55 µL of ethanolamine-HCl, pH8.5, followed by five washes with 50 mM NaOH, 1M NaCl. To measure the binding of anti-CD38 mabs to the human CD38 protein or cyno CD38 protein, antibodies were used at 2 µg/ml, in BIAcore running buffer (HBS-EP). Antigens (human CD38-histag (ID2) or cyno CD38-histag (ID3)) were injected from 3 to 1000 nM. Following completion of the injection phase, dissociation was monitored in a BIAcore running buffer at die same flow rate for 360 sec. The surface was regenerated between injections using 30 µL of 50 mM NaOH-1 M NaCl. Individual sensorgrams wore analyzed using BIAsimulation software.

Binding Affinity to Human CD38-Expressing Pre-B Cells

The binding of anti-CD38 antibodies to CD38 expressed on the surface of recombinant murine preB::300.19 cells was determined by flow cytometry. The recombinant cell line was described by J. Deckket et al. 2014 Clin. Cancer Res 20:4574-4583. Murine preB::300.19 CD38-ex pressing cells were coated at 40,000 cells/well on 96-well High Bind plate (MSD L15XB-3) and 100 µL/well of anti-CD38 antibodies were added for 45 min at 4° C., and washed three times with PBS 1% BSA, 100 µL/well of goat anti-human IgG conjugated with Alexa488 (Jackson ImmunoResearch; #109-545-098) was added for 45 min at 4° C., and washed three times with PBS 1% BSA. Antibody binding was evaluated after centrifugation and resuspension of cells by adding 200 µL/well PBS 1% BSA and read using Guava® easyCyte™ 8HT Flow Cytometry System. Apparent $K_D$ and EC50 values were estimated using BIOST@T-BINDING and BIOST@T-SPEED software, respectively.

Results

Binding of newly isolated mAb1 to human SU-DHL-8 or MOLP-8 cells was compared to that of isatuximab using flow cytometry (FIG. 1A). Both antibodies exhibited high-affinity binding to both cell lines. However, only mAb1 was able to bind to cells expressing cynomolgus monkey CD38 on their surface (FIG. 1B).

Binding to soluble extracellular domains of human and cynomolgus monkey CD38 polypeptides was examined for newly isolated antibodies mAb1 and mAb6 using surface plasmon resonance (SPR). The SPR results are summarized in Table A.

TABLE A

Binding affinity of antibodies to the soluble extracellular domain of hCD38 and cCD38 as determined by SPR assay.

| | hCD38-his (SEQ ID NO: 2) | | cCD38-his (SEQ ID NO: 4) | |
|---|---|---|---|---|
| | Kd (s-1) | KD (M) | Kd (s-1) | KD (M) |
| mAb1 | 2.66E−04 | 3.36E−10 | 9.85E−05 | 3.90E−10 |
| mAb6 | 203E−04 | 1.44E−10 | 1.90E−04 | 1.38E−09 |

Flow cytometry was also used to examine binding of mAb1 and mAb6 anti-CD38 antibodies to murine pre-B cells expressing human or cynomolgus monkey CD38 polypeptide on their cell surface. The results are shown in Table B. Both antibodies tested exhibited high affinity binding to preB::300.19 huCD38- or cCD38-expressing cells.

TABLE B

Binding affinity of antibodies to hCD38 or cCD38 expressed by murine preB::300.10 cells as determined by flow cytometry.

| | Apparent KD FACS (M) | |
|---|---|---|
| | hCD38-expressing cells | cCD38-expressing cells |
| mAb1 | 2.80E−10 | 2.20E−10 |
| mAb6 | 2.07E−09 | 1.14E−09 |

These results demonstrate the generation of antibodies that bind with high affinity to both human and cynomolgus CD38 polypeptides. These antibodies, unlike other anti-CD38 antibodies, cross-react with human and cynomologus CD38 polypeptides in soluble extracellular form or expressed on the surface of mammalian cells.

Example 2: In Silico Design of Humanized Anti-CD38 Variants

This Example describes the humanization of antibodies generated in Example 1.

Sequences of mAb1 variable domains were analysed in-silico. The International ImMunoGeneTics information system for immunoglobulins (IMGT) definition was used to identify Complementarity Determining Regions (CDRs).

First, in parallel, searches were undertaken to identify the closest Mouse germline and Human germline protein sequence combination for each variable chain. This was performed using a Basic Local Alignment Search Tool (BLAST) (Nucleic Acids Res. 25:3389-3402) search against Mouse and Human germline protein sequence databases. For each antibody chain, closest V and J mouse and human protein sequences were found. The qualification of this high protein sequence identity was measured by the V region identity percentage. Results of the searches for mAb1 light and heavy chain are presented in Tables C and D, respectively.

TABLE C mAb1 variable light chain closest human and mouse (V&J) germline protein sequences.

| Species | V Allele | V Region Identity (%) | J Allele |
|---|---|---|---|
| [Homo sapiens] Best Functional Germlines | IGKV4-1*01 (imgt) Functional | 66.34% | IGKJ1*01 (imgt) Functional |
| [Mus musculus] Best Functional Germlines | IGKV3-10*01 (imgt) Functional | 96.97% | IGKJ1*01 (imgt) Functional |

TABLE D mAb1 variable heavy chain closest human and mouse (V&J) germline protein sequences.

| Species | V Allele | V Region Identity (%) | JAllele |
|---|---|---|---|
| [Homo sapiens] Best Functional Germlines | IGHV1-3*01 (imgt) Functional | 69.39 % | IGHJ4*01 (imgt) Functional |
| [Mus musculus] Best Functional Germlines | IGHV1-12*01 (imgt) Functional | 87.76% | IGHJ3*01 (imgt) Functional |

Next mAb1 variable domain sequences were screened for sequence liabilities, such as deamidation, acidic cleavage, oxidation, or iso-aspartate formation sites, mAb1 structure has been analysed by 3D modelling by homology in order to define how amino acid residues interact in intra or intermolecular ways. This step led to the identification of a group of amino acid residues that are structurally important for mAb1 functionalities as CDRs conformation and antigen binding. These amino acid residues were selected to be present in the humanized mAb1 variable sequences.

CDRs from the parental murine mAb1 were grafted onto the relevant frameworks. Based on the above analyses, human IGKV3-20*02 coupled with IGKJ1*01 and human IGHV1-3*01 coupled with IGHJ4*01 were selected to be foundation for mAb1 variable light chain and variable heavy chain humanization, respectively. The mAb1 light chain displayed 64.52% identity over the V region with the selected human IGKV3-20*02 germline. The mAb1 heavy chain displayed 69.39% identify over the V region with the selected human IGHV1-3*01 germline. During humanization process, the parental murine mAb1 CDRs were transplanted between selected germline frameworks in order to recompose standard antibody variable sequences. Attention was provided to the previously identified group of mAb1 amino acid residues that are structurally important for its functionalities, as noted above, if needed those amino acid residues were replaced in the newly created sequences by their exact corresponding mAb1 residue. This corresponds to a back-mutation step to incorporate adequate parental sequence amino acid residues. Some CDR mutations were incorporated for both humanizing and avoiding sequence liabilities in parental CDRs. The newly created light and heavy variable sequences were used to generate 3D homology models of the humanized mAb1 variable region, lire 3D models were built using Model Antibody Framework from BIOVIA Discovery Studio suite.

Based on CDR grafting approach, two variants for the variable light chain (VL1 and VL3) and four variants for the variable heavy chain (VH1, VH3, VH5 and VH6) were generated. The particular combination of amino acid residues which vary between mAb1 variable light and heavy sequences and their humanized versions are set forth in Tables E and Table F, respectively.

TABLE E

Sequence differences between mAb1 variable light chain and humanized variants.

| Ig Regions (IMGT) | parental mAb1 VL | humanized VL1 | humanized VL3 |
|---|---|---|---|
| FR1 | S10 | T | 1 |
| | A12 | S | S |
| | V13 | L | L |

TABLE E-continued

Sequence differences between mAb1 variable light chain and humanized variants.

| Ig Regions (IMGT) | parental mAb1 VL | humanized VL1 | humanized VL3 |
|---|---|---|---|
|  | L15 | P | P |
|  | Q17 | E | E |
| CDR1 | E27 | Q | E |
|  | D30 | S | D |
|  | N34 | Q | N |
| FR2 | K49 | R | R |
| CDR2 | L54 | G | L |
| FR3 | N57 | S | S |
|  | L58 | R | R |
|  | E59 | A | A |
|  | S60 | T | T |
|  | V62 | I | I |
|  | R71 | G | G |
|  | D80 | S | S |
|  | V82 | L | L |
|  | A84 | P | P |
|  | D85 | E | E |
|  | A87 | F | F |
|  | T89 | V | V |

TABLE F

Sequence differences between mAb1 variable heavy chain and humanized variants.

| Ig Regions (IMGT) | parental mAb1 VH | humanized VH1 | humanized VH3 | humanized VH5 | humanized VH6 |
|---|---|---|---|---|---|
| FR1 | Q5 | V | V | V | V |
|  | L11 | V | V | V | V |
|  | R13 | K | K | K | K |
|  | S14 | P | P | S | P |
|  | M20 | V | V | V | M |
| CDR1 | F32 | Y | F | F | F |
|  | N33 | A | N | N | N |
| FR2 | T40 | A | A | A | A |
|  | G44 | R | R | G | R |
| CDR2 | N55 | Q | N | N | N |
| FR3 | K65 | Q | Q | Q | Q |
|  | K67 | R | R | R | R |
|  | S76 | A | A | A | A |
|  | Q82 | E | E | E | E |
|  | I83 | L | L | I | I |
|  | T87 | R | R | R | R |
|  | S91 | T | T | T | T |

The humanized VL1 variant with SEQ ID NO:14 displays a total of 22 mutations (18 in FRs and 4 in CDRs) compared to tire parental VL of mAb1 sequence with SEQ ID NO: 6. This variant derived from frameworks of human germlines IGKV3-20*02 coupled with IGKJ1*01 with 8 back-mutations done due to the risk of negative impact on mAb structure, CDRs conformation and therefore, on binding to its target. Four positions of the parental CDRs were mutated in order to increase humanization rate or avoid sequence liabilities.

The humanized VL3 variant with SEQ ID NO:18 displays a total of 18 mutations (18 in FRs) compared to the parental VL of mAb1 sequence with SEQ ID NO:6. This variant derived from frameworks of human germlines IGKV3-20*02 coupled with IGKJ1*01 with 8 back-mutations done due to the risk of negative impact on mAb structure, CDRs conformation and therefore, on binding to its target.

The humanized VH1 variant with SEQ ID NO:13 displays a total of 17 mutations (14 in FRs and 3 in CDRs) compared to the parental VH of mAb1 sequence with SEQ ID NO: 5. This variant derived from frameworks of human germlines IGHV1-3*01 coupled with IGHJ4*01 with 11 back-mutations done due to the risk of negative impact on mAb structure. CDRs conformation and therefore, on binding to its target. Three positions of the parental CDRs were mutated in order to increase humanization rate or avoid sequence liabilities.

The humanized VH3 variant with SEQ ID NO:17 displays a total of 14 mutations (14 in FRs) compared to the parental VH mAb1 sequence with SEQ ID NO:5. This variant derived from frameworks of human germlines IGHV1-3*01 coupled with IGHJ4*01 with 11 back-mutations done due to the risk of negative impact on mAb structure, CDRs conformation and therefore, on binding to its target.

The humanized VH5 variant with SEQ ID NO: 21 display s a total of 11 mutations (11 in FRs) compared to the parental VH of mAb1 sequence with SEQ ID NO:5. This variant derived from frameworks of human germlines IGHV1-3*01 coupled with IGHJ4*01 with 14 back-mutations done due to the risk of negative impact on mAb structure. CDRs conformation and therefore, on binding to its target.

The humanized VH6 variant with SEQ ID NO:23 displays a total of 12 mutations (12 in FRs) compared to the parental VH of mAb1 sequence with SEQ ID NO:5. This variant derived from frameworks of human germlines IGHV1-3*01 coupled with IGHJ4*01 with 13 back-mutations done due to the risk of negative impact on mAb structure, CDRs conformation and therefore, on binding to its target.

The resulting light and heavy humanized variable sequences w ere blasted for sequence similarity against the Immune Epitope Data Base (IEDB) database ((PLos Biol (2005) 3(3)e91) www.iedb.org) to ensure that none of the sequences contained any known B- or T-cell epitope listed therein.

The complete amino acid variable sequences of mAb land humanized light and heavy variable domains are set forth in Table G. These humanized light and heavy variable domains have been combined to generate several humanized versions of parental variable domains of mAb1, mAb2 variable domains correspond to the association of humanized VH1 combined with humanized VL1, mAb3 variable domains correspond to the association of humanized VH3 combined with humanized VL3, mAb4 variable domains correspond to the association of humanized VH5 combined with humanized VL3, mAb5 variable domains correspond to the association of humanized VH6 combined with humanized VL3. The trispecific binding proteins shown in Table G are described in greater detail in Example 4.

The corresponding coding DNA sequences of the humanized VH and VL variants described above 1 were cloned into a mammalian expression vector encoding respectively the human IgG1 or human Ck domains for transient expression and purification as described in Example 1 The amino sequences of the full length humanized anti-CD38 variants derived from mAb1 are listed as mAb2 (heavy chain: HC1, SEQ ID NO:15; light chain: LC1, SEQ ID NO:16), mAb3 (heavy chain: HC3, SEQ ID NO:19; light chain: LC3, SEQ ID NO:20), mAb4 (heavy chain: HC5, SEQ ID NO:22; light chain: LC3, SEQ ID NO:20), and mAb5 (heavy chain: HC6, SEQ ID NO:24; light chain: LC3, SEQ ID NO:20).

Example 3: Cross-Reactivity and Apoptosis Induction of Anti-CD38 Antibodies

The humanized anti-CD38 variants generated in Example 2 were next characterized for binding to human and cynomolgus CD38 polypeptides and induction of apoptosis.

Materials and Methods

Apoptosis Induction Assay

Cells were incubated at $2\times10^5$ cells/mL in complete medium (RPMI-1640, 10% FBS, 2 mM L-glutamine) with 1.5 µg/mL (10 nM) of indicated antibodies for 20 hours at 37° C. with 5% CO2. Cells were stained with Annexin V-FITC in accordance with the manufacturer's instructions (Life Technologies). Samples were analyzed by flow cytometry on a BD FACS Aria™ flow cytometer with BD FACS-Diva software for acquisition control and data analysis (both BD Biosciences).

Results

Figure 2A:
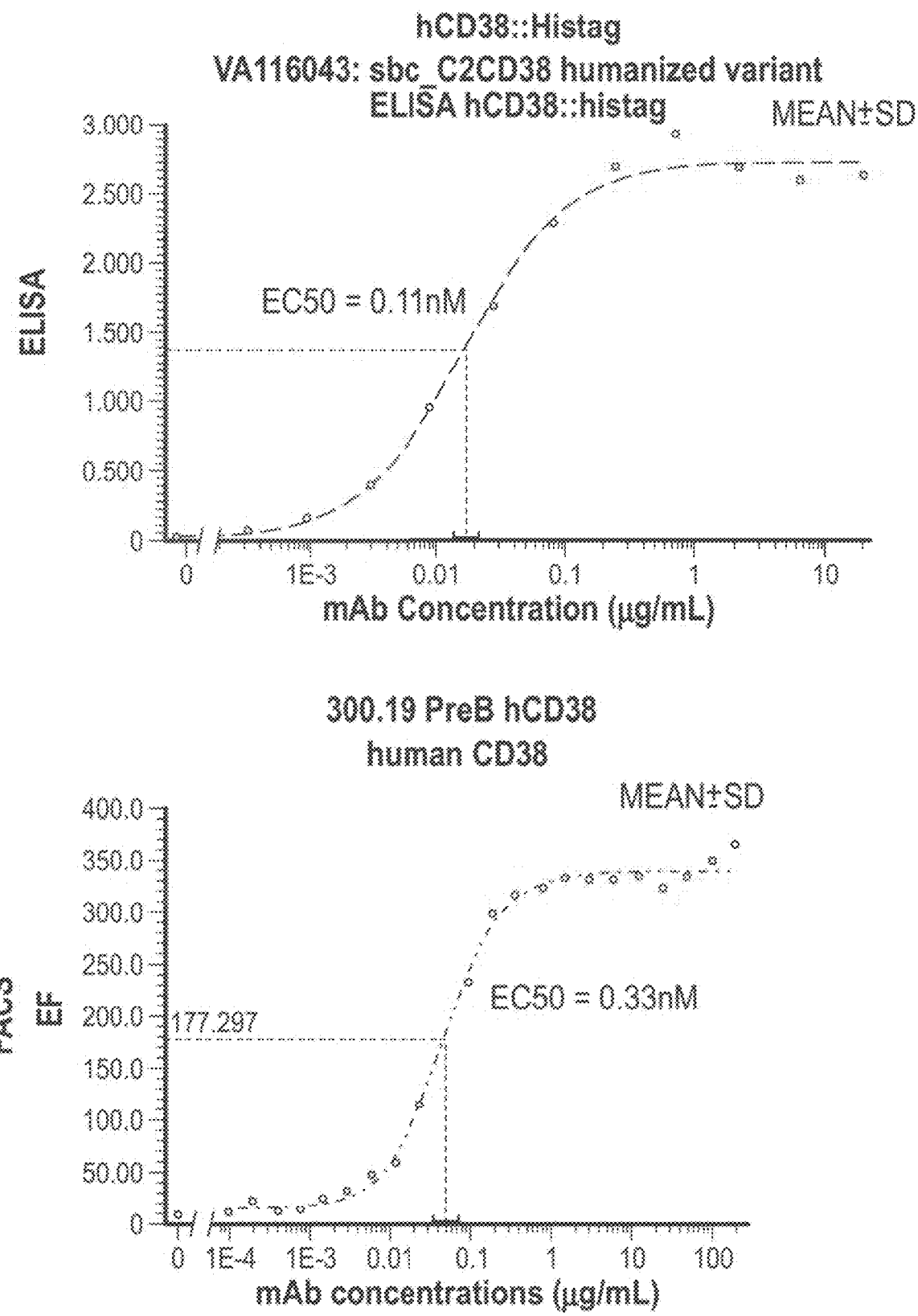
Figure 2A:
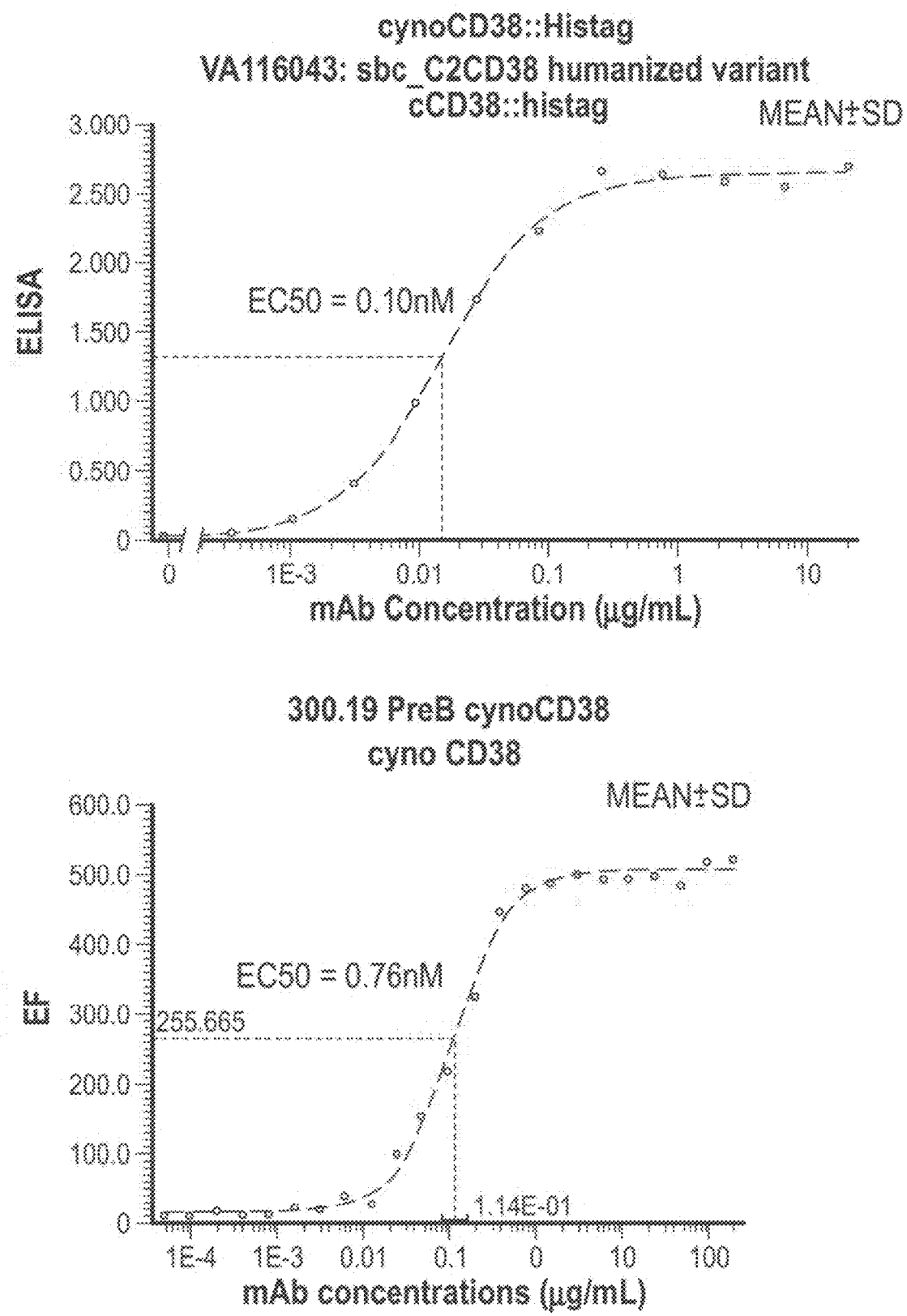
Figure 2C:
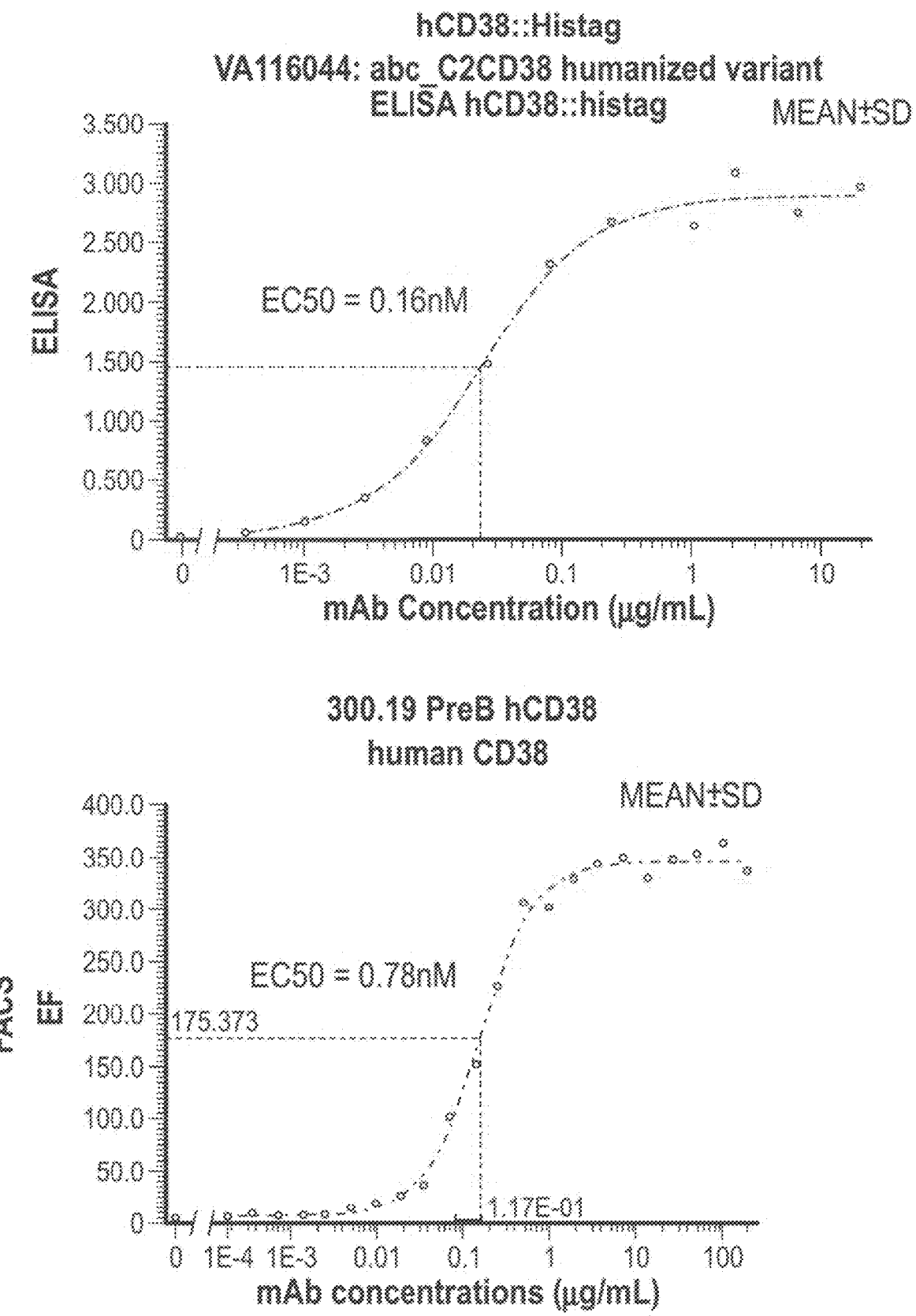
Figure 2C:
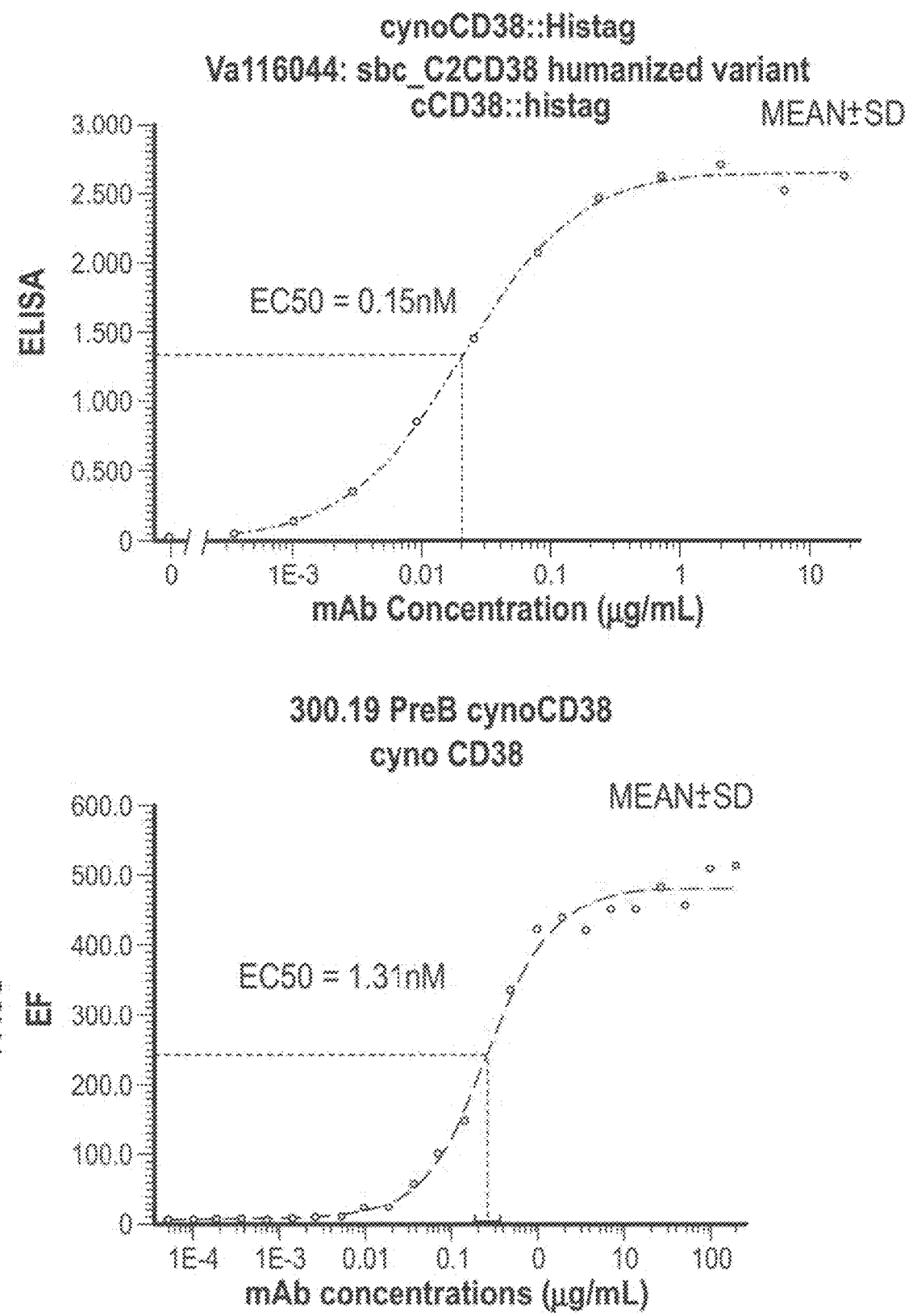
Figure 2E:
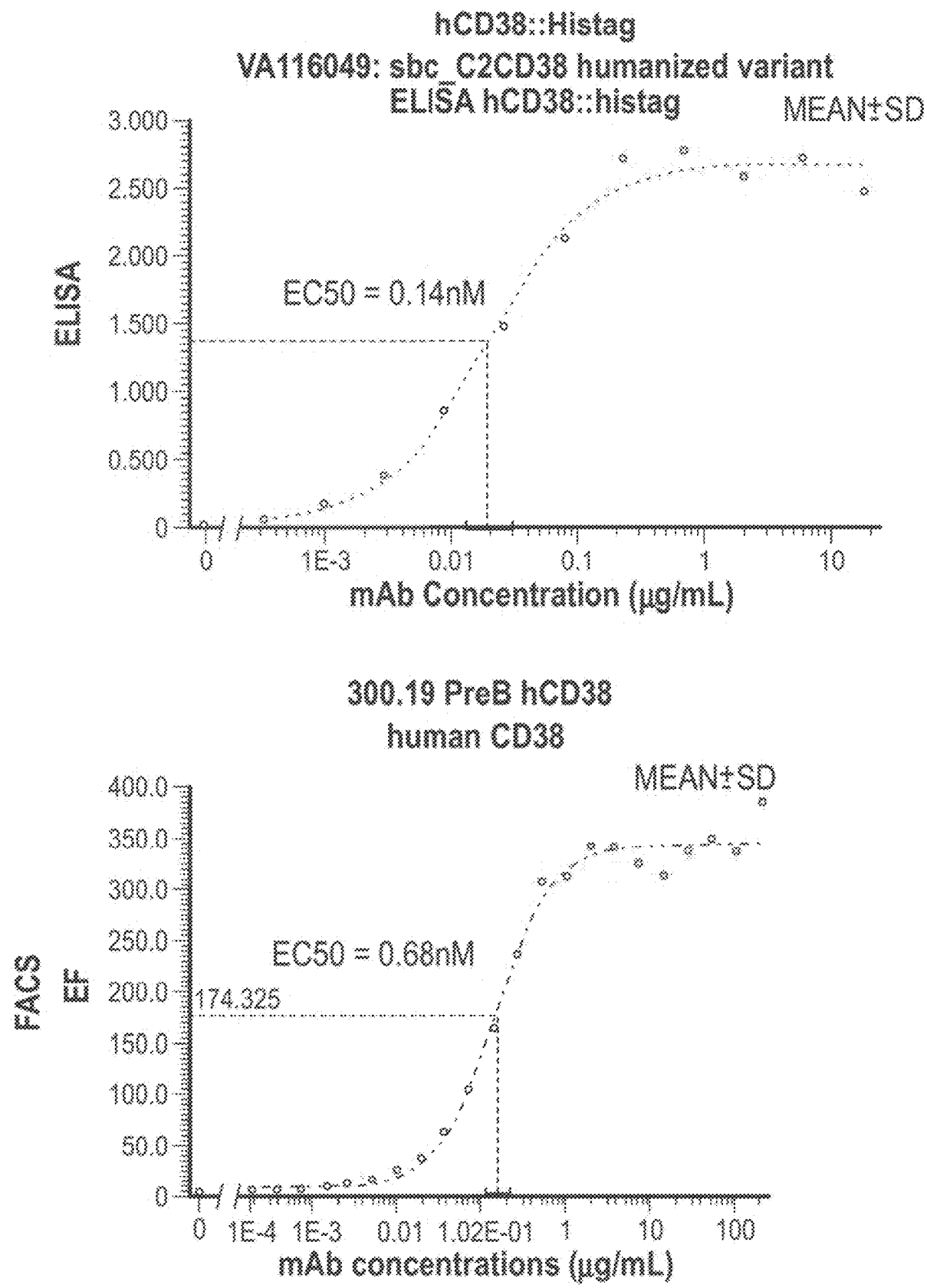
Figure 2E:
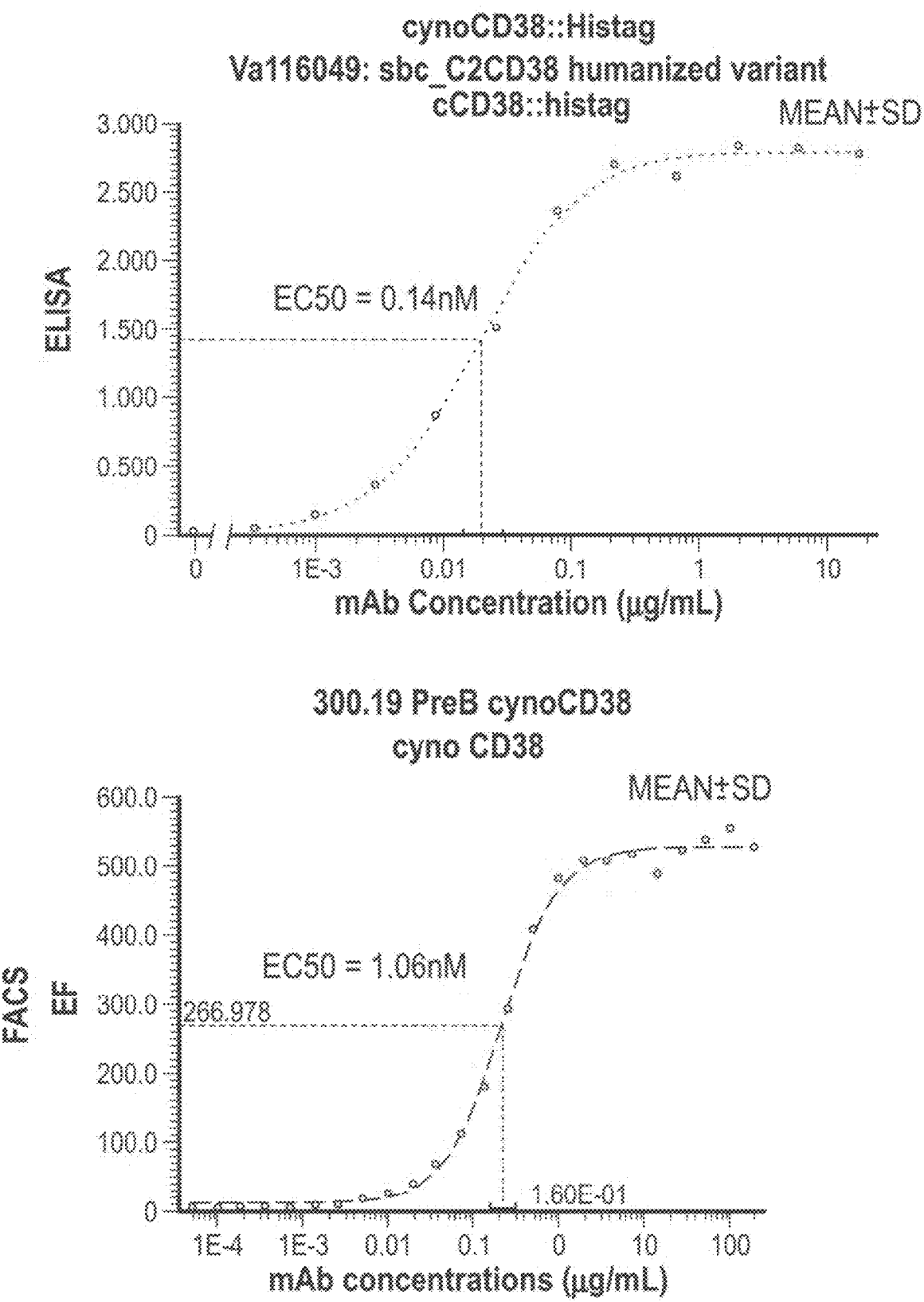

Binding properties of selected anti-human CD38 antibodies produced as described above were examined (FIGS. 2A-2H). Binding of antibodies to soluble human CD38 and cynomolgus monkey CD38 was examined using ELISA and SPR ELISA data were used to determine the EC50 of antibody binding to human and cynomolgus monkey CD38 for humanized anti-CD38 antibodies mAb2 (FIG. 2A), mAb3 (FIG. 2C), mAb4, mAb5 (FIG. 2E), and human anti-CD38 antibody mAb6 (FIG. 2I).

The binding of the humanized anti-CD38 variants or human anti-CD38 mAb to CD38 was also evaluated using the SPR assay described above. SPR data were used to determine the $K_D$ and $k_{off}$ of antibody binding to human and cynomolgus monkey CD38 for humanized anti-CD38 antibodies mAb2 (FIG. 2B), mAb3 (FIG. 2D), mAb4, mAb5 (FIG. 2F), and human anti-CD38 antibody mAb6 (FIG. 2H). The binding data are summarized in Table K show that all the anti-CD38 mAbs bind to CD38 with similar binding characteristics.

TABLE K

Binding affinity of anti-CD38 mAbs to the solible extracellular domain of humanCD38 and cynomolgusCD38 as determined by surface plasmon resonance assay.

| | hCD38-his (SEQ ID NO: 2) | | cCD38-his (SEQ ID NO: 4) | |
|---|---|---|---|---|
| | Kd (s-1) | KD (M) | Kd (s-1) | KD (M) |
| mAb1 | 2.66E−04 | 3.36E−10 | 9.85E−05 | 3.90E−10 |
| mAb2 | 3.90E−04 | 3.32E−10 | 7.84E−04 | 3.44E−09 |
| mAb3 | 2.83E−04 | 4.83E−10 | 1.29E−04 | 7.10E−10 |
| mAb4 | 5.29E−04 | 8.22E−10 | 2.01E−04 | 1.14E−09 |
| mAb5 | 3.33E−04 | 3.12E−10 | 1.25E−04 | 5.63E−10 |
| mAb6 | 2.03E−04 | 1.44E−09 | 1.90E−04 | 1.38E−09 |

Figure 2G:
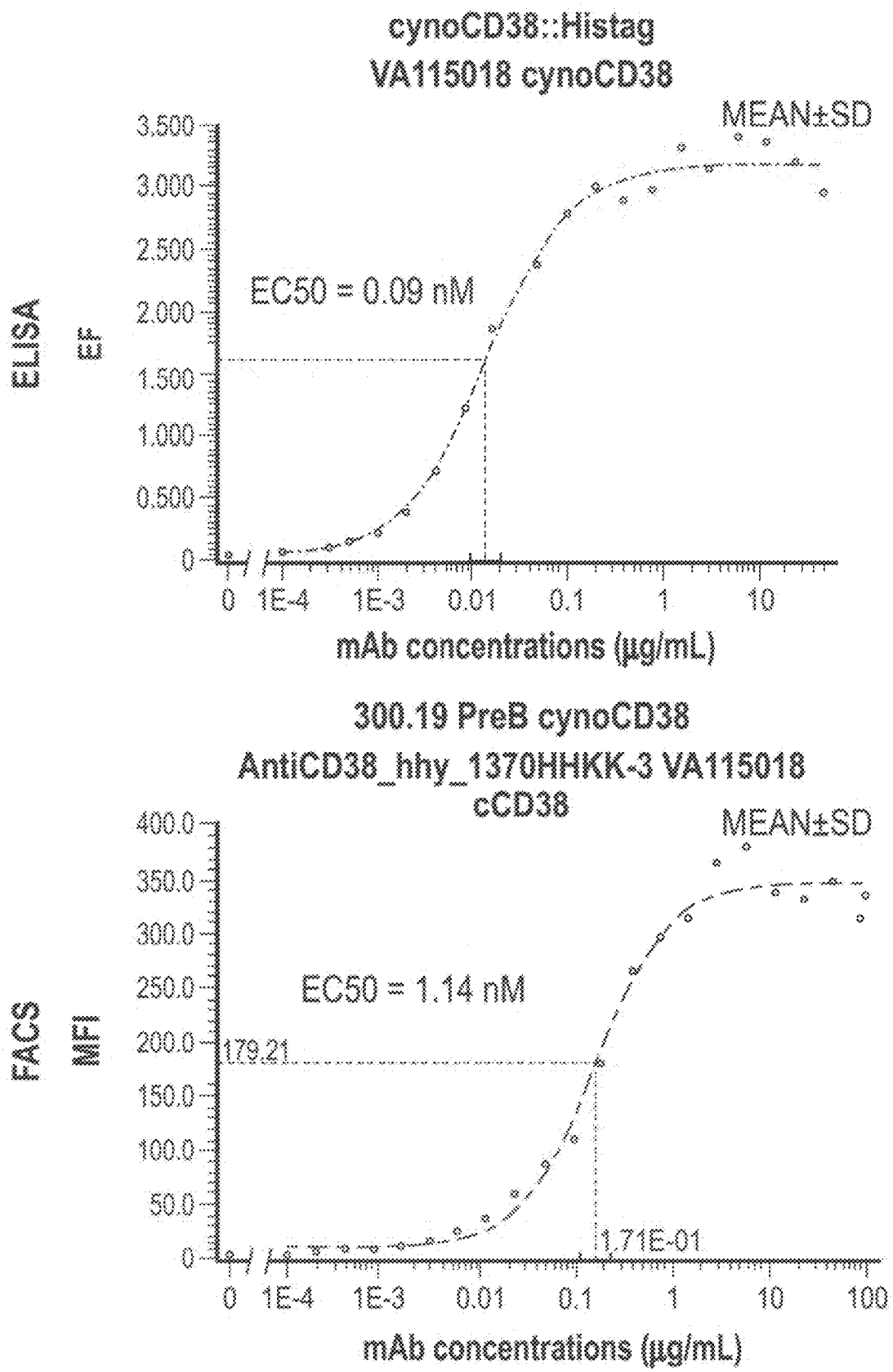

The ability of the humanized anti-CD38 variants to bind to CD38-expressing cells was assessed using the FACS-based binding assay described above. FACS data were used to determine the EC50 of antibody binding to human and cynomolgus monkey CD38 for humanized anti-CD38 antibodies mAb2 (FIG. 2A), mAb3 (FIG. 2C), mAb4, mAb5 (FIG. 2E), and human anti-CD38 antibody mAb6 (FIG. 2G). The binding data, set forth in Table L, shows that all humanized anti-CD38 variants exhibited similar binding affinities for cell surface CD38.

TABLE L

Binding affinity of anti-CD38 mAbs to CD38 expressing murine preB.:300.19 cells.

| | Apparent KD FACS (M) | |
|---|---|---|
| | hCD38-expressing cells | cCD38-expressing cells |
| mAb1 | 2.80E−10 | 2.20E−10 |
| mAb2 | 3.30E−10 | 7.50E−10 |
| mAb3 | 7.80E−10 | 1.31E−09 |
| mAb4 | 3.30E−10 | 1.15E−09 |
| mAb5 | 6.80E−10 | 1.07E−09 |
| mAb6 | 2.07E−09 | 1.14E−09 |

Binding data from the three assays are summarized in FIG. 2I, along with sequence identity of the VH and VL domains to human V regions.

Figure 2J:
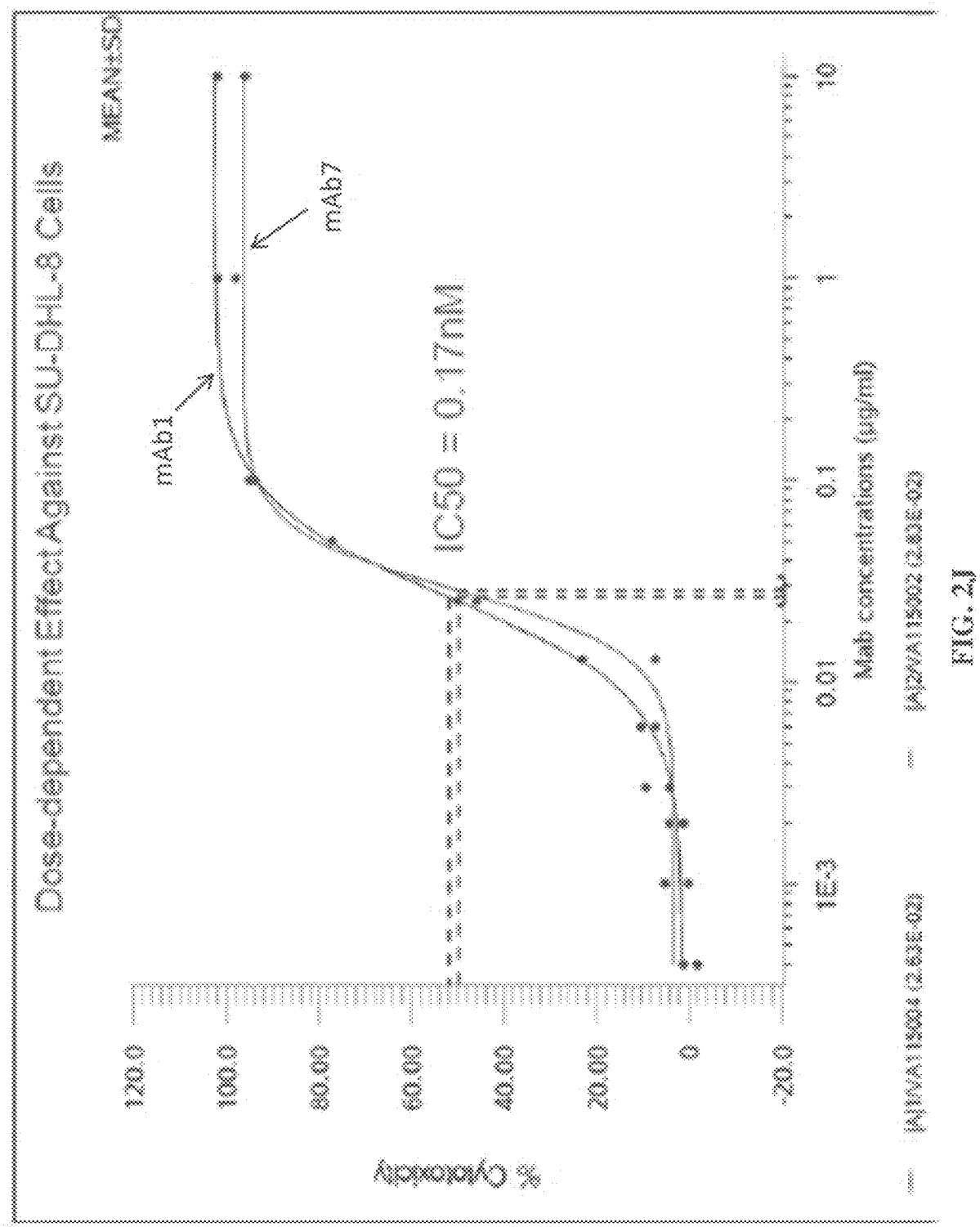
FIG. 2J shows the concentration-dependent induction of SU-DHL-8 cells apoptosis by mAb7 and mAb1 after incubation for 72 hours at 37° C.
Figure 2K:
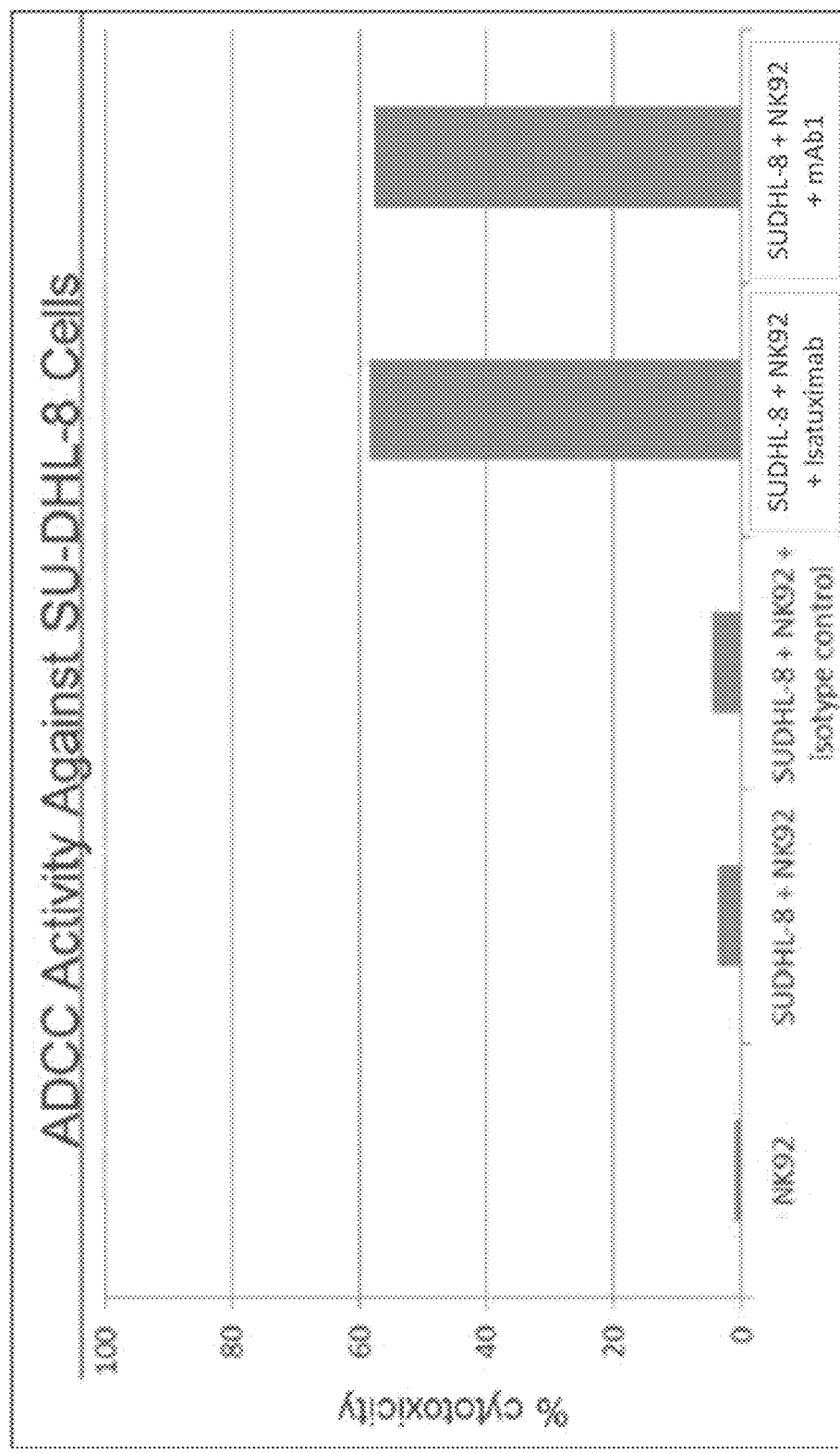
FIG. 2K shows antibody-dependent cell-mediated cytotoxicity (ADCC) activity of isatuximab and mAb1 against SU-DHL-8 cells in the presence of NK92 cells.
Figure 2L:
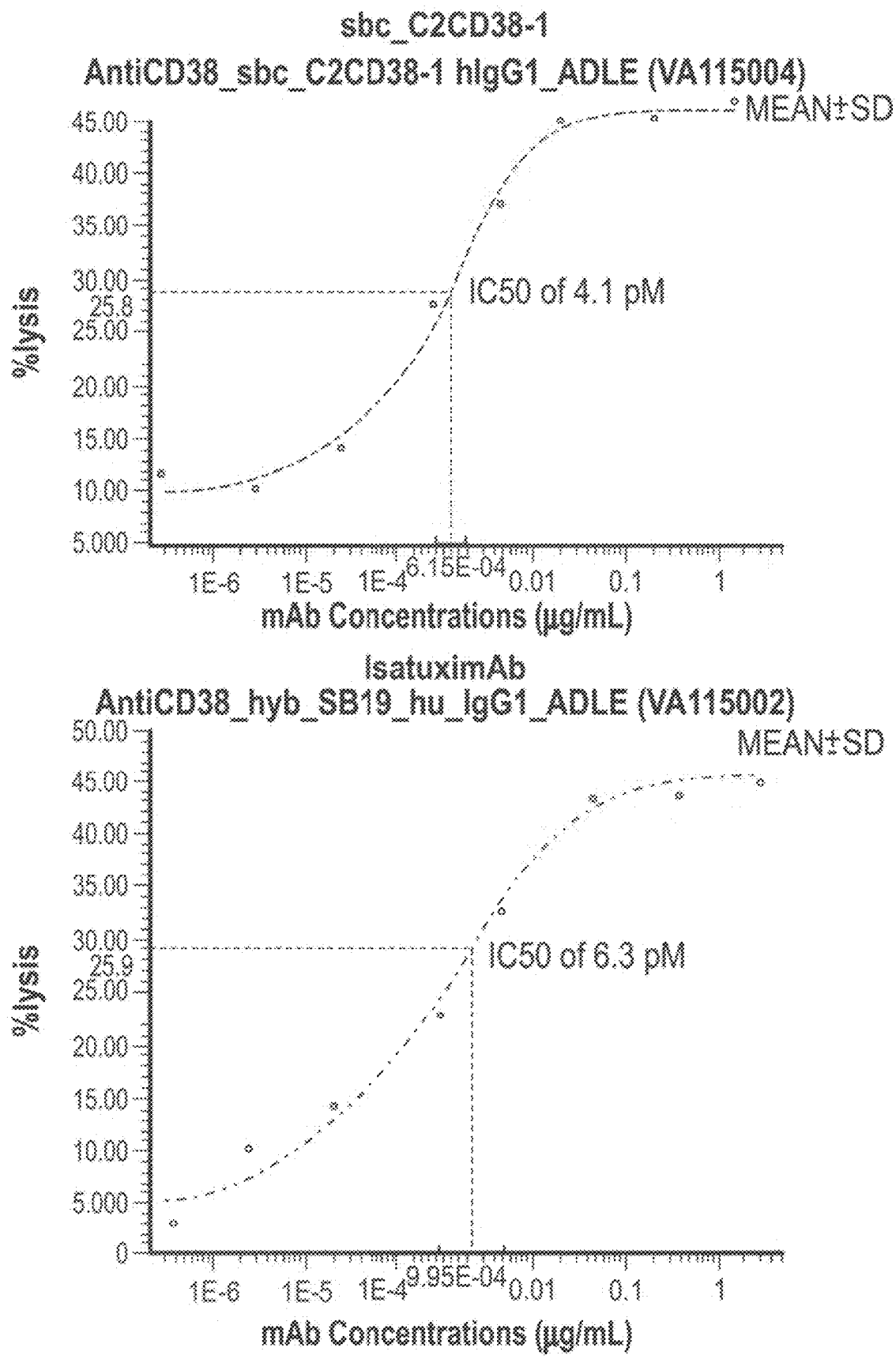
FIG. 2L shows concentration-dependent antibody-dependent cell-mediated cytotoxicity (ADCC) activity of isatuximab (right) and mAb1 (left) against SU-DHL-8 cells in the presence of NK92 cells after 4 hours at 37° C.

The abilities of parental mAb1 antibody and mAb7 to induce apoptosis was next examined. Both antibodies increased Annexin V staining and propidium iodide (PI) uptake. 40% of cells became double-positive for Annexin V and PI after treatment with mAb7, whereas 60% of cells treated with mAb1 were double positive. Both antibodies exhibited a similar concentration-dependent apoptotic effect in SU-DHL-8 cells (FIG. 2J). Similarly, both antibodies promoted ADCC activity against SU-DHL-8 cells in the presence of NK92 cells (FIG. 2K), leading to up to 60% cytotoxicity and an IC50 of 4-6 pM after 4 hours at 37° C. (FIG. 2L).

A CD38 isoform E was identified in silico and validated at the transcript level from NK cells, PBMCs, and BMMCs from multiple myeloma patients and cancer cell lines (MOLP-8, CU1702, and CU2332). CD38 isoform E was evidenced by a nucleic sequence database screening using BLASTN 2.2.26 (Altschul, Stephen F. Thomas L. Madden, Alejandro A. Schaffer, Jinghui Zhang, Zheng Zhang, Webb Miller, and David J. Lipman (1997), "Gapped BLAST and PSI-BLAST: anew generation of protein database search programs". Nucleic Acids Res. 25:3389-3402) program on Human RefSeq transcript database release 20131216 BLASTN program was applied without masking sequence low complexity regions and considering at least: 98.5% identity with human CD38 isoform A nucleic sequence on a stretch of 100 nucleic acid residues long minimum. Sequences highlighted from this screening were realigned with CD38 gene locus in order to be validated as being transcriptional forms of Human CD38 gene (same Intron-Exon genomic structure). CD38 isoform E nucleic sequence was one of sequences validated as being transcriptional forms of the human CD38 gene.

The ability of anti-CD38 antibodies to bind to both human CD38 isoforms A and E was also examined. For evaluating binding to CD38 isoform A and isoform E, an Enzyme-linked immunosorbent assay (ELISA) was performed by using isoform A and isoform E proteins (prepared as described in Example 1) as capturing antigen. 96-well plates were coated with either isoform at 0.5 µg/well in PBS and 100 µL/well of antibodies were added to the plate. The plate was incubated at 37° C. for 1 h and washed five times with PBS containing 0.05% Tween-20 (PBS-T). Then, 100 µL of a 1:25,000 dilution of Anti-human IgG, conjugated with horseradish peroxidase, (Jackson Ref: 109-035-098) was added to each well. Following incubation at 37° C. for 1 h in darkness, plates were washed with PBS-T five times. Antibody binding was visualized by adding TMB-H2O2 buffer and read at a wavelength of 450 nm. EC50 values were estimated using BIOST@T-SPEED software.

The binding affinity of various antibodies to CD38 isoform A (SEQ ID NO:1) and isoform E (SEQ ID NO:105) was determined, as shown in Table L2. Table M provides a comparison of binding properties for various anti-CD38 antibodies.

TABLE L2

Binding affinity of anti-CD38 antibodies for CD38 isoforms A and E, based on EC50 as determined by ELISA.

| Antibody | CD38 isoform A EC50 (nM) | CD38 isoform E EC50 (nM) |
| --- | --- | --- |
| mAb1 | 0.11 (CV 9%) | 0.08 (CV 7%) |
| mAb2 | 0.14 (CV 13%) | 0.10 (CV 12%) |
| mAb6 | 0.47 (CV 3.7%) | 0.32 (CV 5%) |
| mAb7 | 0.10 (CV 7.1%) | No binding |

TABLE M

Binding characteristics of various anti-CD38 antibodies

| Anti-CD3 | H11 (Santa Cruz) | Daratumumab | mAb7 | mAb1 | mAb6 |
| --- | --- | --- | --- | --- | --- |
| Binding to huCD38 isoform A | + | + | + | + | + |
| Binding to huCD38 isoform E | + | − | − | + | + |
| Binding to cyno CD38 | + | − | − | + | + |

In conclusion, both mAb7 and mAb1 induce similar apoptosis in MOLP-8 human multiple myeloma cells, similar concentration-dependent apoptotic effect against SU-DHL-8 cells, and similar concentration-dependent ADCC activity against SU-DHL-8 cells. However, only mAb1 bound to both human and cynomolgus monkey CD38 with sub-nanomolar affinity and bound to CD38 isoforms A and E.

Figure 2M:
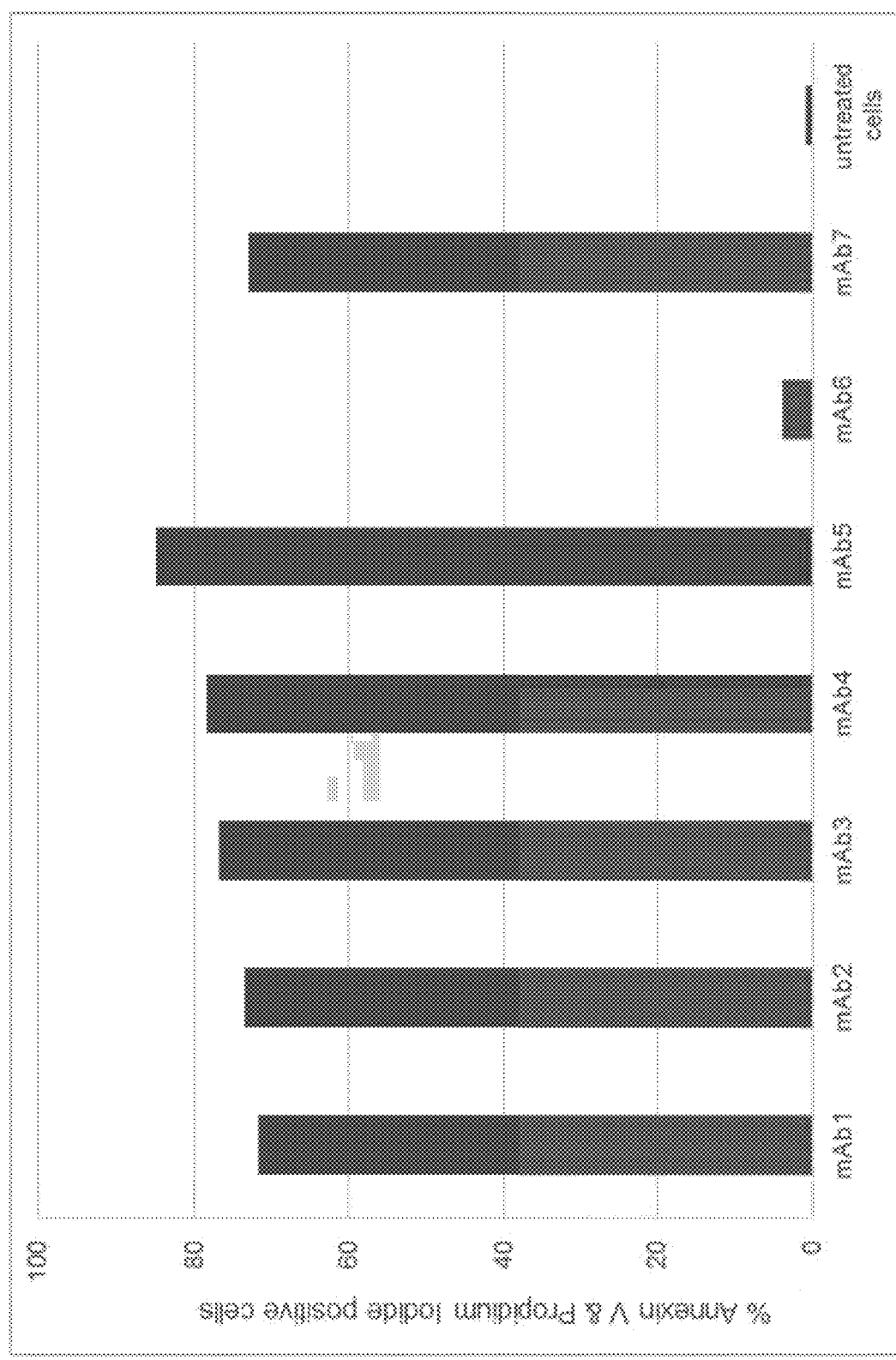
FIGS. 2M-2Q showed the results of apoptosis induction assays using the indicated anti-CD38 antibodies against SU-DHL-8 tumor cells. Apoptosis was quantified by measuring dual Annexin V and Propidium iodide uptake via flow cytometry.
Figure 2N:
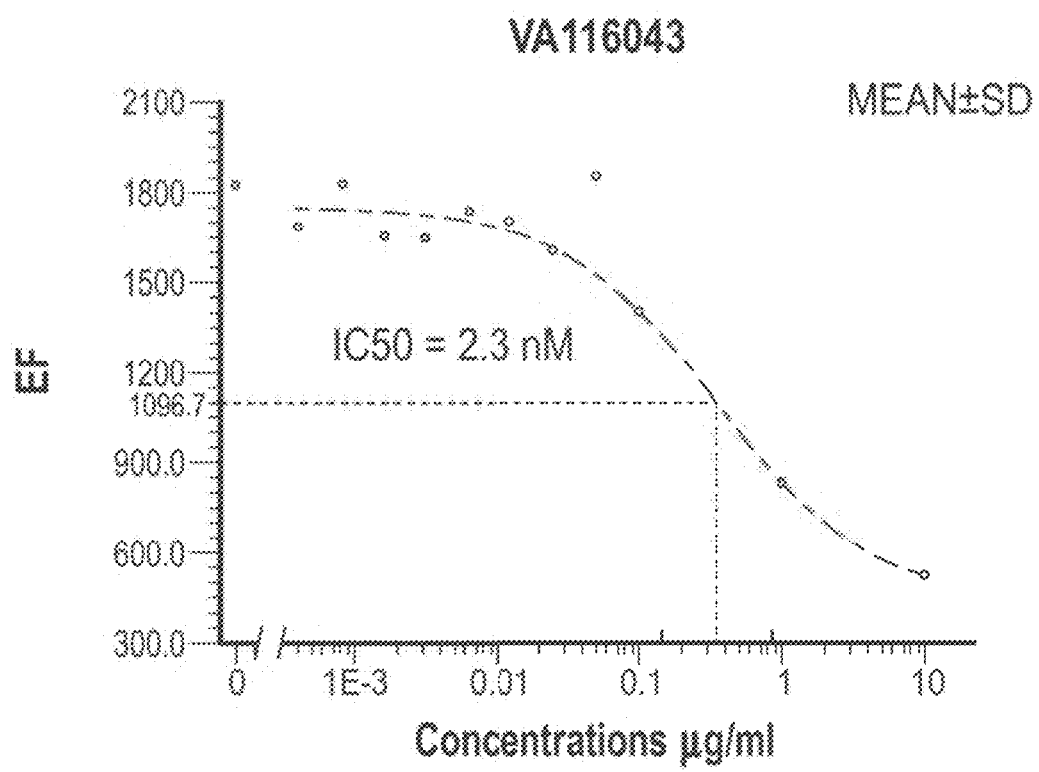
Figure 2O:
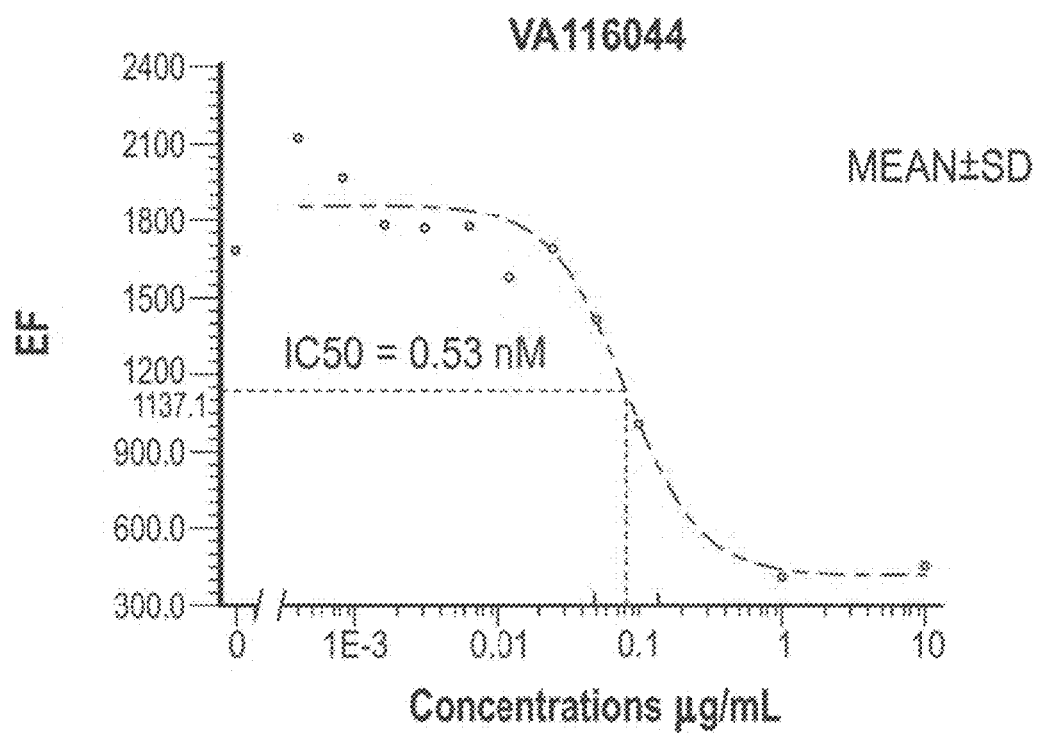
Figure 2P:
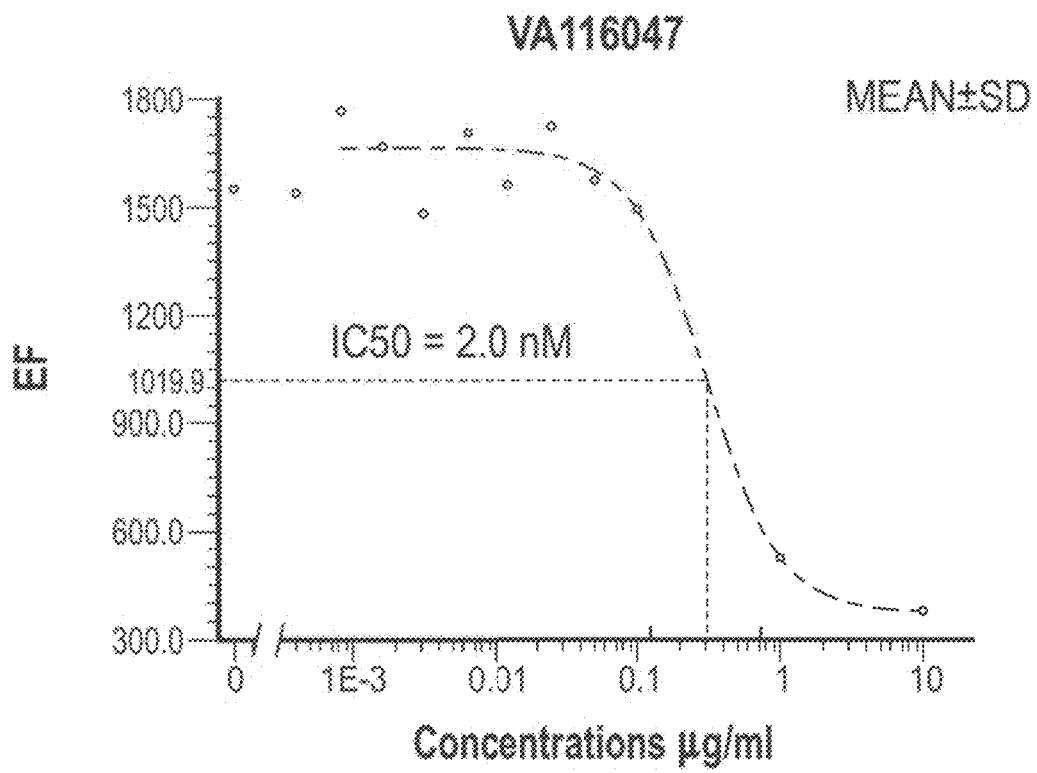
Figure 2Q:
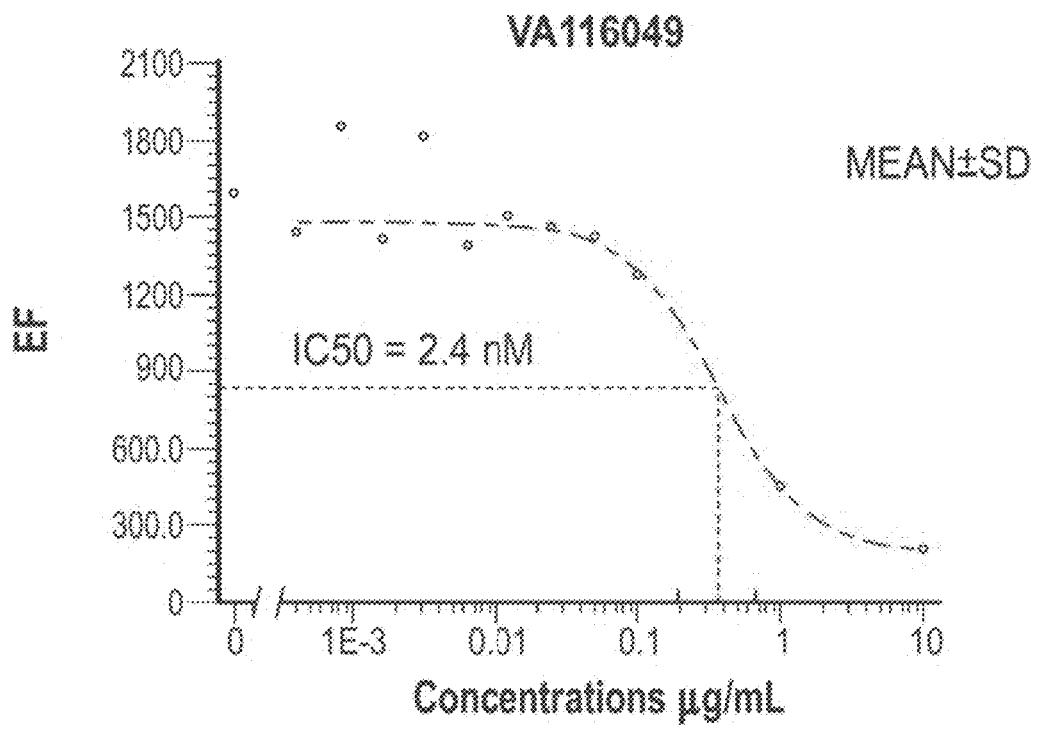

The ability of the humanized anti-CD38 variants to induce apoptosis was also assessed by fluorescence activated cell sorter (FACS) as described above. Several anti-CD38 antibodies with various functional properties have been identified previously, while some of these can mediate in vitro killing of CD38+ cell lines via direct impact on cell proliferation or apoptosis. The results of apoptosis induction assays as shown in FIG. 2M. All antibodies generated in Examples 1 and 2 were able to induce apoptosis except mAb6. Anti-CD38 antibodies mAb2, mAb3, mAb4, and mAb5 led to a dose-dependent induction of apoptosis in SU-DHL-8 lymphoma cells; IC50 for each antibody is provided in FIGS. 2N-2Q.

Example 4: Generation of Trispecific Anti-CD38 Binding Proteins

Figure 3A:
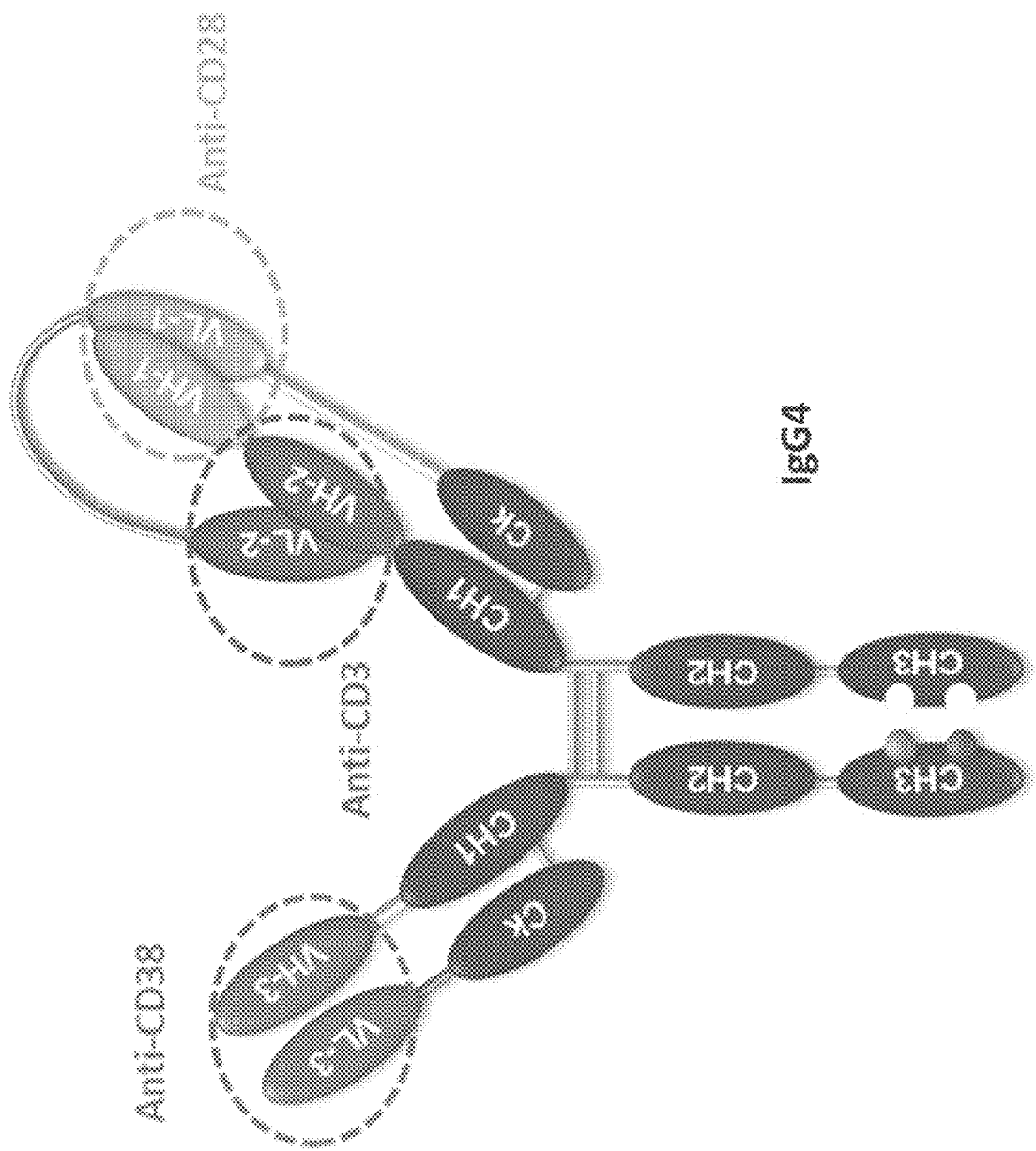
FIG. 3A provides a schematic representation of a trispecific binding protein comprising four polypeptide chains that form three antigen binding sites that binds three target proteins: CD28, CD3, and CD38. A first pair of polypeptides possess dual variable domains having a cross-over orientation (VH1-VH2 and VL2-VL1) forming two antigen binding sites that recognize CD3 and CD28, and a second pair of polypeptides possess a single variable domain (VH3 and VL3) forming a single antigen binding site that recognizes CD38. The trispecific binding protein shown in FIG. 3A uses an IgG4 constant region with a "knobs-into-holes" mutation, where the knob is on the second pair of polypeptides with a single variable domain.
Figure 3D:
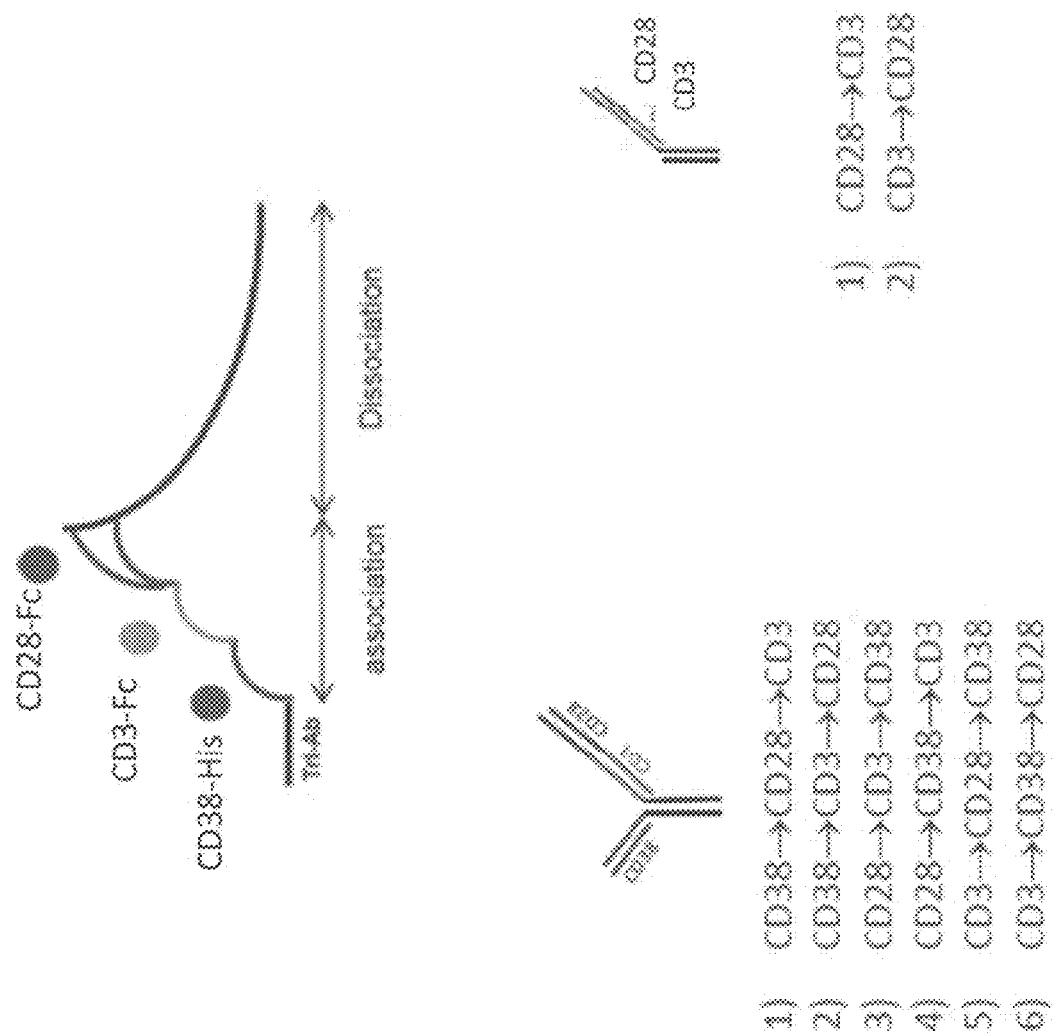
FIG. 3B provides a schematic representation of an SPR-based assay for examining the ability of each antigen binding domain of anti-CD38/anti-CD28/anti-CD3 trispecific binding proteins to bind its cognate antigen.
FIG. 3C shows the results of SPR-based assays for examining CD38 binding to anti-CD38/anti-CD28/anti-CD3 trispecific binding proteins. Binding of human CD38 to trispecific binding proteins was examined done (top led), after pre-binding with CD3 (top center), after pre-binding with CD28 (top right), after pre-binding to CD3 then CD28 (bottom left), or after pre-binding to CD28 then CD3 (bottom right).

Next, binding properties of the antigen binding domains of selected anti-CD38 antibodies described in Examples 1-3 were analyzed in the trispecific format shown in FIG. 3A.

Anti-CD38 antigen binding domains were tested in trispecific format (anti-CD38×anti-CD28×anti-CD3) for ability to bind CD38 when other antigen binding domains are bound to their cognate ligands using SPR. The sequential ligand binding assay is shown in FIG. 3B. For sequential binding of the three antigens to each trispecific Ab, saturating concentration (>10 KD) of each antigen was injected for 8 min followed by 5 min dissociation. Surface regenerate was conducted by injecting 10 mM Glycine-HCl pH 2.5 for 60 sec at 30 μl/min. Data were fitted with 1:1 kinetic binding model and analyzed using Biacore S200 Evaluation Software v 10. Equilibrium dissociation constant ($K_D$) was calculated using association rate constant ($k_{on}$) and dissociation rate constant ($k_{off}$).

Figure 4:
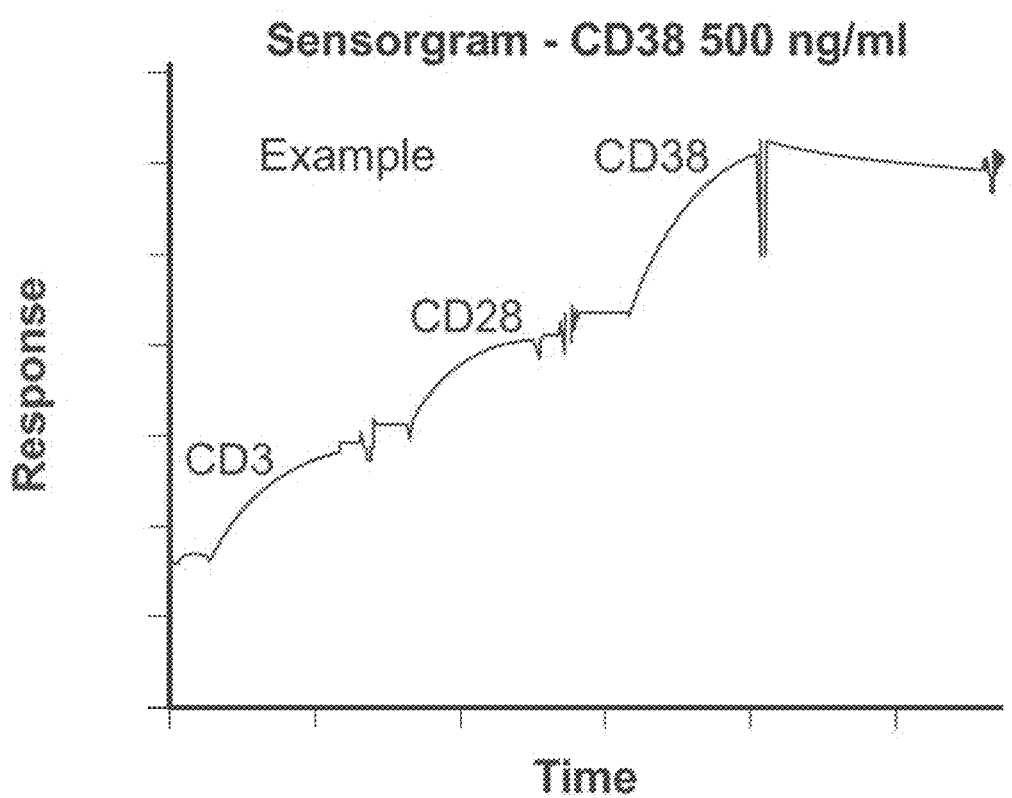
FIG. 4 shows the sequential binding of human CD3, CD28, and CD38 polypeptides to anti-CD38/anti-CD28/anti-CD3 trispecific binding proteins, as assayed by SPR FIG. 5 summarizes the binding affinities of indicated trispecific binding proteins against their cognate antigens (human CD3, CD28, and CD38) as measured by SPR.

As shown in FIG. 3C, this SPR-based assay showed that trispecific binding proteins were able to bind CD38 regardless of whether the CD3 and/or CD28 antigen binding domains were also bound to their cognate antigen. Results of an exemplary sequential binding assay are shown in FIG. 4. Kinetic parameters as measured by SPR are provided in Table M2.

TABLE M2

Binding of trispecific anti-CD38 × anti-CD28 × anti-CD3 binding proteins to 1, 2, or 3 cognate antigens.

| Binding protein state prior to CD38 binding | $k_a$ (M$^{-1}$s$^{-1}$) | $k_d$ (s$^{-1}$) | $K_D$ (M) |
| --- | --- | --- | --- |
| No prebound | 9.02E+05 | 1.42E−03 | 1.57E−09 |
| Prebound CD3 | 8.35E+05 | 1.24E−03 | 1.48E−09 |
| Prebound CD28 | 7.39E+05 | 1.32E−03 | 1.79E−09 |
| Prebound CD3 then CD28 | 8.18E+05 | 1.23E−03 | 1.50E−09 |
| Prebound CD28 then CD3 | 8.37E+05 | 1.23E−03 | 1.47E−09 |

These results demonstrate that all three targets can bind to the trispecific binding proteins simultaneously. Pre-binding the trispecific binding proteins with CD28, CD3, or both (in either order) did not alter binding kinetics or binding affinity to CD38.

Next, each antigen binding domain of the CD38$_{SB19}$×CD28$_{sup}$×CD3$_{mid}$ specific binding protein was evaluated by SPR for the ability to bind cognate antigen with and without the other two antigen binding domains in saturation. Tables M3 and M4 show the results of these assays.

TABLE M3

Target binding without other targets present

| Target | $k_a$ (M$^{-1}$s$^{-1}$) | $k_d$ (s$^{-1}$) | $K_D$ (M) |
| --- | --- | --- | --- |
| CD38 | 8.04E+05 | 1.41E−03 | 1.75E−09 |
| CD28 | 1.16E+05 | 3.14E−04 | 2.71E−09 |
| CD3 | 2.90E+04 | 6.73E−04 | 2.32E−08 |

TABLE M4

Target binding with other targets in saturation

| Target | $k_a$ (M$^{-1}$s$^{-1}$) | $k_d$ (s$^{-1}$) | $K_D$ (M) |
| --- | --- | --- | --- |
| CD38 | 5.93E+05 | 1.44E−03 | 2.42E−09 |
| CD28 | 1.05E+05 | 3.96E−04 | 3.77E−09 |
| CD3 | 1.27E+05 | 2.36E−03 | 1.86E−08 |

As demonstrated in Tables M3 and M4, having two targets saturated by pre-binding with antigen did not impact the kinetics or binding affinity of the third target for CD38 or CD28. In the case of CD3 binding, prebound CD38 and/or CD28 resulted in faster kinetics (approximately 4-fold impact on $k_{on}$ and $k_{off}$ values).

Anti-CD38 antigen binding domains were tested in trispecific format with two anti-CD28 antigen binding domains (super agonist, "sup." and conventional agonist, "cvn") and two anti-CD3 antigen binding domains ("mid" and "low").

Variable domain sequences for these antigen binding domains are provided as follows, anti-CD28$_{sup}$; SEQ ID NO:49 (VH) and SEQ ID NO:50 (VL); anti-CD28$_{evn}$; SEQ ID NO:51 (VH) and SEQ ID NO:52 (VL); anti-CD3$_{mid}$ SEQ ID NO:53 (VH) and SEQ ID NO:54 (VL); anti-CD3$_{low}$; SEQ ID NO:84 (VH) and SEQ ID NO:85 (VL). The results of SPR assays examining binding of trispecific binding proteins are shown in FIG. 5. Three anti-CD38 binding domains had roughly the same binding affinity in the trispecific binding protein format as in a monospecific formal. Both CD3 binding domains had approximately the same binding affinity in mono-, bi-, and trispecific formats. CD28 binding domains should slightly lower (but still nanomolar) binding affinity in bi- or trispecific format as compared with monospecific. When the other two antigen binding domains were saturated, anti-CD38$_{SB19}$ and anti-CD28$_{sup}$ binding domains had similar binding affinities, compared with when the other two antigen binding domains are not bound to antigen. However, the anti-CD3$_{mid}$ binding domain showed faster kinetics when the other two antigen binding domains were saturated. These results demonstrate that anti-CD38, anti-CD28, and anti-CD3 binding domains are compatible for use with the trispecific binding protein format.

The anti-CD38 antigen binding domains generated herein were also compared against the existing anti-CD38 antigen binding domain of mAb7 (see SEQ ID NO:47 for VH and SEQ ID NO:48 for VL sequences, respectively). The binding of trispecific molecules to CD38 expressed on the surface of recombinant murine preB::300.19 cells was determined by flow cytometry and the corresponding anti-CD38 monovalent antibodies were assayed in parallel. The recombinant cell line was described by J. Deckket et al. 2014 Clin. Cancer Res 20:4574-4583. Murine preB::300.19 CD38-expressing cells were coated at 40,000 cells/well on 96-well High Bind plate (MSD L15XB-3) and 100 µL/well of trispecific molecules were added for 45 min at 4° C. and washed three times with PBS 1% BSA. 100 µL/well of goat anti-human IgG conjugated with Alexa488 (Jackson Immu-noResearch: #109-545-098) was added for 45 min at 4*C and washed three times with PBS 1% BSA. Antibody binding was evaluated after centrifugation and resuspension of cells by adding 200 µl/well PBS 1% BSA and read using Guava® easyCyte™ 8HT Flow Cytometry System. Apparent KD and EC50 values were estimated using BIOST@T-BINDING and BIOST@T-SPEED software, respectively.

Figure 6A:
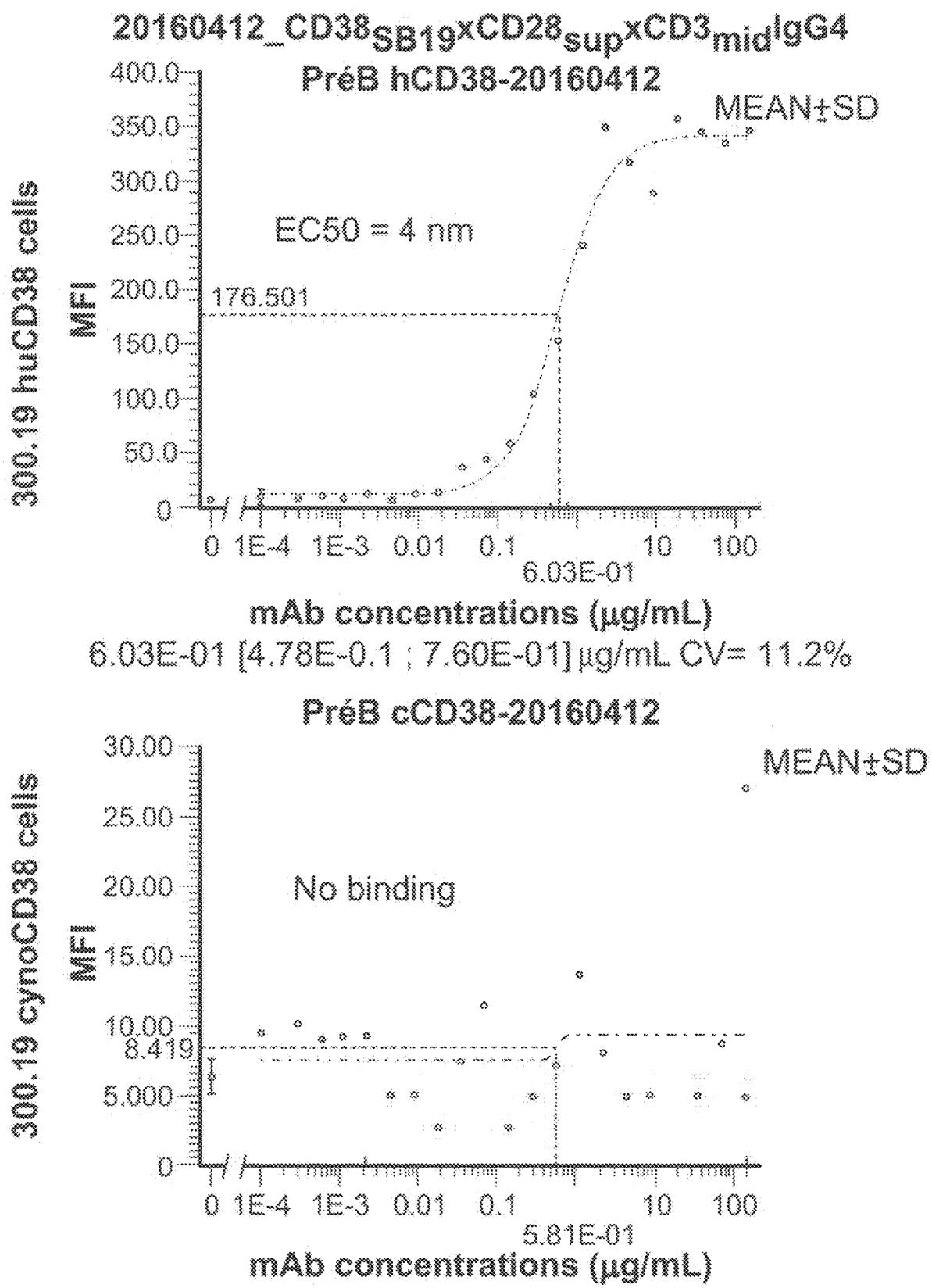
FIG. 6A compares the apparent affinity of isatuximab antigen binding domain in human IgG1 format ($2^{nd}$ sheet) or in a trispecific binding protein format with the isatuximab, anti-CD28, and anti-CD3 antigen binding domains (formal according to FIG. 3A; $1^{st}$ sheet) for binding human (top) or cynomolgus monkey (bottom) CD38 polypeptides, as assayed by flow cytometry.

Flow cytometry was used as described above to examine binding of mAb7 or the trispecific binding protein with the mAb7 anti-CD38 antigen binding domain to murine pre-B cells expressing human or cynomolgus monkey CD38 polypeptide on their cell surface. As shown in FIG. 6A, the CD38×CD28$_{sup}$×CD3$_{mid}$ trispecific binding protein with the mAb7 anti-CD38 antigen binding domain bound to cells expressing human CD38 (upper left) with 8-fold lower apparent affinity than mAb7 monospecific antibody (upper right). Neither mAb7 monospecific antibody (lower right) or the trispecific binding protein with the mAb7 anti-CD38 antigen binding domain (lower left) bound to cells expressing cynomolgus CD38.

Figure 6B:
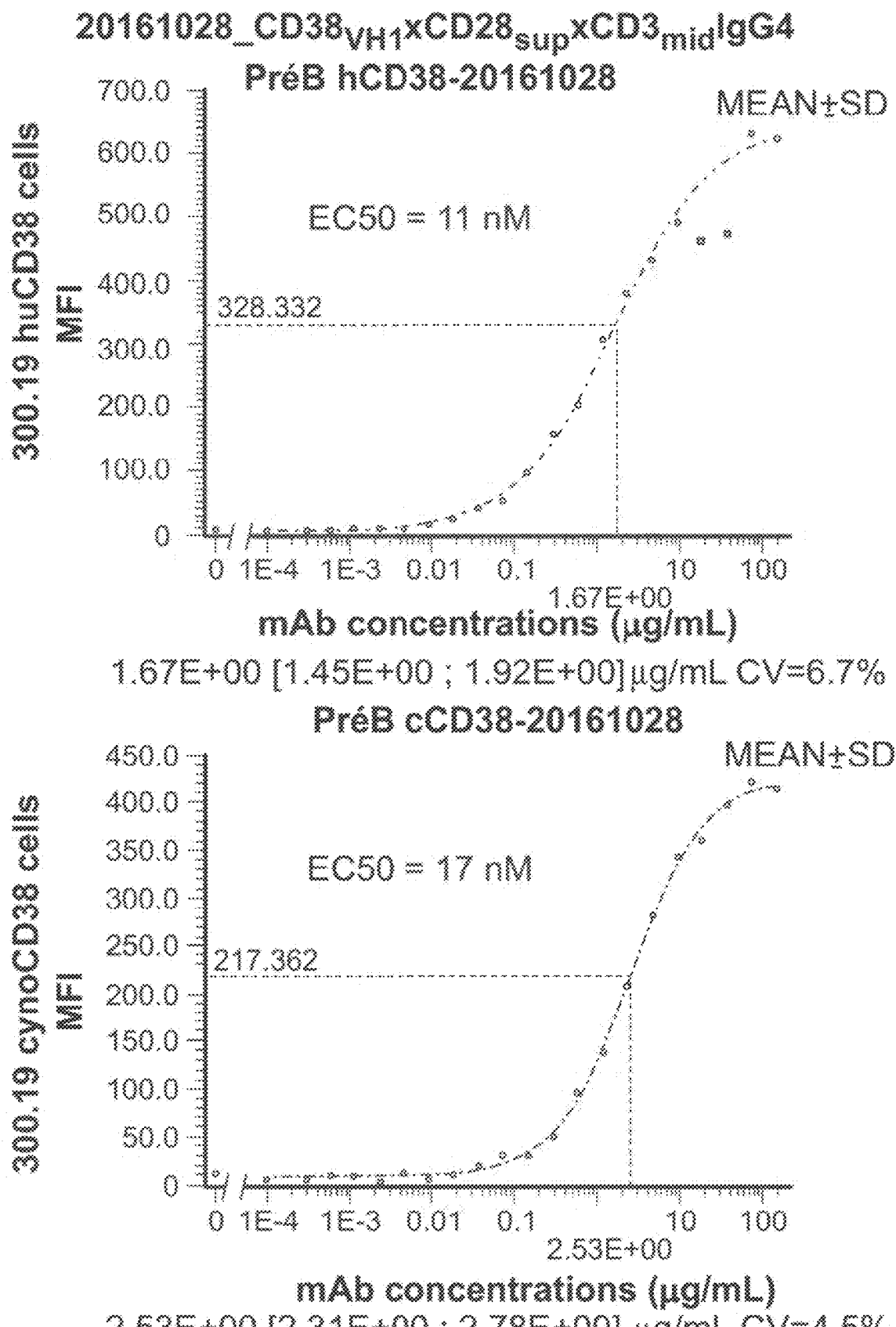
Figure 6D:
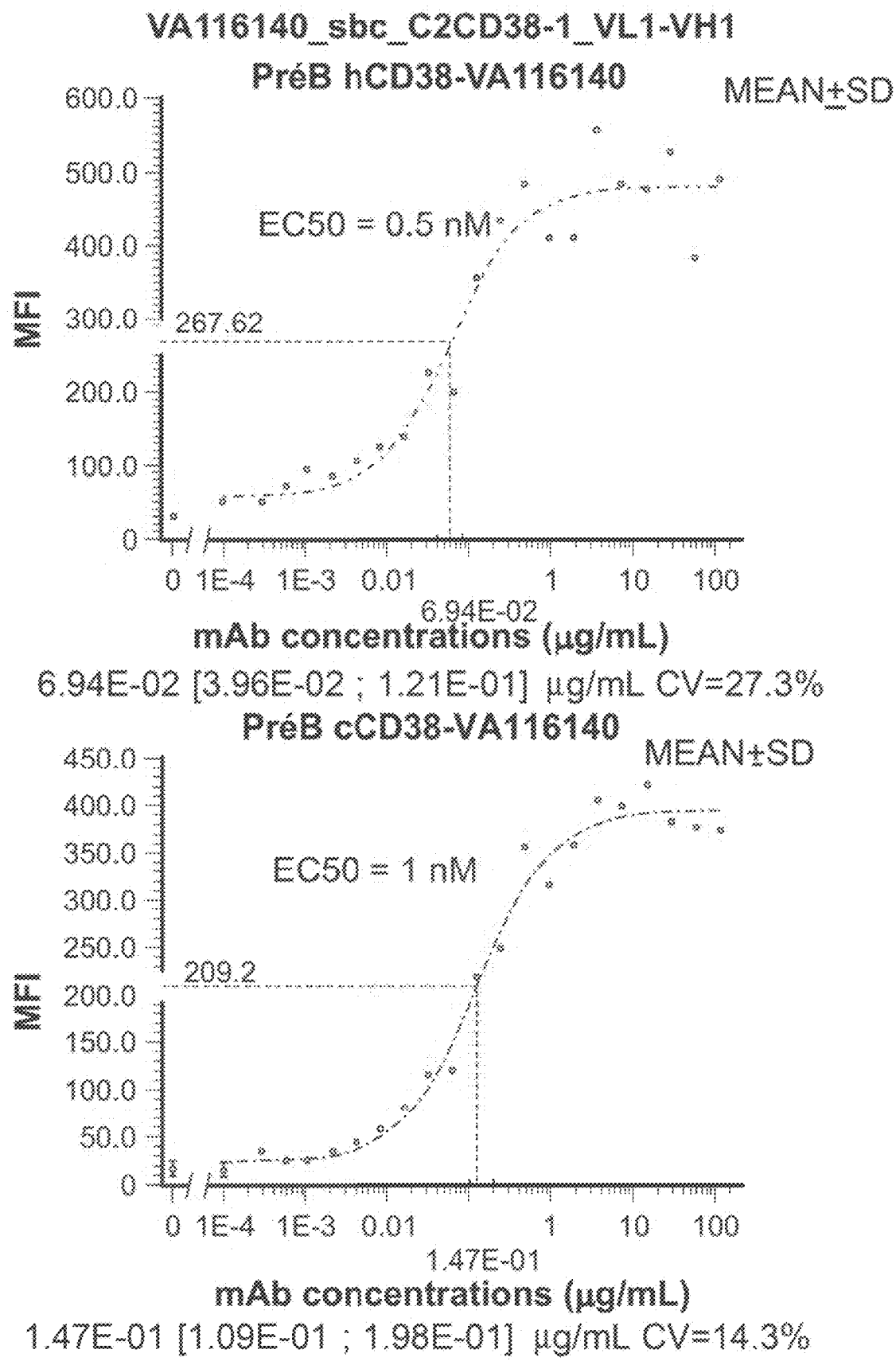

The binding domain of humanized anti-CD38 antibody mAb2 was also tested in trispecific formats for binding to cells expressing human or cynomologus CD38 polypeptides. As shown in FIGS. 6B-6D, and unlike mAb7, CD38×CD28$_{sup}$×CD3$_{mid}$ and CD38×CD28$_{evn}$×CD3$_{mid}$ trispecific binding proteins with mAb2 anti-CD38 antigen binding domain, as well as the mAb2 monospecific antibody, were able to bind both human and cynomolgus monkey CD38 polypeptides. The CD38×CD28$_{evn}$×CD3$_{mid}$ trispecific binding protein with the mAb2 anti-CD38 antigen binding domain bound to cells expressing human CD38 with 9-fold lower apparent affinity than the parental mAb2 antibody (compare FIG. 6C top to FIG. 6D, top). The CD38× CD28$_{evn}$×CD3$_{mid}$ trispecific binding protein with the mAb2 anti-CD38 antigen binding domain bound to cells expressing cynomolgus CD38 with 7.5-fold lower apparent affinity than the parental mAb2 antibody (compare FIG. 6C, bottom to FIG. 6D, bottom). The CD38×CD28$_{sup}$CD3$_{mid}$ trispecific binding protein with the mAb2 anti-CD38 antigen binding domain bound to cells expressing human CD38 with a 2.5-fold lower apparent affinity than the CD38×CD28$_{evn}$× CD3$_{mid}$ trispecific binding protein with the mAb2 anti-CD38 antigen binding domain (compare FIG. 6C, top to FIG. 6B, top).

Figure 6E:
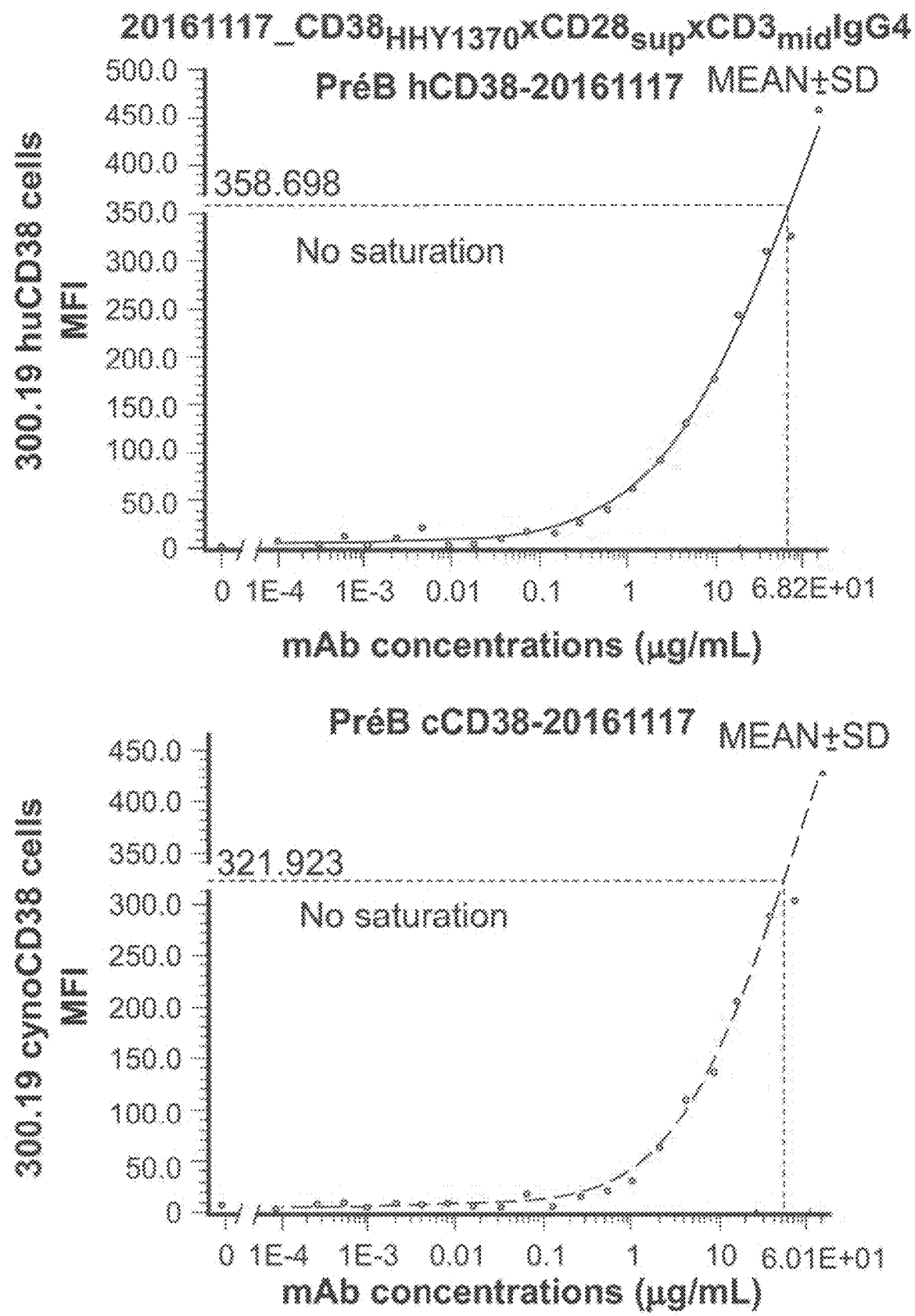
FIG. 6E compares the apparent affinities of trispecific binding protein CD38$_{HHY1370}$×CD28$_{sup}$×CD3$_{mid}$ or monospecific anti-CD38 antibody mAb6 for binding to cells expressing human (top) or cynomolgus monkey (bottom) CD38 polypeptides, as assayed by flow cytometry.

The binding domain of humanized anti-CD38 antibody mAb6 was also compared against the mAb6 monospecific antibody for binding to cells expressing human or cynomologus CD38 polypeptides. While the mAb6 monospecific antibody bound to cells expressing human (upper right) or cynomolgus monkey (lower right) CD38 polypeptides in the nM range (FIG. 6E), the CD38×CD28$_{sup}$×CD3$_{mid}$ trispecific binding protein with the mAb6 anti-CD38 antigen binding domain bound to cells expressing human (upper left) or cynomolgus monkey (lower left) CD38 polypeptides without saturation.

In conclusion, the affinity for CD38$_{SB19}$×CD28$_{sup}$× CD3$_{mid}$ trispecific binding protein binding to human CD38 was found to be in the same range, whether examining binding to recombinant human CD38 by SPR or to human CD38 expressed on a cell surface by flow cytometry (FIG. 6F). Similarly, the affinity of CD38$_{VH1}$×CD28$_{sup}$×CD3$_{mid/low}$ (mAb2 anti-CD38 binding domain) and CD38$_{VH1}$× CD28$_{evn}$×CD3$_{mid/low}$ trispecific binding proteins (mAb2 anti-CD38 binding domain) for binding to human CD38 was also in the same range in both assays. For CD38$_{HHY1370}$× CD28$_{sup}$×CD3$_{mid}$ (mAb6 anti-CD38 binding domain), the K$_D$ for binding human CD38 was determined by SPR to be 1 nM whereas no accurate EC50 value could be estimated by flow cytometry. A summary of apparent KD values (obtained by FACS analyses) of trispecific binding proteins with various anti-CD38 binding domains is provided in Table M5.

TABLE M5

Summary of apparent KD values obtained by flow cytometry assays

| | Apparent KD FACS (M) | |
|---|---|---|
| | hCD38-expressing cells | cCD38-expressing cells |
| Trispecific with antiCD38 mAb2 | 4.4 nM | 7.5 nM |
| Trispecific with antiCD38 mAb6 | No saturation | No saturation |
| Trispecific with antiCD38 mAb7 | 4 nM | No binding |
| mAb2 | 0.5 nM | 1 nM |
| mAb6 | 11.2 nM | 6.6 nM |
| mAb7 | 0.5 nM | No binding |

As expected. ΔCD38×CD28$_{sup}$×CD3$_{mid}$ trispecific binding protein lacking the anti-CD38 binding domain did not bind to cells expressing human or cynomolgus monkey CD38 poly peptides (FIG. 6G). This indicates that the binding observed in this assay was specific for the CD38 antigen binding domains.

Example 5: In Vitro and In Vivo Characterization of Anti-CD38 mAb2 and Anti-CD38 mAb6-Containing Trispecific Binding Proteins The following Example describes experiments characterizing the stability, binding properties, and activities of novel T cell engagers that contain variable domains derived from the mAb2 and mAb6 antibodies. Additional anti-CD38×CD28×CD3 antibodies were generated comprising variants of the anti-CD38, CD3 and CD28 arms of the trispecific binding proteins. The new anti-CD38/CD3/CD28 antibodies differ in: 1) Anti-CD38 binding domain (mAb2 or mAb6); 2) Anti-CD3 binding domain ($CD3_{high}$ or $CD3_{low}$; see SEQ ID NOs: 84 and 85 for anti-$CD3_{low}$ VH and VL sequences, respectively); 3) Anti-CD28 binding domain ($CD28_{sup}$ or $CD28_{evn}$). Within possible combinations, a collection of the anti-CD38×CD28×CD3 was designed, produced, and subsequently tested for various functions.

Materials and Methods

Production and Purification of Trispecific Binding Proteins

Trispecific binding proteins were produced by transient transfection of 4 expression plasmids into Expi293 cells using ExpiFectamine™ 293 Transfection Kit (Thermo Fisher Scientific) according to manufacturer's protocol. Briefly, 23% (w/w) of each plasmid was diluted into Opti-MEM, mixed with pre-diluted ExpiFectamine reagent for 20-30 minutes at room temperature (RT), and added into Expi293 cells ($2.5 \times 10^6$ cells/ml). An optimization of transfection to determine the best ratio of plasmids was often used in order to produce the trispecific binding protein with good yield and purity.

4-5 days post transfection, the supernatant from transfected cells was collected and filtered through 0.45 µm filter unit (Nalgene). The trispecific binding protein in tire supernatant was purified using a 3-step procedure. First, protein A affinity purification was used, and the bound Ab was eluted using "IgG Elution Buffer" (Thermo Fisher Scientific). Second, product was dialyzed against PBS (pH7.4) overnight with 2 changes of PBS buffer. Any precipitate was cleared by filtration through 0.45 µm filter unit (Nalgene) before nest step. Third, size-exclusion chromatography (SEC) purification (Hiload 16/600 Superdex 200 µg, or Hiload 26/600 Superdex 200 µg. GE Healthcare) was used to remove aggregates and different species in the prep. The fractions were analyzed on reduced and non-reduced SDS-PAGE to identify the fractions that contained the monomeric trispecific binding protein before combining them. The purified antibody can be aliquoted and stored at −80° C. long term.

ELISA Assays

The binding properties of the purified antibodies were analyzed either using ELISA or SPR methods. For ELISA, corresponding antigens for each binding site in the trispecific binding protein were used to coat a 96-well Immuno Plate (Nunc 439454, Thermo Fisher Scientific) overnight at 4° C. using 2 µg/ml each antigen in PBS (pH7.4). The coated plate was blocked using 5% skim milk 12% BSA in PBS for one hour at RT, followed by washing with PBS+25% Tween 20 three times (Aqua Max 400, Molecular Devices). Serial dilution of antibodies (trispecific and control Abs) were prepared and added onto the ELISA plates (100 µl/well in duplicate), incubated at RT for one hour, followed by washing 5 times with PBS+0.25% Tween 20.

After washing, the HRP conjugated secondary anti-human Fab (1:5000, Cat. No. 109-035-097, Jackson ImmunoResearch Inc) was added to each well and incubated at RT for 30 minutes. After washing 5 times with PBS+0.25% Tween 20, 100 µl of TMB Microwell Peroxidase Substrate (KPL, Gaithersburg, Md., USA) was added to each well. The reaction was terminated by adding 50 µl 1M $H_2SO_4$, and $OD_{450}$ was measured using SpectraMax M5 (Molecular Devices) and analyzed using SoftMax Pro6.3 software (Molecular Devices). The final data was transferred to GraphPad Prism software (GraphPad Software, CA, USA), and plotted as shown. EC50 was calculated using the same software.

ELISA assay was used to determine the binding of an anti-CD38×CD28×CD3 trispecific antibodies or isotype control antibody (human IgG4) to human CD3 (Cambridge Biologics LLC Cat #03-01-0051), CD28 (Cambridge Biologics LLC Cat*03-01-0303), and CD38 (Cambridge Biologics LLC Cat #03-01-0369). The bound antibodies were detected using a horseradish peroxidase (HRP)-conjugated anti-Fab secondary antibody (Jackson ImmunoResearch Inc #109-035-097).

In Vitro Cell Killing Assay

Purified human PBMCs were using for in vitro killing assays against various cancer cells using different trispecific binding proteins. Briefly, the killing assay was set up in 96-well V-bottom plate. For each plate, 40 ml PBMCs from each donor were plated at $2 \times 10^6$ cells ml, and 30 ml of PKH26 (Sigma #MINI26) labeled target cells at $2.5 \times 10^5$ cells/ml (4 µL of dye to stain up to $1 \times 10^7$ cells) were prepared. First 20 µL/well test proteins at various concentrations or PMA were added into each well, followed by adding 80 µL/well labeled target cells into each well ($2 \times 10^4$ cells/well). 100 µL of PBMC w ere then added to each well, reaching E:T-10:1 well ($2 \times 10^5$ cells/well), and incubated for 24 hours at 37° C. 5% CO2 incubator. The cells were spin down, and the supernatant was either collected for measuring cytokine release, or discarded. The cells were stained with Vivid LIVE/DEAD™ Fixable Violet Dead Cell Staining buffer (Life Technology #1.34955) (staining buffer was prepared by adding 60 µL Vivid reagent into 60 ml PBS). Cells were resuspended into 100 µL staining buffer by incubation for 15 mm at RT in the dark. After washing the cells with 1×PBS, the cells were resuspended in 200 µL PBS with 0.5% Paraformaldehyde, and PKH26+Vivid+ cancer cells were collected by Fortessa flow cytometer (Beckton Dickinson, San Jose, Calif.), followed by analysis using the Flowjo software. The percentage of killing is calculated as specific killing-spontaneous killing/total cells and plotted as shown.

Cytokine Release Assay

For measuring inflammatory cytokine concentrations in the in vitro activation assays, in vitro killing assays, in vim activation assay s in CD34+ umbilical cord cell humanized NSG mice, and the toxicity study, cell culture supernatant was collected, and serum samples were diluted according to manufacturer's protocol using Milliplex Human High Sensitivity T cell 13-plex Kit (EMD Millipore). These were subsequently analyzed by EMD Millipore MAGPIX® System, and MILLIPLEX® Analyst 5.1 software In Vivo Mouse Models and Efficacy Studies Human CD34+ hematopoietic stem cell-engrafted NSG mice (hu-CD34) were used as an in vivo mouse model. These mice develop multi-lineage human immune cells, and are a validated platform for immuno-oncology efficacy studies (see, e.g., Shultz, L. D. et al. (2014) *Cold Spring Harb. Protoc.* 2014:694-708). Hu-CD34+ NSG mice are produced by injecting CD34+ hematopoietic stem cells, showing effective multi-lineage engraftment of human immune cell populations including T cells, B cells and some other populations (McDermott, S. P. et al (2010) *Blood*

116:193-200). Multi-lineage hematopoiesis occurs within 12 weeks. Engraftment is stable for over one year without graft-versus-host disease.

For the efficacy study using hu-CD34 NSG mice, mice were purchased from The Jackson Laboratory (Maine, USA), and human cell populations were validated before use. In general, 5×10$^6$ tumor cells mixed in Matrigel (BD Biosciences) (50% v/v) were used for inoculating tumor in each mouse. Once tumor size reached the range of 100-150 mm$^3$, mice were selected and randomized into each group for study. Antibodies were given intravenously at given doses 3 limes weekly. Body weight was monitored 1-3 times weekly. Tumor size was measured by caliper tumor measurements 1-3 times/week. All mice w ere terminated when the tumor size reached 1,500 mm$^3$, or 24 hours after the last dose. Terminal blood samples (0.3 mL) were collected into serum separator lubes, mixed by gently inverting five times, and placed into a tube rack. Terminal tumors were also collected and weighed before being put into fixative for immunohistochemistry analysis.

Human PBMC humanized (hu-PBMC) NSG mice w ere used as another in vivo mouse model. These mice are produced by injecting purified human PBMC from health donors, which have the fastest engraftment rate using adult peripheral blood mononuclear cells and enable short-term studies requiring a strong effector and memory T cell and NK, cell function, and are suitable for short term efficacy study (3-4 weeks) due to graft-versus-host disease.

For the efficacy study using hu-PBMC NSG mice, 8-10 week old NSG mice (Cat. No: 005557, NOD.Cg-Prkdcscid Il2rgtm1Wj1/SzJ) were purchased from The Jackson Laboratory (Maine, USA). Each mouse was innoculated with 5×10$^6$ tumor cells mixed in Matrigel (BD Biosciences) (50% v/v) subcutaneously. Once tumor size reached the range of 50-100 mm$^3$, 10×10$^6$ human PBMCs from healthy donors were reconstituted to each mouse intraperitoneally (IP). Human cell reconstitution was validated the next day. Once tumor size reached the range of 100-150 mm$^3$, mice w ere selected and randomized into each group for study. Antibodies were given intravenously at given doses 3 times weekly. Body weight was monitored 1-3 times weekly. Tumor size was measured by caliper tumor measurements 1-3 times/week. All mice were terminated when the tumor size reached 1,500 mm$^3$ or 24 hours after the last dose. Terminal blood samples (0.3 mL) were collected into serum separator tubes, mixed by gently inverting five times, and placed into a tube rack. Terminal tumors were also collected and weighed before being put into fixative for immunohistochemistry analysis.

For disseminated hu-PMBC NSG mouse model, 1-5×10$^6$ cells were injected into each mouse intravenously at day 0. At day 3, base line luminance imaging was taken for randomization. At day 4, 10×10$^6$ human PBMCs from healthy donors were reconstituted to each mouse intraperitoneally (IP). Mice were treated weekly at day 5, 12, 19 using indicated doses. Weekly luminance body imaging was taken on day 10, 17, 24 for monitoring tumor volume in each animal. At termination of the study, blood, spleen, bone and bone marrow were collected for histopathology study.

Results

Figure 7A:
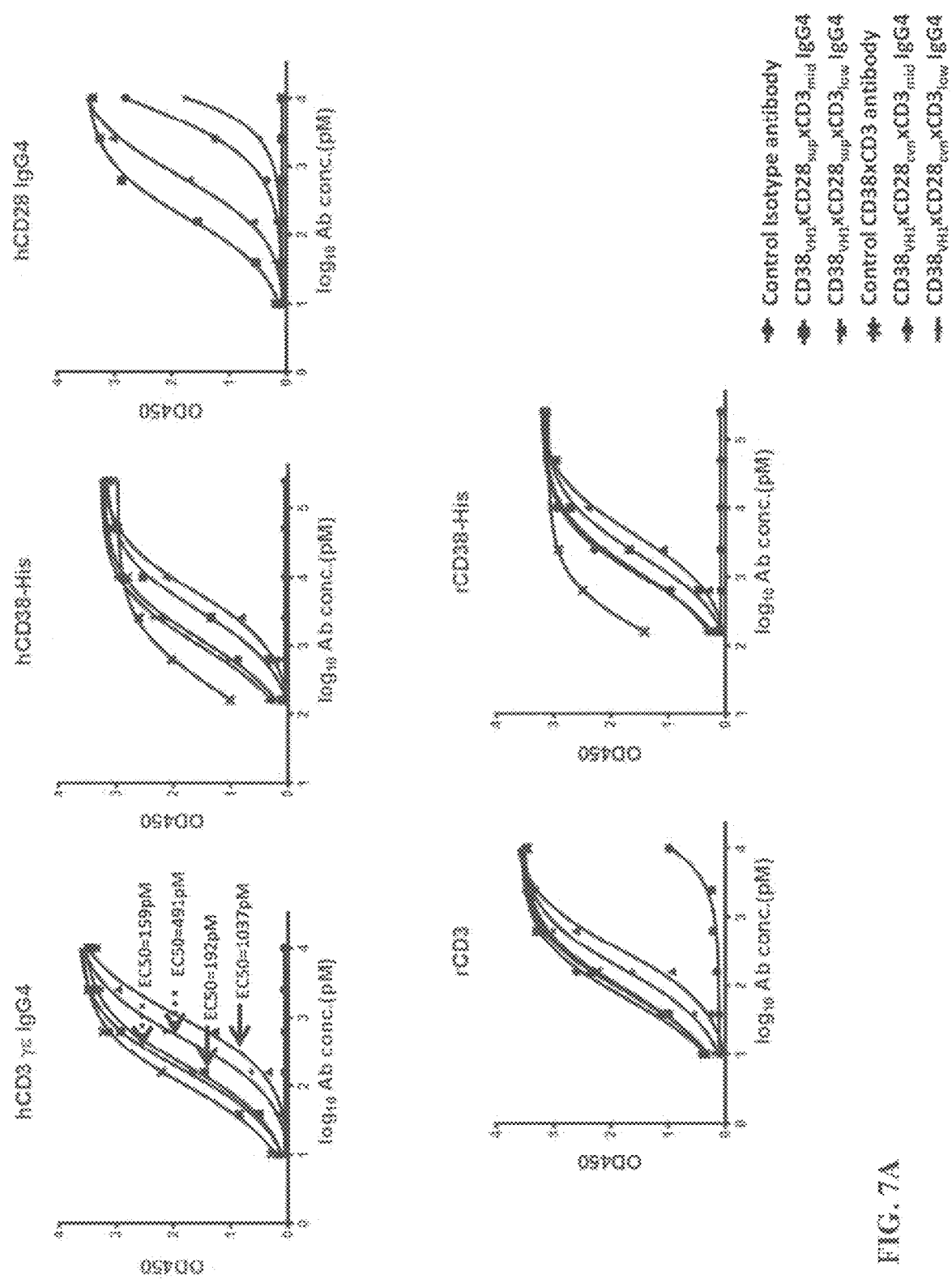
FIGS. 7A & 7B show the results of an ELISA assay determining the binding affinities of various anti-CD38×CD28×CD3 IgG4 trispecific binding proteins, or control antibodies, to human and rhesus monkey CD3, CD28 and CD38 polypeptides.
Figure 7B:
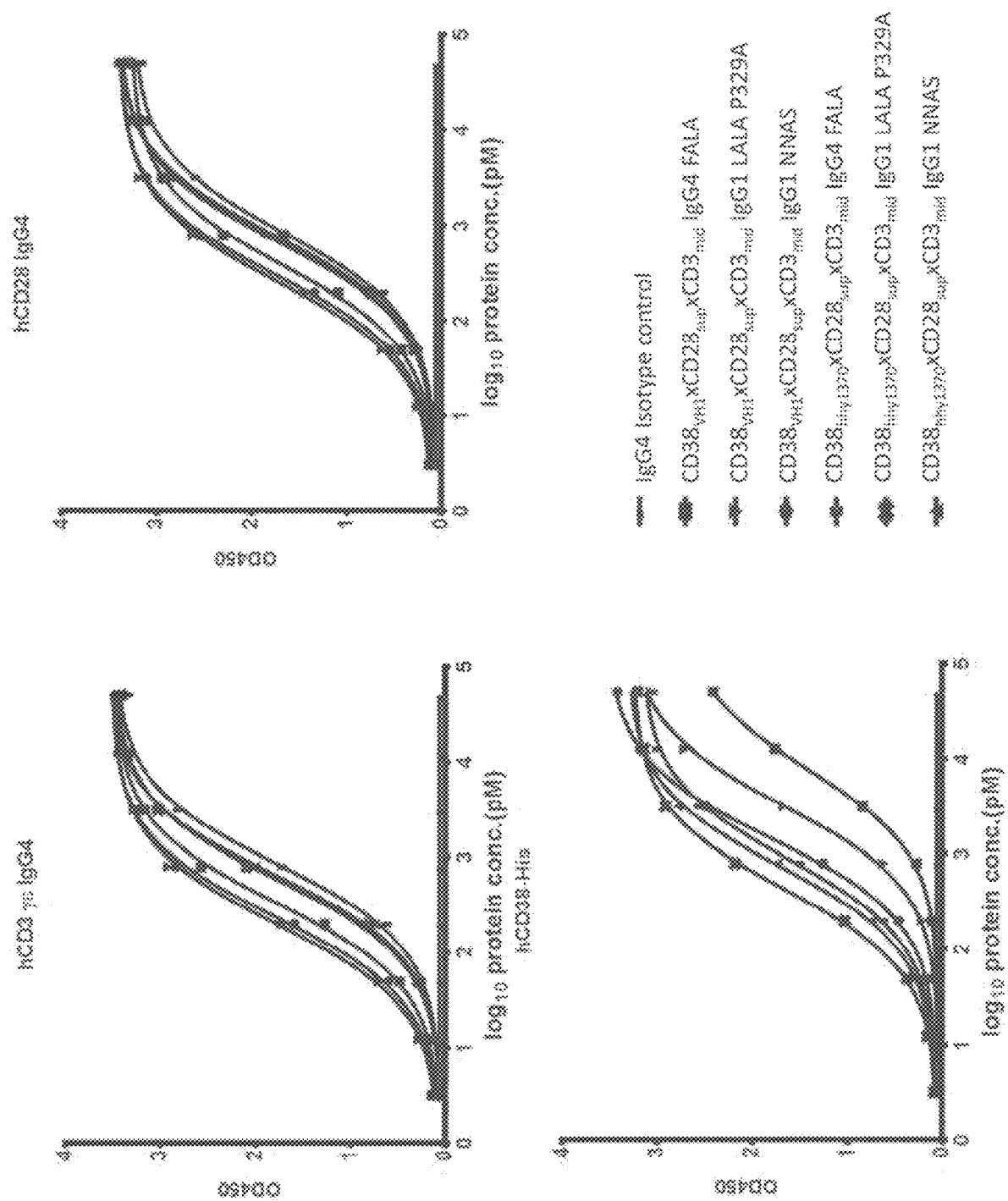

The ability of the antibodies to bind all three target antigens was tested by ELISA assay. $CD38_{VH1} \times CD28_{sup} \times CD3_{mid}$ IgG4, $CD38_{VH1} \times CD28_{sup} \times CD3_{low}$ IgG4, $CD38_{VH1} \times CD28_{evn} \times CD3_{mid}$ IgG4, $CD38_{VH1} \times CD28_{evn} \times CD3_{low}$ IgG4 showed similar binding affinity to human and monkey CD3 and CD38, but variable binding affinity to CD28 (human and monkey have identical extracellular domain) with $CD28_{sup}$ showing better affinity (FIG. 7A). $CD38_{VH1} \times CD28_{sup} \times CD3_{mid}$ and $CD38_{HHY1370} \times CD28_{sup} \times CD3_{mid}$ IgG4 FALA variant and IgG1 LALA P329A and NNAS variants all showed similar binding to human CD3, CD28, and CD38 (FIG. 7B).

Figure 8A:
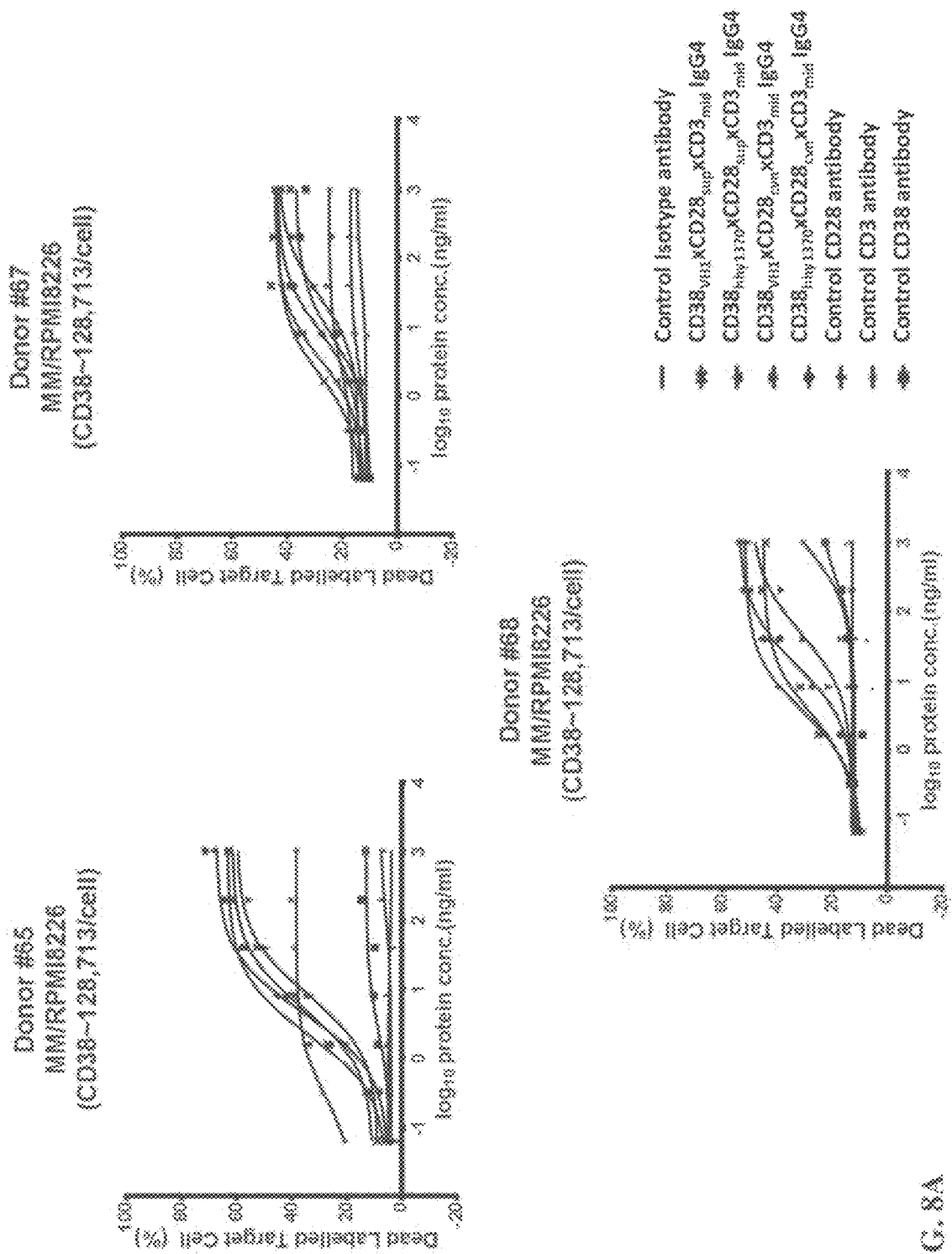
FIGS. 8A-8D show the results of antibody-mediated specific killing of CD38$^+$ cells by PBMCs from three different human donors using the indicated anti-CD38×CD28×CD3 trispecific binding proteins and control antibodies. Representative results using multiple myeloma cell lines RPMI8266 (FIG. 8A), NCI-H929 (FIG. 8B), KMS-26 (FIG. 8C), and KMS-11 cell lines (FIG. 8D) are shown, and EC50 values are provided in Table N. EC50 values obtained by using NCI-H929, KMS-26, and KMS-11 cells are provided in Tables O-Q.
Figure 8B:
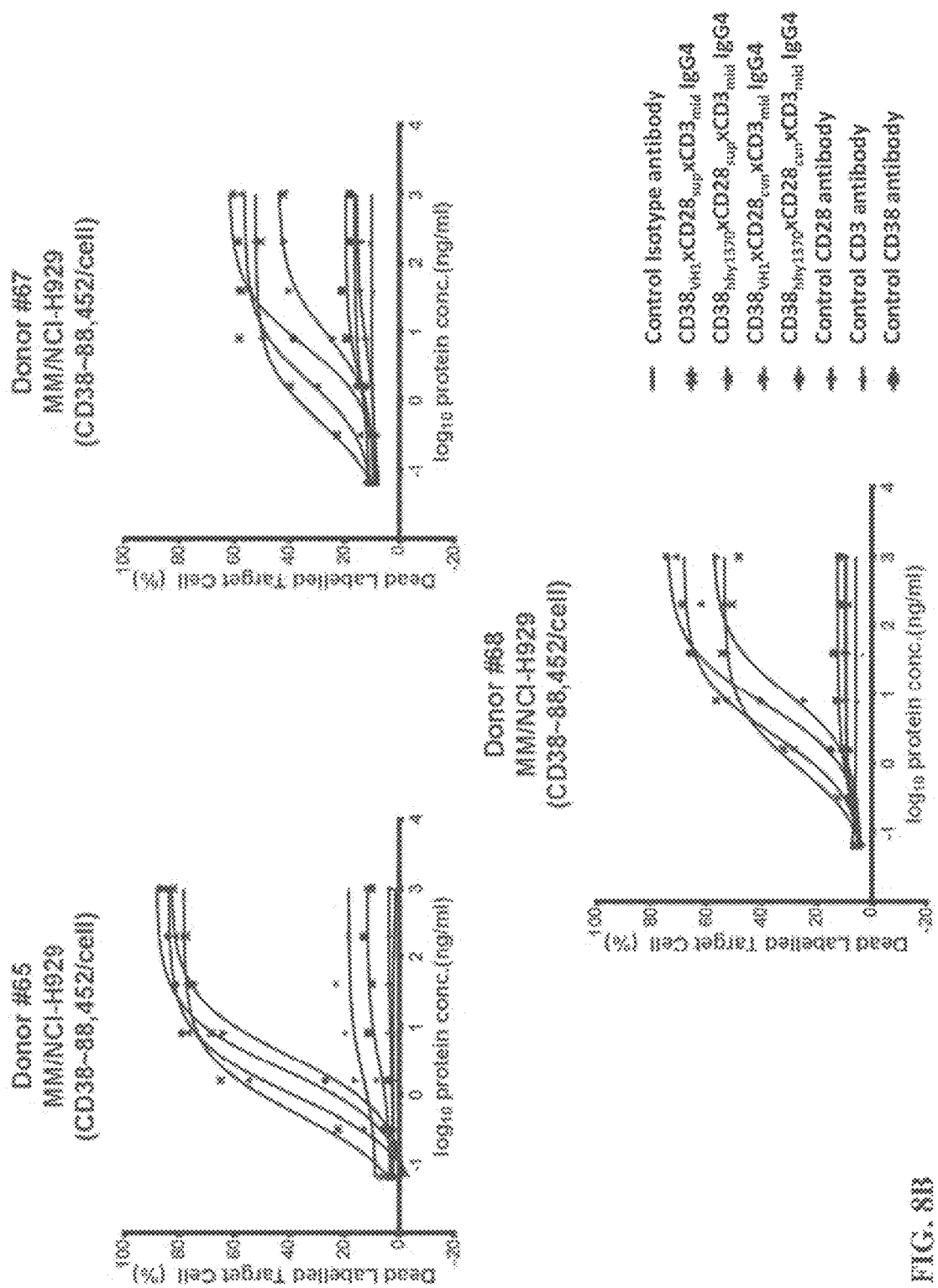
Figure 8C:
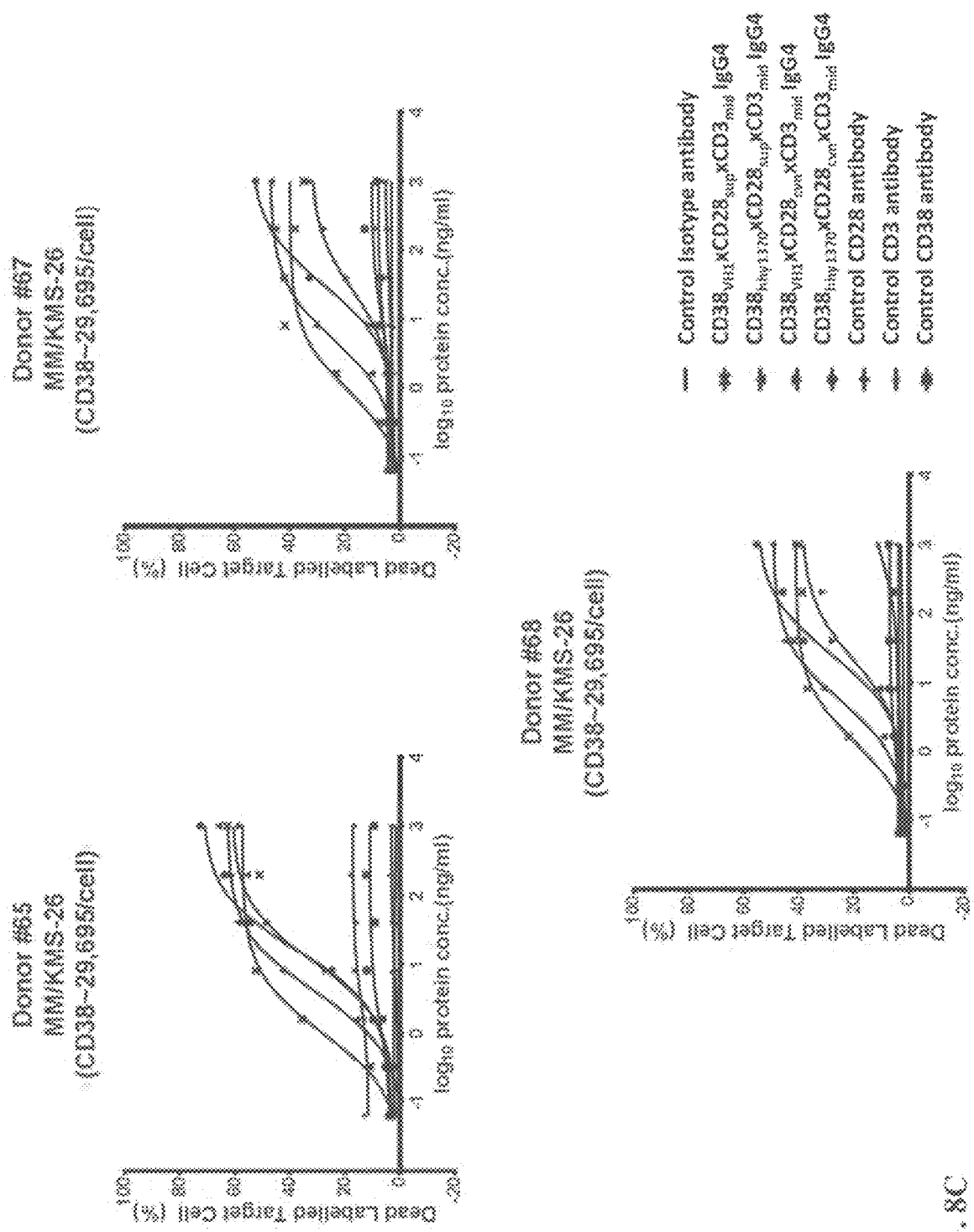
Figure 8D:
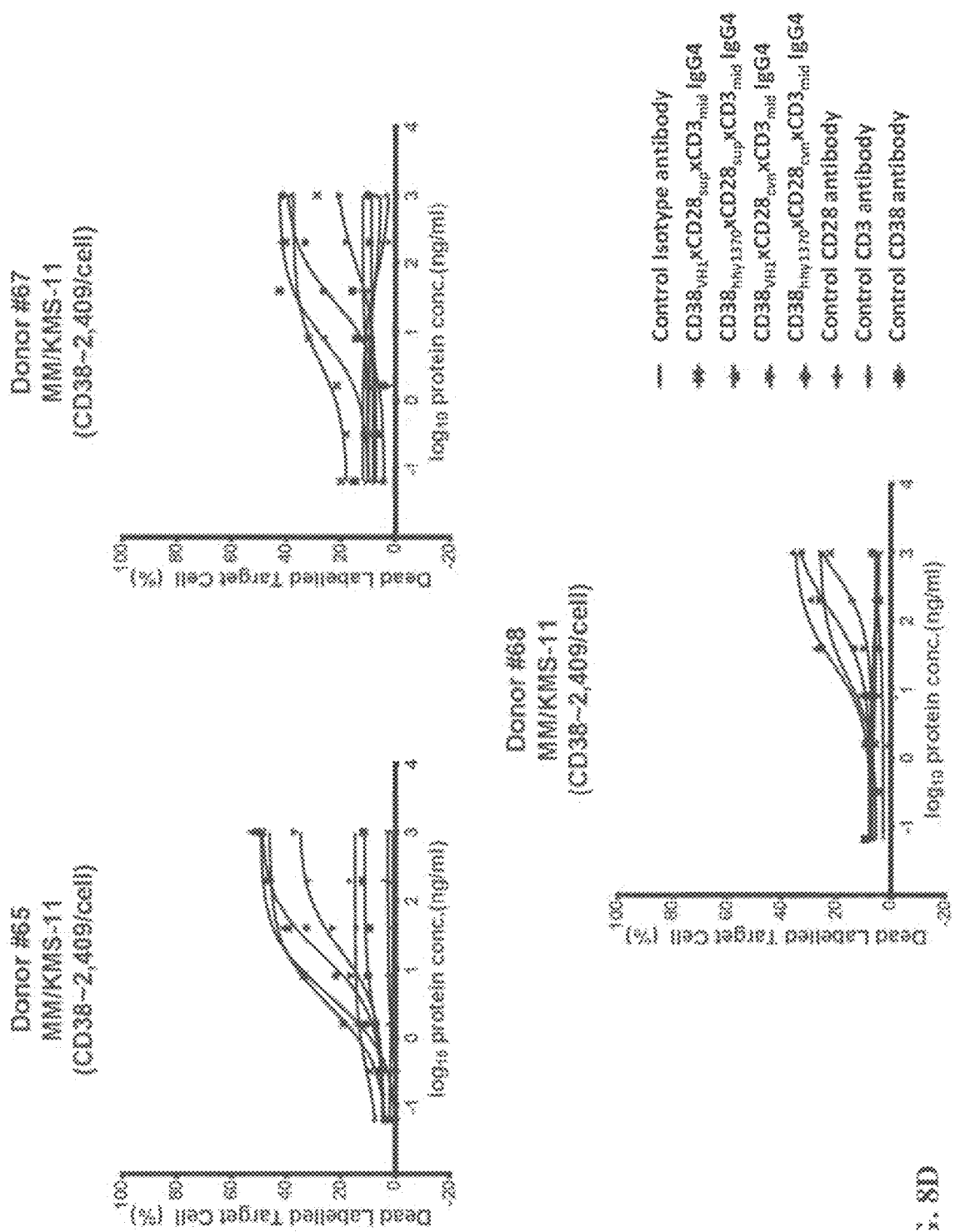

Next the trispecific anti-CD38CD3CD28 binding protein variants were tested for their capability of inducing T cell activation and antibody-mediated tumor cell killing (FIGS. 8A-8D). FIG. 8A shows the in vitro killing activities of $CD38_{VH1} \times CD28_{sup} \times CD3_{mid}$ IgG4, $CD38_{hhy1370} \times CD28_{sup} \times CD3_{mid}$ IgG4, $CD38_{VH1} \times CD28_{evn} \times CD3_{mid}$ IgG4, $CD38_{hhy1370} \times CD28_{evn} \times CD3_{mid}$ IgG4, against human multiple myeloma cell line RPMI-8226 using PBMC from 3 different donors at E:T=10. The EC50 of the killing activity was calculated and summarized in Table N. Both anti-CD38×CD3×CD28 trispecific binding proteins containing $CD28_{sup}$ showed better killing activities. The in vitro killing activities of these molecules was also examined using NCI-H929 (FIG. 8B), KMS-26 (FIG. 8Q, and KMS-11 cell lines. (FIG. 8D).

Anti-CD38×anti-CD3×anti-CD28 trispecific binding proteins with IgG1 LALA P329A and NNAS variants, or IgG4 FALA variant, also displayed in vitro killing of multiple myeloma KMS-11 (FIG. 8E) and U266 (FIG. 8F) cells. The EC50 for each antibody against each cell line was calculated and summarized in Table Q2 (KMS-11) and Q3 (U266).

Figure 9A:
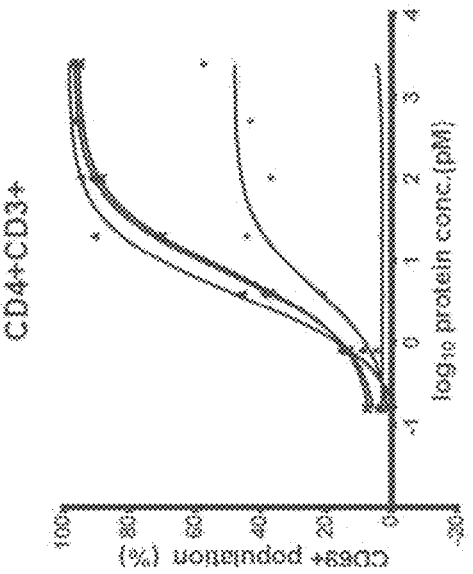
FIGS. 9A, 9B, & 10 show the activation (CD69$^+$) of human T cells treated with various anti-CD38×CD28×CD3 trispecific binding proteins or control antibodies for 24 hours.
Figure 9B:
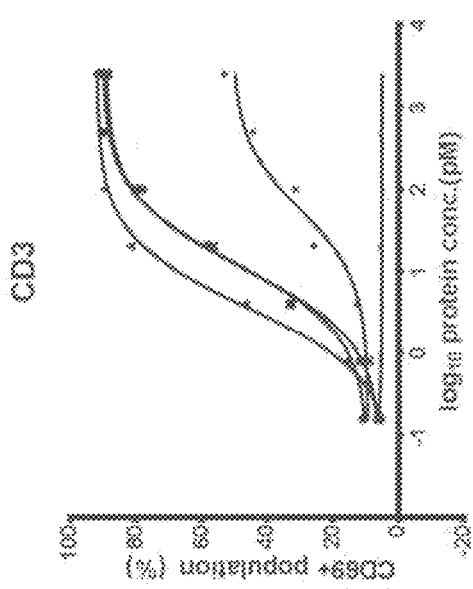
Figure 10:
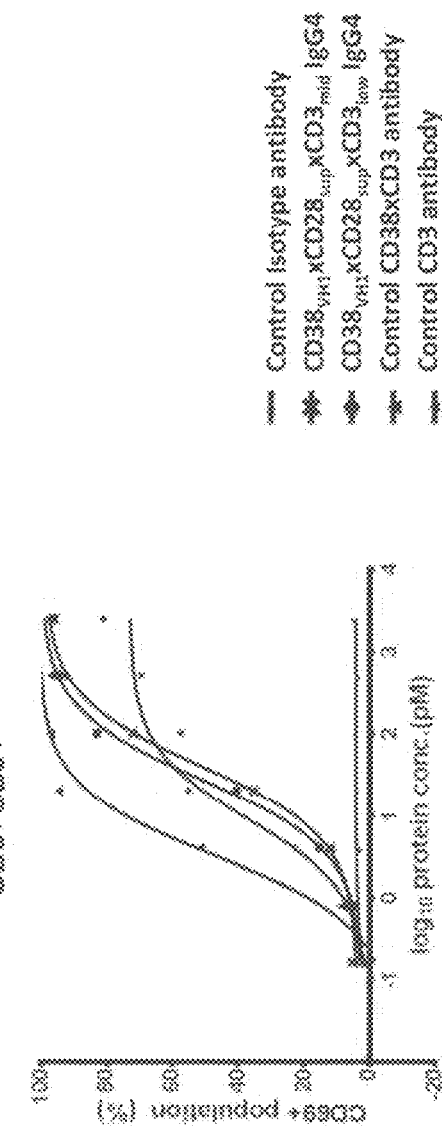

FIGS. 9A, 9B, & 10 show the in vitro T cell activation profile of the $CD38_{VH1} \times CD28_{sup} \times CD3_{mid}$ IgG4 and $CD38_{VH1} \times CD28_{sup} \times CD3_{low}$ IgG4. Both antibodies showed similar activation activities for CD4 and CD8 T cells. The EC50 for each antibody against each cell line was calculated and summarized in Table N (RPMI-8226), Table O (NCI-H929), Table P (KMS-26), and Table Q (KMS-11).

TABLE N

Antibody-mediated specific killing of CD38+ RPMI8266 cells by PBMCs from different donors

| Antibody | EC50 (ng/ml) | | |
|---|---|---|---|
| | Donor #65 | Donor #67 | Donor #68 |
| $CD38_{VH1} \times CD28_{sup} \times CD3_{mid}$ IgG4 | 5.30 | 1.95 | 3.3 |
| $CD38_{hhy1370} \times CD28_{sup} \times CD3_{mid}$ IgG4 | 2.24 | 3.42 | 3.4 |
| $CD38_{VH1} \times CD28_{cyn} \times CD3_{mid}$ IgG4 | 8.31 | 29.52 | 46.8 |
| $CD38_{hhy1370} \times CD28_{cyn} \times CD3_{mid}$ IgG4 | 4.62 | 8.98 | 16.5 |

TABLE O

Antibody-mediated specific killing of CD38+ NCI-H929 cells by PBMCs from different donors

| Antibody | EC50 (ng/ml) | | |
|---|---|---|---|
| | Donor #65 | Donor #67 | Donor #68 |
| $CD38_{VH1} \times CD28_{sup} \times CD3_{mid}$ IgG4 | 0.51 | 0.48 | 0.9 |
| $CD38_{hhy1370} \times CD28_{sup} \times CD3_{mid}$ IgG4 | 0.94 | 1.84 | 2.5 |
| $CD38_{VH1} \times CD28_{cyn} \times CD3_{mid}$ IgG4 | 3.70 | 9.47 | 10.4 |
| $CD38_{hhy1370} \times CD28_{cyn} \times CD3_{mid}$ IgG4 | 2.31 | 6.39 | 7.2 |

TABLE P

Antibody-mediated specific killing of CD38+ KMS-26 cells by PBMCs from different donors

| | EC50 (ng/ml) | | |
|---|---|---|---|
| Antibody | Donor #65 | Donor #67 | Donor #68 |
| $CD38_{VH1} \times CD28_{sup} \times CD3_{mid}$ IgG4 | 1.03 | 0.91 | 1.3 |
| $CD38_{hhy1370} \times CD28_{sup} \times CD3_{mid}$ IgG4 | 3.95 | 5.06 | 5.3 |
| $CD38_{VH1} \times CD28_{cyn} \times CD3_{mid}$ IgG4 | 10.73 | 28.17 | 22.4 |
| $CD38_{hhy1370} \times CD28_{cyn} \times CD3_{mid}$ IgG4 | 15.84 | 32.10 | 25.7 |

TABLE Q

Antibody-mediated specific killing of CD38+ KMS-11 cells by PBMCs from different donors

| | EC50 (ng/ml) | | |
|---|---|---|---|
| Antibody | Donor #65 | Donor #67 | Donor #68 |
| $CD38_{VH1} \times CD28_{sup} \times CD3_{mid}$ IgG4 | 3.05 | 3.40 | 14.7 |
| $CD38_{hhy1370} \times CD28_{sup} \times CD3_{mid}$ IgG4 | 4.17 | 7.74 | 25.1 |
| $CD38_{VH1} \times CD28_{cyn} \times CD3_{mid}$ IgG4 | 18.14 | 98.83 | 566.8 |
| $CD38_{hhy1370} \times CD28_{cyn} \times CD3_{mid}$ IgG4 | 16.30 | 27.63 | 139.2 |

TABLE Q2

Antibody-mediated specific killing of CD38+ KMS-11 cells by PBMCs from different donors (IgG1/4 variant Fcs)

| EC50 (pM) (KMS11) | $CD38_{VH1} \times CD28_{sup} \times CD3_{mid}$ IgG4 FALA | $CD38_{VH1} \times CD28_{sup} \times CD3_{mid}$ IgG1 LALA P329A | $CD38_{VH1} \times CD28_{sup} \times CD3_{mid}$ IgG1 NNAS | $CD38_{VH1} \times CD28_{sup} \times CD3_{mi}$ $CD38_{hhy1370} \times CD28_{sup} \times CD3_{mi}$ IgG4 FALA | $CD38_{hhy1370} \times CD28_{sup} \times CD3_{mi}$ IgG1 LALA P329A | $CD38_{hhy1370} \times CD28_{sup} \times CD3_{mi}$ IgG1 NNAS |
|---|---|---|---|---|---|---|
| KP50901 | 3.879 | 4.375 | 4.411 | 7.731 | 9.311 | 17.71 |
| KP50904 | 4.379 | 6.739 | 8.644 | 19.01 | 18.88 | 24.39 |

TABLE Q3

Antibody-mediated specific killing of CD38+ U266 cells by PBMCs from different donors IgG1/4 variant Fcs)

| EC50 (pM) (U266) | $CD38_{VH1} \times CD28_{sup} \times CD3_{mid}$ IgG4 FALA | $CD38_{VH1} \times CD28_{sup} \times CD3_{mid}$ IgG1 LALA | $CD38_{VH1} \times CD28_{sup} \times CD3_{mid}$ IgG1 NNAS | $CD38_{VH1} \times CD28_{sup} \times CD3_{mi}$ $CD38_{hhy1370}$ IgG4 FALA | $CD38_{hhy1370} \times CD28_{sup} \times CD3_{mi}$ IgG1 LALA P329A | $CD38_{hhy1370} \times CD28_{sup} \times CD3_{mi}$ IgG1 NNAS |
|---|---|---|---|---|---|---|
| KP50901 | 1.879 | 1.031 | 1.150 | 2.691 | 1.597 | 2.816 |
| KP50904 | 0.8657 | 3.570 | 2.018 | 2.112 | 0.8375 | 3.527 |

Figure 11A:
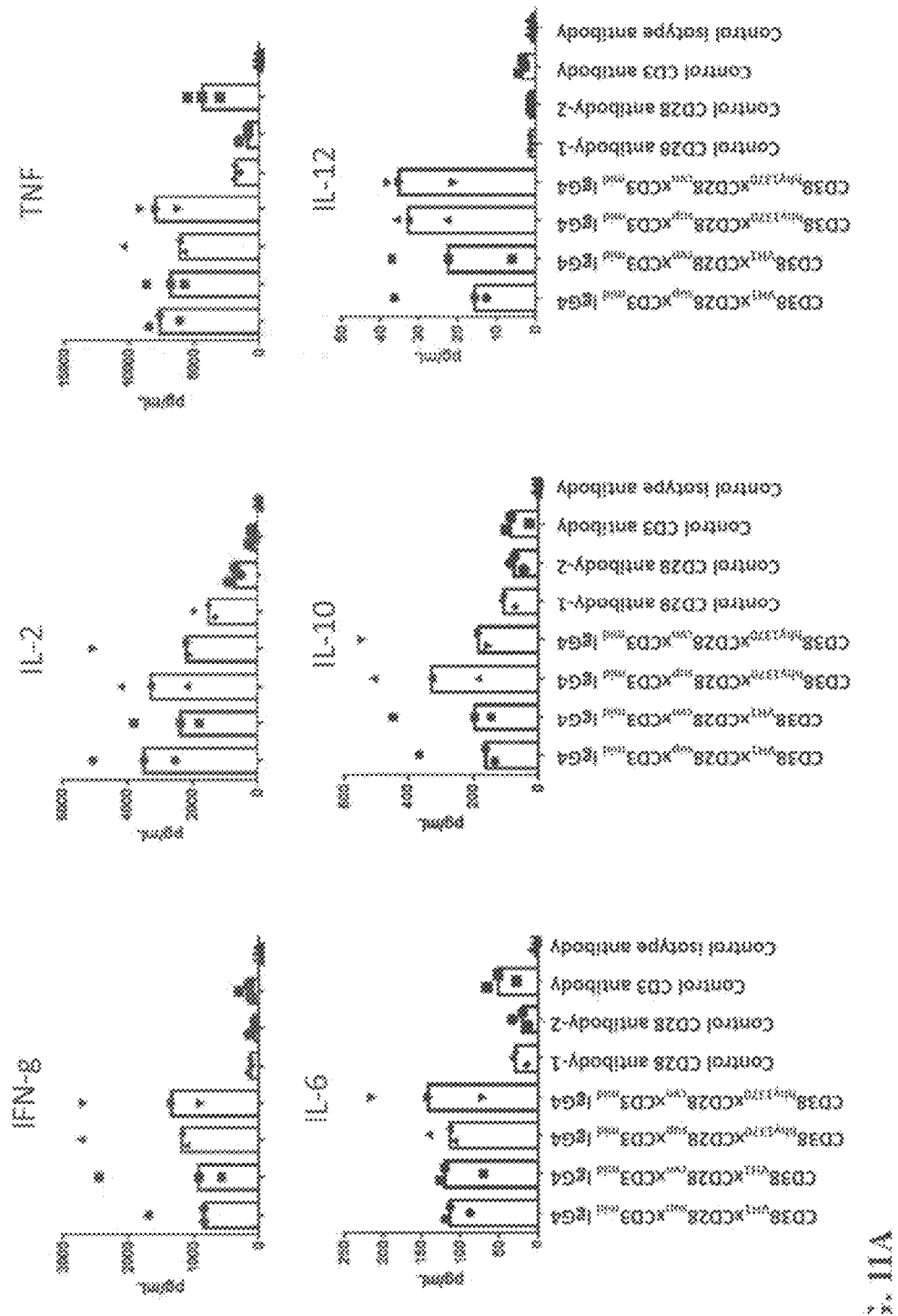
FIGS. 11A-11B show the results of in vitro cytokine release assessments of human PBMCs treated with the indicated anti-CD38×CD28×CD3 trispecific binding proteins or control antibodies based on dried plate method as described in Stebbings, R, et al. (2007) J. Immunol. 179: 3325-3331.
Figure 11B:
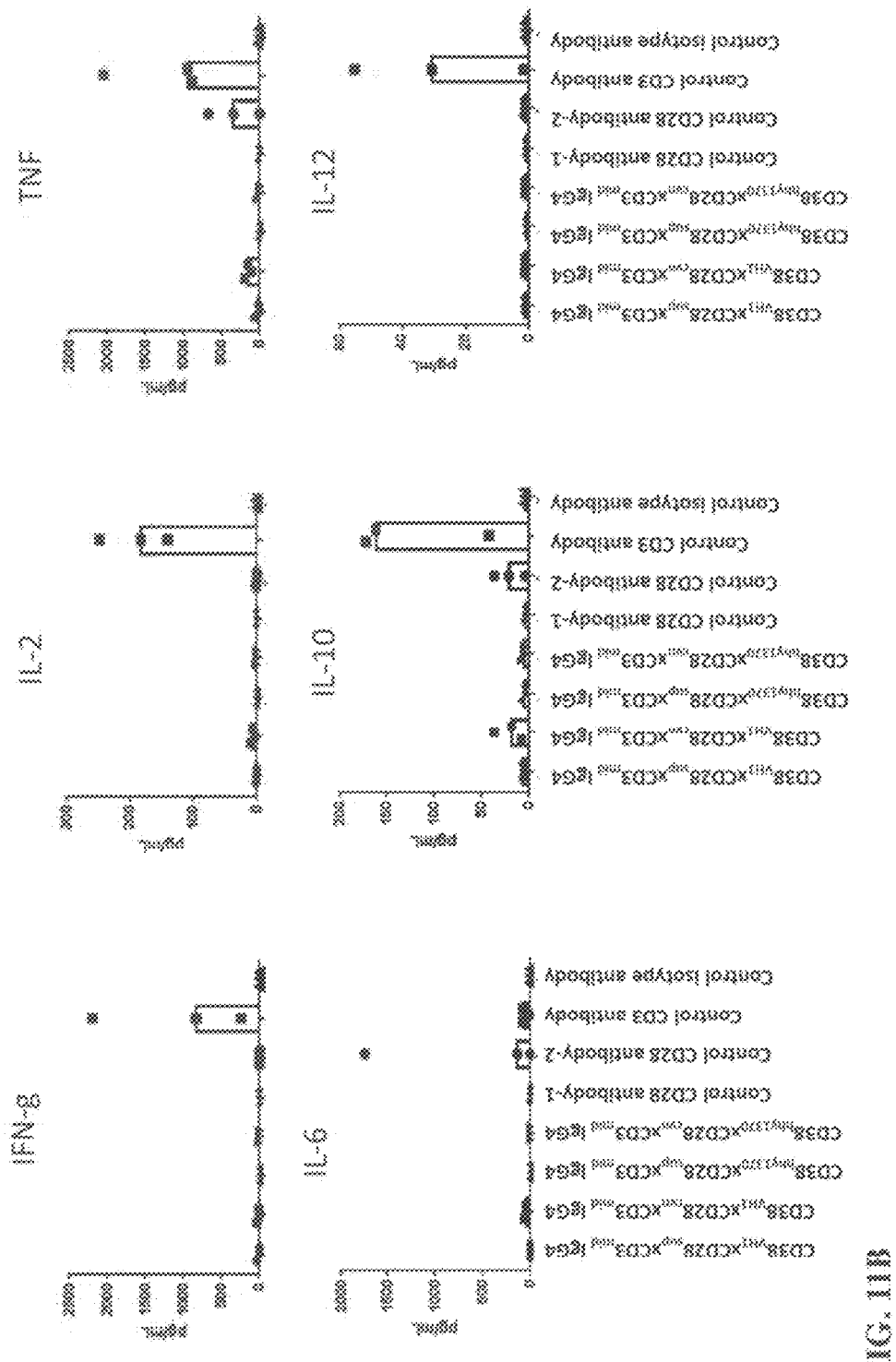

Cytokine production induced by the trispecific binding protein variants was also examined (FIGS. 11A & 11B) using the method described in Stebbings, R. et al. (2007) (*J. Immunol.* 179-3325-3331) by coating the plate with indicated antibodies, followed by incubation with human PBMC for 24 hours using 2 concentrations of the testing antibodies (5 µg/nil and 25 ng/ml). 24-hour culture supernatants were collected and used to measure the IL2, IL6, IL10, IL12, and TNF-α, IFN-γ concentration in the supernatants as described above. $CD38_{VH1} \times CD28_{sup} \times CD3_{mid}$ IgG4, $CD38_{hhy1370} \times CD28_{sup} \times CD3_{mid}$ IgG4, $CD38_{VH1} \times CD28_{evn} \times CD3_{mid}$ IgG4, $CD38_{hhy1370} \times CD28_{evn} \times CD3_{mid}$ IgG4 all stimulated production of significant level of IL2, TNF-α, and IFN-γ at 5 µg-ml, but failed to induce measurable level of any cytokine at 25 ng/ml, a dose showing in vivo efficacy in 2 humanized NSG mouse models.

Figure 12A:
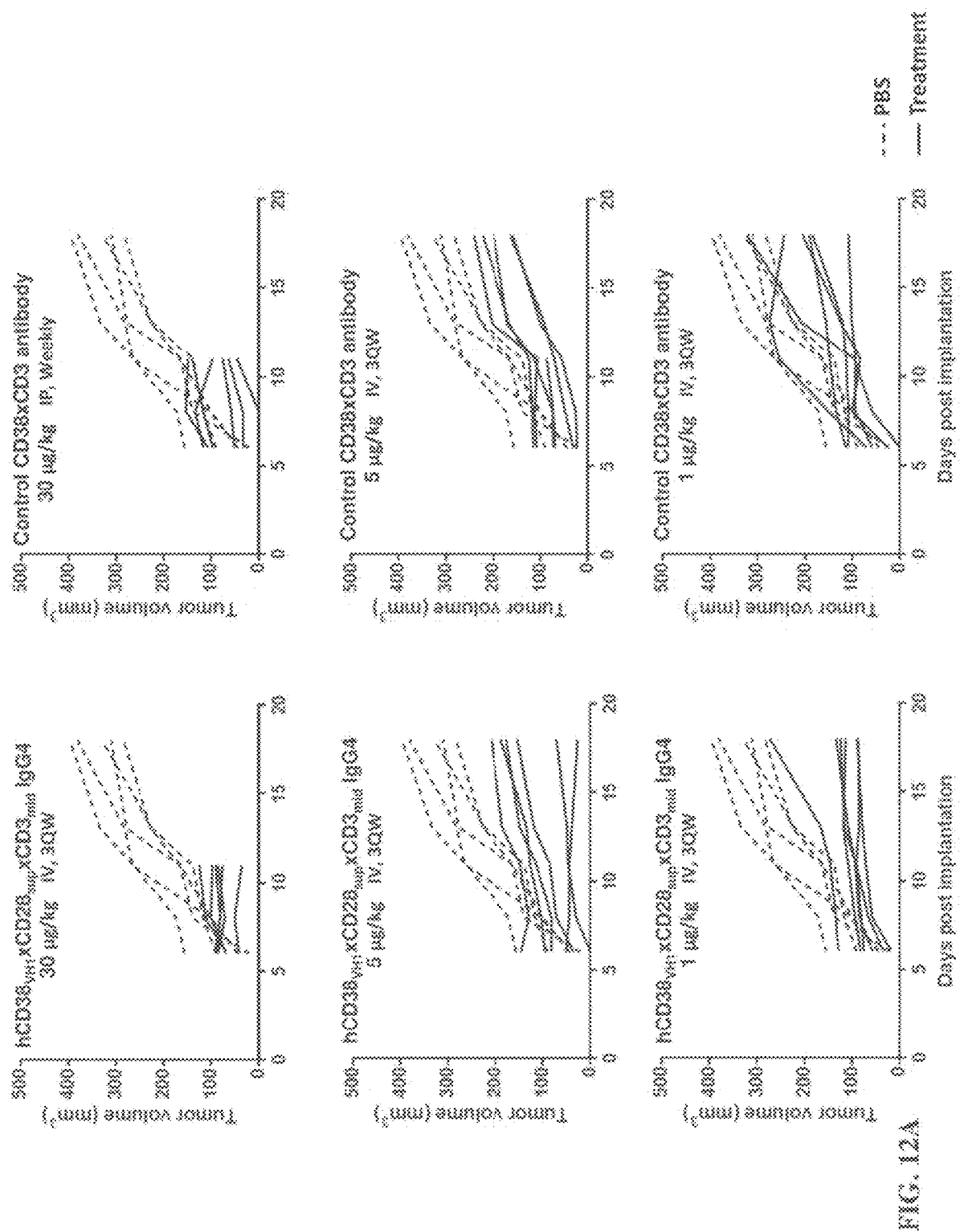
FIGS. 12A-12E show the in vivo activity of the anti-CD38$_{(VH1)}$×CD28$_{(sup)}$×CD3$_{(mid)}$ trispecific binding protein in the CD34+ umbilical cord blood cells humanized NSG mouse model implanted with RPMI-8226 multiple myeloma cells.
Figure 12C:
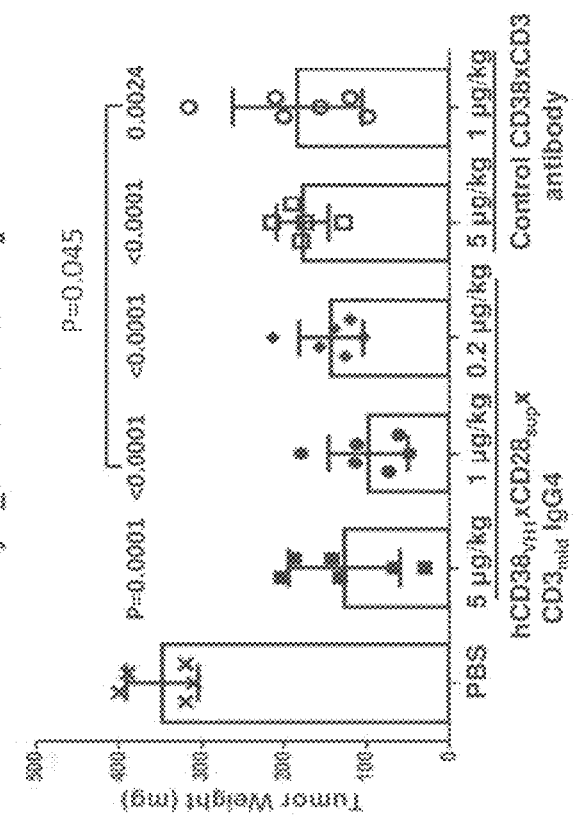
Figure 12B:
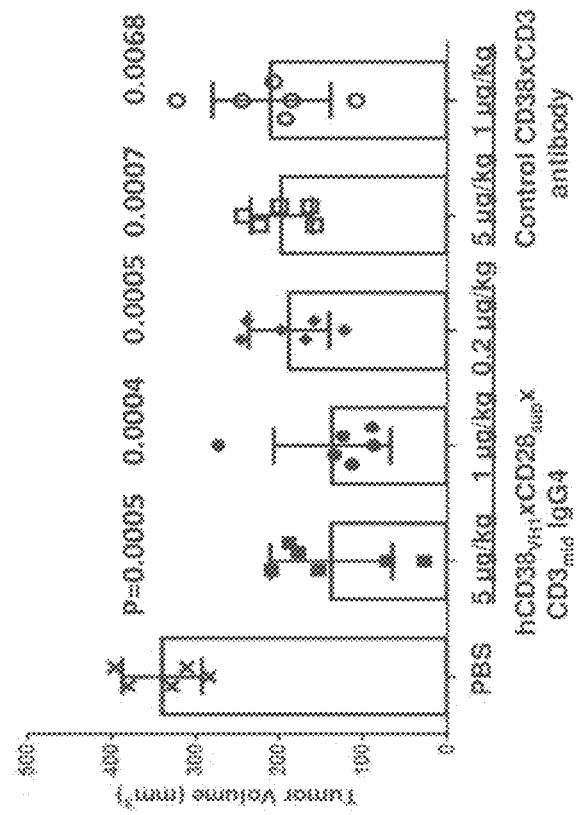
Figure 12D:
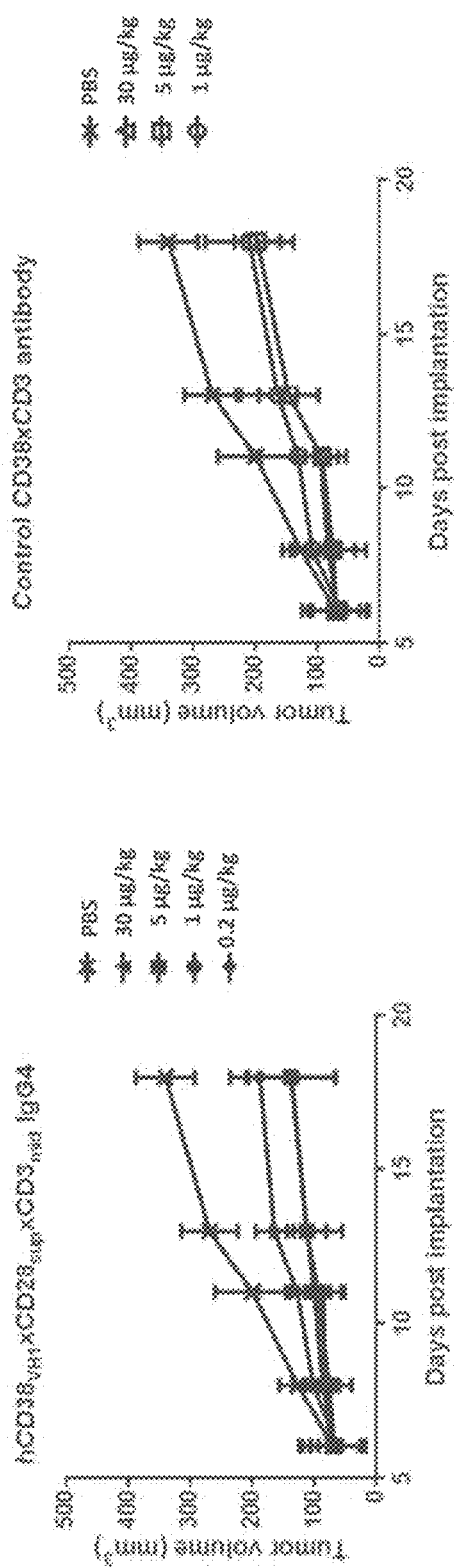
Figure 12E:
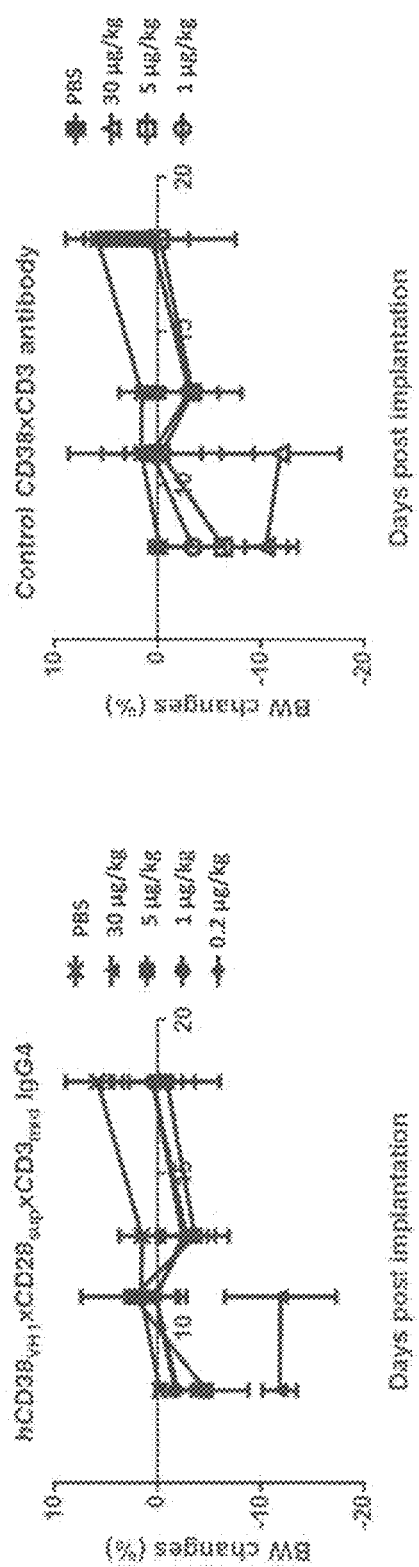

Anti-tumor activity was tested in vivo mouse models for the trispecific binding protein variants (FIGS. 12A-13F) as described above. FIGS. 12A-12E show the results of the in vivo efficacy study using the human CD34+ hematopoietic stem cell-engrafted NSG mouse (hu-CD34) model implanted with human MM cell line RPMI-8226. $CD38_{VH1} \times CD28_{sup} \times CD3_{mid}$ IgG4 and bench marker control CD38×CD3 bispecific antibodies were used to treat tumor bearing mice at indicated doses 3QW (6 doses total). The body-weight and tumor growth for each mouse were measured and plotted (FIGS. 12A & 12E). Average tumor growth curve (FIG. 12D), Day 18 tumor volume (FIG. 12B) and D19 terminal tumor weight (FIG. 12C) for each group were also plotted. All groups treated with $CD38_{VH1} \times CD28_{sup} \times CD3_{mid}$ IgG4 not only showed statistical efficacy compared to PBS control, but also showed statistically better efficacy at 1 µg/kg dose compared to control CD38×CD3 bispecific antibody.

Figure 13A:
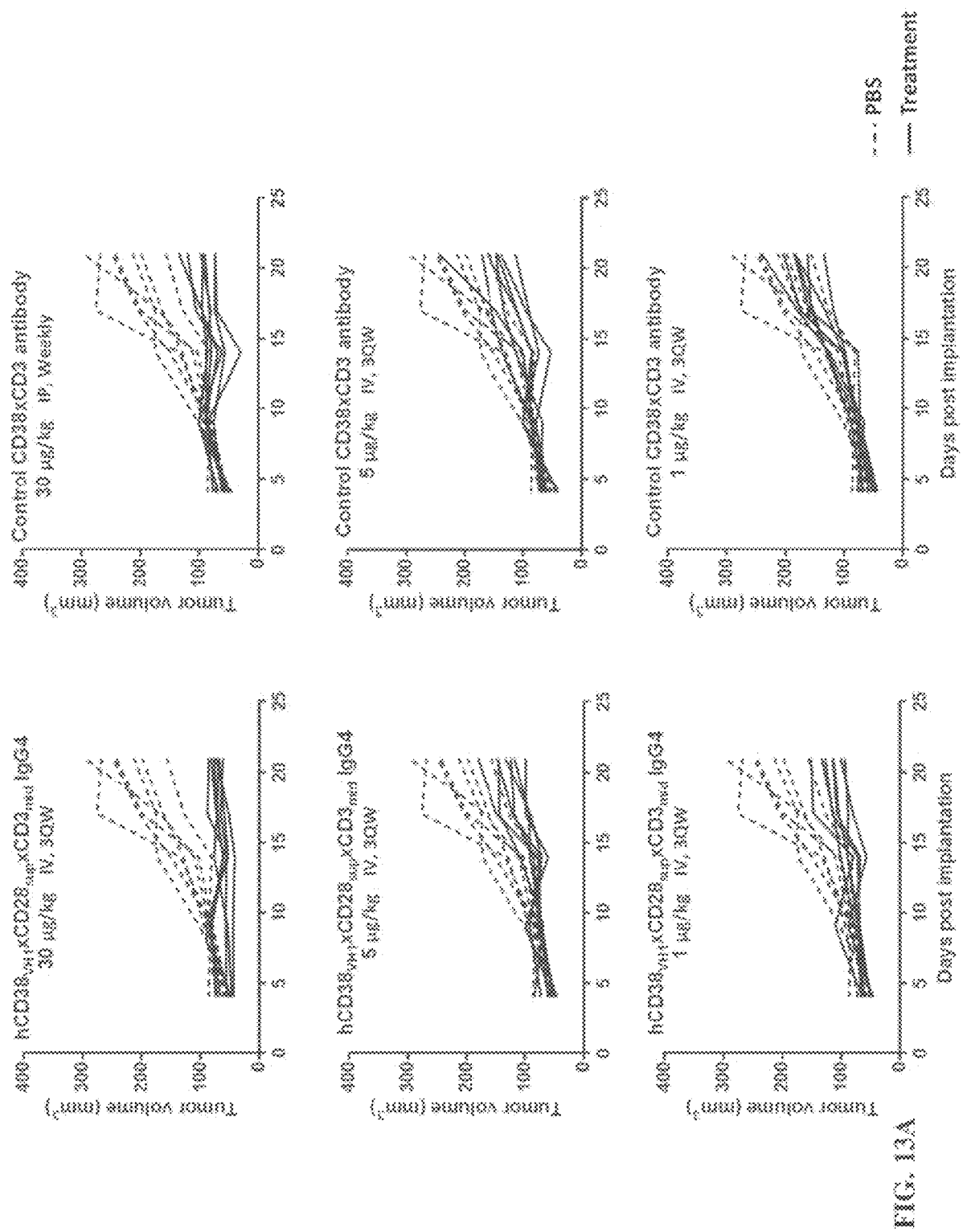
FIGS. 13A-13F show the in vivo activity of the anti-CD38$_{(VH1)}$×CD28$_{(sup)}$×CD3$_{(mid)}$, trispecific binding protein in the PBMCs humanized NSG mouse model implanted with RPMI-8226 multiple myeloma cells.
Figure 13B:
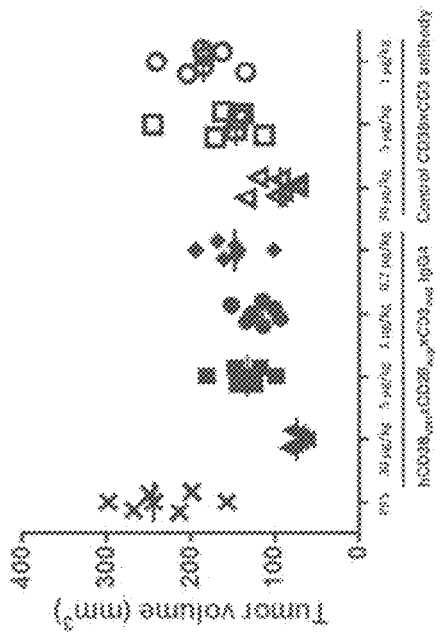
Figure 13C:
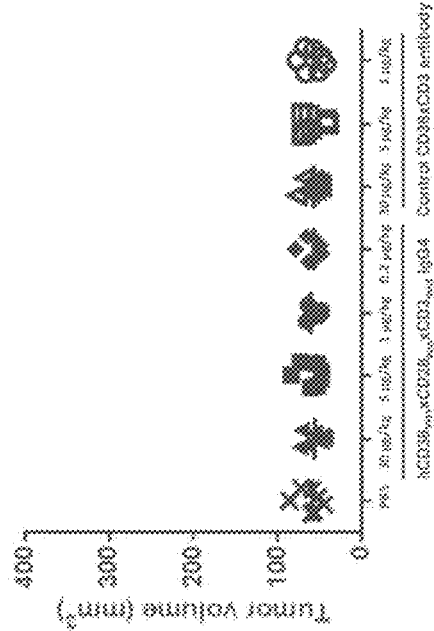
Figure 13D:
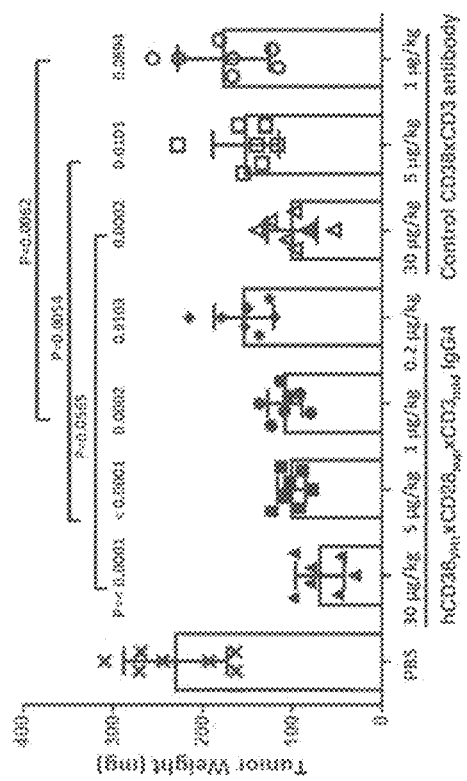
Figure 13E:
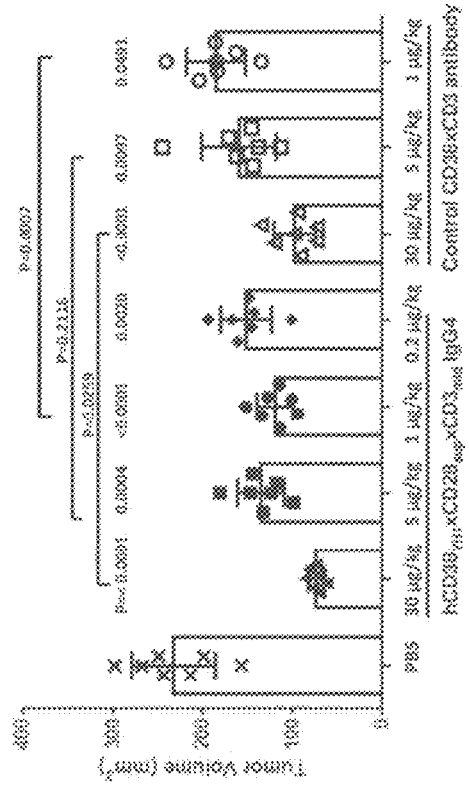
Figure 13F:
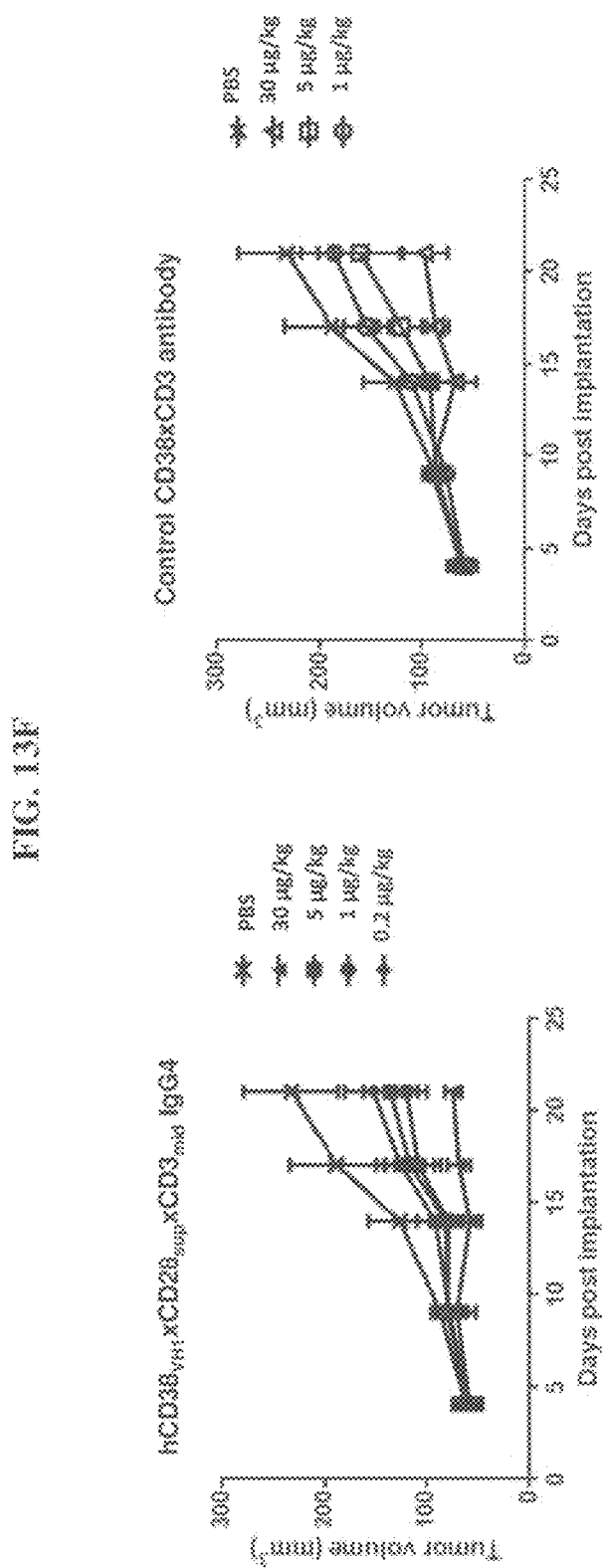

FIGS. 13A-13F show the results of the in vivo efficacy study using the human PBMC humanized NSG mouse model implanted with human MM cell line RPMI-8226. $CD38_{VH1} \times CD28_{sup} \times CD3_{mid}$ IgG4 and benchmark control CD38×CD3 bispecific antibodies were used to treat tumor bearing mice at indicated doses 3QW (8 doses total). The tumor growth for each mouse was measured and plotted (FIG. 13A). Average tumor growth curve (FIG. 13F), Day 4 tumor volume (day of starting the treatment, FIG. 13B), Day 21 tumor volume (day of last treatment; FIG. 13C), Day 21 average tumor volume (FIG. 13D) and Day 22 terminal tumor weight (FIG. 13E) for each group were also plotted. All groups treated with $CD38_{VH1} \times CD28_{sup} \times CD3_{mid}$ IgG4 not only showed statistical efficacy compared to PBS control, but also showed statistically better efficacy at multiple doses compared to control CD38×CD3 bispecific antibody, indicating superior in vivo anti-tumor activity by the trispecific anti-CD38/CD3/CD28 antibody.

Benchmark control CD38×CD3 bispecific antibody comprised the following sequences:

```
SEQ ID NO 108: benchmark heavy chain 1
(binds CD38)
EVQLVESGGGLVQPGGSLRLSCAASGFTFSYSWMNWVRQAPGKGLEWVS

EINPQSSTINYATSVKGRFTISRDNSKNTLYLQMNSLRAEDTAVYYCA

RYGNWFPYWGQGTLVTVSSASTKGPSVFPLAPSSKSTSGGTAALGCLVK

DYFPEPVTVSWNSGALTSGVHTFPAVLQSSGLYSLSSVVTVPSSSLGTQ

TYICNVNHKPSDTKVDKKVEPKSCDKTHTCPPCPAPPVAGPSVFLFPPK

PKDTLMISRTPEVTCVVVDVKHEDPEVKFNWYVDGVEVHNAKTKPREEE

YNSTYRVVSVLTVLHQDWLNGKEYKCKVSNKALPAPIEKTISKAKGQPR

EPQVYTLPPSREEMTKNQVSLTCDVSGFYPSDIAVEWESDGQPENNYKT

TPPVLDSDGSFFLYSKLTVDKSRWEQGDVFSCSVMHEALHNHYTQKSLS

LSPGK

SEQ ID NO 109: benchmark heavy chain 2
(binds CD3)
EVQLVESGGGLVQPGGSLRLSCAASGFTFSTYAMNWVRQAPGKGLEWVG

RIRSKYNNYATYYADSVKGRFTISRDDSKNTLYLQMSLRAEDTAVYYCV

RHGNFGDSYVSWFAYWGQGTLVTVSSGKPGSGKPGSGKPGSGKPGSQAV

VTQEPSLTVSPGGTVTLTCGSSTGAVTTSNYANWVQQKPGKSPRGLIGG

TNKRAPGVPARFSGSLLGGKAALTISGAQPEDEADYYCALWYSNHWVFG

GGTKLTVLEPKSSDKTHTCPPCPAPPVAGPSVFLFPPKPKDTLMISRTP

EVTCVVVDVKHEDPEVKFNWYVDGVEVHNAKTKPREEQYNSTYRVVSVL

TVLHQDWLNGKEYKCKVSNKALPAPIEKTISKAKGQPREPQVYTLPPSR

EQMTKNQVKLTCLVKGFYPSDIAVEWESNGQPENNYKTTPPVLDSDGSF

FLYSKLTVDKSRWQQGNVFSCSVMHEALHNHYTQKSLSLSPGK

SEQ ID NO 110: benchmark light chain (binds CD38)
DIVMTQSPSSLSASVGDRVTITCRASQNVDTWVAWYQQKPGQSKALIYS

ASYRYSGVPDRFTGSGSGTDFTLTISSLQPEDFATYFCQQYDSYPLTFG

GGTKLEIKRTVAAPSVFIFPPSDEQLKSGTASVVCLLNNFYPREAKVQW

KVDNALQSGNSQESVTEQDSKDSTYSLSSTLTLSKADYEKHKVYACEVT

HQGLSSPVTKSFNRGEC
```

Example 6: Dose Escalation Study with Anti-CD38 mAb2 and mAb6-Containing Trispecific Binding Proteins Materials and Methods All NHP studies were carried out by Covance (Princeton, N.J., USA) according to Covance ICUCA protocol. Drug- and protein-naïve or protein-naïve male Cynomolgus Monkeys were used in all studies. Based on study design, monkeys were selected aid grouped for each trispecific binding protein. Antibody was given by intravenous infusion for 1 hour via saphenous vein, increasing doses were given on consecutive days for low doses (<10 µg/kg), but with a 1-2 day interval for higher doses (>10 µg/kg) for observation purposes. Blood samples were collected at 0 hour (Day 1 only), 0.5 hour (mid-infusion), 1, and 6 hours from start of infusion for all animals after each dose, as specified. Additional unscheduled blood samples were collected at the discretion of the study director, pathologist and/or clinical veterinarian. All animals were returned to colony on Day 60. PBMC mid serum from the blood samples were prepared using standard methods, mid preserved for future analysis.

Blood from treated non-human primates was stained with fluorescently conjugated antibodies against T cell markers and human IgG, Fcγ fragment mid analyzed on a flow cytometer.

Results

Figure 14Q:
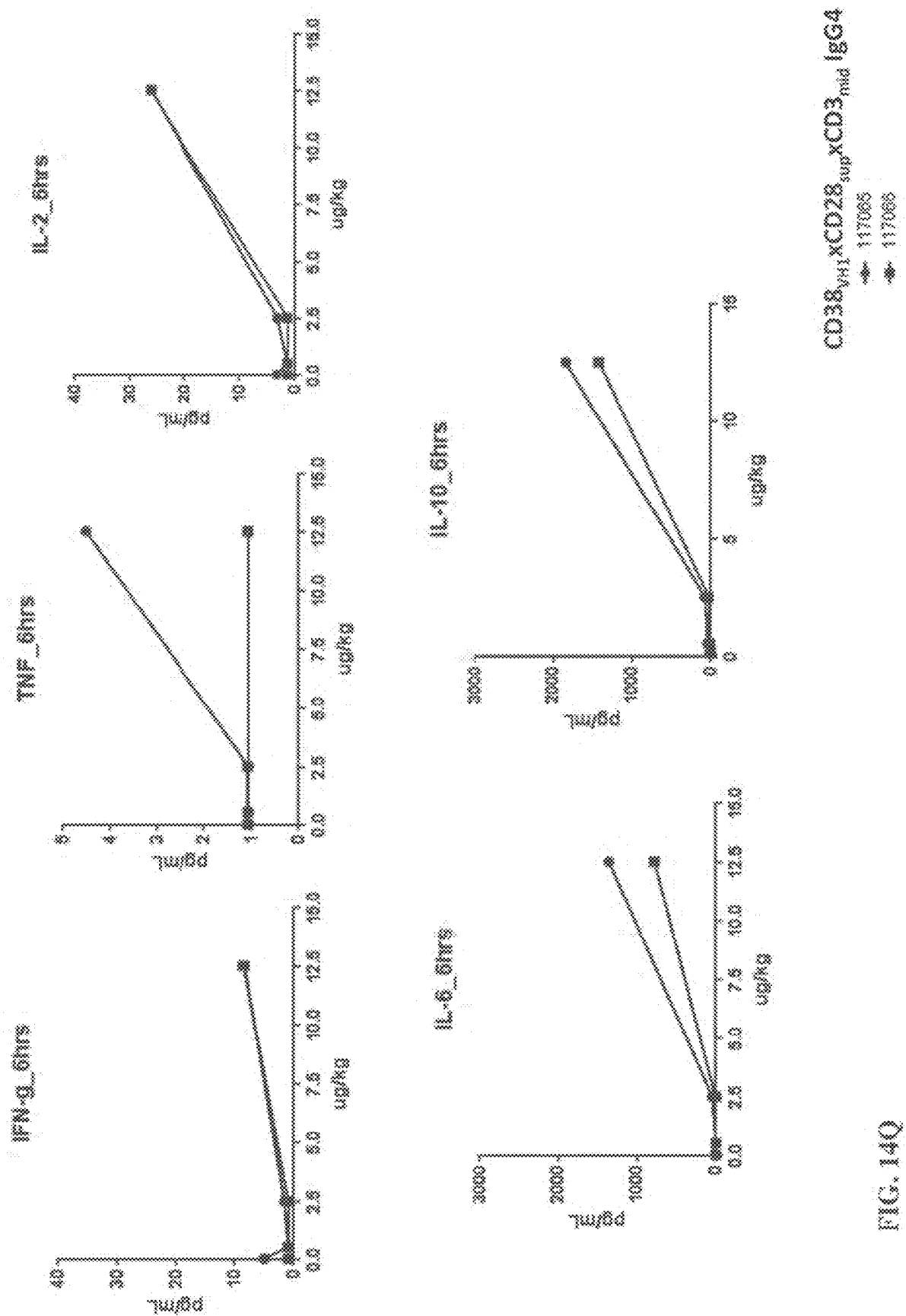
FIG. 14Q shows the changes in cytokine levels 6 hours after administration of the three ascending doses (0.5, 2.5, 12.5 µg/kg) of the anti-CD38$_{(VH1)}$×CD28$_{(sup)}$×CD3$_{(mid)}$ trispecific binding protein (results from different test animals labeled as "117065" and "117066").
Figure 14R:
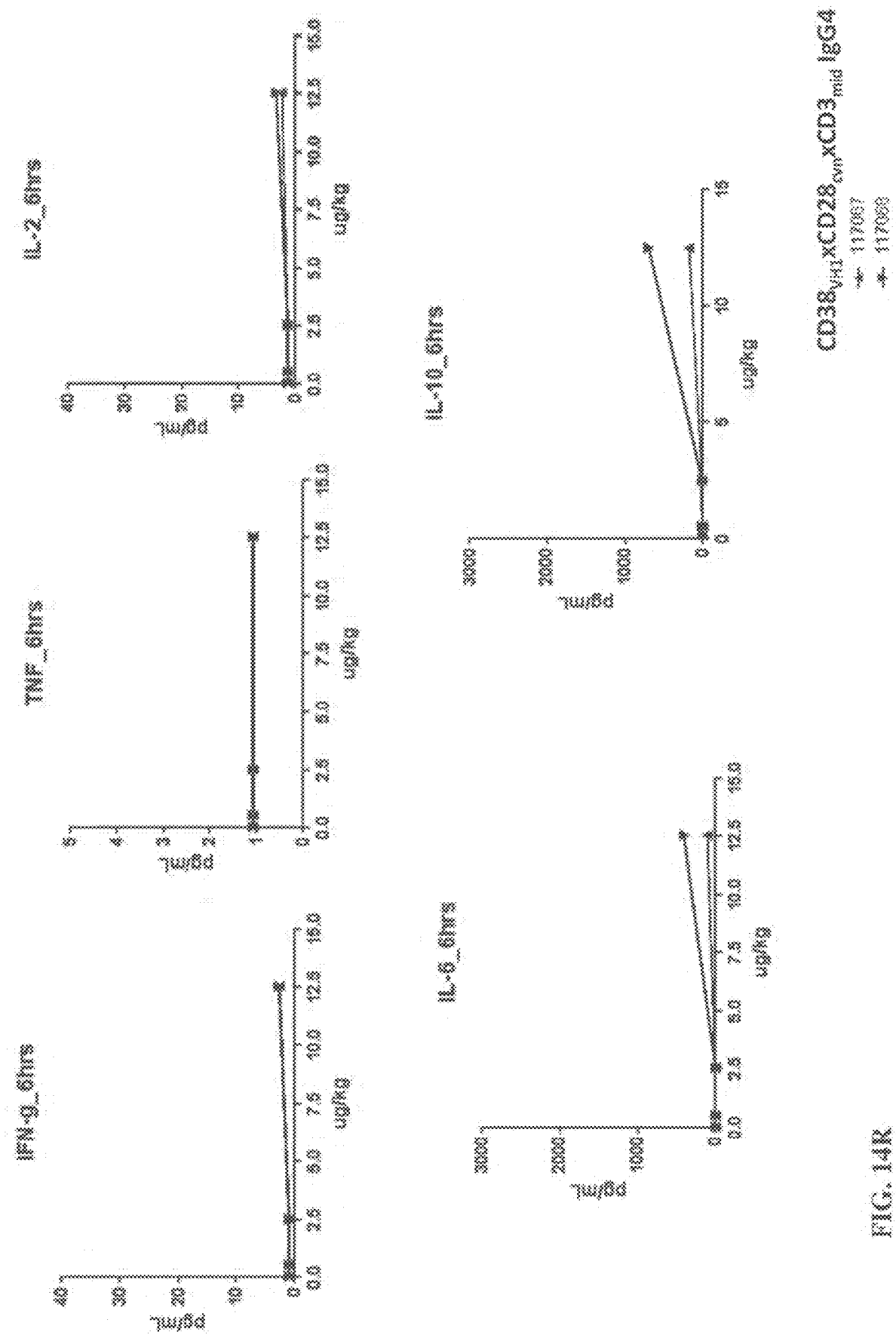
FIG. 14R shows the changes in cytokine levels 6 hours after administration of the three ascending doses (0.5, 2.5, 12.5 µg/kg) of the anti-CD38$_{(VH1)}$×CD28$_{(evn)}$×CD3$_{(mid)}$ trispecific binding protein (results from different test animals labeled as "117067" and "117068").
Figure 14S:
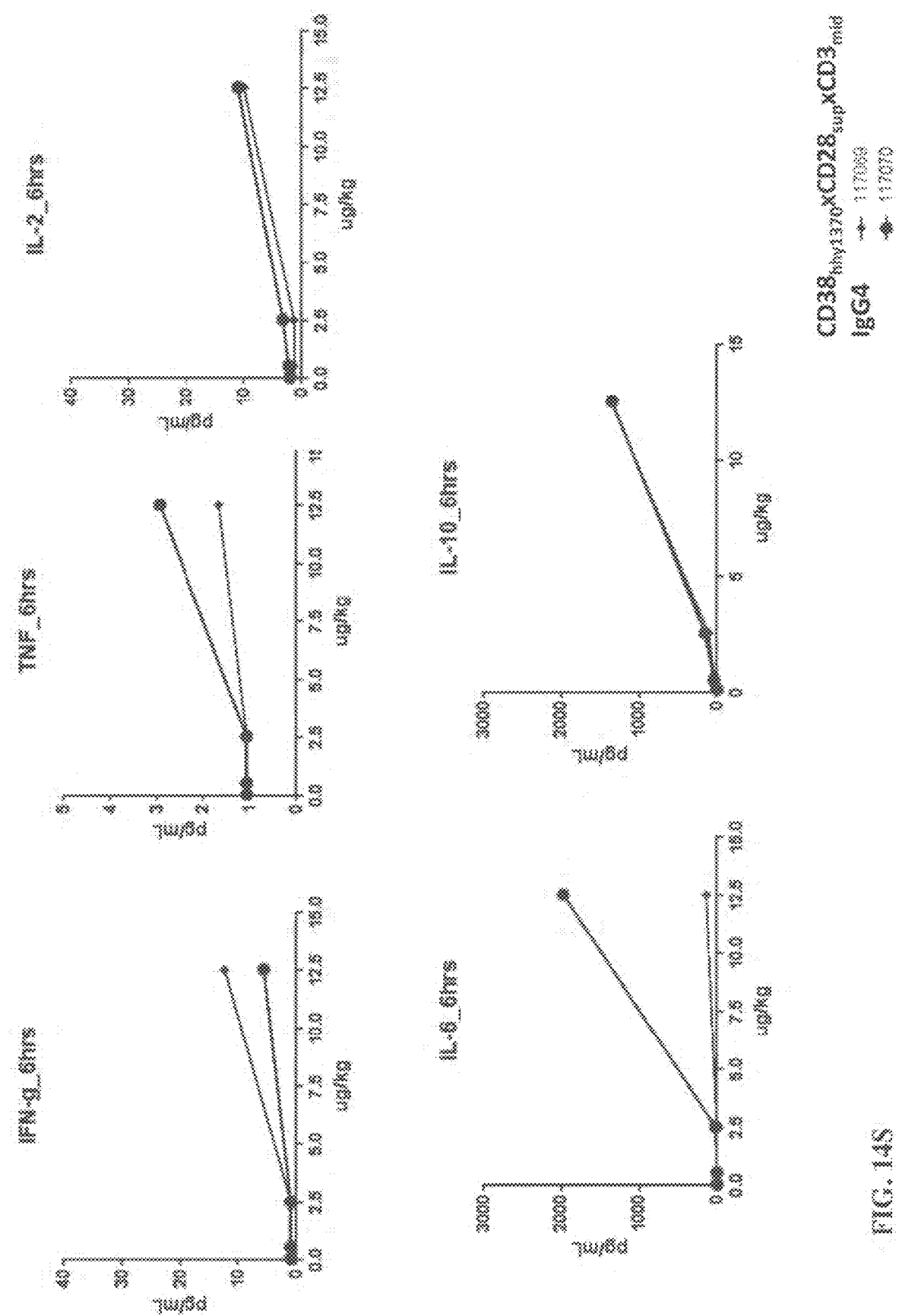
FIG. 14S shows the changes in cytokine levels 6 hours after administration of the three ascending doses (0.5, 2.5, 12.5 µg/kg) of the anti-CD38$_{(hhy1370)}$×CD28$_{(sup)}$×CD3$_{(mid)}$ trispecific binding protein (results from different test animals labeled as "117069" and "117070").
Figure 14T:
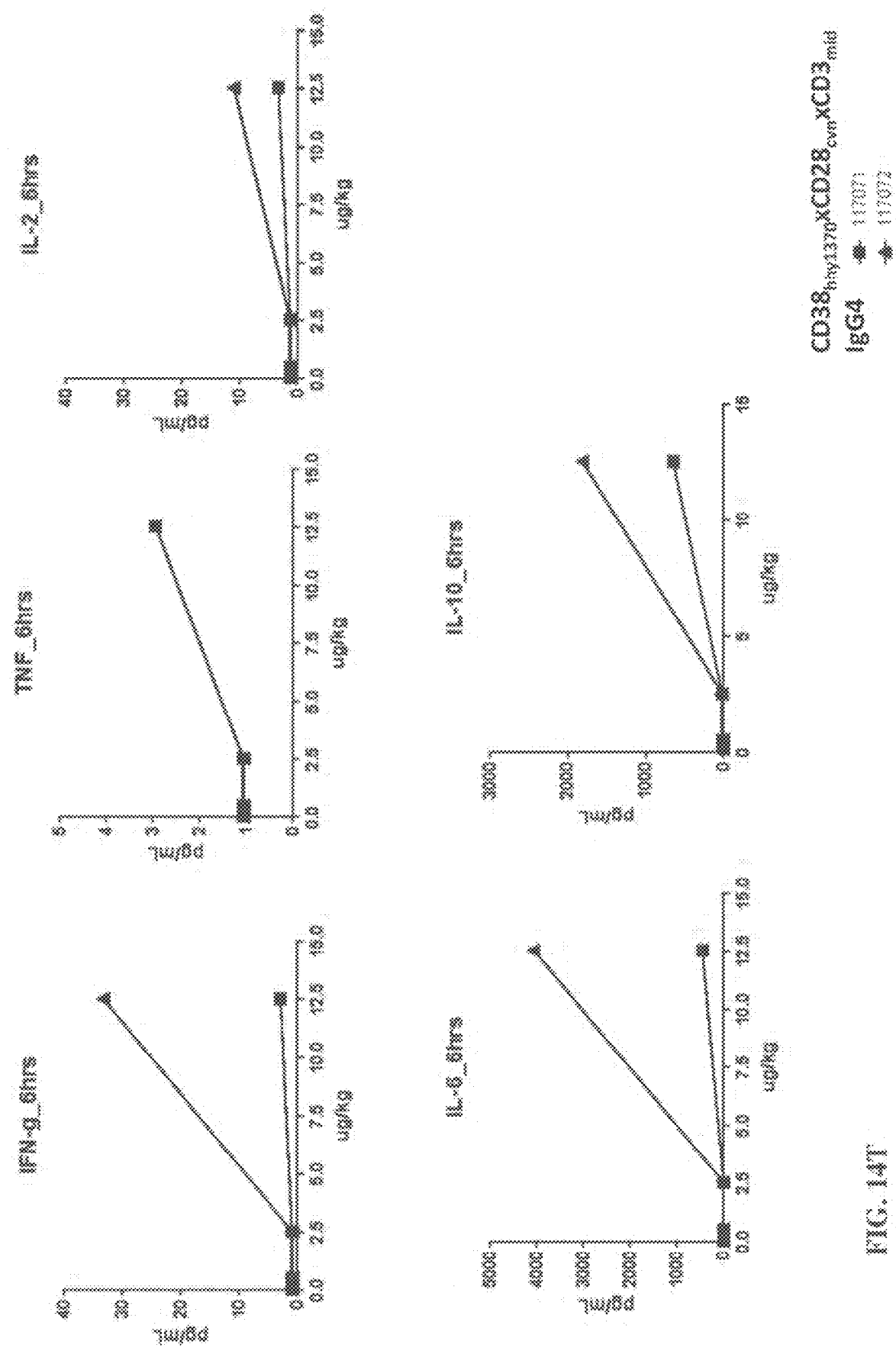
FIG. 14T shows the changes in cytokine levels 6 hours after administration of the three ascending doses (0.5, 2.5.12.5 µg/kg) of the anti-CD38$_{(hhy1370)}$×CD28$_{(evn)}$×CD3$_{(mid)}$ trispecific binding protein (results from different test animals labeled as "117071" and "117072").
Figure 14U:
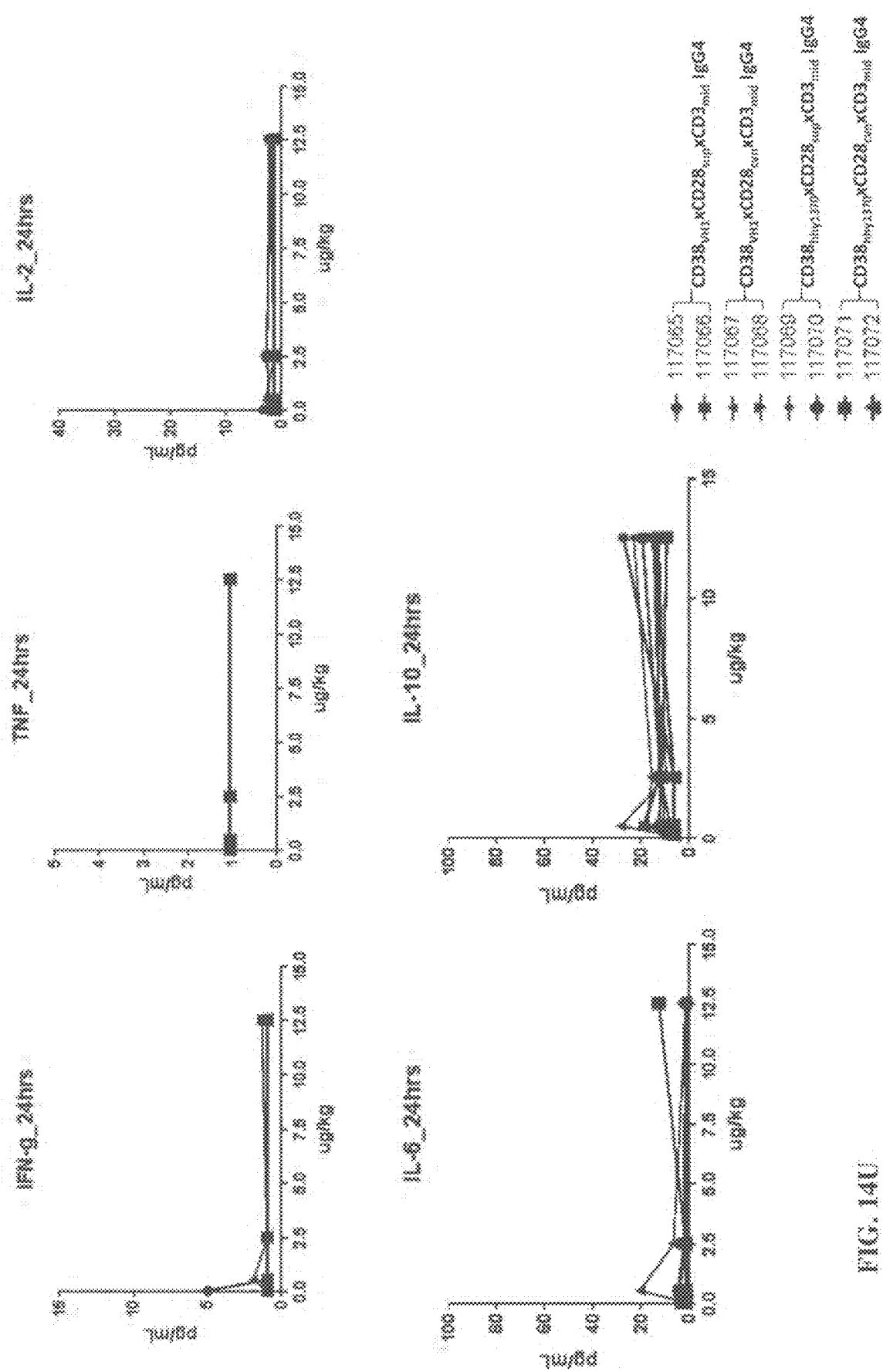
FIGS. 14A-14U show the results of a dose escalation study (0.5, 2.5, 12.5 µg/kg) using the anti-CD38$_{(VH1)}$×CD28$_{(sup)}$×CD3$_{(mid)}$, the anti-CD38$_{(VH1)}$×CD28$_{(evn)}$×CD3$_{(mid)}$, the anti-CD38$_{(hhy1370)}$×CD28$_{(sup)}$×CD3$_{(mid)}$, and the anti-CD38$_{(hhy1370)}$×CD28$_{(evn)}$×CD3$_{(mid)}$ trispecific binding proteins in non-human primates

A dose escalation toxicity study using mAb2-containing $CD38_{VH1} \times CD28_{sup} \times CD3_{mid}$ IgG4, mAb6-containing $CD38_{hhy1370} \times CD28_{sup} \times CD3_{mid}$ IgG4, mAb2-containing $CD38_{VH1} \times CD28_{evn} \times CD3_{mid}$ IgG4, and mAb6-containing $CD38_{hhy1370} \times CD28_{evn} \times CD3_{mid}$ IgG4 trispecific binding proteins was carried out in non-human primates. All three binding domains in 4 binding proteins are cross-reactive with cynomolgus CD38/CD3/CD28 poly peptides. The study was devised to assess the potential toxicity profile of the molecular. Blood samples were collected for serum and PBMC isolations. Circulating T cell populations were investigated after each dosing (FIGS. 14E-14H), along with T cell subpopulation activation (CD69+) (FIGS. 14A-14D). Percentage of CD4 and CD8 T cells in circulation were decreased with dose escalation. Significant CD4 and CD8 T cell activation were prominent starting at 2.5 µg/kg doses, suggesting potent activation ability for mAb2- and mAb6-containing molecules. Significant circulating T cell deletion was seen with all proteins at 12.5 µg/kg (FIGS. 14I-14L), again correlating with potency. Depletion of circulating T cells was rather transient, returning the pre-treatment level after 24-48 hours (FIGS. 14M-14P). Serum level of several cytokines was also measured. Significant IL-6 and IL-10 release were observed at 12.5 µg/kg with all molecules, which was rather transient, returning to baseline at 24 hours (FIG. 14U).

Figure 14W:
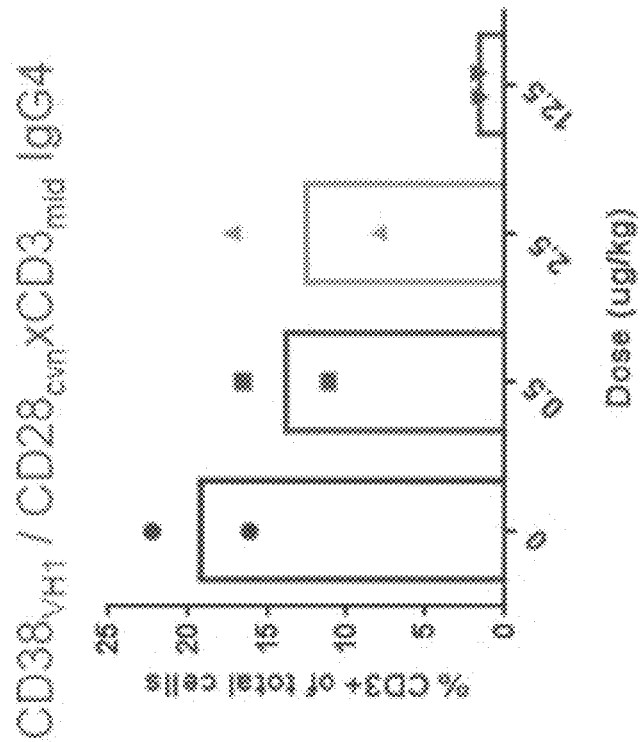
FIGS. 14V & 14W show that anti-CD38$_{(VH1)}$×CD28$_{(sup)}$×CD3$_{(mid)}$ and anti-CD38$_{(VH1)}$×CD28$_{(evn)}$××CD3$_{(mid)}$ trispecific binding proteins induced depletion of T cells in vivo in non-human primate blood at higher doses (6 hours post-dose).
Figure 14V:
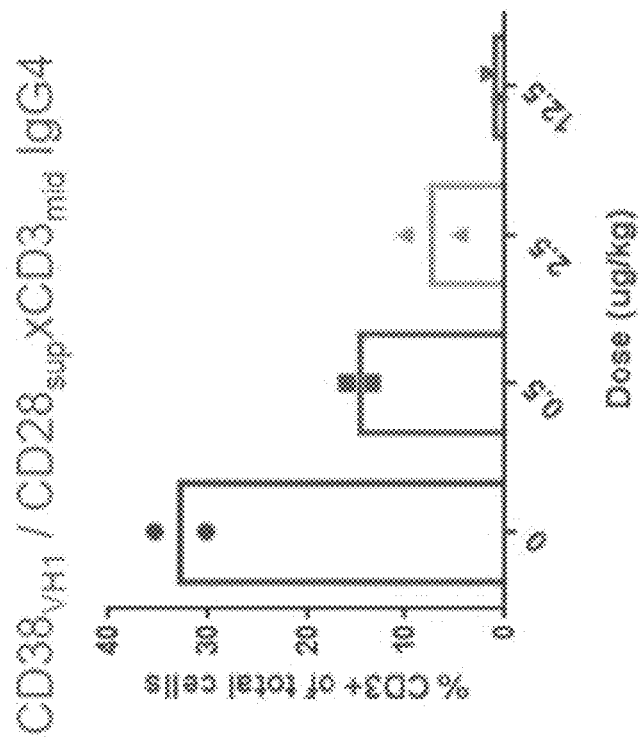
Figure 14Y:
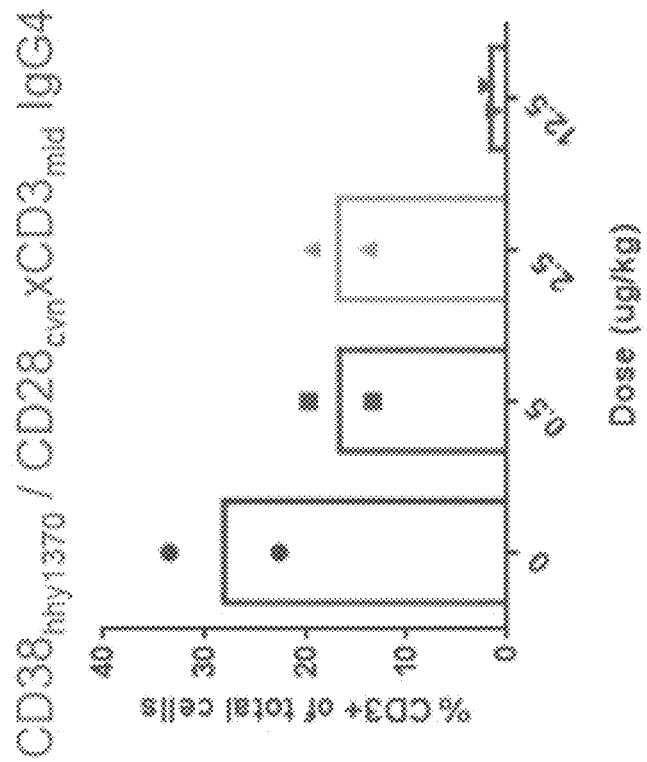
FIGS. 14X & 14Y show that anti-CD38$_{(HHY1370)}$×CD28$_{(sup)}$×CD3$_{(mid)}$ and anti-CD38$_{(HHY1370)}$×CD28$_{(evn)}$×CD3$_{(mid)}$ trispecific binding proteins induced depletion of T cells in vivo in non-human primate blood at higher doses (6 hours post-dose).
Figure 14X:
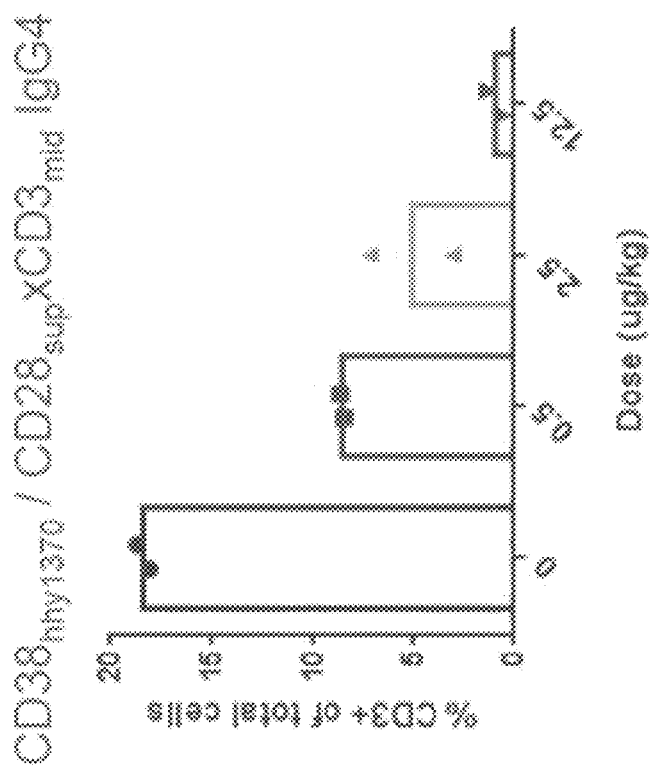
Figure 14A:
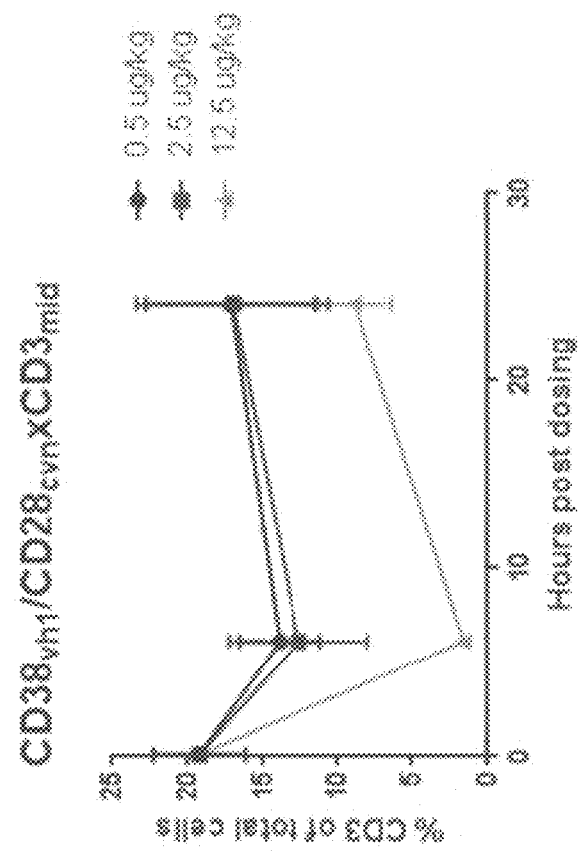
Figure 14Z:
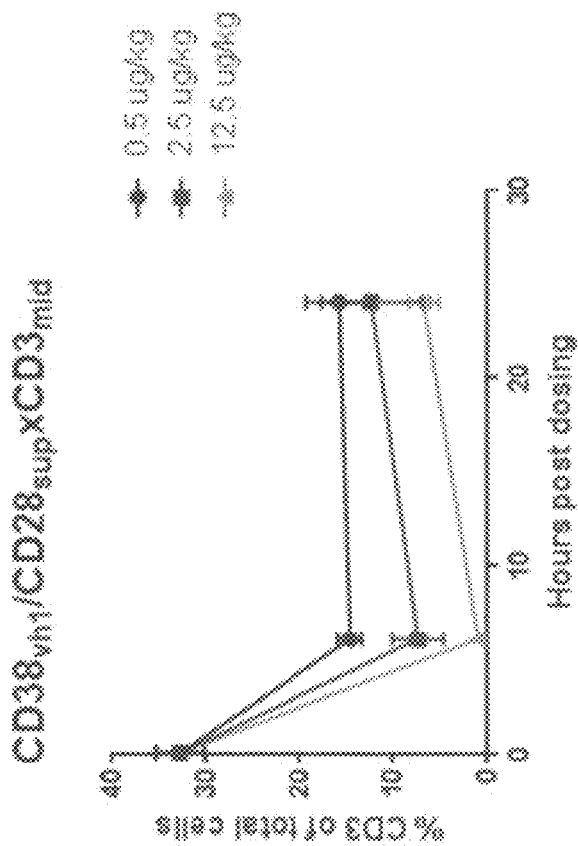
Figure 14A:
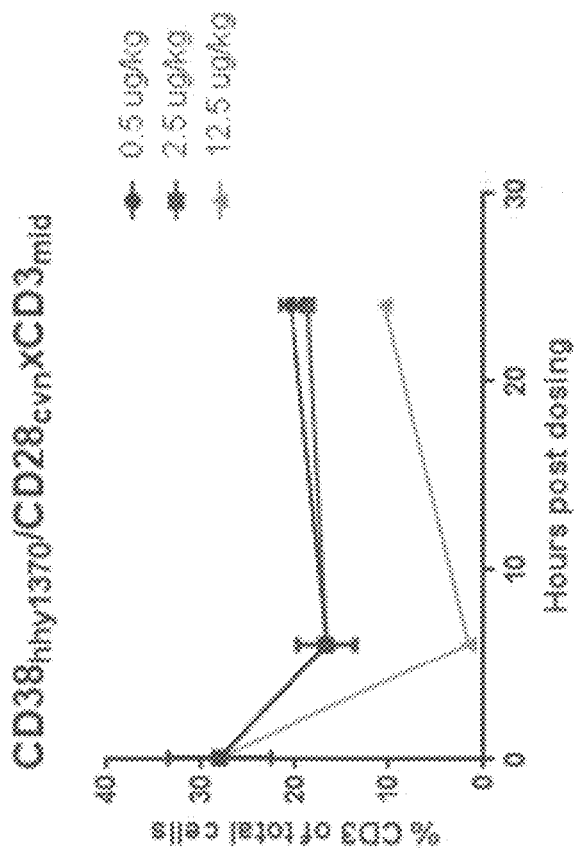
Figure 14A:
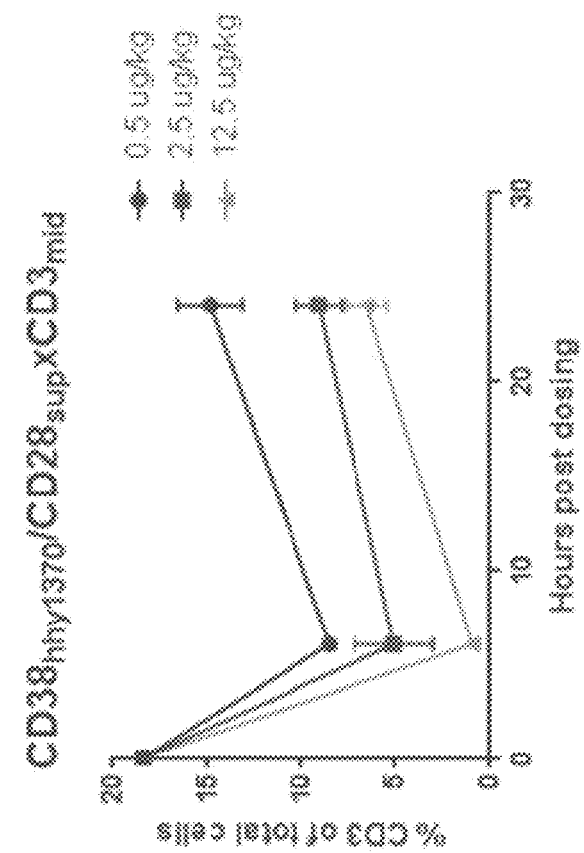
Figure 14A:
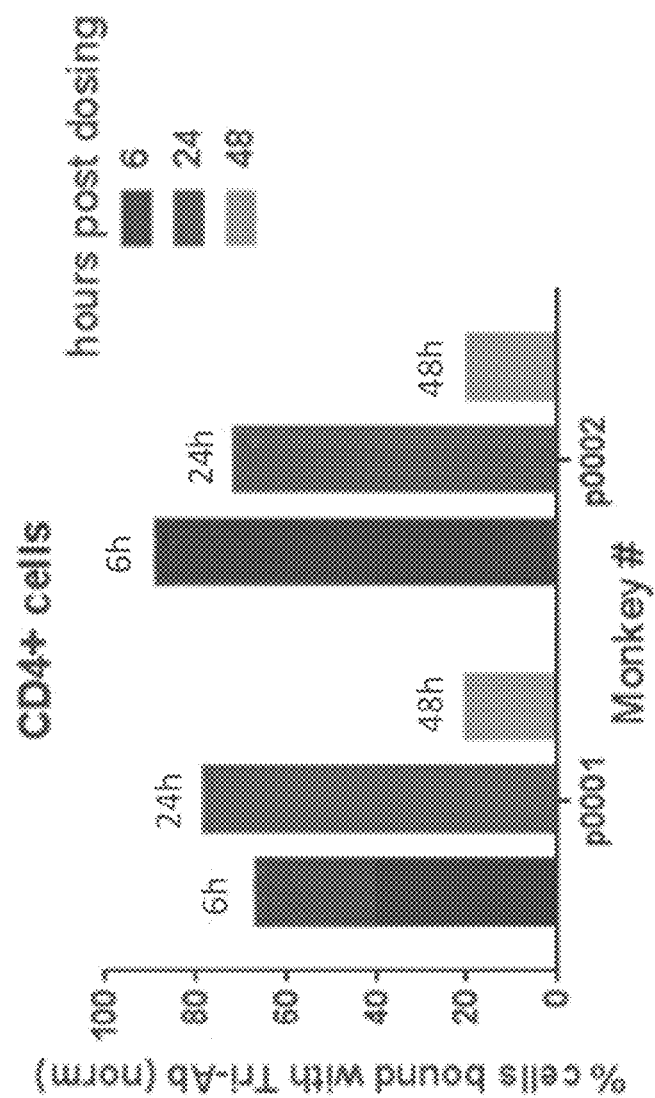
Figure 14A:
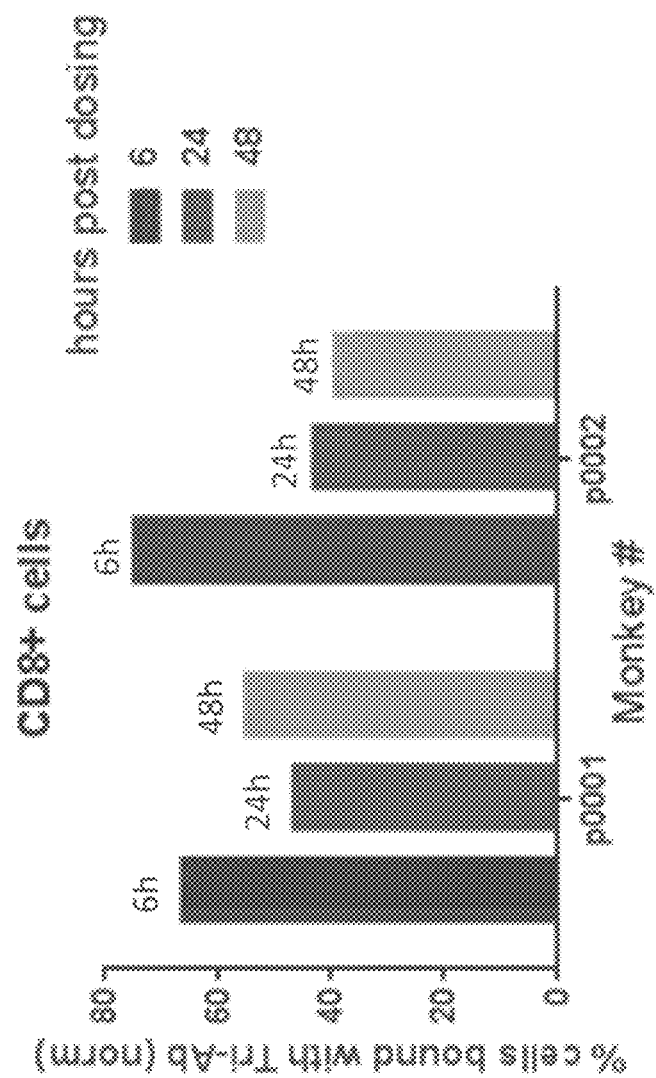

$CD38_{VH1} \times CD28_{sup} \times CD3_{mid}$ IgG4 (FIG. 14V) and $CD38_{VH1} \times CD28_{evn} \times CD3_{mid}$ IgG4 (FIG. 14W) both induced depletion of T cells in blood at higher doses. Similarly, $CD38_{hhy1370} \times CD28_{sup} \times CD3_{mid}$ IgG4 (FIG. 14X) mid $CD38_{hhy1370} \times CD28_{evn} \times CD3_{mid}$ IgG4 (FIG. 14Y) also induced depletion of T cells in blood at higher doses. However, T cells started to reappear in blood 24 hours after treatment with any of the four trispecific binding proteins (FIGS. 14Z-14AC) FIGS. 14AD & 14AE show the amount of $CD38_{VH1} \times CD28_{sup} \times CD3_{mid}$ IgG4 bound to CD4+ T cells after administration of a 100 µg/kg dose. FIGS. 14AF & 14AG show the amount of $CD38_{VH1} \times CD28_{sup} \times CD3_{mid}$ IgG4 bound to CD8+ T cells after administration of a 100 µg/kg dose. These data clearly demonstrated that trispecific Ab $CD38_{VH1} \times CD28_{sup} \times CD3_{mid}$ IgG4 can bind to T cells in vivo with prolonged time (48-72 hours).

Example 7: Optimization of Pharmacokinetics/Pharmacodynamics by Fc Variants

Materials and Methods

C-terminal 6-His tagged recombinant human Fcγ RI (R&D Systems #1257-FC-050), C-terminal 10-His lagged recombinant human Fcγ RIIA (R&D Systems #1330-CD-050/CF) and C-terminal HPC4 tagged recombinant human Fcγ RIII (V158 or F158) were captured to a Biacore chip. Antibodies at 200, 100 & 50 nM were injected for 2 min, followed by 2 min dissociation in HBS-P+, 2 mM CaCl2 pH 7.4 buffer at 30 μL/min flow-rate using Biacore 200. Binding curve at 200 nM was shown.

ELISA assay using C-terminal HPC4 tagged recombinant human Neonatal Fc Receptor (FcRn) was used to measure the binding properties of the trispecific binding proteins with different Fc modifications. Briefly, recombinant human Neonatal Fc Receptor (FcRn) was used to coat the ELISA plate (Nunc 80040LE) (2 ug/ml in PBS) overnight. Serial diluted trispecific binding proteins with different Fc modifications were added into each well and incubated at room temperature for one hour, followed by washing and incubating with HRP labeled anti-human IgG secondary antibody.

Results

Variants of trispecific binding proteins described above were next assayed for binding to various Fc receptors in order to optimize pharmacokinetics (PK)/pharmacodynamics (PD).

Human Fc variants were characterized for binding to FcγR I (FIG. 15A), FcγR IIa (FIG. 15B), and FcγR IIIb/c (FIG. 15C) as described above. Variants tested were human IgG1, human IgG4, and human IgG4 with FALA mutations (F234A and L235A according to EU index) with a control trispecific binding protein.

Figures 15A, 15B, 15C:
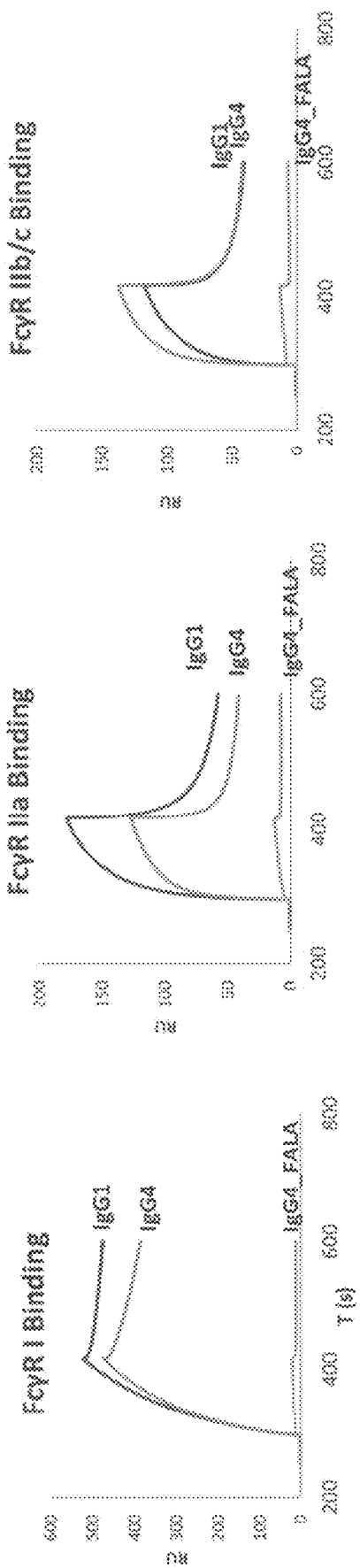
FIGS. 15A-15C show binding or lack thereof of various Fc variants to human Fc receptors FcγR I (FIG. 15A), FcγR IIa (FIG. 15B), and FcγR IIIb/c (FIG. 15C). Variants tested were human IgG1, human IgG4, and human IgG4 with FALA mutations.

As shown in FIGS. 15A-15C wild-type IgG1 and IgG4 were able to bind FcγR I and FcγR IIa, but not FcγR IIIb/c, as previously reported. IgG4 FALA mutations eliminated FcγR I and FcγR IIa binding. Without wishing to be bound to theory, it is thought that eliminating FcγR I and FcγR IIa binding can improve PK/PD by removing unintended clustering through Fc/FcγR interactions.

Figure 16:
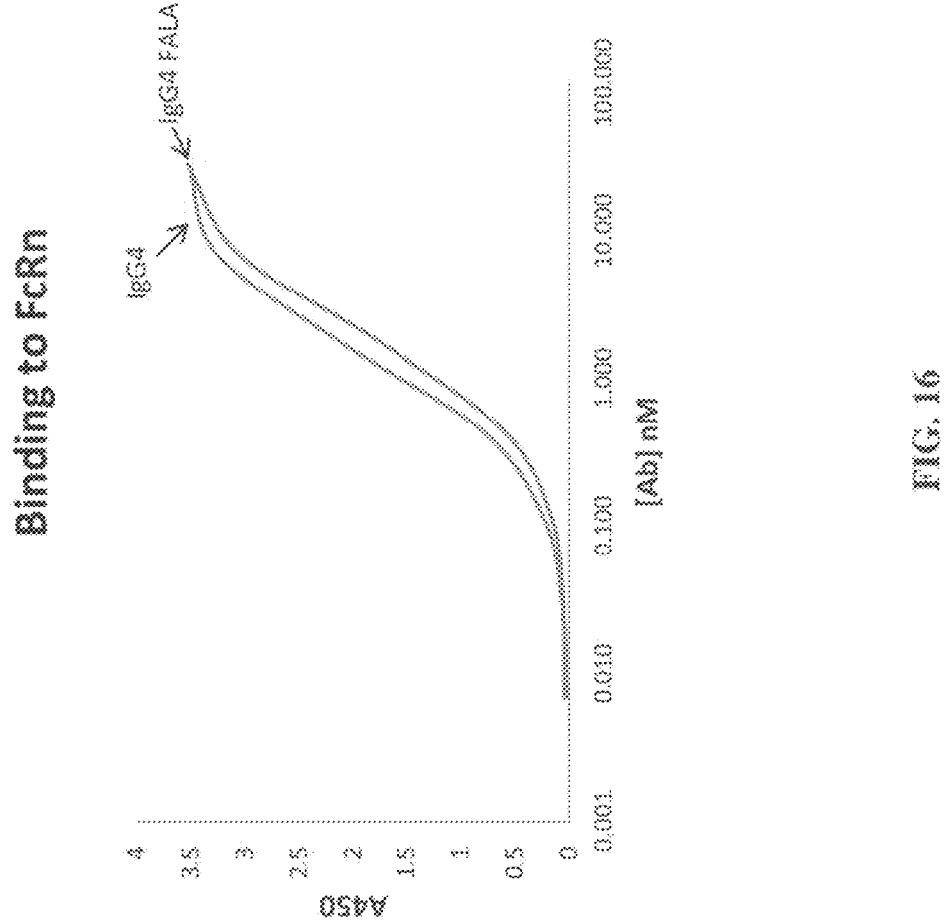
FIG. 16 shows binding of human IgG4, with or without FALA mutations, to FcRn.

Next, the IgG4 FALA variant was examined for binding FcRn. The variant, as well as wild-type IgG4, bound to FcRn (FIG. 16). These results demonstrate that the IgG4 FALA mutations do not affect the interactions between IgG4 Fc and FcRn, implying a minimal impact on binding protein half-life.

The PK parameter of CD38$_{VH1}$×CD28$_{sup}$×CD3$_{mid}$ IgG4, CD38$_{VH1}$×CD28$_{sup}$×CD3$_{mid}$ IgG4 FALA, CD38$_{VH1}$×CD28$_{sup}$×CD3$_{mid}$ IgG1 LALA P329A, and CD38$_{HHY1370}$×CD28$_{sup}$×CD3$_{mid}$ IgG4 FALA, as determined in NSG mice, are summarized in FIG. 17. IgG4 Fc modifications showed significantly improved half-life and AUC in NSG mice by eliminating binding to NSG-specific FcγRI, which is abundant on macrophages.

Example 8: In Vitro Activation and In Vivo Anti-Tumor Efficacy of Anti-CD38 Trispecific Binding Proteins Materials and Methods
Cytokine Release From Human PBMCs Human PMBCs were incubated with 100 pM of binding proteins for 24 hrs. Supernatants were collected and cytokines measured by Luminex using Drop Array plates (in triplicate). For experiments using tumor target cells. Human PMBC were incubated with 100 pM of antibodies and with, or without, RPMI-8226 target cells at 10:1 E:T ratio for 24 hrs. Supernatants were collected after PMBCs incubated with trispecific proteins and assayed for cytokines with MILLIPLEX® MAP kit and analyzed on a MAGPIX® System.

Bcl-xL Assay

Negatively sorted T cells from PBMC (magnetic) were incubated with 100 nM plate-bound Abs for 1 day. T cells were then washed and stained with fluorescently conjugated antibodies specific for T cell markers and Bcl-xL and analyzed on a flow cytometer.

T Cell Proliferation

Negatively sorted T cells from PBMC (magnetic bead cell separation) were incubated with plate-bound Abs (100 nM) for 1 to 6 days. Total cells were counted by flow cytometry using counting beads on specific days after start of incubation. Fold change was calculated from Day 0 cell counts (500 cells/uL). Results from 3 PBMC donors.

IL-2 Expression

GloResponse™ IL2-luc2P Jurkat Cells were incubated with trispecific proteins for 6 hours, then Bio-Glo™ luciferase assay system was used to detect luciferase reporter gene expression.

PBMC In Vitro Activation

The activation (CD69$^+$) of human PBMC cells treated with anti-CD38×CD28×CD3 trispecific antibodies or control IgG4 binding protein was determined.

In Vivo Efficacy in Disseminated Tumor Model

For disseminated hu-PMBC NSG mouse model, 1-5×10$^6$ cells were injected into each mouse intravenously at day 0. At day 3, base line luminance imaging was taken for randomization. At day 4, 10×10$^6$ human PBMCs from healthy donors were reconstituted to each mouse intraperitoneally (IP). Mice were treated weekly at day 5, 12, 19 using indicated doses. Weekly luminance body imaging was taken on day 10, 17, 24 for monitoring tumor volume in each animal. At termination of the study, blood, spleen, bone and bone marrow were collected for histopathology study-.

Figure 18A:
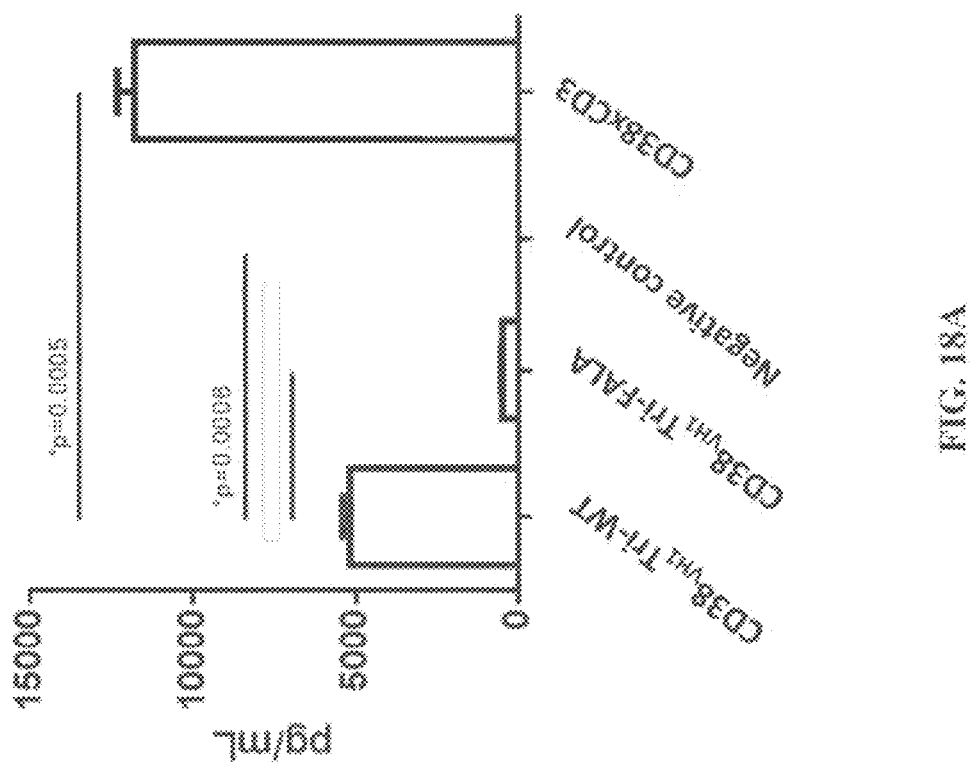
FIGS. 18A-18C show Fc/FcR interaction-mediated (non-specific) release of IFN-γ (FIG. 18A), IL-2 (FIG. 18B), or TNF-α (FIG. 18C) by human PBMCs incubated with trispecific binding proteins having wild-type or FALA variant Fc regions.
Figure 18C:
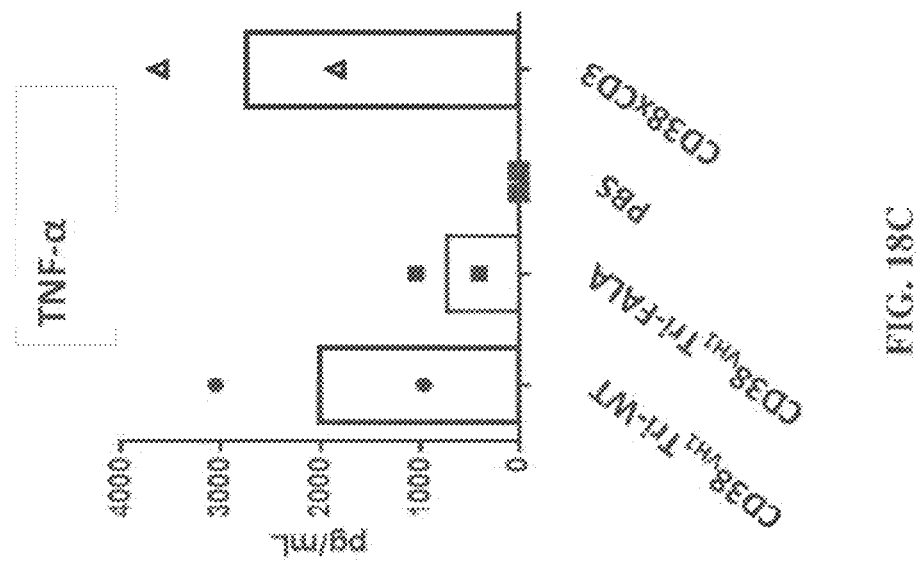
Figure 18B:
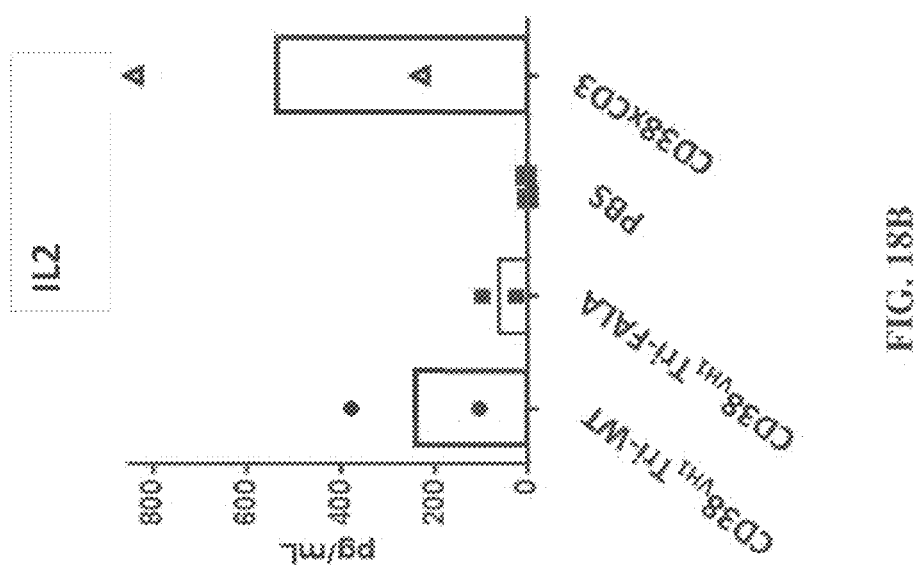

Results mAb2-containing anti-CD38×anti-CD28×anti-CD3 trispecific binding proteins with the IgG4 FALA variant Fc region caused markedly reduced levels of non-specific IFN-γ release in human PBMCs, as compared with similar binding proteins with wild-type Fc regions (FIG. 18A). Similar results were observed with release of IL-2 (FIG. 18B) and TNF-α (FIG. 18C). Importantly, cytokine release was significantly lower for these Fc variant trispecific binding proteins than for the benchmark bispecific anti-CD38× anti-CD3 bispecific antibody-. These results imply improved safety profile of trispecific binding proteins with Fc variants due to a reduction in non-specific cytokine release.

IgG1 and IgG4 Fc variants of both mAb2-containing CD38$_{VH1}$×CD28$_{sup}$×CD3$_{mid}$ and mAb6-containing CD38$_{HHY1370}$×CD28$_{sup}$×CD3$_{mid}$ also led to in vitro activation of human PBMCs (FIG. 18D).

Immune costimulation by ligation of CD28 is required for T cell survival and proliferation; TCR signaling alone does not result in T cell proliferation (Sharmee and Allison (2015) *Science* 348:56-61). Trispecific binding protein CD38$_{VH1}$× CD28$_{sup}$×CD3$_{mid}$ led to induction of Bcl-xL in both CD4+ and CD8+ T cells, whereas removing either the CD28 or the CD3 antigen binding domains eliminated this effect (FIGS. 19A&19B). These results demonstrate, as expected, that both CD3 and CD28 binding arms are required for Bcl-xL induction in T cells by the anti-CD38 trispecific binding proteins, thereby delivering a pro-survival signal to T cells. The anti-CD28 arm of the trispecific binding protein is critical to upregulation of pro-survival Bcl-xL in T cells. When compared with a benchmark anti-CD38×anti-CD3 bispecific antibody. CD38$_{VH1}$×CD28×CD3 trispecific binding protein led to greater upregulation of Bcl-xL in CD4+ and CD8+ T cells (FIGS. 19C & 19D).

Figure 19E:
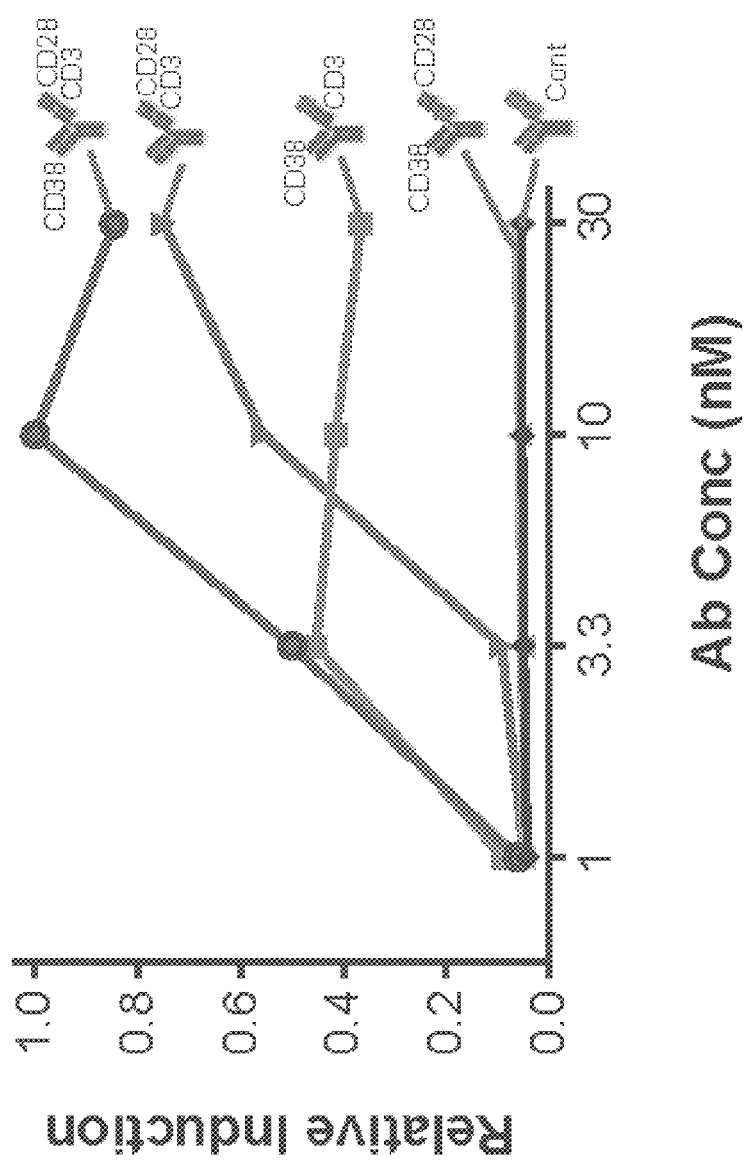
FIG. 19E shows that T cell activation by anti-CD38×anti-CD28×anti-CD3 trispecific binding proteins, as assayed by IL-2 expression in a Jurkat T cell reporter line, is dependent upon the anti-CD3 antigen binding domain.
Figure 10F:
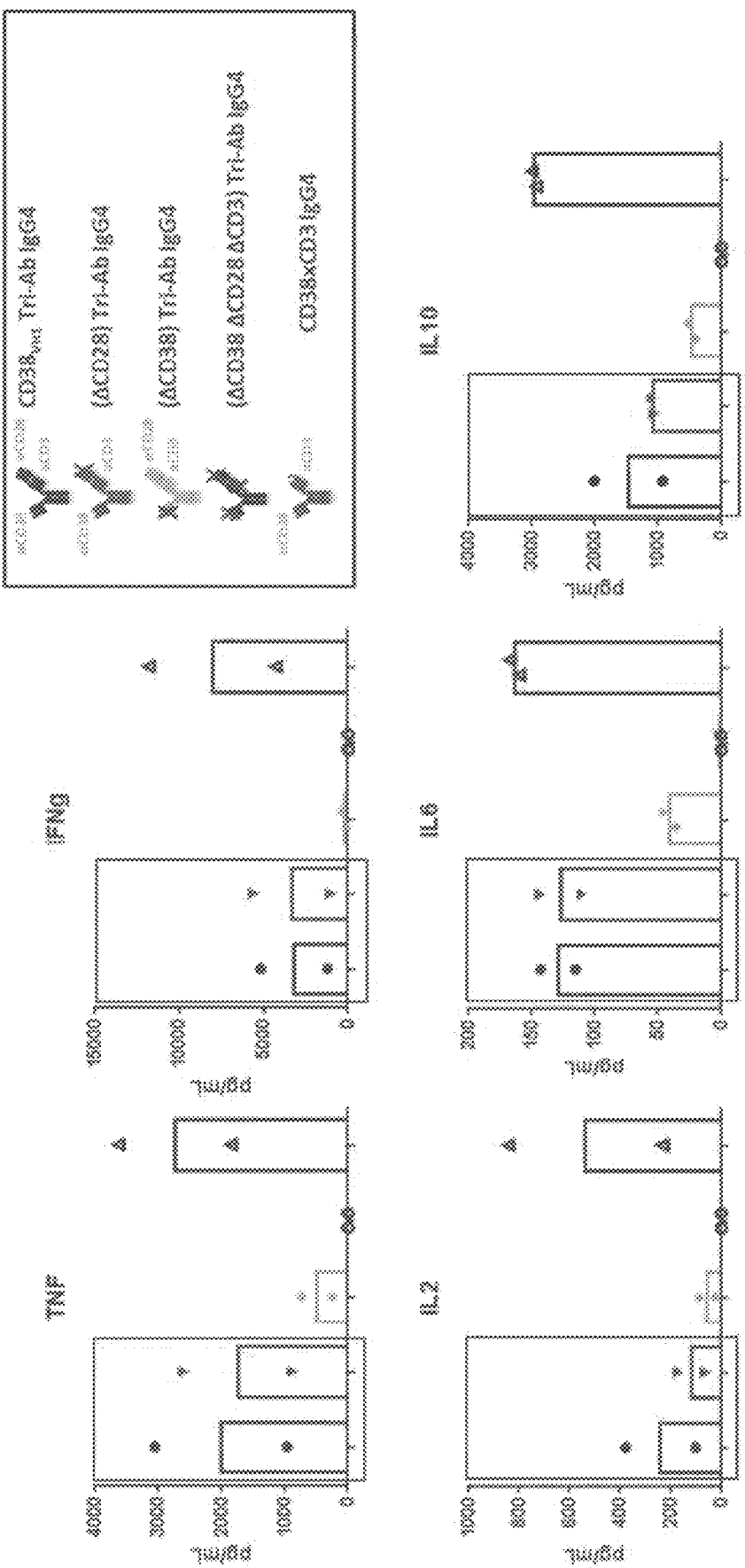

To determine the primary driver of T cell activation by CD38$_{VH1}$×CD28$_{sup}$×CD3$_{mid}$ trispecific binding proteins, IL-2 expression in a Jurkat T cell reporter Jurkat line containing human IL2 promoter driving luciferase reporter was used to measure activation. Knockout mutation of the anti-CD3 binding domain led to elimination of T cell activation, demonstrating that T cell activation is a specific effect of CD3 ligation (FIG. 19E). These results show that anti-CD3 is the primary driver of T cell activation by trispecific binding proteins, and that anti-CD28 also contributes significantly to the T cell activation signal. The primary driver of cytokine release was also examined using human PBMCs (FIG. 19F). By examining release of TNF, IFNg, IL-2, IL-6, and IL-10, it was found that CD3 is the primary determinant of cytokine release. CD28 was found to have the least contribution Trispecific binding proteins with anti-CD38$_{VH1}$ were also found to induce less cytokine release than the benchmark comparator.

Figure 19G:
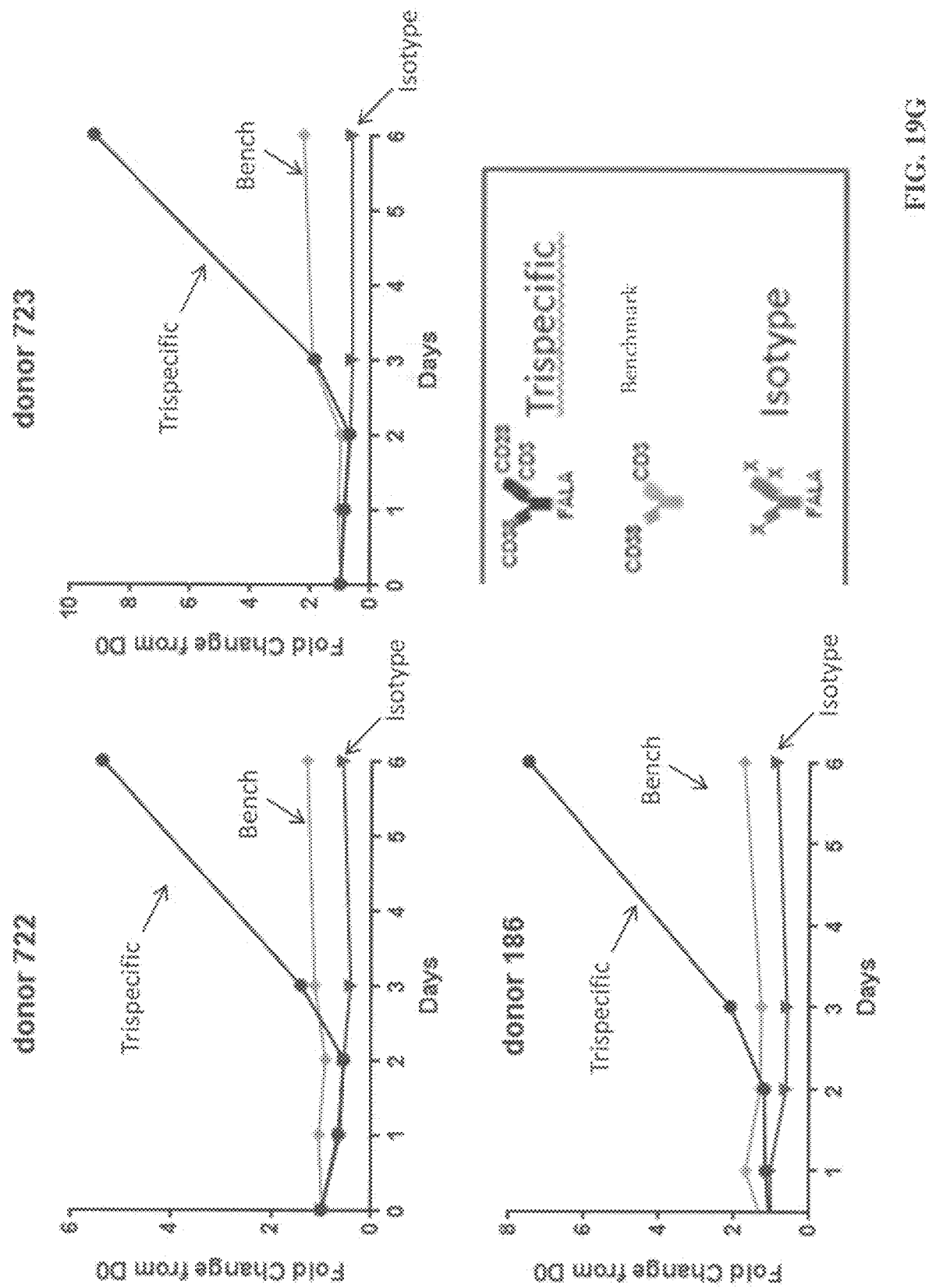
FIG. 19G shows proliferation of T cells activated by anti-CD38×anti-CD28×anti-CD3 trispecific binding protein with IgG4 FALA variant Fc, benchmark anti-CD38×anti-CD3 bispecific antibody, or isotype control (trispecific binding protein with IgG4 FALA variant Fc having mutated binding domains).
Figure 20:
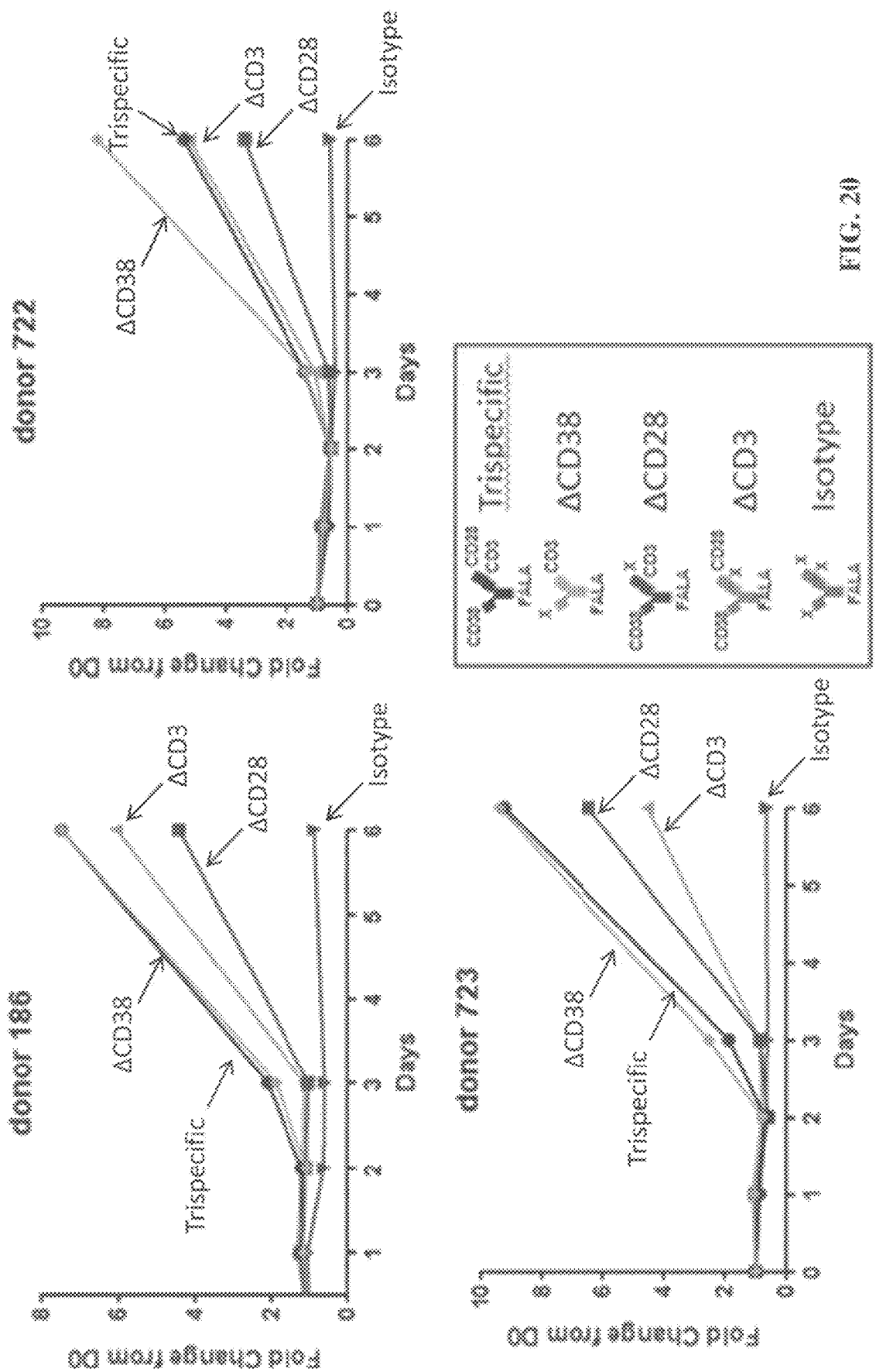
FIG. 20 shows proliferation of T cells activated by anti-CD38×anti-CD28×anti-CD3 trispecific binding protein with IgG4 FALA variant Fc, anti-CD38×anti-CD28×anti-CD3 trispecific binding proteins with IgG4 FALA variant Fc and a mutation in the CD38, CD28, or CD3 antigen binding domain, or isotype control (trispecific binding protein with IgG4 FALA variant Fc having three mutated binding domains).

T cell proliferation was also examined. Activation of T cells using anti-CD38×anti-CD28×anti-CD3 trispecific binding protein with IgG4 FALA variant Fc led to greater proliferation than benchmark or isotype control (FIG. 19G). This activation was reduced upon mutation of the anti-CD28 or anti-CD3 antigen binding domains (FIG. 20).

The humanized NSG mouse model was next used for in vivo solid tumor growth experiments. Mice were implanted at week 6-8 with RPMI8226 human myeloma cells. At week 9, human PBMCs were introduced by ip injection, hPBMCs were reconstituted, and anti-tumor therapy was administered at weeks 10-13. 56 PBMC humanized NSG female mice were implanted with 5 million RPMI8226 cells in 50% matrigel, and mice were selected and randomized into the study at day 5 or 6 post-implantation. This model serves as an in vivo tumor model in mice with human mature T cells.

Figure 21:
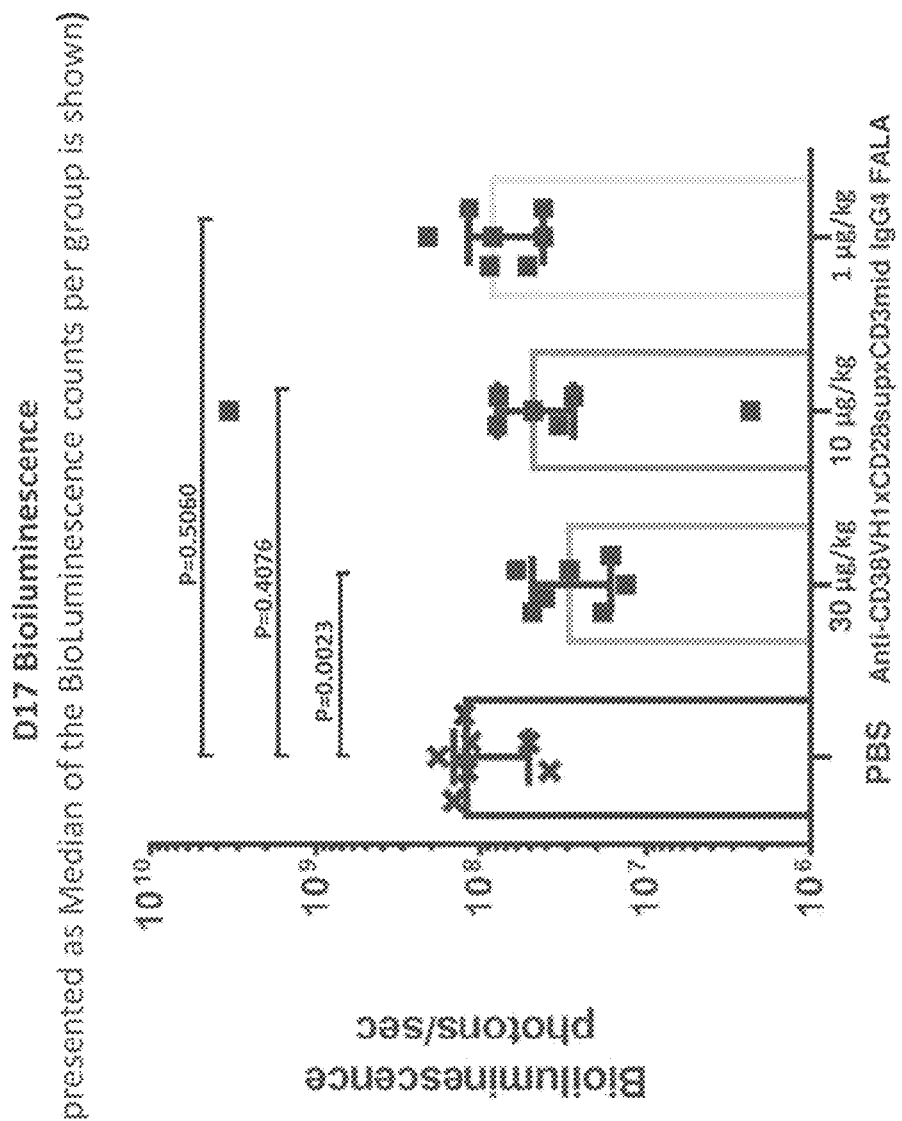
FIG. 21 shows in vivo anti-tumor activity of $CD38_{VH1} \times CD28_{sup} \times CD3_{mid}$ IgG4 FALA trispecific binding protein administered at the indicated doses in an NCI-H929-Luc disseminated tumor model in PBMC humanized NSG mice.
Figure 22:
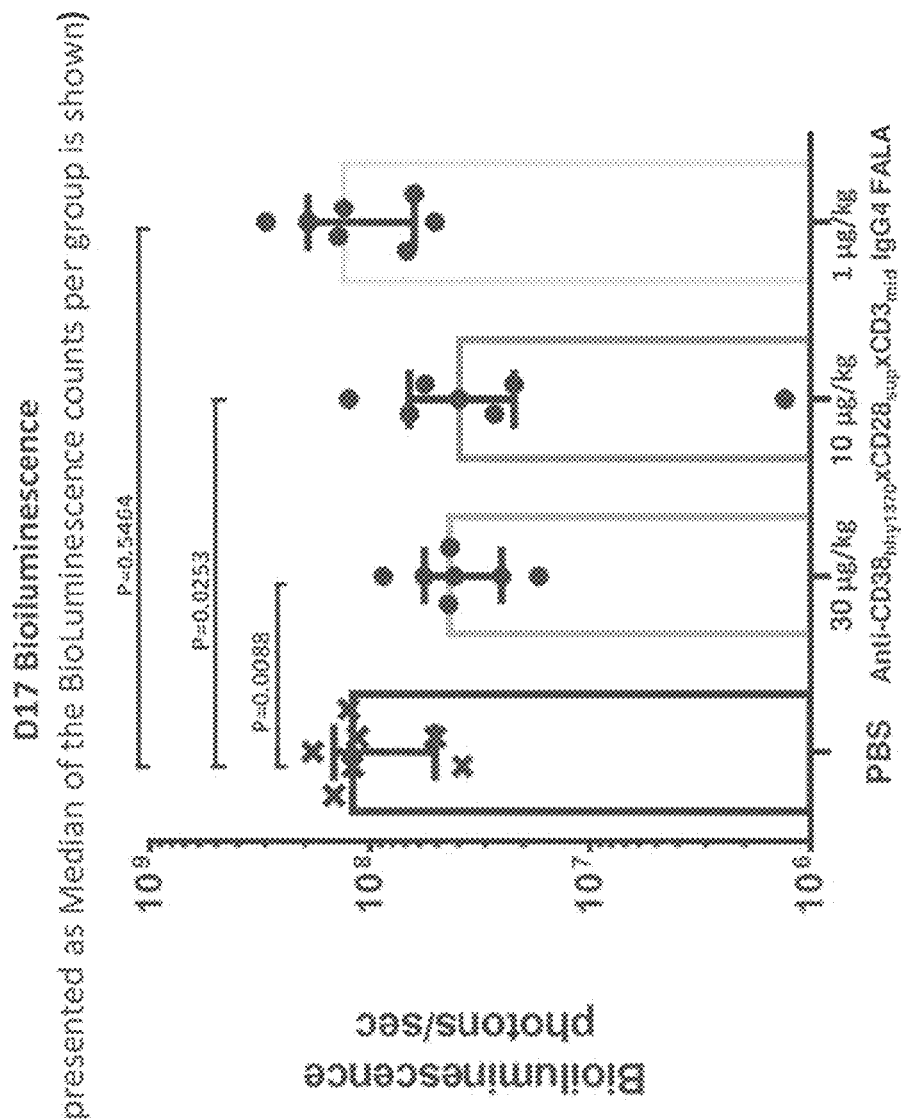
FIG. 22 shows in vivo anti-tumor activity of $CD38_{HHY1370} \times CD28_{sup} \times CD3_{mid}$ IgG4 FALA trispecific binding protein administered at the indicated doses in an NCI-H929-Luc disseminated tumor model in PBMC humanized NSG mice.

Trispecific binding proteins were also assayed in an NSG mouse model of disseminated tumor growth, using NCT-H929-Luc human myeloma cells and assaying tumor growth by bioluminescence. CD38$_{VH1}$×CD28$_{sup}$×CD3$_{mid}$ trispecific binding protein with IgG4 FALA Fc variant showed a statistically significant, dose-dependent anti-tumor efficacy in this disseminated tumor model at 30 µg/kg (FIG. 21). CD38$_{HHY1370}$×CD28$_{sup}$×CD3$_{mid}$ trispecific binding protein with IgG4 FALA Fc variant also showed statistically significant, dose-dependent anti-tumor efficacy in this disseminated tumor model at 30 µg/kg and 10 µg/kg (FIG. 22).

Figures 23A, 23B:
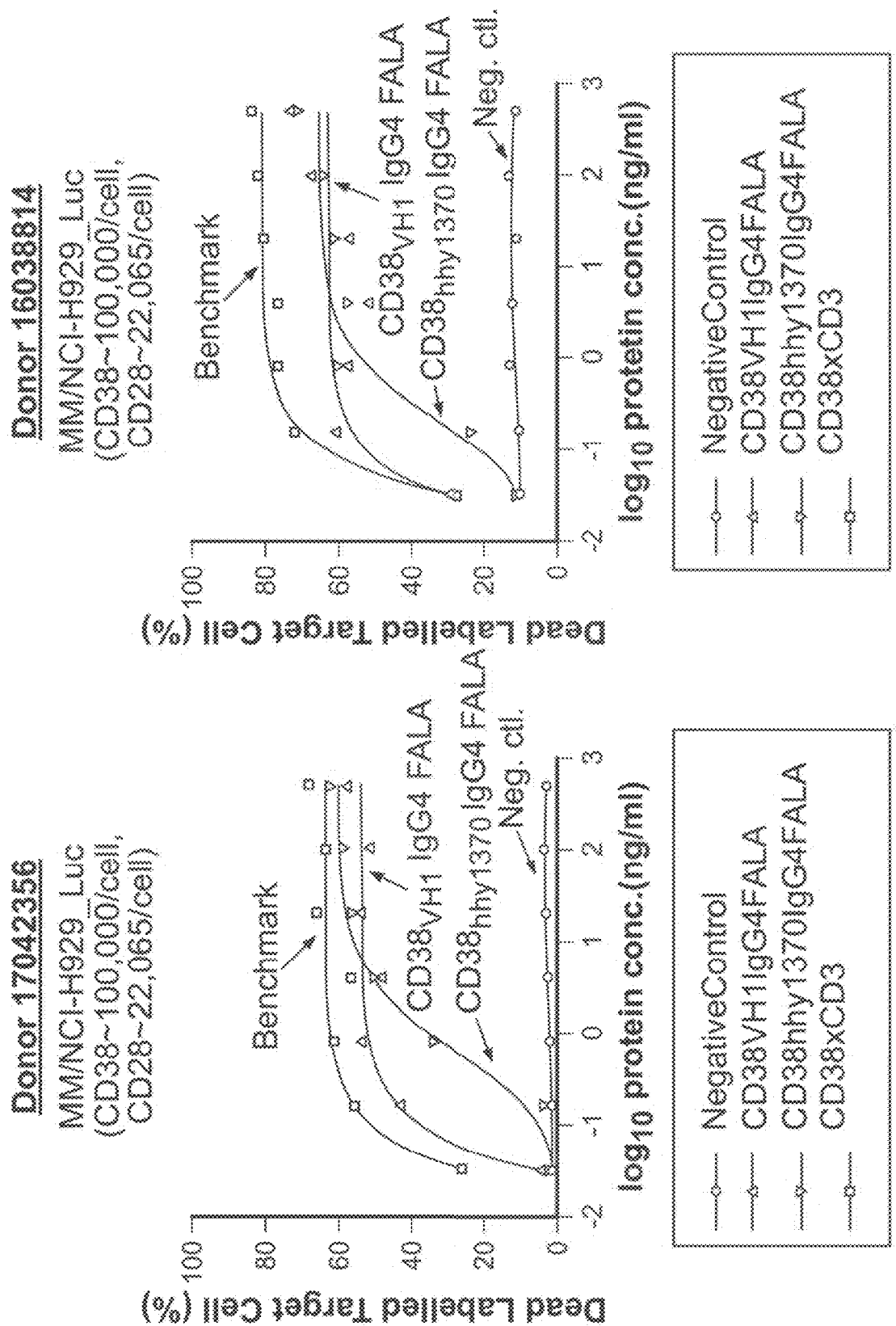
FIGS. 23A & 23B show potent in vitro tumor killing activity of NCI-929-Luc cells with $CD38_{VH1} \times CD28_{sup} \times CD3_{mid}$ and $CD38_{HHY1370} \times CD28_{sup} \times CD3_{mid}$ trispecific binding proteins, and benchmark anti-CD38×anti-CD3 bispecific antibody using the human PBMCs used in the in vivo study. Human PBMCs from two donor humanized NSG mice were used after 24 h. incubation with an effector: PBMC ratio of 10:1.
Figure 23C:
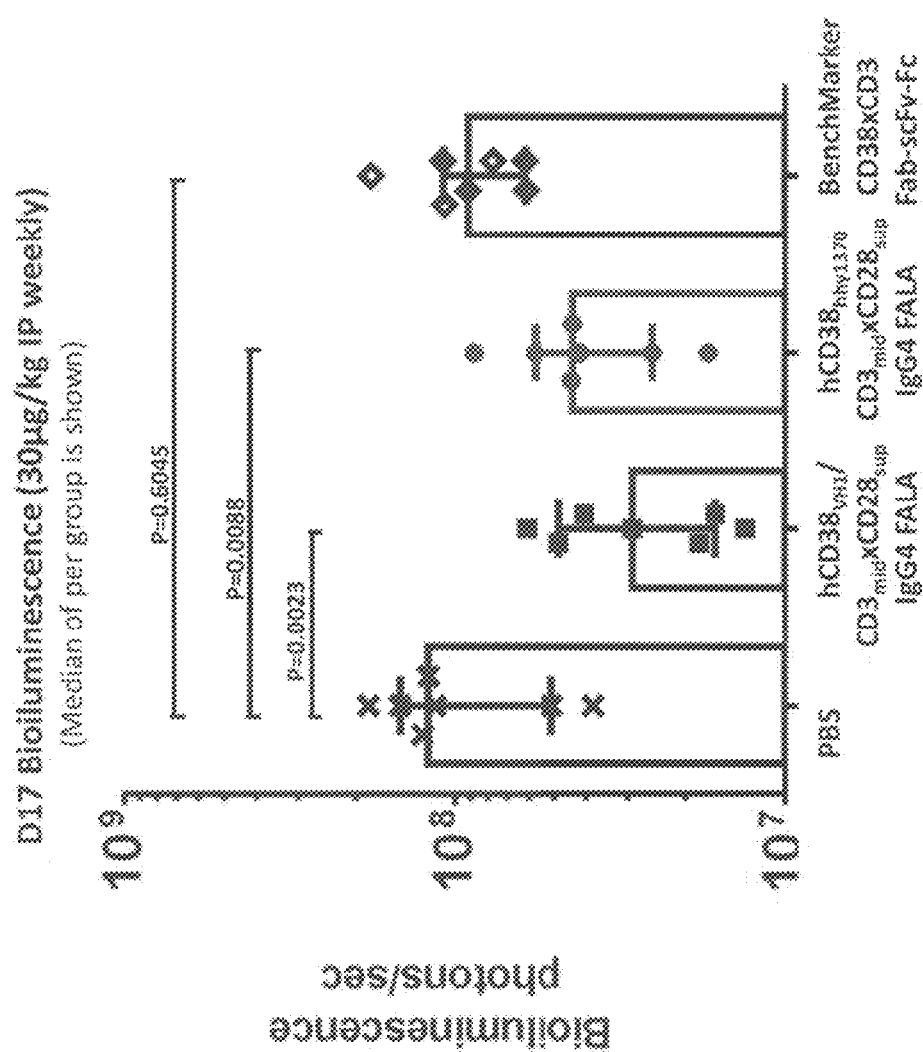
FIG. 23C shows superior in vivo anti-tumor activity of $CD38_{VH1} \times CD28_{sup} \times CD3_{mid}$ and $CD38_{hhy1370} \times CD28_{sup} \times CD3_{mid}$ trispecific binding proteins, as compared to benchmark anti-CD38×anti-CD3 bispecific antibody, administered at the indicated doses in an NCI-H929-Luc disseminated tumor model in PBMC humanized NSG mice. Binding proteins were administered by weekly intraperitoneal (IP) injection at 30 µg/kg.

Trispecific binding proteins mAb2-containing CD38$_{VH1}$×CD28$_{sup}$×CD3$_{mid}$ IgG4 FALA and mAb6-containing CD38$_{hhy1370}$×CD28$_{sup}$×CD3$_{mid}$ IgG4 FALA showed potent in vitro tumor killing activities against NCI-H929-Luc myeloma cells using human PBMCs from two donor humanized NSG mice (FIGS. 23A & 23B). The CD38$_{VH1}$×CD28$_{sup}$×CD3$_{mid}$ IgG4 FALA trispecific binding protein showed superior in vivo tumor activity, as compared to benchmark bispecific antibody, in the disseminated tumor model (FIG. 23C). P-values of comparison with vehicle control (PBS) were determined as follows: CD38$_{VH1}$×CD28$_{sup}$×CD3$_{mid}$ IgG4 FALA: p=0.0023; CD38$_{HHY1370}$×CD28$_{sup}$×CD3$_{mid}$ IgG4 FALA: p=0.0088; benchmark bispecific CD38×CD3 Fab-scFv-Fc: p=0.6045.

Taken together, these results demonstrate an improved anti-0038 candidate with variant Fc region that shows increased half-life, reduced nonspecific cytokine release, and greater in vivo anti-tumor efficacy.

Example 9: Further Characterization of Anti-CD38 Trispecific Binding Proteins

Two signals are required to stimulate T cells for optimal effector function and sustained proliferation. Activation mediated by the T cell receptor (TCR)-CD3 complex induces transcriptional activation leading to cytokine secretion Engagement of a second surface membrane protein. CD28, stimulates an alternative signal transduction pathway and inhibits programmed cell death (Esensten J H, Helou Y A, et al. *Immunity* 44:973-88(2016); Hui E, Cheung J, et al. *Science* 355:1428-1433(2017)). In the absence of a second signal, T cell stimulation through CD3 alone typically leads to activation-induced cell death (Chai J G, Lechler R I. *Int Immunol* 9:935-44(1997)). It was hypothesized that the T cell proliferation could be increased by combining specificities against these two different targets.

Figure 24A:
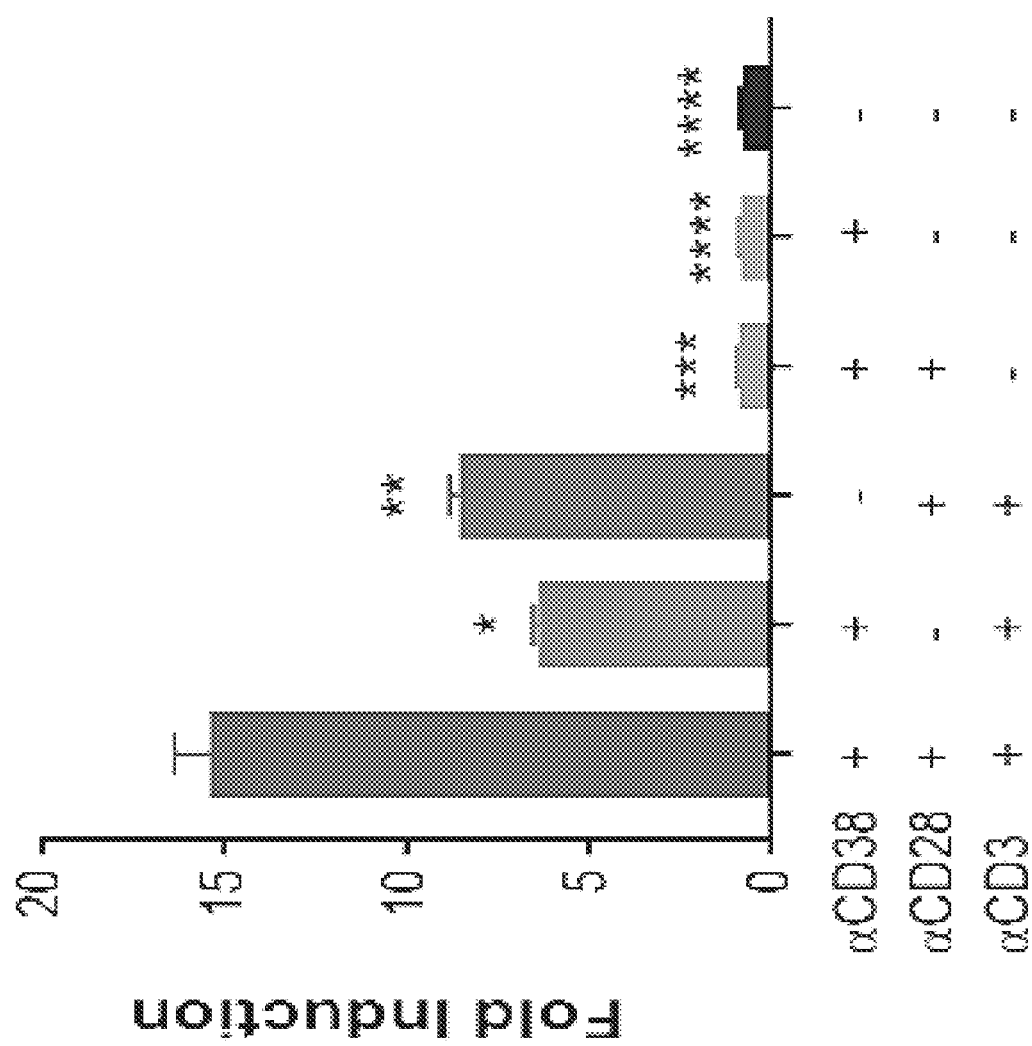
FIG. 24A shows the results of a luciferase reporter assay using GloResponse™ IL2-luc2P Jurkat Cells (Promega) after stimulation by $CD38_{VH1}/CD28_{sup} \times CD3_{mid}$ and its single binding site KO and triple KO mutants at 10 nM concentration.

FIG. 24A shows a luciferase reporter assay that was conducted using GloResponse™ IL2-luc2P Jurkat Cells (Promega) after stimulation by CD38$_{VH1}$/CD28$_{sup}$×CD3$_{mid}$ and its single binding site KO and triple KO mutants at 10 nM concentration. These data illustrate the contribution of CD28 to T cell stimulation (e.g., NFAT signaling).

Figure 24B:
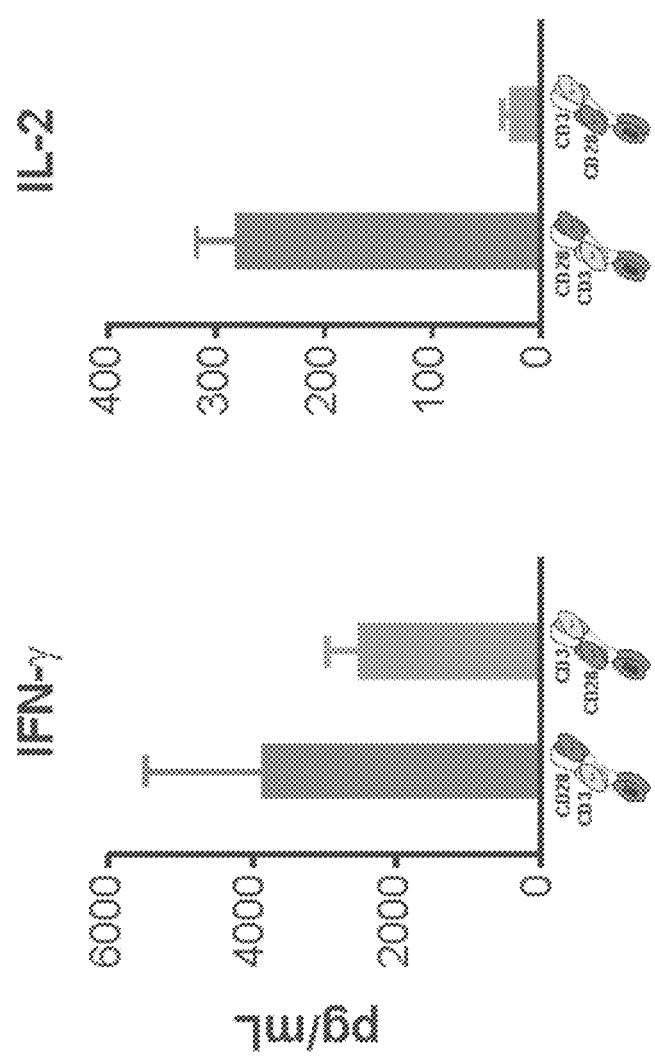
FIG. 24B shows the optimization of anti-CD3×CD28 CODV-Fab antibody. The optimal configuration of the α-CD3 and α-CD28 in alternative positions of the CODV bispecific Fab was evaluated by cytokine release assay s using human PBMCs in vitro. Distal-CD28×proximal CD3 was identified as optimal positioning based on the secretion of IFN-γ and IL-2 in supernatant after 24 hours.

Using the cross-over dual variable (CODV) bispecific Ab format (Steinmetz A, et al. *MAbs* 8: 867-878(2016)), combinations of α-CD3ε (signal 1) and α-CD28 (signal 2) Fv's were evaluated to determine whether dual engagement of these cell surface molecules could stimulate and sustain T cell activation (FIG. 24B). A medium affinity ($K_D$~20 nM) anti-CD3ε Ab was used to avoid high affinity T cell receptor stimulation that causes high level cytokine release and increases the risk of cytokine release syndrome. This CD3 agonist was tested at both positions of the dual arm in combination with a superagonistic CD28 Ab shown previously to support T cell proliferation (Waibler Z, Sender L Y, et al. *PLoS One* 3:e1708(2008)). These monovalent bispecific antibodies wore incubated with human PBMCs in vitro, and T cell stimulation was measured by secretion of interferon-γ and IL-2. While both orientations were active, optimal release of these cytokines was observed with CD3 in the proximal and CD28 in the distal position (FIG. 24B). This dual arm was then selected for pairing with an anti-CD38 antibody in the trispecific Ab formal (Xu L, Pegu A, et al. *Science* 358: 85-90 (2017)).

Figure 25:
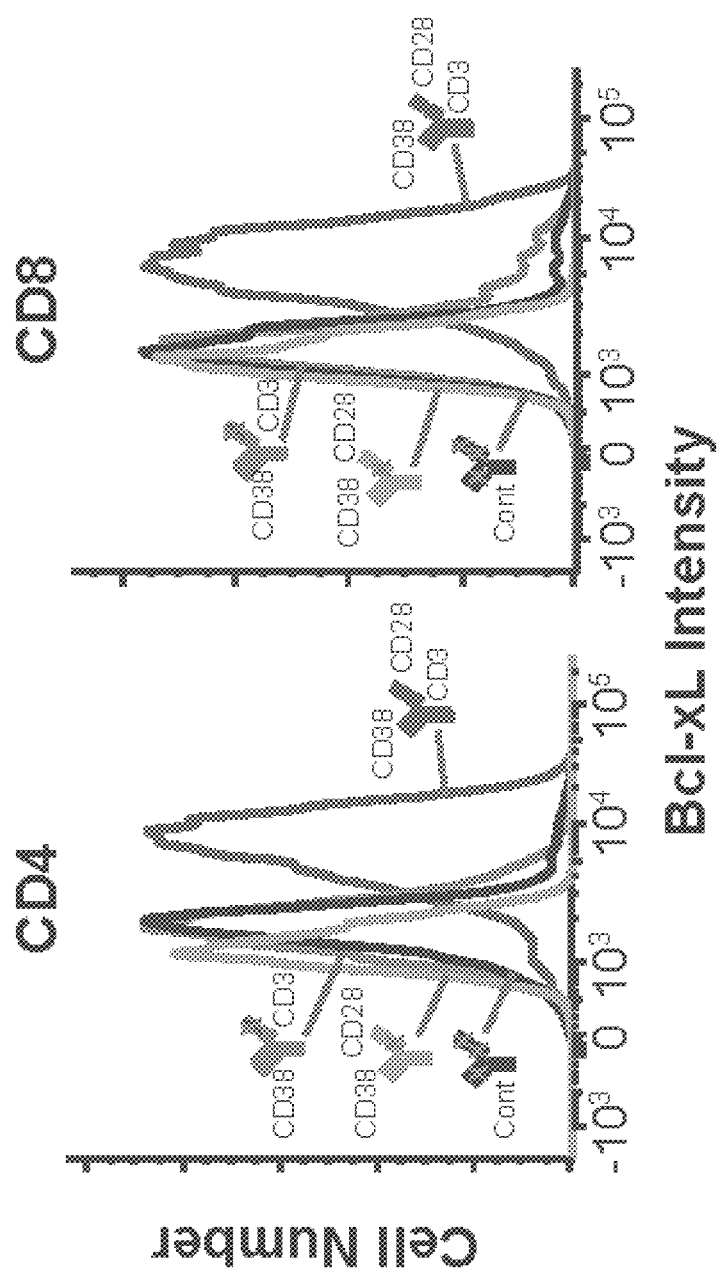
FIG. 25 shows that $CD38_{VH1}/CD28_{sup} \times CD3_{mid}$ induced upregulation of Bcl-2 family member Bcl-xL in primary T cells is CD28 dependent.

FIG. 25 shows that upregulation of Bcl-2 family member Bcl-xL in primary T cells induced by CD38$_{VH1}$/CD28$_{sup}$×CD3$_{mid}$ is CD28-dependent. These data illustrate the contribution of CD28 to T cell survival.

Figure 26:
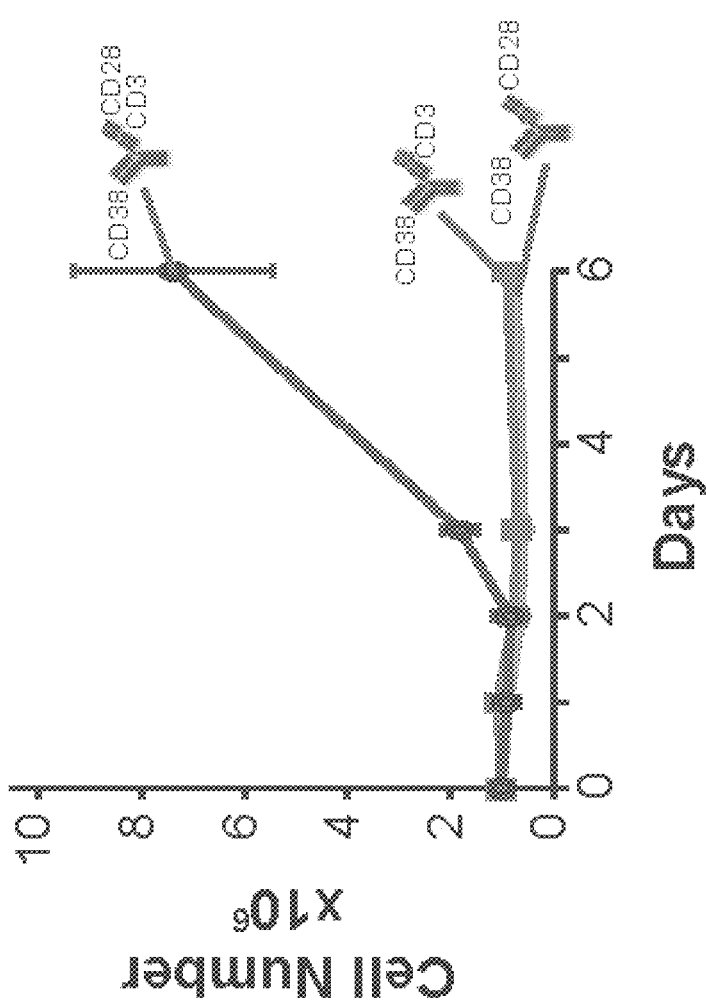
FIG. 26 shows that anti-CD28 in the trispecific Ab provided secondary signaling essential for supporting primary T cell proliferation in vitro.

FIG. 26 shows that anti-CD28 in the trispecific Ab provided secondary signaling essential for supporting primary T cell proliferation in vitro. These data illustrate the contribution of CD28 to T cell proliferation.

Taken together, these data show that anti-C28$_{sup}$ in the CD38$_{VH1}$/CD28$_{sup}$×CD3$_{mid}$ trispecific antibody provides significant functionalities in T cell activation, survival and proliferation in vitro.

FIG. 27 shows the configuration of the trispecific antibody, coded by parental antibody. Also shown is a structure model of the CD38$_{VH1}$/CD28$_{sup}$×CD3$_{mid}$ trispecific Ab obtained based on crystal structures of anti-CD38 VH1 Fab and CD28$_{sup}$/CD3$_{mid}$ CODV Fab (right).

Figures 28A, 28B:
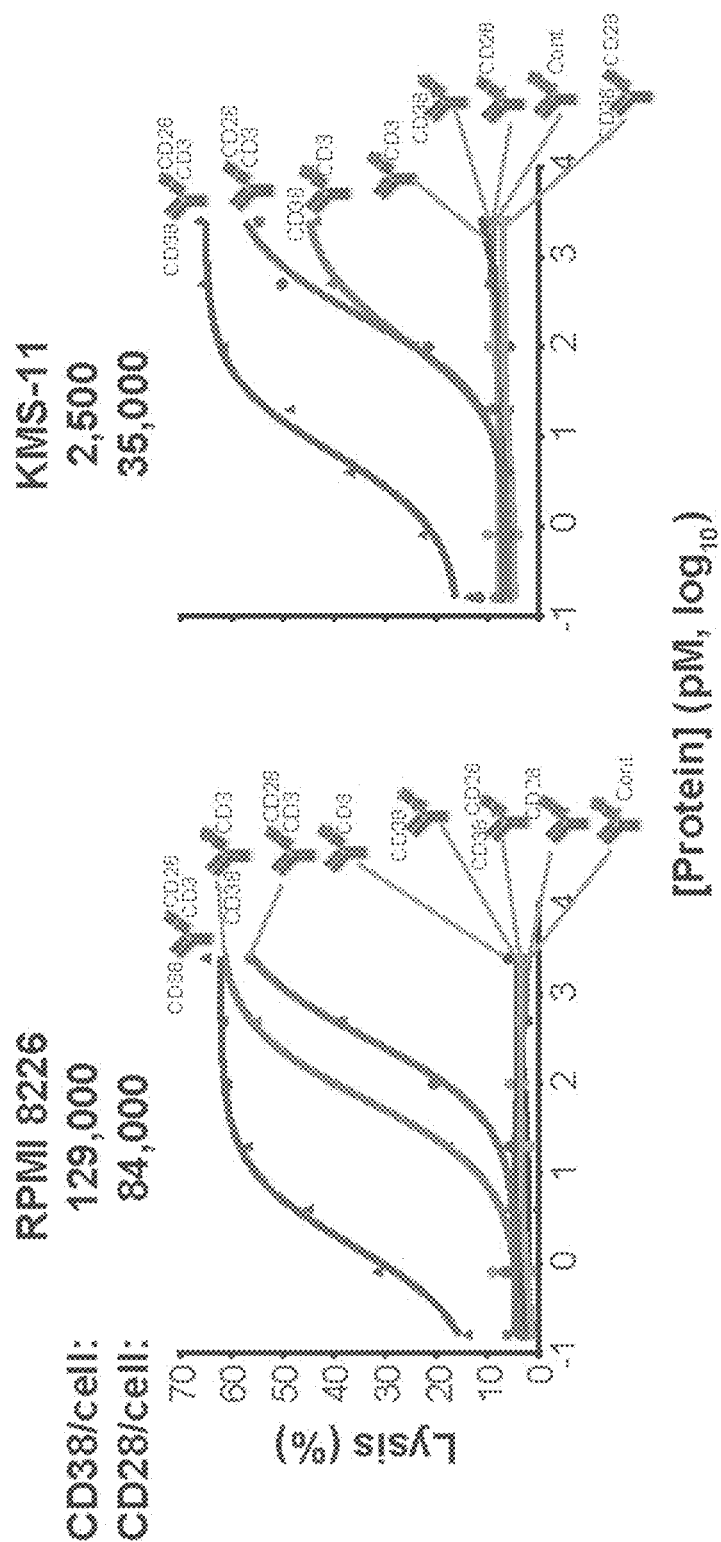
FIGS. 28A & 28B show that multiple myeloma (MM) cells with high (RPMI-8226.

FIGS. 28A & 28B show that multiple myeloma (MM) cells with high (RPMI-8226; FIG. 28A) and low (KMS-11; FIG. 28B) CD38 surface expression were lysed efficiently by human PBMCs (E:T=0:1) incubated with various concentrations of the trispecific Ab. Contribution to the killing activity by each binding site was demonstrated by binding site KO mutations. These data demonstrate that the CD38 trispecific antibody lysed human MM cells through recognition of both CD38 and CD28. CD28 expressed on Multiple Myeloma cells provided a secondary target by the CD38$_{VH1}$/CD28$_{sup}$×CD3$_{mid}$ FALA trispecific antibody, significantly enhancing its killing activity.

Figures 29A, 29B, 29C:
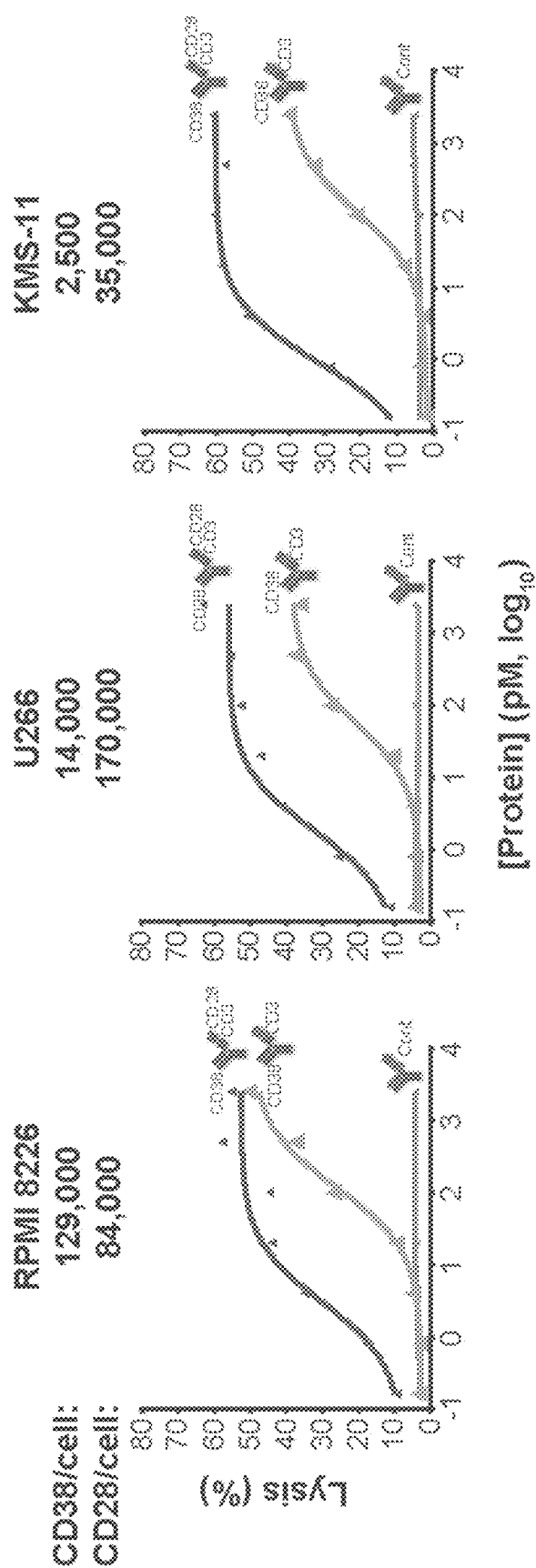
FIGS. 29A-29C show that the anti-$CD28_{sup}$KO mutant of the trispecific Ab exhibited markedly reduced anti-tumor activity against $CD38_{high}$, $CD38_{mid}$ and $CD38_{low}$ MM cells in vitro. Shown are assay s using RPMI-8226 (FIG. 29A), U266 (FIG. 29B), or KMS-11 (no. 290 cells.

FIGS. 29A-29C show that the anti-CD28$_{sup}$KO mutant of the trispecific Ab exhibited markedly reduced anti-tumor activity against CD38$_{high}$, CD38$_{mid}$ and CD38$_{low}$ MM cells in vitro, Shown are assay s using RPMI-8226 (FIG. 29A), U266 (FIG. 29B), or KMS-11 (FIG. 29C) cells. CD28 expression on MM cells increased their susceptibility to cytolysis mediated by the CD38 trispecific antibody.

Figure 30:
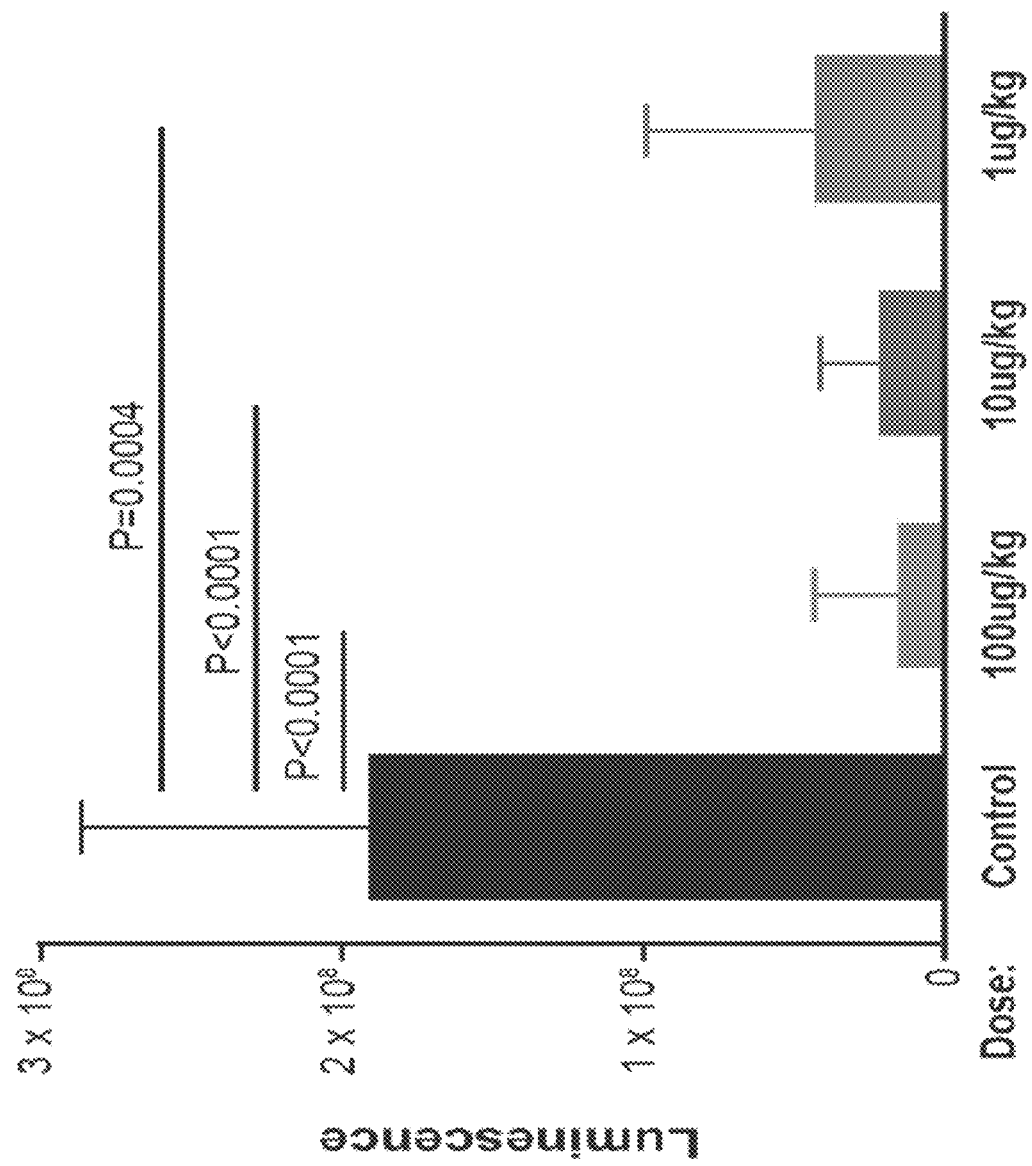
FIG. 30 shows that reduction of tumor burden in $CD38_{VH1}/CD28_{sup} \times CD3_{mid}$_FALA trispecific antibody treatment groups was dose-dependent and statistically different in a disseminated human multiple myeloma cell line model using an NSG mouse reconstituted with in vitro amplified human primary T cells.

FIG. 30 shows the results of an in vivo efficacy study in a disseminated human multiple myeloma cell line model using an NSG mouse reconstituted with in vitro amplified human primary T cells. Reduction of tumor burden in CD38$_{VH1}$/CD28$_{sup}$×CD3$_{mid\_}$FALA trispecific antibody treatment groups was dose-dependent and statistically different. Thus the CD38 trispecific antibody conferred protection against disseminated human MM cell tumor growth in vivo.

Figure 31B:
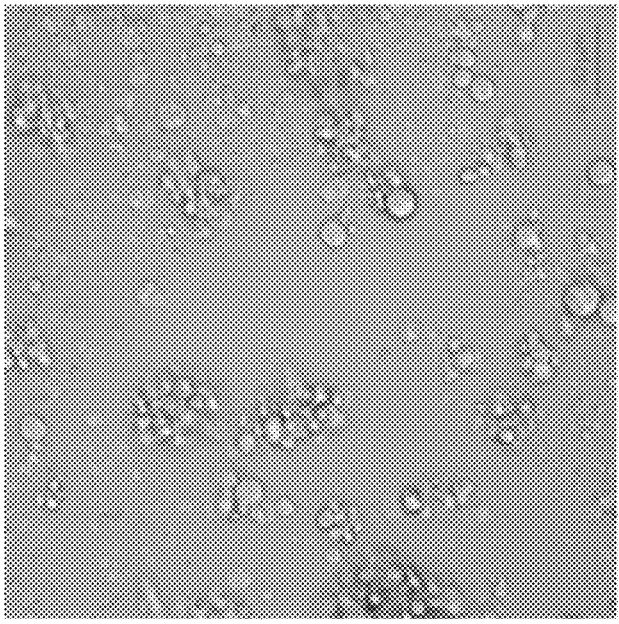
FIGS. 31A & 31B show vital microscopy analysis of myeloma cell cytolysis by the CD38 trispecific Ab in vitro in the presence of primary human T cells. Time lapse photography of microscopic images was performed using a negative control (triple KO trispecific.
Figure 31A:
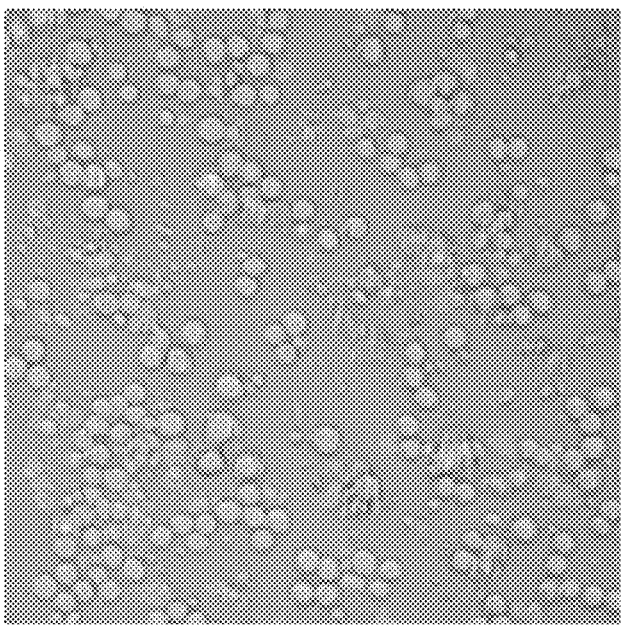

A microscopic study further demonstrated cancer cell killing by primary human T cells mediated by the trispecific antibody in vitro. FIGS. 31A & 31B show microscopic images demonstrating RPMI-8226 (human MM cells, labeled with CellTracker Deep Red dye) lysed by human PBMCs mediated by CD38$_{VH1}$/CD28$_{sup}$×CD3$_{mid\_}$FALA trispecific antibody. FIG. 31A shows control, while FIG. 31B shows lysis mediated by CD38$_{VH1}$/CD28$_{sup}$×CD3$_{mid\_}$FALA trispecific antibody. 10:1 E:T ratio was used with 24 hr. incubation. Exposure to the triple null mutant control Ab induced minimal changes in tumor cell viability over 24 hours (FIG. 31A). In contrast, incubation with the active CD38 trispecific Ab induced substantial clustering of T cells around tumor cells, leading to their nearly complete lysis (FIG. 31B). These data demonstrate that CD38/CD3×CD28 trispecific antibody mediated cytolysis of myeloma cells by T cells.

Example 10: Modification of Fc Receptor Binding Sites in the IgG4 Fc Region of Anti-CD38 Trispecific Binding Proteins Reduces Non-Specific Inflammation The Fc region of antibodies binds to cellular receptors on monocytes and NK cells that induce non-specific inflammation, which could predispose treatment subjects to cytokine release syndrome. The role of Fc receptors in stimulating cytokine release was examined by testing mutants that eliminated FcγI, FcγIIa,b and FcγIII binding. For this purpose, an IgG4 isotype that does not fix complement was used.

Binding in the surface plasmon resonance (SPR) assay using the BIAcore system (Pharmacia Biosensor; Piscataway, N.J.) was used to measure the affinity of the specified IgG4 Fc variants to indicated human Fc receptors immobilized on the chip. IgG4 Fc variants were used at 150 nM. The binding to human FcRn was carried using ELISA by coating the human FcRn antigen on the plate.

Figure 33:
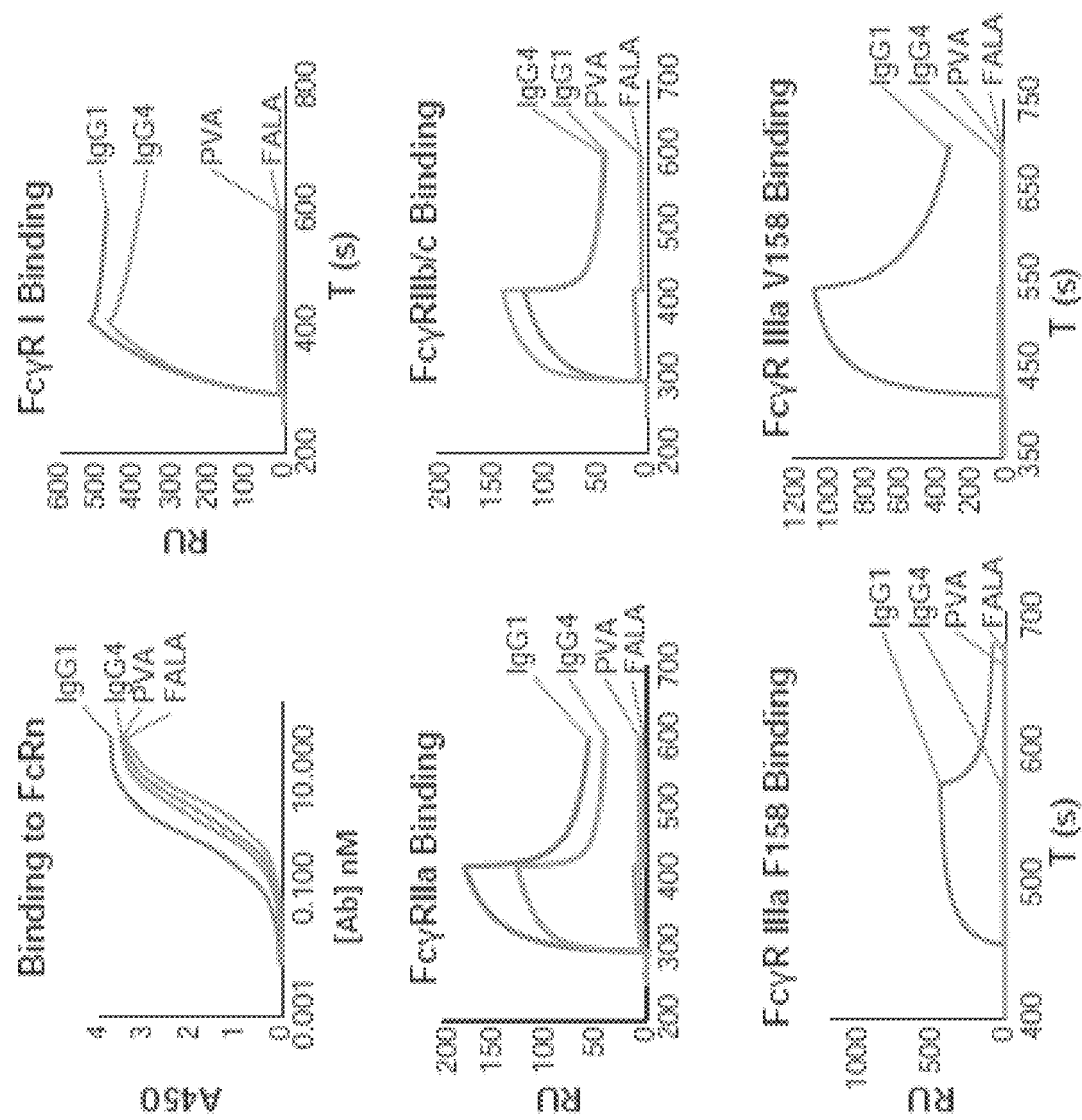
FIG. 33 shows the results of SPR assay s to measure the affinity of the specified IgG4 Fc variants to the indicated human Fc receptors.
Figure 34:
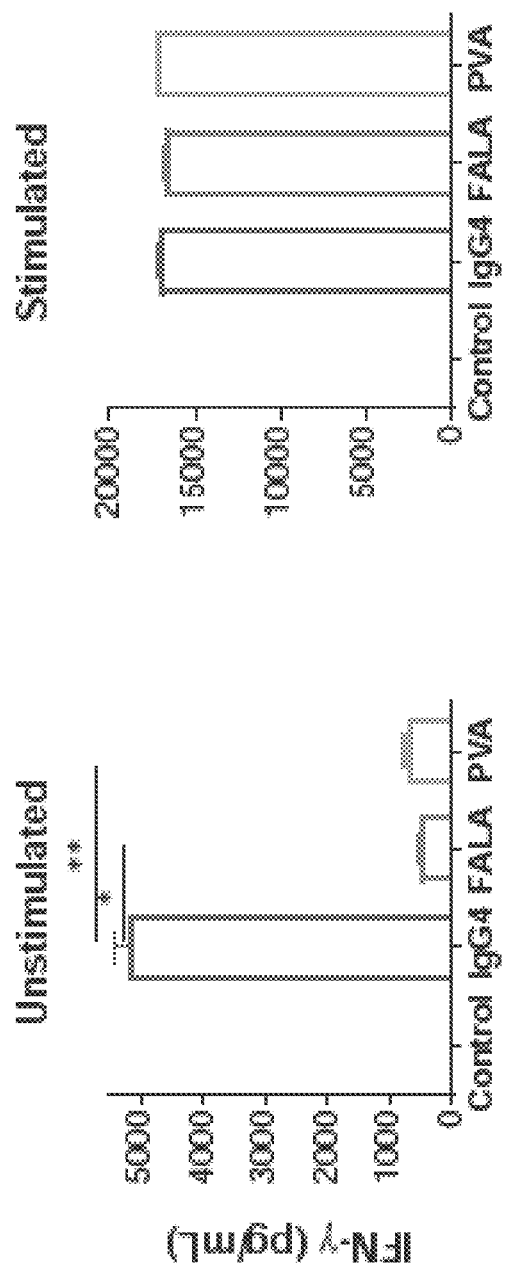
FIG. 34 shows that a CD38 trispecific binding protein with minimal FcR binding reduced non-specific cytokine release by human PBMCs in vitro. Different FcR inactivating mutations (as indicated) were analyzed for their proinflammatory effects in the human IgG4 isotype. Human PBMCs were incubated in media (Unstimulated) or in the presence of the myeloma cells, RPMI-8226 (Stimulated), and bars indicate supernatant IFN-γ levels measured by ELISA.
Figure 35:
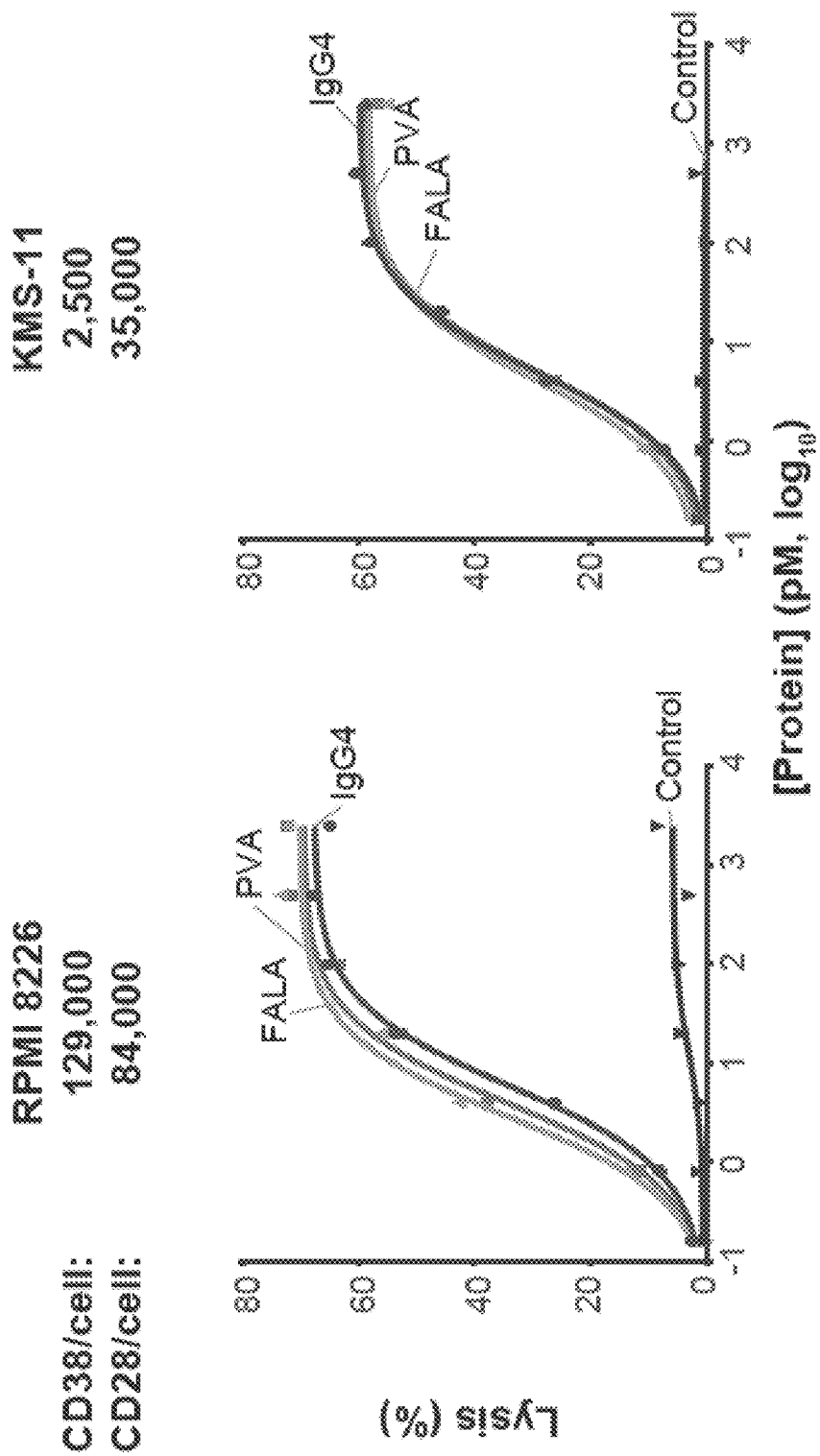
FIG. 35 shows that a CD38 trispecific binding protein with minimal FcR binding lysed human multiple myeloma cells with different CD38 expression levels. Cytolysis of myeloma cells with IgG4 or the indicated Fc mutations was assessed in vitro using human PBMCs with the indicated tumor targets.

A mutation ('FALA') in the Fc region that has been previously described (Alegre M L, Peterson L J, et al. *Transplantation* 57:1537-43(1994); see also Examples 7-9) eliminated binding to all Fc receptors (FIGS. 32 & 33). When tested for non-specific cytokine release, it abrogated IFN-γ release in unstimulated PBMC while allowing for maximal stimulation in the presence of tumor targets that expressed CD38 (FIG. 34, left vs. right, FALA). This Fc mutant retained its cytolytic activity on myeloma tumor targets comparable to Fc wild type control in cells expressing different levels of CD38 (FIG. 35). Similarly, another mutated IgG4 Fc region ("PVA," see FIG. 32) that eliminated binding to Fc receptors (FIG. 33) also abrogated IFN-γ release in unstimulated PBMC while allowing for maximal stimulation in the presence of tumor targets that expressed CD38 (FIG. 34, left vs, right PVA) and retained its cytolytic activity on myeloma tumor targets comparable to Fc wild type control in cells expressing different levels of CD38 (FIG. 35).

Example 11: Contribution of Anti-CD38 and Anti-CD28 to Cytolytic Activity of Trispecific Binding Proteins Trispecific Ab mutants for each binding site or combination of binding sites were generated and tested for their cytolytic activity against multiple myeloma cell lines with high (RPMI-8226) or low (KMS-11) CD38 and CD28 surface expression.

As shown above in FIGS. 28A & 28B, mutation of CD3 specific binding abrogated cytolysis, while anti-CD38 and CD28 null mutations showed markedly reduced killing, but some residual function was retained, indicating that both anti-CD38 and CD28 contributed to tumor cell killing.

Figure 36:
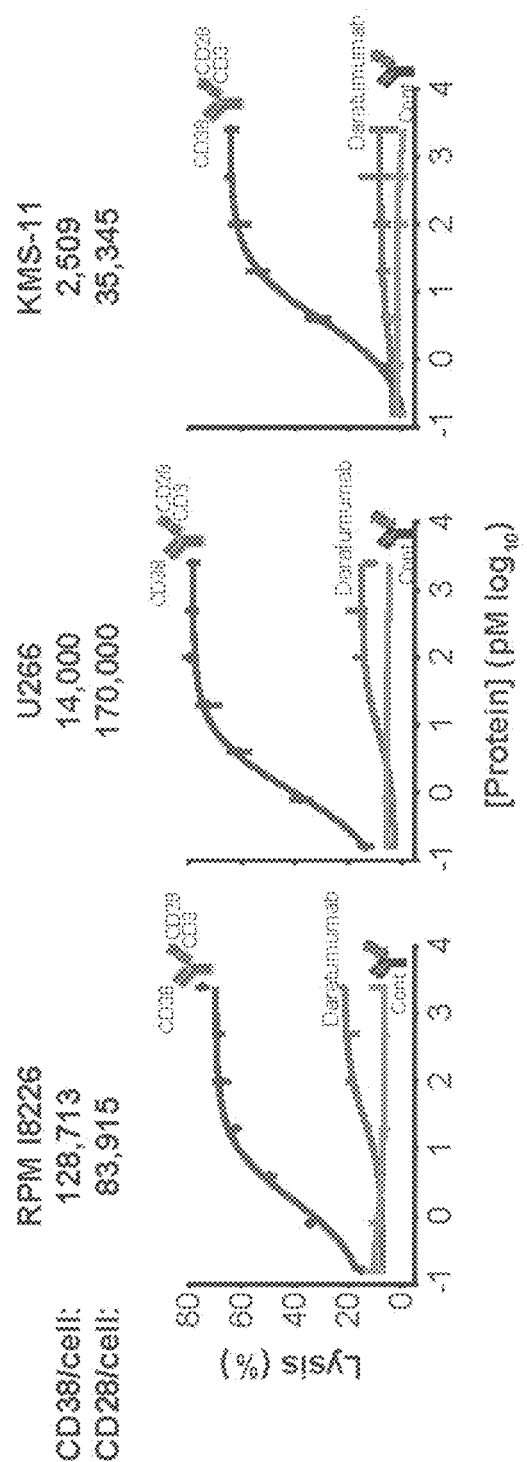
FIG. 36 shows a comparison of in vitro cytolytic activity of the trispecific anti-CD38/CD28/CD3 Ab and the anti-CD38 antibody daratumumab measured using human PBMC as effector cells against cell lines RPMI-8226, U266, and KMS-11 (E:T=10:1).

Compared to daratumumab (the α-CD38 monoclonal antibody approved for the treatment of multiple myeloma; see McKeage K. *Drugs*. 76:275-81(2016)), the trispecific Ab showed a remarkable 3-4 log higher killing potency in vitro against different CD38 expressing cell lines, including both CD38$_{high}$ and CD38$_{low}$ multiple myeloma cells (FIG. 36).

Example 12: CD38/CD3×CD28 Ab Stimulates Central Memory CD4 and CD8, Th1 and Antigen-Specific Responses To determine whether the CD38/CD3×CD28 trispecific Ab could enhance cellular immune function, the phenotype of expanded T cells in vitro was evaluated.

Materials and Methods

Figure 37A:
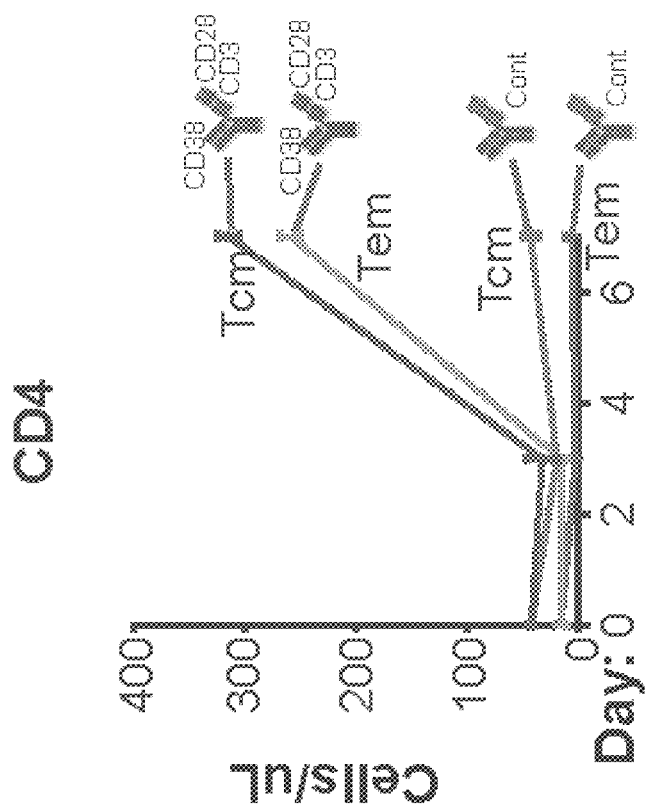
FIGS. 37A-37D show the characterization of in vitro T cell subset expansion in response to CD38/CD3×CD28. Evaluation of T cell subset expansion was performed by coating wells with 350 ng/well of the CD38 trispecific Ab in the absence of exogenous cytokines. T cell populations were measured at indicated time points. The triple mutant trispecific ab was used as negative control. Flow cytometry was used to determine central and effector memory CD4 T cells (FIG. 37A). T helper cells (FIG. 37B), central and effector memory CD8 T cells (FIG. 37C), and CMV pp65-specific CD8 cells (FIG. 37D) as described in Example 12. Analysis of CMV-specific pp65 effector cells was performed by pentamer staining of PBMCs from HLA-A2 CMV+ donors treated with the CD38 trispecific or the triple negative control.
Figure 37B:
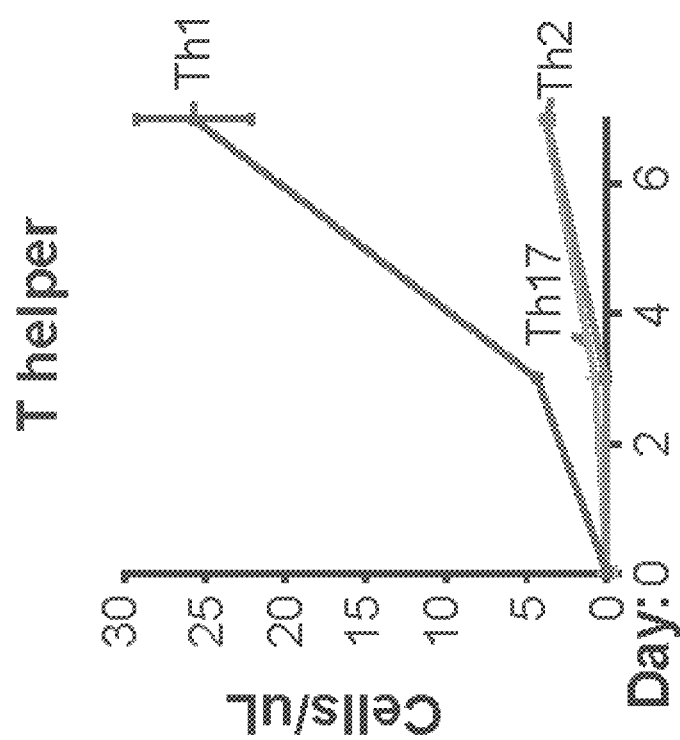
Figure 37C:
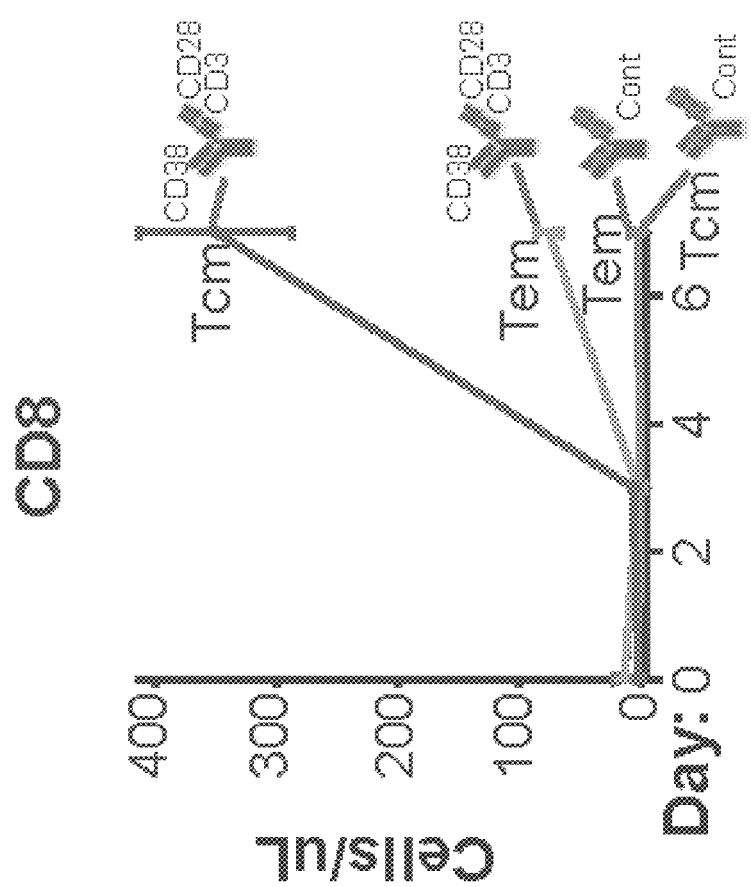
Figure 37D:
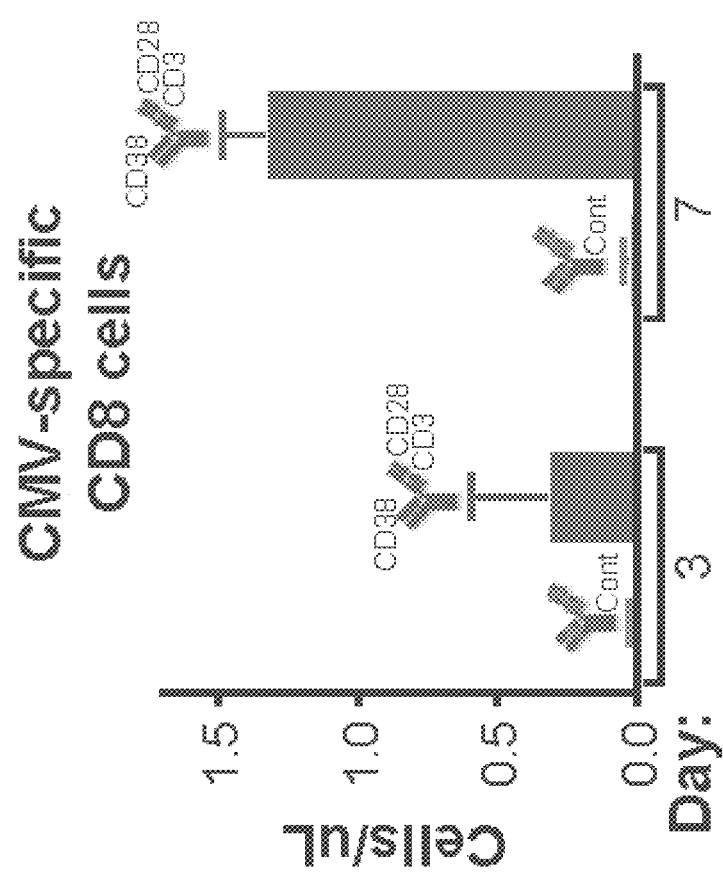

Peripheral blood mononuclear cells were isolated from blood of healthy human donors collected by Research Blood Components, LLC (Boston, Mass.). The PBMC were added to antibody-coated plates (350 ng/well) ($5\times10^5$ cells/mL), as previously described above, and incubated at 37° C. for 3 and 7 days. The cells were collected at specific time points and analyzed by flow cytometry for T cell subsets: naïve (CCR7+ CD45RO−), Tem (CCR7+ CD45RO+), Tem (CCR7− CD45RO+), Tregs (CD4+ Foxp3+CD25hi). Ceils were also treated with monensin (GolgiStop) (BD Biosciences, CA) for at least 6 hours before flow staining to determine intracellular cytokine expression. Th1 (CD4+ IFN-γ+), Th2 (CD4+ IL-4+), and Th17 (CD4+ IL-17+). CMV pp65-specific CD8+ T cells were detected using fluorescent-conjugated pentamer restricted to the PBMC donors' HLA (A*02:01/NLVPMVATV) (ProImmune, Oxford, UK). PBMC was obtained from HemaCare (Van Nuys, Calif.) from donors with known CMV positive populations and HLA types. PMBC from donors negative for the restricting HLA type was used as negative control. Staining was done as per manufacturer's protocol Results Human PBMCs were incubated for 7 days with the trispecific Ab or a triple mutant negative control in the absence of cytokines. Analysis of the CD4 subsets revealed the greatest proliferation in the central memory pool, with a smaller increase in effector memory cells (FIG. 37A). Analysis of the CD4 subset also revealed the greatest proliferation of Th1 cells (>6-fold) compared to Th2 or Th17 cells (FIG. 37B). In the CD8 subset, there was a >150-fold increase in the central memory CD8 subset by day 7, with a lesser increase in effector memory cells (FIG. 37C). Importantly, pre-existing antigen-specific CD8 responses to CMV, directed to the pp65 epitope in seropositive HLA-A2 donors using tetramer staining (Gratama J W, van Esser J W, et al. *Blood* 98: 1358-1364(2001)), increased >44-fold in the presence of the CD38 trispecific compared to negative control (FIG. 37D).

Taken together, these data indicate that the CD38 trispecific Ab stimulates Th1 function and protective CD8 memory T cell responses that are likely to enhance anti-tumor immunity in vivo.

Example 13: CD28 on Multiple Myeloma Cells Increases T Cell Recognition and Cytolysis Materials and Methods
Flow Cytometry Levels of CD28 and CD38 on the indicated tumor cell lines were determined by flow cytometry using QIFI kit (Dako, Denmark, cat. #K007811) as described (S4). Briefly, mouse anti-human CD38 (clone AT13/5, mouse IgG1, Santa Cruz Biotech, cat #59028) and anti-human CD28 (clone CD28.2, mouse IgG1, k, BioLegend, cat #3029123) were used as primary antibodies (at 10 ug/ml) for detecting surface CD38 and CD28 on cell lines using manufacturer's protocol. Surface densities were calculated using QIFI kit calibration standards and formulation provided by the kit.
Generation of CD28KO Human Multiple Myeloma Cell Lines Using CRISPR-Mediated Knockout For KMS-11 cell line, knockout of CD28 was performed using the CRISPR CD28 human knockout kit (Origene). The kit contains a donor vector with a GFP-puromycin functional cassette and two distinct Cas-9 vectors each with a different predesigned guide RNA (gRNA 1: TACCTGTTACTTGAATTGAA (SEQ ID NO:117) and gRNA 2: ATTTTTTGAGGTCTTCCAAT (SEQ ID NO:118) targeting CD28 Exon 1 and Intron 1, respectively). Cells were seeded in a 6-well plate at a density of $3 \cdot 10^5$ cell/well in RPMI1640 GlutaMAX Medium supplemented with 10% FBS and co-transfected after 24 hours with all three vectors using Lipofectamine™ 3000 Transfection Reagent (ThermoFisher Scientific) according to the manufacturer's instructions. Puromycin was added 48 hours after the transfection at a final concentration of 0.5 µg/mL. Transfection efficiency was 30% when using 6.25 µL/well of Lipofectamine™ 3000, 1.25 µg of each Cas-9/gRNA vector and 2.5 µg of the GFP-puromycin donor vector Knockout of CD28 on RPMI 8226 cell line was performed using the CD28 sgRNA CRISPR All-in-One Lentivirus set (Applied Biological Materials Inc.). It consists of a set of 3 lentiviral all-in-one vectors expressing the Cas9 gene, a Puromycin resistance gene and a different sgRNA (sgRNA 1: ATTGTCGTACGCTACAAGCA (SEQ ID NO:119) targeting CD28 exon 2 and sgRNA 2: CAAAAGGGCTTAGAAGGTCC (SEQ ID NO:120) and sgRNA 3: CTATAGCTTGCTAGTAACAG (SEQ ID NO:121) targeting CD28 exon 3). Cells were infected using a spinoculation protocol with $2 \cdot 10^5$ cells mixed with lentiviral particles (10 UI/cell), 8 µg/mL of polybrene and 1:100 ViralPlus Transduction Enhancer (Applied Biological Materials Inc.). The mix was pre-incubated for 20 minutes at room temperature, then centrifuged for 30 minutes at 32° C. and 800×g and seeded in a 12-well plate. Puromycin was added 48 hours after the infection at a final concentration of 0.25 µg/mL. Both cells lines were passaged for at least 5 times (or until cell viability becomes stable) before confirming CD28 knockdown at the protein level by flow cytometry (CD28 PE Clone 28.2 antibody-BioLegend). CD28 negative cells were then sorted on a Sony SH800S Cell Sorter and cultured in media supplemented with 0.25 µg/mL or 0.5 µg/mL puromycin, 100 Unit/mL penicillin and 100 µg/mL streptomycin (ThermoFisher Scientific). Cells w ere then cloned by limiting dilution and CD28 knockout validated by flow cytometry and by PCR and Sanger sequencing using the forward and reverse primers listed below.

TABLE R

List of forward and reverse primers.

| Cell line | Amplicon | Primers | Amplicon size | Comments |
|---|---|---|---|---|
| KMS-11 | CD28_GFP_left | F: CACAACCTGTCCCCATCCTATGAA (SEQ ID NO: 122) R: AAGCTGCCATCCAGATCGTTATCG (SEQ ID NO: 123) | 1475 bp | Validates the insertion of the GFP-puromycin casette (left side) |
| | CD28_PURO_right | F: CCAAATTAAGGGCCAGCTCATTCC (SEQ ID NO: 124) R: ACCTGTACATCCTTGGGCAAATCC (SEQ ID NO: 125) | 1233 bp | Validates the insertion of the GFP-puromycin casette (right side) |
| | CD28_Exon_1 | F: GTCAGGATGCCTTGTGGTTTGAGT (SEQ ID NO: 126) R: CAGAGCTTCCAGAGCCAATCTAC (SEQ ID NO: 127) | Variable; WT = 720 | Region surrounding CD28 exon1-intron 1 junction corresponding to the insertion site of the GFP-puromycin cassette and/or indels following CRISPR cleavage |

TABLE R-continued

List of forward and reverse primers.

| Cell line | Amplicon | Primers | Amplicon size | Comments |
|---|---|---|---|---|
| RPMI 8226 | Exon_2 | F: CCATGTACTGGCCTTCTGGGTGAAAWT (SEQ ID NO: 128) R: CCACTGACCACAACCCAGTTTT (SEQ ID NO: 129) | Variable; WT = 682 bp | Region surrounding CD28 exon 2 corresponding to CRISPR cleavage sites |
| | Exon_3 | F: AGGCCATTGGAAGTCACCGTTT (SEQ ID NO: 130) R: GCCAACATTGTCCATTGGCTTCAG (SEQ ID NO: 131) | Variable; WT = 816 bp | Region surrounding CD28 exon 3 corresponding to CRISPR cleavage sites |

Results

CD28 was incorporated into the trispecific Ab to improve T cell proliferation and survival; however, when cell surface markers were evaluated on multiple myeloma cells, a majority of cell tines (>95%) were found to express the CD28 glycoprotein (Table S).

TABLE S

Cell surface expression of CD28 and CD38 on human multiple myeloma cell lines

| Cell line | CD28 | CD38 |
|---|---|---|
| JJN3 | 1,040 | 50 |
| KMS-11 (p17) | 35,345 | 2,845 |
| U266 | 170,525 | 13,825 |
| L-363 | 9,145 | 17,500 |
| MM.1S | 56,560 | 44,535 |
| MM.1R | 66,220 | 49,160 |
| KMS-12BM | 0 | 62,845 |
| RPMI 8226 | 83,915 | 136,255 |
| NCI-H929 | 22,065 | 153,620 |
| LP-1 | 7,420 | 372,835 |
| U266-CD38++ | 126,465 | 633,805 |
| JJN3-CD38 | 0 | 714,805 |
| MOLP-8 | 245 | 835,030 |
| NCI-H929-CD38++ | 22,935 | 981,310 |
| RPMI 8226-CD38++ | 86,320 | 1,419,120 |

It has been reported that CD28 expression, while absent on normal plasma cells (Almeida J, et al. *British J. of Haematol.* 107: 121-131(1999)), can be detected on primary myeloma plasma cells of in approximately one third of newly diagnosed patients (Mateo G, et al. *Clin. Cancer Res.* 11:3661-3667(2005)). Furthermore, it increases in frequency during myeloma progression and correlates with poor prognosis and aggressive features of myeloma (Robillard N, Jego G, et al. *Clin Cancer Res.* 4:1521-6(1998); Nair J R, Carlson L M, et al. *J Immunol.* 187:1243-53(2011)).

To determine whether CD28 expression on target cells could improve T cell recognition and lysis, the activity of wild type vs CD28 null trispecific Abs on three independent myeloma lines with varying degrees of CD38 and CD28 expression was compared. As noted above in Example 9 and shown in FIGS. 29A-29C, cytolysis was observed on all three lines, regardless of CD28 expression level by the CD38 trispecific Ab; however, against all cell lines, cytolytic activity of the CD28 null trispecific Ab was reduced by 30-100 fold, with the most substantial decrease in the KMS-11 cell line that showed lowest CD38 expression (cf. WT vs. ΔCD28, FIG. 29C vs. FIG. 29A or FIG. 29B).

Figure 38:
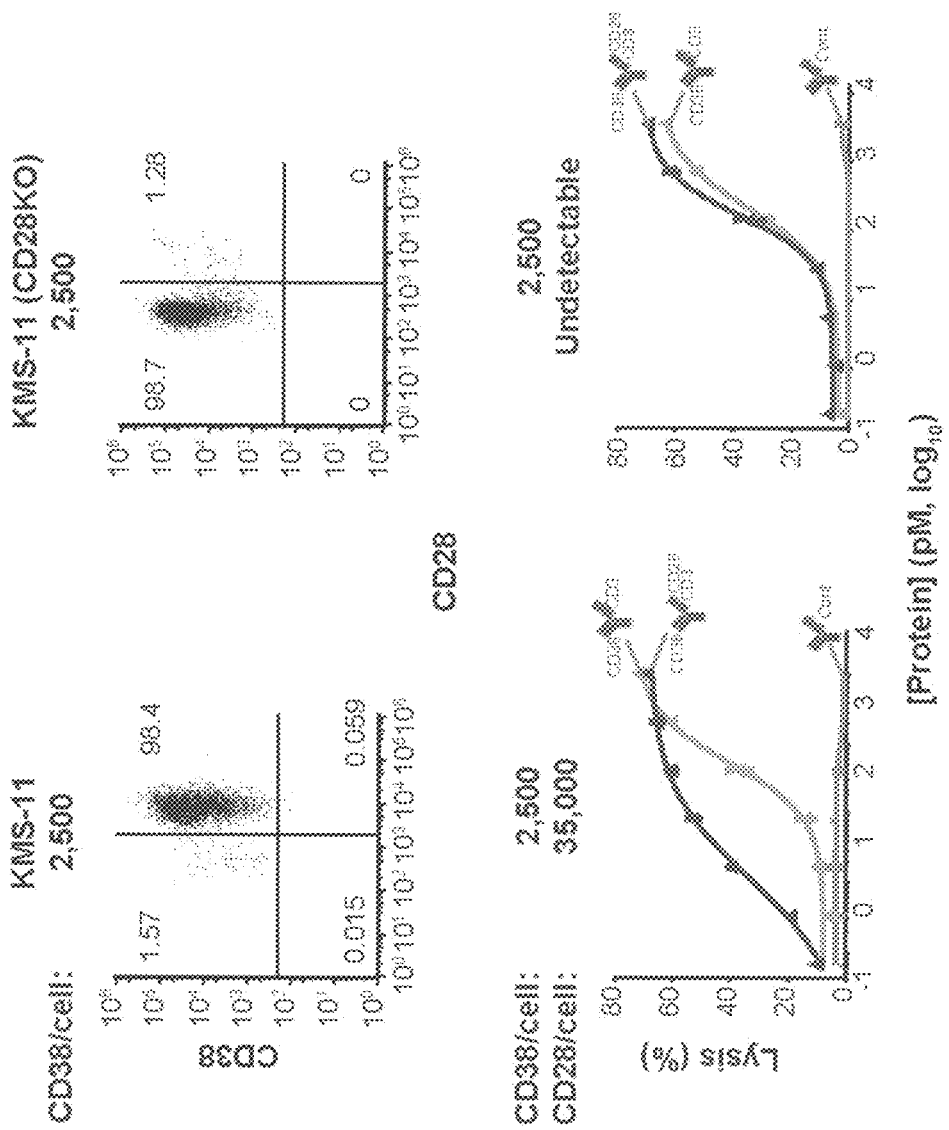
FIG. 38 shows the contribution of CD28 expression on target cells to susceptibility to cytolysis by CD38/CD3×CD28. CD28 was knocked out in KMS-11 cells using CRISPR/Cas 9 gene targeting and used as cytolytic targets in vitro. Compared to parental KMS-11, CD38 expression was preserved while CD28 was eliminated, as demonstrated by flow cytometry (upper panel, KMS-11 vs. KMS-11 (CD28KO). Cytolysis of the CD28 KO cells was examined with the WT or CD28 null trispecific (lower panel; trispecific vs. trispecific (CD28KO)).

The contribution of CD28 to tumor cell recognition and lysis was further confirmed using CRISPR-mediated knock-out of CD28 on the myeloma target cell. CD28 expression was undetectable on CD28KO KMS-11 cells compared to the parental line (FIG. 38, upper panel, right vs. left). The sensitivity of the CD28KO KMS-11 cells to T cell cytolysis was concomitantly reduced 10-100 fold (FIG. 38, lower panel, left). Consistent with this effect, no difference in cytolysis was seen with the CD38 trispecific compared to the CD28 null mutant trispecific on the CD38 KO target cells (FIG. 38, lower panel, right).

Example 14: Cytolysis of the CD38 Trispecific Ab Against $CD38^+$ Hematological Cancer Cell Lines The previous Examples demonstrate trispecific anti-CD38/CD3/CD28 antibodies that promote cytolysis of multiple myeloma cells. The ability of these antibodies to promote cytolysis of other cancer cell lines was tested.

Figure 39:
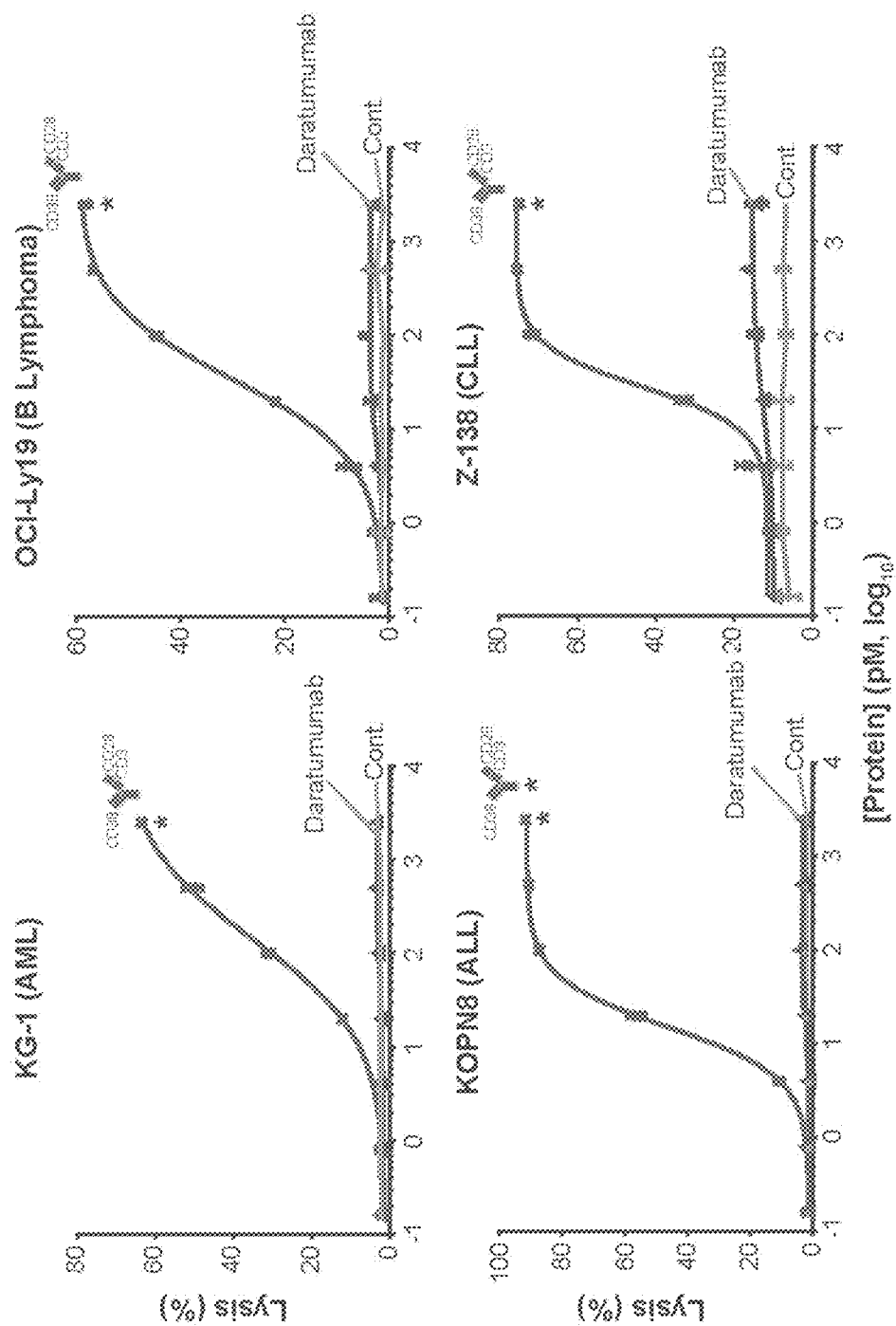
FIG. 39 shows the cytolytic activity of the CD38/CD28×CD3 trispecific FALA mutant Ab against indicated CD38+ CD28− lines, including acute myelocytic leukemia (AML (KG-1)), a B cell lymphoma (OCI-Ly19), acute T lymphocytic leukemia (ALL (KOPN8)), and chronic lymphocytic lymphoma (CLL(Z-138)).

As shown in FIG. 39, CD38/CD28×CD3 trispecific FALA mutant Ab had cytolytic activity targeting $CD38^+CD28^+$ lines, including acute myelocytic leukemia (AML (KG-1)), a B cell lymphoma (OCI-Ly19), acute T lymphocytic leukemia (ALL (KOPN8)), and chronic lymphocytic lymphoma (CLL(Z-138)). This demonstrates that trispecific anti-CD38/CD3/CD28 antibodies have activity against other C038+ hematological cancer cell lines, including those that are CD28−.

Example 15: In Vitro Activation of Human PBMC by α-CD28 Superagonist Requires Bivalency of the Antibody In vitro activation of human PBMC by TGN1412 (TON), single binding arm TON 1412(TGNslg) and single binding arm anti-$CD28_{sup}$($CD28_{sup}$slg) was performed as described (Findlay L, Eastwood D, et al. *J Immunol Methods* 352: 1-12 (2010)). $10^5$ human PBMCs were seeded onto polypropylene 96-well plates dry coated with indicated antibodies (1 ug/well) for 24 hours as previously described. Cytokines such as IFN-γ, TNF-α, and IL2 in the supernatant were measured by Luminex as described in Example 8.

Figure 40:
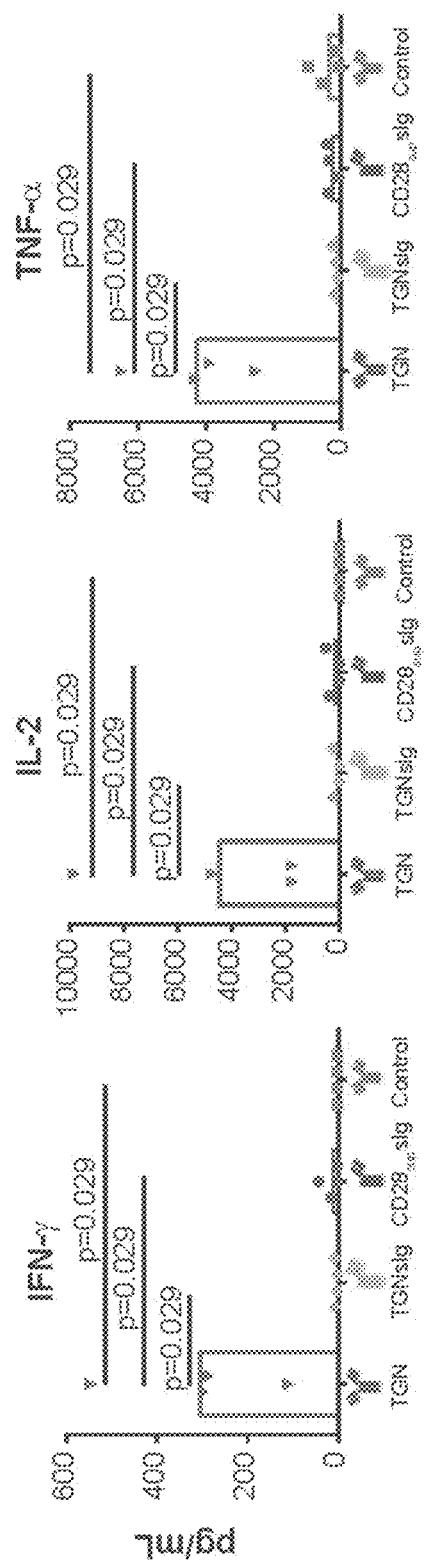
FIG. 40 shows that in vitro activation of human PBMC by α-CD28 superagonist requires bi valency of the antibody.

The inclusion of a single specificity of the CD28 superagonist also reduced non-specific cytokine release seen with the CD28 superagonist mAb (FIG. 40) previously associated with its adverse effects as a native IgG in humans (Suntharalingam G, Perry M R, et al. *N Eng J Med* 355:1018-1028 (2006)). Instead, co-stimulation by the trispecific Ab increased the potency and survival of T cells that lyse and protect against tumors. More interestingly, the CD38 trispecific Ab preferentially amplify Th1 and Tcm cell populations in vitro, exhibiting an important feature that differs from α-CD3 agonist or α-CD28 superagonist monoclonal Abs used to propagate Treg to induce tolerance (Penaranda Cl, Tang Q, Bluestone J A. *J Immunol.* 187:2015-22. (2011); Tabares P, Berr S, et al. *Eur J Immunol.* 44:1225-36(2014)).

Taken together, the data presented in Examples 1-15 demonstrate trispecific anti-CD38/CD3/CD28 antibodies that stimulate potent anti-tumor immunity by engaging two T cell signaling receptors and enhancing target cell recognition. CD3 and CD28 binding triggered T cell receptor signaling that upregulated Bcl-xl and inhibited T cell apoptosis, increasing T cell effector function and survival. The third arm of the trispecific Ab interacted with CD38, which is highly expressed on multiple myeloma cells. Coincidentally, CD28 is also expressed on cells from most myelomas, therefore the trispecific Ab improved targeting at the same time it enhanced T cell activation and cytolysis. The optimized trispecific antibody lysed myeloma cells>1000-fold more effectively than daratumumab, an anti-CD38 mAb therapeutic, and showed potent in vivo anti-tumor activity in a humanized mouse model.

While the disclosure includes various embodiments, it is understood that variations and modifications will occur to those skilled in the art, Therefore, it is intended that tire appended claims cover all such equivalent variations that come within the scope of die disclosure. In addition, the section headings used herein are for organizational purposes only and are not to be construed as limiting the subject matter described.

Each embodiment herein described may be combined with any other embodiment or embodiments unless clearly indicated to the contrary. In particular, any feature or embodiment indicated as being preferred or advantageous may be combined with any other feature or features or embodiment or embodiments indicated as being preferred or advantageous, unless clearly indicated to the contrary.

All references cited in this application are expressly incorporated by reference herein.

What is claimed is:

1. A monospecific binding protein that binds a CD38 polypeptide, wherein the monospecific binding protein comprises:
    (a) an antibody heavy chain that comprises an antibody heavy chain variable (VH) domain comprising a CDR-H1 sequence comprising the amino acid sequence of GYTFTSYA (SEQ ID NO:37), a CDR-H2 sequence comprising the amino acid sequence of IYPGQGGT (SEQ ID NO:38), and a CDR-H3 sequence comprising the amino acid sequence of ARTGGLRRAYFTY (SEQ ID NO:33);
    and
    (b) an antibody light chain that comprises an antibody light chain variable (VL) domain comprising a CDR-L1 sequence comprising the amino acid sequence of QSVSSYGQGF (SEQ ID NO:39), a CDR-L2 sequence comprising the amino acid sequence of GAS (SEQ ID NO:40), and a CDR-L3 sequence comprising the amino acid sequence of QQNKEDPWT (SEQ ID NO:36).

2. The monospecific binding protein of claim 1, wherein the VH domain comprises the sequence, from N-terminus to C-terminus, FR1-CDR-H1-FR2-CDR-H2-FR3-CDR-H3-FR4; wherein FR1 comprises the sequence QVQLVQSGAEVVKPGASVKVSCKAS (SEQ ID NO:86), QVQLVQSGAEVVKSGASVKVSCKAS (SEQ ID NO:87), or QVQLVQSGAEVVKPGASVKMSCKAS (SEQ ID NO:88); wherein FR2 comprises the sequence MHWVKEAPGQRLEWIGY (SEQ ID NO:90) or MHWVKEAPGQGLEWIGY (SEQ ID NO:91); wherein FR3 comprises the sequence NYNQKFQGRATLTADTSASTAYMELSSLRSEDTAVYFC (SEQ ID NO:93) or NYNQKFQGRATLTADTSASTAYMEISSLRSEDTAVYFC (SEQ ID NO:94); and wherein FR4 comprises the sequence WGQGTLVTVSS (SEQ ID NO:96).

3. The monospecific binding protein of claim 1, wherein the VH domain comprises the amino acid sequence of SEQ ID NO:13, and the VL domain comprises the amino acid sequence of SEQ ID NO:14.

4. The monospecific binding protein of claim 3, wherein the antibody heavy chain comprises the amino acid sequence of SEQ ID NO:15, and the antibody light chain comprises the amino acid sequence of SEQ ID NO:16.

5. The monospecific binding protein of claim 1, wherein the monospecific binding protein cross-reacts with an extracellular domain of a human CD38 polypeptide and an extracellular domain of a cynomolgus monkey CD38 polypeptide.

6. The monospecific binding protein of claim 5, wherein the monospecific binding protein binds a human CD38 polypeptide comprising the amino acid sequence of SEQ ID NO:1.

7. The monospecific binding protein of claim 6, wherein the monospecific binding protein binds the human CD38 polypeptide comprising the amino acid sequence of SEQ ID NO:1 with an equilibrium dissociation constant ($K_D$) of 2.1 nM or less.

8. The monospecific binding protein of claim 5, wherein the monospecific binding protein binds a human isoform E CD38 polypeptide comprising the amino acid sequence of SEQ ID NO:105.

9. The monospecific binding protein of claim 5, wherein the monospecific binding protein binds a cynomolgus monkey CD38 polypeptide comprising the amino acid sequence of SEQ ID NO:30.

10. The monospecific binding protein of claim 9, wherein the monospecific binding protein binds the cynomolgus monkey CD38 polypeptide comprising the amino acid sequence of SEQ ID NO:30 with an equilibrium dissociation constant ($K_D$) of 1.3 nM or less.

11. The monospecific binding protein of claim 1, wherein the binding protein is a chimeric or humanized antibody.

12. The monospecific binding protein of claim 1, wherein the binding protein is a monoclonal antibody.

13. The monospecific binding protein of claim 1, wherein the binding protein comprises two full-length antibody heavy chains comprising an Fc region.

14. The monospecific binding protein of claim 13, wherein the Fc region is a human Fc region, and wherein the binding protein induces antibody-dependent cellular cytotoxicity of a cell expressing CD38 on its cell surface.

15. The monospecific binding protein of claim 13, wherein the Fc region is a human IgG1 Fc region.

16. A polynucleotide encoding the monospecific binding protein of claim 1.

17. A vector comprising the polynucleotide of claim 16.

18. A host cell comprising the polynucleotide of claim 16.

19. A method of producing a monospecific binding protein, the method comprising culturing the host cell of claim 18 such that the monospecific binding protein is produced.

20. The method of claim 19, further comprising recovering the monospecific binding protein from the host cell.

21. A pharmaceutical composition comprising the monospecific binding protein of claim 1 and a pharmaceutically acceptable carrier.

22. The monospecific binding protein of claim 15, wherein the human IgG1 Fc region comprises one or more residues involved in Fc receptor binding or antibody-dependent cellular cytotoxicity (ADCC) that have been modified from a native human IgG1 Fc sequence.

23. A monospecific, monoclonal antibody that binds a CD38 polypeptide, wherein the antibody comprises a heavy chain comprising the amino acid sequence of SEQ ID NO:15 and a light chain comprising the amino acid sequence of SEQ ID NO:16.

24. A polynucleotide encoding the antibody of claim 23.

25. A vector comprising the polynucleotide of claim 24.

26. A host cell comprising the polynucleotide of claim 24.

27. A method of producing an antibody, the method comprising culturing the host cell of claim 26 such that the antibody is produced.

28. The method of claim 27, further comprising recovering the antibody from the host cell.

29. A pharmaceutical composition comprising the antibody of claim 23 and a pharmaceutically acceptable carrier.

* * * * *

SEQUENCE LISTING

```
<160> NUMBER OF SEQ ID NOS: 132

<210> SEQ ID NO 1
<211> LENGTH: 256
<212> TYPE: PRT
<213> ORGANISM: Homo sapiens
<220> FEATURE:
<223> OTHER INFORMATION: CD38 extracellular domain (isoform A)

<400> SEQUENCE: 1

Arg Trp Arg Gln Gln Trp Ser Gly Pro Gly Thr Thr Lys Arg Phe Pro
1               5                   10                  15

Glu Thr Val Leu Ala Arg Cys Val Lys Tyr Thr Glu Ile His Pro Glu
            20                  25                  30

Met Arg His Val Asp Cys Gln Ser Val Trp Asp Ala Phe Lys Gly Ala
        35                  40                  45

Phe Ile Ser Lys His Pro Cys Asn Ile Thr Glu Glu Asp Tyr Gln Pro
    50                  55                  60

Leu Met Lys Leu Gly Thr Gln Thr Val Pro Cys Asn Lys Ile Leu Leu
65                  70                  75                  80

Trp Ser Arg Ile Lys Asp Leu Ala His Gln Phe Thr Gln Val Gln Arg
                85                  90                  95

Asp Met Phe Thr Leu Glu Asp Thr Leu Leu Gly Tyr Leu Ala Asp Asp
            100                 105                 110

Leu Thr Trp Cys Gly Glu Phe Asn Thr Ser Lys Ile Asn Tyr Gln Ser
        115                 120                 125

Cys Pro Asp Trp Arg Lys Asp Cys Ser Asn Asn Pro Val Ser Val Phe
    130                 135                 140

Trp Lys Thr Val Ser Arg Arg Phe Ala Glu Ala Ala Cys Asp Val Val
145                 150                 155                 160

His Val Met Leu Asn Gly Ser Arg Ser Lys Ile Phe Asp Lys Asn Ser
                165                 170                 175

Thr Phe Gly Ser Val Glu Val His Asn Leu Gln Pro Glu Lys Val Gln
            180                 185                 190

Thr Leu Glu Ala Trp Val Ile His Gly Gly Arg Glu Asp Ser Arg Asp
        195                 200                 205

Leu Cys Gln Asp Pro Thr Ile Lys Glu Leu Glu Ser Ile Ile Ser Lys
    210                 215                 220
```

```
Arg Asn Ile Gln Phe Ser Cys Lys Asn Ile Tyr Arg Pro Asp Lys Phe
225                 230                 235                 240

Leu Gln Cys Val Lys Asn Pro Glu Asp Ser Ser Cys Thr Ser Glu Ile
                245                 250                 255

<210> SEQ ID NO 2
<211> LENGTH: 265
<212> TYPE: PRT
<213> ORGANISM: Homo sapiens
<220> FEATURE:
<223> OTHER INFORMATION: CD38 extracellular domain containing
      a histag at the C-terminal

<400> SEQUENCE: 2

Arg Trp Arg Gln Gln Trp Ser Gly Pro Gly Thr Thr Lys Arg Phe Pro
1               5                   10                  15

Glu Thr Val Leu Ala Arg Cys Val Lys Tyr Thr Glu Ile His Pro Glu
                20                  25                  30

Met Arg His Val Asp Cys Gln Ser Val Trp Asp Ala Phe Lys Gly Ala
            35                  40                  45

Phe Ile Ser Lys His Pro Cys Asn Ile Thr Glu Glu Asp Tyr Gln Pro
50                  55                  60

Leu Met Lys Leu Gly Thr Gln Thr Val Pro Cys Asn Lys Ile Leu Leu
65                  70                  75                  80

Trp Ser Arg Ile Lys Asp Leu Ala His Gln Phe Thr Gln Val Gln Arg
                85                  90                  95

Asp Met Phe Thr Leu Glu Asp Thr Leu Leu Gly Tyr Leu Ala Asp Asp
            100                 105                 110

Leu Thr Trp Cys Gly Glu Phe Asn Thr Ser Lys Ile Asn Tyr Gln Ser
        115                 120                 125

Cys Pro Asp Trp Arg Lys Asp Cys Ser Asn Asn Pro Val Ser Val Phe
130                 135                 140

Trp Lys Thr Val Ser Arg Arg Phe Ala Glu Ala Cys Asp Val Val
145                 150                 155                 160

His Val Met Leu Asn Gly Ser Arg Ser Lys Ile Phe Asp Lys Asn Ser
                165                 170                 175

Thr Phe Gly Ser Val Glu Val His Asn Leu Gln Pro Glu Lys Val Gln
            180                 185                 190

Thr Leu Glu Ala Trp Val Ile His Gly Gly Arg Glu Asp Ser Arg Asp
        195                 200                 205

Leu Cys Gln Asp Pro Thr Ile Lys Glu Leu Glu Ser Ile Ile Ser Lys
    210                 215                 220

Arg Asn Ile Gln Phe Ser Cys Lys Asn Ile Tyr Arg Pro Asp Lys Phe
225                 230                 235                 240

Leu Gln Cys Val Lys Asn Pro Glu Asp Ser Ser Cys Thr Ser Glu Ile
                245                 250                 255

Ser Ala Ser His His His His His
            260                 265

<210> SEQ ID NO 3
<211> LENGTH: 485
<212> TYPE: PRT
<213> ORGANISM: Homo sapiens
<220> FEATURE:
<223> OTHER INFORMATION: CD38 extracellular domain fused to
      human Fc domain at the C-terminal

<400> SEQUENCE: 3
```

```
Arg Trp Arg Gln Gln Trp Ser Gly Pro Gly Thr Thr Lys Arg Phe Pro
1               5                   10                  15

Glu Thr Val Leu Ala Arg Cys Val Lys Tyr Thr Glu Ile His Pro Glu
            20                  25                  30

Met Arg His Val Asp Cys Gln Ser Val Trp Asp Ala Phe Lys Gly Ala
        35                  40                  45

Phe Ile Ser Lys His Pro Cys Asn Ile Thr Glu Glu Asp Tyr Gln Pro
    50                  55                  60

Leu Met Lys Leu Gly Thr Gln Thr Val Pro Cys Asn Lys Ile Leu Leu
65                  70                  75                  80

Trp Ser Arg Ile Lys Asp Leu Ala His Gln Phe Thr Gln Val Gln Arg
                85                  90                  95

Asp Met Phe Thr Leu Glu Asp Thr Leu Leu Gly Tyr Leu Ala Asp Asp
            100                 105                 110

Leu Thr Trp Cys Gly Glu Phe Asn Thr Ser Lys Ile Asn Tyr Gln Ser
        115                 120                 125

Cys Pro Asp Trp Arg Lys Asp Cys Ser Asn Asn Pro Val Ser Val Phe
    130                 135                 140

Trp Lys Thr Val Ser Arg Arg Phe Ala Glu Ala Ala Cys Asp Val Val
145                 150                 155                 160

His Val Met Leu Asn Gly Ser Arg Ser Lys Ile Phe Asp Lys Asn Ser
                165                 170                 175

Thr Phe Gly Ser Val Glu Val His Asn Leu Gln Pro Glu Lys Val Gln
            180                 185                 190

Thr Leu Glu Ala Trp Val Ile His Gly Gly Arg Glu Asp Ser Arg Asp
        195                 200                 205

Leu Cys Gln Asp Pro Thr Ile Lys Glu Leu Glu Ser Ile Ile Ser Lys
    210                 215                 220

Arg Asn Ile Gln Phe Ser Cys Lys Asn Ile Tyr Arg Pro Asp Lys Phe
225                 230                 235                 240

Leu Gln Cys Val Lys Asn Pro Glu Asp Ser Ser Cys Thr Ser Glu Ile
                245                 250                 255

Gly Ala Leu Asp Lys Thr His Thr Cys Pro Pro Cys Pro Ala Pro Glu
            260                 265                 270

Leu Leu Gly Gly Pro Ser Val Phe Leu Phe Pro Pro Lys Pro Lys Asp
        275                 280                 285

Thr Leu Met Ile Ser Arg Thr Pro Glu Val Thr Cys Val Val Val Asp
    290                 295                 300

Val Ser His Glu Asp Pro Glu Val Lys Phe Asn Trp Tyr Val Asp Gly
305                 310                 315                 320

Val Glu Val His Asn Ala Lys Thr Lys Pro Arg Glu Glu Gln Tyr Asn
                325                 330                 335

Ser Thr Tyr Arg Val Val Ser Val Leu Thr Val Leu His Gln Asp Trp
            340                 345                 350

Leu Asn Gly Lys Glu Tyr Lys Cys Lys Val Ser Asn Lys Ala Leu Pro
        355                 360                 365

Ala Pro Ile Glu Lys Thr Ile Ser Lys Ala Lys Gly Gln Pro Arg Glu
    370                 375                 380

Pro Gln Val Tyr Thr Leu Pro Pro Ser Arg Asp Glu Leu Thr Lys Asn
385                 390                 395                 400

Gln Val Ser Leu Thr Cys Leu Val Lys Gly Phe Tyr Pro Ser Asp Ile
                405                 410                 415
```

```
Ala Val Glu Trp Glu Ser Asn Gly Gln Pro Glu Asn Asn Tyr Lys Thr
            420                 425                 430

Thr Pro Pro Val Leu Asp Ser Asp Gly Ser Phe Phe Leu Tyr Ser Lys
            435                 440                 445

Leu Thr Val Asp Lys Ser Arg Trp Gln Gln Gly Asn Val Phe Ser Cys
450                 455                 460

Ser Val Met His Glu Ala Leu His Asn His Tyr Thr Gln Lys Ser Leu
465                 470                 475                 480

Ser Leu Ser Pro Gly
            485

<210> SEQ ID NO 4
<211> LENGTH: 265
<212> TYPE: PRT
<213> ORGANISM: Macaca fascicularis
<220> FEATURE:
<223> OTHER INFORMATION: CD38 extracellular domain containing
      a histag at the C-terminal

<400> SEQUENCE: 4

Arg Trp Arg Gln Gln Trp Ser Gly Ser Gly Thr Thr Ser Arg Phe Pro
1               5                   10                  15

Glu Thr Val Leu Ala Arg Cys Val Lys Tyr Thr Glu Val His Pro Glu
            20                  25                  30

Met Arg His Val Asp Cys Gln Ser Val Trp Asp Ala Phe Lys Gly Ala
        35                  40                  45

Phe Ile Ser Lys Tyr Pro Cys Asn Ile Thr Glu Glu Asp Tyr Gln Pro
    50                  55                  60

Leu Val Lys Leu Gly Thr Gln Thr Val Pro Cys Asn Lys Thr Leu Leu
65                  70                  75                  80

Trp Ser Arg Ile Lys Asp Leu Ala His Gln Phe Thr Gln Val Gln Arg
                85                  90                  95

Asp Met Phe Thr Leu Glu Asp Met Leu Leu Gly Tyr Leu Ala Asp Asp
            100                 105                 110

Leu Thr Trp Cys Gly Glu Phe Asn Thr Phe Glu Ile Asn Tyr Gln Ser
        115                 120                 125

Cys Pro Asp Trp Arg Lys Asp Cys Ser Asn Asn Pro Val Ser Val Phe
    130                 135                 140

Trp Lys Thr Val Ser Arg Arg Phe Ala Glu Thr Ala Cys Gly Val Val
145                 150                 155                 160

His Val Met Leu Asn Gly Ser Arg Ser Lys Ile Phe Asp Lys Asn Ser
                165                 170                 175

Thr Phe Gly Ser Val Glu Val His Asn Leu Gln Pro Glu Lys Val Gln
            180                 185                 190

Ala Leu Glu Ala Trp Val Ile His Gly Gly Arg Glu Asp Ser Arg Asp
        195                 200                 205

Leu Cys Gln Asp Pro Thr Ile Lys Glu Leu Glu Ser Ile Ile Ser Lys
    210                 215                 220

Arg Asn Ile Arg Phe Phe Cys Lys Asn Ile Tyr Arg Pro Asp Lys Phe
225                 230                 235                 240

Leu Gln Cys Val Lys Asn Pro Glu Asp Ser Ser Cys Leu Ser Gly Ile
                245                 250                 255

Ser Ala Ser His His His His His
            260                 265

<210> SEQ ID NO 5
```

```
<211> LENGTH: 120
<212> TYPE: PRT
<213> ORGANISM: Artificial Sequence
<220> FEATURE:
<223> OTHER INFORMATION: VH amino sequence of the mAb1

<400> SEQUENCE: 5

Gln Val Gln Leu Gln Gln Ser Gly Ala Glu Leu Val Arg Ser Gly Ala
1               5                   10                  15

Ser Val Lys Met Ser Cys Lys Ala Ser Gly Tyr Thr Phe Thr Ser Phe
            20                  25                  30

Asn Met His Trp Val Lys Glu Thr Pro Gly Gln Gly Leu Glu Trp Ile
        35                  40                  45

Gly Tyr Ile Tyr Pro Gly Asn Gly Gly Thr Asn Tyr Asn Gln Lys Phe
    50                  55                  60

Lys Gly Lys Ala Thr Leu Thr Ala Asp Thr Ser Ser Thr Ala Tyr
65                  70                  75                  80

Met Gln Ile Ser Ser Leu Thr Ser Glu Asp Ser Ala Val Tyr Phe Cys
                85                  90                  95

Ala Arg Thr Gly Gly Leu Arg Arg Ala Tyr Phe Thr Tyr Trp Gly Gln
            100                 105                 110

Gly Thr Leu Val Thr Val Ser Ser
        115                 120

<210> SEQ ID NO 6
<211> LENGTH: 111
<212> TYPE: PRT
<213> ORGANISM: Artificial Sequence
<220> FEATURE:
<223> OTHER INFORMATION: VL amino sequence of the mAb1

<400> SEQUENCE: 6

Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Ser Tyr
            20                  25                  30

Gly Asn Gly Phe Met His Trp Tyr Gln Gln Lys Pro Gly Gln Pro Pro
        35                  40                  45

Lys Leu Leu Ile Tyr Leu Ala Ser Asn Leu Glu Ser Gly Val Pro Ala
    50                  55                  60

Arg Phe Ser Gly Ser Gly Ser Arg Thr Asp Phe Thr Leu Thr Ile Asp
65                  70                  75                  80

Pro Val Glu Ala Asp Asp Ala Ala Thr Tyr Tyr Cys Gln Gln Asn Lys
                85                  90                  95

Glu Asp Pro Trp Thr Phe Gly Gly Gly Thr Lys Leu Glu Ile Lys
            100                 105                 110

<210> SEQ ID NO 7
<211> LENGTH: 449
<212> TYPE: PRT
<213> ORGANISM: Artificial Sequence
<220> FEATURE:
<223> OTHER INFORMATION: HC amino sequence of the mAb1

<400> SEQUENCE: 7

Gln Val Gln Leu Gln Gln Ser Gly Ala Glu Leu Val Arg Ser Gly Ala
1               5                   10                  15

Ser Val Lys Met Ser Cys Lys Ala Ser Gly Tyr Thr Phe Thr Ser Phe
            20                  25                  30
```

```
Asn Met His Trp Val Lys Glu Thr Pro Gly Gln Gly Leu Glu Trp Ile
         35                  40                  45
Gly Tyr Ile Tyr Pro Gly Asn Gly Gly Thr Asn Tyr Asn Gln Lys Phe
     50                  55                  60
Lys Gly Lys Ala Thr Leu Thr Ala Asp Thr Ser Ser Ser Thr Ala Tyr
 65                  70                  75                  80
Met Gln Ile Ser Ser Leu Thr Ser Glu Asp Ser Ala Val Tyr Phe Cys
                 85                  90                  95
Ala Arg Thr Gly Gly Leu Arg Arg Ala Tyr Phe Thr Tyr Trp Gly Gln
                100                 105                 110
Gly Thr Leu Val Thr Val Ser Ser Ala Ser Thr Lys Gly Pro Ser Val
            115                 120                 125
Phe Pro Leu Ala Pro Ser Ser Lys Ser Thr Ser Gly Gly Thr Ala Ala
        130                 135                 140
Leu Gly Cys Leu Val Lys Asp Tyr Phe Pro Glu Pro Val Thr Val Ser
145                 150                 155                 160
Trp Asn Ser Gly Ala Leu Thr Ser Gly Val His Thr Phe Pro Ala Val
                165                 170                 175
Leu Gln Ser Ser Gly Leu Tyr Ser Leu Ser Ser Val Val Thr Val Pro
            180                 185                 190
Ser Ser Ser Leu Gly Thr Gln Thr Tyr Ile Cys Asn Val Asn His Lys
        195                 200                 205
Pro Ser Asn Thr Lys Val Asp Lys Lys Val Glu Pro Lys Ser Cys Asp
    210                 215                 220
Lys Thr His Thr Cys Pro Pro Cys Pro Ala Pro Glu Leu Leu Ala Gly
225                 230                 235                 240
Pro Asp Val Phe Leu Phe Pro Pro Lys Pro Lys Asp Thr Leu Met Ile
                245                 250                 255
Ser Arg Thr Pro Glu Val Thr Cys Val Val Val Asp Val Ser His Glu
            260                 265                 270
Asp Pro Glu Val Lys Phe Asn Trp Tyr Val Asp Gly Val Glu Val His
        275                 280                 285
Asn Ala Lys Thr Lys Pro Arg Glu Glu Gln Tyr Asn Ser Thr Tyr Arg
    290                 295                 300
Val Val Ser Val Leu Thr Val Leu His Gln Asp Trp Leu Asn Gly Lys
305                 310                 315                 320
Glu Tyr Lys Cys Lys Val Ser Asn Lys Ala Leu Pro Leu Pro Glu Glu
                325                 330                 335
Lys Thr Ile Ser Lys Ala Lys Gly Gln Pro Arg Glu Pro Gln Val Tyr
            340                 345                 350
Thr Leu Pro Pro Ser Arg Asp Glu Leu Thr Lys Asn Gln Val Ser Leu
        355                 360                 365
Thr Cys Leu Val Lys Gly Phe Tyr Pro Ser Asp Ile Ala Val Glu Trp
    370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Lys Leu Thr Val Asp
                405                 410                 415
Lys Ser Arg Trp Gln Gln Gly Asn Val Phe Ser Cys Ser Val Met His
            420                 425                 430
Glu Ala Leu His Asn His Tyr Thr Gln Lys Ser Leu Ser Leu Ser Pro
        435                 440                 445
Gly
```

<210> SEQ ID NO 8
<211> LENGTH: 218
<212> TYPE: PRT
<213> ORGANISM: Artificial Sequence
<220> FEATURE:
<223> OTHER INFORMATION: LC amino sequence of the mAb1

<400> SEQUENCE: 8

```
Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Ser Tyr
            20                  25                  30

Gly Asn Gly Phe Met His Trp Tyr Gln Gln Lys Pro Gly Gln Pro Pro
        35                  40                  45

Lys Leu Leu Ile Tyr Leu Ala Ser Asn Leu Glu Ser Gly Val Pro Ala
    50                  55                  60

Arg Phe Ser Gly Ser Gly Ser Arg Thr Asp Phe Thr Leu Thr Ile Asp
65                  70                  75                  80

Pro Val Glu Ala Asp Asp Ala Ala Thr Tyr Tyr Cys Gln Gln Asn Lys
                85                  90                  95

Glu Asp Pro Trp Thr Phe Gly Gly Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215
```

<210> SEQ ID NO 9
<211> LENGTH: 117
<212> TYPE: PRT
<213> ORGANISM: Artificial Sequence
<220> FEATURE:
<223> OTHER INFORMATION: VH amino sequence of the mAb6

<400> SEQUENCE: 9

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Gly Asp Asn Ser Lys Asn Thr Leu Tyr
65                  70                  75                  80

Leu Gln Met Asn Ser Leu Arg Ala Glu Asp Thr Ala Val Tyr Tyr Cys
```

```
                    85                  90                  95
Ala Arg Met Phe Arg Gly Ala Phe Asp Tyr Trp Gly Gln Gly Thr Leu
                100                 105                 110

Val Thr Val Ser Ser
            115

<210> SEQ ID NO 10
<211> LENGTH: 107
<212> TYPE: PRT
<213> ORGANISM: Artificial Sequence
<220> FEATURE:
<223> OTHER INFORMATION: VL amino sequence of the mAb6

<400> SEQUENCE: 10

Ala Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Gly Leu Gln Pro
65                  70                  75                  80

Glu Asp Ser Ala Thr Tyr Tyr Cys Leu Gln Asp Tyr Ile Tyr Tyr Pro
                85                  90                  95

Thr Phe Gly Gln Gly Thr Lys Val Glu Ile Lys
            100                 105

<210> SEQ ID NO 11
<211> LENGTH: 446
<212> TYPE: PRT
<213> ORGANISM: Artificial Sequence
<220> FEATURE:
<223> OTHER INFORMATION: HC amino sequence of the mAb6

<400> SEQUENCE: 11

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
50                  55                  60

Lys Gly Arg Phe Thr Ile Ser Gly Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Met Phe Arg Gly Ala Phe Asp Tyr Trp Gly Gln Gly Thr Leu
                100                 105                 110

Val Thr Val Ser Ser Ala Ser Thr Lys Gly Pro Ser Val Phe Pro Leu
            115                 120                 125

Ala Pro Ser Ser Lys Ser Thr Ser Gly Gly Thr Ala Ala Leu Gly Cys
        130                 135                 140

Leu Val Lys Asp Tyr Phe Pro Glu Pro Val Thr Val Ser Trp Asn Ser
145                 150                 155                 160
```

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
            195                 200                 205

Thr Lys Val Asp Lys Lys Val Glu Pro Lys Ser Cys Asp Lys Thr His
210                 215                 220

Thr Cys Pro Pro Cys Pro Ala Pro Glu Leu Leu Ala Gly Pro Asp Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
            275                 280                 285

Thr Lys Pro Arg Glu Glu Gln Tyr Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Leu Pro Glu Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
            355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly
            435                 440                 445

<210> SEQ ID NO 12
<211> LENGTH: 214
<212> TYPE: PRT
<213> ORGANISM: Artificial Sequence
<220> FEATURE:
<223> OTHER INFORMATION: LC amino sequence of the mAb6

<400> SEQUENCE: 12

Ala Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Gly Leu Gln Pro
65                  70                  75                  80

Glu Asp Ser Ala Thr Tyr Tyr Cys Leu Gln Asp Tyr Ile Tyr Tyr Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
            165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
            210

<210> SEQ ID NO 13
<211> LENGTH: 120
<212> TYPE: PRT
<213> ORGANISM: Artificial Sequence
<220> FEATURE:
<223> OTHER INFORMATION: VH1 amino sequence of the mAb2

<400> SEQUENCE: 13

Gln Val Gln Leu Val Gln Ser Gly Ala Glu Val Val Lys Pro Gly Ala
1               5                   10                  15

Ser Val Lys Val Ser Cys Lys Ala Ser Gly Tyr Thr Phe Thr Ser Tyr
            20                  25                  30

Ala Met His Trp Val Lys Glu Ala Pro Gly Gln Arg Leu Glu Trp Ile
            35                  40                  45

Gly Tyr Ile Tyr Pro Gly Gln Gly Gly Thr Asn Tyr Asn Gln Lys Phe
50                  55                  60

Gln Gly Arg Ala Thr Leu Thr Ala Asp Thr Ser Ala Ser Thr Ala Tyr
65                  70                  75                  80

Met Glu Leu Ser Ser Leu Arg Ser Glu Asp Thr Ala Val Tyr Phe Cys
            85                  90                  95

Ala Arg Thr Gly Gly Leu Arg Arg Ala Tyr Phe Thr Tyr Trp Gly Gln
            100                 105                 110

Gly Thr Leu Val Thr Val Ser Ser
            115                 120

<210> SEQ ID NO 14
<211> LENGTH: 111
<212> TYPE: PRT
<213> ORGANISM: Artificial Sequence
<220> FEATURE:
<223> OTHER INFORMATION: VL1 amino sequence of the mAb2

<400> SEQUENCE: 14

Asp Ile Val Leu Thr Gln Ser Pro Ala Thr Leu Ser Leu Ser Pro Gly
1               5                   10                  15

Glu Arg Ala Thr Ile Ser Cys Arg Ala Ser Gln Ser Val Ser Ser Tyr
            20                  25                  30

Gly Gln Gly Phe Met His Trp Tyr Gln Gln Lys Pro Gly Gln Pro Pro
            35                  40                  45

-continued

Arg Leu Leu Ile Tyr Gly Ala Ser Ser Arg Ala Thr Gly Ile Pro Ala
    50                  55                  60

Arg Phe Ser Gly Ser Gly Ser Gly Thr Asp Phe Thr Leu Thr Ile Ser
65                  70                  75                  80

Pro Leu Glu Pro Glu Asp Phe Ala Val Tyr Tyr Cys Gln Gln Asn Lys
                85                  90                  95

Glu Asp Pro Trp Thr Phe Gly Gly Gly Thr Lys Leu Glu Ile Lys
            100                 105                 110

<210> SEQ ID NO 15
<211> LENGTH: 449
<212> TYPE: PRT
<213> ORGANISM: Artificial Sequence
<220> FEATURE:
<223> OTHER INFORMATION: HC1 amino sequence of the mAb2

<400> SEQUENCE: 15

Gln Val Gln Leu Val Gln Ser Gly Ala Glu Val Val Lys Pro Gly Ala
1               5                   10                  15

Ser Val Lys Val Ser Cys Lys Ala Ser Gly Tyr Thr Phe Thr Ser Tyr
            20                  25                  30

Ala Met His Trp Val Lys Glu Ala Pro Gly Gln Arg Leu Glu Trp Ile
        35                  40                  45

Gly Tyr Ile Tyr Pro Gly Gln Gly Gly Thr Asn Tyr Asn Gln Lys Phe
    50                  55                  60

Gln Gly Arg Ala Thr Leu Thr Ala Asp Thr Ser Ala Ser Thr Ala Tyr
65                  70                  75                  80

Met Glu Leu Ser Ser Leu Arg Ser Glu Asp Thr Ala Val Tyr Phe Cys
                85                  90                  95

Ala Arg Thr Gly Gly Leu Arg Arg Ala Tyr Phe Thr Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Ala Gly
225                 230                 235                 240

Pro Asp Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

```
Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Leu Pro Glu Glu
            325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
            355                 360                 365

Thr Cys Leu Val Lys Gly Phe Tyr Pro Ser Asp Ile Ala Val Glu Trp
            370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly

<210> SEQ ID NO 16
<211> LENGTH: 218
<212> TYPE: PRT
<213> ORGANISM: Artificial Sequence
<220> FEATURE:
<223> OTHER INFORMATION: LC1 amino sequence of the mAb2

<400> SEQUENCE: 16

Asp Ile Val Leu Thr Gln Ser Pro Ala Thr Leu Ser Leu Ser Pro Gly
1               5                   10                  15

Glu Arg Ala Thr Ile Ser Cys Arg Ala Ser Gln Ser Val Ser Ser Tyr
            20                  25                  30

Gly Gln Gly Phe Met His Trp Tyr Gln Gln Lys Pro Gly Gln Pro Pro
        35                  40                  45

Arg Leu Leu Ile Tyr Gly Ala Ser Ser Arg Ala Thr Gly Ile Pro Ala
    50                  55                  60

Arg Phe Ser Gly Ser Gly Ser Gly Thr Asp Phe Thr Leu Thr Ile Ser
65                  70                  75                  80

Pro Leu Glu Pro Glu Asp Phe Ala Val Tyr Tyr Cys Gln Gln Asn Lys
                85                  90                  95

Glu Asp Pro Trp Thr Phe Gly Gly Gly Thr Lys Leu Glu Ile Lys Arg
            100                 105                 110

Thr Val Ala Ala Pro Ser Val Phe Ile Phe Pro Pro Ser Asp Glu Gln
            115                 120                 125

Leu Lys Ser Gly Thr Ala Ser Val Val Cys Leu Leu Asn Asn Phe Tyr
130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
            195                 200                 205
```

Val Thr Lys Ser Phe Asn Arg Gly Glu Cys
    210                 215

<210> SEQ ID NO 17
<211> LENGTH: 120
<212> TYPE: PRT
<213> ORGANISM: Artificial Sequence
<220> FEATURE:
<223> OTHER INFORMATION: VH3 amino sequence of the mAb3

<400> SEQUENCE: 17

Gln Val Gln Leu Val Gln Ser Gly Ala Glu Val Val Lys Pro Gly Ala
1               5                   10                  15

Ser Val Lys Val Ser Cys Lys Ala Ser Gly Tyr Thr Phe Thr Ser Phe
            20                  25                  30

Asn Met His Trp Val Lys Glu Ala Pro Gly Gln Arg Leu Glu Trp Ile
        35                  40                  45

Gly Tyr Ile Tyr Pro Gly Asn Gly Gly Thr Asn Tyr Asn Gln Lys Phe
    50                  55                  60

Gln Gly Arg Ala Thr Leu Thr Ala Asp Thr Ser Ala Ser Thr Ala Tyr
65                  70                  75                  80

Met Glu Leu Ser Ser Leu Arg Ser Glu Asp Thr Ala Val Tyr Phe Cys
                85                  90                  95

Ala Arg Thr Gly Gly Leu Arg Arg Ala Tyr Phe Thr Tyr Trp Gly Gln
            100                 105                 110

Gly Thr Leu Val Thr Val Ser Ser
        115                 120

<210> SEQ ID NO 18
<211> LENGTH: 111
<212> TYPE: PRT
<213> ORGANISM: Artificial Sequence
<220> FEATURE:
<223> OTHER INFORMATION: VL3 amino sequence of the mAb3 and mAb4 and
      mAb5

<400> SEQUENCE: 18

Asp Ile Val Leu Thr Gln Ser Pro Ala Thr Leu Ser Leu Ser Pro Gly
1               5                   10                  15

Glu Arg Ala Thr Ile Ser Cys Arg Ala Ser Glu Ser Val Asp Ser Tyr
            20                  25                  30

Gly Asn Gly Phe Met His Trp Tyr Gln Gln Lys Pro Gly Gln Pro Pro
        35                  40                  45

Arg Leu Leu Ile Tyr Leu Ala Ser Ser Arg Ala Thr Gly Ile Pro Ala
    50                  55                  60

Arg Phe Ser Gly Ser Gly Ser Gly Thr Asp Phe Thr Leu Thr Ile Ser
65                  70                  75                  80

Pro Leu Glu Pro Glu Asp Phe Ala Val Tyr Tyr Cys Gln Gln Asn Lys
                85                  90                  95

Glu Asp Pro Trp Thr Phe Gly Gly Gly Thr Lys Leu Glu Ile Lys
            100                 105                 110

<210> SEQ ID NO 19
<211> LENGTH: 449
<212> TYPE: PRT
<213> ORGANISM: Artificial Sequence
<220> FEATURE:
<223> OTHER INFORMATION: HC3 amino sequence of the mAb3

<400> SEQUENCE: 19

-continued

Gln Val Gln Leu Val Gln Ser Gly Ala Glu Val Val Lys Pro Gly Ala
1               5                   10                  15

Ser Val Lys Val Ser Cys Lys Ala Ser Gly Tyr Thr Phe Thr Ser Phe
            20                  25                  30

Asn Met His Trp Val Lys Glu Ala Pro Gly Gln Arg Leu Glu Trp Ile
        35                  40                  45

Gly Tyr Ile Tyr Pro Gly Asn Gly Gly Thr Asn Tyr Asn Gln Lys Phe
    50                  55                  60

Gln Gly Arg Ala Thr Leu Thr Ala Asp Thr Ala Ser Thr Ala Tyr
65                  70                  75                  80

Met Glu Leu Ser Ser Leu Arg Ser Glu Asp Thr Ala Val Tyr Phe Cys
                85                  90                  95

Ala Arg Thr Gly Gly Leu Arg Arg Ala Tyr Phe Thr Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
            165                 170                 175

Leu Gln Ser Ser Gly Leu Tyr Ser Leu Ser Ser Val Val Thr Val Pro
        180                 185                 190

Ser Ser Ser Leu Gly Thr Gln Thr Tyr Ile Cys Asn Val Asn His Lys
    195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Ala Gly
225                 230                 235                 240

Pro Asp Val Phe Leu Phe Pro Pro Lys Pro Lys Asp Thr Leu Met Ile
            245                 250                 255

Ser Arg Thr Pro Glu Val Thr Cys Val Val Val Asp Val Ser His Glu
        260                 265                 270

Asp Pro Glu Val Lys Phe Asn Trp Tyr Val Asp Gly Val Glu Val His
    275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Leu Pro Glu Glu
            325                 330                 335

Lys Thr Ile Ser Lys Ala Lys Gly Gln Pro Arg Glu Pro Gln Val Tyr
        340                 345                 350

Thr Leu Pro Pro Ser Arg Asp Glu Leu Thr Lys Asn Gln Val Ser Leu
    355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
            405                 410                 415

Lys Ser Arg Trp Gln Gln Gly Asn Val Phe Ser Cys Ser Val Met His

```
                420                 425                 430
Glu Ala Leu His Asn His Tyr Thr Gln Lys Ser Leu Ser Leu Ser Pro
            435                 440                 445

Gly

<210> SEQ ID NO 20
<211> LENGTH: 218
<212> TYPE: PRT
<213> ORGANISM: Artificial Sequence
<220> FEATURE:
<223> OTHER INFORMATION: LC3 amino sequence of the mAb3 and mAb4 and
      mAb5

<400> SEQUENCE: 20

Asp Ile Val Leu Thr Gln Ser Pro Ala Thr Leu Ser Leu Ser Pro Gly
1               5                   10                  15

Glu Arg Ala Thr Ile Ser Cys Arg Ala Ser Glu Ser Val Asp Ser Tyr
            20                  25                  30

Gly Asn Gly Phe Met His Trp Tyr Gln Gln Lys Pro Gly Gln Pro Pro
        35                  40                  45

Arg Leu Leu Ile Tyr Leu Ala Ser Ser Arg Ala Thr Gly Ile Pro Ala
    50                  55                  60

Arg Phe Ser Gly Ser Gly Ser Gly Thr Asp Phe Thr Leu Thr Ile Ser
65                  70                  75                  80

Pro Leu Glu Pro Glu Asp Phe Ala Val Tyr Tyr Cys Gln Gln Asn Lys
                85                  90                  95

Glu Asp Pro Trp Thr Phe Gly Gly Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 21
<211> LENGTH: 120
<212> TYPE: PRT
<213> ORGANISM: Artificial Sequence
<220> FEATURE:
<223> OTHER INFORMATION: VH5 amino sequence of the mAb4

<400> SEQUENCE: 21

Gln Val Gln Leu Val Gln Ser Gly Ala Glu Val Val Lys Ser Gly Ala
1               5                   10                  15

Ser Val Lys Val Ser Cys Lys Ala Ser Gly Tyr Thr Phe Thr Ser Phe
            20                  25                  30

Asn Met His Trp Val Lys Glu Ala Pro Gly Gln Gly Leu Glu Trp Ile
        35                  40                  45
```

Gly Tyr Ile Tyr Pro Gly Asn Gly Gly Thr Asn Tyr Asn Gln Lys Phe
            50                  55                  60

Gln Gly Arg Ala Thr Leu Thr Ala Asp Thr Ser Ala Ser Thr Ala Tyr
 65                  70                  75                  80

Met Glu Ile Ser Ser Leu Arg Ser Glu Asp Thr Ala Val Tyr Phe Cys
                 85                  90                  95

Ala Arg Thr Gly Gly Leu Arg Arg Ala Tyr Phe Thr Tyr Trp Gly Gln
                100                 105                 110

Gly Thr Leu Val Thr Val Ser Ser
            115                 120

<210> SEQ ID NO 22
<211> LENGTH: 449
<212> TYPE: PRT
<213> ORGANISM: Artificial Sequence
<220> FEATURE:
<223> OTHER INFORMATION: HC5 amino sequence of the mAb4

<400> SEQUENCE: 22

Gln Val Gln Leu Val Gln Ser Gly Ala Glu Val Val Lys Ser Gly Ala
 1               5                  10                  15

Ser Val Lys Val Ser Cys Lys Ala Ser Gly Tyr Thr Phe Thr Ser Phe
            20                  25                  30

Asn Met His Trp Val Lys Glu Ala Pro Gly Gln Gly Leu Glu Trp Ile
        35                  40                  45

Gly Tyr Ile Tyr Pro Gly Asn Gly Gly Thr Asn Tyr Asn Gln Lys Phe
            50                  55                  60

Gln Gly Arg Ala Thr Leu Thr Ala Asp Thr Ser Ala Ser Thr Ala Tyr
 65                  70                  75                  80

Met Glu Ile Ser Ser Leu Arg Ser Glu Asp Thr Ala Val Tyr Phe Cys
                 85                  90                  95

Ala Arg Thr Gly Gly Leu Arg Arg Ala Tyr Phe Thr Tyr Trp Gly Gln
                100                 105                 110

Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
        130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
                180                 185                 190

Ser Ser Ser Leu Gly Thr Gln Thr Tyr Ile Cys Asn Val Asn His Lys
            195                 200                 205

Pro Ser Asn Thr Lys Val Asp Lys Lys Val Glu Pro Lys Ser Cys Asp
        210                 215                 220

Lys Thr His Thr Cys Pro Cys Pro Ala Pro Glu Leu Leu Ala Gly
225                 230                 235                 240

Pro Asp Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

```
Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Leu Pro Glu Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly

<210> SEQ ID NO 23
<211> LENGTH: 120
<212> TYPE: PRT
<213> ORGANISM: Artificial Sequence
<220> FEATURE:
<223> OTHER INFORMATION: VH6 amino sequence of the mAb5

<400> SEQUENCE: 23

Gln Val Gln Leu Val Gln Ser Gly Ala Glu Val Val Lys Pro Gly Ala
1               5                   10                  15

Ser Val Lys Met Ser Cys Lys Ala Ser Gly Tyr Thr Phe Thr Ser Phe
            20                  25                  30

Asn Met His Trp Val Lys Glu Ala Pro Gly Gln Arg Leu Glu Trp Ile
        35                  40                  45

Gly Tyr Ile Tyr Pro Gly Asn Gly Gly Thr Asn Tyr Asn Gln Lys Phe
    50                  55                  60

Gln Gly Arg Ala Thr Leu Thr Ala Asp Thr Ser Ala Ser Thr Ala Tyr
65                  70                  75                  80

Met Glu Ile Ser Ser Leu Arg Ser Glu Asp Thr Ala Val Tyr Phe Cys
                85                  90                  95

Ala Arg Thr Gly Gly Leu Arg Arg Ala Tyr Phe Thr Tyr Trp Gly Gln
            100                 105                 110

Gly Thr Leu Val Thr Val Ser Ser
        115                 120

<210> SEQ ID NO 24
<211> LENGTH: 449
<212> TYPE: PRT
<213> ORGANISM: Artificial Sequence
<220> FEATURE:
<223> OTHER INFORMATION: HC6 amino sequence of the mAb5

<400> SEQUENCE: 24

Gln Val Gln Leu Val Gln Ser Gly Ala Glu Val Val Lys Pro Gly Ala
1               5                   10                  15
```

Ser Val Lys Met Ser Cys Lys Ala Ser Gly Tyr Thr Phe Thr Ser Phe
            20                  25                  30
Asn Met His Trp Val Lys Glu Ala Pro Gly Gln Arg Leu Glu Trp Ile
        35                  40                  45
Gly Tyr Ile Tyr Pro Gly Asn Gly Thr Asn Tyr Asn Gln Lys Phe
    50                  55                  60
Gln Gly Arg Ala Thr Leu Thr Ala Asp Thr Ser Ala Ser Thr Ala Tyr
65                  70                  75                  80
Met Glu Ile Ser Ser Leu Arg Ser Glu Asp Thr Ala Val Tyr Phe Cys
                85                  90                  95
Ala Arg Thr Gly Gly Leu Arg Arg Ala Tyr Phe Thr Tyr Trp Gly Gln
                100                 105                 110
Gly Thr Leu Val Thr Val Ser Ser Ala Ser Thr Lys Gly Pro Ser Val
            115                 120                 125
Phe Pro Leu Ala Pro Ser Ser Lys Ser Thr Ser Gly Gly Thr Ala Ala
    130                 135                 140
Leu Gly Cys Leu Val Lys Asp Tyr Phe Pro Glu Pro Val Thr Val Ser
145                 150                 155                 160
Trp Asn Ser Gly Ala Leu Thr Ser Gly Val His Thr Phe Pro Ala Val
                165                 170                 175
Leu Gln Ser Ser Gly Leu Tyr Ser Leu Ser Ser Val Val Thr Val Pro
                180                 185                 190
Ser Ser Ser Leu Gly Thr Gln Thr Tyr Ile Cys Asn Val Asn His Lys
            195                 200                 205
Pro Ser Asn Thr Lys Val Asp Lys Lys Val Glu Pro Lys Ser Cys Asp
    210                 215                 220
Lys Thr His Thr Cys Pro Pro Cys Pro Ala Pro Glu Leu Leu Ala Gly
225                 230                 235                 240
Pro Asp Val Phe Leu Phe Pro Pro Lys Pro Lys Asp Thr Leu Met Ile
                245                 250                 255
Ser Arg Thr Pro Glu Val Thr Cys Val Val Val Asp Val Ser His Glu
                260                 265                 270
Asp Pro Glu Val Lys Phe Asn Trp Tyr Val Asp Gly Val Glu Val His
            275                 280                 285
Asn Ala Lys Thr Lys Pro Arg Glu Glu Gln Tyr Asn Ser Thr Tyr Arg
    290                 295                 300
Val Val Ser Val Leu Thr Val Leu His Gln Asp Trp Leu Asn Gly Lys
305                 310                 315                 320
Glu Tyr Lys Cys Lys Val Ser Asn Lys Ala Leu Pro Leu Pro Glu Glu
                325                 330                 335
Lys Thr Ile Ser Lys Ala Lys Gly Gln Pro Arg Glu Pro Gln Val Tyr
            340                 345                 350
Thr Leu Pro Pro Ser Arg Asp Glu Leu Thr Lys Asn Gln Val Ser Leu
    355                 360                 365
Thr Cys Leu Val Lys Gly Phe Tyr Pro Ser Asp Ile Ala Val Glu Trp
370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Lys Leu Thr Val Asp
                405                 410                 415
Lys Ser Arg Trp Gln Gln Gly Asn Val Phe Ser Cys Ser Val Met His
            420                 425                 430
Glu Ala Leu His Asn His Tyr Thr Gln Lys Ser Leu Ser Leu Ser Pro

-continued

```
                435                 440                 445
Gly

<210> SEQ ID NO 25
<400> SEQUENCE: 25
000

<210> SEQ ID NO 26
<400> SEQUENCE: 26
000

<210> SEQ ID NO 27
<400> SEQUENCE: 27
000

<210> SEQ ID NO 28
<400> SEQUENCE: 28
000

<210> SEQ ID NO 29
<400> SEQUENCE: 29
000

<210> SEQ ID NO 30
<211> LENGTH: 256
<212> TYPE: PRT
<213> ORGANISM: Macaca fascicularis
<220> FEATURE:
<223> OTHER INFORMATION: CD38 extracellular domain

<400> SEQUENCE: 30
```

Arg Trp Arg Gln Gln Trp Ser Gly Ser Gly Thr Thr Ser Arg Phe Pro
1               5                   10                  15

Glu Thr Val Leu Ala Arg Cys Val Lys Tyr Thr Glu Val His Pro Glu
            20                  25                  30

Met Arg His Val Asp Cys Gln Ser Val Trp Asp Ala Phe Lys Gly Ala
        35                  40                  45

Phe Ile Ser Lys Tyr Pro Cys Asn Ile Thr Glu Glu Asp Tyr Gln Pro
    50                  55                  60

Leu Val Lys Leu Gly Thr Gln Thr Val Pro Cys Asn Lys Thr Leu Leu
65                  70                  75                  80

Trp Ser Arg Ile Lys Asp Leu Ala His Gln Phe Thr Gln Val Gln Arg
                85                  90                  95

Asp Met Phe Thr Leu Glu Asp Met Leu Leu Gly Tyr Leu Ala Asp Asp
            100                 105                 110

Leu Thr Trp Cys Gly Glu Phe Asn Thr Phe Glu Ile Asn Tyr Gln Ser
        115                 120                 125

Cys Pro Asp Trp Arg Lys Asp Cys Ser Asn Asn Pro Val Ser Val Phe
    130                 135                 140

Trp Lys Thr Val Ser Arg Arg Phe Ala Glu Thr Ala Cys Gly Val Val
145                 150                 155                 160

```
His Val Met Leu Asn Gly Ser Arg Ser Lys Ile Phe Asp Lys Asn Ser
                165                 170                 175

Thr Phe Gly Ser Val Glu Val His Asn Leu Gln Pro Glu Lys Val Gln
            180                 185                 190

Ala Leu Glu Ala Trp Val Ile His Gly Gly Arg Glu Asp Ser Arg Asp
        195                 200                 205

Leu Cys Gln Asp Pro Thr Ile Lys Glu Leu Glu Ser Ile Ser Lys
    210                 215                 220

Arg Asn Ile Arg Phe Phe Cys Lys Asn Ile Tyr Arg Pro Asp Lys Phe
225                 230                 235                 240

Leu Gln Cys Val Lys Asn Pro Glu Asp Ser Ser Cys Leu Ser Gly Ile
                245                 250                 255

<210> SEQ ID NO 31
<211> LENGTH: 8
<212> TYPE: PRT
<213> ORGANISM: Artificial Sequence
<220> FEATURE:
<223> OTHER INFORMATION: mAb1/mAb3/mAb4/mAb5 CDR-H1

<400> SEQUENCE: 31

Gly Tyr Thr Phe Thr Ser Phe Asn
1               5

<210> SEQ ID NO 32
<211> LENGTH: 8
<212> TYPE: PRT
<213> ORGANISM: Artificial Sequence
<220> FEATURE:
<223> OTHER INFORMATION: mAb1/mAb3/mAb4/mAb5 CDR-H2

<400> SEQUENCE: 32

Ile Tyr Pro Gly Asn Gly Gly Thr
1               5

<210> SEQ ID NO 33
<211> LENGTH: 13
<212> TYPE: PRT
<213> ORGANISM: Artificial Sequence
<220> FEATURE:
<223> OTHER INFORMATION: mAb1/mAb2/mAb3/mAb4/mAb5 CDR-H3

<400> SEQUENCE: 33

Ala Arg Thr Gly Gly Leu Arg Arg Ala Tyr Phe Thr Tyr
1               5                   10

<210> SEQ ID NO 34
<211> LENGTH: 10
<212> TYPE: PRT
<213> ORGANISM: Artificial Sequence
<220> FEATURE:
<223> OTHER INFORMATION: mAb1/mAb3/mAb4/mAb5 CDR-L1

<400> SEQUENCE: 34

Glu Ser Val Asp Ser Tyr Gly Asn Gly Phe
1               5                   10

<210> SEQ ID NO 35
<211> LENGTH: 3
<212> TYPE: PRT
<213> ORGANISM: Artificial Sequence
<220> FEATURE:
<223> OTHER INFORMATION: mAb1/mAb3/mAb4/mAb5 CDR-L2

<400> SEQUENCE: 35
```

Leu Ala Ser
1

<210> SEQ ID NO 36
<211> LENGTH: 9
<212> TYPE: PRT
<213> ORGANISM: Artificial Sequence
<220> FEATURE:
<223> OTHER INFORMATION: mAb1/mAb2/mAb3/mAb4/mAb5 CDR-L3

<400> SEQUENCE: 36

Gln Gln Asn Lys Glu Asp Pro Trp Thr
1               5

<210> SEQ ID NO 37
<211> LENGTH: 8
<212> TYPE: PRT
<213> ORGANISM: Artificial Sequence
<220> FEATURE:
<223> OTHER INFORMATION: mAb2 CDR-H1

<400> SEQUENCE: 37

Gly Tyr Thr Phe Thr Ser Tyr Ala
1               5

<210> SEQ ID NO 38
<211> LENGTH: 8
<212> TYPE: PRT
<213> ORGANISM: Artificial Sequence
<220> FEATURE:
<223> OTHER INFORMATION: mAb2 CDR-H2

<400> SEQUENCE: 38

Ile Tyr Pro Gly Gln Gly Gly Thr
1               5

<210> SEQ ID NO 39
<211> LENGTH: 10
<212> TYPE: PRT
<213> ORGANISM: Artificial Sequence
<220> FEATURE:
<223> OTHER INFORMATION: mAb2 CDR-L1

<400> SEQUENCE: 39

Gln Ser Val Ser Ser Tyr Gly Gln Gly Phe
1               5                   10

<210> SEQ ID NO 40
<211> LENGTH: 3
<212> TYPE: PRT
<213> ORGANISM: Artificial Sequence
<220> FEATURE:
<223> OTHER INFORMATION: mAb2 CDR-L2

<400> SEQUENCE: 40

Gly Ala Ser
1

<210> SEQ ID NO 41
<211> LENGTH: 8
<212> TYPE: PRT
<213> ORGANISM: Artificial Sequence
<220> FEATURE:
<223> OTHER INFORMATION: mAb6 CDR-H1

<400> SEQUENCE: 41

Gly Phe Thr Phe Ser Ser Tyr Gly
1               5

<210> SEQ ID NO 42
<211> LENGTH: 8
<212> TYPE: PRT
<213> ORGANISM: Artificial Sequence
<220> FEATURE:
<223> OTHER INFORMATION: mAb6 CDR-H2

<400> SEQUENCE: 42

Ile Trp Tyr Asp Gly Ser Asn Lys
1               5

<210> SEQ ID NO 43
<211> LENGTH: 10
<212> TYPE: PRT
<213> ORGANISM: Artificial Sequence
<220> FEATURE:
<223> OTHER INFORMATION: mAb6 CDR-H3

<400> SEQUENCE: 43

Ala Arg Met Phe Arg Gly Ala Phe Asp Tyr
1               5                   10

<210> SEQ ID NO 44
<211> LENGTH: 6
<212> TYPE: PRT
<213> ORGANISM: Artificial Sequence
<220> FEATURE:
<223> OTHER INFORMATION: mAb6 CDR-L1

<400> SEQUENCE: 44

Gln Gly Ile Arg Asn Asp
1               5

<210> SEQ ID NO 45
<211> LENGTH: 3
<212> TYPE: PRT
<213> ORGANISM: Artificial Sequence
<220> FEATURE:
<223> OTHER INFORMATION: mAb6 CDR-L2

<400> SEQUENCE: 45

Ala Ala Ser
1

<210> SEQ ID NO 46
<211> LENGTH: 9
<212> TYPE: PRT
<213> ORGANISM: Artificial Sequence
<220> FEATURE:
<223> OTHER INFORMATION: mAb6 CDR-L3

<400> SEQUENCE: 46

Leu Gln Asp Tyr Ile Tyr Tyr Pro Thr
1               5

<210> SEQ ID NO 47
<211> LENGTH: 120
<212> TYPE: PRT
<213> ORGANISM: Artificial Sequence
<220> FEATURE:
<223> OTHER INFORMATION: mAb7 VH domain

<400> SEQUENCE: 47

Gln Val Gln Leu Val Gln Ser Gly Ala Glu Val Ala Lys Pro Gly Thr

```
                1               5                   10                  15
Ser Val Lys Leu Ser Cys Lys Ala Ser Gly Tyr Thr Phe Thr Asp Tyr
            20                  25                  30

Trp Met Gln Trp Val Lys Gln Arg Pro Gly Gln Gly Leu Glu Trp Ile
            35                  40                  45

Gly Thr Ile Tyr Pro Gly Asp Gly Asp Thr Gly Tyr Ala Gln Lys Phe
            50                  55                  60

Gln Gly Lys Ala Thr Leu Thr Ala Asp Lys Ser Ser Lys Thr Val Tyr
65                  70                  75                  80

Met His Leu Ser Ser Leu Ala Ser Glu Asp Ser Ala Val Tyr Tyr Cys
            85                  90                  95

Ala Arg Gly Asp Tyr Tyr Gly Ser Asn Ser Leu Asp Tyr Trp Gly Gln
            100                 105                 110

Gly Thr Ser Val Thr Val Ser Ser
            115                 120

<210> SEQ ID NO 48
<211> LENGTH: 107
<212> TYPE: PRT
<213> ORGANISM: Artificial Sequence
<220> FEATURE:
<223> OTHER INFORMATION: mAb7 VL domain

<400> SEQUENCE: 48

Asp Ile Val Met Thr Gln Ser His Leu Ser Met Ser Thr Ser Leu Gly
1               5                   10                  15

Asp Pro Val Ser Ile Thr Cys Lys Ala Ser Gln Asp Val Ser Thr Val
            20                  25                  30

Val Ala Trp Tyr Gln Gln Lys Pro Gly Gln Ser Pro Arg Arg Leu Ile
            35                  40                  45

Tyr Ser Ala Ser Tyr Arg Tyr Ile Gly Val Pro Asp Arg Phe Thr Gly
            50                  55                  60

Ser Gly Ala Gly Thr Asp Phe Thr Phe Thr Ile Ser Ser Val Gln Ala
65                  70                  75                  80

Glu Asp Leu Ala Val Tyr Tyr Cys Gln Gln His Tyr Ser Pro Pro Tyr
            85                  90                  95

Thr Phe Gly Gly Gly Thr Lys Leu Glu Ile Lys
            100                 105

<210> SEQ ID NO 49
<211> LENGTH: 120
<212> TYPE: PRT
<213> ORGANISM: Artificial Sequence
<220> FEATURE:
<223> OTHER INFORMATION: anti-CD28sup VH domain

<400> SEQUENCE: 49

Gln Val Gln Leu Val Gln Ser Gly Ala Glu Val Val Lys Pro Gly Ala
1               5                   10                  15

Ser Val Lys Val Ser Cys Lys Ala Ser Gly Tyr Thr Phe Thr Ser Tyr
            20                  25                  30

Tyr Ile His Trp Val Arg Gln Ala Pro Gly Gln Gly Leu Glu Trp Ile
            35                  40                  45

Gly Ser Ile Tyr Pro Gly Asn Val Asn Thr Asn Tyr Ala Gln Lys Phe
            50                  55                  60

Gln Gly Arg Ala Thr Leu Thr Val Asp Thr Ser Ile Ser Thr Ala Tyr
65                  70                  75                  80
```

Met Glu Leu Ser Arg Leu Arg Ser Asp Asp Thr Ala Val Tyr Tyr Cys
            85                  90                  95

Thr Arg Ser His Tyr Gly Leu Asp Trp Asn Phe Asp Val Trp Gly Lys
        100                 105                 110

Gly Thr Thr Val Thr Val Ser Ser
        115                 120

<210> SEQ ID NO 50
<211> LENGTH: 107
<212> TYPE: PRT
<213> ORGANISM: Artificial Sequence
<220> FEATURE:
<223> OTHER INFORMATION: anti-CD28sup VL domain

<400> SEQUENCE: 50

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asn Ile Tyr Val Trp
            20                  25                  30

Leu Asn Trp Tyr Gln Gln Lys Pro Gly Lys Ala Pro Lys Leu Leu Ile
        35                  40                  45

Tyr Lys Ala Ser Asn Leu His Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Ile Ala Thr Tyr Tyr Cys Gln Gln Gly Gln Thr Tyr Pro Tyr
            85                  90                  95

Thr Phe Gly Gln Gly Thr Lys Leu Glu Ile Lys
        100                 105

<210> SEQ ID NO 51
<211> LENGTH: 120
<212> TYPE: PRT
<213> ORGANISM: Artificial Sequence
<220> FEATURE:
<223> OTHER INFORMATION: anti-CD28cvn VH domain

<400> SEQUENCE: 51

Gln Val Gln Leu Gln Glu Ser Gly Pro Gly Leu Val Lys Pro Ser Gln
1               5                   10                  15

Thr Leu Ser Leu Thr Cys Thr Val Ser Gly Phe Ser Leu Ser Asp Tyr
            20                  25                  30

Gly Val His Trp Val Arg Gln Pro Pro Gly Lys Gly Leu Glu Trp Leu
        35                  40                  45

Gly Val Ile Trp Ala Gly Gly Thr Asn Tyr Asn Pro Ser Leu Lys
    50                  55                  60

Ser Arg Lys Thr Ile Ser Lys Asp Thr Ser Lys Asn Gln Val Ser Leu
65                  70                  75                  80

Lys Leu Ser Ser Val Thr Ala Ala Asp Thr Ala Val Tyr Tyr Cys Ala
            85                  90                  95

Arg Asp Lys Gly Tyr Ser Tyr Tyr Tyr Ser Met Asp Tyr Trp Gly Gln
        100                 105                 110

Gly Thr Thr Val Thr Val Ser Ser
        115                 120

<210> SEQ ID NO 52
<211> LENGTH: 111
<212> TYPE: PRT
<213> ORGANISM: Artificial Sequence

```
<220> FEATURE:
<223> OTHER INFORMATION: anti-CD28cvn VL domain

<400> SEQUENCE: 52

Asp Ile Val Leu Thr Gln Ser Pro Ala Ser Leu Ala Val Ser Pro Gly
1               5                   10                  15

Gln Arg Ala Thr Ile Thr Cys Arg Ala Ser Glu Ser Val Glu Tyr Tyr
            20                  25                  30

Val Thr Ser Leu Met Gln Trp Tyr Gln Gln Lys Pro Gly Gln Pro Pro
        35                  40                  45

Lys Leu Leu Ile Phe Ala Ala Ser Asn Val Glu Ser Gly Val Pro Ala
    50                  55                  60

Arg Phe Ser Gly Ser Gly Ser Gly Thr Asp Phe Thr Leu Thr Ile Asn
65                  70                  75                  80

Pro Val Glu Ala Asn Asp Val Ala Asn Tyr Tyr Cys Gln Gln Ser Arg
                85                  90                  95

Lys Val Pro Tyr Thr Phe Gly Gln Gly Thr Lys Leu Glu Ile Lys
            100                 105                 110

<210> SEQ ID NO 53
<211> LENGTH: 121
<212> TYPE: PRT
<213> ORGANISM: Artificial Sequence
<220> FEATURE:
<223> OTHER INFORMATION: anti-CD3mid VH domain

<400> SEQUENCE: 53

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Thr Lys Ala
            20                  25                  30

Trp Met His Trp Val Arg Gln Ala Pro Gly Lys Gln Leu Glu Trp Val
        35                  40                  45

Ala Gln Ile Lys Asp Lys Ser Asn Ser Tyr Ala Thr Tyr Tyr Ala Asp
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Arg Gly Val Tyr Tyr Ala Leu Ser Pro Phe Asp Tyr Trp Gly
            100                 105                 110

Gln Gly Thr Leu Val Thr Val Ser Ser
        115                 120

<210> SEQ ID NO 54
<211> LENGTH: 112
<212> TYPE: PRT
<213> ORGANISM: Artificial Sequence
<220> FEATURE:
<223> OTHER INFORMATION: anti-CD3mid VL domain

<400> SEQUENCE: 54

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Val His Asn
            20                  25                  30

Asn Ala Asn Thr Tyr Leu Ser Trp Tyr Leu Gln Lys Pro Gly Gln Ser
        35                  40                  45
```

```
Pro Gln Ser Leu Ile Tyr Lys Val Ser Asn Arg Phe Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Gly Gln Gly
                 85                  90                  95

Thr Gln Tyr Pro Phe Thr Phe Gly Ser Gly Thr Lys Val Glu Ile Lys
            100                 105                 110

<210> SEQ ID NO 55
<211> LENGTH: 10
<212> TYPE: PRT
<213> ORGANISM: Artificial Sequence
<220> FEATURE:
<223> OTHER INFORMATION: Linker

<400> SEQUENCE: 55

Gly Gly Gly Gly Ser Gly Gly Gly Gly Ser
1               5                   10

<210> SEQ ID NO 56
<211> LENGTH: 15
<212> TYPE: PRT
<213> ORGANISM: Artificial Sequence
<220> FEATURE:
<223> OTHER INFORMATION: Linker

<400> SEQUENCE: 56

Gly Gly Gly Gly Ser Gly Gly Gly Gly Ser Gly Gly Gly Gly Ser
1               5                   10                  15

<210> SEQ ID NO 57
<211> LENGTH: 5
<212> TYPE: PRT
<213> ORGANISM: Artificial Sequence
<220> FEATURE:
<223> OTHER INFORMATION: Linker

<400> SEQUENCE: 57

Thr Lys Gly Pro Ser
1               5

<210> SEQ ID NO 58
<211> LENGTH: 7
<212> TYPE: PRT
<213> ORGANISM: Artificial Sequence
<220> FEATURE:
<223> OTHER INFORMATION: Linker

<400> SEQUENCE: 58

Gly Gln Pro Lys Ala Ala Pro
1               5

<210> SEQ ID NO 59
<211> LENGTH: 10
<212> TYPE: PRT
<213> ORGANISM: Artificial Sequence
<220> FEATURE:
<223> OTHER INFORMATION: Linker

<400> SEQUENCE: 59

Gly Gly Ser Gly Ser Ser Gly Ser Gly Gly
1               5                   10

<210> SEQ ID NO 60
```

<211> LENGTH: 570
<212> TYPE: PRT
<213> ORGANISM: Artificial Sequence
<220> FEATURE:
<223> OTHER INFORMATION: CD28supxCD3mid IgG4(hole) FALA Heavy1 polypeptide sequence

<400> SEQUENCE: 60

```
Gln Val Gln Leu Val Gln Ser Gly Ala Glu Val Val Lys Pro Gly Ala
1               5                   10                  15

Ser Val Lys Val Ser Cys Lys Ala Ser Gly Tyr Thr Phe Thr Ser Tyr
            20                  25                  30

Tyr Ile His Trp Val Arg Gln Ala Pro Gly Gln Gly Leu Glu Trp Ile
        35                  40                  45

Gly Ser Ile Tyr Pro Gly Asn Val Asn Thr Asn Tyr Ala Gln Lys Phe
    50                  55                  60

Gln Gly Arg Ala Thr Leu Thr Val Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Thr Arg Ser His Tyr Gly Leu Asp Trp Asn Phe Asp Val Trp Gly Lys
            100                 105                 110

Gly Thr Thr Val Thr Val Ser Ser Gln Val Gln Leu Val Glu Ser
        115                 120                 125

Gly Gly Gly Val Val Gln Pro Gly Arg Ser Leu Arg Leu Ser Cys Ala
    130                 135                 140

Ala Ser Gly Phe Thr Phe Thr Lys Ala Trp Met His Trp Val Arg Gln
145                 150                 155                 160

Ala Pro Gly Lys Gln Leu Glu Trp Val Ala Gln Ile Lys Asp Lys Ser
                165                 170                 175

Asn Ser Tyr Ala Thr Tyr Tyr Ala Asp Ser Val Lys Gly Arg Phe Thr
            180                 185                 190

Ile Ser Arg Asp Asp Ser Lys Asn Thr Leu Tyr Leu Gln Met Asn Ser
        195                 200                 205

Leu Arg Ala Glu Asp Thr Ala Val Tyr Tyr Cys Arg Gly Val Tyr Tyr
    210                 215                 220

Ala Leu Ser Pro Phe Asp Tyr Trp Gly Gln Gly Thr Leu Val Thr Val
225                 230                 235                 240

Ser Ser Arg Thr Ala Ser Thr Lys Gly Pro Ser Val Phe Pro Leu Ala
                245                 250                 255

Pro Cys Ser Arg Ser Thr Ser Glu Ser Thr Ala Ala Leu Gly Cys Leu
            260                 265                 270

Val Lys Asp Tyr Phe Pro Glu Pro Val Thr Val Ser Trp Asn Ser Gly
        275                 280                 285

Ala Leu Thr Ser Gly Val His Thr Phe Pro Ala Val Leu Gln Ser Ser
    290                 295                 300

Gly Leu Tyr Ser Leu Ser Ser Val Val Thr Val Pro Ser Ser Ser Leu
305                 310                 315                 320

Gly Thr Lys Thr Tyr Thr Cys Asn Val Asp His Lys Pro Ser Asn Thr
                325                 330                 335

Lys Val Asp Lys Arg Val Glu Ser Lys Tyr Gly Pro Pro Cys Pro Pro
            340                 345                 350

Cys Pro Ala Pro Glu Ala Ala Gly Gly Pro Ser Val Phe Leu Phe Pro
        355                 360                 365

Pro Lys Pro Lys Asp Thr Leu Met Ile Ser Arg Thr Pro Glu Val Thr
```

```
                    370                 375                 380
Cys Val Val Asp Val Ser Gln Glu Asp Pro Glu Val Gln Phe Asn
385                 390                 395                 400

Trp Tyr Val Asp Gly Val Glu Val His Asn Ala Lys Thr Lys Pro Arg
                405                 410                 415

Glu Glu Gln Phe Asn Ser Thr Tyr Arg Val Val Ser Val Leu Thr Val
                420                 425                 430

Leu His Gln Asp Trp Leu Asn Gly Lys Glu Tyr Lys Cys Lys Val Ser
                435                 440                 445

Asn Lys Gly Leu Pro Ser Ser Ile Glu Lys Thr Ile Ser Lys Ala Lys
450                 455                 460

Gly Gln Pro Arg Glu Pro Gln Val Cys Thr Leu Pro Pro Ser Gln Glu
465                 470                 475                 480

Glu Met Thr Lys Asn Gln Val Ser Leu Ser Cys Ala Val Lys Gly Phe
                485                 490                 495

Tyr Pro Ser Asp Ile Ala Val Glu Trp Glu Ser Asn Gly Gln Pro Glu
                500                 505                 510

Asn Asn Tyr Lys Thr Thr Pro Pro Val Leu Asp Ser Asp Gly Ser Phe
                515                 520                 525

Phe Leu Val Ser Lys Leu Thr Val Asp Lys Ser Arg Trp Gln Glu Gly
                530                 535                 540

Asn Val Phe Ser Cys Ser Val Met His Glu Ala Leu His Asn His Tyr
545                 550                 555                 560

Thr Gln Lys Ser Leu Ser Leu Ser Leu Gly
                565                 570

<210> SEQ ID NO 61
<211> LENGTH: 338
<212> TYPE: PRT
<213> ORGANISM: Artificial Sequence
<220> FEATURE:
<223> OTHER INFORMATION: CD28supxCD3mid Light1 polypeptide sequence

<400> SEQUENCE: 61

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Val His Asn
                20                  25                  30

Asn Ala Asn Thr Tyr Leu Ser Trp Tyr Leu Gln Lys Pro Gly Gln Ser
            35                  40                  45

Pro Gln Ser Leu Ile Tyr Lys Val Ser Asn Arg Phe Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Gly Gln Gly
                85                  90                  95

Thr Gln Tyr Pro Phe Thr Phe Gly Ser Gly Thr Lys Val Glu Ile Lys
                100                 105                 110

Gly Gln Pro Lys Ala Ala Pro Asp Ile Gln Met Thr Gln Ser Pro Ser
            115                 120                 125

Ser Leu Ser Ala Ser Val Gly Asp Arg Val Thr Ile Thr Cys Gln Ala
        130                 135                 140

Ser Gln Asn Ile Tyr Val Trp Leu Asn Trp Tyr Gln Gln Lys Pro Gly
145                 150                 155                 160

Lys Ala Pro Lys Leu Leu Ile Tyr Lys Ala Ser Asn Leu His Thr Gly
```

```
                  165                 170                 175

Val Pro Ser Arg Phe Ser Gly Ser Gly Ser Gly Thr Asp Phe Thr Leu
                180                 185                 190

Thr Ile Ser Ser Leu Gln Pro Glu Asp Ile Ala Thr Tyr Tyr Cys Gln
                195                 200                 205

Gln Gly Gln Thr Tyr Pro Tyr Thr Phe Gly Gln Gly Thr Lys Leu Glu
            210                 215                 220

Ile Lys Thr Lys Gly Pro Ser Arg Thr Val Ala Ala Pro Ser Val Phe
225                 230                 235                 240

Ile Phe Pro Pro Ser Asp Glu Gln Leu Lys Ser Gly Thr Ala Ser Val
                245                 250                 255

Val Cys Leu Leu Asn Asn Phe Tyr Pro Arg Glu Ala Lys Val Gln Trp
                260                 265                 270

Lys Val Asp Asn Ala Leu Gln Ser Gly Asn Ser Gln Glu Ser Val Thr
                275                 280                 285

Glu Gln Asp Ser Lys Asp Ser Thr Tyr Ser Leu Ser Ser Thr Leu Thr
            290                 295                 300

Leu Ser Lys Ala Asp Tyr Glu Lys His Lys Val Tyr Ala Cys Glu Val
305                 310                 315                 320

Thr His Gln Gly Leu Ser Ser Pro Val Thr Lys Ser Phe Asn Arg Gly
                325                 330                 335

Glu Cys

<210> SEQ ID NO 62
<211> LENGTH: 446
<212> TYPE: PRT
<213> ORGANISM: Artificial Sequence
<220> FEATURE:
<223> OTHER INFORMATION: CD38VH1 IgG4(knob) FALA Heavy2 polypeptide
      sequence

<400> SEQUENCE: 62

Gln Val Gln Leu Val Gln Ser Gly Ala Glu Val Val Lys Pro Gly Ala
1               5                   10                  15

Ser Val Lys Val Ser Cys Lys Ala Ser Gly Tyr Thr Phe Thr Ser Tyr
                20                  25                  30

Ala Met His Trp Val Lys Glu Ala Pro Gly Gln Arg Leu Glu Trp Ile
            35                  40                  45

Gly Tyr Ile Tyr Pro Gly Gln Gly Thr Asn Tyr Asn Gln Lys Phe
        50                  55                  60

Gln Gly Arg Ala Thr Leu Thr Ala Asp Thr Ser Ala Ser Thr Ala Tyr
65                  70                  75                  80

Met Glu Leu Ser Ser Leu Arg Ser Glu Asp Thr Ala Val Tyr Phe Cys
                85                  90                  95

Ala Arg Thr Gly Gly Leu Arg Arg Ala Tyr Phe Thr Tyr Trp Gly Gln
                100                 105                 110

Gly Thr Leu Val Thr Val Ser Ser Ala Ser Thr Lys Gly Pro Ser Val
            115                 120                 125

Phe Pro Leu Ala Pro Cys Ser Arg Ser Thr Ser Glu Ser Thr Ala Ala
        130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
```

```
              180                 185                 190
Ser Ser Ser Leu Gly Thr Lys Thr Tyr Thr Cys Asn Val Asp His Lys
            195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Ala Ala Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Cys Gln Glu Glu Met Thr Lys Asn Gln Val Ser Leu Trp Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly
        435                 440                 445

<210> SEQ ID NO 63
<211> LENGTH: 218
<212> TYPE: PRT
<213> ORGANISM: Artificial Sequence
<220> FEATURE:
<223> OTHER INFORMATION: CD38VH1 Light2 polypeptide sequence

<400> SEQUENCE: 63

Asp Ile Val Leu Thr Gln Ser Pro Ala Thr Leu Ser Leu Ser Pro Gly
1               5                   10                  15

Glu Arg Ala Thr Ile Ser Cys Arg Ala Ser Gln Ser Val Ser Ser Tyr
            20                  25                  30

Gly Gln Gly Phe Met His Trp Tyr Gln Gln Lys Pro Gly Gln Pro Pro
        35                  40                  45

Arg Leu Leu Ile Tyr Gly Ala Ser Ser Arg Ala Thr Gly Ile Pro Ala
    50                  55                  60

Arg Phe Ser Gly Ser Gly Ser Gly Thr Asp Phe Thr Leu Thr Ile Ser
65                  70                  75                  80

Pro Leu Glu Pro Glu Asp Phe Ala Val Tyr Tyr Cys Gln Gln Asn Lys
                85                  90                  95

Glu Asp Pro Trp Thr Phe Gly Gly Gly Thr Lys Leu Glu Ile Lys Arg
```

```
                    100                 105                 110
Thr Val Ala Ala Pro Ser Val Phe Ile Phe Pro Ser Asp Glu Gln
                115                 120                 125
Leu Lys Ser Gly Thr Ala Ser Val Val Cys Leu Leu Asn Asn Phe Tyr
130                 135                 140
Pro Arg Glu Ala Lys Val Gln Trp Lys Val Asp Asn Ala Leu Gln Ser
145                 150                 155                 160
Gly Asn Ser Gln Glu Ser Val Thr Glu Gln Asp Ser Lys Asp Ser Thr
                165                 170                 175
Tyr Ser Leu Ser Ser Thr Leu Thr Leu Ser Lys Ala Asp Tyr Glu Lys
                180                 185                 190
His Lys Val Tyr Ala Cys Glu Val Thr His Gln Gly Leu Ser Ser Pro
                195                 200                 205
Val Thr Lys Ser Phe Asn Arg Gly Glu Cys
                210                 215

<210> SEQ ID NO 64
<211> LENGTH: 573
<212> TYPE: PRT
<213> ORGANISM: Artificial Sequence
<220> FEATURE:
<223> OTHER INFORMATION: CD28supxCD3mid IgG1(hole) LALA P329A Heavy1
      polypeptide sequence

<400> SEQUENCE: 64

Gln Val Gln Leu Val Gln Ser Gly Ala Glu Val Val Lys Pro Gly Ala
1               5                   10                  15
Ser Val Lys Val Ser Cys Lys Ala Ser Gly Tyr Thr Phe Thr Ser Tyr
                20                  25                  30
Tyr Ile His Trp Val Arg Gln Ala Pro Gly Gln Gly Leu Glu Trp Ile
                35                  40                  45
Gly Ser Ile Tyr Pro Gly Asn Val Asn Thr Asn Tyr Ala Gln Lys Phe
            50                  55                  60
Gln Gly Arg Ala Thr Leu Thr Val Asp Thr Ser Ile Ser Thr Ala Tyr
65              70                  75                  80
Met Glu Leu Ser Arg Leu Arg Ser Asp Asp Thr Ala Val Tyr Tyr Cys
                85                  90                  95
Thr Arg Ser His Tyr Gly Leu Asp Trp Asn Phe Asp Val Trp Gly Lys
                100                 105                 110
Gly Thr Thr Val Thr Val Ser Ser Gln Val Gln Leu Val Glu Ser
                115                 120                 125
Gly Gly Gly Val Val Gln Pro Gly Arg Ser Leu Arg Leu Ser Cys Ala
            130                 135                 140
Ala Ser Gly Phe Thr Phe Thr Lys Ala Trp Met His Trp Val Arg Gln
145                 150                 155                 160
Ala Pro Gly Lys Gln Leu Glu Trp Val Ala Gln Ile Lys Asp Lys Ser
                165                 170                 175
Asn Ser Tyr Ala Thr Tyr Tyr Ala Asp Ser Val Lys Gly Arg Phe Thr
                180                 185                 190
Ile Ser Arg Asp Asp Ser Lys Asn Thr Leu Tyr Leu Gln Met Asn Ser
                195                 200                 205
Leu Arg Ala Glu Asp Thr Ala Val Tyr Tyr Cys Arg Gly Val Tyr Tyr
            210                 215                 220
Ala Leu Ser Pro Phe Asp Tyr Trp Gly Gln Gly Thr Leu Val Thr Val
225                 230                 235                 240
```

```
Ser Ser Arg Thr Ala Ser Thr Lys Gly Pro Ser Val Phe Pro Leu Ala
                245                 250                 255
Pro Ser Ser Lys Ser Thr Ser Gly Gly Thr Ala Ala Leu Gly Cys Leu
            260                 265                 270
Val Lys Asp Tyr Phe Pro Glu Pro Val Thr Val Ser Trp Asn Ser Gly
        275                 280                 285
Ala Leu Thr Ser Gly Val His Thr Phe Pro Ala Val Leu Gln Ser Ser
    290                 295                 300
Gly Leu Tyr Ser Leu Ser Ser Val Val Thr Val Pro Ser Ser Ser Leu
305                 310                 315                 320
Gly Thr Gln Thr Tyr Ile Cys Asn Val Asn His Lys Pro Ser Asn Thr
                325                 330                 335
Lys Val Asp Lys Lys Val Glu Pro Lys Ser Cys Asp Lys Thr His Thr
            340                 345                 350
Cys Pro Pro Cys Pro Ala Pro Glu Ala Ala Gly Gly Pro Ser Val Phe
        355                 360                 365
Leu Phe Pro Pro Lys Pro Lys Asp Thr Leu Met Ile Ser Arg Thr Pro
    370                 375                 380
Glu Val Thr Cys Val Val Val Asp Val Ser His Glu Asp Pro Glu Val
385                 390                 395                 400
Lys Phe Asn Trp Tyr Val Asp Gly Val Glu Val His Asn Ala Lys Thr
                405                 410                 415
Lys Pro Arg Glu Glu Gln Tyr Asn Ser Thr Tyr Arg Val Val Ser Val
            420                 425                 430
Leu Thr Val Leu His Gln Asp Trp Leu Asn Gly Lys Glu Tyr Lys Cys
        435                 440                 445
Lys Val Ser Asn Lys Ala Leu Ala Ala Pro Ile Glu Lys Thr Ile Ser
    450                 455                 460
Lys Ala Lys Gly Gln Pro Arg Glu Pro Gln Val Cys Thr Leu Pro Pro
465                 470                 475                 480
Ser Arg Asp Glu Leu Thr Lys Asn Gln Val Ser Leu Ser Cys Ala Val
                485                 490                 495
Lys Gly Phe Tyr Pro Ser Asp Ile Ala Val Glu Trp Glu Ser Asn Gly
            500                 505                 510
Gln Pro Glu Asn Asn Tyr Lys Thr Thr Pro Pro Val Leu Asp Ser Asp
        515                 520                 525
Gly Ser Phe Phe Leu Val Ser Lys Leu Thr Val Asp Lys Ser Arg Trp
    530                 535                 540
Gln Gln Gly Asn Val Phe Ser Cys Ser Val Met His Glu Ala Leu His
545                 550                 555                 560
Asn His Tyr Thr Gln Lys Ser Leu Ser Leu Ser Pro Gly
                565                 570

<210> SEQ ID NO 65
<211> LENGTH: 449
<212> TYPE: PRT
<213> ORGANISM: Artificial Sequence
<220> FEATURE:
<223> OTHER INFORMATION: CD38VH1 IgG1(knob) LALA P329A Heavy2
      polypeptide sequence

<400> SEQUENCE: 65

Gln Val Gln Leu Val Gln Ser Gly Ala Glu Val Val Lys Pro Gly Ala
1               5                   10                  15
Ser Val Lys Val Ser Cys Lys Ala Ser Gly Tyr Thr Phe Thr Ser Tyr
            20                  25                  30
```

```
Ala Met His Trp Val Lys Glu Ala Pro Gly Gln Arg Leu Glu Trp Ile
         35                  40                  45
Gly Tyr Ile Tyr Pro Gly Gln Gly Thr Asn Tyr Asn Gln Lys Phe
         50                  55                  60
Gln Gly Arg Ala Thr Leu Thr Ala Asp Thr Ser Ala Ser Thr Ala Tyr
 65                  70                  75                  80
Met Glu Leu Ser Ser Leu Arg Ser Glu Asp Thr Ala Val Tyr Phe Cys
                 85                  90                  95
Ala Arg Thr Gly Gly Leu Arg Arg Ala Tyr Phe Thr Tyr Trp Gly Gln
                 100                 105                 110
Gly Thr Leu Val Thr Val Ser Ser Ala Ser Thr Lys Gly Pro Ser Val
                 115                 120                 125
Phe Pro Leu Ala Pro Ser Ser Lys Ser Thr Ser Gly Gly Thr Ala Ala
                 130                 135                 140
Leu Gly Cys Leu Val Lys Asp Tyr Phe Pro Glu Pro Val Thr Val Ser
145                 150                 155                 160
Trp Asn Ser Gly Ala Leu Thr Ser Gly Val His Thr Phe Pro Ala Val
                 165                 170                 175
Leu Gln Ser Ser Gly Leu Tyr Ser Leu Ser Ser Val Val Thr Val Pro
                 180                 185                 190
Ser Ser Ser Leu Gly Thr Gln Thr Tyr Ile Cys Asn Val Asn His Lys
                 195                 200                 205
Pro Ser Asn Thr Lys Val Asp Lys Lys Val Glu Pro Lys Ser Cys Asp
                 210                 215                 220
Lys Thr His Thr Cys Pro Pro Cys Pro Ala Pro Glu Ala Ala Gly Gly
225                 230                 235                 240
Pro Ser Val Phe Leu Phe Pro Pro Lys Pro Lys Asp Thr Leu Met Ile
                 245                 250                 255
Ser Arg Thr Pro Glu Val Thr Cys Val Val Val Asp Val Ser His Glu
                 260                 265                 270
Asp Pro Glu Val Lys Phe Asn Trp Tyr Val Asp Gly Val Glu Val His
                 275                 280                 285
Asn Ala Lys Thr Lys Pro Arg Glu Glu Gln Tyr Asn Ser Thr Tyr Arg
                 290                 295                 300
Val Val Ser Val Leu Thr Val Leu His Gln Asp Trp Leu Asn Gly Lys
305                 310                 315                 320
Glu Tyr Lys Cys Lys Val Ser Asn Lys Ala Leu Ala Ala Pro Ile Glu
                 325                 330                 335
Lys Thr Ile Ser Lys Ala Lys Gly Gln Pro Arg Glu Pro Gln Val Tyr
                 340                 345                 350
Thr Leu Pro Pro Cys Arg Asp Glu Leu Thr Lys Asn Gln Val Ser Leu
                 355                 360                 365
Trp Cys Leu Val Lys Gly Phe Tyr Pro Ser Asp Ile Ala Val Glu Trp
                 370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Lys Leu Thr Val Asp
                 405                 410                 415
Lys Ser Arg Trp Gln Gln Gly Asn Val Phe Ser Cys Ser Val Met His
                 420                 425                 430
Glu Ala Leu His Asn His Tyr Thr Gln Lys Ser Leu Ser Leu Ser Pro
                 435                 440                 445
```

Gly

<210> SEQ ID NO 66
<211> LENGTH: 573
<212> TYPE: PRT
<213> ORGANISM: Artificial Sequence
<220> FEATURE:
<223> OTHER INFORMATION: CD28supxCD3mid IgG1(hole) NNSA Heavy1 polypeptide sequence

<400> SEQUENCE: 66

```
Gln Val Gln Leu Val Gln Ser Gly Ala Glu Val Val Lys Pro Gly Ala
1               5                   10                  15

Ser Val Lys Val Ser Cys Lys Ala Ser Gly Tyr Thr Phe Thr Ser Tyr
            20                  25                  30

Tyr Ile His Trp Val Arg Gln Ala Pro Gly Gln Gly Leu Glu Trp Ile
        35                  40                  45

Gly Ser Ile Tyr Pro Gly Asn Val Asn Thr Asn Tyr Ala Gln Lys Phe
    50                  55                  60

Gln Gly Arg Ala Thr Leu Thr Val Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Thr Arg Ser His Tyr Gly Leu Asp Trp Asn Phe Asp Val Trp Gly Lys
            100                 105                 110

Gly Thr Thr Val Thr Val Ser Ser Gln Val Gln Leu Val Glu Ser
        115                 120                 125

Gly Gly Gly Val Val Gln Pro Gly Arg Ser Leu Arg Leu Ser Cys Ala
    130                 135                 140

Ala Ser Gly Phe Thr Phe Thr Lys Ala Trp Met His Trp Val Arg Gln
145                 150                 155                 160

Ala Pro Gly Lys Gln Leu Glu Trp Val Ala Gln Ile Lys Asp Lys Ser
                165                 170                 175

Asn Ser Tyr Ala Thr Tyr Tyr Ala Asp Ser Val Lys Gly Arg Phe Thr
            180                 185                 190

Ile Ser Arg Asp Asp Ser Lys Asn Thr Leu Tyr Leu Gln Met Asn Ser
        195                 200                 205

Leu Arg Ala Glu Asp Thr Ala Val Tyr Tyr Cys Arg Gly Val Tyr Tyr
    210                 215                 220

Ala Leu Ser Pro Phe Asp Tyr Trp Gly Gln Gly Thr Leu Val Thr Val
225                 230                 235                 240

Ser Ser Arg Thr Ala Ser Thr Lys Gly Pro Ser Val Phe Pro Leu Ala
                245                 250                 255

Pro Ser Ser Lys Ser Thr Ser Gly Gly Thr Ala Ala Leu Gly Cys Leu
            260                 265                 270

Val Lys Asp Tyr Phe Pro Glu Pro Val Thr Val Ser Trp Asn Ser Gly
        275                 280                 285

Ala Leu Thr Ser Gly Val His Thr Phe Pro Ala Val Leu Gln Ser Ser
    290                 295                 300

Gly Leu Tyr Ser Leu Ser Ser Val Val Thr Val Pro Ser Ser Ser Leu
305                 310                 315                 320

Gly Thr Gln Thr Tyr Ile Cys Asn Val Asn His Lys Pro Ser Asn Thr
                325                 330                 335

Lys Val Asp Lys Lys Val Glu Pro Lys Ser Cys Asp Lys Thr His Thr
            340                 345                 350
```

```
Cys Pro Pro Cys Pro Ala Pro Glu Leu Leu Gly Gly Pro Ser Val Phe
            355                 360                 365

Leu Phe Pro Pro Lys Pro Lys Asp Thr Leu Met Ile Ser Arg Thr Pro
370                 375                 380

Glu Val Thr Cys Val Val Val Asp Val Ser His Glu Asp Pro Glu Val
385                 390                 395                 400

Lys Phe Asn Trp Tyr Val Asp Gly Val Glu Val His Asn Ala Lys Thr
                405                 410                 415

Lys Pro Arg Glu Glu Gln Tyr Asn Ala Ser Arg Val Val Ser Val
            420                 425                 430

Leu Thr Val Leu His Gln Asp Trp Leu Asn Gly Lys Glu Tyr Lys Cys
            435                 440                 445

Lys Val Ser Asn Lys Ala Leu Pro Ala Pro Ile Glu Lys Thr Ile Ser
450                 455                 460

Lys Ala Lys Gly Gln Pro Arg Glu Pro Gln Val Cys Thr Leu Pro Pro
465                 470                 475                 480

Ser Arg Asp Glu Leu Thr Lys Asn Gln Val Ser Leu Ser Cys Ala Val
                485                 490                 495

Lys Gly Phe Tyr Pro Ser Asp Ile Ala Val Glu Trp Glu Ser Asn Gly
            500                 505                 510

Gln Pro Glu Asn Asn Tyr Lys Thr Thr Pro Pro Val Leu Asp Ser Asp
            515                 520                 525

Gly Ser Phe Phe Leu Val Ser Lys Leu Thr Val Asp Lys Ser Arg Trp
530                 535                 540

Gln Gln Gly Asn Val Phe Ser Cys Ser Val Met His Glu Ala Leu His
545                 550                 555                 560

Asn His Tyr Thr Gln Lys Ser Leu Ser Leu Ser Pro Gly
                565                 570

<210> SEQ ID NO 67
<211> LENGTH: 449
<212> TYPE: PRT
<213> ORGANISM: Artificial Sequence
<220> FEATURE:
<223> OTHER INFORMATION: CD38VH1 IgG1(knob) NNSA Heavy2 polypeptide
      sequence

<400> SEQUENCE: 67

Gln Val Gln Leu Val Gln Ser Gly Ala Glu Val Val Lys Pro Gly Ala
1               5                   10                  15

Ser Val Lys Val Ser Cys Lys Ala Ser Gly Tyr Thr Phe Thr Ser Tyr
            20                  25                  30

Ala Met His Trp Val Lys Glu Ala Pro Gly Gln Arg Leu Glu Trp Ile
        35                  40                  45

Gly Tyr Ile Tyr Pro Gly Gln Gly Gly Thr Asn Tyr Asn Gln Lys Phe
    50                  55                  60

Gln Gly Arg Ala Thr Leu Thr Ala Asp Thr Ser Ala Ser Thr Ala Tyr
65                  70                  75                  80

Met Glu Leu Ser Ser Leu Arg Ser Glu Asp Thr Ala Val Tyr Phe Cys
                85                  90                  95

Ala Arg Thr Gly Gly Leu Arg Arg Ala Tyr Phe Thr Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140
```

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
                260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ala Ser
        290                 295                 300         Arg

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
                340                 345                 350

Thr Leu Pro Pro Cys Arg Asp Glu Leu Thr Lys Asn Gln Val Ser Leu
            355                 360                 365

Trp Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
            435                 440                 445

Gly

<210> SEQ ID NO 68
<211> LENGTH: 443
<212> TYPE: PRT
<213> ORGANISM: Artificial Sequence
<220> FEATURE:
<223> OTHER INFORMATION: CD38hhy1370 IgG4(knob) FALA P329A Heavy2
      polypeptide sequence

<400> SEQUENCE: 68

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

```
Ala Val Ile Trp Tyr Asp Gly Ser Asn Lys Tyr Tyr Ala Asp Ser Val
         50                  55                  60

Lys Gly Arg Phe Thr Ile Ser Gly Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Met Phe Arg Gly Ala Phe Asp Tyr Trp Gly Gln Gly Thr Leu
                100                 105                 110

Val Thr Val Ser Ser Ala Ser Thr Lys Gly Pro Ser Val Phe Pro Leu
            115                 120                 125

Ala Pro Cys Ser Arg Ser Thr Ser Glu Ser Thr Ala Ala Leu Gly Cys
130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
                180                 185                 190

Leu Gly Thr Lys Thr Tyr Thr Cys Asn Val Asp His Lys Pro Ser Asn
            195                 200                 205

Thr Lys Val Asp Lys Arg Val Glu Ser Lys Tyr Gly Pro Pro Cys Pro
210                 215                 220

Pro Cys Pro Ala Pro Glu Ala Ala Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser Gln Glu Asp Pro Glu Val Gln Phe
                260                 265                 270

Asn Trp Tyr Val Asp Gly Val Glu Val His Asn Ala Lys Thr Lys Pro
            275                 280                 285

Arg Glu Glu Gln Phe Asn Ser Thr Tyr Arg Val Val Ser Val Leu Thr
290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Cys Gln
                340                 345                 350

Glu Glu Met Thr Lys Asn Gln Val Ser Leu Trp Cys Leu Val Lys Gly
            355                 360                 365

Phe Tyr Pro Ser Asp Ile Ala Val Glu Trp Glu Ser Asn Gly Gln Pro
370                 375                 380

Glu Asn Asn Tyr Lys Thr Thr Pro Pro Val Leu Asp Ser Asp Gly Ser
385                 390                 395                 400

Phe Phe Leu Tyr Ser Lys Leu Thr Val Asp Lys Ser Arg Trp Gln Glu
                405                 410                 415

Gly Asn Val Phe Ser Cys Ser Val Met His Glu Ala Leu His Asn His
                420                 425                 430

Tyr Thr Gln Lys Ser Leu Ser Leu Gly
            435                 440

<210> SEQ ID NO 69
<211> LENGTH: 214
```

```
<212> TYPE: PRT
<213> ORGANISM: Artificial Sequence
<220> FEATURE:
<223> OTHER INFORMATION: CD38hhy1370 Light2 polypeptide sequence

<400> SEQUENCE: 69
```

Ala Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Gly Leu Gln Pro
65                  70                  75                  80

Glu Asp Ser Ala Thr Tyr Tyr Cys Leu Gln Asp Tyr Ile Tyr Tyr Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

```
<210> SEQ ID NO 70
<211> LENGTH: 446
<212> TYPE: PRT
<213> ORGANISM: Artificial Sequence
<220> FEATURE:
<223> OTHER INFORMATION: CD38hhy1370 IgG1(knob) LALA P329A Heavy2
      polypeptide sequence

<400> SEQUENCE: 70
```

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Gly Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Met Phe Arg Gly Ala Phe Asp Tyr Trp Gly Gln Gly Thr Leu

```
            100                 105                 110
Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
210                 215                 220

Thr Cys Pro Pro Cys Pro Ala Pro Glu Ala Ala Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Ala Leu Ala Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Cys Arg Asp Glu Leu Thr Lys Asn Gln Val Ser Leu Trp Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly
        435                 440                 445

<210> SEQ ID NO 71
<211> LENGTH: 446
<212> TYPE: PRT
<213> ORGANISM: Artificial Sequence
<220> FEATURE:
<223> OTHER INFORMATION: CD38hhy1370 IgG1(knob) NNSA Heavy2 polypeptide
      sequence

<400> SEQUENCE: 71

Gln Val Gln Leu Val Glu Ser Gly Gly Gly Val Val Gln Pro Gly Arg
1               5                   10                  15
```

Ser Leu Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Val
            35                  40                  45

Ala Val Ile Trp Tyr Asp Gly Ser Asn Lys Tyr Tyr Ala Asp Ser Val
50                  55                  60

Lys Gly Arg Phe Thr Ile Ser Gly Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Met Phe Arg Gly Ala Phe Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
        130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Asn Ala Ser Arg Val Val Ser
        290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Cys Arg Asp Glu Leu Thr Lys Asn Gln Val Ser Leu Trp Cys Leu
        355                 360                 365

Val Lys Gly Phe Tyr Pro Ser Asp Ile Ala Val Glu Trp Glu Ser Asn
        370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly

<210> SEQ ID NO 72
<211> LENGTH: 1710
<212> TYPE: DNA
<213> ORGANISM: Artificial Sequence
<220> FEATURE:
<223> OTHER INFORMATION: CD28supxCD3mid IgG4(hole) FALA Heavy1
polynucleotide sequence

<400> SEQUENCE: 72

```
caggtgcagc tggtgcagtc tggcgccgag gtcgtgaaac ctggcgcctc tgtgaaggtg      60
tcctgcaagg ccagcggcta cacctttacc agctactaca tccactgggt gcgccaggcc     120
cctggacagg gactggaatg gatcggcagc atctaccccg gcaacgtgaa caccaactac     180
gcccagaagt tccagggcag agccaccctg accgtggaca ccagcatcag caccgcctac     240
atggaactga gccggctgag aagcgacgac accgccgtgt actactgcac ccggtcccac     300
tacggcctgg attggaactt cgacgtgtgg ggcaagggca ccaccgtgac agtgtctagc     360
agccaggtgc agctggtgga atctggcggc ggagtggtgc agcctggcag aagcctgaga     420
ctgagctgtg ccgccagcgg cttcaccttc accaaggcct ggatgcactg ggtgcgccag     480
gcccctggaa agcagctgga atgggtggcc agatcaagg acaagagcaa cagctacgcc     540
acctactacg ccgacagcgt gaagggccgg ttcaccatca gccgggacga cagcaagaac     600
accctgtacc tgcagatgaa cagcctgcgg gccgaggaca ccgccgtgta ctactgtcgg     660
ggcgtgtact atgccctgag ccccttcgat tactgggggcc agggaaccct cgtgaccgtg     720
tctagtcgga ccgccagcac aaagggccca tcggtgttcc ctctggcccc ttgcagcaga     780
agcaccagcg aatctacagc cgccctgggc tgcctcgtga aggactactt tcccgagccc     840
gtgaccgtgt cctggaactc tggcgctctg acaagcggcg tgcacacctt ccagccgtg     900
ctccagagca gcggcctgta ctctctgagc agcgtcgtga cagtgcccag cagcagcctg     960
ggcaccaaga cctacacctg taacgtggac cacaagccca gcaacaccaa ggtggacaag    1020
cgggtggaat ctaagtacgg ccctccctgc cctccttgcc cagcccctga agctgccggc    1080
ggaccctccg tgttcctgtt cccccaaag cccaaggaca cctgatgat cagccggacc    1140
cccgaagtga cctgcgtggt ggtggatgtg tcccaggaag atcccgaggt gcagttcaat    1200
tggtacgtgg acggcgtgga agtgcacaac gccaagacca gcccagaga ggaacagttc    1260
aacagcacct accgggtggt gtccgtgctg accgtgctgc accaggactg gctgaacggc    1320
aaagagtaca agtgcaaggt gtccaacaag ggcctgccca gctccatcga aaaaccatc    1380
agcaaggcca agggccagcc ccgcgagcct caagtgtgta ccctgccccc tagccaggaa    1440
gagatgacca gaaccaggt gtccctgagc tgtgccgtga aggcttcta ccccagcgac    1500
attgccgtgg aatgggagag caacggccag cccgagaaca actacaagac cacccccct    1560
gtgctggaca gcgacggctc attcttcctg gtgtccaagc tgaccgtgga caagagccgg    1620
tggcaggaag gcaacgtgtt cagctgctcc gtgatgcacg aggccctgca caaccactac    1680
acccagaagt ccctgtctct gtccctgggc                                    1710
```

<210> SEQ ID NO 73
<211> LENGTH: 1014
<212> TYPE: DNA
<213> ORGANISM: Artificial Sequence
<220> FEATURE:
<223> OTHER INFORMATION: CD28supxCD3mid Light1 polynucleotide sequence

<400> SEQUENCE: 73

```
gacatcgtga tgacccagac cccctgagc ctgagcgtga cacctggaca gcctgccagc    60
atcagctgca agagcagcca gagcctggtg cacaacaacg ccaacaccta cctgagctgg   120
tatctgcaga agcccggcca gagccccag tccctgatct acaaggtgtc caacagattc   180
agcggcgtgc ccgacagatt ctccggcagc ggctctggca ccgacttcac cctgaagatc   240
agccgggtgg aagccgagga cgtgggcgtg tactattgtg ccagggcac ccagtacccc    300
ttcacctttg gcagcggcac caaggtggaa atcaagggcc agcccaaggc cgcccccgac   360
atccagatga cccagagccc cagcagcctg tctgccagcg tgggcgacag agtgaccatc   420
acctgtcagg ccagccagaa catctacgtg tggctgaact ggtatcagca aagcccggc    480
aaggccccca gctgctgat ctacaaggcc agcaacctgc acaccggcgt gcccagcaga   540
ttttctggca gcggctccgg caccgacttc accctgacaa tcagctccct gcagcccgag   600
gacattgcca cctactactg ccagcagggc cagacctacc cctacacctt tggccagggc   660
accaagctgg aaatcaagac caagggcccc agccgtacgg tggccgctcc cagcgtgttc   720
atcttcccac ctagcgacga gcagctgaag tccggcacag cctctgtcgt gtgcctgctg   780
aacaacttct acccccgcga ggccaaagtg cagtggaagg tggacaacgc cctgcagagc   840
ggcaacagcc aggaaagcgt gaccgagcag gacagcaagg actccaccta cagcctgagc   900
agcaccctga cactgagcaa ggccgactac gagaagcaca aggtgtacgc ctgcgaagtg   960
acccaccagg gcctgtctag ccccgtgacc aagagcttca accggggcga gtgt      1014
```

<210> SEQ ID NO 74
<211> LENGTH: 1338
<212> TYPE: DNA
<213> ORGANISM: Artificial Sequence
<220> FEATURE:
<223> OTHER INFORMATION: CD38VH1 IgG4(knob) FALA Heavy2 polynucleotide sequence

<400> SEQUENCE: 74

```
caggtgcagc tggtgcagtc tggcgccgaa gtcgtgaaac ctggcgcctc cgtgaaggtg    60
tcctgcaagg ccagcggcta cacctttacc agctacgcca tgcactgggt caaagaggcc   120
cctggccaga actggaatg gatcggctac atctacccg gccagggcgg caccaactac   180
aaccagaagt tccagggcag agccaccctg accgccgata agagccagca caccgcctac   240
atggaactga gcagcctgcg gagcgaggat accgccgtgt acttctgtgc cagaacaggc   300
ggcctgaggc gggcctactt taccattgg gccagggcca ccctcgtgac cgtgtctagc   360
gctagcacaa agggcccatc ggtgttccct ctggccccct tgcagcagaag caccagcgaa   420
tctacagccg ccctgggctg cctcgtgaag gactactttc ccgagcccgt gaccgtgtcc   480
tggaactctg gcgctctgac aagcggcgtg cacacctttc cagccgtgct ccagagcagc   540
ggcctgtact ctctgagcag cgtcgtgaca gtgcccagca gcagcctggg caccaagacc   600
tacacctgta acgtggacca caagcccagc aacaccaagg tggacaagcg ggtggaatct   660
aagtacggcc ctcccctgcc ctccttgccca gccctgaag ctgccggcgg acctccgtg    720
ttcctgttcc cccaaagcc aaggacacc ctgatgatca gccggacccc cgaagtgacc   780
tgcgtggtgg tggatgtgtc ccaggaagat cccgaggtgc agttcaattg gtacgtggac   840
ggcgtggaag tgcacaacgc caagaccaag cccagagagg aacagttcaa cagcacctac   900
cgggtggtgt ccgtgctgac cgtgctgcac caggactggc tgaacggcaa agagtacaag   960
```

| | |
|---|---|
| tgcaaggtgt ccaacaaggg cctgcccagc tccatcgaga aaaccatcag caaggccaag | 1020 |
| ggccagcccc gcgagcctca agtgtatacc ctgccccctt gccaggaaga gatgaccaag | 1080 |
| aaccaggtgt ccctgtggtg tctcgtgaaa ggcttctacc ccagcgacat tgccgtggaa | 1140 |
| tgggagagca acggccagcc cgagaacaac tacaagacca ccccccctgt gctggacagc | 1200 |
| gacggctcat tcttcctgta ctccaagctg accgtggaca gagccggtg gcaggaaggc | 1260 |
| aacgtgttca gctgctccgt gatgcacgag gccctgcaca accactacac ccagaagtcc | 1320 |
| ctgtctctgt ccctgggc | 1338 |

<210> SEQ ID NO 75
<211> LENGTH: 654
<212> TYPE: DNA
<213> ORGANISM: Artificial Sequence
<220> FEATURE:
<223> OTHER INFORMATION: CD38VH1 Light2 polynucleotide sequence

<400> SEQUENCE: 75

| | |
|---|---|
| gacatcgtgc tgacacagag ccctgccacc ctgtctctga gccctggcga gagagccacc | 60 |
| atcagctgta gagccagcca gagcgtgtcc agctacggcc agggcttcat gcactggtat | 120 |
| cagcagaagc ccggccagcc ccccagactg ctgatctatg cgccagcag cagagccaca | 180 |
| ggcatccccg ccagattttc tggctctggc agcggcaccg acttcaccct gacaatcagc | 240 |
| cccctggaac ccgaggactt cgccgtgtac tactgccagc agaacaaaga ggaccccctgg | 300 |
| accttcggcg gaggcaccaa gctggaaatc aagcgtacgg tggccgctcc cagcgtgttc | 360 |
| atcttcccac ctagcgacga gcagctgaag tccggcacag cctctgtcgt gtgcctgctg | 420 |
| aacaacttct accccgcga ggccaaggtg cagtggaagg tggacaatgc cctgcagagc | 480 |
| ggcaacagcc aggaaagcgt gaccgagcag gacagcaagg actccaccta cagcctgagc | 540 |
| agcaccctga ccctgtccaa ggccgattac gagaagcaca aggtgtacgc ctgcgaagtg | 600 |
| acccaccagg gcctgtctag ccccgtgacc aagagcttca ccggggcga gtgc | 654 |

<210> SEQ ID NO 76
<211> LENGTH: 1719
<212> TYPE: DNA
<213> ORGANISM: Artificial Sequence
<220> FEATURE:
<223> OTHER INFORMATION: CD28supxCD3mid IgG1(hole) LALA P329A Heavy1
      polynucleotide sequence

<400> SEQUENCE: 76

| | |
|---|---|
| caggtgcagc tggtgcagtc tggcgccgag gtcgtgaaac tggcgcctc tgtgaaggtg | 60 |
| tcctgcaagg ccagcggcta cacctttacc agctactaca tccactgggt gcgccaggcc | 120 |
| cctggacagg gactggaatg gatcggcagc atctaccccg gcaacgtgaa caccaactac | 180 |
| gcccagaagt tccagggcag agccaccctg accgtggaca ccagcatcag caccgcctac | 240 |
| atggaactga gccggctgag aagcgacgac accgccgtgt actactgcac ccggtcccac | 300 |
| tacggcctgg attggaactt cgacgtgtgg ggcaagggca ccaccgtgac agtgtctagc | 360 |
| agccaggtgc agctggtgga atctggcggc ggagtggtgc agcctggcag aagcctgaga | 420 |
| ctgagctgtg ccgccagcgg cttcaccttc accaaggcct ggatgcactg ggtgcgccag | 480 |
| gcccctggaa agcagctgga atgggtggcc cagatcaagg acaagagcaa cagctacgcc | 540 |
| acctactacg ccgacagcgt gaagggccgg ttcaccatca gccgggacga cagcaagaac | 600 |
| accctgtacc tgcagatgaa cagcctgcgg gccgaggaca ccgccgtgta ctactgtcgg | 660 |

| | |
|---|---|
| ggcgtgtact atgccctgag ccccttcgat tactggggcc agggaaccct cgtgaccgtg | 720 |
| tctagtcgga ccgccagcac aaagggcccc agcgtgttcc ctctggcccc tagcagcaag | 780 |
| agcacatctg gcggaacagc cgccctgggc tgcctcgtga aggactactt tcccgagccc | 840 |
| gtgaccgtgt cctggaattc tggcgccctg accagcggcg tgcacacctt ccagctgtg | 900 |
| ctgcagtcca gcggcctgta cagcctgagc agcgtcgtga cagtgcccag cagctctctg | 960 |
| ggcacccaga cctacatctg caacgtgaac cacaagccca gcaacaccaa ggtggacaag | 1020 |
| aaggtggaac ccaagagctg cgacaagacc cacacctgtc cccttgtcc tgcccccgaa | 1080 |
| gccgccggag cccttccgt gttcctgttc cccccaaagc caaggacac cctgatgatc | 1140 |
| agccggaccc ccgaagtgac ctgcgtggtg gtggatgtgt cccacgagga ccctgaagtg | 1200 |
| aagttcaatt ggtacgtgga cggcgtggaa gtgcacaacg ccaagaccaa gccaagagag | 1260 |
| gaacagtaca acagcaccta ccgggtggtg tccgtgctga ccgtgctgca ccaggactgg | 1320 |
| ctgaacggca agagtacaa gtgcaaggtg tccaacaagg ccctggccgc ccccatcgag | 1380 |
| aaaaccatca gcaaggccaa ggccagcccc cgcgaacccc aggtgtgcac actgccccca | 1440 |
| agcagggacg agctgaccaa gaaccaggtg tccctgagct gtgccgtgaa aggcttctac | 1500 |
| ccctccgata tcgccgtgga atgggagagc aacggccagc cgagaacaa ctacaagacc | 1560 |
| accccccctg tgctggacag cgacggctca ttcttcctgg tgtccaagct gacagtggac | 1620 |
| aagtcccggt ggcagcaggg caacgtgttc agctgctccg tgatgcacga ggccctgcac | 1680 |
| aaccactaca cccagaagtc cctgagcctg agccccggc | 1719 |

<210> SEQ ID NO 77
<211> LENGTH: 1347
<212> TYPE: DNA
<213> ORGANISM: Artificial Sequence
<220> FEATURE:
<223> OTHER INFORMATION: CD38VH1 IgG1(knob) LALA P329A Heavy2
       polynucleotide sequence

<400> SEQUENCE: 77

| | |
|---|---|
| caggtgcagc tggtgcagtc tggcgccgaa gtcgtgaaac ctggcgcctc cgtgaaggtg | 60 |
| tcctgcaagg ccagcggcta cacctttacc agctacgcca tgcactgggt caaagaggcc | 120 |
| cctggccaga gactggaatg gatcggctac atctaccccg gccagggcgg caccaactac | 180 |
| aaccagaagt tccagggcag agccaccctg accgccgata agtccgccag caccgcctac | 240 |
| atggaactga gcagcctgcg gagcgaggat accgccgtgt acttctgtgc cagaacaggc | 300 |
| ggcctgaggc gggcctactt tacctattgg ggccagggca ccctcgtgac cgtgtctagc | 360 |
| gctagcacaa agggcccag cgtgttccct ctggccccta gcagcaagag cacatctggc | 420 |
| ggaacagccg ccctgggctg cctcgtgaag gactactttc ccgagccgt gaccgtgtcc | 480 |
| tggaattctg gcgccctgac cagcggcgtg cacacctttc agctgtgct gcagtccagc | 540 |
| ggcctgtaca gcctgagcag cgtcgtgaca gtgcccagca gctctctggg cacccagacc | 600 |
| tacatctgca acgtgaacca caagcccagc aacaccaagg tggacaagaa ggtggaaccc | 660 |
| aagagctgcg acaagaccca cacctgtccc cttgtcctg cccccgaagc cgccggaggc | 720 |
| ccttccgtgt tcctgttccc cccaaagccc aaggacaccc tgatgatcag ccggacccc | 780 |
| gaagtgacct gcgtggtggt ggatgtgtcc cacgaggacc ctgaagtgaa gttcaattgg | 840 |
| tacgtggacg gcgtggaagt gcacaacgcc aagaccaagc caagagagga acagtacaac | 900 |
| agcacctacc gggtggtgtc cgtgctgacc gtgctgcacc aggactggct gaacggcaaa | 960 |

```
gagtacaagt gcaaggtgtc caacaaggcc ctggccgccc ccatcgagaa aaccatcagc    1020
aaggccaagg gccagccccg cgaacccag gtgtacacac tgcccccatg cagggacgag    1080
ctgaccaaga accaggtgtc cctgtggtgt ctggtgaaag gcttctaccc ctccgatatc   1140
gccgtggaat gggagagcaa cggccagccc gagaacaact acaagaccac ccccctgtg    1200 ctggacagcg acggctcatt cttcctgtac tccaagctga cagtggacaa gtcccggtgg   1260
cagcagggca acgtgttcag ctgctccgtg atgcacgagg ccctgcacaa ccactacacc   1320
cagaagtccc tgagcctgag ccccggc                                       1347
```

<210> SEQ ID NO 78
<211> LENGTH: 1719
<212> TYPE: DNA
<213> ORGANISM: Artificial Sequence
<220> FEATURE:
<223> OTHER INFORMATION: CD28supxCD3mid IgG1(hole) NNSA Heavy1
      polynucleotide sequence

<400> SEQUENCE: 78

```
caggtgcagc tggtgcagtc tggcgccgag gtcgtgaaac ctggcgcctc tgtgaaggtg     60
tcctgcaagg ccagcggcta caccttacc agctactaca tccactgggt gcgccaggcc    120
cctggacagg gactggaatg gatcggcagc atctaccccg gcaacgtgaa caccaactac    180
gcccagaagt tccagggcag agccaccctg accgtggaca ccagcatcag caccgcctac    240
atggaactga gccggctgag aagcgacgac accgccgtgt actactgcac ccggtcccac    300
tacggcctgg attggaactt cgacgtgtgg ggcaagggca ccaccgtgac agtgtctagc    360
agccaggtgc agctggtgga atctggcggc ggagtggtgc agcctggcag aagcctgaga    420
ctgagctgtg ccgccagcgg cttcaccttc accaaggcct ggatgcactg ggtgcgccag    480
gcccctggaa agcagctgga atgggtggcc cagatcaagg acaagagcaa cagctacgcc    540
acctactacg ccgacagcgt gaagggccgg ttcaccatca gccgggacga cagcaagaac    600
accctgtacc tgcagatgaa cagcctgcgg gccgaggaca ccgccgtgta ctactgtcgg    660
ggcgtgtact atgccctgag cccttcgat tactggggcc agggaaccct cgtgaccgtg    720
tctagtcgga ccgccagcac aaagggcccc agcgtgttcc ctctggcccc tagcagcaag    780
agcacatctg gcggaacagc cgccctgggc tgcctcgtga aggactactt tcccgagccc    840
gtgaccgtgt cctggaattc tggcgccctg accagcggcg tgcacacctt ccagcctgtg    900
ctgcagtcca gcggcctgta cagcctgagc agcgtcgtga cagtgcccag cagctctctg    960
ggcacccaga cctacatctg caacgtgaac cacaagccca gcaacaccaa ggtggacaag   1020
aaggtggaac ccaagagctg cgacaagacc cacacctgtc cccttgtcc tgcccccgaa    1080 ctgctgggag gcccttccgt gttcctgttc ccccaaagc ccaaggacac cctgatgatc    1140
agccggaccc ccgaagtgac ctgcgtggtg gtggatgtgt cccacgagga ccctgaagtg   1200
aagttcaatt ggtacgtgga cggcgtggaa gtgcacaacg ccaagaccaa gccaagagag   1260
gaacagtaca acagtgcctc ccgggtggtg tccgtgctga ccgtgctgca ccaggactgg   1320
ctgaacggca aagagtacaa gtgcaaggtg tccaacaagg ccctgcctgc ccccatcgag   1380
aaaaccatca gcaaggccaa gggccagccc cgcgaacccc aggtgtgcac actgcccca    1440 agcagggacg agctgaccaa gaaccaggtg tccctgagct gtgccgtgaa aggcttctac   1500
ccctccgata tcgccgtgga atgggagagc aacggccagc ccgagaacaa ctacaagacc   1560 acccccctg tgctggacag cgacggctca ttcttcctgg tgtccaagct gacagtggac   1620
```

<210> SEQ ID NO 79
<211> LENGTH: 1347
<212> TYPE: DNA
<213> ORGANISM: Artificial Sequence
<220> FEATURE:
<223> OTHER INFORMATION: CD38VH1 IgG1(knob) NNSA Heavy2 polynucleotide sequence

<400> SEQUENCE: 79

```
caggtgcagc tggtgcagtc tggcgccgaa gtcgtgaaac ctggcgcctc cgtgaaggtg      60
tcctgcaagg ccagcggcta cacctttacc agctacgcca tgcactgggt caaagaggcc     120
cctggccaga ctggaatg gatcggctac atctaccccg gccagggcgg caccaactac     180
aaccagaagt ccagggcag agccaccctg accgccgata agcgccag caccgcctac     240
atggaactga gcagcctgcg gagcgaggat accgccgtgt acttctgtgc cagaacaggc     300
ggcctgaggc gggcctactt tacctattgg ggccagggca cctcgtgac cgtgtctagc     360
gctagcacaa agggcccatc ggtcttcccc ctggcaccct cctccaagag cacctctggg     420
ggcacagcgg ccctgggctg cctggtcaag gactacttcc ccgaaccggt gacggtgtcg     480
tggaactcag gcgccctgac cagcggcgtg cacaccttcc cggctgtcct acagtcctca     540
ggactctact ccctcagcag cgtggtgacc gtgccctcca gcagcttggg cacccagacc     600
tacatctgca acgtgaatca caagcccagc aacaccaagg tggacaagaa agttgagccc     660
aaatcttgtg acaaaactca cacatgccca ccgtgcccag cacctgaact cctggggga     720
ccgtcagtct tcctcttccc cccaaaaccc aaggacaccc tcatgatctc ccggacccct     780
gaggtcacat gcgtggtggt ggacgtgagc cacgaagacc ctgaggtcaa gttcaactgg     840
tatgttgacg gcgtggaggt gcataatgcc aagacaaagc cgcgggagga gcagtacaac     900
aatgcctccc gtgtggtcag cgtcctcacc gtcctgcacc aggactggct gaatggcaag     960
gagtacaagt gcaaggtctc caacaaagcc ctcccagccc ccatcgagaa aaccatctcc    1020
aaagccaaag ggcagccccg agaaccacag gtgtacaccc tgcccccatg ccgggatgag    1080
ctgaccaaga tcaagtcag cctgtggtgc ctggtaaaag gcttctatcc cagcgacatc    1140
gccgtggagt gggagagcaa tgggcagccg gagaacaact acaagaccac gcctcccgtg    1200
ctggactccg acggctcctt cttcctctac tcaaaactca ccgtggacaa gagcaggtgg    1260
cagcagggga acgtcttctc atgctccgtg atgcatgagg ctctgcacaa ccactacacg    1320
cagaagagcc tctccctgtc tccgggt                                       1347
```

<210> SEQ ID NO 80
<211> LENGTH: 1329
<212> TYPE: DNA
<213> ORGANISM: Artificial Sequence
<220> FEATURE:
<223> OTHER INFORMATION: CD38hhy1370 IgG4(knob) FALA P329A Heavy2 polynucleotide sequence

<400> SEQUENCE: 80

```
caggtgcagc tggtggaaag cggcggaggc gtggtgcagc ctggcaggtc tctgagactg      60
agctgtgccg ccagcggctt cacctcagc agctacggaa tgcactgggt gcgccaggcc     120
cctggcaaag actggaatg ggtggccgtg atttggtacg acggcagcaa caagtactac     180
gccgacagcg tgaagggccg gttcaccatc agcgccgaca acagcaagaa caccctgtac     240
```

```
ctgcagatga acagcctgcg ggccgaggac accgccgtgt actactgcgc cagaatgttc      300
agaggcgcct tcgactactg gggccagggc acactcgtga ccgtgtctag tgcgtcgacc      360
aagggcccat cggtgttccc tctggcccct gcagcagaa gcaccagcga atctacagcc       420
gccctgggct gcctcgtgaa ggactacttt cccgagcccg tgaccgtgtc ctggaactct      480
ggcgctctga caagcggcgt gcacaccttt ccagccgtgc tccagagcag cggcctgtac      540
tctctgagca gcgtcgtgac agtgccagc agcagcctgg gcaccaagac ctacacctgt       600
aacgtggacc acaagcccag caacaccaag gtggacaagc gggtggaatc taagtacggc      660 cctcccctgcc ctccttgccc agcccctgaa gctgccggcg acccctccgt gttcctgttc     720
cccccaaagc ccaaggacac cctgatgatc agccggaccc ccgaagtgac ctgcgtggtg      780
gtggatgtgt cccaggaaga tcccgagtg cagttcaatt ggtacgtgga cggcgtggaa       840
gtgcacaacg ccaagaccaa gccagagag gaacagttca acagcaccta ccgggtggtg      900
tccgtgctga ccgtgctgca ccaggactgg ctgaacggca agagtacaa gtgcaaggtg       960 tccaacaagg gcctgcccag ctccatcgag aaaaccatca gcaaggccaa gggccagccc     1020
cgcgagcctc aagtgtatac cctgccccct gccaggaag agatgaccaa gaaccaggtg      1080
tccctgtggt gtctcgtgaa aggcttctac cccagcgaca ttgccgtgga atgggagagc     1140
aacggccagc cgagaacaa ctacaagacc accccccctg tgctggacag cgacggctca     1200
ttcttcctgt actccaagct gaccgtggac aagagccggt ggcaggaag caacgtgttc     1260 agctgctccg tgatgcacga ggccctgcac aaccactaca cccagaagtc cctgtctctg    1320
tccctgggc                                                              1329

<210> SEQ ID NO 81
<211> LENGTH: 642
<212> TYPE: DNA
<213> ORGANISM: Artificial Sequence
<220> FEATURE:
<223> OTHER INFORMATION: CD38hhy1370 Light2 polynucleotide sequence

<400> SEQUENCE: 81
gccatccaga tgacccagag ccccagcagc ctgtctgcca gcgtgggcga cagagtgacc       60
atcacctgta gagccagcca gggcatccgg aacgacctgg gctggtatca gcagaagcct      120
ggcaaggccc ccaagctgct gatctacgcc gctagctctc tgcagtccgg cgtgcccagc      180 agatttctg gcagcggctc cggcaccgac ttcaccctga caatctctgg cctgcagccc      240
gaggacagcg ccacctacta ctgtctgcaa gactacatct actaccccac cttcggccag      300
ggcaccaagg tggaaatcaa gcgtacggtg gccgctccca gcgtgttcat cttcccacct      360
agcgacgagc agctgaagtc cggcacagcc tctgtcgtgt gcctgctgaa caacttctac      420
ccccgcgagg ccaaagtgca gtggaaggtg gacaacgccc tgcagagcgg caacagccag     480
gaaagcgtga ccgagcagga cagcaaggac tccacctaca gcctgagcag caccctgaca    540
ctgagcaagg ccgactacga gaagcacaag gtgtacgcct gcgaagtgac ccaccagggc    600
ctgtctagcc ccgtgaccaa gagcttcaac cggggcgagt gt                         642

<210> SEQ ID NO 82
<211> LENGTH: 1338
<212> TYPE: DNA
<213> ORGANISM: Artificial Sequence
<220> FEATURE:
<223> OTHER INFORMATION: CD38hhy1370 IgG1(knob) LALA P329A Heavy2
      polynucleotide sequence
```

<400> SEQUENCE: 82

```
caggtgcagc tggtggaaag cggcggaggc gtggtgcagc tggcaggtc tctgagactg      60
agctgtgccg ccagcggctt caccttcagc agctacggaa tgcactgggt gcgccaggcc    120
cctggcaaag gactggaatg ggtggccgtg atttggtacg acggcagcaa caagtactac    180
gccgacagcg tgaagggccg gttcaccatc agcggcgaca acagcaagaa caccctgtac    240
ctgcagatga acagcctgcg ggccgaggac accgccgtgt actactgcgc cagaatgttc    300
agaggcgcct tcgactactg gggccagggc acactcgtga ccgtgtctag tgcgtcgacc    360
aagggcccca gcgtgttccc tctggcccct agcagcaaga gcacatctgg cggaacagcc    420
gccctgggct gcctcgtgaa ggactacttt cccgagcccg tgaccgtgtc ctggaattct    480
ggcgccctga ccagcggcgt gcacaccttt ccagctgtgc tgcagtccag cggcctgtac    540
agcctgagca gcgtcgtgac agtgcccagc agctctctgg cacccagac ctacatctgc    600
aacgtgaacc acaagcccag caacaccaag gtggacaaga aggtggaacc caagagctgc    660
gacaagaccc acacctgtcc cccttgtcct gcccccgaag ccgccggagg cccttccgtg    720
ttcctgttcc ccccaaagcc caaggacacc ctgatgatca gccggacccc cgaagtgacc    780
tgcgtggtgg tggatgtgtc ccacgaggac cctgaagtga agttcaattg gtacgtggac    840
ggcgtggaag tgcacaacgc caagaccaag ccaagagagg aacagtacaa cagcacctac    900
cgggtggtgt ccgtgctgac cgtgctgcac caggactggc tgaacggcaa agagtacaag    960
tgcaaggtgt ccaacaaggc cctggccgcc cccatcgaga aaaccatcag caaggccaag   1020
ggccagcccc gcgaacccca ggtgtacaca ctgcccccat gcagggacga gctgaccaag   1080
aaccaggtgt ccctgtggtg tctggtgaaa ggcttctacc cctccgatat cgccgtggaa   1140
tgggagagca acggccagcc cgagaacaac tacaagacca cccccctgt gctggacagc   1200
gacggctcat tcttcctgta ctccaagctg acagtggaca agtccggtg cagcagggc    1260
aacgtgttca gctgctccgt gatgcacgag gccctgcaca accactacac ccagaagtcc   1320
ctgagcctga gccccggc                                                  1338
```

<210> SEQ ID NO 83
<211> LENGTH: 1338
<212> TYPE: DNA
<213> ORGANISM: Artificial Sequence
<220> FEATURE:
<223> OTHER INFORMATION: CD38hhy1370 IgG1(knob) NNSA Heavy2 polynucleotide sequence

<400> SEQUENCE: 83

```
caggtgcagc tggtggaaag cggcggaggc gtggtgcagc tggcaggtc tctgagactg      60
agctgtgccg ccagcggctt caccttcagc agctacggaa tgcactgggt gcgccaggcc    120
cctggcaaag gactggaatg ggtggccgtg atttggtacg acggcagcaa caagtactac    180
gccgacagcg tgaagggccg gttcaccatc agcggcgaca acagcaagaa caccctgtac    240
ctgcagatga acagcctgcg ggccgaggac accgccgtgt actactgcgc cagaatgttc    300
agaggcgcct tcgactactg gggccagggc acactcgtga ccgtgtctag tgcgtcgacc    360
aagggcccat cggtcttccc cctggcaccc tcctccaaga gcacctctgg gggcacagcg    420
gccctgggct gcctggtcaa ggactacttc cccgaaccgg tgacggtgtc gtggaactca    480
ggcgccctga ccagcggcgt gcacaccttc ccggctgtcc tacagtcctc aggactctac    540
tccctcagca gcgtggtgac cgtgccctcc agcagcttgg gcacccagac ctacatctgc    600
```

```
aacgtgaatc acaagcccag caacaccaag gtggacaaga agttgagccc caaatcttgt     660
gacaaaactc acacatgccc accgtgccca gcacctgaac tcctgggggg accgtcagtc     720
ttcctcttcc ccccaaaacc caaggacacc ctcatgatct cccggacccc tgaggtcaca     780
tgcgtggtgg tggacgtgag ccacgaagac cctgaggtca agttcaactg gtatgttgac     840
ggcgtggagg tgcataatgc caagacaaag ccgcgggagg agcagtacaa caatgcctcc     900
cgtgtggtca gcgtcctcac cgtcctgcac caggactggc tgaatggcaa ggagtacaag     960
tgcaaggtct ccaacaaagc cctcccagcc cccatcgaga aaccatctc caaagccaaa     1020 gggcagcccc gagaaccaca ggtgtacacc ctgcccccat gccgggatga gctgaccaag    1080
aatcaagtca gcctgtggtg cctggtaaaa ggcttctatc ccagcgacat cgccgtggag    1140
tgggagagca atgggcagcc ggagaacaac tacaagacca cgcctcccgt gctggactcc    1200
gacggctcct tcttcctcta ctcaaaactc accgtggaca agagcaggtg gcagcagggg    1260
aacgtcttct catgctccgt gatgcatgag gctctgcaca accactacac gcagaagagc    1320 ctctcccctgt ctccgggt                                                  1338
```

<210> SEQ ID NO 84
<211> LENGTH: 121
<212> TYPE: PRT
<213> ORGANISM: Artificial Sequence
<220> FEATURE:
<223> OTHER INFORMATION: anti-CD3low VH domain

<400> SEQUENCE: 84

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Thr Lys Ala
            20                  25                  30

Trp Met His Trp Val Arg Gln Ala Pro Gly Lys Gly Leu Glu Trp Val
        35                  40                  45

Ala Gln Ile Lys Asp Lys Ser Asn Ser Tyr Ala Thr Tyr Tyr Ala Asp
    50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Arg Gly Val Tyr Tyr Ala Leu Ser Pro Phe Asp Tyr Trp Gly
            100                 105                 110

Gln Gly Thr Leu Val Thr Val Ser Ser
        115                 120
```

<210> SEQ ID NO 85
<211> LENGTH: 112
<212> TYPE: PRT
<213> ORGANISM: Artificial Sequence
<220> FEATURE:
<223> OTHER INFORMATION: anti-CD3low VL domain

<400> SEQUENCE: 85

```
Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Val His Asn
            20                  25                  30

Asn Gly Asn Thr Tyr Leu Ser Trp Tyr Leu Gln Lys Pro Gly Gln Ser
        35                  40                  45
```

```
Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Gly Gln Gly
                85                  90                  95

Thr Gln Tyr Pro Phe Thr Phe Gly Gly Gly Thr Lys Val Glu Ile Lys
            100                 105                 110
```

<210> SEQ ID NO 86
<211> LENGTH: 25
<212> TYPE: PRT
<213> ORGANISM: Artificial Sequence
<220> FEATURE:
<223> OTHER INFORMATION: mAb2/mAb3 VH FW1

<400> SEQUENCE: 86

```
Gln Val Gln Leu Val Gln Ser Gly Ala Glu Val Val Lys Pro Gly Ala
1               5                   10                  15

Ser Val Lys Val Ser Cys Lys Ala Ser
            20                  25
```

<210> SEQ ID NO 87
<211> LENGTH: 25
<212> TYPE: PRT
<213> ORGANISM: Artificial Sequence
<220> FEATURE:
<223> OTHER INFORMATION: mAb4 VH FW1

<400> SEQUENCE: 87

```
Gln Val Gln Leu Val Gln Ser Gly Ala Glu Val Val Lys Ser Gly Ala
1               5                   10                  15

Ser Val Lys Val Ser Cys Lys Ala Ser
            20                  25
```

<210> SEQ ID NO 88
<211> LENGTH: 25
<212> TYPE: PRT
<213> ORGANISM: Artificial Sequence
<220> FEATURE:
<223> OTHER INFORMATION: mAb5 VH FW1

<400> SEQUENCE: 88

```
Gln Val Gln Leu Val Gln Ser Gly Ala Glu Val Val Lys Pro Gly Ala
1               5                   10                  15

Ser Val Lys Met Ser Cys Lys Ala Ser
            20                  25
```

<210> SEQ ID NO 89
<211> LENGTH: 25
<212> TYPE: PRT
<213> ORGANISM: Artificial Sequence
<220> FEATURE:
<223> OTHER INFORMATION: mAb6 VH FW1

<400> SEQUENCE: 89

```
Gln Val Gln Leu Val Glu Ser Gly Gly Gly Val Val Gln Pro Gly Arg
1               5                   10                  15

Ser Leu Arg Leu Ser Cys Ala Ala Ser
            20                  25
```

<210> SEQ ID NO 90

```
<211> LENGTH: 17
<212> TYPE: PRT
<213> ORGANISM: Artificial Sequence
<220> FEATURE:
<223> OTHER INFORMATION: mAb2/mAb3/mAb5 VH FW2

<400> SEQUENCE: 90

Met His Trp Val Lys Glu Ala Pro Gly Gln Arg Leu Glu Trp Ile Gly
1               5                   10                  15
Tyr

<210> SEQ ID NO 91
<211> LENGTH: 17
<212> TYPE: PRT
<213> ORGANISM: Artificial Sequence
<220> FEATURE:
<223> OTHER INFORMATION: mAb4 VH FW2

<400> SEQUENCE: 91

Met His Trp Val Lys Glu Ala Pro Gly Gln Gly Leu Glu Trp Ile Gly
1               5                   10                  15
Tyr

<210> SEQ ID NO 92
<211> LENGTH: 17
<212> TYPE: PRT
<213> ORGANISM: Artificial Sequence
<220> FEATURE:
<223> OTHER INFORMATION: mAb6 VH FW2

<400> SEQUENCE: 92

Met His Trp Val Arg Gln Ala Pro Gly Lys Gly Leu Glu Trp Val Ala
1               5                   10                  15
Val

<210> SEQ ID NO 93
<211> LENGTH: 38
<212> TYPE: PRT
<213> ORGANISM: Artificial Sequence
<220> FEATURE:
<223> OTHER INFORMATION: mAb2/mAb3 VH FW3

<400> SEQUENCE: 93

Asn Tyr Asn Gln Lys Phe Gln Gly Arg Ala Thr Leu Thr Ala Asp Thr
1               5                   10                  15

Ser Ala Ser Thr Ala Tyr Met Glu Leu Ser Ser Leu Arg Ser Glu Asp
            20                  25                  30

Thr Ala Val Tyr Phe Cys
        35

<210> SEQ ID NO 94
<211> LENGTH: 38
<212> TYPE: PRT
<213> ORGANISM: Artificial Sequence
<220> FEATURE:
<223> OTHER INFORMATION: mAb4/mAb5 VH FW3

<400> SEQUENCE: 94

Asn Tyr Asn Gln Lys Phe Gln Gly Arg Ala Thr Leu Thr Ala Asp Thr
1               5                   10                  15

Ser Ala Ser Thr Ala Tyr Met Glu Ile Ser Ser Leu Arg Ser Glu Asp
            20                  25                  30

Thr Ala Val Tyr Phe Cys
```

```
<210> SEQ ID NO 95
<211> LENGTH: 38
<212> TYPE: PRT
<213> ORGANISM: Artificial Sequence
<220> FEATURE:
<223> OTHER INFORMATION: mAb6 VH FW3

<400> SEQUENCE: 95

Tyr Tyr Ala Asp Ser Val Lys Gly Arg Phe Thr Ile Ser Gly Asp Asn
1               5                   10                  15

Ser Lys Asn Thr Leu Tyr Leu Gln Met Asn Ser Leu Arg Ala Glu Asp
            20                  25                  30

Thr Ala Val Tyr Tyr Cys
        35

<210> SEQ ID NO 96
<211> LENGTH: 11
<212> TYPE: PRT
<213> ORGANISM: Artificial Sequence
<220> FEATURE:
<223> OTHER INFORMATION: mAb2/mAb3/mAb4/mAb5/mAb6 VH FW4

<400> SEQUENCE: 96

Trp Gly Gln Gly Thr Leu Val Thr Val Ser Ser
1               5                   10

<210> SEQ ID NO 97
<211> LENGTH: 26
<212> TYPE: PRT
<213> ORGANISM: Artificial Sequence
<220> FEATURE:
<223> OTHER INFORMATION: mAb2/mAb3/mAb4/mAb5 VL FW1

<400> SEQUENCE: 97

Asp Ile Val Leu Thr Gln Ser Pro Ala Thr Leu Ser Leu Ser Pro Gly
1               5                   10                  15

Glu Arg Ala Thr Ile Ser Cys Arg Ala Ser
            20                  25

<210> SEQ ID NO 98
<211> LENGTH: 26
<212> TYPE: PRT
<213> ORGANISM: Artificial Sequence
<220> FEATURE:
<223> OTHER INFORMATION: mAb6 VL FW1

<400> SEQUENCE: 98

Ala Ile Gln Met Thr Gln Ser Pro Ser Ser Leu Ser Ala Ser Val Gly
1               5                   10                  15

Asp Arg Val Thr Ile Thr Cys Arg Ala Ser
            20                  25

<210> SEQ ID NO 99
<211> LENGTH: 17
<212> TYPE: PRT
<213> ORGANISM: Artificial Sequence
<220> FEATURE:
<223> OTHER INFORMATION: mAb2/mAb3/mAb4/mAb5 VL FW2

<400> SEQUENCE: 99

Met His Trp Tyr Gln Gln Lys Pro Gly Gln Pro Pro Arg Leu Leu Ile
1               5                   10                  15
```

Tyr

<210> SEQ ID NO 100
<211> LENGTH: 16
<212> TYPE: PRT
<213> ORGANISM: Artificial Sequence
<220> FEATURE:
<223> OTHER INFORMATION: mAb6 VL FW2

<400> SEQUENCE: 100

Gly Trp Tyr Gln Gln Lys Pro Gly Lys Ala Pro Lys Leu Leu Ile Tyr
1               5                   10                  15

<210> SEQ ID NO 101
<211> LENGTH: 36
<212> TYPE: PRT
<213> ORGANISM: Artificial Sequence
<220> FEATURE:
<223> OTHER INFORMATION: mAb2/mAb3/mAb4/mAb5 VL FW3

<400> SEQUENCE: 101

Ser Arg Ala Thr Gly Ile Pro Ala Arg Phe Ser Gly Ser Gly Ser Gly
1               5                   10                  15

Thr Asp Phe Thr Leu Thr Ile Ser Pro Leu Glu Pro Glu Asp Phe Ala
            20                  25                  30

Val Tyr Tyr Cys
        35

<210> SEQ ID NO 102
<211> LENGTH: 36
<212> TYPE: PRT
<213> ORGANISM: Artificial Sequence
<220> FEATURE:
<223> OTHER INFORMATION: mAb6 VL FW3

<400> SEQUENCE: 102

Ser Leu Gln Ser Gly Val Pro Ser Arg Phe Ser Gly Ser Gly Ser Gly
1               5                   10                  15

Thr Asp Phe Thr Leu Thr Ile Ser Gly Leu Gln Pro Glu Asp Ser Ala
            20                  25                  30

Thr Tyr Tyr Cys
        35

<210> SEQ ID NO 103
<211> LENGTH: 10
<212> TYPE: PRT
<213> ORGANISM: Artificial Sequence
<220> FEATURE:
<223> OTHER INFORMATION: mAb2/mAb3/mAb4/mAb5 VL FW4

<400> SEQUENCE: 103

Phe Gly Gly Gly Thr Lys Leu Glu Ile Lys
1               5                   10

<210> SEQ ID NO 104
<211> LENGTH: 11
<212> TYPE: PRT
<213> ORGANISM: Artificial Sequence
<220> FEATURE:
<223> OTHER INFORMATION: mAb6 VL FW4

<400> SEQUENCE: 104

Trp Gly Gln Gly Thr Leu Val Thr Val Ser Ser
1               5                   10

```
<210> SEQ ID NO 105
<211> LENGTH: 159
<212> TYPE: PRT
<213> ORGANISM: Artificial Sequence
<220> FEATURE:
<223> OTHER INFORMATION: CD38 isoform E sequence

<400> SEQUENCE: 105

Arg Trp Arg Gln Gln Trp Ser Gly Pro Gly Thr Thr Lys Arg Phe Pro
1               5                   10                  15

Glu Thr Val Leu Ala Arg Cys Val Lys Tyr Thr Glu Ile His Pro Glu
            20                  25                  30

Met Arg His Val Asp Cys Gln Ser Val Trp Asp Ala Phe Lys Gly Ala
        35                  40                  45

Phe Ile Ser Lys His Pro Cys Asn Ile Thr Glu Glu Asp Tyr Gln Pro
    50                  55                  60

Leu Met Lys Leu Gly Thr Gln Thr Val Pro Cys Asn Lys Ile Leu Leu
65                  70                  75                  80

Trp Ser Arg Ile Lys Asp Leu Ala His Gln Phe Thr Gln Val Gln Arg
                85                  90                  95

Asp Met Phe Thr Leu Glu Asp Thr Leu Leu Gly Tyr Leu Ala Asp Asp
            100                 105                 110

Leu Thr Trp Cys Gly Glu Phe Asn Thr Ser Lys Ile Asn Tyr Gln Ser
        115                 120                 125

Cys Pro Asp Trp Arg Lys Asp Cys Ser Asn Asn Pro Val Ser Val Phe
    130                 135                 140

Trp Lys Thr Val Ser Arg Arg His Phe Trp Glu Cys Gly Ser Pro
145                 150                 155

<210> SEQ ID NO 106
<211> LENGTH: 214
<212> TYPE: PRT
<213> ORGANISM: Artificial Sequence
<220> FEATURE:
<223> OTHER INFORMATION: mAb7 light chain

<400> SEQUENCE: 106

Asp Ile Val Met Thr Gln Ser His Leu Ser Met Ser Thr Ser Leu Gly
1               5                   10                  15

Asp Pro Val Ser Ile Thr Cys Lys Ala Ser Gln Asp Val Ser Thr Val
            20                  25                  30

Val Ala Trp Tyr Gln Gln Lys Pro Gly Gln Ser Pro Arg Arg Leu Ile
        35                  40                  45

Tyr Ser Ala Ser Tyr Arg Tyr Ile Gly Val Pro Asp Arg Phe Thr Gly
    50                  55                  60

Ser Gly Ala Gly Thr Asp Phe Thr Phe Thr Ile Ser Ser Val Gln Ala
65                  70                  75                  80

Glu Asp Leu Ala Val Tyr Tyr Cys Gln Gln His Tyr Ser Pro Pro Tyr
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160
```

Glu Ser Val Thr Glu Gln Asp Ser Lys Asp Ser Thr Tyr Ser Leu Ser
            165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
            210

<210> SEQ ID NO 107
<211> LENGTH: 450
<212> TYPE: PRT
<213> ORGANISM: Artificial Sequence
<220> FEATURE:
<223> OTHER INFORMATION: mAb7 heavy chain

<400> SEQUENCE: 107

Gln Val Gln Leu Val Gln Ser Gly Ala Glu Val Ala Lys Pro Gly Thr
1               5                   10                  15

Ser Val Lys Leu Ser Cys Lys Ala Ser Gly Tyr Thr Phe Thr Asp Tyr
            20                  25                  30

Trp Met Gln Trp Val Lys Gln Arg Pro Gly Gln Gly Leu Glu Trp Ile
            35                  40                  45

Gly Thr Ile Tyr Pro Gly Asp Gly Asp Thr Gly Tyr Ala Gln Lys Phe
    50                  55                  60

Gln Gly Lys Ala Thr Leu Thr Ala Asp Lys Ser Ser Lys Thr Val Tyr
65                  70                  75                  80

Met His Leu Ser Ser Leu Ala Ser Glu Asp Ser Ala Val Tyr Tyr Cys
                85                  90                  95

Ala Arg Gly Asp Tyr Tyr Gly Ser Asn Ser Leu Asp Tyr Trp Gly Gln
            100                 105                 110

Gly Thr Ser Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
            130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
            165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
            195                 200                 205

Pro Ser Asn Thr Lys Val Asp Lys Lys Val Glu Pro Lys Ser Cys Asp
            210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
            245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
            290                 295                 300

```
Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
            325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
            355                 360                 365

Thr Cys Leu Val Lys Gly Phe Tyr Pro Ser Asp Ile Ala Val Glu Trp
        370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 108
<211> LENGTH: 445
<212> TYPE: PRT
<213> ORGANISM: Artificial Sequence
<220> FEATURE:
<223> OTHER INFORMATION: benchmark heavy chain 1 (binds CD38)

<400> SEQUENCE: 108

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Tyr Ser
            20                  25                  30

Trp Met Asn Trp Val Arg Gln Ala Pro Gly Lys Gly Leu Glu Trp Val
        35                  40                  45

Ser Glu Ile Asn Pro Gln Ser Ser Thr Ile Asn Tyr Ala Thr Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Arg Tyr Gly Asn Trp Phe Pro Tyr Trp Gly Gln Gly Thr Leu Val
            100                 105                 110

Thr Val Ser Ser Ala Ser Thr Lys Gly Pro Ser Val Phe Pro Leu Ala
            115                 120                 125

Pro Ser Ser Lys Ser Thr Ser Gly Gly Thr Ala Ala Leu Gly Cys Leu
        130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
            165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asp Thr
            195                 200                 205
```

```
Lys Val Asp Lys Lys Val Glu Pro Lys Ser Cys Asp Lys Thr His Thr
            210                 215                 220

Cys Pro Pro Cys Pro Ala Pro Pro Val Ala Gly Pro Ser Val Phe Leu
225                 230                 235                 240

Phe Pro Pro Lys Pro Lys Asp Thr Leu Met Ile Ser Arg Thr Pro Glu
            245                 250                 255

Val Thr Cys Val Val Val Asp Val Lys His Glu Asp Pro Glu Val Lys
            260                 265                 270

Phe Asn Trp Tyr Val Asp Gly Val Glu Val His Asn Ala Lys Thr Lys
            275                 280                 285

Pro Arg Glu Glu Glu Tyr Asn Ser Thr Tyr Arg Val Val Ser Val Leu
            290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
            325                 330                 335

Ala Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Asp Val Ser
            355                 360                 365

Gly Phe Tyr Pro Ser Asp Ile Ala Val Glu Trp Glu Ser Asp Gly Gln
            370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Glu
            405                 410                 415

Gln Gly Asp Val Phe Ser Cys Ser Val Met His Glu Ala Leu His Asn
            420                 425                 430

His Tyr Thr Gln Lys Ser Leu Ser Leu Ser Pro Gly Lys
            435                 440                 445

<210> SEQ ID NO 109
<211> LENGTH: 485
<212> TYPE: PRT
<213> ORGANISM: Artificial Sequence
<220> FEATURE:
<223> OTHER INFORMATION: benchmark heavy chain 2 (binds CD3)

<400> SEQUENCE: 109

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Gly Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
            85                  90                  95

Tyr Cys Val Arg His Gly Asn Phe Gly Asp Ser Tyr Val Ser Trp Phe
            100                 105                 110

Ala Tyr Trp Gly Gln Gly Thr Leu Val Thr Val Ser Ser Gly Lys Pro
        115                 120                 125
```

```
Gly Ser Gly Lys Pro Gly Ser Gly Lys Pro Gly Ser Gly Lys Pro Gly
        130                 135                 140

Ser Gln Ala Val Val Thr Gln Glu Pro Ser Leu Thr Val Ser Pro Gly
145                 150                 155                 160

Gly Thr Val Thr Leu Thr Cys Gly Ser Ser Thr Gly Ala Val Thr Thr
                165                 170                 175

Ser Asn Tyr Ala Asn Trp Val Gln Gln Lys Pro Gly Lys Ser Pro Arg
            180                 185                 190

Gly Leu Ile Gly Gly Thr Asn Lys Arg Ala Pro Gly Val Pro Ala Arg
        195                 200                 205

Phe Ser Gly Ser Leu Leu Gly Gly Lys Ala Ala Leu Thr Ile Ser Gly
210                 215                 220

Ala Gln Pro Glu Asp Glu Ala Asp Tyr Tyr Cys Ala Leu Trp Tyr Ser
225                 230                 235                 240

Asn His Trp Val Phe Gly Gly Gly Thr Lys Leu Thr Val Leu Glu Pro
                245                 250                 255

Lys Ser Ser Asp Lys Thr His Thr Cys Pro Pro Cys Pro Ala Pro Pro
            260                 265                 270

Val Ala Gly Pro Ser Val Phe Leu Phe Pro Pro Lys Pro Lys Asp Thr
        275                 280                 285

Leu Met Ile Ser Arg Thr Pro Glu Val Thr Cys Val Val Val Asp Val
290                 295                 300

Lys His Glu Asp Pro Glu Val Lys Phe Asn Trp Tyr Val Asp Gly Val
305                 310                 315                 320

Glu Val His Asn Ala Lys Thr Lys Pro Arg Glu Glu Gln Tyr Asn Ser
                325                 330                 335

Thr Tyr Arg Val Val Ser Val Leu Thr Val Leu His Gln Asp Trp Leu
            340                 345                 350

Asn Gly Lys Glu Tyr Lys Cys Lys Val Ser Asn Lys Ala Leu Pro Ala
        355                 360                 365

Pro Ile Glu Lys Thr Ile Ser Lys Ala Lys Gly Gln Pro Arg Glu Pro
370                 375                 380

Gln Val Tyr Thr Leu Pro Pro Ser Arg Glu Gln Met Thr Lys Asn Gln
385                 390                 395                 400

Val Lys Leu Thr Cys Leu Val Lys Gly Phe Tyr Pro Ser Asp Ile Ala
                405                 410                 415

Val Glu Trp Glu Ser Asn Gly Gln Pro Glu Asn Asn Tyr Lys Thr Thr
            420                 425                 430

Pro Pro Val Leu Asp Ser Asp Gly Ser Phe Phe Leu Tyr Ser Lys Leu
        435                 440                 445

Thr Val Asp Lys Ser Arg Trp Gln Gln Gly Asn Val Phe Ser Cys Ser
450                 455                 460

Val Met His Glu Ala Leu His Asn His Tyr Thr Gln Lys Ser Leu Ser
465                 470                 475                 480

Leu Ser Pro Gly Lys
                485

<210> SEQ ID NO 110
<211> LENGTH: 214
<212> TYPE: PRT
<213> ORGANISM: Artificial Sequence
<220> FEATURE:
<223> OTHER INFORMATION: benchmark light chain (binds CD38)

<400> SEQUENCE: 110
```

```
Asp Ile Val Met Thr Gln Ser Pro Ser Ser Leu Ser Ala Ser Val Gly
1               5                   10                  15

Asp Arg Val Thr Ile Thr Cys Arg Ala Ser Gln Asn Val Asp Thr Trp
            20                  25                  30

Val Ala Trp Tyr Gln Gln Lys Pro Gly Gln Ser Pro Lys Ala Leu Ile
        35                  40                  45

Tyr Ser Ala Ser Tyr Arg Tyr Ser Gly Val Pro Asp Arg Phe Thr Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Phe Cys Gln Gln Tyr Asp Ser Tyr Pro Leu
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
            210

<210> SEQ ID NO 111
<211> LENGTH: 14
<212> TYPE: PRT
<213> ORGANISM: Artificial Sequence
<220> FEATURE:
<223> OTHER INFORMATION: Synthetic Construct

<400> SEQUENCE: 111

Cys Pro Pro Cys Pro Ala Pro Glu Leu Leu Gly Gly Pro Ser
1               5                   10

<210> SEQ ID NO 112
<211> LENGTH: 13
<212> TYPE: PRT
<213> ORGANISM: Artificial Sequence
<220> FEATURE:
<223> OTHER INFORMATION: Synthetic Construct

<400> SEQUENCE: 112

Cys Pro Pro Cys Pro Ala Pro Pro Val Ala Gly Pro Ser
1               5                   10

<210> SEQ ID NO 113
<211> LENGTH: 14
<212> TYPE: PRT
<213> ORGANISM: Artificial Sequence
<220> FEATURE:
<223> OTHER INFORMATION: Synthetic Construct

<400> SEQUENCE: 113
```

Cys Pro Pro Cys Pro Ala Pro Glu Phe Leu Gly Gly Pro Ser
1               5                   10

<210> SEQ ID NO 114
<211> LENGTH: 14
<212> TYPE: PRT
<213> ORGANISM: Artificial Sequence
<220> FEATURE:
<223> OTHER INFORMATION: Synthetic Construct

<400> SEQUENCE: 114

Cys Pro Pro Cys Pro Ala Pro Glu Ala Ala Gly Gly Pro Ser
1               5                   10

<210> SEQ ID NO 115
<211> LENGTH: 12
<212> TYPE: PRT
<213> ORGANISM: Artificial Sequence
<220> FEATURE:
<223> OTHER INFORMATION: Synthetic Construct

<400> SEQUENCE: 115

Cys Pro Pro Cys Pro Ala Pro Val Ala Gly Pro Ser
1               5                   10

<210> SEQ ID NO 116
<211> LENGTH: 14
<212> TYPE: PRT
<213> ORGANISM: Artificial Sequence
<220> FEATURE:
<223> OTHER INFORMATION: Synthetic Construct

<400> SEQUENCE: 116

Cys Pro Pro Cys Pro Ala Pro Glu Ala Ala Gly Gly Pro Ser
1               5                   10

<210> SEQ ID NO 117
<211> LENGTH: 20
<212> TYPE: DNA
<213> ORGANISM: Artificial Sequence
<220> FEATURE:
<223> OTHER INFORMATION: Synthetic Construct

<400> SEQUENCE: 117
tacctgttac ttgaattgaa                                              20

<210> SEQ ID NO 118
<211> LENGTH: 20
<212> TYPE: DNA
<213> ORGANISM: Artificial Sequence
<220> FEATURE:
<223> OTHER INFORMATION: Synthetic Construct

<400> SEQUENCE: 118
attttttgag gtcttccaat                                              20

<210> SEQ ID NO 119
<211> LENGTH: 20
<212> TYPE: DNA
<213> ORGANISM: Artificial Sequence
<220> FEATURE:
<223> OTHER INFORMATION: Synthetic Construct

<400> SEQUENCE: 119
attgtcgtac gctacaagca                                              20

```
<210> SEQ ID NO 120
<211> LENGTH: 20
<212> TYPE: DNA
<213> ORGANISM: Artificial Sequence
<220> FEATURE:
<223> OTHER INFORMATION: Synthetic Construct

<400> SEQUENCE: 120
caaaagggct tagaaggtcc                                              20

<210> SEQ ID NO 121
<211> LENGTH: 20
<212> TYPE: DNA
<213> ORGANISM: Artificial Sequence
<220> FEATURE:
<223> OTHER INFORMATION: Synthetic Construct

<400> SEQUENCE: 121
ctatagcttg ctagtaacag                                              20

<210> SEQ ID NO 122
<211> LENGTH: 24
<212> TYPE: DNA
<213> ORGANISM: Artificial Sequence
<220> FEATURE:
<223> OTHER INFORMATION: Synthetic Construct

<400> SEQUENCE: 122
cacaacctgt ccccatccta tgaa                                         24

<210> SEQ ID NO 123
<211> LENGTH: 24
<212> TYPE: DNA
<213> ORGANISM: Artificial Sequence
<220> FEATURE:
<223> OTHER INFORMATION: Synthetic Construct

<400> SEQUENCE: 123
aagctgccat ccagatcgtt atcg                                         24

<210> SEQ ID NO 124
<211> LENGTH: 24
<212> TYPE: DNA
<213> ORGANISM: Artificial Sequence
<220> FEATURE:
<223> OTHER INFORMATION: Synthetic Construct

<400> SEQUENCE: 124
ccaaattaag ggccagctca ttcc                                         24

<210> SEQ ID NO 125
<211> LENGTH: 24
<212> TYPE: DNA
<213> ORGANISM: Artificial Sequence
<220> FEATURE:
<223> OTHER INFORMATION: Synthetic Construct

<400> SEQUENCE: 125
acctgtacat ccttgggcaa atcc                                         24

<210> SEQ ID NO 126
<211> LENGTH: 24
<212> TYPE: DNA
<213> ORGANISM: Artificial Sequence
<220> FEATURE:
<223> OTHER INFORMATION: Synthetic Construct
```

```
<400> SEQUENCE: 126
gtcaggatgc cttgtggttt gagt                                         24

<210> SEQ ID NO 127
<211> LENGTH: 23
<212> TYPE: DNA
<213> ORGANISM: Artificial Sequence
<220> FEATURE:
<223> OTHER INFORMATION: Synthetic Construct

<400> SEQUENCE: 127
cagagcttcc agagccaatc tac                                          23

<210> SEQ ID NO 128
<211> LENGTH: 24
<212> TYPE: DNA
<213> ORGANISM: Artificial Sequence
<220> FEATURE:
<223> OTHER INFORMATION: Synthetic Construct

<400> SEQUENCE: 128
ccatgtactg ccttctgggt gaaa                                         24

<210> SEQ ID NO 129
<211> LENGTH: 22
<212> TYPE: DNA
<213> ORGANISM: Artificial Sequence
<220> FEATURE:
<223> OTHER INFORMATION: Synthetic Construct

<400> SEQUENCE: 129
ccactgacca caacccagtt tt                                           22

<210> SEQ ID NO 130
<211> LENGTH: 22
<212> TYPE: DNA
<213> ORGANISM: Artificial Sequence
<220> FEATURE:
<223> OTHER INFORMATION: Synthetic Construct

<400> SEQUENCE: 130
aggccattgg aagtcaccgt tt                                           22

<210> SEQ ID NO 131
<211> LENGTH: 24
<212> TYPE: DNA
<213> ORGANISM: Artificial Sequence
<220> FEATURE:
<223> OTHER INFORMATION: Synthetic Construct

<400> SEQUENCE: 131
gccaacattg tccattggct tcag                                         24

<210> SEQ ID NO 132
<211> LENGTH: 9
<212> TYPE: PRT
<213> ORGANISM: Artificial Sequence
<220> FEATURE:
<223> OTHER INFORMATION: Synthetic Construct

<400> SEQUENCE: 132

Gln Ser Val Ser Ser Tyr Gly Gln Gly
1               5
```

UNITED STATES PATENT AND TRADEMARK OFFICE
CERTIFICATE OF CORRECTION

PATENT NO. : 11,365,261 B2  
APPLICATION NO. : 17/503038  
DATED : June 21, 2022  
INVENTOR(S) : Béatrice Cameron et al.

Page 1 of 1

It is certified that error appears in the above-identified patent and that said Letters Patent is hereby corrected as shown below:

On the Title Page

Page 2, Item (56) "Other Publications", Column 1 Line 19 please replace: "Interleukin-?" with --Interleukin-7--.

Signed and Sealed this  
Eighteenth Day of March, 2025

Coke Morgan Stewart  
*Acting Director of the United States Patent and Trademark Office*